(12) United States Patent
Azuma et al.

(10) Patent No.: US 9,888,688 B2
(45) Date of Patent: *Feb. 13, 2018

(54) TETRAZOLINONE COMPOUNDS AND APPLICATIONS THEREOF

(71) Applicant: Sumitomo Chemical Company, Limited, Tokyo (JP)

(72) Inventors: Shuhei Azuma, Takarazuka (JP); Sadayuki Arimori, Takarazuka (JP); Nao Maehata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/903,841

(22) PCT Filed: Jul. 10, 2014

(86) PCT No.: PCT/JP2014/069120
§ 371 (c)(1),
(2) Date: Jan. 8, 2016

(87) PCT Pub. No.: WO2015/005499
PCT Pub. Date: Jan. 15, 2015

(65) Prior Publication Data
US 2016/0150787 A1  Jun. 2, 2016

(30) Foreign Application Priority Data

Jul. 12, 2013 (JP) ................................. 2013-146105
Oct. 23, 2013 (JP) ................................. 2013-219865

(51) Int. Cl.
| | |
|---|---|
| A01N 43/54 | (2006.01) |
| A01N 43/64 | (2006.01) |
| A01N 43/713 | (2006.01) |
| C07D 403/12 | (2006.01) |
| C07D 401/12 | (2006.01) |
| C07D 257/04 | (2006.01) |
| C07F 5/02 | (2006.01) |
| C07D 213/30 | (2006.01) |

(52) U.S. Cl.
CPC ......... *A01N 43/713* (2013.01); *C07D 213/30* (2013.01); *C07D 257/04* (2013.01); *C07D 401/12* (2013.01); *C07D 403/12* (2013.01); *C07F 5/02* (2013.01)

(58) Field of Classification Search
CPC .... C07D 211/00; C07D 257/00; A01N 43/54; A01N 43/64
USPC ......................................... 546/245; 548/253
See application file for complete search history.

(56) References Cited

U.S. PATENT DOCUMENTS

| | | | |
|---|---|---|---|
| 6,583,090 B1 * | 6/2003 | Gewehr ............... | C07D 231/12 504/280 |
| 7,056,941 B1 | 6/2006 | Muller et al. | |
| 2004/0157740 A1 | 8/2004 | Maurer et al. | |
| 2005/0065197 A1 | 3/2005 | Gusmeroli et al. | |
| 2015/0299146 A1 | 10/2015 | Hasegawa et al. | |
| 2015/0336908 A1 | 11/2015 | Shioda et al. | |

(Continued)

FOREIGN PATENT DOCUMENTS

| | | |
|---|---|---|
| JP | H09208565 A | 8/1997 |
| JP | 2001510840 A | 8/2001 |

(Continued)

OTHER PUBLICATIONS

International Search Report and Written Opinion dated Sep. 30, 2014 in International Application No. PCT/JP2014/069120.

(Continued)

*Primary Examiner* — Timothy P Thomas
*Assistant Examiner* — George W Kosturko
(74) *Attorney, Agent, or Firm* — Panitch Schwarze Belisario & Nadel LLP

(57) ABSTRACT

A tetrazolinone compound represented by formula (1):

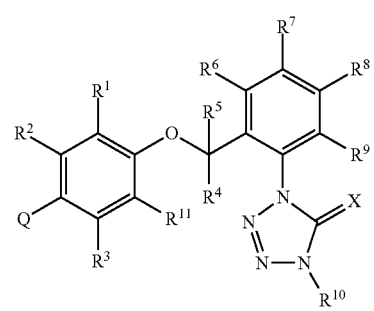

wherein Q represents a 6-membered aromatic heterocyclic group optionally having one or more atoms or groups selected from Group $P^1$, provided that a heteroatom constituting the heterocyclic group is a nitrogen atom, and the number of nitrogen atom is 1, 2, or 3; $R^1$, $R^2$, $R^3$, and $R^{11}$ each represents a C1-C6 alkyl group optionally having one or more atoms or groups selected from Group $P^2$; $R^4$ and $R^5$ each represents a hydrogen atom, etc.; $R^6$ represents a C1-C6 alkyl group optionally having one or more halogen atoms, etc.; $R^7$, $R^8$, and $R^9$ each represents a hydrogen atom, etc.; and X represents an oxygen atom or a sulfur atom, has excellent control activity against pests.

10 Claims, No Drawings

(56) References Cited

U.S. PATENT DOCUMENTS

| | | |
|---|---|---|
| 2016/0081339 A1 | 3/2016 | Yoshimoto et al. |
| 2016/0081340 A1 | 3/2016 | Arimori et al. |

FOREIGN PATENT DOCUMENTS

| | | | |
|---|---|---|---|
| JP | 2002506060 A | 2/2002 | |
| JP | 2004531551 A | 10/2004 | |
| JP | 2005511739 A | 4/2005 | |
| JP | 2014097979 A | 5/2014 | |
| WO | 96036229 A1 | 11/1996 | |
| WO | WO-9636229 A1 * | 11/1996 | ............. A01N 43/56 |
| WO | 9940076 A1 | 8/1999 | |
| WO | 9946246 A1 | 9/1999 | |
| WO | WO 9946246 A1 * | 9/1999 | ........... C07D 231/12 |
| WO | WO 03050096 A1 * | 6/2003 | ............. A01N 43/78 |
| WO | 2013092224 A1 | 6/2013 | |
| WO | 2013162072 A1 | 10/2013 | |
| WO | 2013162077 A1 | 10/2013 | |
| WO | 2014051161 A1 | 4/2014 | |
| WO | 2014051165 A1 | 4/2014 | |
| WO | 2014084223 A1 | 6/2014 | |
| WO | 2014104268 A1 | 7/2014 | |
| WO | 2014104382 A1 | 7/2014 | |
| WO | 2014104384 A1 | 7/2014 | |
| WO | 2014175465 A1 | 10/2014 | |
| WO | 2014192953 A1 | 12/2014 | |
| WO | 2015016335 A1 | 2/2015 | |
| WO | 2015016372 A1 | 2/2015 | |
| WO | 2015016373 A1 | 2/2015 | |
| WO | 2015030217 A1 | 3/2015 | |
| WO | 2015046480 A1 | 4/2015 | |
| WO | 2015056806 A1 | 4/2015 | |
| WO | 2015056811 A1 | 4/2015 | |
| WO | 2015060461 A1 | 4/2015 | |
| WO | 2015064727 A1 | 5/2015 | |

OTHER PUBLICATIONS

Office Action dated Oct. 20, 2016 in CN Application No. 201480036577.6.

Extended Search Report dated Jan. 4, 2017 in EP Application No. 14822209.4.

\* cited by examiner

TETRAZOLINONE COMPOUNDS AND APPLICATIONS THEREOF

CROSS-REFERENCE TO RELATED APPLICATION

This application is a Section 371 of International Application No. PCT/JP2014/069120, filed Jul. 10, 2014, which was published in the Japanese language on Jan. 15, 2015, under International Publication No. WO 2015/005499 A1, and the disclosures of which are incorporated herein by reference.

TECHNICAL FIELD

The present invention relates to tetrazolinone compounds and applications thereof.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by 1-methyl-4-[2-(4-phenyl-phenoxymethyl)-phenyl]-1,4-dihydrotetrazol-5-one (the following formula (A)):

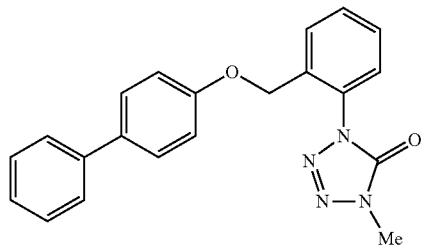

(A)

(see WO 96/36229 A)

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus completing the present invention.

The present invention includes the followings [1] to [19].

[1] A tetrazolinone compound represented by formula (1):

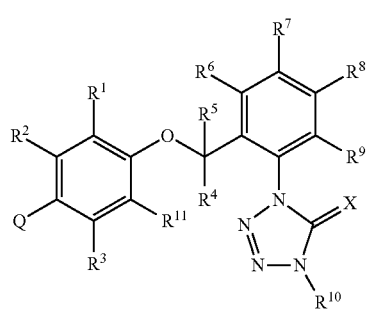

(1)

wherein Q represents a 6-membered aromatic heterocyclic group optionally having one or more atoms or groups selected from Group $P^1$, provided that a heteroatom constituting the heterocyclic group is a nitrogen atom, and the number of nitrogen atom is 1, 2, or 3;

$R^1$, $R^2$, $R^3$, and $R^{11}$ each independently represents a C1-C6 alkyl group optionally having one or more atoms or groups selected from Group $P^2$, a C3-C6 cycloalkyl group optionally having one or more atoms or groups selected from Group $P^2$, a halogen atom, a hydrogen atom, a C1-C6 alkoxy group optionally having one or more halogen atoms, a cyano group, a nitro group, an amino group, a hydroxy group, a sulfanyl group, a C2-C6 alkenyl group optionally having one or more halogen atoms, a C2-C6 alkynyl group optionally having one or more halogen atoms, an amino group optionally having one or two C1-C8 alkyl groups (optionally having a halogen atom), a C1-C6 alkylthio group optionally having one or more halogen atoms, a C1-C6 alkylsulfinyl group optionally having one or more halogen atoms, a C1-C6 alkylsulfonyl group optionally having one or more halogen atoms, a pentafluorosulfanyl group, a C3-C9 trialkylsilyl group, a C2-C6 alkylcarbonyl group, a C2-C6 alkoxycarbonyl group, or an aminocarbonyl group optionally having one or more C2-C8 alkyl; $R^4$ and $R^5$ each independently represents a hydrogen atom, a halogen atom, or a C1-C3 alkyl group; $R^6$ represents a C1-C6 alkyl group optionally having one or more halogen atoms, a C3-C6 cycloalkyl group optionally having one or more halogen atoms, a halogen atom, a hydrogen atom, a C2-C6 alkenyl group optionally having one or more halogen atoms, a C1-C6 alkoxy group optionally having one or more halogen atoms, a C1-C6 alkylthio group optionally having one or more halogen atoms, a C2-C6 alkynyl group optionally having one or more halogen atoms, a nitro group, a cyano group, an aminocarbonyl group optionally having one or two C1-C6 alkyl groups, a C3-C6 cycloalkoxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group, a C2-C6 alkylcarbonylthio group, a C2-C6 alkoxycarbonyl group, a hydroxy group, a sulfanyl group, an amino group optionally having one or two C1-C6 alkyl groups, a pentafluorosulfanyl group, a C3-C9 trialkylsilyl group, a C5-C14 trialkylsilylethynyl group, a C1-C4 alkylsulfonyl group optionally having one or more halogen atoms, a C1-C4 alkylsulfinyl group optionally having one or more halogen atoms, a C2-C5 alkoxyalkyl group, or a C2-C5 alkylthioalkyl group;

$R^7$, $R^8$, and $R^9$ each independently represents a hydrogen atom, a halogen atom, a C1-C3 alkyl group optionally having one or more halogen atoms, a C2-C3 alkenyl group optionally having one or more halogen atoms, or a C1-C3 alkoxy group optionally having one or more halogen atoms;

$R^{10}$ represents a C1-C3 alkyl group optionally having one or more halogen atoms, a C2-C3 alkenyl group optionally having one or more halogen atoms, a C2-C3 alkynyl group optionally having one or more halogen atoms, or a C3-C5 cycloalkyl group optionally having one or more halogen atoms; and X represents an oxygen atom or a sulfur atom:
Group P$^1$: Group consisting of a C1-C6 alkyl group optionally having one or more halogen atoms, a halogen atom, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C6-C16 aryl group optionally having one or more halogen atoms, a C6-C16 aryloxy group optionally having one or more halogen atoms, a C6-C16 arylthio group optionally having one or more halogen atoms, a C7-C18 aralkyl group optionally having one or more halogen atoms, a C7-C18 arylalkoxy group optionally having one or more halogen atoms, a sulfanyl group, a pentafluorosulfanyl group, a C3-C12 trialkylsilyl group, a C5-C14 trialkylsilylethynyl group, a C1-C6 alkylsulfonyl group optionally having one or more halogen atoms, a C6-C16 arylsulfonyl group optionally having one or more halogen atoms, a C1-C6 alkylsulfinyl group optionally having one or more halogen atoms, a C6-C16 arylsulfinyl group optionally having one or more halogen atoms, an aminosulfonyl group optionally having a C1-C6 alkyl group and/or a C6-C12 aryl group, an amino group, an amino group optionally having one or two C1-C8 alkyl groups (optionally having a halogen atom), and an aminocarbonyl group optionally having one or two C1-C6 alkyl groups; and
Group P$^2$: Group consisting of a halogen atom, a cyano group, a C3-C6 cycloalkyl group optionally having one or more halogen atoms, a C1-C4 alkoxy group optionally having one or more halogen atoms, and a C1-C4 alkylthio group optionally having one or more halogen atoms.
[2] The tetrazolinone compound according to [1], wherein Q is the following group Q1;

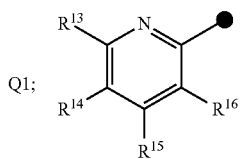

R$^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms;
R$^2$, R$^4$, R$^5$, R$^7$, R$^8$, R$^9$, and R$^{11}$ are hydrogen atoms;
R$^3$ is a hydrogen atom, a halogen atom, or a C1-C3 alkyl group optionally having one or more halogen atoms;
R$^6$ is a C1-C3 alkyl group optionally having one or more halogen atoms, a C3-C4 cycloalkyl group optionally having one or more halogen atoms, a halogen atom, a hydrogen atom, a C1-C3 alkoxy group optionally having one or more halogen atoms, or a C2-C4 alkenyl group optionally having one or more halogen atoms;
R$^{10}$ is a methyl group;
X is an oxygen atom; and
R$^{13}$, R$^{14}$, R$^{15}$, and R$^{16}$ each independently represents a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, a C6-C16 arylthio group optionally having one or more halogen atoms, or a sulfanyl group.
[3] The tetrazolinone compound according to [1] or [2], wherein R$^1$ is a C1-C3 alkyl group optionally having one or more halogen atoms, or a halogen atom;
R$^3$ is a hydrogen atom or a methyl group;
R$^6$ is a C1-C3 alkyl group optionally having one or more halogen atoms, a C3-C4 cycloalkyl group, a halogen atom, or a C1-C3 alkoxy group optionally having one or more halogen atoms; and
R$^{13}$, R$^{14}$, R$^{15}$ and R$^{16}$ each independently represents a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.
[4] The tetrazolinone compound according to [1], wherein Q is the following group Q2;

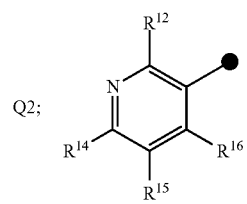

R$^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms;
R$^2$, R$^4$, R$^5$, R$^7$, R$^8$, R$^9$, and R$^{11}$ are hydrogen atoms;
R$^3$ is a hydrogen atom, a halogen atom, or a C1-C3 alkyl group optionally having one or more halogen atoms;
R$^6$ is a C1-C3 alkyl group optionally having one or more halogen atoms, a C3-C4 cycloalkyl group optionally having one or more halogen atoms, a halogen atom, a hydrogen atom, a C1-C3 alkoxy group optionally having one or more halogen atoms, or a C2-C4 alkenyl group optionally having one or more halogen atoms; and $R^{12}$, $R^{14}$, $R^{15}$, and $R^{16}$ each independently represents a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, a C6-C16 arylthio group optionally having one or more halogen atoms, or a sulfanyl group.

[5] The tetrazolinone compound according to [1] or [4], wherein $R^1$ is a C1-C3 alkyl group optionally having one or more halogen atoms, or a halogen atom;

$R^3$ is a hydrogen atom or a methyl group;

$R^6$ is a C1-C3 alkyl group optionally having one or more halogen atoms, a C3-C4 cycloalkyl group, a halogen atom, or a C1-C3 alkoxy group optionally having one or more halogen atoms; and $R^{12}$, $R^{14}$, $R^{15}$, and $R^{16}$ each independently represents a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

[6] The tetrazolinone compound according to [1], wherein Q is the following group Q4;

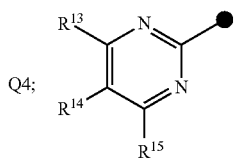

$R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms;

$R^2$, $R^4$, $R^5$, $R^7$, $R^8$, $R^9$, and $R^{11}$ are hydrogen atoms;

$R^3$ is a hydrogen atom, a halogen atom, or a C1-C3 alkyl group optionally having one or more halogen atoms;

$R^6$ is a C1-C3 alkyl group optionally having one or more halogen atoms, a C3-C4 cycloalkyl group optionally having one or more halogen atoms, a halogen atom, a hydrogen atom, a C1-C3 alkoxy group optionally having one or more halogen atoms, or a C2-C4 alkenyl group optionally having one or more halogen atoms; and $R^{13}$, $R^{14}$, and $R^{15}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, a C6-C16 arylthio group optionally having one or more halogen atoms, or a sulfanyl group.

[7] The tetrazolinone compound according to [1] or [6], wherein $R^1$ is a C1-C3 alkyl group optionally having one or more halogen atoms, or a halogen atom;

$R^3$ is a hydrogen atom or a methyl group;

$R^6$ is a C1-C3 alkyl group optionally having one or more halogen atoms, a C3-C4 cycloalkyl group, a halogen atom, or a C1-C3 alkoxy group optionally having one or more halogen atoms; and $R^{13}$, $R^{14}$, and $R^{15}$ each independently represents a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

[8] The tetrazolinone compound according to [1] or [2], wherein $R^1$ is a C1-C3 alkyl group optionally having one or more halogen atoms, or a halogen atom;

$R^6$ is a C1-C3 alkyl group optionally having one or more halogen atoms, a C3-C4 cycloalkyl group optionally having one or more halogen atoms, a halogen atom, a hydrogen atom, or a C1-C3 alkoxy group optionally having one or more halogen atoms; and $R^{13}$, $R^{14}$, $R^{15}$, and $R^{16}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

[9] The tetrazolinone compound according to [1] or [4], wherein $R^1$ is a C1-C3 alkyl group optionally having one or more halogen atoms, or a halogen atom;

$R^6$ is a C1-C3 alkyl group optionally having one or more halogen atoms, a C3-C4 cycloalkyl group optionally having one or more halogen atoms, a halogen atom, a hydrogen atom, or a C1-C3 alkoxy group optionally having one or more halogen atoms; and $R^{12}$, $R^{14}$, $R^{15}$, and $R^{16}$ each independently represents a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

[10] The tetrazolinone compound according to [1] or [6], wherein $R^1$ is a C1-C3 alkyl group optionally having one or more halogen atoms, or a halogen atom;

$R^6$ is a C1-C3 alkyl group optionally having one or more halogen atoms, a C3-C4 cycloalkyl group optionally having one or more halogen atoms, a halogen atom, a hydrogen atom, or a C1-C3 alkoxy group optionally having one or more halogen atoms; and $R^{12}$, $R^{14}$, $R^{15}$, and $R^{16}$ each independently represents a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

[11] The tetrazolinone compound according to [1], wherein Q is the following group Q7; 7; R

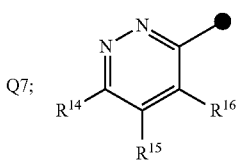

R¹ is a C1-C3 alkyl group optionally having one or more halogen atoms, a halogen atom, a C3-C5 cycloalkyl group optionally having one or more halogen atoms, a hydrogen atom, or a C1-C3 alkoxy group optionally having one or more halogen atoms;

$R^2$, $R^4$, $R^5$, $R^7$, $R^8$, $R^9$, and $R^{11}$ are hydrogen atoms;

$R^3$ is a hydrogen atom, a halogen atom, or a C1-C3 alkyl group optionally having one or more halogen atoms;

$R^6$ is a C1-C3 alkyl group optionally having one or more halogen atoms, a C3-C4 cycloalkyl group optionally having one or more halogen atoms, a halogen atom, a hydrogen atom, or a C1-C3 alkoxy group optionally having one or more halogen atoms; and $R^{14}$, $R^{15}$, and $R^{16}$ each independently represents a C1-C3 alkyl group optionally having one or more halogen atoms, a hydrogen atom, a halogen atom, a C3-C4 cycloalkyl group optionally having one or more halogen atoms, or a C1-C3 alkoxy group optionally having one or more halogen atoms.

[12] The tetrazolinone compound according to [1] or [11], wherein $R^1$ is a C1-C3 alkyl group optionally having one or more halogen atoms, or a halogen atom;

$R^2$, $R^4$, $R^5$, $R^7$, $R^8$, $R^9$, and $R^{11}$ are hydrogen atoms; and $R^{14}$, $R^{15}$, and $R^{16}$ are the same or different and represent a C1-C3 alkyl group optionally having one or more halogen atoms, a hydrogen atom, a halogen atom, or a C1-C3 alkoxy group optionally having one or more halogen atoms.

[13] A pyridine compound represented by formula (2):

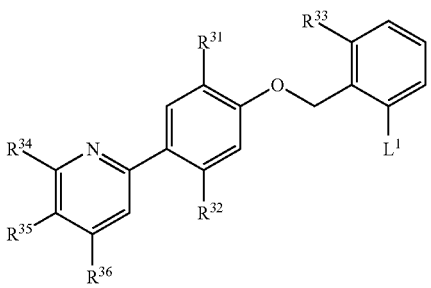

wherein $R^{31}$ represents a C1-C3 alkyl group optionally having one or more halogen atoms;

$R^{32}$ represents a C1-C3 alkyl group optionally having one or more halogen atoms, a hydrogen atom, or a halogen atom;

$R^{33}$ represents a C1-C3 alkyl group optionally having one or more halogen atoms, a C3-C4 cycloalkyl group, a halogen atom, or a C1-C3 alkoxy group optionally having one or more halogen atoms;

$R^{34}$, $R^{35}$, and $R^{36}$ each independently represents a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms; and $L^1$ represents a nitro group, an amino group, an isocyanate group, a carboxyl group, a C2-C6 alkoxycarbonyl group, a halogen atom, a halocarbonyl group, 1,4-dihydrotetrazol-5-on-1-yl, NSO, $C(O)N_3$, $C(O)NH_2$, $C(O)NHCl$, $C(O)NHBr$, or $C(O)NHOH$.

[14] The pyridine compound according to [13], wherein $R^{31}$ is a methyl group;

$R^{32}$ is a methyl group, a fluoro group, a chloro group, or a hydrogen atom;

$R^{33}$ is a methyl group, an ethyl group, a chloro group, a cyclopropyl group, or a methoxy group;

$R^{34}$, $R^{35}$, and $R^{36}$ each independently represents a C1-C3 alkyl group optionally having one or more halogen atoms, a halogen atom, or a hydrogen atom; and $L^1$ is a nitro group, an amino group, an isocyanate group, or a 1,4-dihydrotetrazol-5-on-1-yl group.

[15] A tetrazolinone compound represented by formula (3):

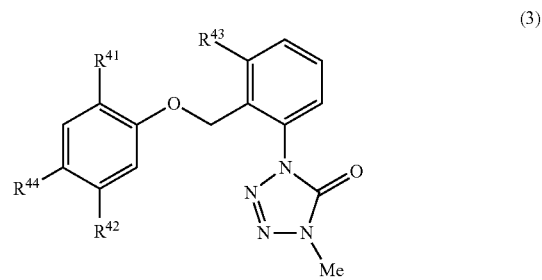

wherein $R^{41}$ represents a C1-C3 alkyl group optionally having one or more halogen atoms, a hydrogen atom, a cyano group, a halogen atom, or a C1-C3 alkoxy group optionally having one or more halogen atoms;

$R^{42}$ represents a C1-C3 alkyl group optionally having one or more halogen atoms, a hydrogen atom, or a halogen atom;

$R^{43}$ represents a C1-C3 alkyl group optionally having one or more halogen atoms, a C3-C4 cycloalkyl group, a hydrogen atom, a halogen atom, or a C1-C3 alkoxy group optionally having one or more halogen atoms; and $R^{44}$ represents a bromine atom, an iodine atom, a borono group, or a 4,4,5,5-tetramethyl-1,3,2-dioxaborolan-2-yl group.

[16] The tetrazolinone compound according to [15], wherein $R^{41}$ is a methyl group;

$R^{42}$ is a methyl group, a fluoro group, a chloro group, or a hydrogen atom; and $R^{43}$ is a methyl group, an ethyl group, a chloro group, a cyclopropyl group, or a methoxy group.

[17] A pest control agent comprising the tetrazolinone compound according to any one of [1] to [12].

[18] A method for controlling pests, which comprises treating plants or soil with an effective amount of the tetrazolinone compound according to any one of [1] to [12].

[19] Use of the tetrazolinone compound according to any one of [1] to [12] for controlling pests.

According to the present invention, pests can be controlled.

MODE FOR CARRYING OUT THE INVENTION

The compound of the present invention (hereinafter referred to as the present compound) is a tetrazolinone compound represented by formula (1):

Formula (1)

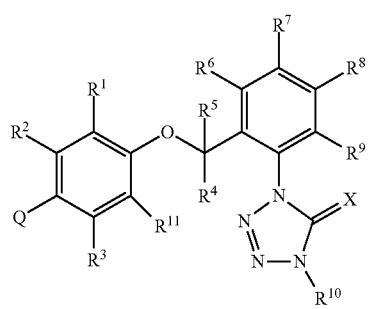

wherein symbols are the same as defined above.

A pest control agent containing a tetrazolinone compound represented by formula (1) is referred to as the present control agent.

Substituents as used herein will be mentioned below.

Q represents a 6-membered aromatic heterocyclic group optionally having one or more atoms or groups selected from Group $P^1$, provided that a heteroatom constituting the heterocyclic group is a nitrogen atom, and the number of nitrogen atoms is 1, 2, or 3, and examples thereof include the following Group Q1, Q2, Q3, Q4, Q5, Q6, Q7, Q8, Q9, Q10, Q11, Q012, Q13, Q014, Q15, or Q016, in which the symbol ● represents a binding site for a carbon atom;

Q1
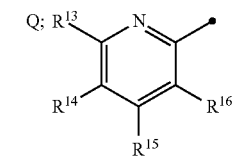

Q2
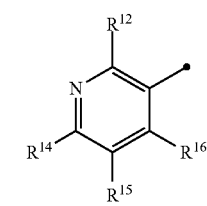

Q3
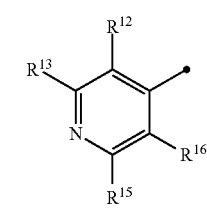

Q4
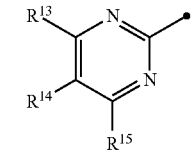

Q5
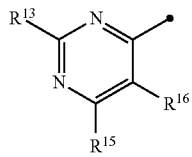

Q6
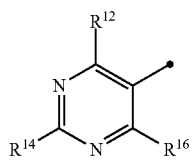

Q7
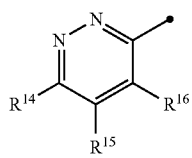

Q8
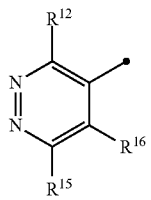

Q9
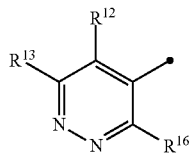

Q10
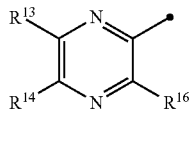

Q11
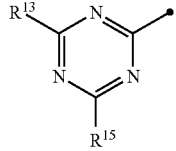

Q12
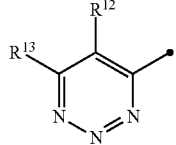

Q13
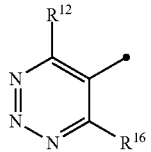

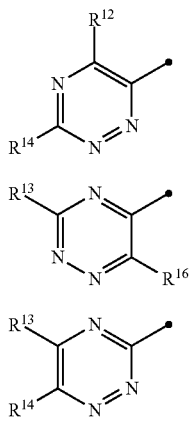

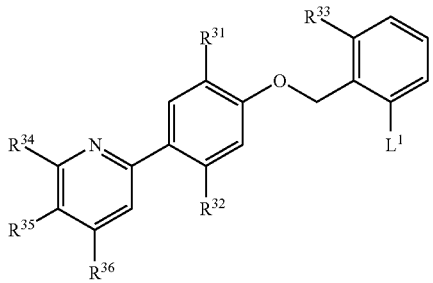

wherein $R^{12}$, $R^{13}$, $R^{14}$, $R^{15}$, and $R^{16}$ each independently represents a halogen atom, a hydrogen atom, a C1-C6 alkyl group optionally having one or more halogen atoms, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 cycloalkyloxy group optionally having one or more halogen atoms, a C3-C6 cycloalkylthio group, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C6-C16 aryl group optionally having one or more halogen atoms, a C6-C16 aryloxy group optionally having one or more halogen atoms, a C6-C16 arylthio group optionally having one or more halogen atoms, a C7-C18 aralkyl group optionally having one or more halogen atoms, a C7-C18 arylalkoxy group optionally having one or more halogen atoms, a sulfanyl group, a pentafluorosulfuranyl group, a C3-C12 trialkylsilyl group, a C5-C14 trialkylsilylethynyl group, a C1-C6 alkylsulfonyl group optionally having one or more halogen atoms, a C6-C16 arylsulfonyl group optionally having one or more halogen atoms, a C1-C6 alkylsulfinyl group optionally having one or more halogen atoms, a C6-C16 arylsulfinyl group optionally having one or more halogen atoms, an aminosulfonyl group optionally having a C1-C6 alkyl group and/or a C6-C12 aryl group, an amino group, an amino group optionally having one or two C1-C8 alkyl groups (optionally having a halogen atom), or an aminocarbonyl group optionally having one or two C1-C6 alkyl groups.

The present invention also includes a pyridine compound (hereinafter referred to as the present compound A) represented by formula (2):

wherein symbols are the same as defined above, which is used in the production of the present compound.

The present invention also includes a tetrazolinone compound (hereinafter referred to as the present compound B) represented by formula (3):

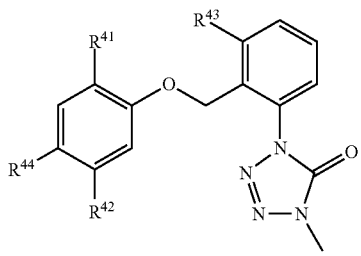

wherein symbols are the same as defined above, which is used in the production of the present compound.

Examples of the halogen atom include a fluorine atom, a chlorine atom, a bromine atom, and an iodine atom.

Examples of the C1-C3 alkyl group include a methyl group, an ethyl group, a propyl group, and an isopropyl group.

Examples of the C1-C6 alkyl group include a methyl group, an ethyl group, a propyl group, a tert-butyl group, and a hexyl group.

The C1-C6 alkyl group optionally having one or more halogen atoms represents a C1-C6 alkyl group one or more hydrogen atoms of which are optionally substituted with a halogen atom, and examples thereof include a methyl group, an ethyl group, a propyl group, an isopropyl group, a butyl group, an isobutyl group, a sec-butyl group, a tert-butyl group, a pentyl group, a hexyl group, a fluoromethyl group, a chloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2,2-dichloro-2-fluoroethyl group, a 2-fluoropropyl group, a 3-fluoropropyl group, a 3,3,3-trifluoropropyl group, a 4-fluorobutyl group, and a 2,2-difluorohexyl group.

Examples of the C2-C6 alkenyl group include a vinyl group, a 1-propenyl group, an isopropenyl group, a 2-butenyl group, and a 1-hexenyl group.

The C2-C6 alkenyl group optionally having one or more halogen atoms represents a C2-C6 alkenyl group one or more hydrogen atoms of which are optionally substituted with a halogen atom, and examples thereof include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, a 5-hexenyl group, a 2-chlorovinyl group, a 2-bromovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 4,4-difluoro-3-methyl-3-butenyl group, a 4,5,5-trifluoro-4-pentenyl group, a 3,4,4,4-tetrafluoro-3-trifluoromethyl-1-butenyl group, a 4,4,4-trifluoro-3-methyl-2-butenyl group, a 3,5,5-trifluoro-2,4-pentadienyl group, and a 4,4,5,5,6,6,6-heptafluoro-2-hexenyl group.

Examples of the C2-C6 alkynyl group include an ethynyl group, a propargyl group, a 2-butynyl group, and a 1-hexynyl group.

The C2-C6 alkynyl group optionally having one or more halogen atoms represents a C2-C6 alkynyl group one or more hydrogen atoms of which are optionally substituted with a halogen atom, and examples thereof include an ethynyl group, a propargyl group, a 1-butyn-3-yl group, a 3-methyl-1-butyn-3-yl group, a 2-butynyl group, a 3-butynyl group, a 2-pentynyl group, a 3-pentynyl group, a 4-pentynyl group, a 1-hexynyl group, a 5-hexynyl group, a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3-fluoro-2-propynyl group, a perfluoro-2-butynyl group, a perfluoro-2-pentynyl group, a perfluoro-3-pentynyl group, and a perfluoro-1-hexynyl group.

Examples of the C3-C6 cycloalkyl group include a cyclopropyl group, a cyclobutyl group, a cyclopentyl group, and a cyclohexyl group.

The C3-C6 cycloalkyl group optionally having one or more halogen atoms represents a C3-C6 cycloalkyl group one or more hydrogen atoms of which are optionally substituted with a halogen atom, and examples thereof include a cyclopropyl group, a cyclobutyl group, a cyclopentyl group, a cyclohexyl group, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclohexyl group, a 4,4-difluorocyclohexyl group, and a 4-chlorocyclohexyl group.

Examples of the C1-C6 alkoxy group include a methoxy group, an ethoxy group, a propyloxy group, a tert-butyloxy group, a pentyloxy group, and a hexyloxy group.

The C1-C6 alkoxy group optionally having one or more halogen atoms is a C1-C6 alkoxy group one or more hydrogen atoms of which are optionally substituted with a halogen atom, and examples thereof include a methoxy group, an ethoxy group, a propyloxy group, an isopropyloxy group, a butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group, a 4-methylpentyloxy, a trifluoromethoxy group, a trichloromethoxy group, chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a 3,3,3-trifluoropropoxy group, a 3,3,3-trichloropropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a perfluoropentyloxy group, a perchloropentyloxy group, a perfluorohexyloxy group, and a perchlorohexyloxy group.

Examples of the C1-C6 alkylthio group include a methylthio group, an ethylthio group, a propylthio group, a butylthio group, a tert-butylthio group, and a hexylthio group.

The C1-C6 alkylthio group optionally having one or more halogen atoms represents a C1-C6 alkylthio group one or more hydrogen atoms of which are optionally substituted with a halogen atom, and examples thereof include a methylthio group, an ethylthio group, a propylthio group, an isopropylthio group, a butylthio group, a sec-butylthio group, a tert-butylthio group, a pentylthio group, an isopentylthio group, a neopentylthio group, a hexylthio group, an isohexylthio group, a sec-hexylthio group, a fluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a 2,2,2-trichloroethylthio group, a 2,2,2-trifluoroethylthio group, a 2,2-difluoroethylthio group, a heptafluoropropylthio group, a heptachloropropylthio group, a 3,3,3-trifluoropropylthio group, a 3,3,3-trichloropropylthio group, a 2,2-difluoropropylthio group, a 2,3,3-trifluoropropylthio group, a nonafluorobutylthio group, a nonachlorobutylthio group, a perfluoropentylthio group, a perfluorohexylthio group, and a perchlorohexylthio group.

Examples of the C3-C6 cycloalkyloxy group include a cyclopropyloxy group, a cyclobutyloxy group, a cyclopentyloxy group, and a cyclohexyloxy group.

The C3-C6 cycloalkyloxy group optionally having one or more halogen atoms represents a C3-C6 cycloalkyloxy group one or more hydrogen atoms of which are optionally substituted with a halogen atom, and examples thereof include a cyclopropyloxy group, a cyclobutyloxy group, a cyclopentyloxy group, a cyclohexyloxy group, a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group.

Examples of the C3-C6 cycloalkylthio group include a cyclopropylthio group, a cyclobutylthio group, a cyclopentylthio group, and a cyclohexylthio group.

The C3-C6 cycloalkylthio group optionally having one or more halogen atoms represents a C3-C6 cycloalkylthio group one or more hydrogen atoms of which are optionally substituted with a halogen atom, and examples thereof include a cyclopropylthio group, a cyclobutylthio group, a cyclopentylthio group, a cyclohexylthio group, a 2-fluorocyclopropylthio group, a 2,2-difluorocyclopropylthio group, a 2-chloro-2-fluorocyclopropylthio group, a 2,2-dichlorocyclopropylthio group, a 2,2-dibromocyclopropylthio group, a 2,2,3,3-tetrafluorocyclobutylthio group, a 2-chlorocyclohexylthio group, a 4,4-difluorocyclohexylthio group, and a 4-chlorocyclohexylthio group.

Examples of the C3-C6 alkenyloxy group include a 2-propenyloxy group, a 2-butenyloxy group, a 3-pentenyloxy group, and a 5-hexenyloxy group.

The C3-C6 alkenyloxy group optionally having one or more halogen atoms represents a C3-C6 alkenyloxy group one or more hydrogen atoms of which are optionally substituted with a halogen atom, an examples thereof include a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, a 5-hexenyloxy group, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, and a 4,4,5,5,6,6,6-heptafluoro-2-hexenyloxy group.

Examples of the C3-C6 alkynyloxy group include a propargyloxy group, a 1-butyn-3-yloxy group, a 2-butynyloxy group, and a 5-hexynyloxy group.

The C3-C6 alkynyloxy group optionally having one or more halogen atoms represents a C3-C6 alkynyloxy group one or more hydrogen atoms of which are optionally substituted with a halogen atom, and examples thereof include a propargyloxy group, a 1-butyn-3-yloxy group, a 3-methyl-1-butyn-3-yloxy group, a 2-butynyloxy group, a 3-butynyloxy group, a 2-pentynyloxy group, a 3-pentynyloxy group, a 4-pentynyloxy group, a 5-hexynyloxy group, a 3-chloro-2-propynyloxy group, a 3-bromo-2-propynyloxy group, a 3-iodo-2-propynyloxy group, a 5-chloro-4-pentynyloxy group, a 3-fluoro-2-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

Examples of the C3-C6 alkenylthio group include a 2-propenylthio group, a 2-butenylthio group, a 4-pentenylthio group, and a 5-hexenylthio group.

The C3-C6 alkenylthio group optionally having one or more halogen atoms represents a C3-C6 alkenylthio group one or more hydrogen atoms of which are optionally substituted with a halogen atom, and examples thereof include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, a 5-hexenylthio group, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4,5,5,5-tetrafluoro-4-trifluoromethyl-2-pentenylthio group, and a 5-bromo-4,5,5-trifluoro-4-trifluoromethyl-2-pentenylthio group.

Examples of the C3-C6 alkynylthio group include a propargylthio group, a 1-butyn-3-ylthio group, a 4-pentynylthio group, and a 5-hexynylthio group.

The C3-C6 alkynylthio group optionally having one or more halogen atoms represents a C3-C6 alkynylthio group one or more hydrogen atoms of which are optionally substituted with a halogen atom, and examples thereof include a propargylthio group, a 1-butyn-3-ylthio group, a 3-methyl-1-butyn-3-ylthio group, a 2-butynylthio group, a 3-butynylthio group, a 2-pentynylthio group, a 3-pentynylthio group, a 4-pentynylthio group, a 5-hexynylthio group, a 3-chloro-2-propynylthio group, a 3-bromo-2-propynylthio group, a 3-iodo-2-propynylthio group, a 5-chloro-4-pentynylthio group, a 3-fluoro-2-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group.

Examples of the C2-C6 alkylcarbonyl group include an acetyl group, a propionyl group, a butanoyl group, a pentanoyl group, and a hexanoyl group.

The C2-C6 alkylcarbonyl group optionally having one or more halogen atoms is a straight or branched C2-C6 alkylcarbonyl group optionally having one or more halogen atoms, and examples thereof include an acetyl group, a propionyl group, a butanoyl group, a pentanoyl group, a hexanoyl group, a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a heptafluorobutanoyl group, a heptachlorobutanoyl group, a 4,4,4-trifluorobutanoyl group, a 4,4,4-trichlorobutanoyl group, a nonafluoropentanoyl group, and a perfluorohexanoyl group.

Examples of the C2-C6 alkoxycarbonyl group include a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutyloxycarbonyl group.

Examples of the C6-C16 aryl group include a phenyl group, a 1-naphthyl group, a 2-naphthyl group, a 1-anthryl group, a 2-anthryl group, a 9-anthryl group, a 1-pyrenyl group, a 2-pyrenyl group, and a 4-pyrenyl group.

The C6-C16 aryl group optionally having one or more halogen atoms represents a group in which one or more hydrogen atoms of a C6-C16 aryl group are optionally substituted with a halogen atom, and examples thereof include a phenyl group, a 1-naphthyl group, a 2-naphthyl group, a 1-acenaphthyl group, a 1-phenanthryl group, a 9-anthryl group, a 1-pyrenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-bromo-3-fluorophenyl group, a 2-chloro-4-fluorophenyl group, a 2-fluoro-1-naphthyl group, a 4-chloro-2-naphthyl group, a 3-fluoro-1-acenaphthyl group, a 9-fluoro-1-phenanthryl group, a 10-fluoro-9-anthryl group, and a 6-fluoro-1-pyrenyl group.

Examples of the C6-C16 aryloxy group include a phenyloxy group, a 1-naphthyloxy group, a 2-naphthyloxy group, a 1-anthryloxy group, a 2-anthryloxy group, a 9-anthryloxy group, a 1-pyrenyloxy group, a 2-pyrenyloxy group, and a 4-pyrenyloxy group.

The C6-C16 aryloxy group optionally having one or more halogen atoms represents a C6-C16 aryloxy group one or more hydrogen atoms of which are optionally substituted with a halogen atom, and examples thereof include a phenyloxy group, a 1-naphthyloxy group, a 2-naphthyloxy group, a 1-acenaphthyloxy group, a 1-phenanthryloxy group, a 9-anthryloxy group, a 1-pyrenyloxy group, a 2-fluorophenyloxy group, a 3-fluorophenyloxy group, a 4-fluorophenyloxy group, a 2-chlorophenyloxy group, a 3-chlorophenyloxy group, a 4-chlorophenyloxy group, a 2-bromophenyloxy group, a 3-bromophenyloxy group, a 4-bromophenyloxy group, a 2-iodophenyloxy group, a 3-iodophenyloxy group, a 4-iodophenyloxy group, a 2,4-difluorophenyloxy group, a 2,5-dichlorophenyloxy group, a 2,4,6-trifluorophenyloxy group, a 2,3,4-trichlorophenyloxy group, a pentafluorophenyloxy group, a pentachlorophenyloxy group, a 2-bromo-4-fluorophenyloxy group, a 2-chloro-3-fluorophenyloxy group, a 2-fluoro-1-naphthyloxy group, a 3-chloro-1-naphthyloxy group, a 3-fluoro-1-acenaphthyloxy group, a 9-fluoro-1-phenanthryloxy group, a 10-fluoro-9-anthryloxy group, and a 6-fluoro-1-pyrenyloxy group.

Examples of the C6-C16 arylthio group include a phenylthio group, a 1-naphthylthio group, a 2-naphthylthio group, a 1-anthrylthio group, a 2-anthrylthio group, a 9-anthrylthio group, a 1-pyrenylthio group, a 2-pyrenylthio group, and a 4-pyrenylthio group.

The C6-C16 arylthio group optionally having one or more halogen atoms represents a C6-C16 arylthio group one or more hydrogen atoms of which are optionally substituted with a halogen atom, and examples thereof include a phenylthio group, a 1-naphthylthio group, a 2-naphthylthio group, a 1-acenaphthylthio group, a 1-phenanthrylthio group, a 9-anthrylthio group, a 1-pyrenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, a 2-iodophenylthio group, a 3-iodophenylthio group, a 4-iodophenylthio group, a 2,4-difluorophenylthio group, a 2,5-dichlorophenylthio group, a 2,3,4-trifluorophenylthio group, a pentachlorophenylthio group, a 2-bromo-3-fluorophenylthio group, a 2-chloro-4-fluorophenylthio group, a 3-chloro-4-fluorophenylthio group, a 3-fluoro-1-naphthylthio group, a 4-chloro-1-naphthylthio group, a 1-fluoro-2-naphthylthio group, a 1-chloro-2-naphthylthio group, a heptafluoro-2-naphthylthio group, a 3-fluoro-1-acenaphthylthio group, a 9-fluoro-1-phenanthrylthio group, a 10-fluoro-9-anthrylthio group, and a 6-fluoro-1-pyrenylthio group.

The C7-C18 aralkyl group is composed of a C1-C12 alkyl group and an aryl group bound to each other, and examples thereof include a benzyl group, a phenethyl group, a 3-phenylpropyl group, a 4-phenylbutyl group, a 12-phenyldodecyl group, a 1-naphthylmethyl group, a 2-(1-naphthyl)ethyl group, a 3-(1-naphthyl)propyl group, a 8-(2-naphthyl)octyl group, a 1-anthrylmethyl group, a 2-(1-anthryl)ethyl group, a 4-(1-anthryl)butyl group, a 2-anthrylmethyl group, a 2-(2-anthryl)ethyl group, a 4-(2-anthryl)butyl group, a 9-anthrylmethyl group, a 2-(9-anthryl)ethyl group, and a 4-(9-anthryl) butyl group.

The C7-C18 aralkyl group optionally having one or more halogen atoms represents a C7-C18 aralkyl group one or more hydrogen atoms of which are optionally substituted with a halogen atom, and examples thereof include a benzyl group, a phenethyl group, a 3-phenylpropyl group, a 4-phenylbutyl group, a 12-phenyldodecyl group, a 1-naphthylmethyl group, a 2-(1-naphthyl)ethyl group, a 3-(1-naphthyl)propyl group, a 4-(1-naphthyl)butyl group, a 8-(1-naphthyl)octyl group, a 2-naphthylmethyl group, a 2-(2-naphthyl)ethyl group, a 3-(2-naphthyl)propyl group, a 8-(2-naphthyl)octyl group, a 1-anthrylmethyl group, a 2-(1-anthryl)ethyl group, a 3-(1-anthryl)propyl group, a 4-(1-anthryl)butyl group, a 2-anthrylmethyl group, a 2-(2-anthryl)ethyl group, a 3-(2-anthryl)propyl group, a 4-(2-anthryl)butyl group, a 9-anthrylmethyl group, a 2-(9-anthryl)ethyl group, a 3-(9-anthryl)propyl group, a 4-(9-anthryl)butyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2,4-difluorobenzyl group, a 2,5-dichlorobenzyl group, a 2,4,6-trifluorobenzyl group, a 2,3,4-trichlorobenzyl group, a pentafluorobenzyl group, a 2-bromo-3-fluorobenzyl group, a 2-chloro-4-fluorobenzyl group, a 2-(4-bromophenyl)ethyl group, a 6-fluoro-1-naphthylmethyl group, a 4-chloro-2-naphthylmethyl group, a 3-(6-bromo-2-naphthyl)propyl group, a 6-(6-chloro-2-naphthyl)octyl group, a 3-fluoro-1-acenaphthylmethyl group, a 9-fluoro-1-phenanthrylmethyl group, a 10-fluoro-9-anthrylmethyl group, a 6-fluoro-1-pyrenylmethyl group, and a 1,1-difluoro-1-phenylmethyl group.

The C7-C18 arylalkoxy group is composed of a C1-C12 alkoxy group and an aryl group bound to each other, and examples thereof include a benzyloxy group, a phenethyloxy group, a 3-phenylpropyloxy group, a 4-phenylbutyloxy group, a 11-phenylundecyloxy group, a 12-phenyldodecyloxy group, a 1-naphthylmethyloxy group, a 2-naphthylmethyloxy group, a 1-naphthylethyloxy group, a 2-naphthylethyloxy group, a 1-naphthylpropyloxy group, a 2-naphthylpropyloxy group, a 1-anthrylmethyloxy group, a 2-anthrylmethyloxy group, a 9-anthrylmethyloxy group, and a 1-anthrylbutyloxy group, a 2-anthrylbutyloxy group, and a 9-anthrylbutyloxy group.

The C7-C18 arylalkoxy group optionally having one or more halogen atoms represents a C7-C18 arylalkoxy group one or more hydrogen atoms of which are optionally substituted with a halogen atom, and examples thereof include a benzyloxy group, a phenethyloxy group, a 3-phenylpropyloxy group, a 4-phenylbutyloxy group, a 11-phenylundecyloxy group, a 12-phenyldodecyloxy group, a 1-naphthylmethyloxy group, a 2-naphthylmethyloxy group, a 1-naphthylethyloxy group, a 2-naphthylethyloxy group, a 1-naphthylpropyloxy group, a 2-naphthylpropyloxy group, a 1-anthrylmethyloxy group, a 2-anthrylmethyloxy group, a 9-anthrylmethyloxy group, a 1-anthrylbutyloxy group, a 2-anthrylbutyloxy group, a 9-anthrylbutyloxy group, a 4-fluorobenzyloxy group, a 2-chlorobenzyloxy group, a 3-bromobenzyloxy group, a 4-iodobenzyloxy group, a 2,4-difluorobenzyloxy group, a 2,5-dichlorobenzyloxy group, a 3,4,5-trifluorobenzyloxy group, a 2,3,4-trichlorobenzyloxy group, a pentafluorobenzyloxy group, a 4-bromo-2-fluorobenzyloxy group, a 2-chloro-3-fluorobenzyloxy group, a 6-chloro-2-fluorobenzyloxy group, a 2-(4-fluorophenyl)ethyloxy group, a 2-(3-chlorophenyl)ethyloxy group, a 2-(2-bromophenyl)ethyloxy group, a 3-(4-iodophenyl)propyloxy group, a 12-(4-bromophenyl)dodecyloxy group, a 4-fluoro-1-naphthylmethyloxy group, a 1-chloro-2-naphthylmethyloxy group, a 2-(5-fluoro-1-naphthyl)ethyloxy group, a 6-(6-bromo-2-naphthyl)octyloxy group, a 3-fluoro-1-acenaphthylmethyloxy group, a 9-fluoro-1-phenanthrylmethyloxy group, a 10-fluoro-9-anthrylmethyloxy group, a 6-fluoro-1-pyrenylmethyloxy group, and a 1,1-difluoro-1-phenylmethyloxy group.

The C3-C12 trialkylsilyl group represents an alkylsilyl group, three hydrogen atoms of a silyl group are substituted with the same or different alkyl groups, and examples thereof include a trimethylsilyl group, a tert-butyldimethylsilyl group, a triethylsilyl group, an isopropyldimethylsilyl group, a triisopropylsilyl group, a tri(tert-butyl)silyl group, and a tri(n-butyl)silyl group.

The C5-C14 trialkylsilylethynyl group represents a group in which a C3-C12 trialkylsilyl group and an ethynyl group are bound to each other, and examples thereof include a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tri(n-butyl)silylethynyl group.

The aminosulfonyl group optionally having a C1-C6 alkyl group and/or a C6-C12 aryl group represents an aminosulfonyl group in which one or two hydrogen atoms on nitrogen are optionally substituted with the same or different C1-C6 alkyl groups and/or C6-C12 aryl groups, and examples thereof include an aminosulfonyl group, an N-methylaminosulfonyl group, an N-ethylaminosulfonyl group, an N-propylaminosulfonyl group, an N-isopropylaminosulfonyl group, an N-butylaminosulfonyl group, an N-pentylaminosulfonyl group, an N-hexylaminosulfonyl group, an N,N-dimethylaminosulfonyl group, an N,N-diethylaminosulfonyl group, an N,N-dipropylaminosulfonyl group, an N,N-diisopropylaminosulfonyl group, an N-ethyl-N-methylaminosulfonyl group, an N-propyl-N-methylaminosulfonyl group, an N-phenylaminosulfonyl group, an N,N-diphenylaminosulfonyl group, an N-methyl-N-phenylaminosulfonyl group, an N-ethyl-N-phenylaminosulfonyl group, an N-propyl-N-phenylaminosulfonyl group, an N-hexyl-N-phenylaminosulfonyl group, an N-(1-naphthyl)aminosulfonyl group, an N-(1-naphthyl)N-methylaminosulfonyl group, an N-(2-naphthyl)aminosulfonyl group, and an N-(2-naphthyl)N-methylaminosulfonyl group.

Examples of the C1-C6 alkylsulfonyl group include a methylsulfonyl group, an ethylsulfonyl group, a propylsulfonyl group, an isopropylsulfonyl group, a butylsulfonyl group, an isobutylsulfonyl group, a sec-butylsulfonyl group, a pentylsulfonyl group, a hexylsulfonyl group, a 3-methylpentylsulfonyl group, and a 4-methylpentylsulfonyl group.

The C1-C6 alkylsulfonyl group optionally having one or more halogen atoms represents a C1-C6 alkylsulfonyl group one or more hydrogen atoms of which are optionally substituted with a halogen atom, and examples thereof include a methylsulfonyl group, an ethylsulfonyl group, a propylsulfonyl group, an isopropylsulfonyl group, a butylsulfonyl group, an isobutylsulfonyl group, a sec-butylsulfonyl group, a pentylsulfonyl group, a hexylsulfonyl group, a 3-methylpentylsulfonyl group, a 4-methylpentylsulfonyl group, a trifluoromethylsulfonyl group, a trichloromethylsulfonyl group, a pentafluoroethylsulfonyl group, a pentachloroethylsulfonyl group, a 2,2,2-trichloroethylsulfonyl group, a 2,2,2-trifluoroethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a nonafluorobutylsulfonyl group, a nonachlorobutylsulfonyl group, a perfluoropentylsulfonyl group, and a perfluorohexylsulfonyl group.

Examples of the C6-C16 arylsulfonyl group include a phenylsulfonyl group, a 1-naphthylsulfonyl group, a 2-naphthylsulfonyl group, a 1-acenaphthylsulfonyl group, a 1-phenanthrylsulfonyl group, a 9-anthrylsulfonyl group, and a 1-pyrenylsulfonyl group.

The C6-C16 arylsulfonyl group optionally having one or more halogen atoms represents a C6-C16 arylsulfonyl group one or more hydrogen atoms of which are optionally substituted with a halogen atom, and examples thereof include a phenylsulfonyl group, a 1-naphthylsulfonyl group, a 2-naphthylsulfonyl group, a 1-acenaphthylsulfonyl group, a 1-phenanthrylsulfonyl group, a 9-anthrylsulfonyl group, a 1-pyrenylsulfonyl group, a 2-fluorophenylsulfonyl group, a 3-fluorophenylsulfonyl group, a 4-fluorophenylsulfonyl group, a 2-chlorophenylsulfonyl group, a 3-chlorophenylsulfonyl group, a 4-chlorophenylsulfonyl group, a 4-bromophenylsulfonyl group, a 4-iodophenylsulfonyl group, a 2,4-difluorophenylsulfonyl group, a 2,4-dichlorophenylsulfonyl group, a 2,6-dichlorophenylsulfonyl group, a 2,4,6-trifluorophenylsulfonyl group, a 3,4,5-trifluorophenylsulfonyl group, a 2,4,6-trichlorophenylsulfonyl group, a 3,4,5-trichlorophenylsulfonyl group, a pentafluorophenylsulfonyl group, a 2-chloro-4-fluorophenylsulfonyl group, a 2-chloro-6-fluorophenylsulfonyl group, a 2-fluoro-1-naphthylsulfonyl group, a 3-chloro-1-naphthylsulfonyl group, a 5-fluoro-2-naphthylsulfonyl group, a 3-fluoro-1-acenaphthylsulfonyl group, a 9-fluoro-1-phenanthrylsulfonyl group, a 10-fluoro-9-anthrylsulfonyl group, and a 6-fluoro-1-pyrenylsulfonyl group.

Examples of the C1-C6 alkylsulfinyl group include a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, an isoamylsulfinyl group, a neopentylsulfinyl group, and a hexylsulfinyl group.

The C1-C6 alkylsulfinyl group optionally having one or more halogen atoms represents a C1-C6 alkylsulfinyl group one or more hydrogen atoms of which are optionally substituted with a halogen atom, and examples thereof include a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, a hexylsulfinyl group, a 3-methylpentylsulfinyl group, a 4-methylpentylsulfinyl group, a trifluoromethylsulfinyl group, a trichloromethylsulfinyl group, a pentafluoroethylsulfinyl group, a pentachloroethylsulfinyl group, a 2,2,2-trichloroethylsulfinyl group, a 2,2,2-trifluoroethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a nonafluorobutylsulfinyl group, a nonachlorobutylsulfinyl group, a perfluoropentylsulfinyl group, and a perfluorohexylsulfinyl group.

Examples of the C6-C16 arylsulfinyl group include a phenylsulfinyl group, a 1-naphthylsulfinyl group, a 2-naphthylsulfinyl group, a 1-acenaphthylsulfinyl group, a 1-phenanthrylsulfinyl group, a 9-anthrylsulfinyl group, and a 1-pyrenylsulfinyl group.

The C6-C16 arylsulfinyl group optionally having one or more halogen atoms represents a C6-C16 arylsulfinyl group one or more hydrogen atoms of which are optionally substituted with a halogen atom, and examples thereof include a phenylsulfinyl group, a 1-naphthylsulfinyl group, a 2-naphthylsulfinyl group, a 1-acenaphthylsulfinyl group, a 1-phenanthrylsulfinyl group, a 9-anthrylsulfinyl group, a 1-pyrenylsulfinyl group, a 2-fluorophenylsulfinyl group, a 3-fluorophenylsulfinyl group, a 4-fluorophenylsulfinyl group, a 2-chlorophenylsulfinyl group, a 3-chlorophenylsulfinyl group, a 4-chlorophenylsulfinyl group, a 4-bromophenylsulfinyl group, a 4-iodophenylsulfinyl group, a 2,4-difluorophenylsulfinyl group, a 2,4-dichlorophenylsulfinyl group, a 2,6-dichlorophenylsulfinyl group, a 2,4,6-trifluorophenylsulfinyl group, a 3,4,5-trifluorophenylsulfinyl group, a 2,4,6-trichlorophenylsulfinyl group, a 3,4,5-trichlorophenylsulfinyl group, a pentafluorophenylsulfinyl group, a 2-chloro-4-fluorophenylsulfinyl group, a 2-chloro-6-fluorophenylsulfinyl group, a 2-fluoro-1-naphthylsulfinyl group, a 3-chloro-1-naphthylsulfinyl group, a 5-fluoro-2-naphthylsulfinyl group, a 3-fluoro-1-acenaphthylsulfinyl group, a 9-fluoro-1-phenanthrylsulfinyl group, a 10-fluoro-9-anthrylsulfinyl group, and a 6-fluoro-1-pyrenylsulfinyl group.

Examples of the C3-C5 cycloalkyl group include a cyclopropyl group, a cyclobutyl group, and a cyclopentyl group.

The C3-C5 cycloalkyl group optionally having one or more halogen atoms represents a C3-C5 cycloalkyl group one or more hydrogen atoms of which are optionally substituted with a halogen atom, and examples thereof include a cyclopropyl group, a cyclobutyl group, a cyclopentyl group, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclopentyl group, and a 3-chlorocyclopentyl group.

Examples of the C1-C4 alkoxy group include a methoxy group, an ethoxy group, a propyloxy group, and a tert-butyloxy group.

The C1-C4 alkoxy group optionally having one or more halogen atoms represents a C1-C4 alkoxy group one or more hydrogen atoms of which are optionally substituted with a halogen atom, and examples thereof include a methoxy group, an ethoxy group, a propyloxy group, an isopropyloxy group, a butyloxy group, an isobutyloxy group, a sec-butyloxy group, a tert-butyloxy group, a trifluoromethoxy group, a trichloromethoxy group, a chloromethoxy group, a dichloromethoxy group, a fluoromethoxy group, a difluoromethoxy group, a chlorofluoromethoxy group, a pentafluoroethoxy group, a pentachloroethoxy group, a 2-fluoroethoxy group, a 2-chloroethoxy group, a 2,2,2-trifluoroethoxy group, a 2-chloro-2,2-difluoroethoxy group, a heptafluoropropoxy group, a heptachloropropoxy group, a 3,3,3-trifluoropropoxy group, a 3,3,3-trichloropropoxy group, a 3,3,3-tribromopropoxy group, a 2,3,3-trifluoropropoxy group, a nonafluorobutoxy group, and a nonachlorobutoxy group.

The amino group optionally having one or two C1-C6 alkyl groups represents an amino group in which one or two hydrogen atoms on nitrogen are optionally substituted with the same or different C1-C6 alkyl groups, and examples thereof include an amino group, an N-methylamino group, an N-ethylamino group, an N-propylamino group, an N-isopropylamino group, an N-butylamino group, an N,N-dimethylamino group, an N,N-diethylamino group, an N,N-dipropylamino group, an N-ethyl-N-methylamino group, and an N-propyl-N-methylamino group.

Examples of the C3-C9 trialkylsilyl group include a trimethylsilyl group, a tert-butyldimethylsilyl group, a triethylsilyl group, an isopropyldimethylsilyl group, and a triisopropylsilyl group.

Examples of the C1-C4 alkylsulfonyl group include a methylsulfonyl group, an ethylsulfonyl group, a propylsulfonyl group, an isopropylsulfonyl group, a butylsulfonyl group, an isobutylsulfonyl group, and a sec-butylsulfonyl group.

The C1-C4 alkylsulfonyl group optionally having one or more halogen atoms represents a C1-C4 alkylsulfonyl group one or more hydrogen atoms of which are optionally substituted with a halogen atom, and examples thereof include a methylsulfonyl group, an ethylsulfonyl group, a propylsulfonyl group, an isopropylsulfonyl group, a butylsulfonyl group, an isobutylsulfonyl group, a sec-butylsulfonyl group, a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a 2,2,2-trichloroethylsulfonyl group, a 2,2,2-trifluoroethylsulfonyl group, a heptafluoropropylsulfonyl group, a heptachloropropylsulfonyl group, a 3,3,3-trifluoropropylsulfonyl group, a 3,3,3-triiodopropylsulfonyl group, a nonafluorobutylsulfonyl group, and a nonachlorobutylsulfonyl group.

Examples of the C1-C4 alkylsulfinyl group include a methylsulfinyl group, an ethylsulfinyl group, a propylsulfinyl group, an isopropylsulfinyl group, a butylsulfinyl group, an isobutylsulfinyl group, and a sec-butylsulfinyl group.

The C1-C4 alkylsulfinyl group optionally having one or more halogen atoms represents a C1-C4 alkylsulfinyl group one or more hydrogen atoms of which are optionally substituted with a halogen atom, and examples thereof include a methylsulfinyl group, an ethylsulfinyl group, a propylsulfinyl group, an isopropylsulfinyl group, a butylsulfinyl group, an isobutylsulfinyl group, a sec-butylsulfinyl group, a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a 2,2,2-trichloroethylsulfinyl group, a 2,2,2-trifluoroethylsulfinyl group, a heptafluoropropylsulfinyl group, a heptachloropropylsulfinyl group, a 3,3,3-trifluoropropylsulfinyl group 3,3,3-triiodopropylsulfinyl group, a nonafluorobutylsulfinyl group, and a nonachlorobutylsulfinyl group.

The C2-C5 alkoxyalkyl group has 2 to 5 carbon atoms as the total of carbon atoms in the alkoxy and alkyl moieties, and examples thereof include a methoxymethyl group, an ethoxymethyl group, a propyloxymethyl group, an isopropyloxymethyl group, a butyloxymethyl group, an isobutyloxymethyl group, a sec-butyloxymethyl group, a 1-methoxyethyl group, a 2-methoxyethyl group, a 2-propyloxyethyl group, a 2-isopropyloxyethyl group, a 3-methoxypropyl group, a 3-ethoxypropyl group, a 3-methoxybutyl group, and a 4-methoxybutyl group.

The C2-C5 alkylthioalkyl group has a total of 2 to 5 carbon atoms in the whole C2-C5 alkylthioalkyl group, and examples thereof include a methylthiomethyl group, an ethylthiomethyl group, a propylthiomethyl group, an isopropylthiomethyl group, a butylthiomethyl group, an isobutylthiomethyl group, a sec-butylthiomethyl group, a 1-methylthioethyl group, a 2-methylthioethyl group, a 2-propylthioethyl group, a 2-isopropylthioethyl group, a 3-methylthiopropyl group, a 3-ethylthiopropyl group, a 3-methylthiobutyl group, and a 4-methylthiobutyl group.

Examples of the C3-C4 cycloalkyl group include a cyclopropyl group and a cyclobutyl group.

The C3-C4 cycloalkyl group optionally having one or more halogen atoms represents a C3-C4 cycloalkyl group one or more hydrogen atoms of which are optionally substituted with a halogen atom, and examples thereof include a cyclopropyl group, a cyclobutyl group, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, and a 2,2,3,3-tetrafluorocyclobutyl group.

Examples of the C1-C3 alkoxy group include a methoxy group, an ethoxy group, a propyloxy group, and an isopropyloxy group.

The C1-C3 alkoxy group optionally having one or more halogen atoms represents a C1-C3 alkoxy group one or more hydrogen atoms of which are optionally substituted with a halogen atom, and examples thereof include a methoxy group, an ethoxy group, a propyloxy group, an isopropyloxy group, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2-fluoroethoxy group, a 2-chloroethoxy group, a 2,2-difluoroethoxy group, a 2,2,2-trifluoroethoxy group, a 3,3,3-trifluoropropoxy group, a 3,3,3-trichloropropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, and a 3,3,3-trifluoropropoxy group.

Examples of the C1-C4 alkylthio group include a methylthio group, an ethylthio group, a propylthio group, an isopropylthio group, a butylthio group, an isobutylthio group, and a tert-butylthio group.

The C1-C4 alkylthio group optionally having one or more halogen atoms represents a C1-C4 alkylthio group one or more hydrogen atoms of which are optionally substituted with a halogen atom, and examples thereof include a methylthio group, an ethylthio group, a propylthio group, an isopropylthio group, a butylthio group, an isobutylthio group, a tert-butylthio group, a fluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a 2,2,2-trichloroethylthio group, a 2,2,2-trifluoroethylthio group, a 2,2,2-trifluoroethylthio group, and a 2,2-difluoroethylthio group.

Examples of the C2-C4 alkylcarbonylthio group include an acetylthio group, a propionylthio group, and a butanoylthio group.

The C2-C4 alkylcarbonyloxy group represents a group in which the whole number of carbon atoms including carbon atoms of carbonyl is within a range of 2 to 4, and examples thereof include an acetyloxy group, a propionyloxy group, and a butanoyloxy group.

Examples of the C3-C5 cycloalkyloxy group include a cyclopropyloxy group, a cyclobutyloxy group, and a cyclopentyloxy group.

The C3-C5 cycloalkyloxy group optionally having one or more halogen atoms represents a C3-C5 cycloalkyloxy group one or more hydrogen atoms of which are optionally substituted with a halogen atom, and examples thereof include a cyclopropyloxy group, a cyclobutyloxy group, a cyclopentyloxy group, a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2,3,3-tetrafluorocyclobutyloxy group, a 2-chlorocyclopentyloxy group, and a 2-chlorocyclopentyloxy group.

Examples of the C2-C4 alkenyl group include a vinyl group, a 1-propenyl group, an isopropenyl group, and a 2-butenyl group.

The C2-C4 alkenyl group optionally having one or more halogen atoms represents a C2-C4 alkenyl group one or more hydrogen atoms of which are optionally substituted with a halogen atom, and examples thereof include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 2-chloro-2-propenyl group, a 3,3-difluoro-2-propenyl group, a 2,3,3-trichloro-2-propenyl group, a 3-chloro-2-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, and a 3,4,4-trifluoro-1,3-butadienyl group.

Examples of the C2-C4 alkylcarbonyl group include an acetyl group, a propionyl group, and a butanoyl group.

The C2-C4 alkylcarbonyl group optionally having one or more halogen atoms represents a C2-C4 alkylcarbonyl group one or more hydrogen atoms of which are optionally substituted with a halogen atom, and examples thereof include an acetyl group, a propionyl group, a butanoyl group, a trichloroacetyl group, a fluoroacetyl group, a difluoroacetyl group, a trifluoroacetyl group, a pentafluoropropionyl group, a pentachloropropionyl group, a 3,3,3-trichloropropionyl group, a 3,3,3-trifluoropropionyl group, a 3,3,3-tribromopropionyl group, a 3,3,3-triiodopropionyl group, a heptafluorobutanoyl group, a heptachlorobutanoyl group, a 4,4,4-trifluorobutanoyl group, and a 4,4,4-trichlorobutanoyl group.

Examples of the C2-C4 alkynyl group include an ethynyl group, a propargyl group, and a 2-butynyl group.

The C2-C4 alkynyl group optionally having one or more halogen atoms represents a C2-C4 alkynyl group one or more hydrogen atoms of which are optionally substituted with a halogen atom, and examples thereof include an ethynyl group, a propargyl group, a 1-butyn-3-yl group, a 3-methyl-1-butyn-3-yl group, a 2-butynyl group, a 3-butynyl group, a fluoroethynyl group, a 3-chloro-2-propynyl group, a 3-bromo-2-propynyl group, a 3-iodo-2-propynyl group, a 3-chloro-1-propynyl group, a 3,3,3-trifluoro-1-propynyl group, a 3-fluoro-2-propynyl group, and a perfluoro-2-butynyl group.

Examples of the C2-C3 alkenyl group include a vinyl group and an isopropenyl group.

The C2-C3 alkenyl group optionally having one or more halogen atoms represents a C2-C3 alkenyl group one or more hydrogen atoms of which are optionally substituted with a halogen atom, and examples thereof include a vinyl group, a 1-propenyl group, a 2-propenyl group, a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, and a 2,3,3-trichloro-2-propenyl group.

Examples of the C2-C3 alkynyl group include an ethynyl group and a propargyl group.

The C2-C3 alkynyl group optionally having one or more halogen atoms represents a C2-C3 alkynyl group one or more hydrogen atoms of which are optionally substituted with a halogen atom, and examples thereof include an ethynyl group, a propargyl group, a fluoroethynyl group, a 3-chloro-2-propynyl group, a 3-bromo-2-propynyl group, a 3-iodo-2-propynyl group, and a 3-chloro-1-propynyl group.

The amino group optionally having one or two C1-C8 alkyl groups (optionally having a halogen atom) represents an amino group in which one or two hydrogen atoms on nitrogen are substituted with the same or different alkyl groups, the total number of carbon atoms of the alkyl group on the nitrogen is within a range of 1 to 8 and one or more hydrogen atoms on the carbon atom are optionally substituted with a halogen atom.

Examples thereof include a methylamino group, an ethylamino group, a propylamino group, an isopropylamino group, an N,N-dimethylamino group, an N,N-diethylamino group, an N-ethyl-N-methylamino group, a butylamino group, a pentylamino group, a hexylamino group, an N,N-dibutylamino group, an N-sec-butyl-N-methylamino group, a 2,2,2-trifluoroethylamino group, an N,N-(2,2-ditrifluoroethyl)-amino group, an N,N-(2,2-ditrichloroethyl)-amino group, and a pentafluoropropylamino group.

Examples of the C1-C3 alkylthio group include a methylthio group, an ethylthio group, a propylthio group, and an isopropylthio group.

The C1-C3 alkylthio group optionally having one or more halogen atoms represents a C1-C3 alkylthio group one or more hydrogen atoms of which are optionally substituted with a halogen atom, and examples thereof include a methylthio group, an ethylthio group, a propylthio group, an isopropylthio group, a fluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a 2,2,2-trichloroethylthio group, a 2,2,2-trifluoroethylthio group, a 2,2,2-trifluoroethylthio group, and a 2,2-difluoroethylthio group.

The aminocarbonyl group optionally having one or two C1-C6 alkyl groups represents an aminocarbonyl group in which one or two hydrogen atoms on nitrogen are optionally substituted with the same or different alkyl groups, and examples thereof include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a diisopropylaminocarbonyl group, a pentylaminocarbonyl group, and a hexylaminocarbonyl group.

The C1-C6 alkyl group optionally having an atom or a group selected from Group $P^2$ represents a C1-C6 alkyl a hydrogen atom of which is optionally substituted with an atom or a group selected from Group $P^2$ and, when a C1-C6 alkyl group has two or more atoms or groups selected from Group $P^2$, those atoms and groups may be the same or different with each other.

Examples of the C1-C6 alkyl group optionally having an atom or a group selected from Group $P^2$ include a trifluoromethyl group, a trichloromethyl group, a tribromomethyl group, a 2,2,2-trifluoroethyl group, a 2,2,2-trichloroethyl group, a 3,3,3-trifluoropropyl group, a difluoromethyl group, a 2,2-difluoroethyl group, a 1,1-difluoroethyl group, a pentafluoroethyl group, a heptafluoroisopropyl group, a 1,1,2,2-tetrafluoroethyl group, a cyclopropylmethyl group, a cyclopropylethyl group, a cyclopropylpropyl group, a cyclopropylhexyl group, a cyclobutylmethyl group, a cyclobutylethyl group, a cyclobutylpropyl group, a cyclopentylmethyl group, a 1-fluorocyclopropylmethyl group, a 1-fluorocyclopropylethyl group, a 1-fluorocyclopropylpropyl group, a 2,2-difluorocyclopropylmethyl group, a 2,2-difluorocyclopropylethyl group, a pentafluorocyclopropylmethyl group, a pentafluorocyclopropylethyl group, a 1-chlorocyclopropylmethyl group, a 1-chlorocyclopropylethyl group, a 2,2-dichlorocyclopropylmethyl group, a 2,2-dichlorocyclopropylethyl group, a pentachlorocyclopropylmethyl group, a 1-fluorocyclobutylmethyl group, a 1-fluorocyclobutylethyl group, a 2,2-difluorocyclobutylmethyl group, a 2,2-difluorocyclobutylethyl group, a 1-chlorocyclobutylmethyl group, a 1-chlorocyclobutylethyl group, a 2,2-dichlorocyclobutylmethyl group, a 2,2-dichlorocyclobutylethyl group, a 1-fluorocyclopentylmethyl group, a 1-fluorocyclopentylethyl group, a 2,2-difluorocyclopentylmethyl group, a 2,2-difluorocyclopentylethyl group, a 3,3-difluorocyclopentylmethyl group, a 3,3-difluorocyclopentylethyl group, a 1-chlorocyclopentylmethyl group, a 1-chlorocyclopentylethyl group, a 2,2-dichlorocyclopentylmethyl group, a 2,2-dichlorocyclopentylethyl group, a 3,3-dichlorocyclopentylmethyl group, a 3,3-dichlorocyclopentylethyl group, a 1-fluorocyclohexylmethyl group, a 1-fluorocyclohexylethyl group, a 2,2-difluorocyclohexylmethyl group, a 2,2-difluorocyclohexylethyl group, a 3,3-difluorocyclohexylmethyl group, a 3,3-difluorocyclohexylethyl group, a 4,4-difluorocyclohexylmethyl group, a 4,4-difluorocyclohexylethyl group, a 4,4-difluorocyclohexylpropyl group, a 1-chlorocyclohexylmethyl group, a 1-chlorocyclohexylethyl group, a 1-chlorocyclohexylpropyl group, a 2,2-dichlorocyclohexylmethyl group, a 2,2-dichlorocyclohexylethyl group, a 2,2-dichlorocyclohexylpropyl group, a 3,3-dichlorocyclohexylmethyl group, a 3,3-dichlorocyclohexylethyl group, a 3,3-dichlorocyclohexylpropyl group, a methoxymethyl group, an ethoxymethyl group, an isopropoxymethyl group, a tert-butoxymethyl group, a 2-methoxyethyl group, a 2-ethoxyethyl group, a 2-tert-butoxyethyl group, a trifluoromethoxymethyl group, a 2-trifluoromethoxyethyl group, a difluoromethoxymethyl group, a 2-difluoromethoxyethyl group, a 2-pentafluoroethoxyethyl group, a 1,1,2,2-tetrafluoroethoxymethyl group, a 2-(1,1,2,2-tetrafluoroethoxy)-ethyl group, a methylthiomethyl group, a 2-methylthioethyl group, an ethylthiomethyl group, a 2-ethylthioethyl group, a 3-ethylthiopropyl group, a tert-butylthiomethyl group, a 2-(tert-butylthio)-ethyl group, a trifluoromethylthiomethyl group, a 2-trifluoromethylthioethyl group, a cyanomethyl group, a 2-cyanoethyl group, a 3-cyanopropyl group, a 1-cyanoethyl group, a 2-cyano-2-methylethyl group, and a 2-cyano-2-methylpropyl group.

The C3-C6 cycloalkyl group optionally having an atom or a group selected from Group $P^2$ represents a C3-C6 cycloalkyl a hydrogen atom of which is optionally substituted with an atom or a group selected from Group $P^2$ and, when a C3-C6 cycloalkyl group has two or more atoms or groups selected from Group $P^2$, those atoms and groups may be the same as or different from each other.

Examples of the C3-C6 cycloalkyl group optionally having an atom or a group selected from Group $P^2$ include a 1-fluorocyclopropyl group, a 2,2-difluorocyclopropyl group, a 1-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group, a 2,2,3,3-tetrafluorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group, a 4,4-difluorocyclohexyl group, a 1-cyclopropylcyclopropyl group, a 2-cyclopropylcyclopropyl group, a 1-(1-fluorocyclopropyl)-cyclopropyl group, a 1-(2,2-difluorocyclopropyl)-cyclopropyl group, a 1-(1-chlorocyclopropyl)-cyclopropyl group, a 1-(2,2-dichlorocyclopropyl)-cyclopropyl group, a 1-methoxycyclopropyl group, a 1-methoxycyclobutyl group, a 1-methoxycyclopentyl group, a 2-methoxycyclopropyl group, a 2-methoxycyclobutyl group, a 2-methoxycyclopentyl group, a 2-ethoxycyclopropyl group, a 2-ethoxycyclobutyl group, a 1-ethoxycyclopropyl group, a 1-ethoxycyclobutyl group, a 1-isopropoxycyclopropyl group, a 1-trifluoromethoxycyclopropyl group, a 2-trifluoromethoxycyclopropyl group, a 1-difluoromethoxycyclopropyl group, a 2-difluoromethoxycyclopropyl group, a 2-(2,2-difluoroethoxy)-cyclopropyl group, a 1-methylthiocyclopropyl group, a 1-ethylthiocyclopropyl group, a 2-methylthiocyclopropyl group, a 2-ethylthiocyclopropyl group, a 1-trifluoromethylthiocyclopropyl group, a 2-trifluoromethylthiocyclopropyl group, a 1-cyanocyclopropyl group, a 2-cyanocyclopropyl group, and a 2,2-dicyanocyclopropyl group.

Examples of the C1-C5 alkyl group include a methyl group, an ethyl group, a propyl group, an isopropyl group, a butyl group, a tert-butyl group, and a pentyl group.

Examples of the present compound, in one aspect, include compounds having the substituents shown below in formula (1).

A tetrazolinone compound in which Q is an 6-membered aromatic heterocyclic group (provided that Q optionally has one or more atoms or groups selected from the group consisting of a C1-C6 alkyl group optionally having one or more halogen atoms, a halogen atom, a C2-C6 alkynyl group, a C3-C6 cycloalkyl group, a C1-C6 alkoxy group, and a cyano group); $R^1$ is a C1-C6 alkyl group optionally having one or more halogen atoms, a C3-C6 cycloalkyl group, a halogen atom, or a hydrogen atom; $R^2$ is a C1-C6 alkyl group or a hydrogen atom; $R^3$, $R^4$, $R^5$, $R^7$, $R^8$, $R^9$, and $R^{11}$ are hydrogen atoms; $R^6$ is a C1-C6 alkyl group, a C1-C6 alkoxy group, a C1-C6 alkylthio group, a C3-C6 cycloalkyl group, a halogen atom, or a hydrogen atom; $R^{10}$ is a C1-C3 alkyl group; and X is an oxygen atom.

A tetrazolinone compound in which Q is Q1; $R^{13}$, $R^{14}$, $R^{15}$, and $R^{16}$ are the same or different and represent a C1-C6 alkyl group optionally having one or more halogen atoms, a halogen atom, a C3-C6 cycloalkyl group, a C1-C6 alkoxy group, a hydrogen atom, or a cyano group; $R^1$ is a C1-C6 alkyl group optionally having one or more halogen atoms, a C3-C6 cycloalkyl group, a halogen atom, or a hydrogen atom; $R^2$ is a C1-C6 alkyl group or a hydrogen atom; $R^3$, $R^4$, $R^5$, $R^7$, $R^8$, $R^9$, and $R^{11}$ are hydrogen atoms; $R^6$ is a C1-C6 alkyl group, a C1-C6 alkoxy group, a C3-C6 cycloalkyl group, a halogen atom, or a hydrogen atom; $R^{10}$ is a C1-C3 alkyl group; and X is an oxygen atom.

A tetrazolinone compound in which Q is Q2; $R^{12}$, $R^{14}$, $R^{15}$, and $R^{16}$ are the same or different and represent a C1-C6 alkyl group, a hydrogen atom, or a halogen atom; $R^1$ is a C1-C6 alkyl group; $R^2$, $R^3$, $R^4$, $R^5$, $R^7$, $R^8$, $R^9$, and $R^{11}$ are hydrogen atoms; $R^6$ is a C1-C6 alkyl group, a C1-C6 alkoxy group, a C3-C6 cycloalkyl group, a halogen atom, or a hydrogen atom; $R^{10}$ is a C1-C3 alkyl group; and X is an oxygen atom.

A tetrazolinone compound in which Q is Q3; $R^{12}$, $R^{13}$, $R^{15}$, and $R^{16}$ are the same or different and represent a C1-C6 alkyl group, a hydrogen atom, or a halogen atom; $R^1$ and $R^6$ are the same or different and represent a C1-C6 alkyl group; $R^2$, $R^3$, $R^4$, $R^5$, $R^7$, $R^8$, $R^9$, and $R^{11}$ are hydrogen atoms; $R^{10}$ is a C1-C3 alkyl group; and X is an oxygen atom.

A tetrazolinone compound in which Q is Q4; $R^{13}$, $R^{14}$, and $R^{15}$ are the same or different and represent a C1-C6 alkyl group or a hydrogen atom; $R^1$ is a C1-C6 alkyl group; $R^2$, $R^3$, $R^4$, $R^5$, $R^7$, $R^8$, $R^9$, and $R^{11}$ are hydrogen atoms; $R^6$ is a 1-C6 alkyl group, a C1-C6 alkoxy group, a C1-C6 alkylthio group, a C3-C6 cycloalkyl group, a halogen atom, or a hydrogen atom; $R^{10}$ is a C1-C3 alkyl group; and X is an oxygen atom.

A tetrazolinone compound in which Q is Q5; $R^{13}$, $R^{15}$, and $R^{16}$ are the same or different and represent a C1-C6 alkyl group or a hydrogen atom; $R^1$ is a C1-C6 alkyl group; $R^2$, $R^3$, $R^4$, $R^5$, $R^7$, $R^8$, $R^9$, and $R^{11}$ are hydrogen atoms; $R^6$ is a C1-C6 alkyl group, a C1-C6 alkoxy group, a C3-C6 cycloalkyl group, a halogen atom, or a hydrogen atom; $R^{10}$ is a C1-C3 alkyl group; and X is an oxygen atom.

A tetrazolinone compound in which Q is Q6; $R^{12}$, $R^{14}$, and $R^{16}$ are the same or different and represent a C1-C6 alkyl group or a hydrogen atom; $R^1$, and $R^6$ are the same or different and represent a C1-C6 alkyl group; $R^2$, $R^3$, $R^4$, $R^5$, $R^7$, $R^8$, $R^9$, and $R^{11}$ are hydrogen atoms; $R^{10}$ is a C1-C3 alkyl group; and X is an oxygen atom.

A tetrazolinone compound in which Q is Q7; $R^{14}$, $R^{15}$, and $R^{16}$ are the same or different and represent a C1-C6 alkyl group, a C1-C6 alkoxy group, or a C2-C6 alkynyl group; $R^1$ and $R^6$ are the same or different and represent a C1-C6 alkyl group; $R^2$, $R^3$, $R^4$, $R^5$, $R^7$, $R^8$, $R^9$, and $R^{11}$ are hydrogen atoms; $R^{10}$ is a C1-C3 alkyl group; and X is an oxygen atom.

A tetrazolinone compound in which Q is Q10; $R^{13}$, $R^{14}$, and $R^{16}$ are hydrogen atoms; $R^1$ and $R^6$ are the same or different and represent a C1-C6 alkyl group; $R^2$, $R^3$, $R^4$, $R^5$, $R^7$, $R^8$, $R^9$, and $R^{11}$ are hydrogen atoms; $R^{10}$ is a C1-C3 alkyl group; and X is an oxygen atom.

[Aspect 1A]

A tetrazolinone compound in which Q is Q1; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^{13}$, $R^{14}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, or a C6-C16 arylthio group optionally having one or more halogen atoms.

A tetrazolinone compound in which $R^1$ is a C1-C3 alkyl group optionally having one or more halogen atoms, or a halogen atom in [Aspect 1A].

A tetrazolinone compound in which $R^1$ is a C1-C3 alkyl group optionally having one or more halogen atoms in [Aspect 1A].

A tetrazolinone compound in which $R^1$ is a halogen atom in [Aspect 1A].

A tetrazolinone compound in which $R^1$ is a methyl group in [Aspect 1A].

A tetrazolinone compound in which $R^1$ is a chlorine atom in [Aspect 1A].

A tetrazolinone compound in which $R^1$ is a trifluoromethyl group in [Aspect 1A].

[Aspect 1B]

A tetrazolinone compound in which Q is Q1; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^{13}$, $R^{14}$, $R^{15}$, and $R^{16}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

A tetrazolinone compound in which $R^1$ is a C1-C3 alkyl group optionally having one or more halogen atoms, or a halogen atom in [Aspect 1B].

A tetrazolinone compound in which $R^1$ is a C1-C3 alkyl group optionally having one or more halogen atoms in [Aspect 1B].

A tetrazolinone compound in which $R^1$ is a halogen atom in [Aspect 1B].

A tetrazolinone compound in which $R^1$ is a methyl group in [Aspect 1B].

A tetrazolinone compound in which $R^1$ is a chlorine atom in [Aspect 1B].

A tetrazolinone compound in which $R^1$ is a trifluoromethyl group in [Aspect 1B].

[Aspect 1C]

A tetrazolinone compound in which Q is Q1; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{13}$, $R^{14}$, $R^{15}$, and $R^{16}$ are the same or different and represent a C1-C3 alkyl group optionally having one or more a halogen atom, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, or a C6-C16 arylthio group optionally having one or more halogen atoms.

A tetrazolinone compound in which $R^6$ is a C1-C3 alkyl group optionally having one or more halogen atoms in [Aspect 1C].

A tetrazolinone compound in which $R^6$ is a C3-C4 cycloalkyl group optionally having one or more halogen atoms in [Aspect 1C].

A tetrazolinone compound in which $R^6$ is a C1-C3 alkoxy group optionally having one or more halogen atoms in [Aspect 1C].

A tetrazolinone compound in which $R^6$ is a halogen atom in [Aspect 1C].

A tetrazolinone compound in which $R^6$ is a hydrogen atom in [Aspect 1C].

A tetrazolinone compound in which $R^6$ is a methyl group in [Aspect 1C].

A tetrazolinone compound in which $R^6$ is an ethyl group in [Aspect 1C].

A tetrazolinone compound in which $R^6$ is a chlorine atom in [Aspect 1C].

A tetrazolinone compound in which $R^6$ is a cyclopropyl group in [Aspect 1C].

[Aspect 1D]

A tetrazolinone compound in which Q is Q1; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{13}$, $R^{14}$, $R^{15}$, and $R^{16}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy groups optionally having one or more halogen atoms.

A tetrazolinone compound in which $R^6$ is a C1-C3 alkyl group optionally having one or more halogen atoms in [Aspect 1D].

A tetrazolinone compound in which $R^6$ is a C3-C4 cycloalkyl group optionally having one or more halogen atoms in [Aspect 1D].

A tetrazolinone compound in which $R^6$ is a C1-C3 alkoxy group optionally having one or more halogen atoms in [Aspect 1D].

A tetrazolinone compound in which $R^6$ is a halogen atom in [Aspect 1D].

A tetrazolinone compound in which $R^6$ is a hydrogen atom in [Aspect 1D].

A tetrazolinone compound in which $R^6$ is a methyl group in [Aspect 1D].

A tetrazolinone compound in which $R^6$ is an ethyl group in [Aspect 1D].

A tetrazolinone compound in which $R^6$ is a chlorine atom in [Aspect 1D].

A tetrazolinone compound in which $R^6$ is a cyclopropyl group in [Aspect 1D].

[Aspect 2A]

A tetrazolinone compound in which Q is Q2; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^{12}$, $R^{14}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, or a C6-C16 arylthio group optionally having one or more halogen atoms.

A tetrazolinone compound in which $R^1$ is a C1-C3 alkyl group optionally having one or more halogen atoms, or a halogen atom in [Aspect 2A].

A tetrazolinone compound in which $R^1$ is a C1-C3 alkyl group optionally having one or more halogen atoms in [Aspect 2A].

A tetrazolinone compound in which $R^1$ is a halogen atom in [Aspect 2A].

A tetrazolinone compound in which $R^1$ is a methyl group in [Aspect 2A].

A tetrazolinone compound in which $R^1$ is a chlorine atom in [Aspect 2A].

A tetrazolinone compound in which $R^1$ is a trifluoromethyl group in [Aspect 2A].

[Aspect 2B]

A tetrazolinone compound in which Q is Q2; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^{12}$, $R^{14}$, $R^{15}$, and $R^{16}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atom.

A tetrazolinone compound in which $R^1$ is a C1-C3 alkyl group optionally having one or more halogen atoms, or a halogen atom in [Aspect 2B].

A tetrazolinone compound in which $R^1$ is a C1-C3 alkyl group optionally having one or more halogen atoms in [Aspect 2B].

A tetrazolinone compound in which $R^1$ is a halogen atom in [Aspect 2B].

A tetrazolinone compound in which $R^1$ is a methyl group in [Aspect 2B].

A tetrazolinone compound in which $R^1$ a chlorine atom in [Aspect 2B].

A tetrazolinone compound in which $R^1$ is a trifluoromethyl group in [Aspect 2B].

[Aspect 2C]

A tetrazolinone compound in which Q is Q2; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{12}$, $R^{14}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, or a C6-C16 arylthio group optionally having one or more halogen atoms.

A tetrazolinone compound in which $R^6$ is a C1-C3 alkyl group optionally having one or more halogen atoms in [Aspect 2C].

A tetrazolinone compound in which $R^6$ is a C3-C4 cycloalkyl group optionally having one or more halogen atoms in [Aspect 2C].

A tetrazolinone compound in which $R^6$ is a C1-C3 alkoxy group optionally having one or more halogen atoms in [Aspect 2C].

A tetrazolinone compound in which $R^6$ is a halogen atom in [Aspect 2C].

A tetrazolinone compound in which $R^6$ is a hydrogen atom in [Aspect 2C].

A tetrazolinone compound in which $R^6$ is a methyl group in [Aspect 2C].

A tetrazolinone compound in which $R^6$ is an ethyl group in [Aspect 2C].

A tetrazolinone compound in which $R^6$ is a chlorine atom in [Aspect 2C].

A tetrazolinone compound in which $R^6$ is a cyclopropyl group in [Aspect 2C].

[Aspect 2D]

A tetrazolinone compound in which Q is Q2; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{12}$, $R^{14}$, $R^{15}$, and $R^{16}$ are the same or different and represent a C1-C3 alkyl group optionally having one or more halogen atoms, a halogen atom, a hydrogen atom, a C3-C4 cycloalkyl group optionally having one or more halogen atoms, cyano groups, or a C1-C3 alkoxy group optionally having one or more halogen atoms.

A tetrazolinone compound in which $R^6$ is a C1-C3 alkyl group optionally having one or more halogen atoms in [Aspect 2D]. A tetrazolinone compound in which $R^6$ is a C3-C4 cycloalkyl group optionally having one or more halogen atoms in [Aspect 2D].

A tetrazolinone compound in which $R^6$ is a C1-C3 alkoxy group optionally having one or more halogen atoms in [Aspect 2D].

A tetrazolinone compound in which $R^6$ is a halogen atom in [Aspect 2D].

A tetrazolinone compound in which $R^6$ is a hydrogen atom in [Aspect 2D].

A tetrazolinone compound in which $R^6$ is a methyl group in [Aspect 2D].

A tetrazolinone compound in which $R^6$ is an ethyl group in [Aspect 2D].

A tetrazolinone compound in which $R^6$ is a chlorine atom in [Aspect 2D].

A tetrazolinone compound in which $R^6$ is a cyclopropyl group in [Aspect 2D].

[Aspect 3A]

A tetrazolinone compound in which Q is Q3; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^{12}$, $R^{13}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, or a C6-C16 arylthio group optionally having one or more halogen atoms.

A tetrazolinone compound in which $R^1$ is a C1-C3 alkyl group optionally having one or more halogen atoms, or a halogen atom in [Aspect 3A].

A tetrazolinone compound in which $R^1$ is a C1-C3 alkyl group optionally having one or more halogen atoms in [Aspect 3A].

A tetrazolinone compound in which $R^1$ is a halogen atom in [Aspect 3A].

A tetrazolinone compound in which $R^1$ is a methyl group in [Aspect 3A].

A tetrazolinone compound in which $R^1$ is a chlorine atom in [Aspect 3A].

A tetrazolinone compound in which $R^1$ is a trifluoromethyl group in [Aspect 3A].

[Aspect 3B]

A tetrazolinone compound in which Q is Q3; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^{12}$, $R^{13}$, $R^{15}$, and $R^{16}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

A tetrazolinone compound in which $R^1$ is a C1-C3 alkyl group optionally having one or more halogen atoms, or a halogen atom in [Aspect 3B].

A tetrazolinone compound in which $R^1$ is a C1-C3 alkyl group optionally having one or more halogen atoms in [Aspect 3B].

A tetrazolinone compound in which $R^1$ is a halogen atom in [Aspect 3B].

A tetrazolinone compound in which $R^1$ is a methyl group in [Aspect 3B].

A tetrazolinone compound in which $R^1$ is a chlorine atom in [Aspect 3B].

A tetrazolinone compound in which $R^1$ is a trifluoromethyl group in [Aspect 3B].

[Aspect 3C]

A tetrazolinone compound in which Q is Q3; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{12}$, $R^{13}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, C6-C16 aryloxy group optionally having one or more halogen atoms, or a C6-C16 arylthio group optionally having one or more halogen atoms.

A tetrazolinone compound in which $R^6$ is a C1-C3 alkyl group optionally having one or more halogen atoms in [Aspect 3C].

A tetrazolinone compound in which $R^6$ is a C3-C4 cycloalkyl group optionally having one or more halogen atoms in [Aspect 3C].

A tetrazolinone compound in which $R^6$ is a C1-C3 alkoxy group optionally having one or more halogen atoms in [Aspect 3C].

A tetrazolinone compound in which $R^6$ is a halogen atom in [Aspect 3C].

A tetrazolinone compound in which $R^6$ is a hydrogen atom in [Aspect 3C].

A tetrazolinone compound in which $R^6$ is a methyl group in [Aspect 3C].

A tetrazolinone compound in which $R^6$ is an ethyl group in [Aspect 3C].

A tetrazolinone compound in which $R^6$ is a chlorine atom in [Aspect 3C].

A tetrazolinone compound in which $R^6$ is a cyclopropyl group in [Aspect 3C].

[Aspect 3D]

A tetrazolinone compound in which Q is Q3; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{12}$, $R^{13}$, $R^{15}$, and $R^{16}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

A tetrazolinone compound in which $R^6$ is a C1-C3 alkyl group optionally having one or more halogen atoms in [Aspect 3D]. A tetrazolinone compound in which $R^6$ is a C3-C4 cycloalkyl group optionally having one or more halogen atoms in [Aspect 3D].

A tetrazolinone compound in which $R^6$ is a C1-C3 alkoxy group optionally having one or more halogen atoms in [Aspect 3D]. A tetrazolinone compound in which $R^6$ is a halogen atom in [Aspect 3D].

A tetrazolinone compound in which $R^6$ is a hydrogen atom in [Aspect 3D].

A tetrazolinone compound in which $R^6$ is a methyl group in [Aspect 3D].

A tetrazolinone compound in which $R^6$ is an ethyl group in [Aspect 3D].

A tetrazolinone compound in which $R^6$ is a chlorine atom in [Aspect 3D].

A tetrazolinone compound in which $R^6$ is a cyclopropyl group in [Aspect 3D].

[Aspect 4A]

A tetrazolinone compound in which Q is Q4; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^1$, $R^{14}$, and $R^{15}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, or a C6-C16 arylthio group optionally having one or more halogen atoms.

A tetrazolinone compound in which $R^1$ is a C1-C3 alkyl group optionally having one or more halogen atoms, or a halogen atom in [Aspect 4A].

A tetrazolinone compound in which $R^1$ is a C1-C3 alkyl group optionally having one or more halogen atoms in [Aspect 4A].

A tetrazolinone compound in which $R^1$ is a halogen atom in [Aspect 4A].

A tetrazolinone compound in which $R^1$ is a methyl group in [Aspect 4A].

A tetrazolinone compound in which $R^1$ is a chlorine atom in [Aspect 4A].

A tetrazolinone compound in which $R^1$ is a trifluoromethyl group in [Aspect 4A].

[Aspect 4B]

A tetrazolinone compound in which Q is Q4; $R^2$, $R^4$, $R^5$, $R^7$, $R^8$, $R^9$, and $R^{11}$ are hydrogen atoms; $R^3$ is a hydrogen atom or a methyl group; $R^6$ is a C1-C3 alkyl group optionally having one or more halogen atoms, a C3-C4 cycloalkyl group optionally having one or more halogen atoms, a C1-C3 alkoxy group optionally having one or more halogen atoms, a C2-C4 alkenyl group optionally having one or more halogen atoms, a halogen atom, a hydrogen atom, or a cyano group; $R^{10}$ is a methyl group; and $R^{13}$, $R^{14}$, and $R^{15}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

A tetrazolinone compound in which $R^1$ is a C1-C3 alkyl group optionally having one or more halogen atoms, or a halogen atom in [Aspect 4B].

A tetrazolinone compound in which $R^1$ is a C1-C3 alkyl group optionally having one or more halogen atoms in [Aspect 4B].

A tetrazolinone compound in which $R^1$ is a halogen atom in [Aspect 4B].

A tetrazolinone compound in which $R^1$ is a methyl group in [Aspect 4B].

A tetrazolinone compound in which $R^1$ is a chlorine atom in [Aspect 4B].

A tetrazolinone compound in which $R^1$ is a trifluoromethyl group in [Aspect 4B].

[Aspect 4C]

A tetrazolinone compound Q is Q4; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{13}$, $R^{14}$, and $R^{15}$ are the same or different and represent a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, or a C6-C16 arylthio group optionally having one or more halogen atoms.

A tetrazolinone compound in which $R^6$ is a C1-C3 alkyl group optionally having one or more halogen atoms in [Aspect 4C].

A tetrazolinone compound in which $R^6$ is a C3-C4 cycloalkyl group optionally having one or more halogen atoms in [Aspect 4C].

A tetrazolinone compound in which $R^6$ is a C1-C3 alkoxy group optionally having one or more halogen atoms in [Aspect 4C].

A tetrazolinone compound in which $R^6$ is a halogen atom in [Aspect 4C].

A tetrazolinone compound in which $R^6$ is a hydrogen atom in [Aspect 4C].

A tetrazolinone compound in which $R^6$ is a methyl group in [Aspect 4C].

A tetrazolinone compound in which $R^6$ is an ethyl group in [Aspect 4C].

A tetrazolinone compound in which $R^6$ is a chlorine atom in [Aspect 4C].

A tetrazolinone compound in which $R^6$ is a cyclopropyl group in [Aspect 4C].

[Aspect 4D]

A tetrazolinone compound in which Q is Q4; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{13}$, $R^{14}$, and $R^{15}$ are the same or different and represent a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms.

A tetrazolinone compound in which $R^6$ is a C1-C3 alkyl group optionally having one or more halogen atoms in [Aspect 4D]. A tetrazolinone compound in which $R^6$ is a C3-C4 cycloalkyl group optionally having one or more halogen atoms in [Aspect 4D].

A tetrazolinone compound in which $R^6$ is a C1-C3 alkoxy group optionally having one or more halogen atoms in [Aspect 4D]. A tetrazolinone compound in which $R^6$ is a halogen atom in [Aspect 4D].

A tetrazolinone compound in which $R^6$ is a hydrogen atom in [Aspect 4D].

A tetrazolinone compound in which $R^6$ is a methyl group in [Aspect 4D].

A tetrazolinone compound in which $R^6$ is an ethyl group in [Aspect 4D].

A tetrazolinone compound in which $R^6$ is a chlorine atom in [Aspect 4D].

A tetrazolinone compound in which $R^6$ is a cyclopropyl group in [Aspect 4D].

[Aspect E]

A tetrazolinone compound in which $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms; $R^2$, $R^4$, $R^5$, $R^7$, $R^8$, $R^9$, and $R^{11}$ are hydrogen atoms; $R^3$ is a hydrogen atom, a halogen atom, or a C1-C3 alkyl group optionally having one or more halogen atoms; and $R^6$ is a C1-C3 alkyl group optionally having one or more halogen atoms, a C3-C4 cycloalkyl group optionally having one or more halogen atoms, a halogen atom, a hydrogen atom, a C1-C3 alkoxy group optionally having one or more halogen atoms, or a C2-C4 alkenyl group optionally having one or more halogen atoms.

A tetrazolinone compound in which Q is Q3; and $R^{12}$, $R^{13}$, $R^{15}$, and $R^{16}$ are the same or different and represent an atom or a group selected from Group E in [Aspect E]:

Group E: Group consisting of a C1-C3 alkyl group optionally having one or more halogen atoms, a hydrogen atom, a halogen atom, a C3-C4 cycloalkyl group optionally having one or more halogen atoms, a cyano group, a C1-C3 alkoxy group optionally having one or more halogen atoms, a C1-C3 alkylthio group optionally having one or more halogen atoms, a C3-C5 cycloalkyloxy group optionally having one or more halogen atoms, a C2-C4 alkylcarbonyl group optionally having one or more halogen atoms, a C2-C4 alkylcarbonyloxy group, a C2-C4 alkylcarbonylthio group, a nitro group, a hydroxy group, a C6-C16 aryl group optionally having one or more halogen atoms, a C6-C16 aryloxy group optionally having one or more halogen atoms, a C6-C16 arylthio group optionally having one or more halogen atoms, and a sulfanyl group.

A tetrazolinone compound in which Q is Q5, and $R^{13}$, $R^{15}$, and $R^{16}$ are the same or different and represent an atom or a group selected from Group E in [Aspect E].

A tetrazolinone compound in which Q is Q6, and $R^{12}$, $R^{14}$, and $R^{16}$ are the same or different and represent an atom or a group selected from Group E in [Aspect E].

A tetrazolinone compound in which Q is Q7, and $R^{14}$, $R^{15}$, and $R^{16}$ are the same or different and represent an atom or a group selected from Group E in [Aspect E].

A tetrazolinone compound in which Q is Q8, and $R^{12}$, $R^{15}$, and $R^{16}$ are the same or different and represent an atom or a group selected from Group E in [Aspect E].

A tetrazolinone compound in which Q is Q9, and $R^{12}$, $R^{13}$, and $R^{16}$ are the same or different and represent an atom or a group selected from Group E in [Aspect E].

A tetrazolinone compound in which Q is Q10, and $R^{12}$, $R^{14}$, and $R^{16}$ are the same or different and represent an atom or a group selected from Group E in [Aspect E].

A tetrazolinone compound in which Q is Q11, and $R^{13}$ and $R^{15}$ are the same or different and represent an atom or a group selected from Group E in [Aspect E].

A tetrazolinone compound in which Q is Q12, and $R^{12}$ and $R^{13}$ are the same or different and represent an atom or a group selected from Group E in [Aspect E].

A tetrazolinone compound in which Q is Q13, and $R^{12}$ and $R^{16}$ are the same or different and represent an atom or a group selected from Group E in [Aspect E].

A tetrazolinone compound in which Q is Q14, and $R^{12}$ and $R^{14}$ are the same or different and represent an atom or a group selected from Group E in [Aspect E].

A tetrazolinone compound in which Q is Q15, and $R^{13}$ and $R^{16}$ are the same or different and represent an atom or a group selected from Group E tetrazolinone compound.

A tetrazolinone compound in which Q is Q16, and $R^{13}$ and $R^{14}$ are the same or different and represent an atom or a group selected from Group E in [Aspect E].

[Aspect 7A]

A tetrazolinone compound in which Q is Q7; $R^2$, $R^4$, $R^5$, $R^7$, $R^8$, $R^9$, and $R^{11}$ are hydrogen atoms; $R^3$ is a hydrogen atom, a halogen atom, or a C1-C3 alkyl group optionally having one or more halogen atoms; and $R^6$ is a C1-C3 alkyl group optionally having one or more halogen atoms, a C3-C4 cycloalkyl group optionally having one or more halogen atoms, a halogen atom, a hydrogen atom, or a C1-C3 alkoxy group optionally having one or more halogen atoms; $R^{10}$ is a methyl group; and $R^{14}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, or a C1-C3 alkoxy group optionally having one or more halogen atoms.

A tetrazolinone compound in which $R^1$ is a C1-C3 alkyl group optionally having one or more halogen atoms, or a halogen atom in [Aspect 7A].

A tetrazolinone compound in which $R^1$ is a C1-C3 alkyl group optionally having one or more halogen atoms in [Aspect 7A].

A tetrazolinone compound in which $R^1$ is a halogen atom in [Aspect 7A].

A tetrazolinone compound in which $R^1$ is a methyl group in [Aspect 7A].

A tetrazolinone compound in which $R^1$ is a chlorine atom in [Aspect 7A].

A tetrazolinone compound in which $R^1$ is a trifluoromethyl group in [Aspect 7A].

[Aspect 7B]

A tetrazolinone compound in which Q is Q7; $R^2$, $R^4$, $R^5$, $R^7$, $R^8$, $R^9$, and $R^{11}$ are hydrogen atoms; $R^3$ is a hydrogen atom, a halogen atom, or a C1-C3 alkyl group optionally having one or more halogen atoms; $R^6$ is a C1-C3 alkyl group optionally having one or more halogen atoms, a C3-C4 cycloalkyl group optionally having one or more halogen atoms, a halogen atom, a hydrogen atom, or a C1-C3 alkoxy group optionally having one or more halogen atoms; $R^{10}$ is a methyl group; and $R^{14}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, or a C1-C3 alkoxy group optionally having one or more halogen atoms.

A tetrazolinone compound in which $R^1$ is a C1-C3 alkyl group optionally having one or more halogen atoms, or a halogen atom in [Aspect 7B].

A tetrazolinone compound in which $R^1$ is a C1-C3 alkyl group optionally having one or more halogen atoms in [Aspect 7B]. A tetrazolinone compound in which $R^1$ is a halogen atom in [Aspect 7B].

A tetrazolinone compound in which $R^1$ is a methyl group in [Aspect 7B].

A tetrazolinone compound in which $R^1$ is a chlorine atom in [Aspect 7B].

A tetrazolinone compound in which $R^1$ is a trifluoromethyl group in [Aspect 7B].

[Aspect 7C]

A tetrazolinone compound in which Q is Q7; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom, a halogen atom, or a C1-C3 alkyl group optionally having one or more halogen atoms; $R^{10}$ is a methyl group; and $R^{14}$, $R^{15}$, and $R^{16}$ are the same or different and represent a C1-C3 alkyl group optionally having one or more halogen atoms, a hydrogen atom, a halogen atom, a C3-C4 cycloalkyl group optionally having one or more halogen atoms, or a C1-C3 alkoxy group optionally having one or more halogen atoms.

A tetrazolinone compound in which $R^6$ is a C1-C3 alkyl group optionally having one or more halogen atoms in [Aspect 7C].

A tetrazolinone compound in which $R^6$ is a C3-C4 cycloalkyl group optionally having one or more halogen atoms in [Aspect 7C].

A tetrazolinone compound in which $R^6$ is a C1-C3 alkoxy group optionally having one or more halogen atoms in [Aspect 7C].

A tetrazolinone compound in which $R^6$ is a halogen atom in [Aspect 7C].

A tetrazolinone compound in which $R^6$ is a hydrogen atom in [Aspect 7C].

A tetrazolinone compound in which $R^6$ is a methyl group in [Aspect 7C].

A tetrazolinone compound in which $R^6$ is an ethyl group in [Aspect 7C].

A tetrazolinone compound in which $R^6$ is a chlorine atom in [Aspect 7C].

A tetrazolinone compound in which $R^6$ is a cyclopropyl group in [Aspect 7C].

[Aspect 7D]

A tetrazolinone compound in which Q is Q7; $R^1$ is a C1-C3 alkyl group optionally having one or more halogen atoms, or a halogen atom; $R^2$, $R^4$, $R^5$, $R^7$, $R^8$, $R^9$, and $R^{11}$ are hydrogen atoms; $R^3$ is a hydrogen atom or a methyl group; $R^{10}$ is a methyl group; and $R^{14}$, $R^{15}$, and $R^{16}$ are the same or different and represent a C1-C3 alkyl group optionally having one or more halogen atoms, a hydrogen atom, a halogen atom, or a C1-C3 alkoxy group optionally having one or more halogen atoms.

A tetrazolinone compound in which $R^6$ is a C1-C3 alkyl group optionally having one or more halogen atoms in [Aspect 7D].

A tetrazolinone compound in which $R^6$ is a C3-C4 cycloalkyl group optionally having one or more halogen atoms in [Aspect 7D].

A tetrazolinone compound in which $R^6$ is a C1-C3 alkoxy group optionally having one or more halogen atoms in [Aspect 7D].

A tetrazolinone compound in which $R^6$ is a halogen atom in [Aspect 7D].

A tetrazolinone compound in which $R^6$ is a hydrogen atom in [Aspect 7D].

A tetrazolinone compound in which $R^6$ is a methyl group in [Aspect 7D].

A tetrazolinone compound in which $R^6$ is an ethyl group in [Aspect 7D].

A tetrazolinone compound in which $R^6$ is a chlorine atom in [Aspect 7D].

A tetrazolinone compound in which $R^6$ is a cyclopropyl group in [Aspect 7D].

A tetrazolinone compound in which Q is a 6-membered aromatic heterocyclic group (provided that Q optionally has one or more atoms or groups selected from the group consisting of a C1-C6 alkyl group optionally having one or more halogen atoms, a halogen atom, a C2-C6 alkenyl group, a C2-C6 alkynyl group, a C3-C6 cycloalkyl group, a C1-C6 alkoxy group, and a cyano group); $R^1$ is a C1-C6 alkyl group optionally having one or more halogen atoms, a C3-C6 cycloalkyl group, a halogen atom, or a hydrogen atom; $R^2$ is a C1-C6 alkyl group or a hydrogen atom; $R^3$ is a hydrogen atom or a C1-C6 alkyl group; $R^4$, $R^5$, $R^7$, $R^8$, $R^9$, and $R^{11}$ are hydrogen atoms; $R^6$ is a C1-C6 alkyl group, a C1-C6 alkoxy group, a C1-C6 alkylthio group, a C3-C6 cycloalkyl group, a halogen atom, or a hydrogen atom; $R^{10}$ is a C1-C3 alkyl group; and X is an oxygen atom.

A tetrazolinone compound in which Q is Q1; $R^{13}$, $R^{14}$, $R^{15}$ and $R^{16}$ are the same or different and represent a C1-C6 alkyl group optionally having one or more halogen atoms, a halogen atom, a C2-C6 alkenyl group, a C3-C6 cycloalkyl group, a C1-C6 alkoxy group, a hydrogen atom, or a cyano group; $R^1$ is a C1-C6 alkyl group optionally having one or more halogen atoms, a C3-C6 cycloalkyl group, a halogen atom, or a hydrogen atom; $R^2$ is a C1-C6 alkyl group or a hydrogen atom; $R^3$ is a hydrogen atom or a C1-C6 alkyl group; $R^4$, $R^5$, $R^7$, $R^8$, $R^9$, and $R^{11}$ are hydrogen atoms; $R^6$ is a C1-C6 alkyl group, a C1-C6 alkoxy group, a C3-C6 cycloalkyl group, a halogen atom, or a hydrogen atom; $R^{10}$ is a C1-C3 alkyl group; and X is an oxygen atom.

A tetrazolinone compound in which Q is Q4; $R^{13}$, $R^{14}$, and $R^{15}$ are the same or different and represent a C1-C6 alkyl group or a hydrogen atom; $R^1$ is a C1-C6 alkyl group optionally having one or more halogen atoms; $R^2$, $R^3$, $R^4$, $R^5$, $R^7$, $R^8$, $R^9$, and $R^{11}$ are hydrogen atoms; $R^6$ is a C1-C6 alkyl group, a C1-C6 alkoxy group, a C1-C6 alkylthio group, a C3-C6 cycloalkyl group, a halogen atom, or a hydrogen atom; $R^{10}$ is a C1-C3 alkyl group; and X is an oxygen atom.

Next, a process for producing the present compound will be described.

The present compound can be produced, for example, by the following Production Processes.

(Production Process A)

A compound represented by formula (1) (hereinafter sometimes referred to as the compound (1)) can be produced by reacting a compound represented by formula (A1) (hereinafter referred to as the compound (A1)) with a compound represented by formula (A2) (hereinafter referred to as the compound (A2)) in the presence of a base:

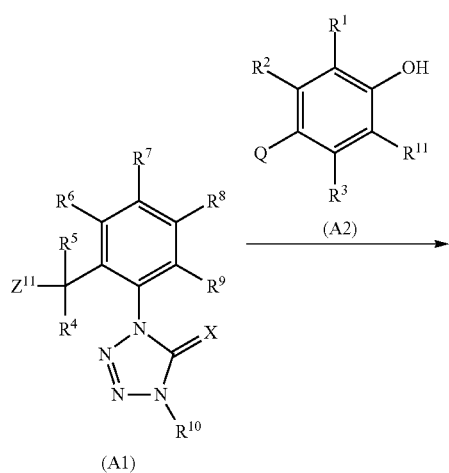

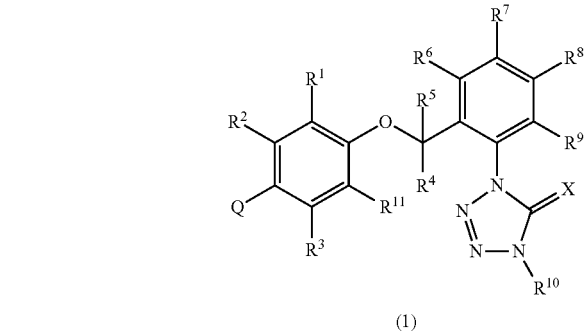

wherein $R^1$, $R^2$, $R^3$, $R^4$, $R^5$, $R^6$, $R^7$, $R^8$, $R^9$, $R^{10}$, $R^{11}$, Q, and X are the same as defined above, and $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used in the proportion of 0.001 to 1.2 mols based on 1 mol of the compound (A1).

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

The compound (1) can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

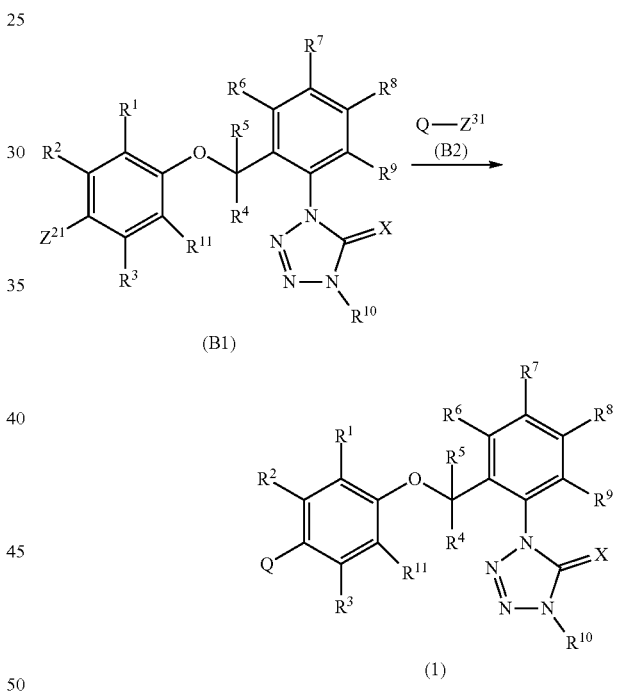

wherein $R^1$, $R^2$, $R^3$, $R^4$, $R^5$, $R^6$, $R^7$, $R^8$, $R^9$, $R^{10}$, $R^{11}$, Q, and X are the same as defined above, $Z^{21}$ represents a chlorine atom, a bromine atom, or an iodine atom, and $Z^{31}$ represents $B(OH)_2$, an alkoxyboranyl group, or a trifluoroborate ($BF_3^-$ $K^+$).

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. It is possible to produce, as the compound (B2) to be used in the reaction, a boric acid ester derivative, for example, by reacting an iodine compound (Q-I) of Q, a bromo compound (Q-Br) of Q, or a chloro compound (Q-Cl) of Q with an alkyllithium such as butyllithium, followed by a reaction with a boric acid ester. It is possible to produce a boric acid ester derivative by optionally hydrolyzing the boric acid ester derivative obtained in the above-mentioned reaction. It is also possible to produce a trifluoroborate ($BF_3^-K^+$) by fluorinating the boric acid ester with potassium hydrogen fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine-ferrocenyl)palladium(II) dichloride, 1,3-bis(2,6-diisopropylphenyl)imidazol-2-ylidene(1,4-naphthoquinone) palladium dimer, allyl(chloro)(1,3-dimesityl-1,3-dihydro-2H-imidazol-2-ylidene)palladium or palladium (II) acetate/ dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time of the reaction is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process C)

The compound (1) can be produced by subjecting a compound represented by formula (C1) (hereinafter referred to as the compound (C1)) and a compound represented by formula (C2) (hereinafter referred to as the compound (C2)) to a coupling reaction in the presence of a base and a catalyst:

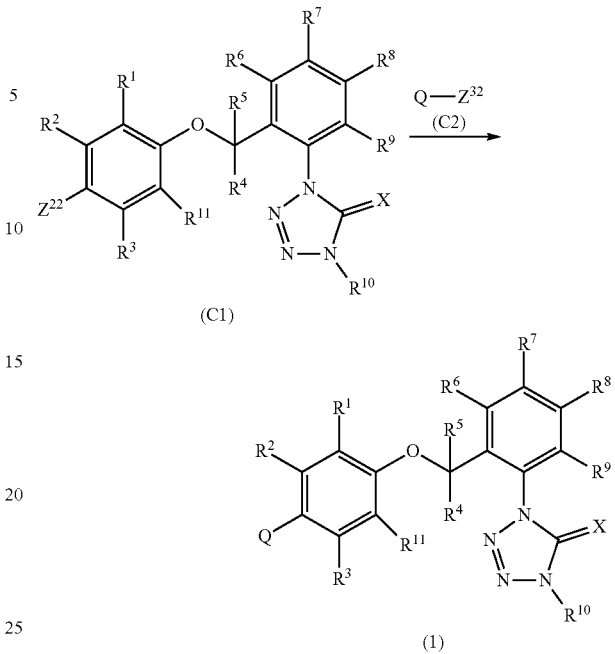

wherein $R^1$, $R^2$, $R^3$, $R^4$, $R^5$, $R^6$, $R^7$, $R^8$, $R^9$, $R^{10}$, $R^{11}$, Q, and X are the same as defined above, $Z^{22}$ represents $B(OH)_2$, an alkoxyboranyl group, or a trifluoroborate ($BF_3^-K+$), and $Z^{32}$ represents a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is usually possible to use, as the compound (C2) to be used in the reaction, commercially available compounds. Specific examples thereof include bromobenzene, iodobenzene, 1-bromo-2-methylbenzene, and the like.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine-ferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/ dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (C2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (C1).

The reaction temperature of the reaction is usually within a range of 0 to 150° C. The reaction time of the reaction is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process D)

The compound (1) can be produced by reacting the compound (1-3) with a compound represented by formula (E1) (hereinafter referred to as the compound (E1)) in the presence of a base:

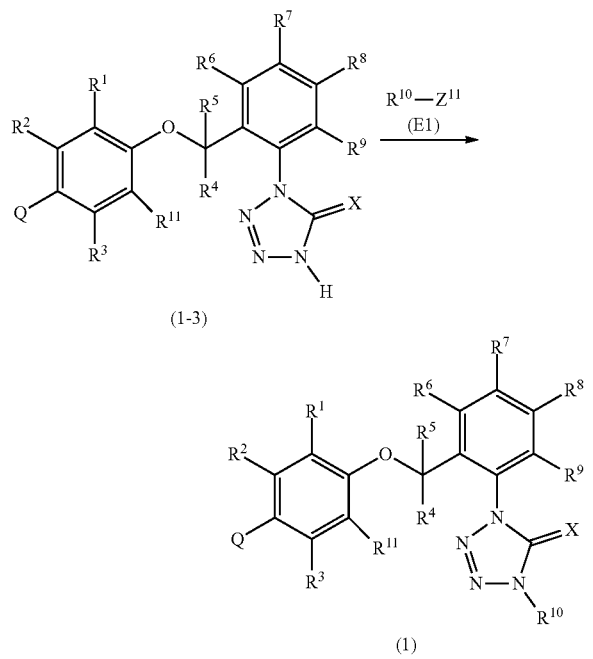

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually use, as the compound (E1) to be used in the reaction, commercially available compounds. Specific examples thereof include alkyl halides such as chlorodifluoromethane, methyl bromide, ethyl bromide, propyl bromide, methyl iodide, ethyl iodide, propyl bromide, allyl bromide, cyclopropyl bromide, and 1,1-difluoro-2-iodoethane; sulfuric acid esters such as dimethyl sulfate; and sulfonic acid esters such as methyl p-toluenesulfonate, ethyl p-toluenesulfonate, propyl toluenesulfonate, methyl methanesulfonate, ethyl methanesulfonate, and propyl methanesulfonate.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; alkali metal alkoxides such as sodium tert-butoxide and potassium tert-butoxide.

In the reaction, the compound (E1) is usually used in the proportion within a range of 1 to 10 mols, and the base is usually used in the proportion within a range of 1 to 10 mols, based on 1 mol of the compound (1-3).

The reaction temperature of the reaction is usually within a range of −20 to 150° C. The reaction time is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process E)

Among the compound (1), a compound in which X is a sulfur atom (hereinafter referred to as the compound (1-S)) can be produced from a compound in which X is an oxygen atom (hereinafter referred to as the compound (1-O)) of the compounds (1) by a known sulfidation reaction using a sulfurizing agent:

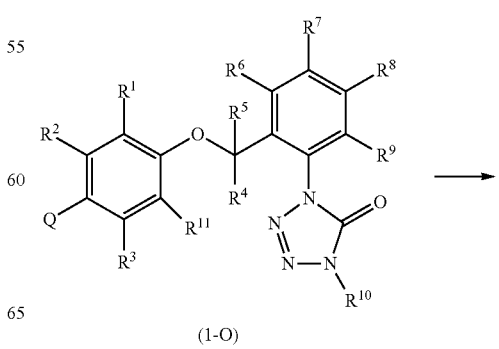

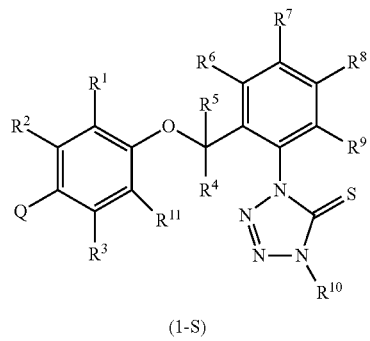

(1-S)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-O).

The reaction temperature of the reaction is usually within a range of −20 to 150° C. The reaction time is usually within a range of 0.1 to 24 hours.

If necessary, organic bases such as pyridine and trimethylamine; and inorganic bases such as alkali metal hydroxide and alkali metal carbonate may be added in the reaction, and the amount of the base to be added is within a range of 0.5 to 1.5 mols based on the compound (1-O).

After completion of the reaction, the present compound represented by formula (1-S) can be isolated by performing post-treatment operations such as extraction of the reaction mixture with an organic solvent, and drying and concentration of the organic layer. The isolated present compound can be further purified by chromatography, recrystallization, and the like.

(Production Process F)

Among the compounds (1), a compound represented by formula (1-4) (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

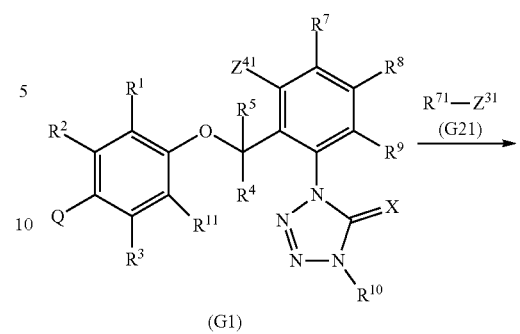

(G1)

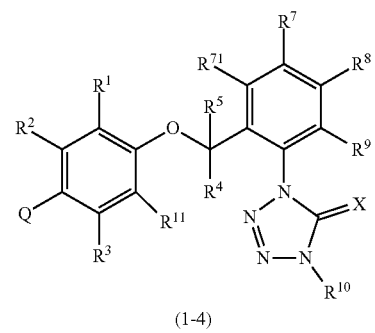

(1-4)

wherein $R^1$, $R^2$, $R^3$, $R^4$, $R^5$, $R^7$, $R^8$, $R^9$, $R^{10}$, $R^{11}$, Q, and $Z^{31}$ are the same as defined above, $Z^{41}$ represents a chlorine atom, a bromine atom, an iodine atom, or a trifluoromethanesulfonyloxy group, and $R^{71}$ represents a C1-C6 alkyl group optionally having one or more halogen atoms, a C2-C6 alkenyl group optionally having one or more halogen atoms, a C2-C6 alkynyl group optionally having one or more halogen atoms, or a C3-C6 cycloalkyl group optionally having one or more halogen atoms.

The reaction can be carried out in accordance with the reaction mentioned in Production Process B.

Among the compounds (1), a compound represented by formula (1-5) (hereinafter referred to as the compound (1-5)) can be produced by subjecting a compound represented by formula (G2) (hereinafter referred to as the compound (G2)) and a compound represented by formula (G22) (hereinafter referred to as the compound (G22)) to a coupling reaction in the presence of a base and a catalyst:

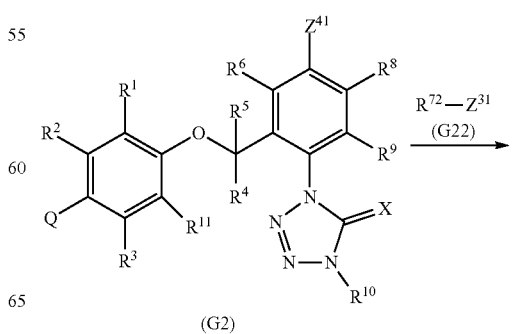

(G2)

-continued

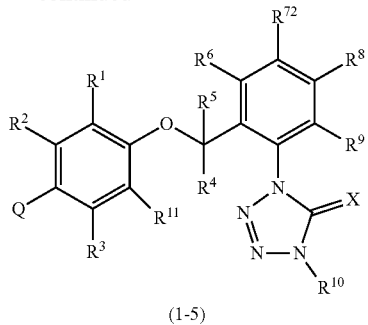

(1-5)

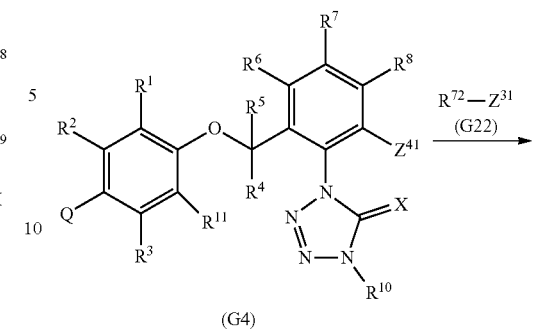

(G4)

wherein $R^1$, $R^2$, $R^3$, $R^4$, $R^5$, $R^6$, $R^8$, $R^9$, $R^{10}$, $R^{11}$, Q, $Z^{31}$, and $Z^{41}$ are the same as defined above, $R^{72}$ represents a C1-C4 alkyl group optionally having one or more halogen atoms, or a C3-C5 cycloalkyl group optionally having one or more halogen atoms.

The reaction can be carried out in accordance with the reaction mentioned in Production Process B.

Among the compounds (1), a compound represented by formula (1-6) (hereinafter referred to as the compound (1-6)) can be produced by subjecting a compound represented by formula (G3) (hereinafter referred to as the compound (G3)) and the compound (G22) to a coupling reaction in the presence of a base and a catalyst:

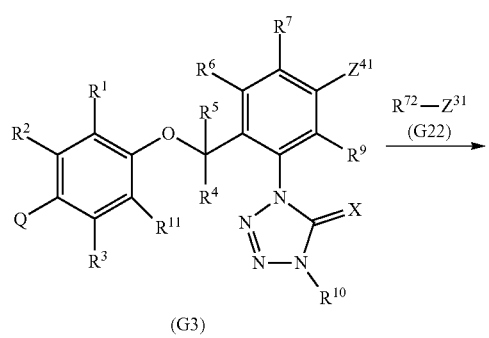

(G3)

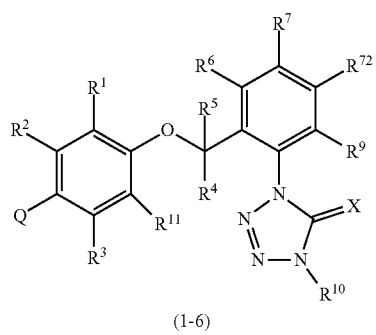

(1-6)

wherein symbols are the same as defined above.

The reaction can be carried out in accordance with the reaction mentioned in Production Process B.

Among the compounds (1), a compound represented by formula (1-7) (hereinafter referred to as the compound (1-7)) can be produced by subjecting a compound represented by formula (G4) (hereinafter referred to as the compound (G4)) and the compound (G22) to a coupling reaction in the presence of a base and a catalyst:

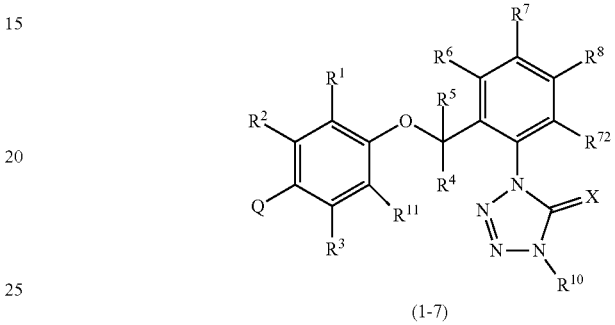

(1-7)

wherein symbols are the same as defined above.

The reaction can be carried out in accordance with the reaction mentioned in Production Process B.

In accordance with Production Process B, it is possible to produce a compound in which two or more substituents selected from $R^6$, $R^7$, $R^8$, and $R^9$ are $R^{71}$ and/or $R^{72}$, among the compounds (1).

It is also possible to produce the compound (1) by using the other known coupling reaction in place of the coupling reaction of the Production Process B.

(Production Process G)

Among the compounds (1), a compound represented by formula (1-8) (hereinafter referred to as the compound (1-8)) can be produced by subjecting a compound represented by formula (H1) (hereinafter referred to as the compound (H1)) and a compound represented by formula (H21) (hereinafter referred to as the compound (H21)) to a coupling reaction in the presence of a base and a catalyst:

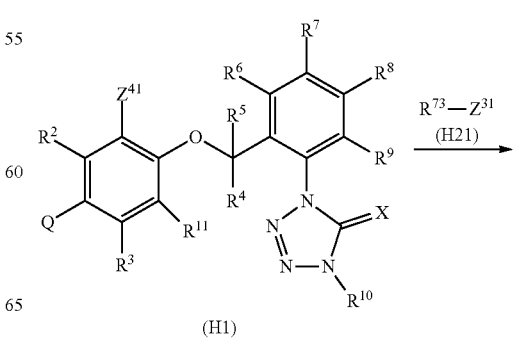

(H1)

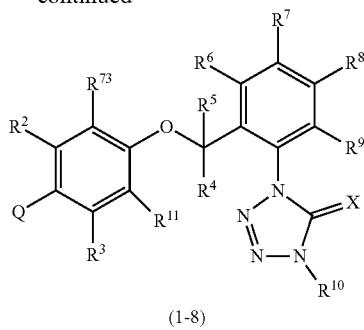

(1-8)

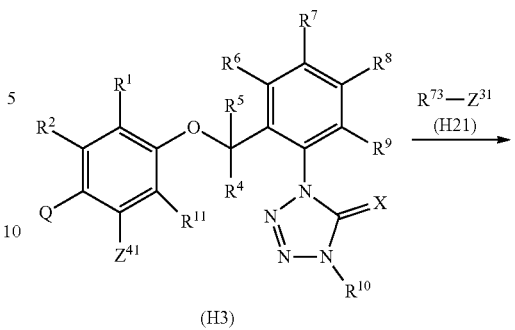

(H3)

wherein $R^2$, $R^3$, $R^4$, $R^5$, $R^6$, $R^7$, $R^8$, $R^9$, $R^{10}$, $R^{11}$, Q, $Z^{31}$, and $Z^{41}$ are the same as defined above, and $R^{73}$ represents a C1-C6 alkyl group optionally having one or more atoms or groups selected from Group $P^1$; a C3-C6 cycloalkyl group optionally having one or more atoms or groups selected from Group $P^1$, or a C2-C6 alkenyl group optionally having one or more halogen atoms.

The reaction can be carried out in accordance with the reaction mentioned in Production Process B.

Among the compounds (1), a compound represented by formula (1-9) (hereinafter referred to as the compound (1-9)) can be produced by subjecting a compound represented by formula (H2) (hereinafter referred to as the compound (H2)) and the compound (H21) to a coupling reaction in the presence of a base and a catalyst:

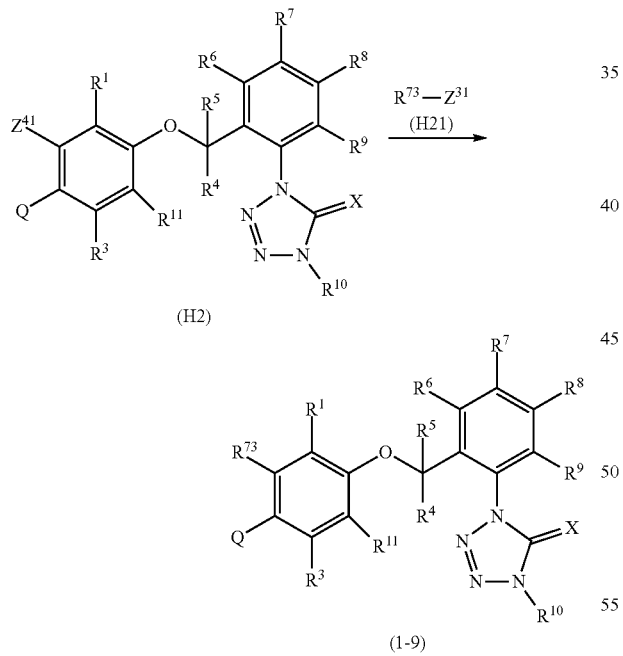

wherein symbols are the same as defined above.

The reaction can be carried out in accordance with the reaction mentioned in Production Process B.

Among the compounds (1), a compound represented by formula (1-10) (hereinafter referred to as the compound (1-10)) can be produced by subjecting a compound represented by formula (H3) (hereinafter referred to as the compound (H3)) and the compound (H21) to a coupling reaction in the presence of a base and a catalyst:

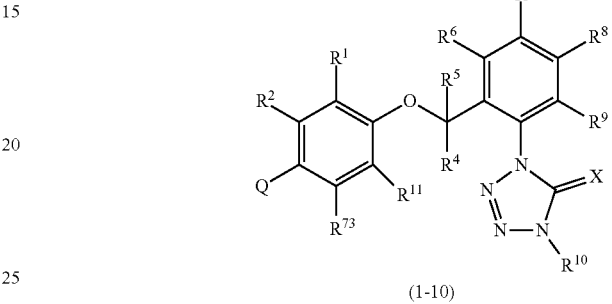

(1-10)

wherein symbols are the same as defined above.

The reaction can be carried out in accordance with the reaction mentioned in Production Process B.

Among the compounds (1), a compound represented by formula (1-11) (hereinafter referred to as the compound (1-11)) can be produced by subjecting a compound represented by formula (H4) (hereinafter referred to as the compound (H4)) and the compound (H21) to a coupling reaction in the presence of a base and a catalyst:

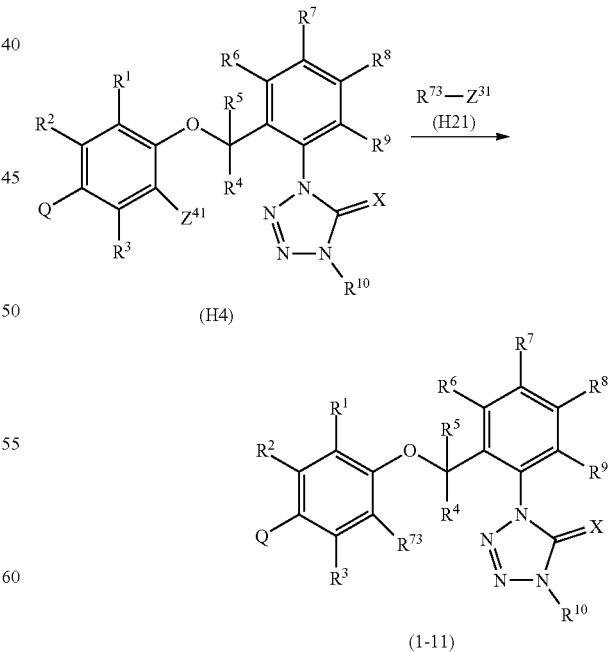

(1-11)

wherein symbols are the same as defined above.

The reaction can be carried out in accordance with the reaction mentioned in Production Process B.

In accordance with Production Process B, it is possible to produce a compound in which two or more substituents selected from $R^1$, $R^2$, $R^3$, and $R^{11}$ are $R^{73}$, among the compounds (1).

It is also possible to produce the compound (1) by using the other known coupling reaction in place of the coupling reaction of the Production Process B.

The process for producing the present compound A will be mentioned below.

(Synthesis Process A)

A compound represented by formula (2-1) in which $L^1$ is a nitro group in the compound (2) (hereinafter referred to as the compound (2-1)) can be produced by reacting a compound represented by formula (B-1) (hereinafter referred to as the compound (B-1)) with a compound represented by formula (A-2) (hereinafter referred to as the compound (A-2)) in the presence of a base:

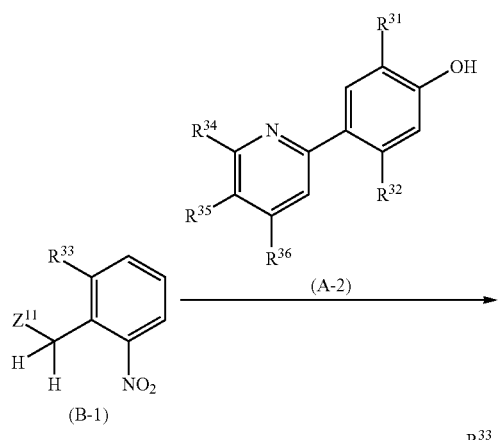

wherein $R^{31}$, $R^{32}$, $R^{33}$, $R^{34}$, $R^{35}$, $R^{36}$, and $Z^{11}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A-2) is usually used in the proportion within a range of 1 to 10 mols, and the base is usually used in the proportion within a range of 0.5 to 5 mols, based on 1 mol of the compound (B-1).

The reaction temperature of the reaction is usually within a range of –20 to 150° C. The reaction time is usually within a range of 0.1 to 24 hours.

If necessary, sodium iodide, tetrabutylammonium iodide, and the like may be added in the reaction, and the amount to be added is usually within a range of 0.001 to 1.2 mols based on 1 mol of the compound (B-1).

After completion of the reaction, the compound (2-1) can be isolated by performing post-treatment operations such as extraction of the reaction mixture with an organic solvent, and drying and concentration of the organic layer. The isolated compound (2-1) can be further purified by chromatography, recrystallization, and the like.

(Synthesis Process B1)

A compound represented by formula (2-2) in which $L^1$ is an amino group in the compound (2) (hereinafter referred to as the compound (2-2)) can be produced by reacting the compound (2-1) with hydrogen in the presence of a catalyst:

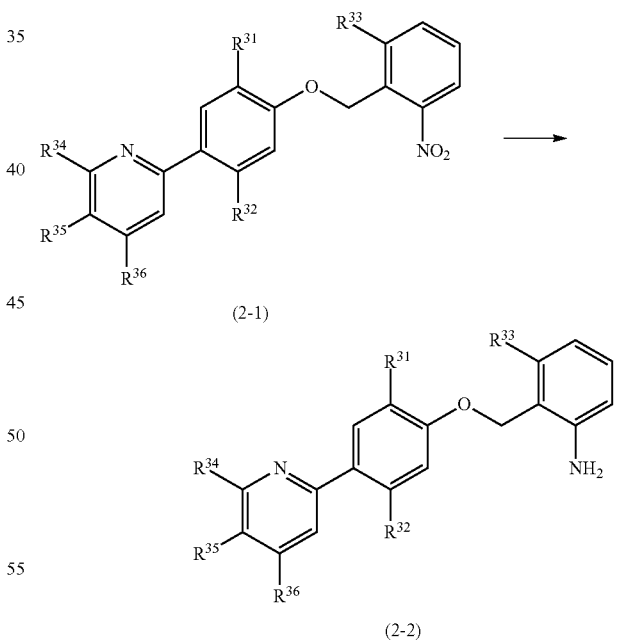

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as n-heptane, n-hexane, cyclohexane, toluene, and xylene; water; and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), Raney nickel, and the like.

The reaction temperature of the reaction is usually within a range of −20 to 150° C. The reaction time is usually within a range of 0.1 to 24 hours.

In the reaction, the catalyst is usually used in the proportion within a range of 0.01 to 1 mol, and hydrogen is usually used in the proportion within a range of 3 mols to a large excess, based on 1 mol of the compound (2-1).

After completion of the reaction, the compound (2-2) can be isolated by performing post-treatment operations such as extraction of the reaction mixture with an organic solvent, and drying and concentration of the organic layer. The isolated compound (2-2) can be further purified by operations such as distillation, chromatography, and recrystallization.

(Synthesis Process B2)

The compound (2-2) can be produced by reacting the compound (2-1) with a reducing agent, if necessary, in the presence of a catalyst:

Examples of the reducing agent to be used in the reaction include metal borohydride salt compounds such as lithium borohydride, sodium borohydride, potassium borohydride, and the like.

Examples of the catalyst usable in the reaction include copper(I) chloride, copper(I) bromide, copper(I) acetate, and the like.

In the reaction, the catalyst is usually used in the proportion within a range of 1 to 10 mols, and the reducing agent is usually used in the proportion within a range of 1 to mols or a large excess, based on 1 mol of the compound (2-1).

The reaction temperature of the reaction is usually within a range of −20 to 100° C. The reaction time is usually within a range of 0.1 to 24 hours.

After completion of the reaction, the present compound represented by formula (2-2) can be isolated by performing post-treatment operations such as extraction of the reaction mixture with an organic solvent, and drying and concentration of the organic layer. Alternatively, the present compound represented by formula (2-2) can be isolated by performing post-treatment operations such as filtration and concentration of the reaction mixture. The isolated present compound can be further purified by chromatography, recrystallization, and the like.

(Synthesis Process B3)

The compound (2-2) can also be produced by reacting the compound (2-1) with a reducing agent in the presence of an acid:

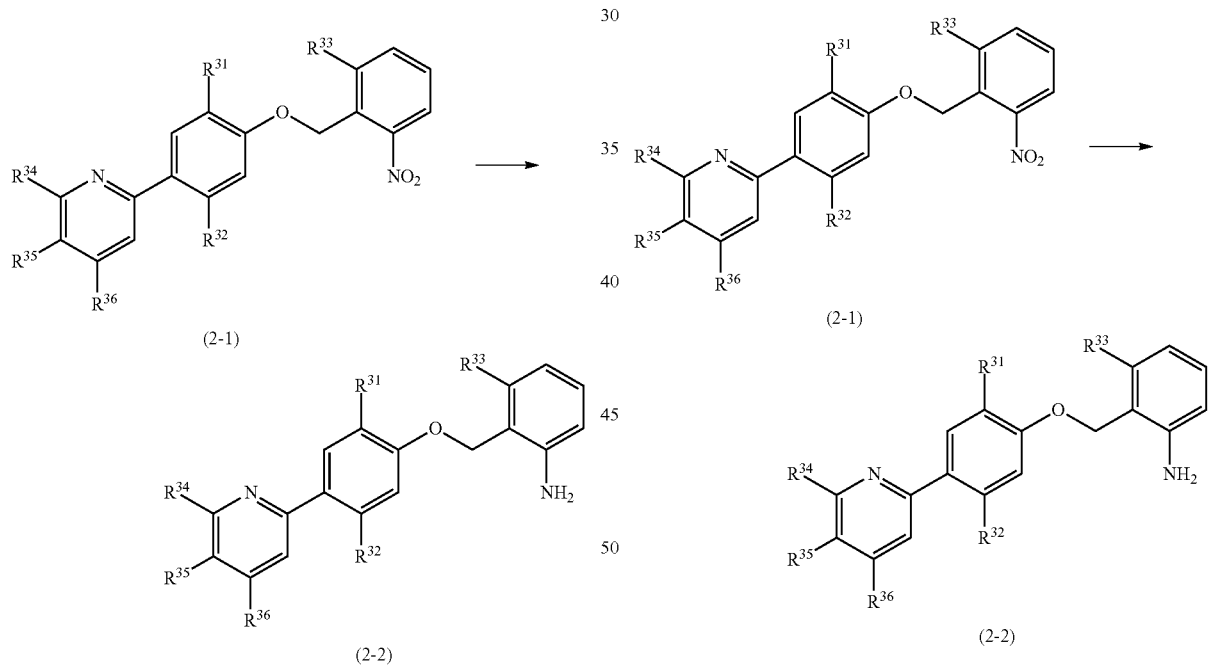

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include alcohols such as methanol, ethanol, propanol, and butanol; n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; hydrocarbons such as heptane, hexane, cyclohexane, pentane, toluene, and xylene; water; and mixtures thereof.

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include solvent include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, an aqueous ammonium chloride solution, and the like.

In the reaction, the reducing agent is usually used in the proportion within a range of 1 to 30 mols and the acid is usually used in the proportion within a range of 1 to 30 mols, based on 1 mol of the compound (2-1), and the acid can also be used as the solvent.

The reaction temperature of the reaction is usually within a range of −20 to 150° C. The reaction time is usually within a range of 0.1 to 24 hours.

After completion of the reaction, the compound (2-2) can be isolated by performing post-treatment operations such as extraction of the reaction mixture with an organic solvent, and drying and concentration of the organic layer. The isolated compound can be further purified by operations such as chromatography and recrystallization.

(Synthesis Process C)

A compound represented by formula (2-3) in which $L^1$ is an isocyanate group in the compound (2) (hereinafter referred to as the compound (2-3)) can be produced by reacting the compound (2-2) with phosgenes:

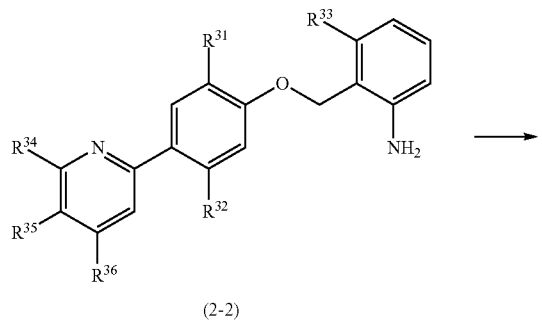

(2-2)

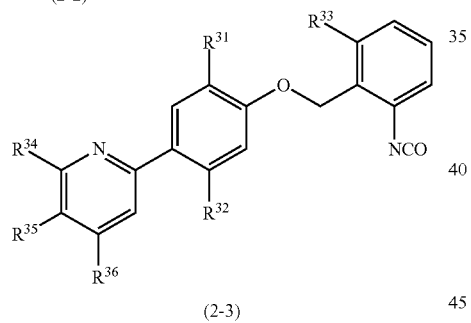

(2-3)

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of phosgenes to be used in the reaction include phosgene, diphosgene, and triphosgene.

In the reaction, phosgenes are usually used in the proportion within a range of 1 to 10 mols, based on 1 mol of the compound (2-2).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (2-2).

After completion of the reaction, the compound (2-3) can be isolated by performing post-treatment operations such as extraction of the reaction mixture with an organic solvent, and drying and concentration of the organic layer. The isolated compound (2-3) can be further purified by operations such as chromatography and recrystallization.

(Synthesis Process D)

A compound represented by formula (2-4) in which $L^1$ is NSO in the compound (2) (hereinafter referred to as the compound (2-4)) can be produced by reacting the compound (2-2) with thionyl chloride:

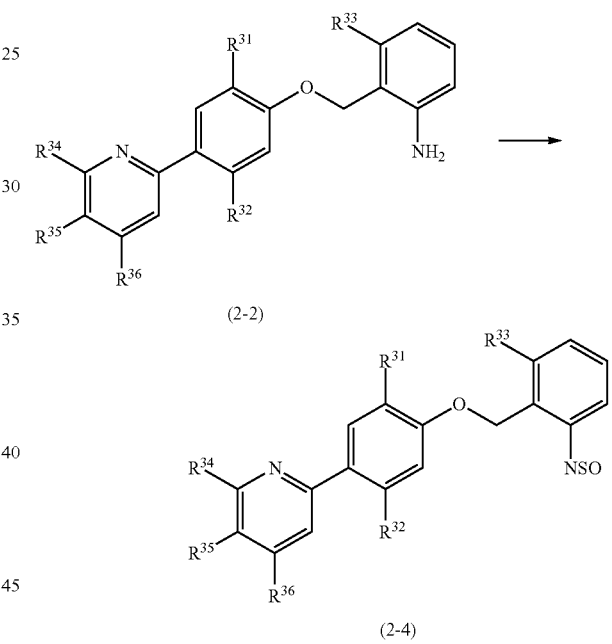

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

In the reaction, thionyl chloride is usually used in the proportion within a range of 1 to 10 mols based on 1 mol of the compound (2-2).

The reaction temperature of the reaction is usually within a range of −20 to 150° C. The reaction time is usually within a range of 0.1 to 24 hours.

After completion of the reaction, the compound (2-4) can be isolated by performing post-treatment operations such as extraction of the reaction mixture with an organic solvent, and drying and concentration of the organic layer. The isolated compound (2-4) can be further purified by operations such as distillation, chromatography, and recrystallization.

(Synthesis Process E)

The compound (2-3) can also be produced by reacting the compound (2-4) with phosgenes:

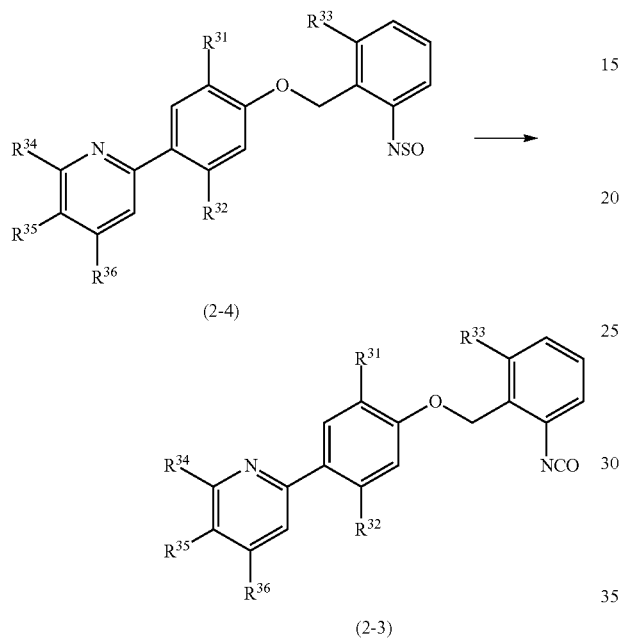

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of phosgenes to be used in the reaction include phosgene, diphosgene, and triphosgene.

In the reaction, phosgenes are usually used in the proportion within a range of 1 to 10 mols based on 1 mol of the compound (2-4).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used within a range of 0.05 to 5 mols based on 1 mol of the compound (2-4).

After completion of the reaction, the compound (2-3) can be isolated by performing post-treatment operations such as extraction of the reaction mixture with an organic solvent, and drying and concentration of the organic layer. The isolated compound (2-3) can be further purified by operations such as chromatography and recrystallization.

(Synthesis Process F)

A compound represented by formula (2-5) in which $L^1$ is a C2-C6 alkoxycarbonyl group in the compound (2) (hereinafter referred to as the compound (2-5)) can be produced by reacting the compound (A-2) with a compound represented by formula (B-2) (hereinafter referred to as the compound (B-2)) in the presence of a base:

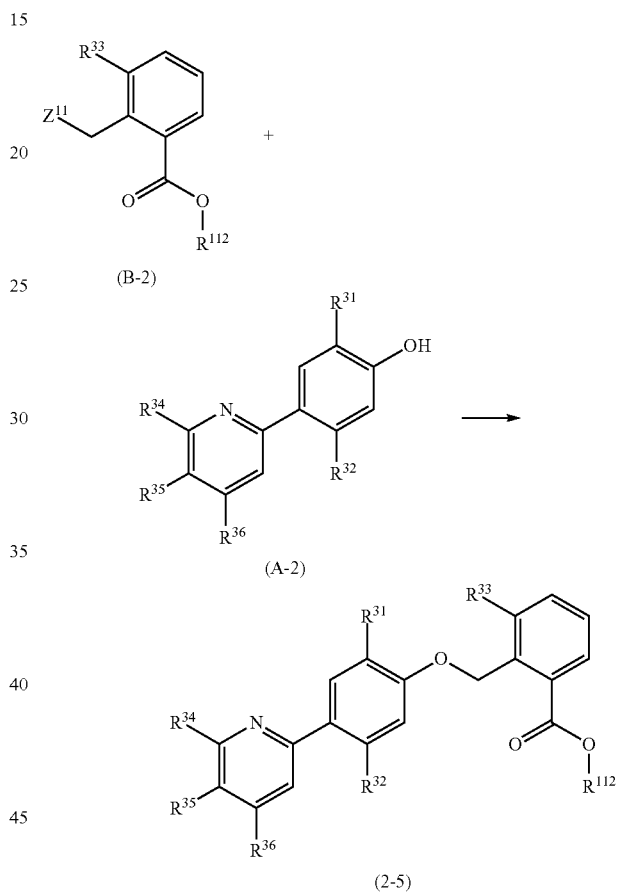

wherein $R^{31}$, $R^{32}$, $R^{33}$, $R^{34}$, $R^{35}$, $R^{36}$, and $Z^{11}$ are the same as defined above, and $R^{112}$ represents a C1-C5 alkyl group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A-2) is usually used in the proportion within a range of 1 to 10 mols, and the base is usually used in the proportion within a range of 0.5 to 5 mols, based on 1 mol of the compound (B-2).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used within a range of 0.001 to 1.2 mols based on 1 mol of the compound (B-2).

After completion of the reaction, the compound (2-5) can be isolated by performing post-treatment operations such as extraction of the reaction mixture with an organic solvent, and drying and concentration of the organic layer. The isolated compound (2-5) can be further purified by chromatography, recrystallization, and the like.

(Synthesis Process G)

A compound represented by formula (2-6) in which $L^1$ is a carboxyl group in the compound (2) (hereinafter referred to as the compound (2-6)) can be produced by reacting the compound (2-5) with a hydrolyzing agent:

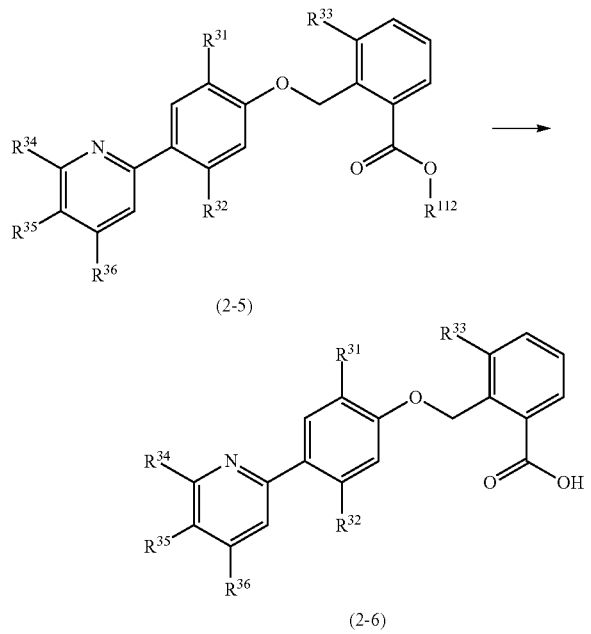

wherein $R^{31}$, $R^{32}$, $R^{33}$, $R^{34}$, $R^{35}$, $R^{36}$, and $R^{112}$ are the same as defined above.

The reaction is usually performed in a solvent.

Examples of the solvent to be used in the reaction include water; alcohols such as methanol, ethanol, propanol, and butanol; n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; ketones such as acetone, methyl ethyl ketone, and methyl isobutyl ketone; and mixtures thereof.

Examples of the hydrolyzing agent to be used in the reaction include bases such as an aqueous potassium hydroxide solution and an aqueous sodium hydroxide solution; and acids such as hydrochloric acid and sulfuric acid.

In the reaction, the hydrolyzing agent is usually used in the proportion within a range of 0.5 to 20 mols based on 1 mol of the compound (2-5).

The reaction temperature of the reaction is usually within a range of −20 to 150° C. The reaction time is usually within a range of 0.1 to 72 hours.

After completion of the reaction, the compound (2-6) can be isolated by performing post-treatment operations such as extraction of the reaction mixture with an organic solvent, and drying and concentration of the organic layer. The isolated compound (2-6) can be further purified by operations such as chromatography and recrystallization.

(Synthesis Process H)

A compound represented by formula (2-7) in which $L^1$ is a halocarbonyl group in the compound (2) (hereinafter referred to as the compound (2-7)) can be produced by reacting the compound (2-6) with a halogenating agent:

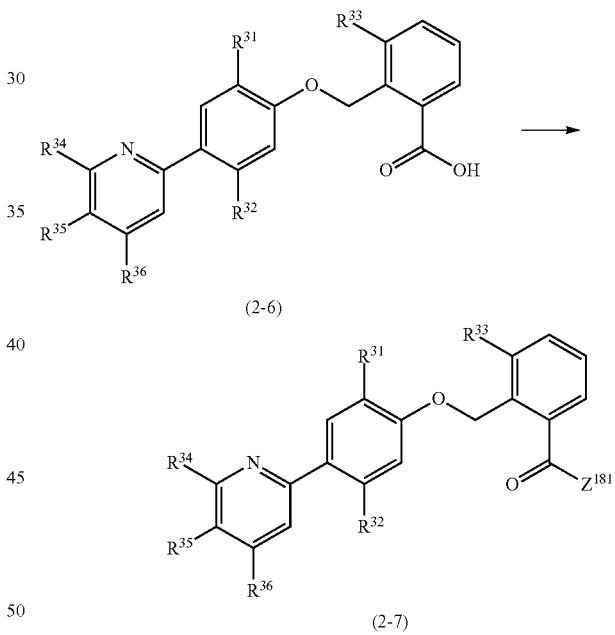

wherein $R^{31}$, $R^{32}$, $R^{33}$, $R^{34}$, $R^{35}$, and $R^{36}$ are the same as defined above, and $Z^{181}$ represents a chlorine atom, a bromine atom, or an iodine atom.

The reaction is usually performed in a solvent.

Examples of the solvent to be used in the reaction include n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (2-6).

The reaction temperature of the reaction is usually within a range of −20 to 150° C. The reaction time is usually within a range of 0.1 to 24 hours.

In the reaction, the catalyst may be added, and N,N-dimethylformamide, triethylamine, diisopropylethylamine, and the like are used. The catalyst is used in the proportion within a range of 0.001 to 1 mol based on 1 mol of the compound (2-6).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (2-6).

After completion of the reaction, the compound (2-7) can be isolated by performing post-treatment operations such as extraction of the reaction mixture with an organic solvent, and drying and concentration of the organic layer. The isolated compound (2-7) may be further purified by operations such as chromatography and recrystallization.

(Synthesis Process I)

A compound represented by formula (2-8) in which $L^1$ is $C(O)N_3$ in the compound (2) (hereinafter referred to as the compound (2-8)) can be produced by reacting the compound (2-7) with sodium azide:

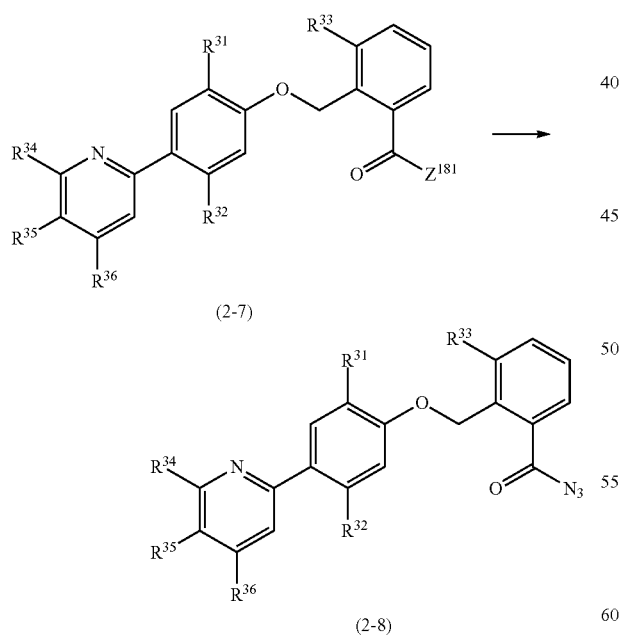

(2-7)

(2-8)

wherein $R^{31}$, $R^{32}$, $R^{33}$, $R^{34}$, $R^{35}$, $R^{36}$, and $Z^{181}$ are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; n-heptane, hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

In the reaction, sodium azide is usually used in the proportion within a range of 1 to 10 mols based on 1 mol of the compound (2-7).

The reaction temperature of the reaction is usually within a range of −20 to 50° C. The reaction time is usually within a range of 0.1 to 24 hours.

After completion of the reaction, the compound (2-8) can be isolated by performing post-treatment operations such as extraction of the reaction mixture with an organic solvent, and drying and concentration of the organic layer. The isolated compound (2-8) can be further purified by chromatography, recrystallization, and the like.

(Synthesis Process J)

The compound (2-3) can also be produced by heating the compound (2-8):

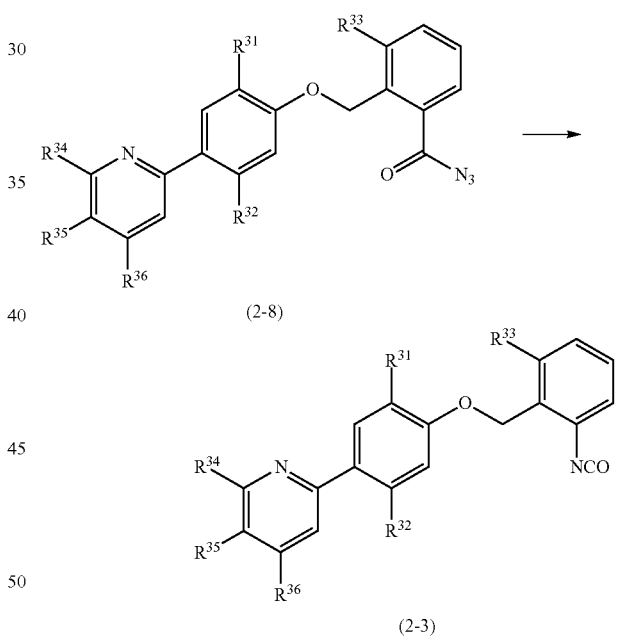

(2-8)

(2-3)

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; n-heptane, hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

The reaction temperature of the reaction is usually within a range of room temperature to 150° C. The reaction time is usually within a range of 0.1 to 24 hours.

After completion of the reaction, the compound (2-3) can be isolated by performing post-treatment operations such as extraction of the reaction mixture with an organic solvent, and drying and concentration of the organic layer. The isolated compound (2-3) can be further purified by chromatography, recrystallization, and the like.

(Synthesis Process K)

A compound represented by formula (2-9) $L^1$ is $C(O)NH_2$ in the compound (2) (hereinafter referred to as the compound (2-9)) can be produced by reacting the compound (2-7) with ammonia:

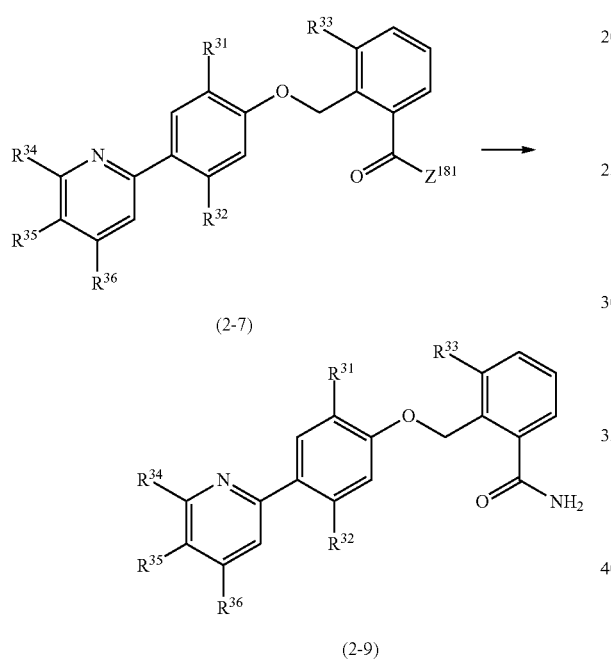

(2-7)

(2-9)

wherein $R^{31}$, $R^{32}$, $R^{33}$, $R^{34}$, $R^{35}$, $R^{36}$, and $Z^{181}$ are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; n-heptane; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Ammonia to be used in the reaction may be in the form of a gas, or a solution prepared by dissolving in a solvent such as water, methanol, ethanol, tetrahydrofuran, 1,4-dioxane, or diethyl ether.

In the reaction, ammonia is usually used in the proportion within a range of 1 mol to large excess based on 1 mol of the compound (2-7).

The reaction temperature of the reaction is usually within a range of −20 to 50° C. The reaction time is usually within a range of 0.1 to 24 hours.

After completion of the reaction, the compound (2-9) can be isolated by performing post-treatment operations such as extraction of the reaction mixture with an organic solvent, and drying and concentration of the organic layer. The isolated present compound (2-9) can be further purified by chromatography, recrystallization, and the like.

(Synthesis Process L)

The compound (2-3) can also be produced by reacting the compound (2-9) with a hypochlorite or a hypobromite:

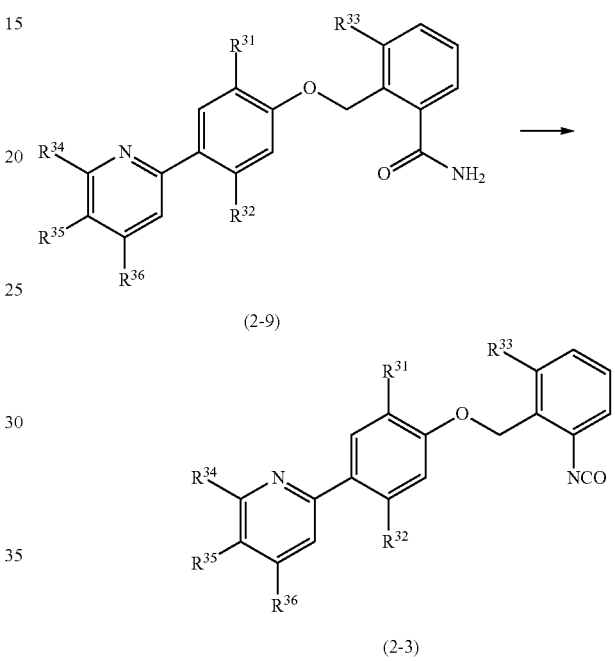

(2-9)

(2-3)

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; n-heptane, hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; water; and mixtures thereof.

Examples of the hypochlorite and hypobromous acid to be used in the reaction include sodium hypobromite, sodium hypochlorite, potassium hypobromite, potassium hypochlorite, barium hypobromite, barium hypochlorite, calcium hypobromite, calcium hypochlorite, and the like.

It is possible to use, as the hypochlorite and hypobromite to be used in the reaction, those produced by mixing chlorine or bromine with sodium hydroxide, potassium hydroxide, barium hydroxide, calcium hydroxide, or the like.

The reaction temperature of the reaction is usually within a range of 0 to 150° C. The reaction time of the reaction is usually within a range of 0.1 to 24 hours.

In the reaction, the hypochlorite is usually used in the proportion within a range of 1 to 10 mols based on 1 mol of the compound (2-9).

After completion of the reaction, the compound (2-3) can be isolated by performing post-treatment operations such as extraction of the reaction mixture with an organic solvent, and drying and concentration of the organic layer. The isolated compound (2-3) can be further purified by chromatography, recrystallization, and the like.

(Synthesis Process M)

A compound represented by formula (2-10) in which $L^1$ is C(O)NHOH in the compound (2) (hereinafter referred to as the compound (2-10)) can be produced by reacting the compound (2-7) with hydroxylamine:

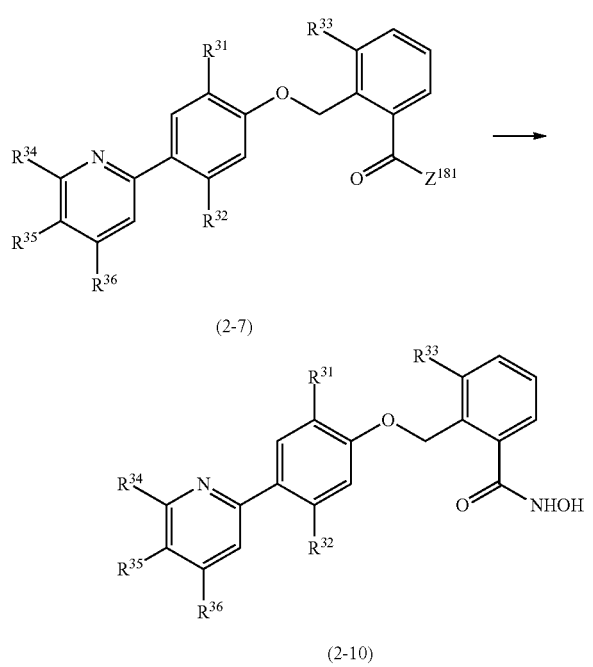

wherein $R^{31}$, $R^{32}$, $R^{33}$, $R^{34}$, $R^{35}$, $R^{36}$, and $Z^{181}$ are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; n-heptane, hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

In the reaction, hydroxylamine is usually used in the proportion within a range of 1 to 10 mols based on 1 mol of the compound (2-7).

The reaction temperature of the reaction is usually within a range of −20 to 50° C. The reaction time is usually within a range of 0.1 to 24 hours.

After completion of the reaction, the compound (2-10) can be isolated by performing post-treatment operations such as extraction of the reaction mixture with an organic solvent, and drying and concentration of the organic layer. The isolated compound (2-10) can be further purified by chromatography, recrystallization, and the like.

(Synthesis Process N)

The compound (2-3) can be produced by reacting the compound (2-10) with an acid halide:

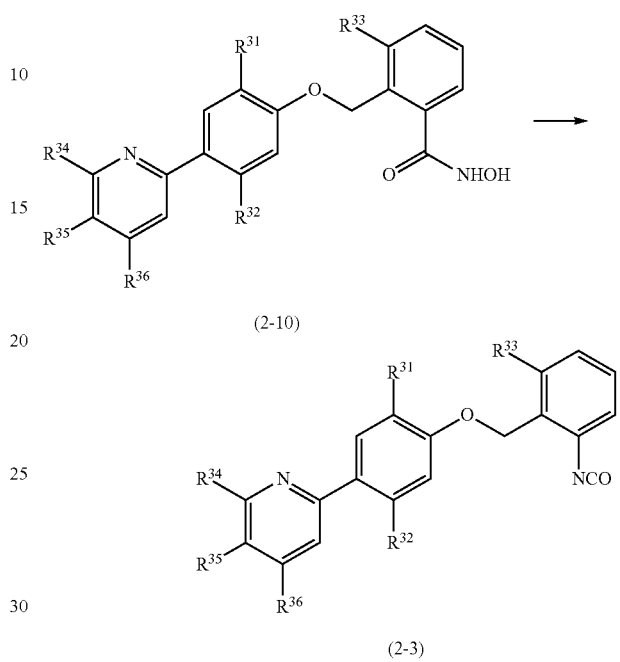

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; n-heptane, hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; water; and mixtures thereof.

Examples of the acid halide to be used in the reaction include acid anhydrides such as acetic anhydride and propionic anhydride; acid halides such as acetyl chloride, acetyl bromide, and benzoyl chloride; sulfonyl chlorides such as paratoluenesulfonyl chloride and methanesulfonyl chloride; pyridine-sulfur trichloride complex and thionyl chloride.

In the reaction, if necessary, bases such as pyridine, triethylamine, tributylamine, diazabicycloundecene, sodium hydroxide, and potassium hydroxide may be added, and these compounds are usually used in the proportion within a range of 1 to 10 mols based on 1 mol of the compound (2-10).

The reaction temperature of the reaction is usually within a range of −20 to 150° C. The reaction time is usually within a range of 0.1 to 24 hours.

In the reaction, the acid halide is usually used in the proportion within a range of 1 to 10 mols based on 1 mol of the compound (2-10).

After completion of the reaction, the compound (2-3) can be isolated by performing post-treatment operations such as extraction of the reaction mixture with an organic solvent, and drying and concentration of the organic layer. The isolated compound (2-3) can be further purified by chromatography, recrystallization, and the like.

(Synthesis Process O)

A compound represented by formula (2-11) in which $L^1$ is C(O)NHCl in the compound (2) (hereinafter referred to as the compound (2-11)), and a compound represented by formula (2-12) in which $L^1$ is C(O)NHBr (hereinafter referred to as the compound (2-12)) can be produced by reacting the compound (2-9) with a chlorinating agent or a brominating agent:

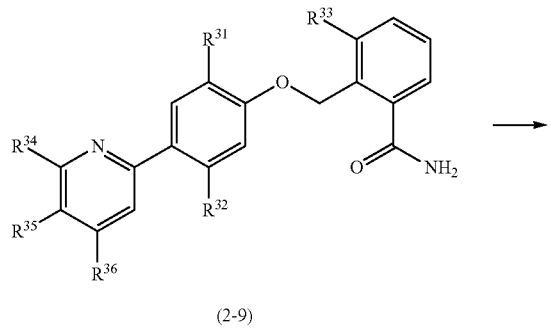

(2-9)

Examples of the chlorinating agent or brominating agent to be used in the reaction include sodium hypochlorite, tert-butyl hypochlorite, trichloroisocyanuric acid, chlorine, sulfuryl chloride, sodium bromate, sodium bromite, hydrogen bromide, sodium bromide, and bromine.

In the reaction, the halogenating agent is usually used in the proportion within a range of 1 to 10 mols based on 1 mol of the compound (2-9).

The reaction temperature of the reaction is usually within a range of −20 to 150° C. The reaction time is usually within a range of 0.1 to 24 hours.

In the reaction, the catalyst may be added and N,N-dimethylformamide, or the like is used. The catalyst is

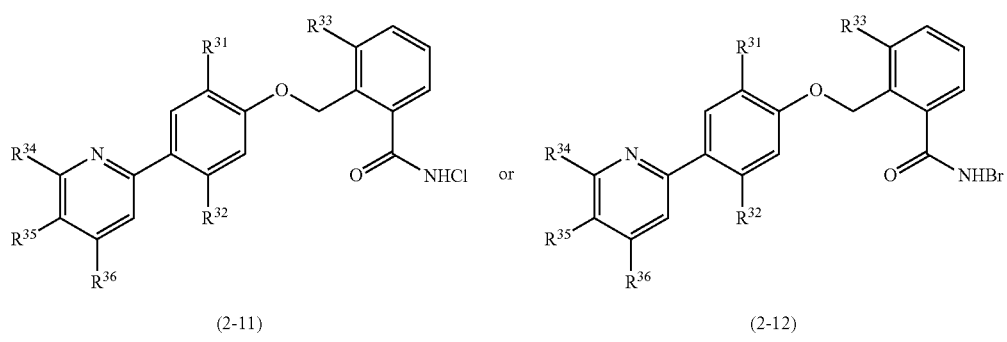

(2-11)      (2-12)

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

usually used in the proportion within a range of 0.001 to 1 mol based on 1 mol of the compound (2-9).

After completion of the reaction, the compound (2-11) and the compound (2-12) can be isolated by performing post-treatment operations such as extraction of the reaction mixture with an organic solvent, and drying and concentration of the organic layer. The isolated compounds (2-11) and (2-12) can be further purified by chromatography, recrystallization, and the like.

(Synthesis Process P)

The compound (2-3) can be produced by reacting the compound (2-11) or the compound (2-12) with a base:

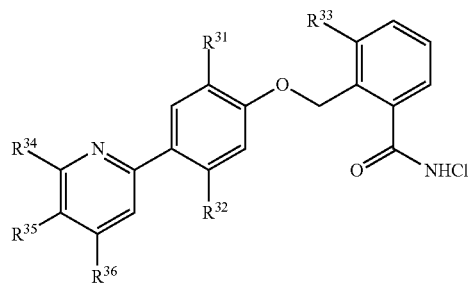
(2-11)

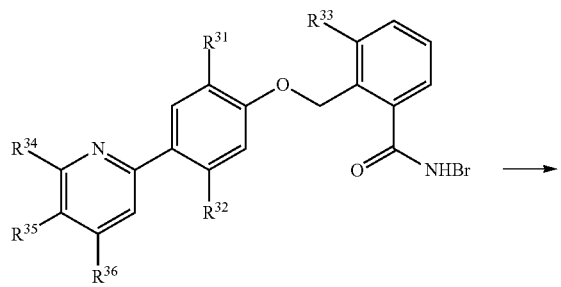
(2-12)

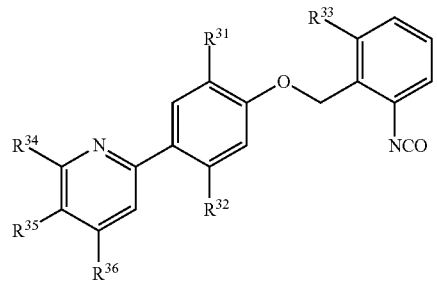
(2-3)

wherein $R^{31}$, $R^{32}$, $R^{33}$, $R^{34}$, $R^{35}$, and $R^{36}$ are the same as defined above.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; n-heptane, hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; water; and mixtures thereof.

Examples of the base to be used in the reaction include pyridine, triethylamine, tributylamine, diazabicycloundecene, sodium hydroxide, potassium hydroxide, and the like.

In the reaction, the base is usually used in the proportion within a range of 1 to 10 mols based on 1 mol of the compound (2-11) or the compound (2-12).

The reaction temperature of the reaction is usually within a range of −20 to 150° C. The reaction time is usually within a range of 0.1 to 24 hours.

In the reaction, the base is usually used in the proportion within a range of 1 to 10 mols based on 1 mol of the compound (2-11) or the compound (2-12).

After completion of the reaction, the compound (2-3) can be isolated by performing post-treatment operations such as extraction of the reaction mixture with an organic solvent, and drying and concentration of the organic layer. The isolated compounds (2-3) can be further purified by chromatography, recrystallization, and the like.

(Synthesis Process Q)

A compound represented by formula (2-13) in which $L^1$ is a halogen atom in the compound represented by formula (2) (hereinafter referred to as the compound (2-13)) can be produced by reacting the compound (A-2) with a compound represented by formula (B-3) (hereinafter referred to as the compound (B-3)) in the presence of a base:

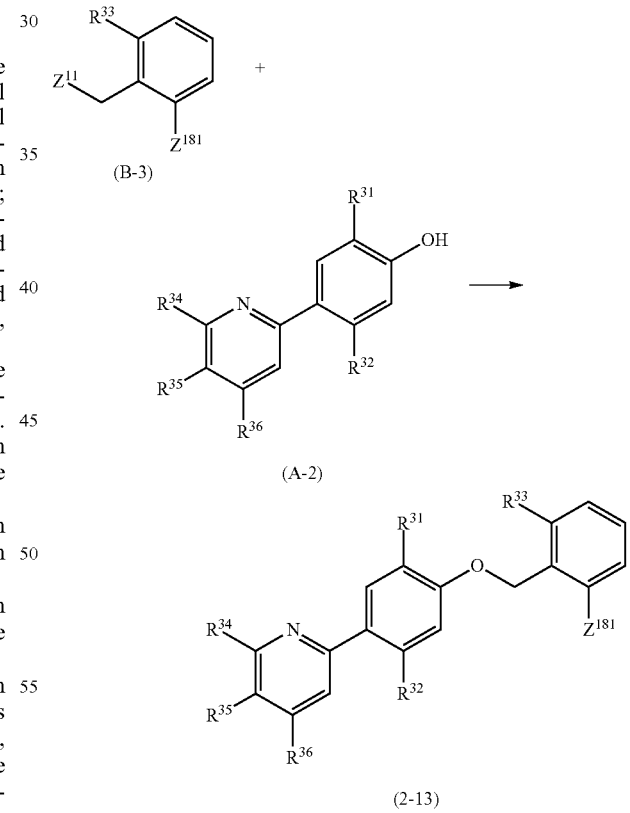

wherein $R^{31}$, $R^{32}$, $R^{33}$, $R^{34}$, $R^{35}$, $R^{36}$, $Z^{11}$ and $Z^{181}$ are the same as defined above.

The reaction is usually performed in a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, compounds are usually used within a range of 0.001 to 1.2 mols based on 1 mol of the compound (B-3).

After completion of the reaction, the compound (2-13) can be isolated by performing post-treatment operations such as extraction of the reaction mixture with an organic solvent, and drying and concentration of the organic layer. The isolated compounds (2-13) can be further purified by chromatography, recrystallization, and the like.

(Synthesis Process R)

A compound represented by formula (2-16) (hereinafter referred to as the compound (2-16)) can be produced by reacting a compound represented by formula (2-15) (hereinafter referred to as the compound (2-15)) or the compound (2-7) with an azidation agent:

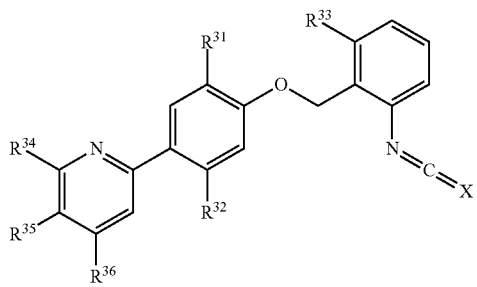 or 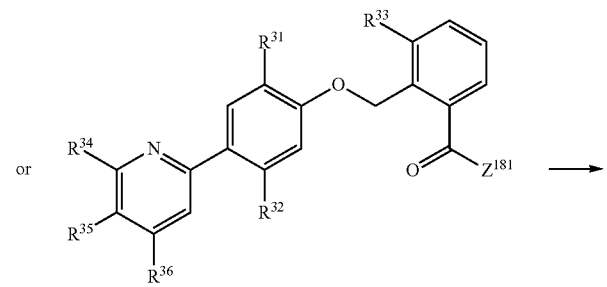

(2-15) (2-7)

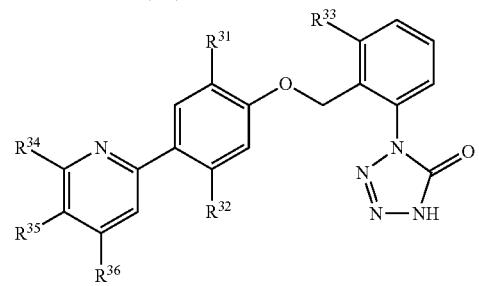

(2-16)

wherein $R^{31}$, $R^{32}$, $R^{33}$, $R^{34}$, $R^{35}$, $R^{36}$, $Z^{181}$, and X are the same as defined above.

The reaction is usually performed in a solvent.

Examples of the solvent to be used in the reaction include n-heptane, hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the compound (2-15) or the azidation agent is usually used in the proportion within a range of 1 to mols based on 1 mol of the compound (2-7).

diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A-2) is usually used in the proportion within a range of 1 to 10 mols, and the base is usually used in the proportion within a range of 0.5 to 5 mols, based on 1 mol of the compound (B-3).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (2-15) or the compound (2-7).

After completion of the reaction, the compound (2-16) can be isolated by performing post-treatment operations such as extraction of the reaction mixture with an organic solvent, and drying and concentration of the organic layer. The isolated compounds (2-16) can be further purified by chromatography, recrystallization, and the like.

(Synthesis Process X)

Next, the process for producing the present compound B will be mentioned.

A compound represented by formula (3-1) in which $R^{44}$ is a chlorine atom, a bromine atom, or an iodine atom in the compound (3) (hereinafter referred to as the compound (3-1)) can be produced by reacting a compound represented by formula (C-1) (hereinafter referred to as the compound (C-1)) with a compound represented by formula (C-2) (hereinafter referred to as the compound (C-2)) in the presence of a base:

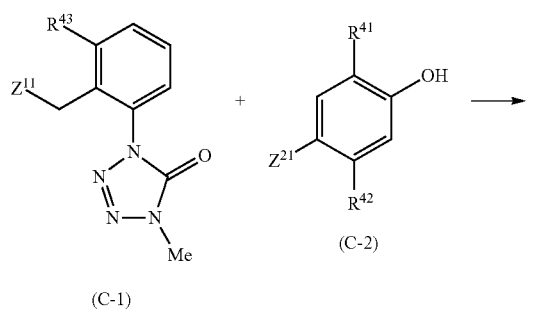

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; and alkali metal hydrides such as lithium hydride, sodium hydride, and potassium hydride; alkali metal alkoxides such as sodium tert-butoxide and potassium tert-butoxide.

In the reaction, the compound (C-2) is usually used in the proportion within a range of 1 to 10 mols, and the base is usually used in the proportion within a range of 0.5 to 5 mols, based on 1 mol of the compound (C-1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used within a range of 0.001 to 1.2 mols based on 1 mol of the compound (C-1).

After completion of the reaction, the compound (3-1) can be isolated by performing post-treatment operations such as extraction of the reaction mixture with an organic solvent, and drying and concentration of the organic layer. The isolated compounds (3-1) can be further purified by chromatography, recrystallization, and the like.

(Synthesis Process Y)

A compound represented by formula (3-2) in which $R^{44}$ is a 4,4,5,5-tetramethyl-1,3,2-dioxaborolan-2-yl group in the compound (3) (hereinafter referred to as the compound (3-2)) can be produced by reacting the compound (3-1) with a Borylation reagent in the presence of a catalyst:

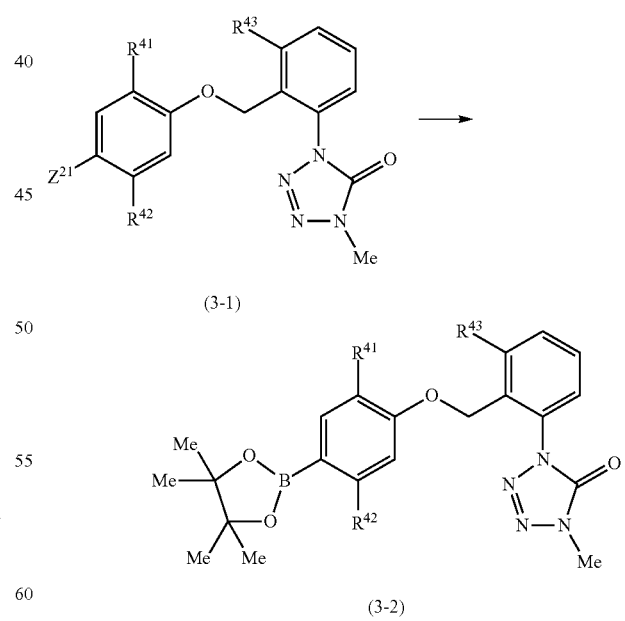

wherein $R^{41}$, $R^{42}$, $R^{43}$, $Z^{11}$, and $Z^{21}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

wherein $R^{41}$, $R^{42}$, $R^{43}$, and $Z^{21}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the Borylation reagent to be used in the reaction include bis(pinacolato)diboron, pinacolborane, and the like.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshineferrocenyl)palladium(II) dichloride, 1,3-bis(2,6-diisopropylphenyl)imidazol-2-ylidene(1,4-naphthoquinone) palladium dimer, allyl(chloro)(1,3-dimesityl-1,3-dihydro-2H-imidazol-2-ylidene)palladium or palladium (II) acetate/ dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, potassium carbonate, and cesium carbonate; potassium acetate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the Borylation reagent is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (3-1).

The reaction temperature of the reaction is usually within a range of 0 to 150° C. The reaction time of the reaction is usually within a range of 0.1 to 24 hours.

After completion of the reaction, the compound (3-2) can be isolated by performing post-treatment operations such as extraction of the reaction mixture with an organic solvent, and drying and concentration of the organic layer. The isolated compound may be further purified by operations such as distillation, chromatography, and recrystallization.

(Synthesis Process Z)

A compound represented by formula (3-2) in which $R^{44}$ is a borono group in the compound (3) (hereinafter referred to as the compound (3-2)) can be produced by reacting the compound (3-1) with the Borylation reagent in the presence of a catalyst:

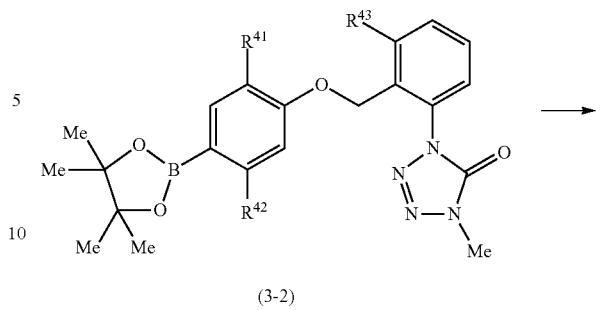

(3-2)

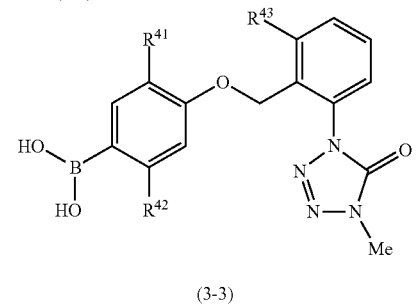

(3-3)

wherein $R^{41}$, $R^{42}$, and $R^{43}$ are the same as defined above.

Examples of the solvent to be used in the reaction include alcohols such as methanol, ethanol, propanol, and butanol; water, acetic acid; and mixtures thereof.

Examples of the acid to be used in the reaction include acetic acid, hydrochloric acid, hydrobromic acid, and the like, and aqueous solutions thereof can also be used as the solvent.

In the reaction, an excess amount of the acid is usually used based on 1 mol of the compound (3-2).

The reaction temperature of the reaction is usually within a range of −20 to 150° C. The reaction time is usually within a range of 0.1 to 100 hours.

After completion of the reaction, the compound (3-3) can be isolated by performing post-treatment operations such as extraction of the reaction mixture with an organic solvent, and drying and concentration of the organic layer. The isolated compound may be further purified by operations such as distillation, chromatography, and recrystallization.

The process for synthesizing an intermediate compound will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by (XA2) (hereinafter referred to as the compound (XA2)) with an azidation agent:

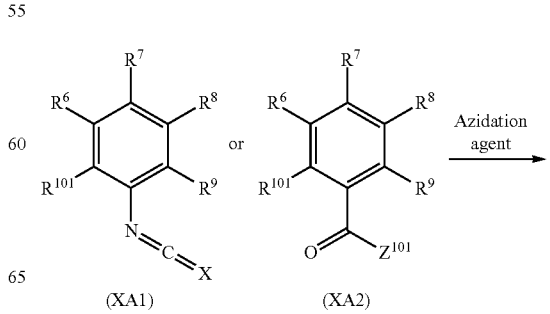

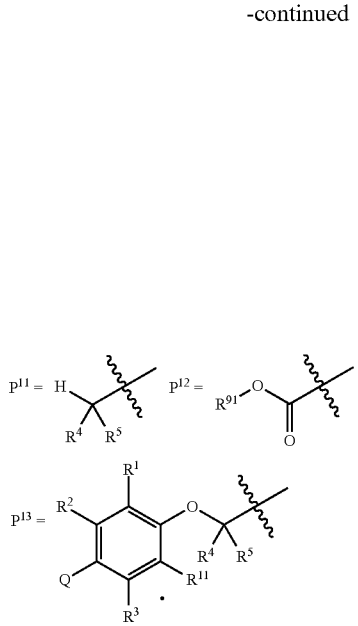

(XA3)

wherein $R^1$, $R^2$, $R^3$, $R^4$, $R^5$, $R^6$, $R^7$, $R^8$, $R^9$, $R^{10}$, $R^{11}$, Q, and X are the same as defined above, R represents $P^{11}$, $P^{12}$, or $P^{13}$, $R^{91}$ represents a C1-C5 alkyl group, $Z^{101}$ represents a chlorine atom or a bromine atom, and the wavy line represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by formula (XB1) (hereinafter referred to as the compound (XB1)) with an isocyanating agent:

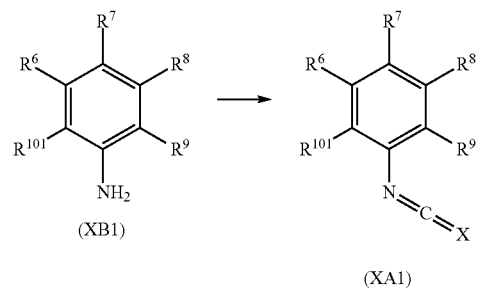

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

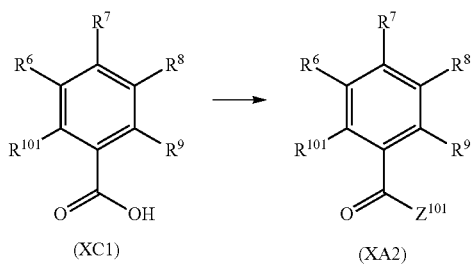

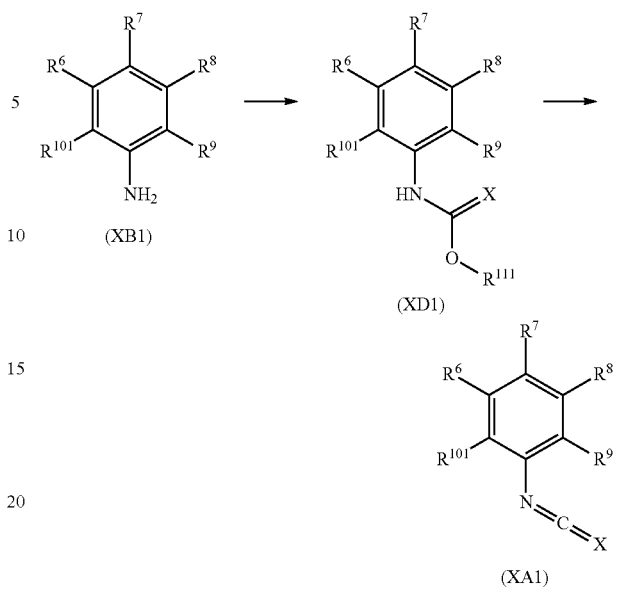

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time is usually within a range of 0.1 to 24 hours.

In the reaction, the catalyst may be added and N,N-dimethylformamide, or the like is used. The catalyst is usually used in the proportion within a range of 0.001 to 1 mol based on 1 mol of the compound (XC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by formula (XD1) (hereinafter referred to as the compound (XD1)), and then reacting the compound (XD1) with an isocyanating agent:

wherein $R^6$, $R^7$, $R^8$, $R^9$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, 1,4-dioxane, ethylene glycol dimethyl ether, and methyl tert-butyl ether; aromatic hydrocarbons such as toluene and xylene; halogenated hydrocarbons such as carbon tetrachloride, chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the isocyanating agent to be used in the reaction include phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by formula (XE2) (hereinafter referred to as the compound (XE2)) can be produced by reacting a compound represented by formula (XE1) (hereinafter referred to as the compound (XE1)) with hydrogen in the presence of a catalyst:

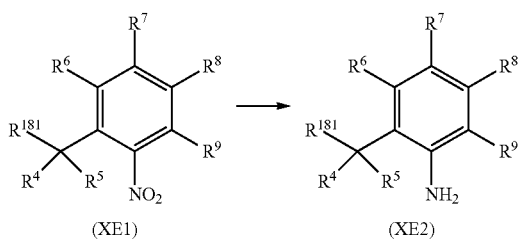

(XE1) → (XE2)

-continued

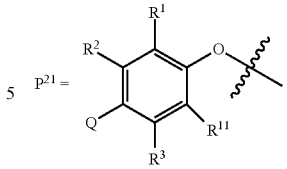

wherein $R^1$, $R^2$, $R^3$, $R^4$, $R^5$, $R^6$, $R^7$, $R^8$, $R^9$, $R^{10}$, $R^{11}$, and Q are the same as defined above, $R^{181}$ represents a hydrogen atom or $P^{21}$, and the wavy line represents a binding site.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; water; and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), Raney nickel, and the like.

In the reaction, the catalyst is usually used in the proportion within a range of 0.0001 to 1 mol based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as filtration and concentration of the organic layer. The isolated compound may be further purified by operations such as distillation, chromatography, and recrystallization.

(Reference Production Process F)

The compound (XE2) can be produced by reacting the compound (XE1) with a reducing agent in the presence of an acid:

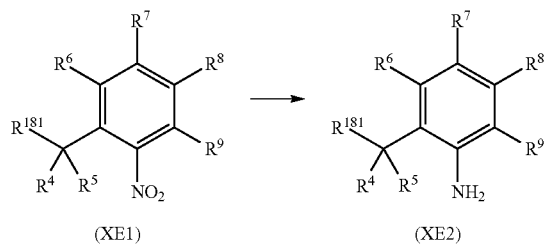

(XE1) → (XE2)

wherein symbols are the same as defined above.

The reaction is usually performed in a solvent.

Examples of the solvent to be used in the reaction include solvent include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, an aqueous ammonium chloride solution, and the like.

In the reaction, the reducing agent is usually used in the proportion within a range from 1 to 30 mols based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with the compound (E1) in the presence of a base:

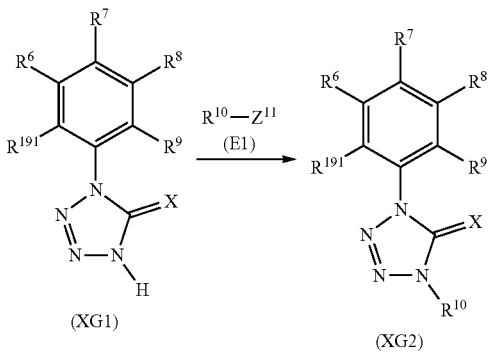

wherein $R^6$, $R^7$, $R^8$, $R^9$, $R^{10}$, and $Z^{11}$ are the same as defined above, and $R^{19}$ represents $P^{11}$ or $P^{12}$.

The reaction can be carried out in accordance with the reaction mentioned in Production Process D.

(Reference Production Process H) A compound represented by formula (XH2) (hereinafter referred to as the compound (XH2)) can be produced by reacting a compound represented by formula (XH1) (hereinafter referred to as the compound (XH1)) with a halogenating agent:

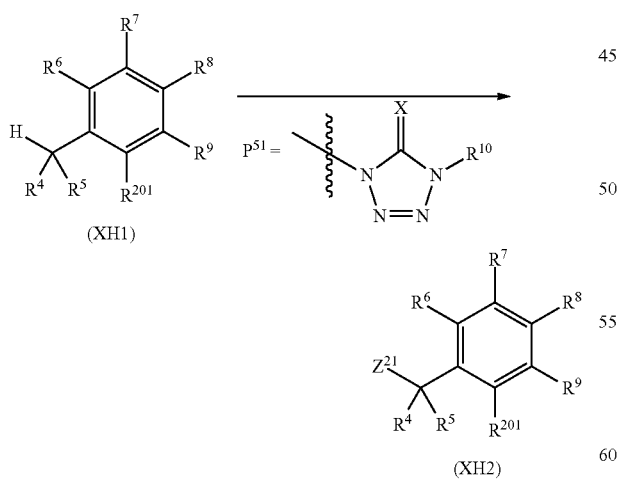

wherein $R^4$, $R^5$, $R^6$, $R^7$, $R^8$, $R^9$, $R^{10}$, $Z^{21}$, and X are the same as defined above, and $R^{201}$ represents $P^{51}$ or a nitro group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, and N-bromophthalimide.

It is also possible to use a radical initiator in the reaction.

Examples of the radical initiator to be used in the reaction include benzoyl peroxide, azobisisobutyronitrile (AIBN), diacyl peroxide, dialkyl peroxydicarbonate, tert-alkyl peroxyester, monoperoxycarbonate, di(tert-alkylperoxy)ketal and ketone peroxide, and the like.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XJ2) (hereinafter referred to as the compound (XJ2)) can be produced by reacting the compound (XH2) with a compound represented by formula (XJ1) (hereinafter referred to as the compound (XJ1)):

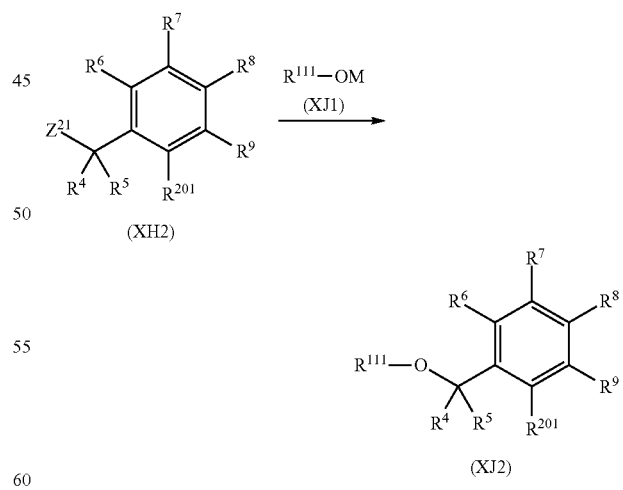

wherein $R^4$, $R^5$, $R^6$, $R^7$, $R^8$, $R^9$, $R^{111}$, and $Z^{21}$ are the same as defined above, and M represents sodium, potassium, or lithium.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction include sodium methoxide, sodium ethoxide, sodium n-propoxide, sodium n-butoxide, sodium isopropoxide, sodium sec-butoxide, sodium tert-butoxide, potassium methoxide, potassium methoxide, potassium n-propoxide, potassium n-butoxide, potassium isopropoxide, potassium sec-butoxide, potassium tert-butoxide, sodium phenoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XK1) (hereinafter referred to as the compound (XK1)) can be produced by reacting the compound (XH2) with water in the presence of a base:

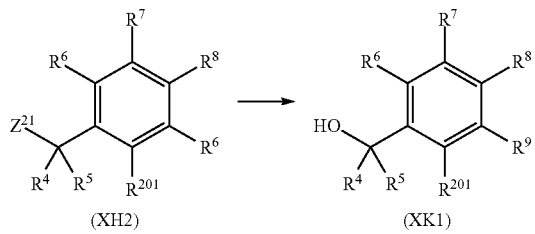

wherein symbols are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, 4-dimethylaminopyridine, diisopropylethylamine, and diazabicycloundecene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

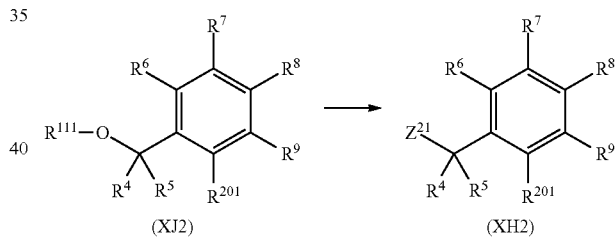

wherein symbols are the same as defined above.

The reaction is usually performed in a solvent.

Examples of the solvent to be used in the reaction include hydrocarbons such as n-hexane, cyclohexane, toluene, and xylene; halogenated hydrocarbons such as chloroform, 1,2-dichloroethane, and chlorobenzene; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer.

The isolated compound may be further purified by operations such as distillation, chromatography, and recrystallization.
(Reference Production Process L)
The compound (XH2) can be produced by reacting the compound (XK1) with a halogenating agent:

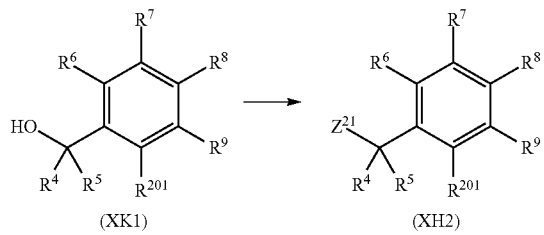

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, acetyl bromide, and the like.

In the reaction, the halogenating agent is usually used in the proportion within a range of 1 to 10 mols based on 1 mol of the compound (XK1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. Any additives are usually used in the proportion within a range of 0.01 to 5 mols based on 1 mol of the compound (XK1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)
A compound represented by formula (XM3) (hereinafter referred to as the compound (XM3)) can be produced by reacting the compound (XK1) with a compound represented by formula (XM2) (hereinafter referred to as the compound (XM2)) in the presence of a base:

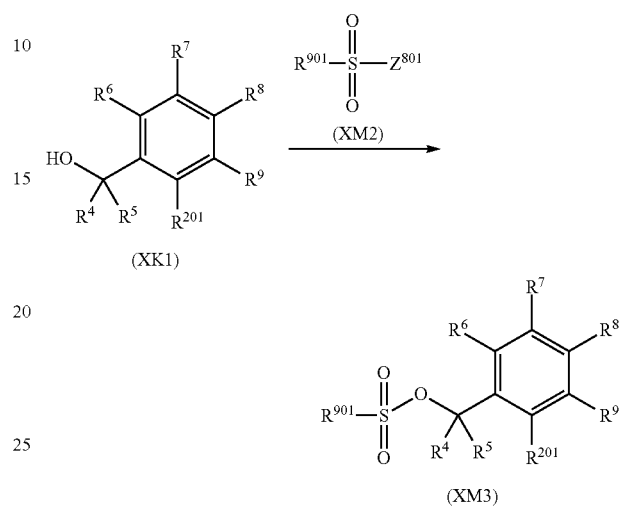

wherein $R^4$, $R^5$, $R^6$, $R^7$, $R^8$, $R^9$, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, the compound (XM2) is usually used in the proportion within a range of 1 to 10 mols, and the base is usually used in the proportion within a range of 1 to 5 mols, based on 1 mol of the compound (XK1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

A compound represented by formula (XN12) (hereinafter referred to as the compound (XN12)) can be produced by subjecting a compound represented by formula (XN11) (hereinafter referred to as the compound (XN11)) and the compound (G21) to a coupling reaction in the presence of a base and a catalyst:

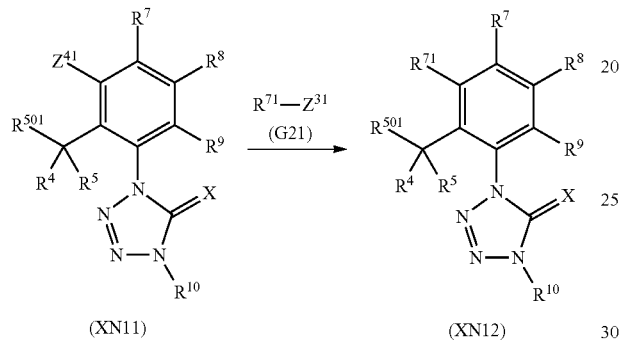

(XN11)    (XN12)

wherein $R^{501}$ represents a hydrogen atom or $OR^{111}$, and $R^{111}$, $R^4$, $R^5$, $R^7$, $R^8$, $R^9$, $R^{10}$, $R^{71}$, X, $Z^{31}$, and $Z^{41}$ are the same as defined above.

The reaction can be carried out in accordance with the reaction mentioned in Production Process B.

A compound represented by formula (XN22) (hereinafter referred to as the compound (XN22)) can be produced by subjecting a compound represented by formula (XN21) (hereinafter referred to as the compound (XN21)) and the compound (G22) to a coupling reaction in the presence of a base and a catalyst:

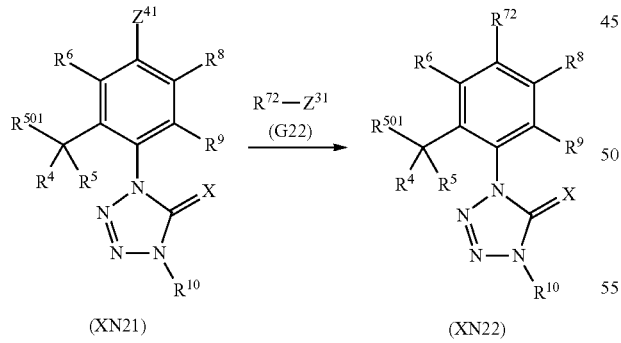

(XN21)    (XN22)

wherein symbols are the same as defined above.

The reaction can be carried out in accordance with the reaction mentioned in Production Process B.

A compound represented by formula (XN32) (hereinafter referred to as the compound (XN32)) can be produced by subjecting a compound represented by formula (XN31) (hereinafter referred to as the compound (XN31)) and the compound (G22) to a coupling reaction in the presence of a base and a catalyst:

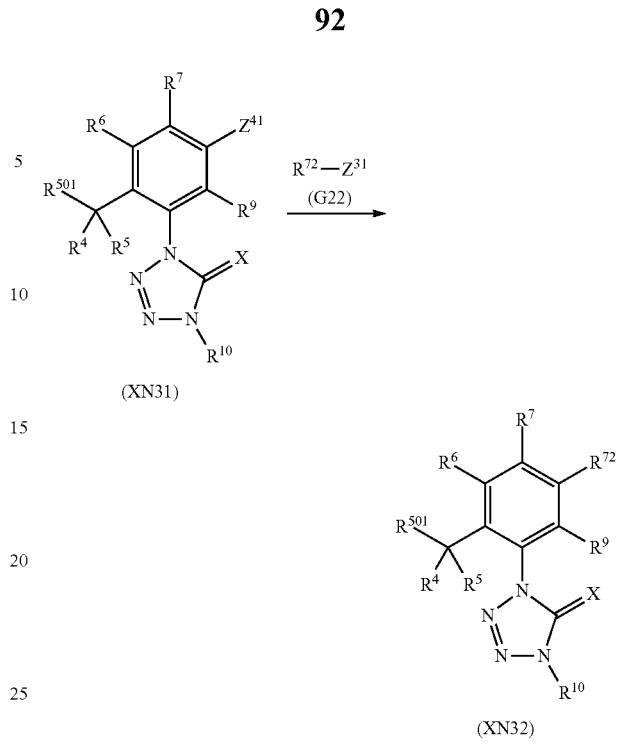

(XN31)

(XN32)

wherein symbols are the same as defined above.

The reaction can be carried out in accordance with the reaction mentioned in Production Process B.

A compound represented by formula (XN42) (hereinafter referred to as the compound (XN42)) can be produced by subjecting a compound represented by formula (XN41) (hereinafter referred to as the compound (XN41)) and the compound (G22) to a coupling reaction in the presence of a base and a catalyst:

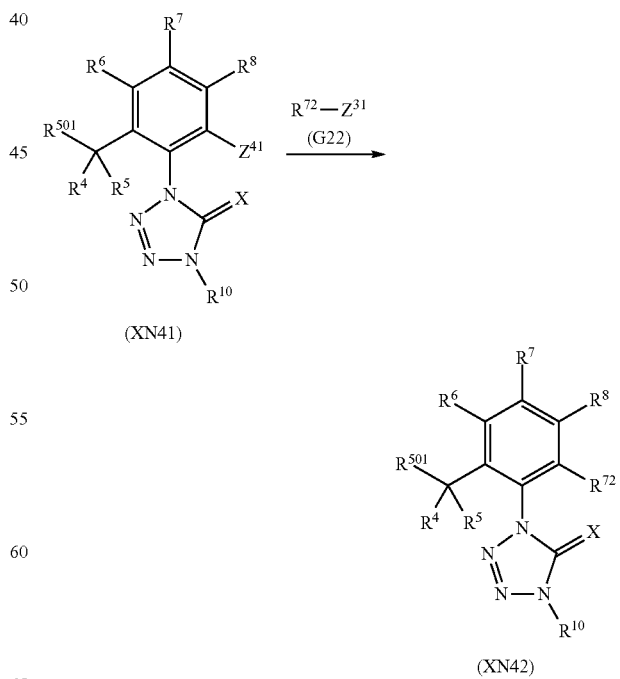

(XN41)

(XN42)

wherein symbols are the same as defined above.

The reaction can be carried out in accordance with the reaction mentioned in Production Process B.

In accordance with the reaction mentioned in Production Process B, it is possible to produce a compound in which two or more substituents selected from $R^3$, $R^4$, $R^5$, and $R^6$ are $R^{71}$ and/or $R^{72}$, among the compounds represented by formula (XN50):

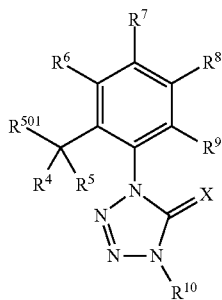

(XN50)

wherein symbols are the same as defined above.

It is also possible to use the other known coupling reaction in place of the coupling reaction of the Production Process B.

(Reference Production Process O)

A compound represented by formula (XW2) (hereinafter referred to as the compound (XW2)) can be produced by reacting a compound represented by formula (XW1) (hereinafter referred to as the compound (XW1)) with a compound represented by formula (XW3) (hereinafter referred to as the compound (XW3)) in the presence of a reaction accelerator:

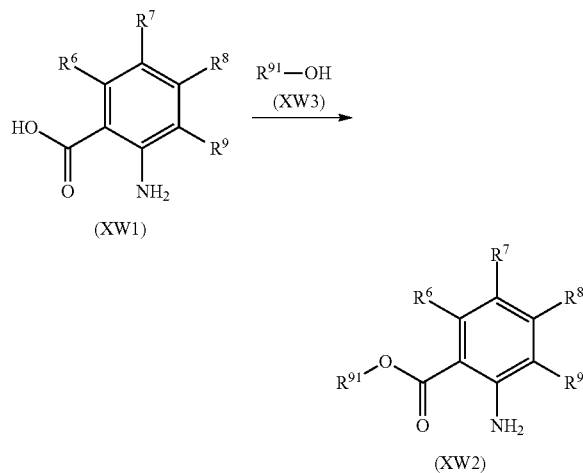

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) usable in the reaction include methyl alcohol, ethyl alcohol, propyl alcohol, isopropyl alcohol, n-butyl alcohol, sec-butyl alcohol, t-butanol, n-pentanol, and the like.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.001 to 5 mols based on 1 mol of the compound (XW1).

In the reaction, an excess amount of the compound (XW3) is used based on the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by the following formula (XV1) (hereinafter referred to as the compound (XV1)), and then reacting the compound (XV1) with the compound (XW3):

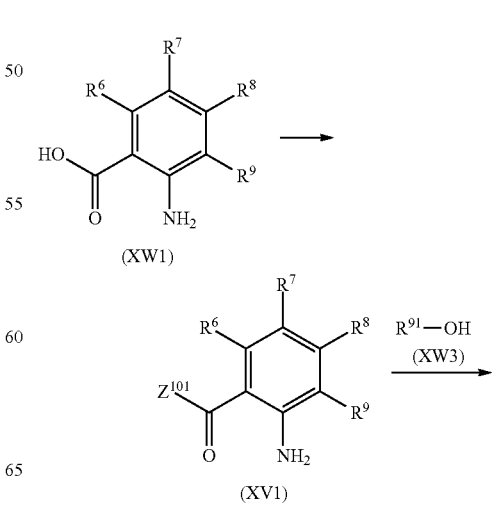

-continued

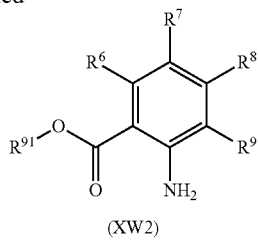

wherein symbols are the same as defined above.

The process for producing the compound (XV1) by reacting the compound (XW1) with the halogenating agent can be carried out in accordance with the reaction mentioned in Reference Production Process C.

The process for producing the compound (XW2) from the compound (XV1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) usable in the reaction include methyl alcohol, ethyl alcohol, propyl alcohol, isopropyl alcohol, n-butyl alcohol, sec-butyl alcohol, t-butanol, and n-pentanol.

In the reaction, an excess amount of the compound (XW3) is used based on the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

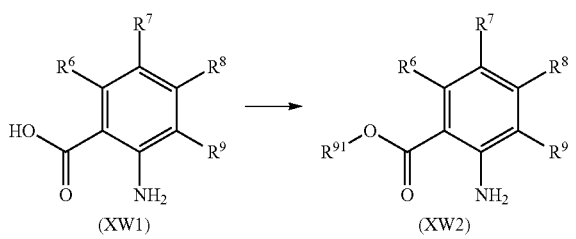

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the alkylating agent usable in the reaction include halogenated alkyls such as diazomethane, trimethylsilyldiazomethane, chlorodifluoromethane, methyl bromide, ethyl bromide, propyl bromide, methyl iodide, ethyl iodide, propyl bromide, allyl bromide, cyclopropyl bromide, benzyl bromide, and 1,1-difluoro-2-iodoethane; dialkyl sulfates such as dimethyl sulfate, diethyl sulfate, and di-propyl sulfate; and alkyl or arylsulfonic acid esters, such as methyl p-toluenesulfonate, ethyl p-toluenesulfonate, propyl p-toluenesulfonate, methyl methanesulfonate, ethyl methanesulfonate, and propyl methanesulfonate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; quaternary ammonium salts such as tetra(n-butyl)ammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process R)

A compound represented by formula (XS2) (hereinafter referred to as the compound (XS2)) can be produced by reacting a compound represented by formula (XS1) (hereinafter referred to as the compound (XS1)) with the compound (A2) in the presence of a base:

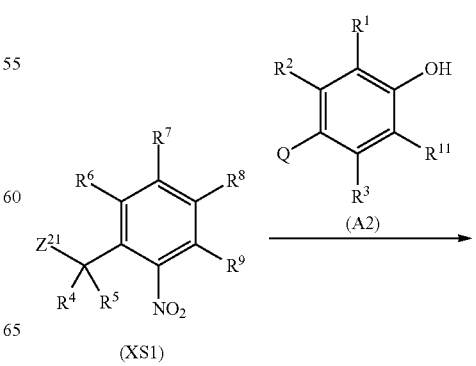

-continued

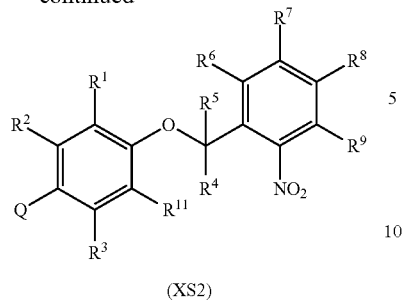

(XS2)

wherein $R^1$, $R^2$, $R^3$, $R^4$, $R^5$, $R^6$, $R^7$, $R^8$, $R^9$, $R^{11}$, Q, and $Z^{21}$ are the same as defined above.

The reaction can be carried out in accordance with the reaction mentioned in Production Process A.

(Reference Production Process S)

The compound (A2) can be produced by subjecting a compound represented by formula (XU1) (hereinafter referred to as the compound (XU1)) and the compound (B2) to a coupling reaction in the presence of a base and a catalyst:

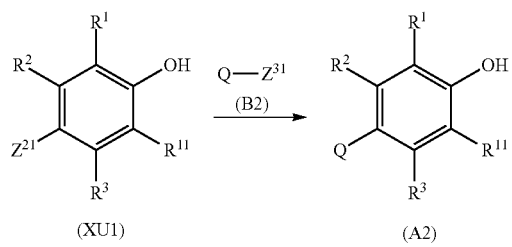

wherein symbols are the same as defined above.

The reaction can be carried out in accordance with the reaction mentioned in Production Process B.

(Reference Production Process T)

The compound (B1) can be produced by reacting the compound (A1) with the compound (XU1) in the presence of a base:

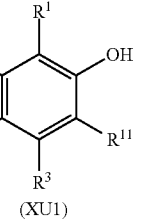
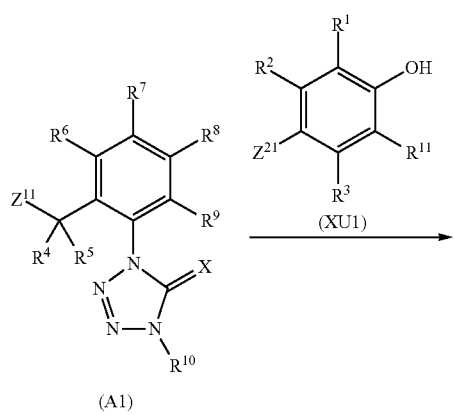

-continued

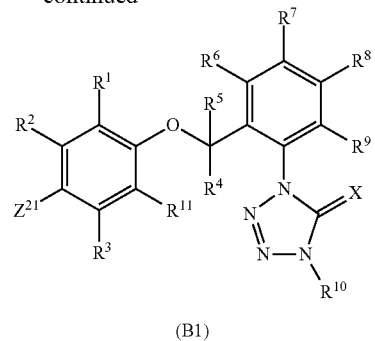

(B1)

wherein symbols are the same as defined above.

The reaction can be carried out in accordance with the reaction mentioned in Production Process A.

(Reference Production Process U)

The compound (C1) can be produced by reacting the compound (B1) with a Borylation reagent in the presence of a base:

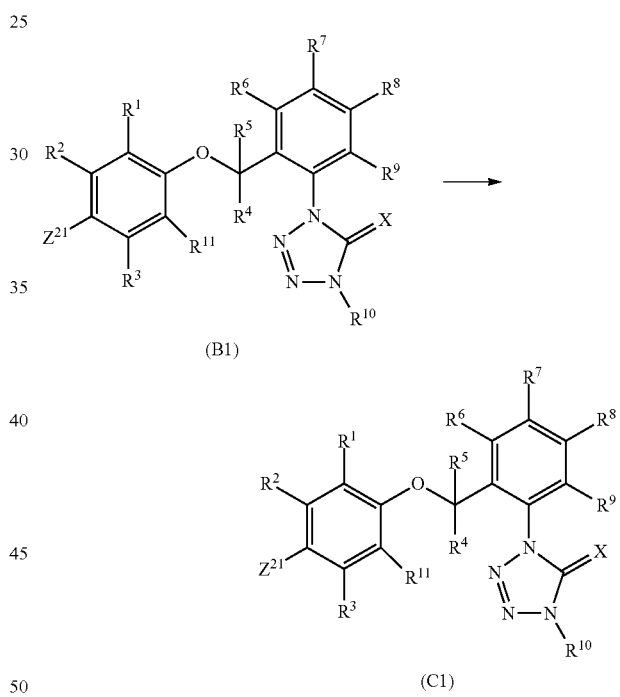

wherein $Z^{51}$ represents an alkoxyboranyl group, and other symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the Borylation reagent to be used in the reaction include bis(pinacolato)diboron, pinacolborane, and the like.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshineferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, potassium carbonate, and cesium carbonate; potassium acetate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the Borylation reagent is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time of the reaction is usually within a range of 0.1 to 24 hours.

After completion of the reaction, the compound (C1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process V)

A compound represented by formula (XX2) (hereinafter referred to as the compound (XX2)) can be produced by reacting a compound represented by formula (XX1) (hereinafter referred to as the compound (XX1)) with the compound (X1) in the presence of a base:

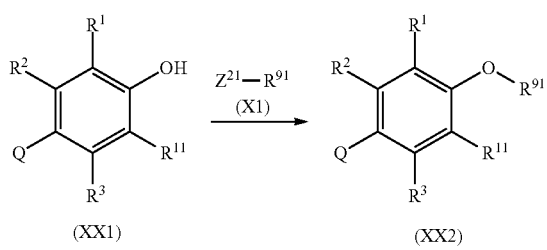

wherein $R^1$, $R^2$, $R^3$, $R^{11}$, Q, and $Z^{21}$ are the same as defined above, and $R^{91}$ represents a C1-C5 alkyl group.

The reaction can be carried out in accordance with the reaction mentioned in Production Process A.

(Reference Production Process W)

A compound represented by formula (XY2) (hereinafter referred to as the compound (XY2)) can be produced by subjecting a compound represented by formula (XY1) (hereinafter referred to as the compound (XY1)) and the compound (Y1) to a coupling reaction in the presence of a base and a catalyst:

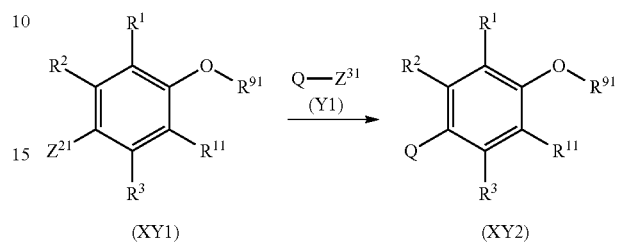

wherein symbols are the same as defined above.

The reaction can be carried out in accordance with the reaction mentioned in Production Process B.

(Reference Production Process X)

The compound (A2) can be produced by reacting a compound represented by formula (XZ1) (hereinafter referred to as the compound (XZ1)) with an acid:

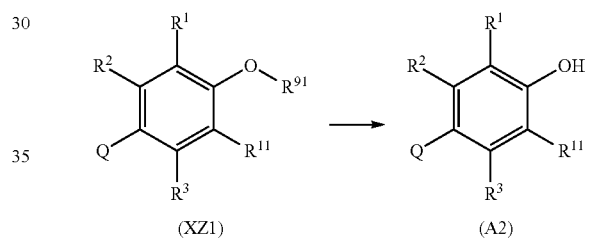

wherein symbols are the same as defined above.

The reaction is usually performed in a solvent.

Examples of the solvent to be used in the reaction include alcohols such as methanol, ethanol, propanol, and butanol; water, acetic acid; and mixtures thereof.

Examples of the acid to be used in the reaction include acetic acid, hydrochloric acid, hydrobromic acid, and the like, and aqueous solutions thereof can also be used as the solvent.

In the reaction, an excess amount of the acid is usually used based on 1 mol of the compound (XZ1).

The reaction temperature of the reaction is usually within a range of −20 to 150° C. The reaction time is usually within a range of 0.1 to 100 hours.

After completion of the reaction, the compound (A2) can be isolated by performing post-treatment operations such as extraction of the reaction mixture with an organic solvent, and drying and concentration of the organic layer. Alternatively, the compound (A2) can be isolated by performing post-treatment operations such as concentration of the reaction mixture. The isolated compound can be further purified by chromatography, recrystallization, and the like.

(Reference Production Process Y)

A compound represented by formula (XAA2) can be produced by reacting a compound represented by formula (XAA1) with a reducing agent:

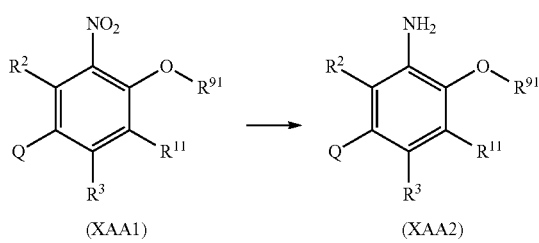

(XAA1) → (XAA2)

wherein symbols are the same as defined above.

The reaction can be carried out in accordance with the reaction mentioned in Production Process F.

(Reference Production Process Z)

A compound represented by formula (XAB2) (hereinafter referred to as the compound (XAB2)) can be produced by reacting a compound represented by formula (XAB1) (hereinafter referred to as the compound (XAB1)) with an acid, a diazotizing agent, and a compound represented by formula (AB1) (hereinafter referred to as the compound (AB1)):

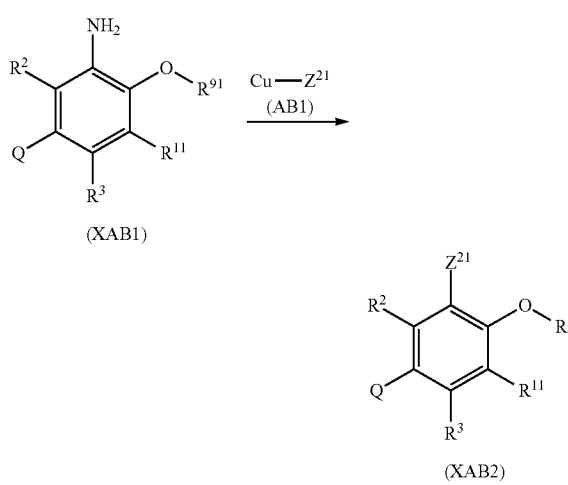

wherein symbols are the same as defined above.

The reaction is usually performed in a solvent.

Examples of the solvent to be used in the reaction include water; ethers such as tetrahydrofuran, 1,4-dioxane, ethylene glycol dimethyl ether, methyl tert-butyl ether, and diisopropyl ether; nitriles such as acetonitrile; and mixtures thereof.

Examples of the acid to be used in the reaction include hydrochloric acid, hydrobromic acid, and the like, and aqueous solutions thereof can also be used as the solvent.

Examples of the diazotizing agent to be used in the reaction include sodium nitrite, tert-butyl nitrite, and the like.

In the reaction, an excess amount of the acid is usually used, the diazotizing agent is usually used in the proportion within a range of 1 to 10 mols, and the compound (AB1) is used in the proportion within a range of 1 to 10 mols, based on 1 mol of the compound (XAB1).

The reaction temperature of the reaction is usually within a range of −20 to 60° C. The reaction time is usually within a range of 0.1 to 100 hours.

After completion of the reaction, the compound (XAB2) can be isolated by performing post-treatment operations such as extraction of the reaction mixture with an organic solvent, and drying and concentration of the organic layer.

Alternatively, the compound (XAB2) can be isolated by performing post-treatment operations such as concentration of the reaction mixture. The isolated compound can be further purified by chromatography, recrystallization, and the like.

(Reference Production Process AA)

A compound represented by formula (XAC2) (hereinafter referred to as the compound (XAC2)) can be produced by reacting a compound represented by formula (XAC1) (hereinafter referred to as the compound (XAC1)) with an acid, a diazotizing agent, and a fluorinating agent:

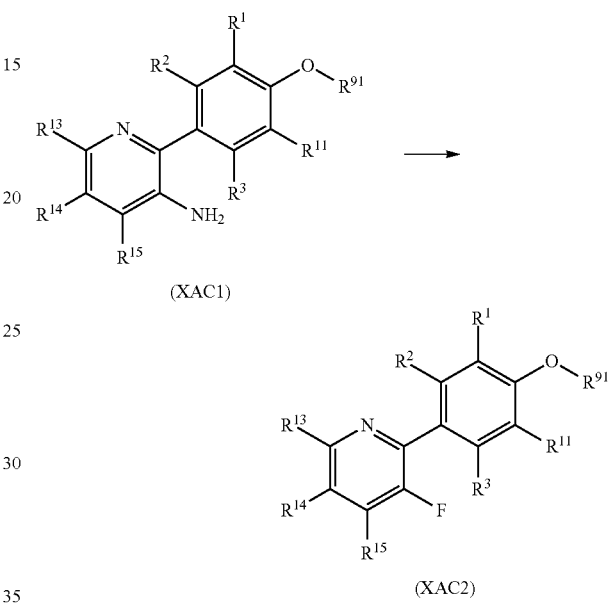

wherein symbols are the same as defined above.

The reaction is usually performed in a solvent.

Examples of the solvent to be used in the reaction include water; ethers such as tetrahydrofuran, 1,4-dioxane, ethylene glycol dimethyl ether, methyl tert-butyl ether, and diisopropyl ether; nitriles such as acetonitrile; and mixtures thereof.

Examples of the acid to be used in the reaction include hydrochloric acid, hydrobromic acid, and the like, and aqueous solutions thereof can also be used as the solvent.

Examples of the diazotizing agent include sodium nitrite, tert-butyl nitrite, and the like.

Examples of the fluorinating agent include tetrafluoroboric acid, hexafluorophosphoric acid, hexafluoroantimonic acid, and the like.

In the reaction, an excess amount of the acid is usually used, the diazotizing agent is used in the proportion within a range of 1 to 10 mols, and the fluorinating agent is used in the proportion within a range of 1 to 10 mols, based on 1 mol of the compound (XAC1).

The reaction temperature of the reaction is usually within a range of −20 to 60° C. The reaction time is usually within a range of 0.1 to 100 hours.

After completion of the reaction, the compound (XAC2) can be isolated by performing post-treatment operations such as extraction of the reaction mixture with an organic solvent, and drying and concentration of the organic layer.

Alternatively, the compound (XAC2) can be isolated by performing post-treatment operations such as concentration of the reaction mixture. The isolated compound can be further purified by chromatography, recrystallization, and the like.

(Reference Production Process AB)

A compound represented by formula (1-3) (hereinafter referred to as the compound (1-3)) can be produced by reacting a compound represented by formula (D1) (hereinafter referred to as the compound (D1)) with an azidation agent:

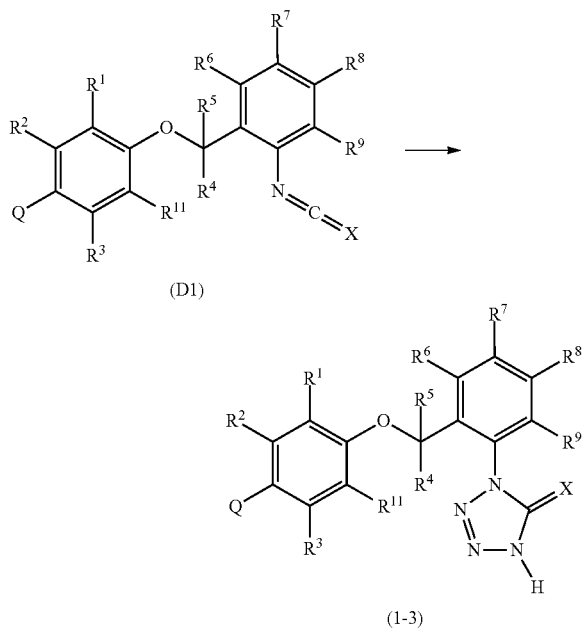

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (D1).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (D1).

After completion of the reaction, the present compound represented by formula (1-3) can be isolated by performing post-treatment operations such as extraction of the reaction mixture with an organic solvent, and drying and concentration of the organic layer. The isolated present compound can be further purified by chromatography, recrystallization, and the like.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutyronitrile), ethers (for example, 1,4-dioxane and diisopropylether), acid amides (for example, DMF and dimethylacetamide), and halogenated hydrocarbons (for example, 1,2-dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers, dispersers and stabilizers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The method for applying the present control compound is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

The present control agent may be used as a mixture with various oils or surfactants such as mineral oils or vegetable oils. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the like.

The present control agent can also be used as a mixture with or together with other fungicides, insecticides, acaricides, nematicides, and plant growth regulators.

Examples of these other fungicides include the followings.

It is also possible to use the present control agent with or without mixing with other fungicides, insecticides, acaricides, nematicides, herbicides, and plant growth regulators.

Examples of these other fungicides include:
(1) Azole Fungicides
such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, ipconazole, azaconazole, diniconazole-M, etaconazole, imibenconazole, oxpoconazole, triadimefon, and uniconazole;
(2) Amine Fungicides
such as fenpropimorph, tridemorph, fenpropidin, spiroxamine, aldimorph, dodemorph, and piperalin;
(3) Benzimidazole Fungicides
such as carbendazim, benomyl, thiabendazole, thiophanate-methyl, fuberidazole, and thiophanate;
(4) Dicarboxyimide Fungicides
such as procymidone, iprodione, and vinclozolin;
(5) Anilinopyrimidine Fungicides
such as cyprodinil, pyrimethanil, and mepanipyrim;
(6) Phenylpyrrole Fungicides
such as fenpiclonil and fludioxonil;
(7) Strobilurin Fungicides
such as kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, fenaminstrobin, enoxastrobin, coumoxystrobin, triclopyricarb, and mandestrobin;
(8) Phenylamide Fungicides
such as metalaxyl, metalaxyl-M or mefenoxam, benalaxyl, benalaxyl-M or kiralaxyl, furalaxyl, ofurace, and oxadixyl;
(9) Carbocylic Acid Amide Fungicides
such as dimethomorph, iprovalicarb, benthivalicarb-isopropyl, mandipropamid, valiphenal or valifenalate, and flumorph;
(10) Carboxamide Fungicides
such as carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, N-[2-(3,4-difluorophenyl)phenyl]-3-trifluoromethylpyrazine-2-carboxylic acid amide, N-(1,1,3-trimethylindan-4-yl)-1-methyl-3-difluoromethylpyrazole-4-carboxylic acid amide (including a mixture of a racemic body or an enantiomer, an enantiomer of an R-form, and an enantiomer of an S-form at any ratio), benodamil, fenfuram, and oxycarboxin;
(11) Other Fungicides
such as diethofencarb; thiram; fluazinam; mancozeb; chlorothalonil; captan; dichlofluanid; folpet; quinoxyfen; fenhexanid; fanoxadon; fenamidon; zoxamide; ethaboxam; amisulbrom; cyazofamid; metrafenone; pyriofenone; cyflufenamid; proquinazid; flusulfamide; fluopicolide; fosetyl-aluminum; propamocarb hydrochloride; cymoxanil; pencycuron; tolclofos-methyl; carpropamid; diclocymet; fenoxanil; tricyclazole; pyroquilon; probenazole; isotianil; tiadinil; tebufloquin; diclomezine; kasugamycin; ferimzone; fthalide; validamycin; hydroxyisoxazole; iminoctadine acetate; and isoprothiolane;

oxolinic acid; oxytetracycline; streptomycin; copper oxychloride; copper hydroxide; copper hydroxide sulfate; organocopper; Bordeaux mixture; sulfur; ametoctradin; fenpyrazamine; oxathiapiprolin; picarbutrazox; 3-chloro-4-(2,6-difluorophenyl)-6-methyl-5-phenylpyridazine; 3-cyano-4-(2,6-difluorophenyl)-6-methyl-5-phenylpyridazine;

acibenzolar-S-methyl; anilazine; bethoxadin; binapacryl; biphenyl; blasticidin-S; bupirimate; captafol; chloroneb; dicloran; diflumetrim; dimethirimol; dinocap; dithianon; dodin; edifenphos; ethirimol; etridiazole; fenarimol; fentin-acetate; fentin-hydroxide; ferbam; flumetver; fluoroimide; flutianil; furmecyclox; iodocarb; iprobenfos; laminarin; maneb; meptyldinocap; methasulfocarb; metiram; naftifin; nuarimol; octhilinone; pefurazoate;

phosphorous acid; potassium salt of phosphorous acid; sodium salt of phosphorous acid; ammonium salt of phosphorous acid; polyoxin; propineb; prothiocarb; pyrazophos; pyributicarb; pyrifenox; pyrrolnitrin; chinomethionate; PCNB; TCNB; silthiofam; tecloftalam; terbinafin; tolprocarb; tolylfluanid; triarimol; triazoxide; triforine; trimorphamide; zineb; ziram;

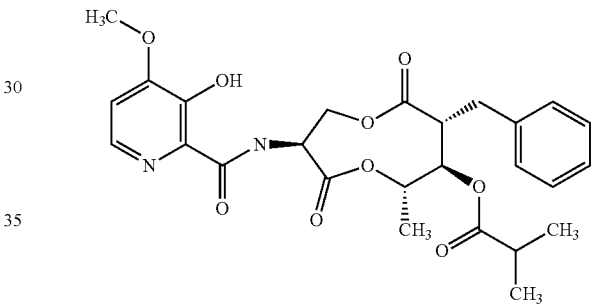

or
(3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate;

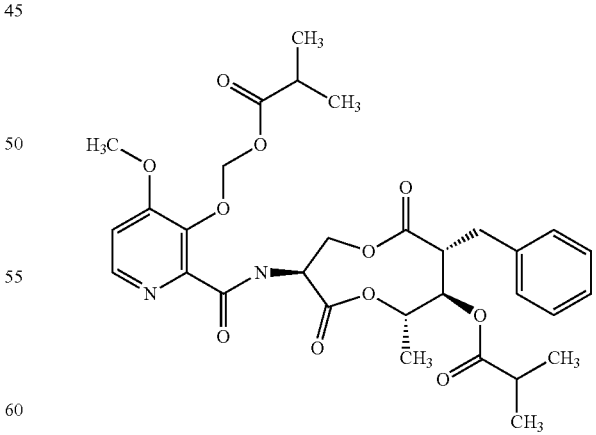

or
{[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate;

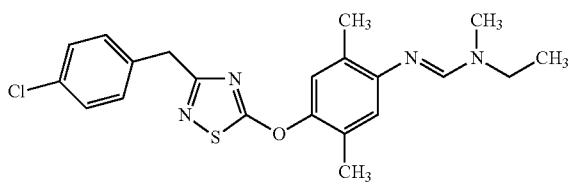 [SMILES: CCN(C)/C=N/c1cc(C)c(Oc2nc(Cc3ccc(Cl)cc3)ns2)cc1C]

or

N'-[4-({3-[(4-chlorophenyl)methyl]-1,2,4-thiadiazol-5-yl}oxy)-2,5-dimethylphenyl]-N-ethyl-N-methylmethanimidamide;

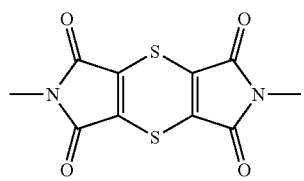

or 2,6-dimethyl-1H,5H-[1,4]dithiino[2,3-c:5,6-c']dipyrrole-1,3,5,7(2H,6H)-tetrone;

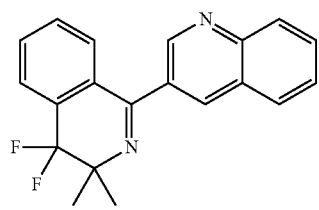 [SMILES: CC1(C)N=C(c2cnc3ccccc3c2)c2ccccc2C1(F)F]

or 3-(4,4-difluoro-3,3-dimethyl-3,4-dihydroisoquinolin-1-yl)quinoline;

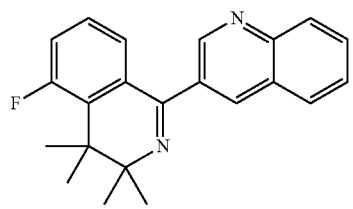 [SMILES: CC1(C)N=C(c2cnc3ccccc3c2)c2cccc(F)c2C1(C)C]

or 3-(5-fluoro-3,3,4,4-tetramethyl-3,4-dihydroisoquinolin-1-yl)quinoline;

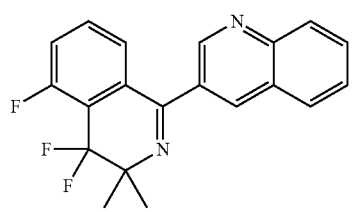 [SMILES: CC1(C)N=C(c2cnc3ccccc3c2)c2cccc(F)c2C1(F)F]

or
3-(4,4,5-trifluoro-3,3-dimethyl-3,4-dihydroisoquinolin-1-yl)quinoline;

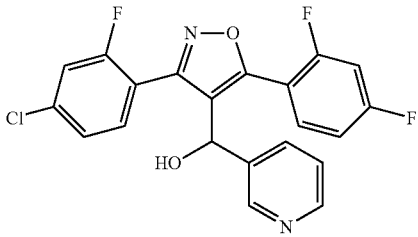 [SMILES: OC(c1cccnc1)c1c(-c2ccc(Cl)cc2F)noc1-c1ccc(F)cc1F]

or
[3-(4-chloro-2-fluorophenyl)-5-(2,4-difluorophenyl)-1,2-oxazol-4-yl](pyridin-3-yl)methanol;
(S)-[3-(4-chloro-2-fluorophenyl)-5-(2,4-difluorophenyl)-1,2-oxazol-4-yl](pyridin-3-yl)methanol;
(R)-[3-(4-chloro-2-fluorophenyl)-5-(2,4-difluorophenyl)-1,2-oxazol-4-yl](pyridin-3-yl)methanol;

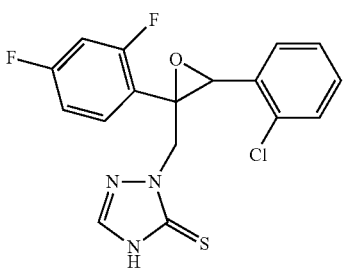 [SMILES: Fc1ccc(C2(Cn3nc[nH]c3=S)OC2c2ccccc2Cl)c(F)c1]

or
2-{[3-(2-chlorophenyl)-2-(2,4-difluorophenyl)oxiran-2-yl]methyl}-2,4-dihydro-3H-1,2,4-triazol-3-thione;
2-{[rel-(2R,3S)-3-(2-chlorophenyl)-2-(2,4-difluorophenyl)oxiran-2-yl]methyl}-2,4-dihydro-3H-1,2,4-triazole-3-thione;
2-{[rel-(2R,3R)-3-(2-chlorophenyl)-2-(2,4-difluorophenyl)oxiran-2-yl]methyl}-2,4-dihydro-3H-1,2,4-triazole-3-thione;
2-{[(2R,3S)-3-(2-chlorophenyl)-2-(2,4-difluorophenyl)oxiran-2-yl]methyl}-2,4-dihydro-3H-1,2,4-triazole-3-thione;
2-{[(2S,3R)-3-(2-chlorophenyl)-2-(2,4-difluorophenyl)oxiran-2-yl]methyl}-2,4-dihydro-3H-1,2,4-triazole-3-thione;
2-{[(2R,3R)-3-(2-chlorophenyl)-2-(2,4-difluorophenyl)oxiran-2-yl]methyl}-2,4-dihydro-3H-1,2,4-triazole-3-thione;
2-{[(2S,3S)-3-(2-chlorophenyl)-2-(2,4-difluorophenyl)oxiran-2-yl]methyl}-2,4-dihydro-3H-1,2,4-triazole-3-thione;

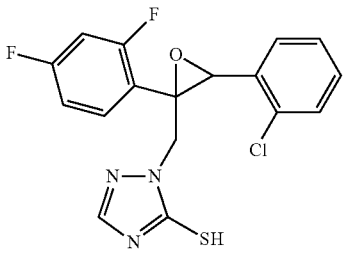 [SMILES: Fc1ccc(C2(Cn3ncnc3S)OC2c2ccccc2Cl)c(F)c1]

or
1-{[3-(2-chlorophenyl)-2-(2,4-difluorophenyl)oxiran-2-yl]methyl}-1H-1,2,4-triazole-5-thiol;

1-{[rel-(2R,3S)-3-(2-chlorophenyl)-2-(2,4-difluorophenyl)oxiran-2-yl]methyl}-1H-1,2,4-triazole-5-thiol;
1-{[rel-(2R,3R)-3-(2-chlorophenyl)-2-(2,4-difluorophenyl)oxiran-2-yl]methyl}-1H-1,2,4-triazole-5-thiol;
1-{[(2R,3S)-3-(2-chlorophenyl)-2-(2,4-difluorophenyl)oxiran-2-yl]methyl}-1H-1,2,4-triazole-5-thiol;
1-{[(2S,3R)-3-(2-chlorophenyl)-2-(2,4-difluorophenyl)oxiran-2-yl]methyl}-1H-1,2,4-triazole-5-thiol;
1-{[(2R,3R)-3-(2-chlorophenyl)-2-(2,4-difluorophenyl)oxiran-2-yl]methyl}-1H-1,2,4-triazole-5-thiol;
1-{[(2S,3S)-3-(2-chlorophenyl)-2-(2,4-difluorophenyl)oxiran-2-yl]methyl}-1H-1,2,4-triazole-5-thiol;

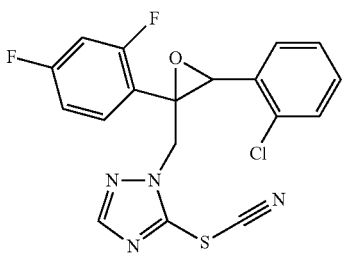 [SMILES: N#CSc1ncnn1CC1(c2ccc(F)cc2F)OC1c1ccccc1Cl]

or
1-{[3-(2-chlorophenyl)-2-(2,4-difluorophenyl)oxiran-2-yl]methyl}-1H-1,2,4-triazol-5-yl thiocyanate;
1-{[rel-(2R,3S)-3-(2-chlorophenyl)-2-(2,4-difluorophenyl)oxiran-2-yl]methyl}-1H-1,2,4-triazol-5-yl thiocyanate;
1-{[rel-(2R,3R)-3-(2-chlorophenyl)-2-(2,4-difluorophenyl)oxiran-2-yl]methyl}-1H-1,2,4-triazol-5-yl thiocyanate;
1-{[(2R,3S)-3-(2-chlorophenyl)-2-(2,4-difluorophenyl)oxiran-2-yl]methyl}-1H-1,2,4-triazol-5-yl thiocyanate;
1-{[(2S,3R)-3-(2-chlorophenyl)-2-(2,4-difluorophenyl)oxiran-2-yl]methyl}-1H-1,2,4-triazol-5-yl thiocyanate;
1-{[(2R,3R)-3-(2-chlorophenyl)-2-(2,4-difluorophenyl)oxiran-2-yl]methyl}-1H-1,2,4-triazol-5-yl thiocyanate;
1-{[(2S,3S)-3-(2-chlorophenyl)-2-(2,4-difluorophenyl)oxiran-2-yl]methyl}-1H-1,2,4-triazol-5-yl thiocyanate;

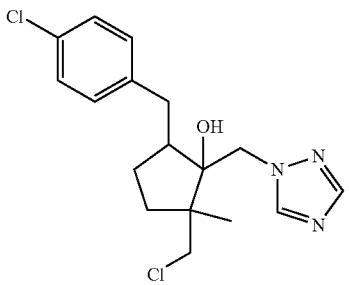 [SMILES: CC1(CCl)CCC(Cc2ccc(Cl)cc2)C1(O)Cn1cncn1]

or
5-(4-chlorobenzyl)-2-chloromethyl-2-methyl-1-(1H-1,2,4-triazol-1-ylmethyl)cyclopentanol;
(1RS,2SR,5SR)-5-(4-chlorobenzyl)-2-chloromethyl-2-methyl-1-(1H-1,2,4-triazol-1-ylmethyl)cyclopentanol;
(1RS,2RS,5RS)-2-chloromethyl-5-(4-fluorobenzyl)-2-methyl-1-(1H-1,2,4-triazol-1-ylmethy)cyclopentanol;
(1RS,2RS,5SR)-2-chloromethyl-5-(4-fluorobenzyl)-2-methyl-1-(1H-1,2,4-triazol-1-ylmethy)cyclopentanol;
(1RS,2SR,5RS)-2-chloromethyl-5-(4-fluorobenzyl)-2-methyl-1-(1H-1,2,4-triazol-1-ylmethy)cyclopentanol;
(1R,2S,5S)-2-chloromethyl-5-(4-fluorobenzyl)-2-methyl-1-(1H-1,2,4-triazol-1-ylmethy)cyclopentanol;
(1S,2R,5R)-2-chloromethyl-5-(4-fluorobenzyl)-2-methyl-1-(1H-1,2,4-triazol-1-ylmethy)cyclopentanol;
(1R,2R,5R)-2-chloromethyl-5-(4-fluorobenzyl)-2-methyl-1-(1H-1,2,4-triazol-1-ylmethy)cyclopentanol;
(1S,2S,5S)-2-chloromethyl-5-(4-fluorobenzyl)-2-methyl-1-(1H-1,2,4-triazol-1-ylmethy)cyclopentanol;
(1R,2R,5S)-2-chloromethyl-5-(4-fluorobenzyl)-2-methyl-1-(1H-1,2,4-triazol-1-ylmethy)cyclopentanol;
(1S,2S,5R)-2-chloromethyl-5-(4-fluorobenzyl)-2-methyl-1-(1H-1,2,4-triazol-1-ylmethy)cyclopentanol;
(1R,2S,5R)-2-chloromethyl-5-(4-fluorobenzyl)-2-methyl-1-(1H-1,2,4-triazol-1-ylmethy)cyclopentanol;
(1S,2R,5S)-2-chloromethyl-5-(4-fluorobenzyl)-2-methyl-1-(1H-1,2,4-triazol-1-ylmethy)cyclopentanol;

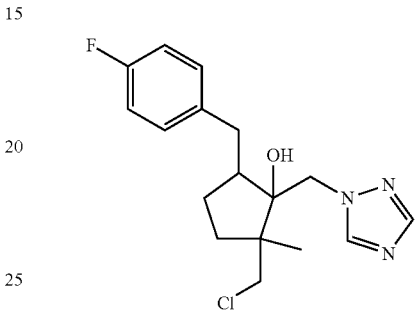

or
2-chloromethyl-5-(4-fluorobenzyl)-2-methyl-1-(1H-1,2,4-triazol-1-ylmethy)cyclopentanol;
(1RS,2SR,5SR)-2-chloromethyl-5-(4-fluorobenzyl)-2-methyl-1-(1H-1,2,4-triazol-1-ylmethy)cyclopentanol;
(1RS,2RS,5RS)-2-chloromethyl-5-(4-fluorobenzyl)-2-methyl-1-(1H-1,2,4-triazol-1-ylmethy)cyclopentanol;
(1RS,2RS,5SR)-2-chloromethyl-5-(4-fluorobenzyl)-2-methyl-1-(1H-1,2,4-triazol-1-ylmethy)cyclopentanol;
(1RS,2SR,5RS)-2-chloromethyl-5-(4-fluorobenzyl)-2-methyl-1-(1H-1,2,4-triazol-1-ylmethy)cyclopentanol;
(1R,2S,5S)-2-chloromethyl-5-(4-fluorobenzyl)-2-methyl-1-(1H-1,2,4-triazol-1-ylmethy)cyclopentanol;
(1S,2R,5R)-2-chloromethyl-5-(4-fluorobenzyl)-2-methyl-1-(1H-1,2,4-triazol-1-ylmethy)cyclopentanol;
(1R,2R,5R)-2-chloromethyl-5-(4-fluorobenzyl)-2-methyl-1-(1H-1,2,4-triazol-1-ylmethy)cyclopentanol;
(1S,2S,5S)-2-chloromethyl-5-(4-fluorobenzyl)-2-methyl-1-(1H-1,2,4-triazol-1-ylmethy)cyclopentanol;
(1R,2R,5S)-2-chloromethyl-5-(4-fluorobenzyl)-2-methyl-1-(1H-1,2,4-triazol-1-ylmethy)cyclopentanol;
(1S,2S,5R)-2-chloromethyl-5-(4-fluorobenzyl)-2-methyl-1-(1H-1,2,4-triazol-1-ylmethy)cyclopentanol;
(1R,2S,5R)-2-chloromethyl-5-(4-fluorobenzyl)-2-methyl-1-(1H-1,2,4-triazol-1-ylmethy)cyclopentanol;
(1S,2R,5S)-2-chloromethyl-5-(4-fluorobenzyl)-2-methyl-1-(1H-1,2,4-triazol-1-ylmethy)cyclopentanol;

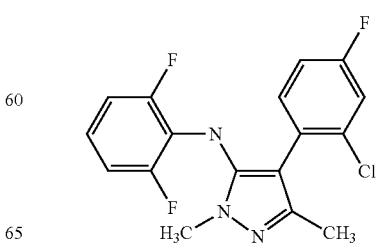

or 5-amino-4-(2-chloro-4-fluorophenyl)-N-(2,6-difluorophenyl)-1,3-dimethyl-1H-pyrazole;

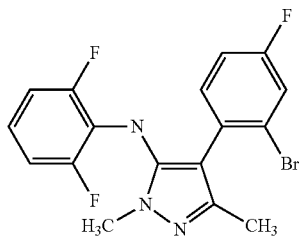 [SMILES: Cc1nn(C)c(Nc2c(F)cccc2F)c1-c1ccc(F)cc1Br]

or 5-amino-4-(2-bromo-4-fluorophenyl)-N-(2,6-difluorophenyl)-1,3-dimethyl-1H-pyrazole;

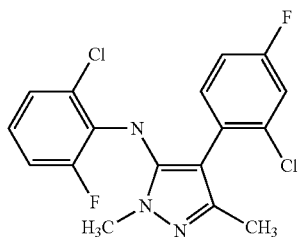 [SMILES: Cc1nn(C)c(Nc2c(F)cccc2Cl)c1-c1ccc(F)cc1Cl]

or 5-amino-4-(2-chloro-4-fluorophenyl)-N-(2-chloro-6-fluorophenyl)-1,3-dimethyl-1H-pyrazole;

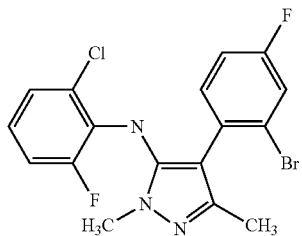 [SMILES: Cc1nn(C)c(Nc2c(F)cccc2Cl)c1-c1ccc(F)cc1Br]

or 5-amino-4-(2-bromo-4-fluorophenyl)-N-(2-chloro-6-fluorophenyl)-1,3-dimethyl-1H-pyrazole;

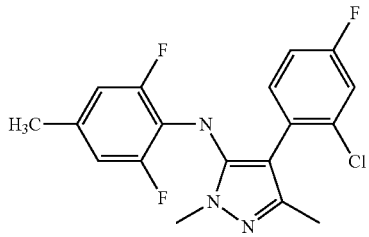 [SMILES: Cc1cc(F)c(Nc2c(-c3ccc(F)cc3Cl)c(C)nn2C)c(F)c1]

or 5-amino-4-(2-chloro-4-fluorophenyl)-N-(2,6-difluoro-4-methylphenyl)-1,3-dimethyl-1H-pyrazole;

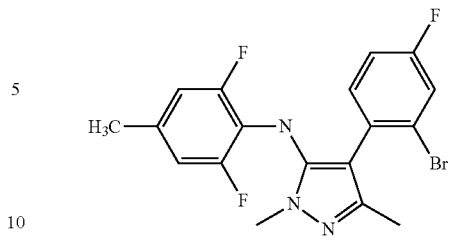

or 5-amino-4-(2-bromo-4-fluorophenyl)-N-(2,6-difluoro-4-methylphenyl)-1,3-dimethyl-1H-pyrazole;

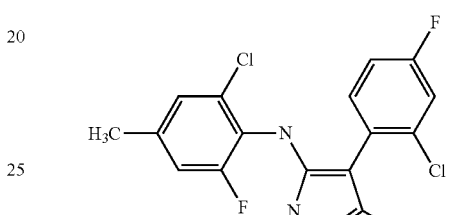

or 5-amino-N-(2-chloro-6-fluoro-4-methylphenyl)-4-(2-chloro-4-fluorophenyl)-1,3-dimethyl-1H-pyrazole;

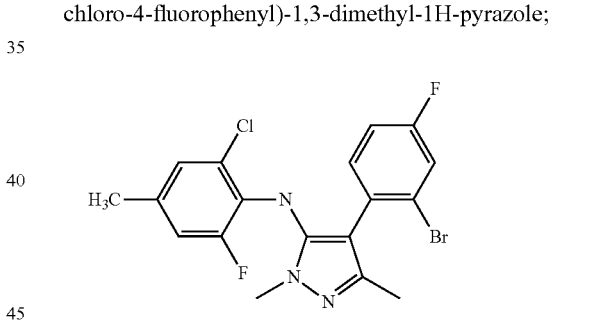

or 5-amino-4-(2-bromo-4-fluorophenyl)-N-(2-chloro-6-fluoro-4-methylphenyl)-1,3-dimethyl-1H-pyrazole;

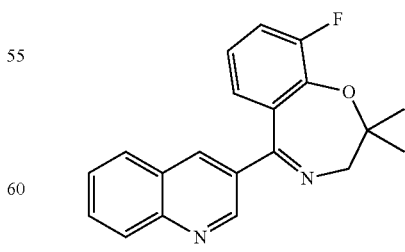

or 9-fluoro-2,3-dihydro-2,2-dimethyl-5-(quinolin-3-yl)-1,4-benzoxazepine;

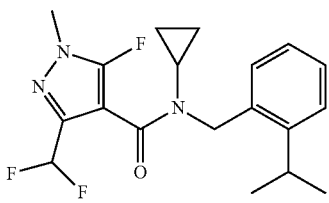 [SMILES: CC(C)c1ccccc1CN(C(=O)c1c(C(F)F)nn(C)c1F)C1CC1]

or
N-cyclopropyl-3-(difluoromethyl)-5-fluoro-N-(2-isopropylbenzyl)-1-methyl-1H-pyrazole-4-carboxamide;

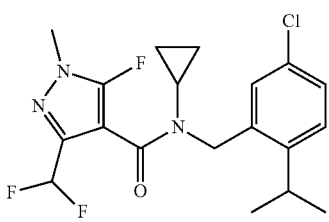 [SMILES: CC(C)c1ccc(Cl)cc1CN(C(=O)c1c(C(F)F)nn(C)c1F)C1CC1]

or
N-cyclopropyl-3-(difluoromethyl)-5-fluoro-N-(5-chloro-2-isopropylbenzyl)-1-methyl-1H-pyrazole-4-carboxamide;

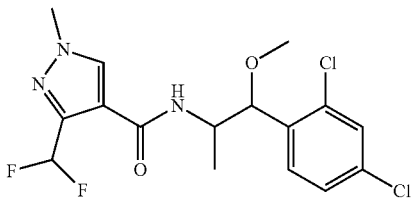 [SMILES: COC(c1ccc(Cl)cc1Cl)C(C)NC(=O)c1cn(C)nc1C(F)F]

or
N-[1-(2,4-dichlorophenyl)-1-methoxypropan-2-yl]-3-difluoromethyl-1-methyl-1H-pyrazole-4-carboxamide;
N-[(1R,2R)-1-(2,4-dichlorophenyl)-1-methoxypropan-2-yl]-3-difluoromethyl-1-methyl-1H-pyrazole-4-carboxamide;
N-[(1R,2S)-1-(2,4-dichlorophenyl)-1-methoxypropan-2-yl]-3-difluoromethyl-1-methyl-1H-pyrazole-4-carboxamide;
N-[(1S,2R)-1-(2,4-dichlorophenyl)-1-methoxypropan-2-yl]-3-difluoromethyl-1-methyl-1H-pyrazole-4-carboxamide;
N-[(1S,2S)-1-(2,4-dichlorophenyl)-1-methoxypropan-2-yl]-3-difluoromethyl-1-methyl-1H-pyrazole-4-carboxamide;
rel-N-[(1R,2R)-1-(2,4-dichlorophenyl)-1-methoxypropan-2-yl]-3-difluoromethyl-1-methyl-1H-pyrazole-4-carboxamide;
rel-N-[(1R,2S)-1-(2,4-Dichlorophenyl)-1-methoxypropan-2-yl]-3-difluoromethyl-1-methyl-1H-pyrazole-4-carboxamide;
N-[(1R,2RS)-1-(2,4-dichlorophenyl)-1-methoxypropan-2-yl]-3-difluoromethyl-1-methyl-1H-pyrazole-4-carboxamide;
N-[(1R,2RS)-1-(2,4-dichlorophenyl)-1-methoxypropan-2-yl]-3-difluoromethyl-1-methyl-1H-pyrazole-4-carboxamide;
N-[(1RS,2R)-1-(2,4-dichlorophenyl)-1-methoxypropan-2-yl]-3-difluoromethyl-1-methyl-1H-pyrazole-4-carboxamide;
N-[(1RS,2S)-1-(2,4-dichlorophenyl)-1-methoxypropan-2-yl]-3-difluoromethyl-1-methyl-1H-pyrazole-4-carboxamide;

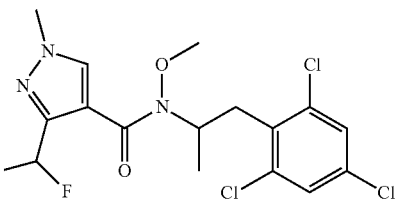

or
3-difluoromethyl-N-methoxy-1-methyl-N-[1-methyl-2-(2,4,6-trichlorophenyl)ethyl]-1H-pyrazole-4-carboxamide;
3-difluoromethyl-N-methoxy-1-methyl-N-[(1R)-1-methyl-2-(2,4,6-trichlorophenyl)ethyl]-1H-pyrazole-4-carboxamide;
3-difluoromethyl-N-methoxy-1-methyl-N-[(1S)-1-methyl-2-(2,4,6-trichlorophenyl)ethyl]-1H-pyrazole-4-carboxamide;

or
2-[6-(3-fluoro-4-methoxyphenyl)-5-methylpyridin-2-yl]quinazoline;

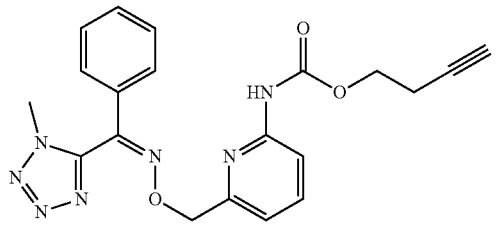 [SMILES: C#CCCOC(=O)Nc1cccc(CO/N=C(/c2ccccc2)c2nnnn2C)n1]

or
3-butyn-1-yl N-{6-[({(Z)-[(1-methyl-1H-tetrazol-5-yl)phenylmethylene]amino}oxy)methyl]-2-pyridinyl}carbamate;

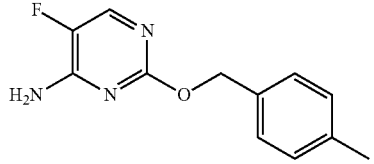 [SMILES: Cc1ccc(COc2ncc(F)c(N)n2)cc1]

or
5-fluoro-2-[(4-methylphenyl)methoxy]-4-pyrimidinamine.

Examples of these other insecticides, acaricides, and nematicides include the followings:
(1) Organophosphorus Compounds
such as acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos:CYAP, demeton-S-methyl, diazinon, dichlorvos: DDVP, dicrotophos, dimethoate, dimethylvinphos, disulfoton, EPN, ethion, ethoprophos, famphur, fenamiphos, fenitrothion:MEP, fenthion:MPP, heptenophos, isofenphos, isopropyl-O-(methoxyaminothiophosphoryl)salicylate or isocarbophos, isoxathion, malathion, mecarbam, methamidophos, methidathion:DMTP, mevinphos, monocrotophos, naled:BRP, omethoate, oxydemeton-methyl, parathion, parathion-methyl or methyl parathion, phenthoate:PAP, phorate, phosalone, phosmet:PMP, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon:DEP, and vamidothion;

(2) Carbamate Compounds such as alanycarb, aldicarb, bendiocarb, benfuracarb, butocarboxim, butoxycarboxim, carbaryl:NAC, carbofuran, carbosulfan, ethiofencarb, fenobucarb:BPMC, formetanate, furathiocarb, isoprocarb:MIPC, methiocarb, methomyl, metolcarb, oxamyl, pirimicarb, propoxur:PHC, thiodicarb, thiofanox, triazamate, trimethacarb, XMC, and xylylcarb;

(3) Synthetic Pyrethroid Compounds such as acrinathrin, allethrin, bifenthrin, bioallethrin, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, fluvalinate, tau-fluvalinate, halfenprox, heptafluthrin, imiprothrin, kadethrin, meperfluthrin, momfluorothrin, permethrin, phenothrin, prallethrin, pyrethrins, resmethrin, silafluofen, tefluthrin, tetramethrin, tetramethylfluthrin, tralomethrin, and transfluthrin;

(4) Nereistoxin Compounds such as bensultap, cartap, cartap hydrochloride, thiocyclam, thiosultap-disodium or bisultap, and thiosultap-monosodium or monosultap;

(5) Neonicotinoid Compounds such as acetamiprid, clothianidin, dinotefuran, flupyradifurone, imidacloprid, nitenpyram, sulfoxaflor, thiacloprid, and thiamethoxam;

(6) Benzoylurea Compounds such as bistrifluron, chlorfluazuron, diflubenzuron, flucycloxuron, flufenoxuron, hexaflumuron, lufenuron, novaluron, noviflumuron, teflubenzuron, and triflumuron;

(7) Phenylpyrazole Compounds such as ethiprole, fipronil, and flufiprole;

(8) Hydrazine Compounds such as chromafenozide, halofenozide, methoxyfenozide, and tebufenozide;

(9) Organochlorine Compounds such as chlordane, endosulfan, and alpha-endosulfan;

(10) Diamide Compounds such as chlorantraniliprole, cyantraniliprole, cycloniliprole, flubendiamide, and tetraniliprole;

(11) Natural Insecticides such as machine oil, nicotine-sulfate, and rotenone;

(12) Agricultural Inoculants such as live spores and produced crystal toxin derived from *bacillus thuringiensis*, var. *aizawai*, var. *kurstaki*, var. *israelensis*, and var. *tenebriosis*, and mixtures thereof; *Bacillus firmus*, strain CNCM 1-1582, *Bacillus sphaericus*, *Beauveria bassiana*, strain GHA, *Beauveria brongniartii*, *Paecilomyces fumosoroseus*, *Paecilomyces lilacinus*, *Paecilomyces tenuipes*, *Trichoderma harzianum*, *Verticillium lecani*, and *Pasteuria penetrans*;

(13) Nematicidally Active Compounds such as dazomet, fluensulfone, fosthiazate, imicyafos, metam, potassium antimonyl tartrate trihydrate, tioxazafen, *Arthrobotrys dactyloides*, *Bacilus firmus*, strain CNCM 1-1582, *Bacillus megaterium*, *Hirsutella rhossiliensis*, *Hirsutella minnesotensis*, *Monacrosporium phymatopagus*, *Pasteuria nishizawae*, *Pasteuria penetrans*, *Pasteuria usgae*, *Verticillium chlamydosporium*, Harpin protein,

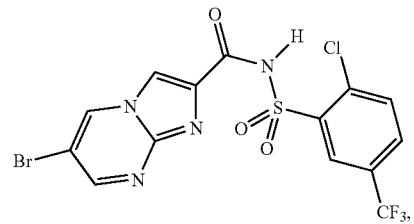 [SMILES: O=C(NS(=O)(=O)c1cc(C(F)(F)F)ccc1Cl)c1cn2cc(Br)cnc2n1]

or
6-bromo-N-{[2-chloro-5-(trifluoromethyl)phenyl]sulfonyl}-imidazo[1,2-a]pyrimidine-2-carboxamide,

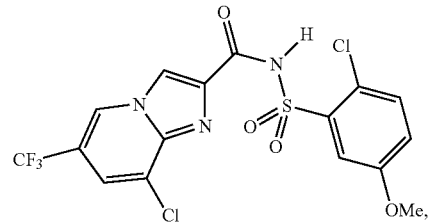 [SMILES: COc1ccc(Cl)c(S(=O)(=O)NC(=O)c2cn3cc(C(F)(F)F)cc(Cl)c3n2)c1]

or
8-chloro-N-[(2-chloro-5-methoxyphenyl)sulfonyl]-6-(trifluoromethyl)-imidazo[1,2-a]pyridine-2-carboxamide;

(14) Other Acaricidal Compounds such as acequinocyl, amitraz, benzoximate, bifenazate, bromopropylate, chinomethionat, clofentezine, cyenopyrafen, cyflumetofen, cyhexatin or tricyclohexyltin hydroxide, dicofol, etoxazole, fenazaquin, fenbutatin oxide, fenpyroximate, fluacrypyrim, fluazuron, flufenoxystrobin, hexythiazox, propargite:BPPS, pyflubumide, pyridaben, pyrimidifen, pyriminostrobin, spirodiclofen, spiromesifen, tebufenpyrad, and tetradifon;

(15) Other Insecticides such as abamectin, emamectin-benzoate, lepimectin, milbemectin, spinetoram, spinosad, afidopyropen, aluminium phosphide, calcium phosphide, phosphine, zinc phosphide, azadirachtin, buprofezin, chlorfenapyr, chloropicrin, cyromazine, diafenthiuron, DNOC, fenoxycarb, flometoquin, flonicamid, hydramethylnon, hydroprene, indoxacarb, kinoprene, metaflumizone, methoprene, methoxychlor, methyl bromide, metoxadiazone, pymetrozine, pyrazophos, pyridalyl, pyrifluquinazone, pyriproxyfen, sodium aluminium fluoride or chiolite, spirotetramat, sulfluramid, sulfuryl fluoride, tolfenpyrad, and triflumezopyrim.

Examples of these other herbicides or plant growth regulators include the followings:

2,4-D, 2,4-DB, acetochlor, acifluorfen, alachlor, ametryn, amicarbazone, aminopyralid, atrazine, benefin, bentazon, bromoxynil, carfentrazone, carfentrazone-ethyl, chloransulam, chlorimuron, chlorimuron-ethyl, chloridazon, clethodim, clodinafop, clomazone, clopyralid, cloransulam-methyl, desmedipham, dicamba, diclofop, diclosulam, diflufenzopyr, dimethanamid, diquat, diuron, EPTC, ethalfluralin, ethofumesate, fenoxaprop, fenoxaprop-P-ethyl, florasulam, fluazifop-P-butyl, flufenacet, flumetsulam, flumiclorac, flumioxazin, fluthiacet, fomesafen, foramsulfuron, glufosinate, glufosinate-ammonium, glyphosate, glyphosate-trimesium, glyphosate-isopropylamine, glyphosate-potassium, halosulfuron, halosulfuron-methyl, haloxyfop-R-methyl, hexazinone, imazamox, imazapic, imazaquin, imazethapyr, iodosulfuron, isoxaflutole, lactofen, lenacil, linuron, mesosulfuron, mesotrione, metam, metamitron, metolachlor, metribuzin, metsulfuron, MPCA, MSMA, nicosulfuron, oryzalin, oxyfluorfen, paraquat, pendimethalin, phenmedipham, picloram, pyrimisulfuron, pinoxaden, promethryn, pyrafulfen-ethyl, pyrithiobac, pyroxsulam, pyroxasulfone, quizalofop-p-ethyl, salflufenacil, sethoxydim, simazine, sulfentrazone, tebuthiuron, tembotrione, tepraloxydim, thifensulfuron, tribenuron-methyl, triclopyr, trifloxysulfuron, trifluaralin, triflusulfuron-methyl, ethephon, chlormequat-chloride, mepiquat-chloride, Gibberellin A typified by Gibberellin A3, abscisic acid, Kinetin, benzyladenine, 1,3-diphenylurea, forchlorfenuron, thidiazuron, 4-oxo-4-(2-phenylethyl)aminobutyric acid, and methyl 5-(trifluoromethyl)benzo[b]thiophene-2-carboxylate.

The method for applying the present control agent is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

The application dose of the present control agent varies depending on weather conditions, dosage forms, timing of application, methods of application, areas to be applied, target diseases, target crops, and the like, and is usually within a range of 1 to 500 g, and preferably 2 to 200 g, per 1,000 m$^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present control agent can be ingested to a livestock animal so as to exterminate sanitary insects which occur in the excrement of the animal.

When the present control agent is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present control agent can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: olanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers, Ornamental foliage plants Fruits: pomaceous fruits (for example, apple, pear, Japanese pear, Chinese quince, and quince), stone fruits (for example, peach, plum, nectarine, *Prunus mume*, cherry fruit, apricot, and prune), *citrus* fruits (for example, *Citrus unshiu*, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate); and the like.

The above-mentioned "plants" include genetically modified crops.

The pests which can be controlled by the present control agent include plant pathogens such as filamentous fungus, as well as harmful arthropods such as harmful insects and harmful mites, and nemathelminth such as nematodes, and specifically include the following examples, but are not limited thereto.

The method for applying the present compound is not particularly limited, as long as the applying form is a form by which the present compound may be applied substantially, and includes, for example, an application to plants such as a foliage application; an application to area for cultivating plants such as a submerged treatment; and an application to soil such as seed disinfection.

The application dose of the present compound varies depending on weather conditions, dosage forms, timing of application, methods of application, areas to be applied, target diseases, target crops, and the like, and is usually within a range of 1 to 500 g, and preferably 2 to 200 g, per 1,000 m$^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present compound can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: olanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica*, *colocasia*, and the like; Flowers; Ornamental foliage plants:

Fruits: pomaceous fruits (for example, apple, pear, Japanese pear, Chinese quince, and quince), stone fruits (for example, peach, plum, nectarine, *Prunus mume*, cherry fruit, apricot, and prune), *citrus* fruits (for example, *Citrus unshiu*, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like;

Trees other than fruit trees: tea, mulberry, flowering plant, roadside trees (for example, ash, birch, dogwood, *Eucalyptus*, *Ginkgo biloba*, lilac, maple, *Quercus*, poplar, Judas tree, *Liquidambar formosana*, plane tree, *zelkova*, Japanese arborvitae, fir wood, hemlock, juniper, *Pinus*, *Picea*, and *Taxus* cuspidate); and the like.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), seeding blight caused by bacteria of the genus (*Rhizoctonia solani*), and take all disease (*Gaeumannomyces graminis*); Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia* collo-*cygni*), and seeding blight caused by bacteria of the genus (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum graminicola*), gray leaf spot (*Cercospora zeae-maydis*), eyespot (*Kabatiella zeae*), and phaeosphaeria leaf spot (*Phaeosphaeria maydis*);

Cotton diseases: anthracnose (*Colletotrichum gossypii*), grey mildew (*Ramuraria areola*), and alternaria leaf spot (*Alternaria macrospora, A. gossypii*); Coffee diseases: rust (*Hemileia vastatrix*); Rape seed diseases: sclerotinia rot (*Sclerotinia sclerotiorum*), black spot (*Alternaria brassicae*), and black leg (*Phoma lingam*); Citrus diseases: melanose (*Diaporthe citri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata, Colletotrichum acutatum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and Phomopsis rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: *alternaria* leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), *sphaceloma* scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia aerial blight (*Rhizoctonia solani*), septoria brown spot (*Septoria glycines*), and frog eye leaf spot (*Cercospora sojina*); Kindney bean diseases: anthracnose (*Colletotrichum lindemthianum*);

Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and *verticillium* wilt (*verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytis cinerea, B. byssoidea, B. squamosa*), gray-mold neck rot (*Botrytis slli*), and small sclerotial rot (*Botrytis squamosa*); various crops diseases: gray mold (*Botrytis cinerea*) and *sclerotinia* rot (*Sclerotinia sclerotiorum*); Japanese radish diseases: *alternaria* leaf spot (*Alternaria brassicicola*); Turfgrass diseases: dollar spot (*Sclerotinia homeocarpa*) and brown patch and large patch (*Rhizoctonia solani*); and Banana diseases: Sigatoka disease (*Mycosphaerella fijiensis, Mycosphaerella musicola*).

Hemiptera: planthoppers (*Delphacidae*) such as small brown planthopper (*Laodelphax striatellus*), brown rice planthopper (*Nilaparvata lugens*), and white-backed rice planthopper (*Sogatella furcifera*); leafhoppers (*Deltocephalidae*) such as green rice leafhopper (*Nephotettix cincticeps*) and green rice leafhopper (*Nephotettix virescens*); aphids (*Aphididae*) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical *citrus* aphid (*Toxoptera citricidus*); stink bugs (*Pentatomidae*) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (*Aleyrodidae*) such as greenhouse whitefly (*Trialeurodes vaporariorum*) and silverleaf whitefly (*Bemisia argentifolii*); scales (*Coccidae*) such as Calformia red scale (*Aonidiella aurantii*), San Jose scale (*Comstockaspis perniciosa*), *citrus* north scale (*Unaspis citri*), red wax scale (*Ceroplastes rubens*), and cottonycushion scale (*Icerya purchasi*); lace bugs (*Tingidae*); jumping plant lices (*Homoptera, Psylloidea*); and bed bugs (*Cimex lectularius*).

Lepidoptera: pyralid moths (*Pyralidae*) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (*Noctuidae*) such as common cutworm (*Spodoptera litura*), beet armyworm (*Spodoptera exigua*), armvworm (*Pseudaletia separata*), cabbage armyworm (*Mamestra brassicae*), black cutworm (*Agrotis ipsilon*), beet semi-looper (*Plusia nigrisigna*), Thoricoplusia spp., *Heliothis* spp., and *Helicoverpa* spp.; white butterflies (*Pieridae*) such as common white (*Pieris rapae*); tortricid moths (*Tortricidae*) such as *Adoxophyes* spp., oriental fruit moth (*Grapholita molesta*), soybean pod borer (*Leguminivora glycinivorella*), azuki bean podworm (*Matsumuraeses azukivora*), summer fruit *tortrix* (*Adoxophyes orana fasciata*), smaller tea *tortrix* (*Adoxophyes* sp.), oriental tea *tortrix* (*Homona magnanima*), apple *tortrix* (*Archips fuscocupreanus*), and codling moth (*Cydia pomonella*); leafblotch miners (*Gracillariidae*) such as tea leafroller (*Caloptilia theivora*), and apple leafminer (*Phyllonorycter ringoneella*); leaf miners (*Gracillariidae*) such as tea leafroller (*Caloptilia theivora*) and apple leafminer (*Phyllonorycter ringoneella*); codling moths (*Carposimidae*) such as peach fruit moth (*Carposina niponensis*); lyonetiid moths (*Lyonetiidae*) such as *Lyonetia* spp.; tussock moths (*Lymantriidae*) such as *Lymantria* spp. and *Euproctis* spp.; yponomeutid moths (*Yponomeutidae*) such as diamondback (*Plutella xylostella*); gelechild moths (*Gelechiidae*) such as pink bollworm (*Pectinophora gossypiella*) and potato tuberworm (*Phthorimaea operculella*); tiger moths and allies (*Arctiidae*) such as fall webworm (*Hyphantria cunea*); and tineid moths (*Tineidae*) such as casemaking clothes moth (*Tinea translucens*), and webbing clothes moth (*Tineola bisselliella*).

Thysanoptera: yellow *citrus* thrips (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*), and tobacco *thrips* (*Frankliniella fusca*).

Diptera: houseflies (*Musca domestica*), common mosquito (*Culex pipiens pallens*), horsefly (*Tabanus trigonus*), onion maggot (*Hylemya anitgua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta America*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink *citrus* rust mite (*Aculops pelekassi*)); Tarsonemidae (for example, broad mite (*Polyphagotarsonemus latus*));

Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides ptrenyssnus*)); Cheyletidae (for example, cheyletid mite (*Cheyletus eruditus*), Cheyletus *malaccensis*, and Cheyletus *moorei*); and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *dermacentor* spp., Ornithodoros spp. (for example, Ornithodoros *moubata*), red mite (*Dermahyssus gallinae*), ghost ant (*Ornithonyssus sylviarum*), Sarcoptes spp. (for example, *Sarcoptes scabiei*), *Psoroptes* spp., Chorioptes spp., Demodex spp., Eutrombicula spp., Ades spp. (for example, Asian tiger mosquito (*Aedes albopictus*)), *Anopheles* spp., *Culex* spp., Culicodes spp., *Musca* spp., *Hypoderma* spp., Gasterophilus spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) Xenosylla spp., Pharaoh's ant (*monomorium pharaonis*) and nematodes [for example, hairworm (for example, *Nippostrongylus brasiliensis*, *Trichostrongylus axei*, *Trichostrongylus colubriformis*), *Trichinella* spp. (for example, *Trichinella spiriralis*), barber pole worm (*Haemonchus contortus*), *Nematodirus* spp. (for example, *Nematodirus battus*), *Ostertagia circumcincta*, *Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 0.28 g of CA55 mentioned in Reference Production Example 55, 0.27 g of the intermediate (HP27) mentioned in Reference Production Example 38, 0.20 g of potassium carbonate, and 10 mL of acetonitrile was stirred with heating under reflux for 5 hours. After cooling to room temperature, the reaction mixture was filtered and the filtrate was concentrated. The residue thus obtained was subjected to silica gel column chromatography to obtain 0.27 g of 1-{2-[2-methyl-4-(4-methylpyridin-2-yl)-phenoxymethyl]phenyl}-4-methyl-1,4-dihydrotetrazol-5-one (hereinafter referred to as the present compound 1).

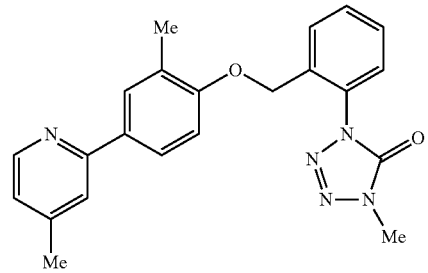 [SMILES: Cc1ccnc(-c2ccc(OCc3ccccc3-n3nnn(C)c3=O)c(C)c2)c1]

$^1$H-NMR (CDCl$_3$) δ: 2.25 (3H, s), 2.34 (3H, s), 3.62 (3H, s), 5.20 (2H, s), 6.86 (1H, d, J=8.5 Hz), 6.95 (1H, ddd, J=5.0, 1.5, 0.7 Hz), 7.42-7.53 (4H, m), 7.67-7.73 (2H, m), 7.82 (1H, dd, J=1.5, 0.7 Hz), 8.48 (1H, d, J=5.0 Hz).

Production Example 2

Using the compounds mentioned in Reference Production Examples, the following present compounds were synthesized by the same reaction as in Production Example 1. Structural formulas and $^1$H-NMR data of the thus obtained present compounds are shown below.

Present Compound 2

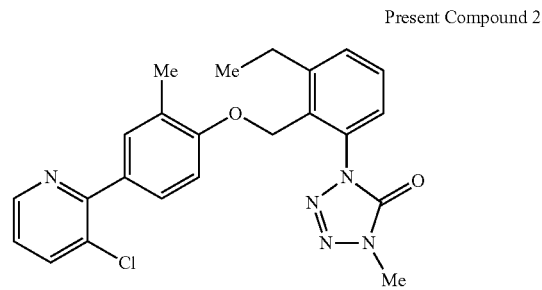

Present Compound 3
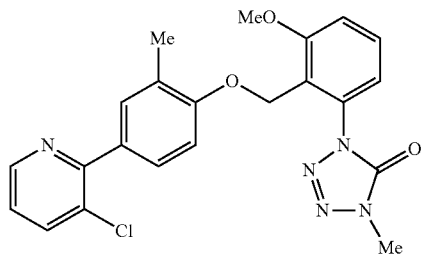
Present Compound 4
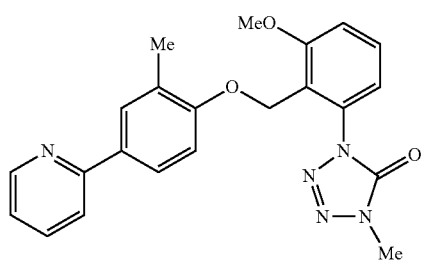
Present Compound 5
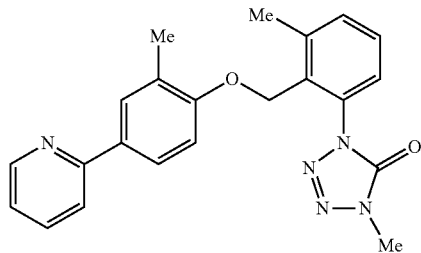
Present Compound 6
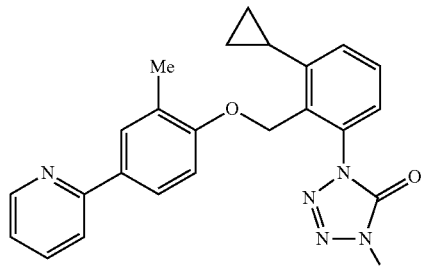
Present Compound 7
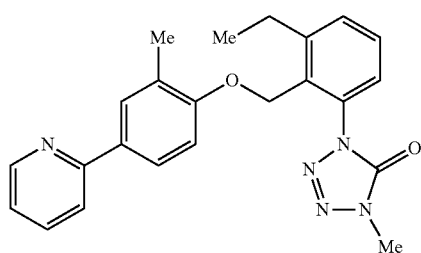
Present Compound 8
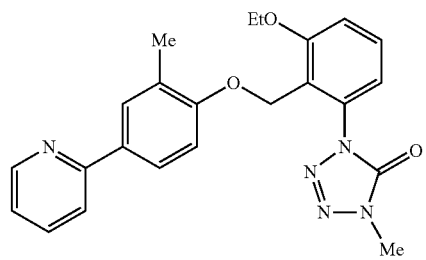
Present Compound 9
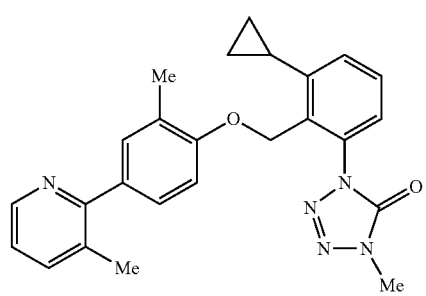
Present Compound 10
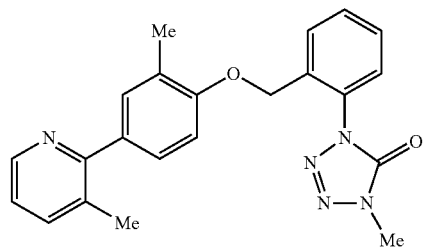
Present Compound 11
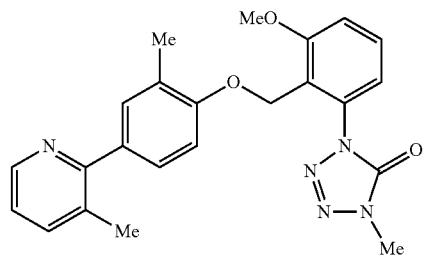
Present Compound 12
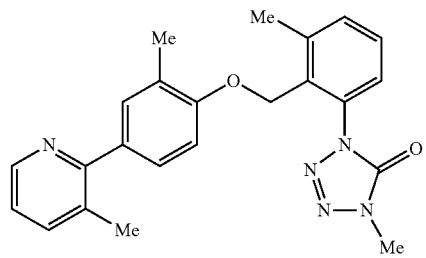

Present Compound 13
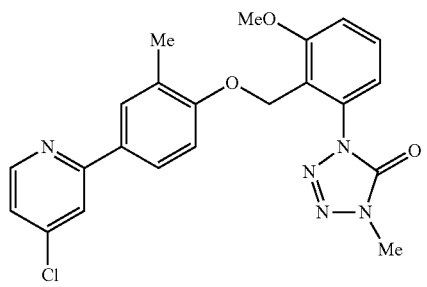
Present Compound 14
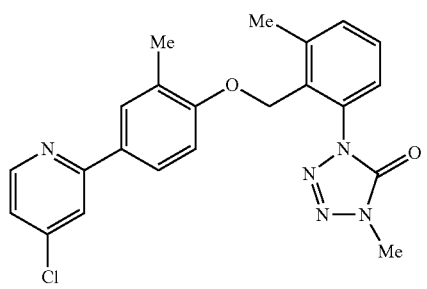
Present Compound 15
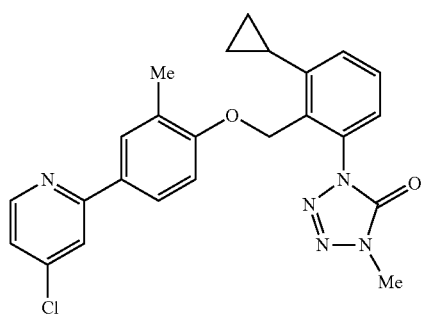
Present Compound 16
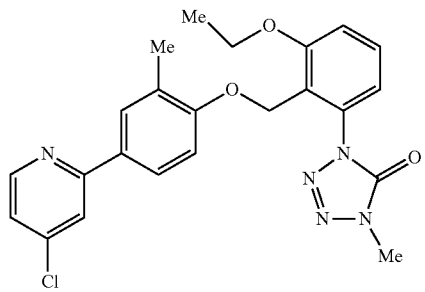
Present Compound 17
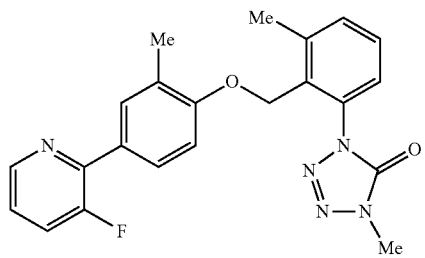
Present Compound 18
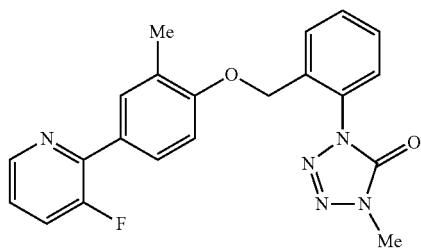
Present Compound 19
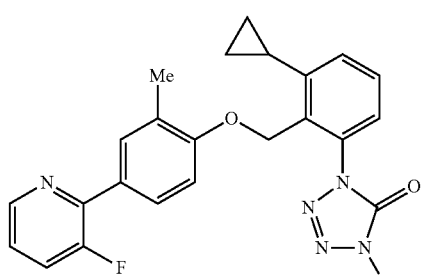
Present Compound 20
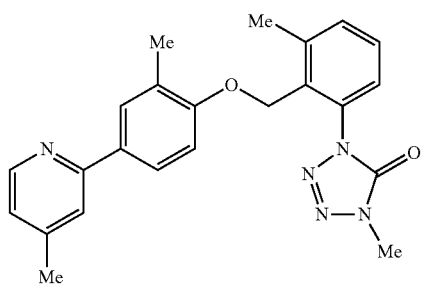
Present Compound 21
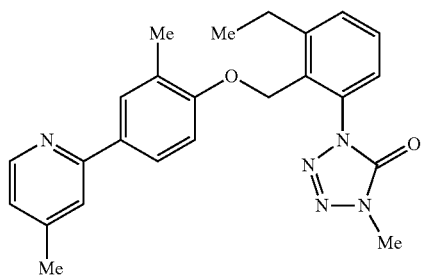
Present Compound 22
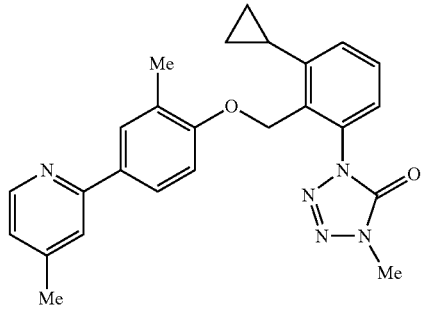

Present Compound 23
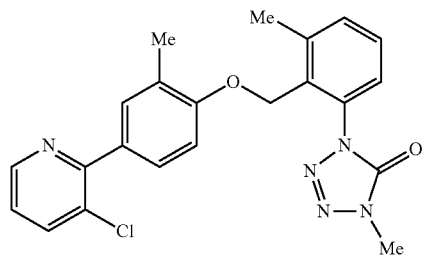
Present Compound 24
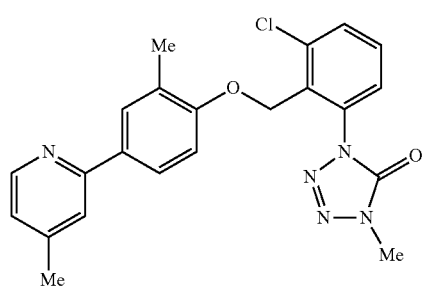
Present Compound 25
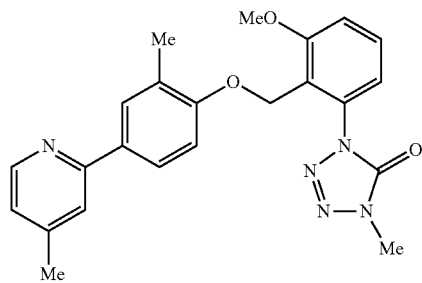
Present Compound 26
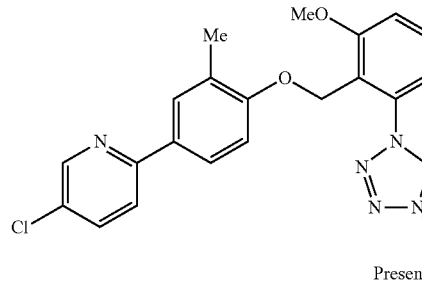
Present Compound 27
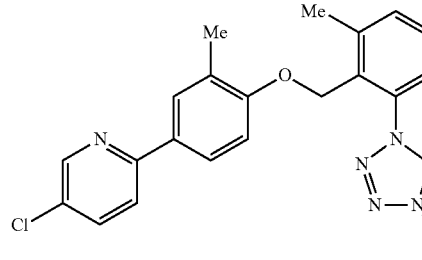
Present Compound 28
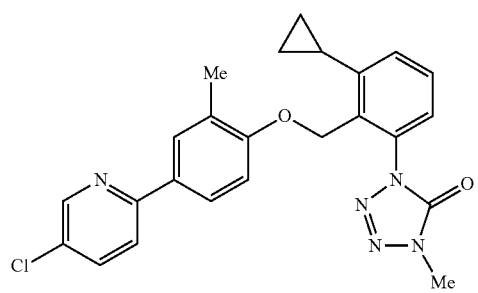
Present Compound 29
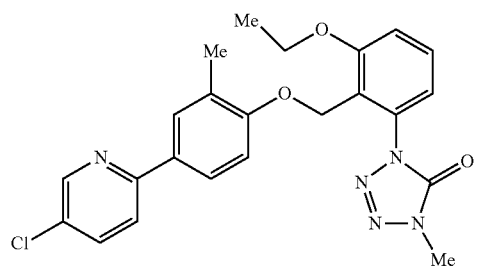
Present Compound 30
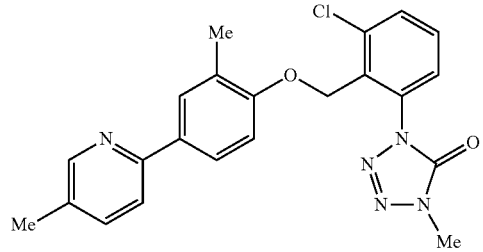
Present Compound 31
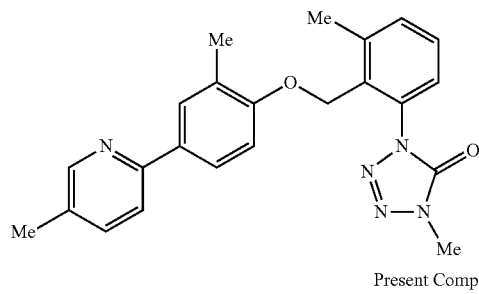
Present Compound 32
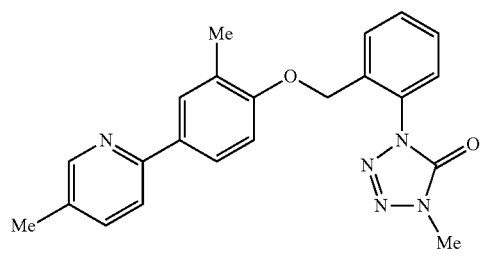

Present Compound 33
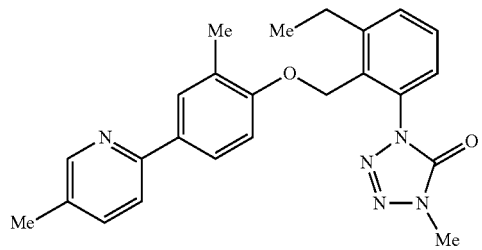
Present Compound 34
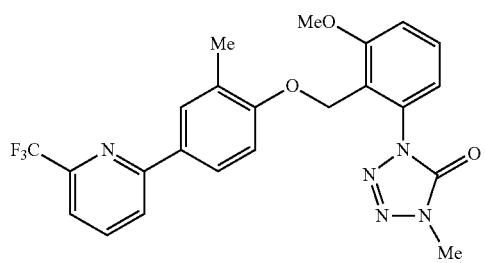
Present Compound 35
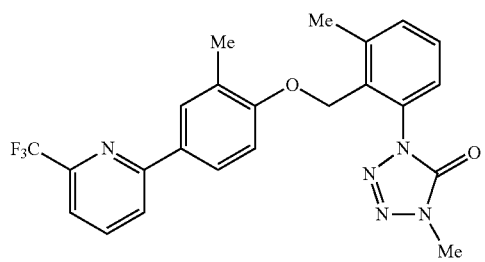
Present Compound 36
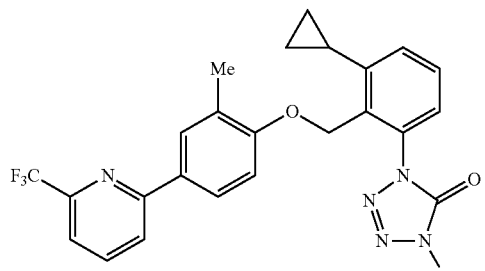
Present Compound 37
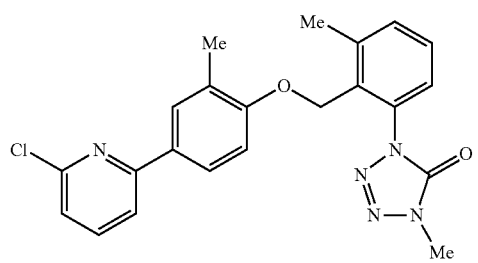
Present Compound 38
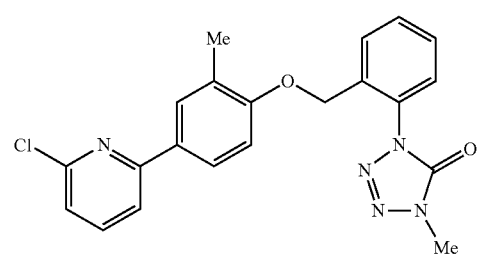
Present Compound 39
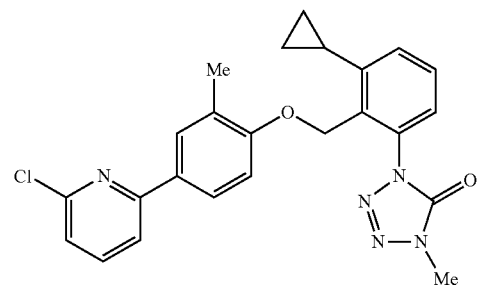
Present Compound 40
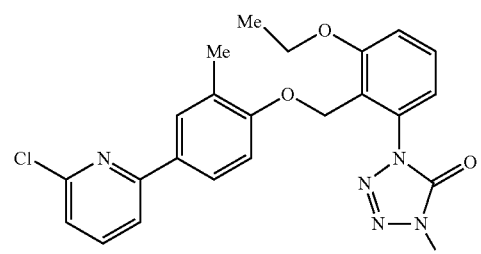
Present Compound 41
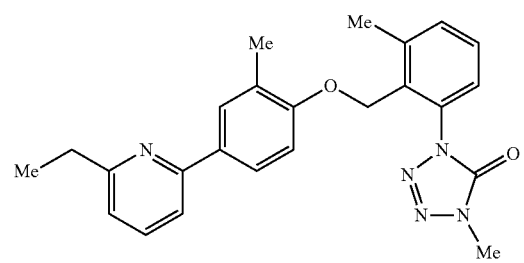
Present Compound 42

Present Compound 43

Present Compound 44

Present Compound 45
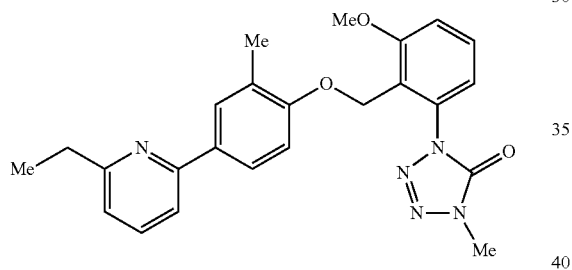
Present Compound 46
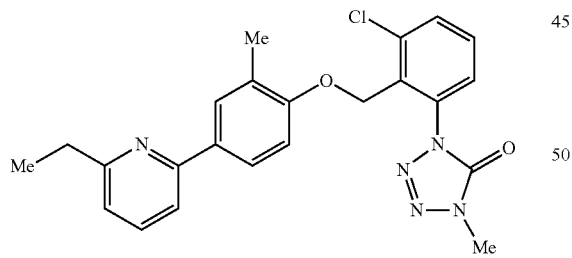
Present Compound 47
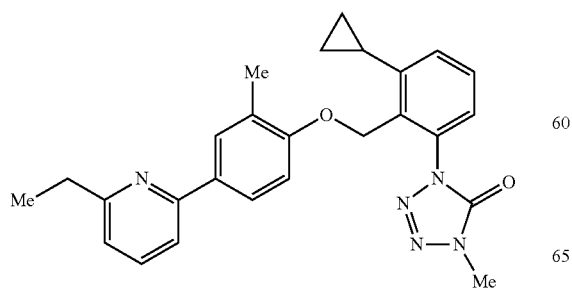
Present Compound 48
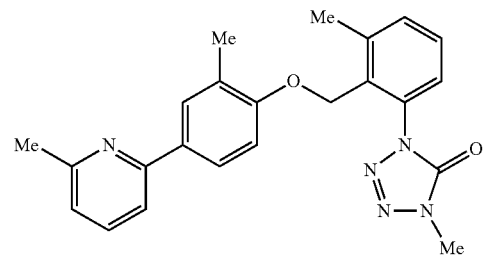
Present Compound 49
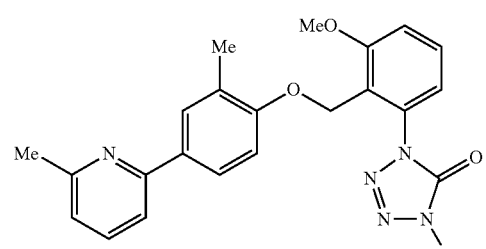
Present Compound 50
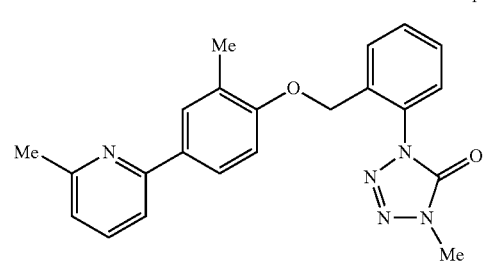
Present Compound 51
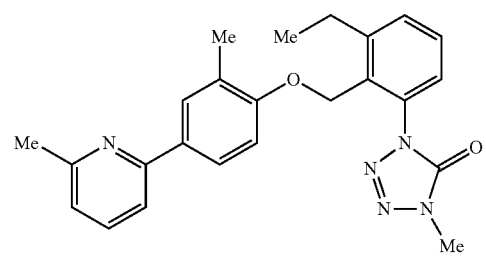
Present Compound 52
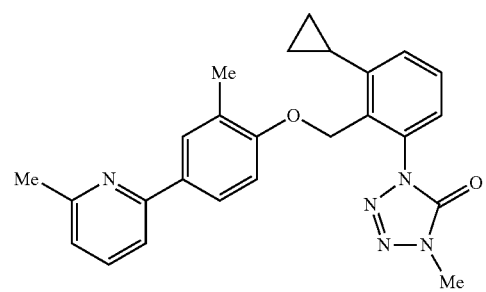

Present Compound 53
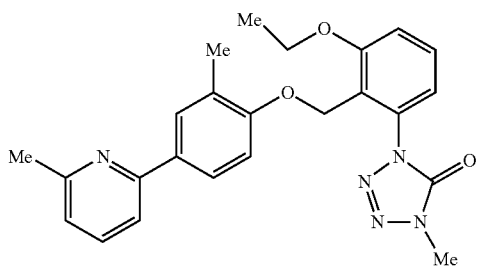
Present Compound 54
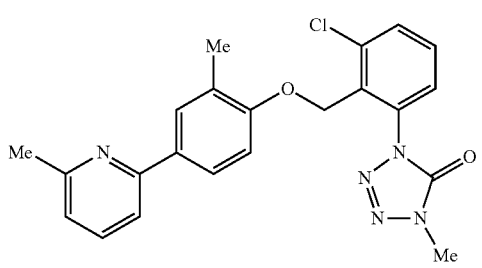
Present Compound 55
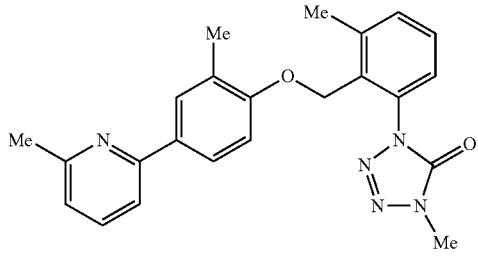
Present Compound 56
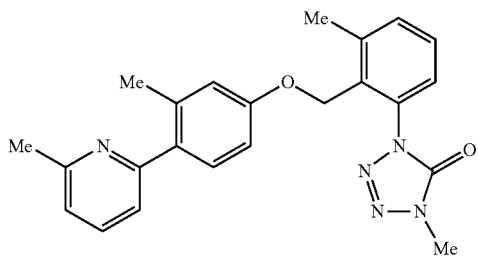
Present Compound 57
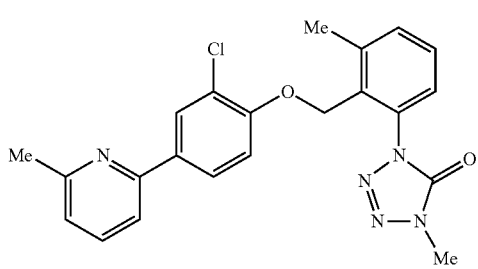
Present Compound 58
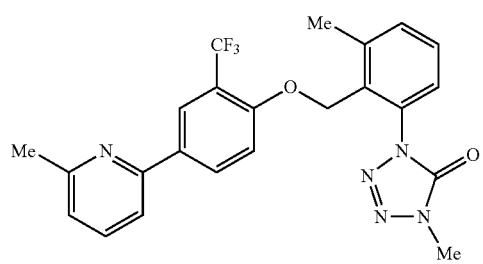
Present Compound 59
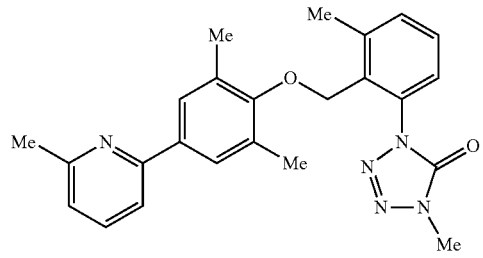
Present Compound 60
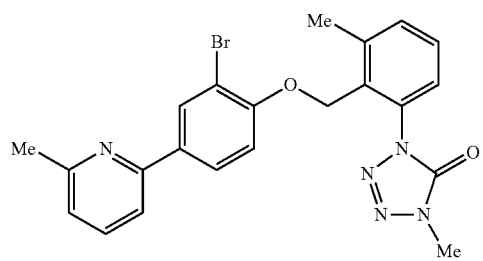
Present Compound 61
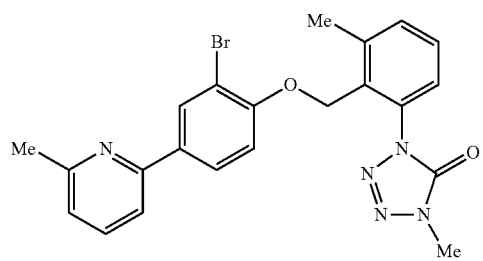
Present Compound 62
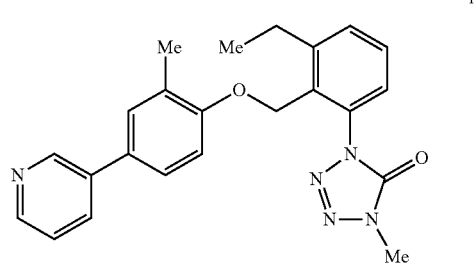

Present Compound 63
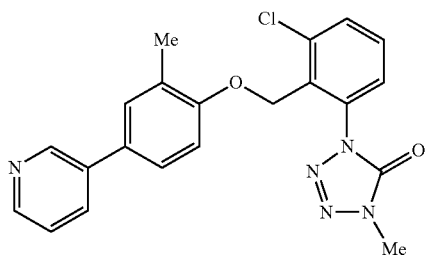
Present Compound 64
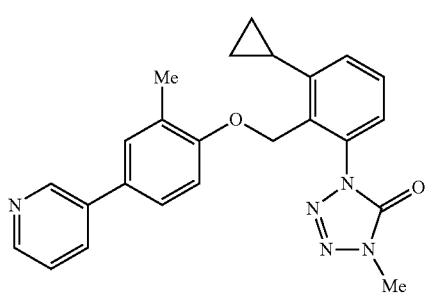
Present Compound 65
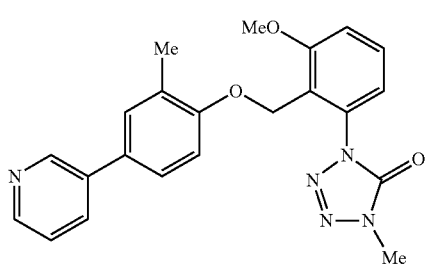
Present Compound 66
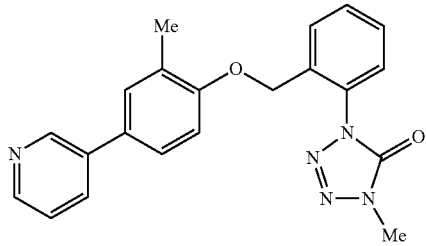
Present Compound 67
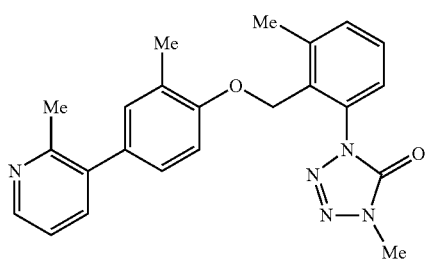
Present Compound 68
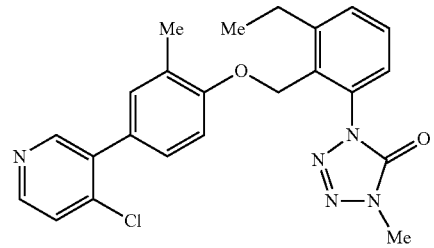
Present Compound 69
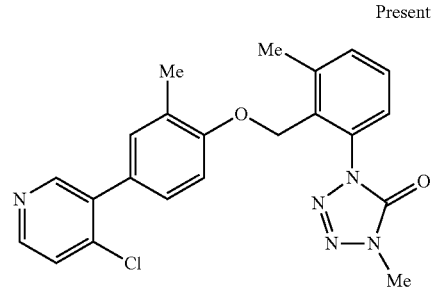
Present Compound 70
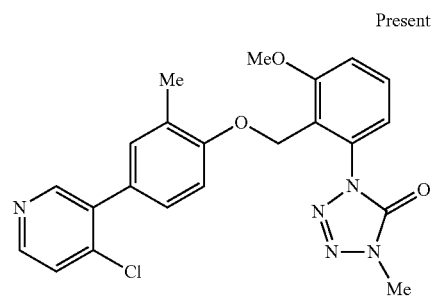
Present Compound 71
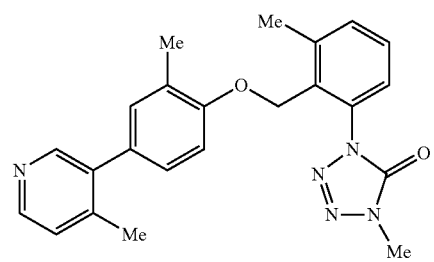
Present Compound 72
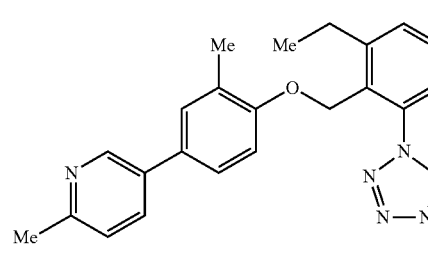

Present Compound 73
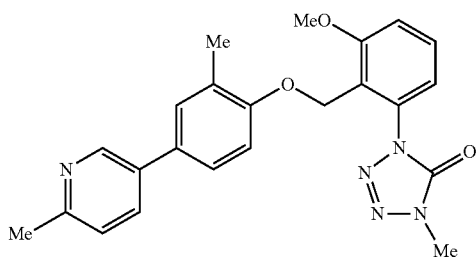
Present Compound 74
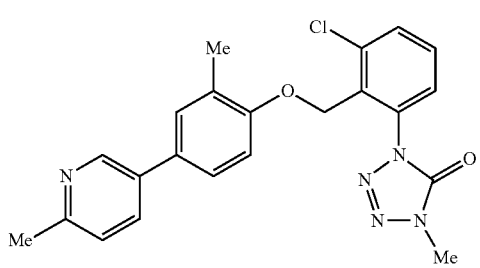
Present Compound 75
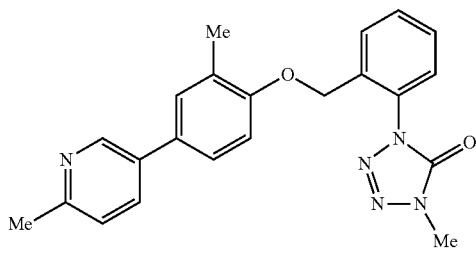
Present Compound 76
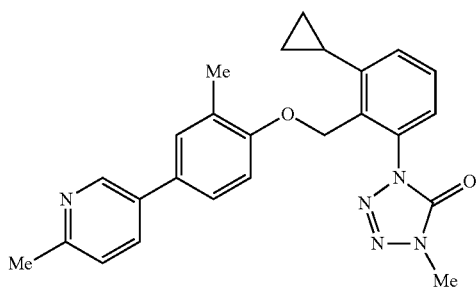
Present Compound 77
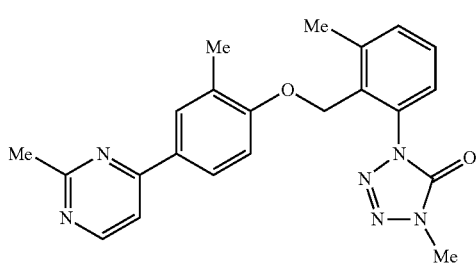
Present Compound 78
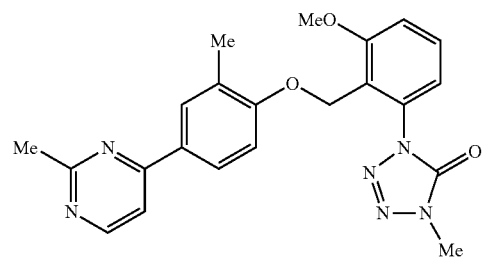
Present Compound 79
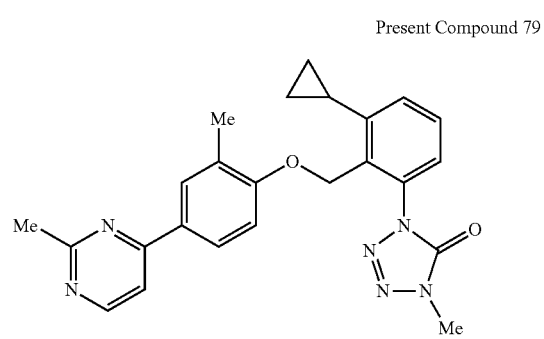
Present Compound 80
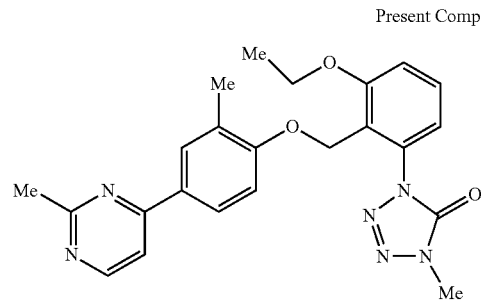
Present Compound 81
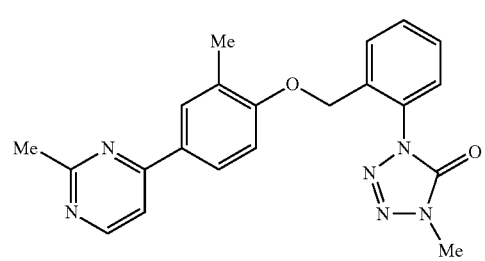
Present Compound 82
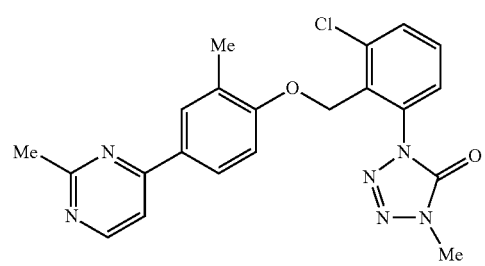

Present Compound 83
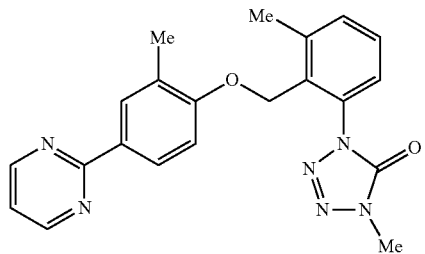
Present Compound 84
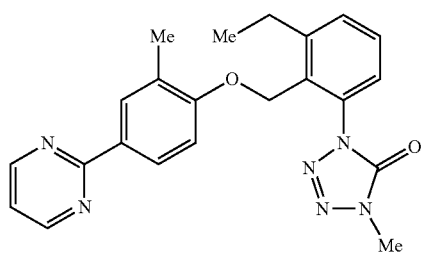
Present Compound 85
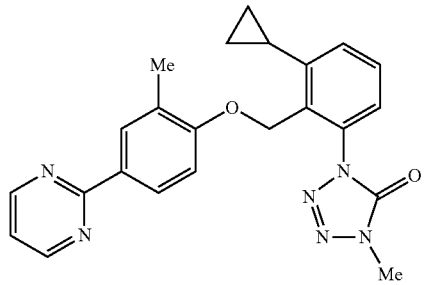
Present Compound 86
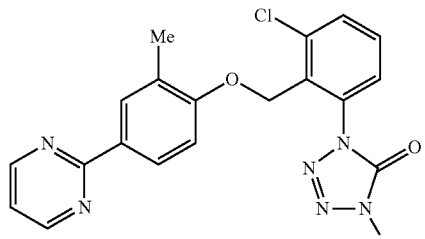
Present Compound 87
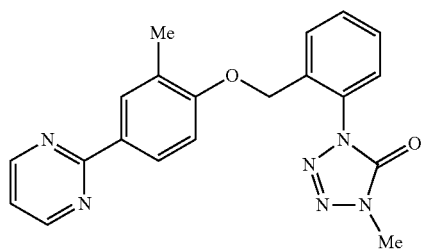
Present Compound 88
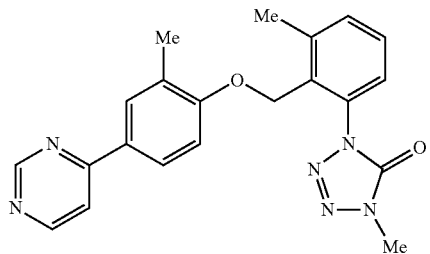
Present Compound 89
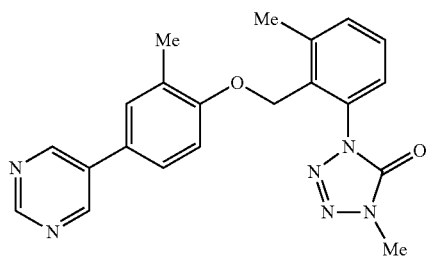
Present Compound 90
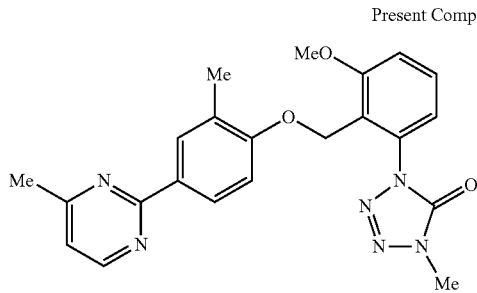
Present Compound 91
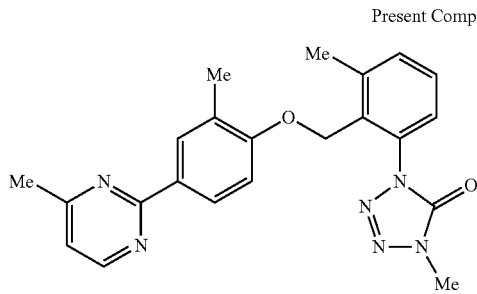
Present Compound 92
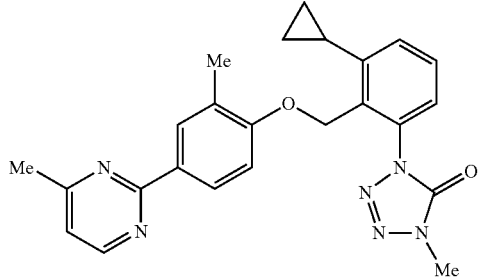

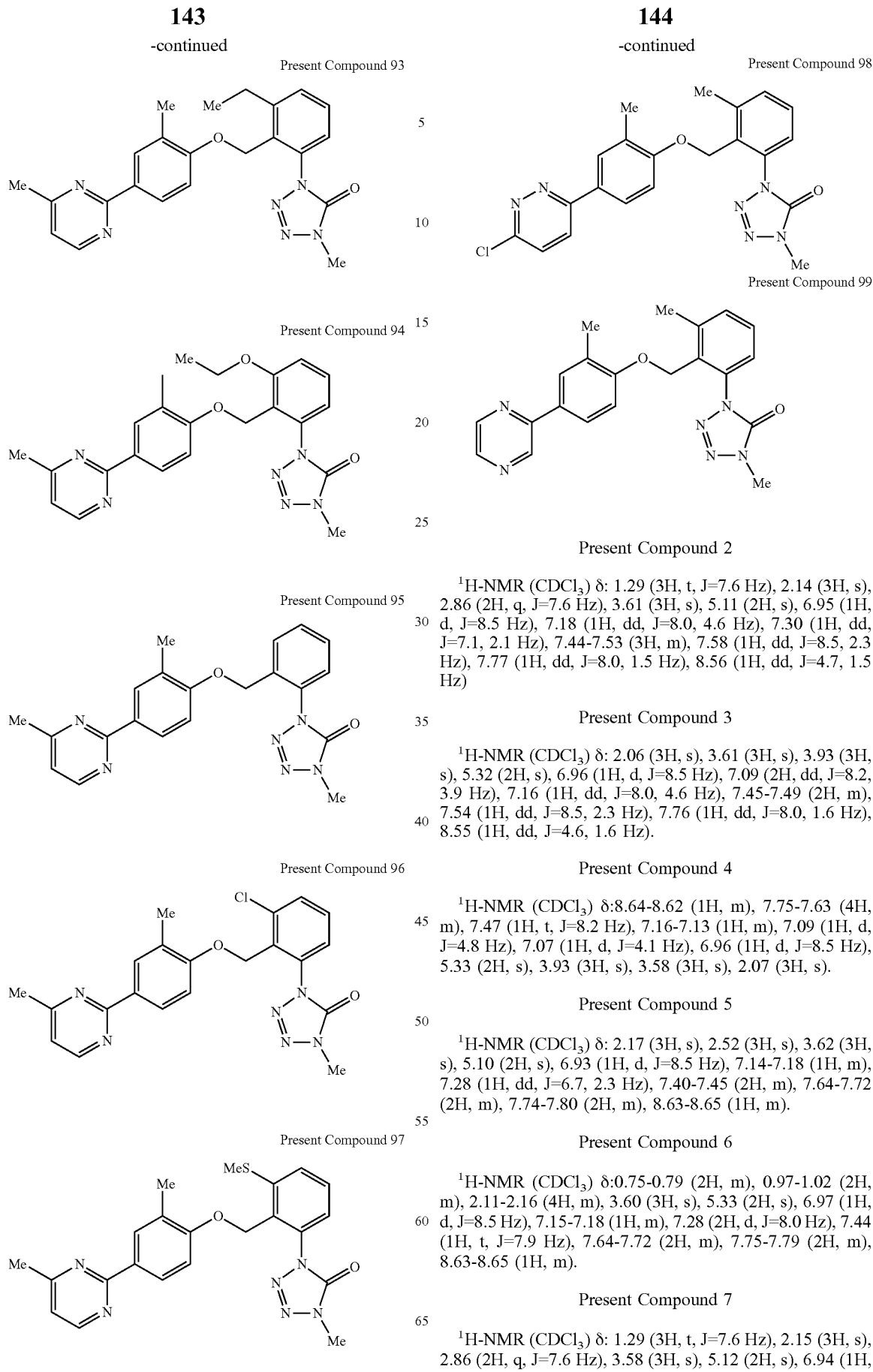

Present Compound 2

¹H-NMR (CDCl₃) δ: 1.29 (3H, t, J=7.6 Hz), 2.14 (3H, s), 2.86 (2H, q, J=7.6 Hz), 3.61 (3H, s), 5.11 (2H, s), 6.95 (1H, d, J=8.5 Hz), 7.18 (1H, dd, J=8.0, 4.6 Hz), 7.30 (1H, dd, J=7.1, 2.1 Hz), 7.44-7.53 (3H, m), 7.58 (1H, dd, J=8.5, 2.3 Hz), 7.77 (1H, dd, J=8.0, 1.5 Hz), 8.56 (1H, dd, J=4.7, 1.5 Hz)

Present Compound 3

¹H-NMR (CDCl₃) δ: 2.06 (3H, s), 3.61 (3H, s), 3.93 (3H, s), 5.32 (2H, s), 6.96 (1H, d, J=8.5 Hz), 7.09 (2H, dd, J=8.2, 3.9 Hz), 7.16 (1H, dd, J=8.0, 4.6 Hz), 7.45-7.49 (2H, m), 7.54 (1H, dd, J=8.5, 2.3 Hz), 7.76 (1H, dd, J=8.0, 1.6 Hz), 8.55 (1H, dd, J=4.6, 1.6 Hz).

Present Compound 4

¹H-NMR (CDCl₃) δ:8.64-8.62 (1H, m), 7.75-7.63 (4H, m), 7.47 (1H, t, J=8.2 Hz), 7.16-7.13 (1H, m), 7.09 (1H, d, J=4.8 Hz), 7.07 (1H, d, J=4.1 Hz), 6.96 (1H, d, J=8.5 Hz), 5.33 (2H, s), 3.93 (3H, s), 3.58 (3H, s), 2.07 (3H, s).

Present Compound 5

¹H-NMR (CDCl₃) δ: 2.17 (3H, s), 2.52 (3H, s), 3.62 (3H, s), 5.10 (2H, s), 6.93 (1H, d, J=8.5 Hz), 7.14-7.18 (1H, m), 7.28 (1H, dd, J=6.7, 2.3 Hz), 7.40-7.45 (2H, m), 7.64-7.72 (2H, m), 7.74-7.80 (2H, m), 8.63-8.65 (1H, m).

Present Compound 6

¹H-NMR (CDCl₃) δ:0.75-0.79 (2H, m), 0.97-1.02 (2H, m), 2.11-2.16 (4H, m), 3.60 (3H, s), 5.33 (2H, s), 6.97 (1H, d, J=8.5 Hz), 7.15-7.18 (1H, m), 7.28 (2H, d, J=8.0 Hz), 7.44 (1H, t, J=7.9 Hz), 7.64-7.72 (2H, m), 7.75-7.79 (2H, m), 8.63-8.65 (1H, m).

Present Compound 7

¹H-NMR (CDCl₃) δ: 1.29 (3H, t, J=7.6 Hz), 2.15 (3H, s), 2.86 (2H, q, J=7.6 Hz), 3.58 (3H, s), 5.12 (2H, s), 6.94 (1H, d, J=8.5 Hz), 7.15-7.18 (1H, m), 7.29 (1H, dd, J=7.1, 2.0 Hz), 7.44-7.50 (2H, m), 7.65-7.73 (2H, m), 7.75-7.79 (2H, m), 8.63-8.65 (1H, m).

Present Compound 8

¹H-NMR (CDCl₃) δ: 1.46 (3H, t, J=6.9 Hz), 2.07 (3H, s), 3.59 (3H, s), 4.15 (2H, q, J=6.9 Hz), 5.35 (2H, s), 6.99 (1H, d, J=8.5 Hz), 7.05 (1H, d, J=3.6 Hz), 7.07 (1H, d, J=3.9 Hz), 7.13-7.17 (1H, m), 7.44 (1H, t, J=8.2 Hz), 7.63-7.74 (4H, m), 8.62-8.64 (1H, m).

Present Compound 9

¹H-NMR (CDCl₃) δ:0.75-0.79 (2H, m), 0.98-1.02 (2H, m), 2.12-2.16 (4H, m), 2.37 (3H, s), 3.63 (3H, s), 5.30 (2H, s), 6.94-6.96 (1H, m), 7.13 (1H, dd, J=7.7, 4.8 Hz), 7.27-7.32 (4H, m), 7.44 (1H, t, J=7.8 Hz), 7.55 (1H, d, J=7.6 Hz), 8.48-8.50 (1H, m).

Present Compound 10

¹H-NMR (CDCl₃) δ: 2.25 (3H, s), 2.36 (3H, s), 3.70 (3H, s), 5.21 (2H, s), 6.85 (1H, d, J=8.5 Hz), 7.13 (1H, dd, J=7.6, 4.7 Hz), 7.27-7.29 (1H, m), 7.35 (1H, d, J=1.9 Hz), 7.49-7.57 (4H, m), 7.73 (1H, d, J=7.5 Hz), 8.48-8.50 (1H, m).

Present Compound 11

¹H-NMR (CDCl₃) δ: 2.05 (3H, s), 2.36 (3H, s), 3.61 (3H, s), 3.93 (3H, s), 5.31 (2H, s), 6.93-6.95 (1H, m), 7.07-7.14 (3H, m), 7.27-7.29 (2H, m), 7.45-7.49 (1H, m), 7.53-7.55 (1H, m), 8.47-8.49 (1H, m).

Present Compound 12

¹H-NMR (CDCl₃) δ: 2.14 (3H, s), 2.37 (3H, s), 2.52 (3H, s), 3.65 (3H, s), 5.08 (2H, s), 6.90 (1H, d, J=8.0 Hz), 7.13 (1H, dd, J=7.7, 4.8 Hz), 7.27-7.32 (3H, m), 7.40-7.45 (2H, m), 7.54-7.56 (1H, m), 8.48-8.50 (1H, m).

Present Compound 13

¹H-NMR (CDCl₃) δ: 2.06 (3H, s), 3.59 (3H, s), 3.94 (3H, s), 5.33 (2H, s), 6.96 (1H, d, J=9.2 Hz), 7.09 (2H, t, J=7.6 Hz), 7.15-7.17 (1H, m), 7.47 (1H, t, J=8.2 Hz), 7.64 (1H, d, J=1.9 Hz), 7.70-7.73 (2H, m), 8.51 (1H, d, J=5.3 Hz).

Present Compound 14

¹H-NMR (CDCl₃) δ: 2.16 (3H, s), 2.52 (3H, s), 3.62 (3H, s), 5.10 (2H, s), 6.92 (1H, d, J=8.2 Hz), 7.17 (1H, dd, J=5.3, 1.9 Hz), 7.29 (1H, dd, J=7.0, 2.2 Hz), 7.40-7.45 (2H, m), 7.66 (1H, dd, J=1.8, 0.6 Hz), 7.74-7.78 (2H, m), 8.53 (1H, dd, J=5.3, 0.7 Hz).

Present Compound 15

¹H-NMR (CDCl₃) δ:0.75-0.79 (2H, m), 0.97-1.02 (2H, m), 2.10-2.20 (4H, m), 3.61 (3H, s), 5.33 (2H, s), 6.97 (1H, d, J=8.9 Hz), 7.17 (1H, dd, J=5.3, 1.9 Hz), 7.28 (2H, d, J=8.0 Hz), 7.44 (1H, t, J=7.5 Hz), 7.66 (1H, d, J=1.9 Hz), 7.74-7.77 (2H, m), 8.53 (1H, d, J=5.3 Hz).

Present Compound 16

¹H-NMR (CDCl₃) δ: 1.46 (3H, t, J=7.0 Hz), 2.07 (3H, s), 3.60 (3H, s), 4.16 (2H, q, J=7.0 Hz), 5.36 (2H, s), 6.98-7.00 (1H, m), 7.05-7.08 (2H, m), 7.16 (1H, dd, J=5.3, 1.9 Hz), 7.44 (1H, t, J=8.2 Hz), 7.64 (1H, d, J=1.4 Hz), 7.70-7.72 (2H, m), 8.51 (1H, d, J=5.3 Hz).

Present Compound 17

¹H-NMR (CDCl₃) δ: 2.17 (3H, s), 2.52 (3H, s), 3.64 (3H, s), 5.11 (2H, s), 6.94 (1H, d, J=9.2 Hz), 7.18-7.24 (1H, m), 7.29 (1H, dd, J=6.9, 2.3 Hz), 7.41-7.48 (3H, m), 7.75-7.80 (2H, m), 8.49-8.47 (1H, m).

Present Compound 18

¹H-NMR (CDCl₃) δ: 2.27 (3H, s), 3.68 (3H, s), 5.23 (2H, s), 6.90 (1H, d, J=8.7 Hz), 7.18-7.22 (1H, m), 7.45 (1H, ddd, J=11.2, 8.2, 1.6 Hz), 7.48-7.57 (3H, m), 7.70-7.77 (2H, m), 7.80 (1H, brs), 8.49-8.46 (1H, m).

Present Compound 19

¹H-NMR (CDCl₃) δ:0.75-0.80 (2H, m), 0.97-1.03 (2H, m), 2.13-2.17 (4H, m), 3.62 (3H, s), 5.33 (2H, s), 6.99 (1H, d, J=8.2 Hz), 7.18-7.23 (1H, m), 7.27 (1H, s), 7.29 (1H, s), 7.49-7.42 (2H, m), 7.75-7.80 (2H, m), 8.46-8.49 (1H, m).

Present Compound 20

¹H-NMR (CDCl₃) δ: 2.16 (3H, s), 2.35 (3H, s), 2.49 (3H, s), 3.58 (3H, s), 5.09 (2H, s), 6.91 (1H, d, J=8.5 Hz), 6.96 (1H, d, J=5.0 Hz), 7.28 (1H, d, J=2.7 Hz), 7.39 (2H, d, J=7.1 Hz), 7.46 (1H, s), 7.75 (1H, d, J=8.2 Hz), 7.79 (1H, s), 8.48 (1H, d, J=5.0 Hz).

Present Compound 21

¹H-NMR (CDCl₃) δ: 1.28 (3H, t, J=7.6 Hz), 2.15 (3H, s), 2.39 (3H, s), 2.85 (2H, q, J=7.6 Hz), 3.58 (3H, s), 5.11 (2H, s), 6.93 (1H, d, J=8.5 Hz), 6.99 (1H, d, J=4.8 Hz), 7.29 (1H, dd, J=7.1, 2.1 Hz), 7.42-7.50 (3H, m), 7.75 (1H, dd, J=8.0, 2.5 Hz), 7.78 (1H, s), 8.50 (1H, d, J=4.8 Hz).

Present Compound 22

¹H-NMR (CDCl₃) δ:0.73-0.79 (2H, m), 0.95-1.01 (2H, m), 2.10-2.17 (4H, m), 2.37 (3H, s), 3.58 (3H, s), 5.33 (2H, s), 6.94-6.99 (2H, m), 7.26 (2H, t, J=6.9 Hz), 7.41 (1H, t, J=7.8 Hz), 7.47 (1H, s), 7.76 (1H, dd, J=8.5, 2.3 Hz), 7.78 (1H, s), 8.49 (1H, d, J=5.0 Hz).

Present Compound 23

¹H-NMR (CDCl₃) δ: 2.15 (3H, s), 2.52 (3H, s), 3.64 (3H, s), 5.09 (2H, s), 6.93 (1H, d, J=8.5 Hz), 7.17 (1H, dd, J=8.0, 4.8 Hz), 7.29 (1H, dd, J=6.8, 2.3 Hz), 7.46-7.40 (2H, m), 7.52 (1H, dd, J=1.6, 0.6 Hz), 7.57 (1H, dd, J=8.5, 2.3 Hz), 7.77 (1H, dt, J=8.0, 0.6 Hz), 8.56 (1H, dt, J=4.7, 0.7 Hz).

Present Compound 24

¹H-NMR (CDCl₃) δ: 2.10 (3H, s), 2.38 (3H, d, J=1.6 Hz), 3.58 (3H, d, J=1.6 Hz), 5.37 (2H, s), 6.92 (1H, d, J=8.5 Hz), 6.98 (1H, d, J=5.0 Hz), 7.38-7.49 (3H, m), 7.60 (1H, dt, J=8.0, 1.8 Hz), 7.73 (1H, dd, J=8.5, 2.1 Hz), 7.76 (1H, d, J=1.8 Hz), 8.49 (1H, d, J=4.8 Hz).

Present Compound 25

¹H-NMR (CDCl₃) δ: 2.07 (3H, s), 2.37 (3H, d, J=2.3 Hz), 3.57 (3H, d, J=2.3 Hz), 3.91 (3H, d, J=3.4 Hz), 5.33 (2H, s), 6.94-6.99 (2H, m), 7.07 (2H, dd, J=8.1, 1.9 Hz), 7.48-7.41 (2H, m), 7.77-7.70 (2H, m), 8.48 (1H, d, J=5.0 Hz).

Present Compound 26

¹H-NMR (CDCl₃) δ: 2.06 (3H, s), 3.59 (3H, s), 3.95 (3H, s), 5.33 (2H, s), 6.95 (1H, d, J=9.0 Hz), 7.06-7.10 (2H, m), 7.46 (1H, t, J=8.3 Hz), 7.57-7.59 (1H, m), 7.64-7.70 (3H, m), 8.56-8.57 (1H, m).

Present Compound 27

¹H-NMR (CDCl₃) δ: 2.16 (3H, s), 2.52 (3H, s), 3.62 (3H, s), 5.10 (2H, s), 6.92 (1H, d, J=8.5 Hz), 7.29 (1H, dd, J=6.8, 2.4 Hz), 7.40-7.45 (2H, m), 7.60 (1H, d, J=8.5 Hz), 7.67 (1H, dd, J=8.6, 2.5 Hz), 7.72-7.75 (2H, m), 8.58 (1H, d, J=2.4 Hz).

Present Compound 28

¹H-NMR (CDCl₃) δ:0.75-0.79 (2H, m), 0.97-1.02 (2H, m), 2.11-2.15 (4H, m), 3.60 (3H, s), 5.32 (2H, s), 6.96 (1H, d, J=9.0 Hz), 7.28 (2H, d, J=8.0 Hz), 7.44 (1H, t, J=7.8 Hz), 7.60 (1H, dd, J=8.5, 0.7 Hz), 7.67 (1H, dd, J=8.5, 2.4 Hz), 7.72-7.75 (2H, m), 8.58 (1H, dd, J=2.6, 0.6 Hz).

Present Compound 29

¹H-NMR (CDCl₃) δ: 1.46 (3H, t, J=6.9 Hz), 2.06 (3H, s), 3.60 (3H, s), 4.16 (2H, q, J=6.9 Hz), 5.35 (2H, s), 6.97-6.99 (1H, m), 7.05 (1H, d, J=4.6 Hz), 7.07 (1H, d, J=5.1 Hz), 7.44 (1H, t, J=8.2 Hz), 7.58 (1H, d, J=8.7 Hz), 7.64-7.70 (3H, m), 8.56 (1H, d, J=2.7 Hz).

Present Compound 30

¹H-NMR (CDCl₃) δ: 2.10 (3H, s), 2.35 (3H, s), 3.59 (3H, d, J=1.1 Hz), 5.37 (2H, s), 6.92 (1H, d, J=8.5 Hz), 7.41 (1H, dt, J=8.0, 1.3 Hz), 7.47 (1H, td, J=8.0, 1.1 Hz), 7.52 (1H, s), 7.55 (1H, d, J=8.2 Hz), 7.62 (1H, dt, J=8.0, 1.3 Hz), 7.71 (1H, d, J=8.7 Hz), 7.75 (1H, d, J=0.9 Hz), 8.46 (1H, d, J=0.7 Hz).

Present Compound 31

¹H-NMR (CDCl₃) δ: 2.16 (3H, s), 2.35 (3H, s), 2.52 (3H, s), 3.62 (3H, s), 5.09 (2H, s), 6.91 (1H, d, J=8.5 Hz), 7.28 (1H, dd, J=6.9, 2.3 Hz), 7.39-7.46 (2H, m), 7.51 (1H, ddd, J=8.2, 2.3, 0.7 Hz), 7.56 (1H, dd, J=8.2, 0.7 Hz), 7.72 (1H, dd, J=8.5, 2.1 Hz), 7.76 (1H, dd, J=2.1, 0.5 Hz), 8.47 (1H, dd, J=1.4, 0.7 Hz).

Present Compound 32

¹H-NMR (CDCl₃) δ: 2.26 (3H, s), 2.35 (3H, s), 3.68 (3H, s), 5.22 (2H, s), 6.87 (1H, d, J=8.7 Hz), 7.57-7.48 (5H, m), 7.69 (1H, dd, J=8.5, 2.1 Hz), 7.72 (1H, t, J=3.9 Hz), 7.80 (1H, d, J=2.1 Hz), 8.47 (1H, t, J=0.7 Hz).

Present Compound 33

¹H-NMR (CDCl₃) δ: 1.29 (3H, t, J=7.6 Hz), 2.15 (3H, s), 2.35 (3H, s), 2.86 (2H, q, J=7.6 Hz), 3.59 (3H, s), 5.11 (2H, s), 6.93 (1H, d, J=8.2 Hz), 7.29 (1H, dd, J=7.1, 2.1 Hz), 7.44-7.53 (3H, m), 7.56 (1H, d, J=7.8 Hz), 7.73 (1H, dd, J=8.2, 2.5 Hz), 7.76 (1H, s), 8.47 (1H, s).

Present Compound 34

¹H-NMR (CDCl₃) δ: 2.07 (3H, s), 3.60 (3H, s), 3.95 (3H, s), 5.35 (2H, s), 6.96 (1H, d, J=8.3 Hz), 7.06-7.10 (2H, m), 7.47 (1H, t, J=8.3 Hz), 7.51 (1H, dd, J=7.1, 1.5 Hz), 7.78-7.86 (4H, m).

Present Compound 35

¹H-NMR (CDCl₃) δ: 2.17 (3H, s), 2.52 (3H, s), 3.63 (3H, s), 5.11 (2H, s), 6.92-6.94 (1H, m), 7.29 (1H, dd, J=6.8, 2.4 Hz), 7.40-7.45 (2H, m), 7.53 (1H, dd, J=7.1, 1.5 Hz), 7.81-7.88 (4H, m).

Present Compound 36

¹H-NMR (CDCl₃) δ:0.76-0.80 (2H, m), 0.98-1.02 (2H, m), 2.11-2.16 (4H, m), 3.61 (3H, s), 5.34 (2H, s), 6.97 (1H, d, J=8.3 Hz), 7.28 (2H, d, J=7.8 Hz), 7.44 (1H, t, J=7.8 Hz), 7.53 (1H, dd, J=7.0, 1.3 Hz), 7.82-7.88 (4H, m).

Present Compound 37

¹H-NMR (CDCl₃) δ: 2.16 (3H, s), 2.52 (3H, s), 3.63 (3H, s), 5.10 (2H, s), 6.90 (1H, d, J=8.5 Hz), 7.19 (1H, d, J=7.7 Hz), 7.27-7.30 (1H, m), 7.40-7.45 (2H, m), 7.57 (1H, d, J=7.7 Hz), 7.65 (1H, t, J=7.7 Hz), 7.76-7.79 (2H, m).

Present Compound 38

¹H-NMR (DMSO-D₆) δ: 1.99 (3H, s), 3.54 (3H, s), 3.95 (3H, s), 5.21 (2H, s), 7.05 (1H, d, J=8.2 Hz), 7.15 (1H, d, J=8.0 Hz), 7.34-7.38 (2H, m), 7.59 (1H, t, J=8.2 Hz), 7.81-7.85 (2H, m), 7.86-7.88 (2H, m).

Present Compound 39

¹H-NMR (CDCl₃) δ: 2.26 (3H, s), 3.68 (3H, s), 5.23 (2H, s), 6.86 (1H, d, J=8.7 Hz), 7.18 (1H, d, J=7.7 Hz), 7.49-7.57 (4H, m), 7.64 (1H, t, J=7.4 Hz), 7.70-7.75 (2H, m), 7.82-7.83 (1H, m).

Present Compound 40

¹H-NMR (CDCl₃) δ:0.75-0.79 (2H, m), 0.97-1.02 (2H, m), 2.10-2.14 (4H, m), 3.61 (3H, s), 5.33 (2H, s), 6.95 (1H, d, J=9.2 Hz), 7.18 (1H, dd, J=7.7, 0.7 Hz), 7.28 (2H, d, J=8.0 Hz), 7.44 (1H, t, J=7.8 Hz), 7.56 (1H, dd, J=7.7, 0.7 Hz), 7.65 (1H, t, J=7.7 Hz), 7.76-7.78 (2H, m).

Present Compound 41

¹H-NMR (CDCl₃) δ: 1.46 (3H, t, J=7.1 Hz), 2.06 (3H, s), 3.60 (3H, s), 4.16 (2H, q, J=7.1 Hz), 5.35 (2H, s), 6.97 (1H, d, J=9.0 Hz), 7.04-7.08 (2H, m), 7.17 (1H, d, J=7.6 Hz), 7.44 (1H, t, J=8.2 Hz), 7.55 (1H, d, J=7.8 Hz), 7.63 (1H, t, J=7.8 Hz), 7.72-7.75 (2H, m).

Present Compound 42

¹H-NMR (CDCl₃) δ: 1.36 (3H, t, J=7.7 Hz), 2.16 (3H, s), 2.52 (3H, s), 2.87 (2H, q, J=7.7 Hz), 3.63 (3H, s), 5.09 (2H, s), 6.91 (1H, d, J=8.2 Hz), 7.04 (1H, d, J=7.8 Hz), 7.28 (1H, dd, J=6.9, 2.5 Hz), 7.47-7.39 (3H, m), 7.61 (1H, t, J=7.8 Hz), 7.77 (2H, d, J=10.2 Hz).

Present Compound 43

¹H-NMR (CDCl₃) δ: 1.28 (3H, t, J=7.7 Hz), 1.36 (3H, t, J=7.6 Hz), 2.15 (3H, s), 2.83-2.91 (4H, m), 3.60 (3H, s), 5.11

(2H, s), 6.93 (1H, d, J=8.7 Hz), 7.05 (1H, d, J=7.7 Hz), 7.29 (1H, dd, J=7.1, 2.2 Hz), 7.51-7.42 (3H, m), 7.61 (1H, t, J=7.7 Hz), 7.77 (2H, d, J=7.5 Hz).

Present Compound 44

¹H-NMR (CDCl₃) δ: 1.36 (3H, t, J=7.6 Hz), 2.27 (3H, s), 2.87 (2H, q, J=7.6 Hz), 3.68 (3H, s), 5.22 (2H, s), 6.87 (1H, d, J=8.6 Hz), 7.04 (1H, d, J=7.7 Hz), 7.44 (1H, d, J=7.7 Hz), 7.48-7.57 (3H, m), 7.61 (1H, t, J=7.8 Hz), 7.71-7.75 (2H, m), 7.82 (1H, dd, J=2.0, 0.7 Hz).

Present Compound 45

¹H-NMR (CDCl₃) δ: 1.35 (3H, t, J=7.6 Hz), 2.06 (3H, s), 2.87 (2H, q, J=7.6 Hz), 3.59 (3H, s), 3.94 (3H, s), 5.32 (2H, s), 6.95 (1H, d, J=9.3 Hz), 7.03 (1H, d, J=7.5 Hz), 7.07 (1H, d, J=6.1 Hz), 7.09 (1H, d, J=6.1 Hz), 7.43 (1H, d, J=8.3 Hz), 7.48 (1H, d, J=8.3 Hz), 7.60 (1H, t, J=7.5 Hz), 7.71-7.76 (2H, m).

Present Compound 46

¹H-NMR (CDCl₃) δ: 1.35 (3H, t, J=7.6 Hz), 2.10 (3H, s), 2.87 (2H, q, J=7.6 Hz), 3.61 (3H, s), 5.38 (2H, s), 6.92 (1H, d, J=7.9 Hz), 7.04 (1H, d, J=7.7 Hz), 7.41 (1H, dd, J=7.9, 1.1 Hz), 7.44 (1H, d, J=8.2 Hz), 7.47 (1H, t, J=8.2 Hz), 7.59-7.64 (2H, m), 7.73-7.78 (2H, m).

Present Compound 47

¹H-NMR (CDCl₃) δ:0.75-0.80 (2H, m), 0.96-1.02 (2H, m), 1.36 (3H, t, J=7.7 Hz), 2.13-2.16 (4H, m), 2.88 (2H, q, J=7.6 Hz), 3.62 (3H, s), 5.31 (2H, s), 6.96 (1H, d, J=9.3 Hz), 7.04 (1H, d, J=7.5 Hz), 7.28 (2H, d, J=7.9 Hz), 7.43 (1H, d, J=7.7 Hz), 7.45 (1H, d, J=7.9 Hz), 7.61 (1H, t, J=7.7 Hz), 7.75-7.79 (2H, m).

Present Compound 48

¹H-NMR (CDCl₃) δ: 2.16 (3H, s), 2.51 (3H, s), 2.60 (3H, s), 3.63 (3H, s), 5.09 (2H, s), 6.90 (1H, d, J=8.3 Hz), 7.03 (1H, d, J=7.6 Hz), 7.28 (1H, dd, J=7.0, 2.3 Hz), 7.40-7.44 (3H, m), 7.58 (1H, t, J=7.8 Hz), 7.73 (1H, dd, J=8.4, 2.3 Hz), 7.76-7.77 (1H, m).

Present Compound 49

¹H-NMR (CDCl₃) δ: 2.06 (3H, s), 2.60 (3H, s), 3.59 (3H, s), 3.94 (3H, s), 5.32 (2H, s), 6.94 (1H, d, J=8.3 Hz), 7.01 (1H, d, J=7.6 Hz), 7.06-7.10 (2H, m), 7.41-7.48 (2H, m), 7.57 (1H, t, J=7.6 Hz), 7.69-7.72 (2H, m).

Present Compound 50

¹H-NMR (CDCl₃) δ: 2.26 (3H, s), 2.60 (3H, s), 3.68 (3H, s), 5.22 (2H, s), 6.86 (1H, d, J=8.3 Hz), 7.03 (1H, d, J=7.1 Hz), 7.43 (1H, d, J=7.8 Hz), 7.48-7.60 (4H, m), 7.69-7.72 (2H, m), 7.80-7.81 (1H, m).

Present Compound 51

¹H-NMR (CDCl₃) δ: 1.28 (3H, t, J=7.6 Hz), 2.15 (3H, s), 2.60 (3H, s), 2.85 (2H, q, J=7.6 Hz), 3.59 (3H, s), 5.10 (2H, s), 6.92 (1H, d, J=8.5 Hz), 7.03 (1H, d, J=7.6 Hz), 7.29 (1H, dd, J=7.1, 2.0 Hz), 7.42-7.49 (3H, m), 7.58 (1H, t, J=7.7 Hz), 7.72-7.76 (2H, m).

Present Compound 52

¹H-NMR (CDCl₃) δ:0.75-0.79 (2H, m), 0.97-1.02 (2H, m), 2.11-2.16 (4H, m), 2.60 (3H, s), 3.61 (3H, s), 5.31 (2H, s), 6.95 (1H, d, J=8.3 Hz), 7.03 (1H, d, J=7.6 Hz), 7.28 (2H, d, J=8.0 Hz), 7.41-7.45 (2H, m), 7.58 (1H, t, J=7.8 Hz), 7.72-7.76 (2H, m).

Present Compound 53

¹H-NMR (CDCl₃) δ: 1.45 (3H, t, J=7.0 Hz), 2.07 (3H, s), 2.59 (3H, s), 3.59 (3H, s), 4.15 (2H, q, J=7.0 Hz), 5.34 (2H, s), 6.95 (1H, d, J=8.2 Hz), 7.01 (1H, d, J=7.3 Hz), 7.05 (2H, dd, J=8.3, 2.4 Hz), 7.43 (2H, t, J=8.2 Hz), 7.56 (1H, t, J=7.7 Hz), 7.69-7.71 (2H, m).

Present Compound 54

¹H-NMR (CDCl₃) δ: 2.09 (3H, s), 2.60 (3H, s), 3.60 (3H, d, J=0.9 Hz), 5.37 (2H, s), 6.91 (1H, d, J=8.5 Hz), 7.03 (1H, d, J=7.6 Hz), 7.39-7.44 (2H, m), 7.47 (1H, t, J=8.0 Hz), 7.58 (1H, t, J=7.8 Hz), 7.62 (1H, dd, J=7.9, 1.3 Hz), 7.72 (1H, dd, J=8.5, 2.3 Hz), 7.75-7.75 (1H, m).

Present Compound 55

¹H-NMR (CDCl₃) δ: 2.51 (3H, s), 2.60 (3H, s), 3.62 (3H, s), 5.08 (2H, s), 6.95 (2H, dt, J=9.4, 2.4 Hz), 7.04 (1H, d, J=7.7 Hz), 7.29 (1H, dd, J=6.9, 2.4 Hz), 7.39-7.45 (3H, m), 7.60 (1H, t, J=7.7 Hz), 7.91 (2H, dt, J=9.4, 2.4 Hz).

Present Compound 56

¹H-NMR (CDCl₃) δ: 2.34 (3H, s), 2.50 (3H, s), 2.60 (3H, s), 3.66 (3H, s), 5.05 (2H, s), 6.76-6.81 (2H, m), 7.08 (1H, d, J=7.7 Hz), 7.15 (1H, d, J=7.7 Hz), 7.33-7.27 (2H, m), 7.39-7.44 (2H, m), 7.60 (1H, t, J=7.7 Hz).

Present Compound 57

¹H-NMR (CDCl₃) δ: 2.55 (3H, s), 2.61 (3H, s), 3.68 (3H, s), 5.23 (2H, s), 6.97 (1H, d, J=8.5 Hz), 7.07 (1H, d, J=7.6 Hz), 7.31 (1H, dd, J=7.2, 2.0 Hz), 7.39-7.45 (3H, m), 7.61 (1H, t, J=7.6 Hz), 7.80 (1H, dd, J=8.5, 2.2 Hz), 8.02 (1H, d, J=2.2 Hz).

Present Compound 58

¹H-NMR (CDCl₃) δ: 2.54 (3H, s), 2.60 (3H, s), 3.67 (3H, s), 5.18 (2H, s), 7.00 (1H, t, J=8.5 Hz), 7.07 (1H, d, J=7.7 Hz), 7.29 (1H, dd, J=7.1, 2.2 Hz), 7.45-7.38 (3H, m), 7.61 (1H, t, J=7.7 Hz), 7.64-7.66 (1H, m), 7.75 (1H, dd, J=12.6, 2.2 Hz).

Present Compound 59

¹H-NMR (CDCl₃) δ: 2.51 (3H, s), 2.61 (3H, s), 3.68 (3H, s), 5.21 (2H, s), 7.04 (1H, d, J=8.6 Hz), 7.08 (1H, d, J=7.8 Hz), 7.30 (1H, dd, J=7.2, 1.8 Hz), 7.47-7.38 (3H, m), 7.62 (1H, t, J=7.8 Hz), 8.08 (1H, dd, J=8.6, 2.3 Hz), 8.19 (1H, d, J=2.3 Hz).

Present Compound 60

¹H-NMR (CDCl₃) δ: 2.12 (6H, s), 2.57 (3H, s), 2.61 (3H, s), 3.61 (3H, s), 5.00 (2H, s), 7.05 (1H, d, J=7.6 Hz), 7.23

(1H, dd, J=6.0, 3.2 Hz), 7.38-7.41 (2H, m), 7.44 (1H, d, J=7.9 Hz), 7.54 (2H, s), 7.59 (1H, t, J=7.9 Hz).

Present Compound 61

$^1$H-NMR (CDCl$_3$) δ: 2.56 (3H, s), 2.60 (3H, s), 3.68 (3H, s), 5.22 (2H, s), 6.93 (1H, d, J=8.7 Hz), 7.07 (1H, d, J=7.6 Hz), 7.31 (1H, dd, J=7.3, 2.2 Hz), 7.37-7.46 (3H, m), 7.61 (1H, t, J=7.8 Hz), 7.84 (1H, dd, J=8.5, 2.2 Hz), 8.18 (1H, d, J=2.2 Hz).

Present Compound 62

$^1$H-NMR (CDCl$_3$) δ: 1.30 (3H, t, J=7.6 Hz), 2.16 (3H, s), 2.87 (2H, q, J=7.6 Hz), 3.61 (3H, s), 5.10 (2H, s), 6.96 (1H, d, J=8.2 Hz), 7.28-7.40 (3H, m), 7.50-7.45 (3H, m), 7.82 (1H, dt, J=7.9, 1.9 Hz), 8.54 (1H, dd, J=4.8, 1.4 Hz), 8.80 (1H, d, J=2.3 Hz).

Present Compound 63

$^1$H-NMR (CDCl$_3$) δ: 2.10 (3H, s), 3.62 (3H, s), 5.36 (2H, s), 6.95 (1H, d, J=8.2 Hz), 7.30-7.37 (3H, m), 7.41 (1H, dd, J=8.0, 1.0 Hz), 7.48 (1H, t, J=8.0 Hz), 7.63 (1H, d, J=8.2 Hz), 7.81 (1H, dt, J=8.0, 1.7 Hz), 8.53 (1H, dd, J=4.8, 1.0 Hz), 8.79 (1H, d, J=2.3 Hz).

Present Compound 64

$^1$H-NMR (CDCl$_3$) δ:0.75-0.80 (2H, m), 0.97-1.03 (2H, m), 2.14-2.17 (4H, m), 3.62 (3H, s), 5.31 (2H, s), 6.99 (1H, d, J=8.2 Hz), 7.27-7.39 (5H, m), 7.44 (1H, t, J=7.8 Hz), 7.83-7.80 (1H, m), 8.53 (1H, dd, J=4.8, 1.6 Hz), 8.80 (1H, d, J=2.3 Hz).

Present Compound 65

$^1$H-NMR (CDCl$_3$) δ: 2.07 (3H, s), 3.62 (3H, s), 3.95 (3H, s), 5.32 (2H, s), 6.98 (1H, d, J=8.5 Hz), 7.09 (2H, t, J=8.6 Hz), 7.36-7.29 (3H, m), 7.48 (1H, t, J=8.1 Hz), 7.78-7.83 (1H, m), 8.52 (1H, dd, J=4.8, 1.4 Hz), 8.78 (1H, d, J=2.3 Hz).

Present Compound 66

$^1$H-NMR (CDCl$_3$) δ: 2.27 (3H, s), 3.69 (3H, s), 5.22 (2H, s), 6.90 (1H, d, J=8.5 Hz), 7.31-7.36 (2H, m), 7.37 (1H, d, J=1.6 Hz), 7.49-7.52 (2H, m), 7.53-7.58 (1H, m), 7.73 (1H, d, J=7.9 Hz), 7.81 (1H, ddd, J=7.9, 2.4, 1.6 Hz), 8.54 (1H, dd, J=4.8, 1.6 Hz), 8.79 (1H, dd, J=2.4, 0.8 Hz).

Present Compound 67

$^1$H-NMR (CDCl$_3$) δ: 2.14 (3H, s), 2.52 (3H, s), 2.54 (3H, s), 3.66 (3H, s), 5.08 (2H, s), 6.90 (1H, d, J=8.0 Hz), 7.06-7.11 (2H, m), 7.16 (1H, dd, J=7.8, 4.8 Hz), 7.29 (1H, dd, J=6.5, 2.6 Hz), 7.41-7.46 (2H, m), 7.48 (1H, dd, J=7.8, 1.8 Hz), 8.47 (1H, dd, J=4.8, 1.8 Hz).

Present Compound 68

$^1$H-NMR (CDCl$_3$) δ: 1.30 (3H, t, J=7.6 Hz), 2.14 (3H, s), 2.87 (2H, q, J=7.6 Hz), 3.62 (3H, s), 5.11 (2H, s), 6.96 (1H, d, J=8.5 Hz), 7.22 (1H, d, J=1.4 Hz), 7.26 (1H, dd, J=8.2, 2.1 Hz), 7.30 (1H, dd, J=7.1, 2.1 Hz), 7.40 (1H, d, J=5.3 Hz), 7.45-7.52 (2H, m), 8.43 (1H, d, J=5.3 Hz), 8.53 (1H, s).

Present Compound 69

$^1$H-NMR (CDCl$_3$) δ: 2.16 (3H, s), 2.54 (3H, s), 3.65 (3H, s), 5.09 (2H, s), 6.95 (1H, d, J=8.5 Hz), 7.23 (2H, dd, J=8.9, 2.1 Hz), 7.29 (1H, dd, J=7.0, 2.4 Hz), 7.40 (1H, d, J=5.3 Hz), 7.47-7.41 (2H, m), 8.43 (1H, d, J=5.3 Hz), 8.53 (1H, s).

Present Compound 70

$^1$H-NMR (CDCl$_3$) δ: 2.06 (3H, s), 3.62 (3H, s), 3.94 (3H, s), 5.32 (2H, s), 6.98 (1H, d, J=8.5 Hz), 7.08 (1H, d, J=7.1 Hz), 7.10 (1H, d, J=7.1 Hz), 7.17 (1H, d, J=2.2 Hz), 7.21 (1H, dd, J=8.2, 2.2 Hz), 7.38 (1H, d, J=5.4 Hz), 7.48 (1H, t, J=8.2 Hz), 8.41 (1H, d, J=5.4 Hz), 8.51 (1H, s).

Present Compound 71

$^1$H-NMR (CDCl$_3$) δ: 2.14 (3H, s), 2.29 (3H, s), 2.54 (3H, s), 3.65 (3H, s), 5.08 (2H, s), 6.91 (1H, d, J=8.0 Hz), 7.06-7.11 (2H, m), 7.16 (1H, dd, J=5.0, 0.7 Hz), 7.29 (1H, dd, J=6.4, 2.7 Hz), 7.41-7.47 (2H, m), 8.40 (1H, s), 8.40 (1H, d, J=5.3 Hz).

Present Compound 72

$^1$H-NMR (CDCl$_3$) δ: 1.29 (3H, t, J=7.5 Hz), 2.15 (3H, s), 2.58 (3H, s), 2.86 (2H, q, J=7.5 Hz), 3.60 (3H, s), 5.10 (2H, s), 6.94 (1H, d, J=8.2 Hz), 7.18 (1H, d, J=8.0 Hz), 7.28-7.35 (3H, m), 7.51-7.44 (2H, m), 7.71 (1H, dd, J=8.0, 2.4 Hz), 8.67 (1H, d, J=2.2 Hz).

Present Compound 73

$^1$H-NMR (CDCl$_3$) δ: 2.05 (3H, s), 2.58 (3H, s), 3.61 (3H, s), 3.94 (3H, s), 5.31 (2H, s), 6.96 (1H, d, J=8.1 Hz), 7.09 (2H, t, J=8.1 Hz), 7.17 (1H, d, J=8.1 Hz), 7.27 (1H, d, J=2.3 Hz), 7.30 (1H, dd, J=8.1, 2.3 Hz), 7.47 (1H, t, J=8.1 Hz), 7.69 (1H, dd, J=8.1, 2.3 Hz), 8.65 (1H, d, J=2.3 Hz).

Present Compound 74

$^1$H-NMR (CDCl$_3$) δ: 2.10 (3H, s), 2.58 (3H, s), 3.62 (3H, d, J=0.5 Hz), 5.36 (2H, s), 6.93 (1H, d, J=8.5 Hz), 7.18 (1H, d, J=8.0 Hz), 7.35-7.29 (2H, m), 7.41 (1H, d, J=7.8 Hz), 7.48 (1H, t, J=8.0 Hz), 7.63 (1H, d, J=8.0 Hz), 7.70 (1H, dd, J=8.0, 2.3 Hz), 8.66 (1H, d, J=2.3 Hz).

Present Compound 75

$^1$H-NMR (CDCl$_3$) δ: 2.26 (3H, s), 2.58 (3H, s), 3.69 (3H, s), 5.21 (2H, s), 6.88 (1H, d, J=8.5 Hz), 7.18 (1H, d, J=8.0 Hz), 7.31 (1H, dd, J=8.5, 2.5 Hz), 7.34 (1H, d, J=2.1 Hz), 7.49-7.51 (2H, m), 7.58-7.52 (1H, m), 7.68-7.76 (2H, m), 8.66 (1H, d, J=2.5 Hz).

Present Compound 76

$^1$H-NMR (CDCl$_3$) δ:0.76-0.80 (2H, m), 0.97-1.04 (2H, m), 2.14-2.17 (4H, m), 2.58 (3H, s), 3.62 (3H, s), 5.30 (2H, s), 6.97 (1H, d, J=8.5 Hz), 7.18 (1H, d, J=8.0 Hz), 7.27 (1H, s), 7.29 (1H, s), 7.32 (1H, d, J=1.8 Hz), 7.34 (1H, d, J=8.4, 2.4 Hz), 7.44 (1H, t, J=8.0 Hz), 7.71 (1H, dd, J=8.0, 2.4 Hz), 8.67 (1H, d, J=2.4 Hz).

Present Compound 77

¹H-NMR (CDCl₃) δ: 2.17 (3H, s), 2.51 (3H, s), 2.77 (3H, s), 3.62 (3H, s), 5.12 (2H, s), 6.93 (1H, d, J=9.2 Hz), 7.29 (1H, dd, J=7.0, 2.2 Hz), 7.40-7.44 (3H, m), 7.86-7.88 (2H, m), 8.59 (1H, d, J=5.3 Hz).

Present Compound 78

¹H-NMR (CDCl₃) δ: 2.07 (3H, s), 2.76 (3H, s), 3.59 (3H, s), 3.94 (3H, s), 5.35 (2H, s), 6.97 (1H, d, J=8.5 Hz), 7.09 (2H, t, J=7.7 Hz), 7.40 (1H, d, J=5.3 Hz), 7.47 (1H, t, J=8.2 Hz), 7.83-7.85 (2H, m), 8.57 (1H, d, J=5.3 Hz).

Present Compound 79

¹H-NMR (CDCl₃) δ: 0.76-0.80 (2H, m), 0.97-1.02 (2H, m), 2.10-2.16 (4H, m), 2.77 (3H, s), 3.61 (3H, s), 5.34 (2H, s), 6.98 (1H, d, J=9.2 Hz), 7.29 (2H, d, J=8.0 Hz), 7.42-7.47 (2H, m), 7.87-7.90 (2H, m), 8.59 (1H, d, J=5.6 Hz).

Present Compound 80

¹H-NMR (CDCl₃) δ: 1.46 (3H, t, J=7.0 Hz), 2.07 (3H, s), 2.76 (3H, s), 3.60 (3H, s), 4.17 (2H, q, J=7.0 Hz), 5.37 (2H, s), 6.99 (1H, d, J=8.5 Hz), 7.05-7.08 (2H, m), 7.41 (1H, d, J=5.6 Hz), 7.45 (1H, t, J=8.3 Hz), 7.83-7.85 (2H, m), 8.57 (1H, d, J=5.4 Hz).

Present Compound 81

¹H-NMR (CDCl₃) δ: 2.27 (3H, s), 2.77 (3H, s), 3.68 (3H, s), 5.24 (2H, s), 6.89 (1H, d, J=8.7 Hz), 7.41 (1H, d, J=5.5 Hz), 7.49-7.56 (3H, m), 7.70 (1H, d, J=6.6 Hz), 7.83 (1H, dd, J=8.5, 2.3 Hz), 7.90-7.91 (1H, m), 8.58 (1H, d, J=5.5 Hz).

Present Compound 82

¹H-NMR (CDCl₃) δ: 2.10 (3H, s), 2.77 (3H, s), 3.60 (3H, s), 5.39 (2H, s), 6.93-6.95 (1H, m), 7.40-7.42 (2H, m), 7.48 (1H, t, J=8.0 Hz), 7.63 (1H, d, J=8.0 Hz), 7.85-7.87 (2H, m), 8.59 (1H, d, J=5.5 Hz).

Present Compound 83

¹H-NMR (CDCl₃) δ: 2.17 (3H, s), 2.52 (3H, s), 3.62 (3H, s), 5.12 (2H, s), 6.95 (1H, d, J=8.6 Hz), 7.12 (1H, t, J=4.9 Hz), 7.29 (1H, dd, J=6.9, 2.3 Hz), 7.40-7.47 (2H, m), 8.20-8.22 (1H, m), 8.25 (1H, dd, J=8.6, 2.3 Hz), 8.75 (2H, d, J=4.9 Hz).

Present Compound 84

¹H-NMR (CDCl₃) δ: 1.28 (3H, t, J=7.6 Hz), 2.16 (3H, s), 2.85 (2H, q, J=7.6 Hz), 3.57 (3H, s), 5.14 (2H, s), 6.96 (1H, d, J=8.7 Hz), 7.10 (1H, t, J=4.8 Hz), 7.30 (1H, dd, J=7.1, 1.8 Hz), 7.43-7.51 (2H, m), 8.21 (1H, d, J=1.6 Hz), 8.26 (1H, dd, J=8.7, 2.2 Hz), 8.74 (2H, d, J=4.8 Hz).

Present Compound 85

¹H-NMR (CDCl₃) δ: 0.74-0.80 (2H, m), 0.96-1.02 (2H, m), 2.09-2.14 (1H, brm), 2.16 (3H, s), 3.60 (3H, s), 5.35 (2H, s), 6.99 (1H, d, J=8.6 Hz), 7.11 (1H, td, J=4.8, 1.5 Hz), 7.27-7.30 (2H, m), 7.44 (1H, t, J=7.8 Hz), 8.20 (1H, d, J=1.5 Hz), 8.25 (1H, dd, J=8.6, 2.3 Hz), 8.75 (2H, dd, J=4.8, 1.5 Hz).

Present Compound 86

¹H-NMR (CDCl₃) δ: 2.11 (3H, s), 3.59 (3H, s), 5.40 (2H, s), 6.96 (1H, d, J=8.7 Hz), 7.12 (1H, t, J=4.8 Hz), 7.41 (1H, dd, J=8.0, 1.4 Hz), 7.48 (1H, t, J=8.0 Hz), 7.62 (1H, dd, J=8.0, 1.4 Hz), 8.19 (1H, d, J=2.2 Hz), 8.24 (1H, dd, J=8.7, 2.2 Hz), 8.75 (2H, d, J=4.8 Hz).

Present Compound 87

¹H-NMR (CDCl₃) δ: 2.27 (3H, s), 3.67 (3H, s), 5.25 (2H, s), 6.91 (1H, d, J=9.2 Hz), 7.11 (1H, t, J=4.8 Hz), 7.47-7.57 (3H, m), 7.73 (1H, d, J=7.2 Hz), 8.25-8.20 (2H, m), 8.75 (2H, d, J=4.8 Hz).

Present Compound 88

¹H-NMR (CDCl₃) δ: 2.18 (3H, s), 2.52 (3H, s), 3.63 (3H, s), 5.13 (2H, s), 6.95 (1H, d, J=9.2 Hz), 7.30 (1H, dd, J=7.0, 2.2 Hz), 7.40-7.47 (2H, m), 7.64 (1H, dd, J=5.4, 1.4 Hz), 7.90 (2H, d, J=6.6 Hz), 8.69 (1H, d, J=5.4 Hz), 9.20 (1H, d, J=1.4 Hz).

Present Compound 89

¹H-NMR (CDCl₃) δ: 2.18 (3H, s), 2.53 (3H, s), 3.65 (3H, s), 5.10 (2H, s), 6.97 (1H, d, J=8.2 Hz), 7.30 (1H, dd, J=6.9, 2.3 Hz), 7.33-7.39 (1H, m), 7.41-7.49 (2H, m), 7.64-7.71 (1H, m), 8.90 (2H, s), 9.15 (1H, s).

Present Compound 90

¹H-NMR (CDCl₃) δ: 2.07 (3H, s), 2.55 (3H, s), 3.58 (3H, s), 3.94 (3H, s), 5.35 (2H, s), 6.97 (2H, dd, J=6.9, 1.6 Hz), 7.07-7.10 (2H, m), 7.47 (1H, t, J=8.3 Hz), 8.15-8.15 (1H, m), 8.20 (1H, dd, J=8.6, 2.3 Hz), 8.58 (1H, d, J=5.1 Hz).

Present Compound 91

¹H-NMR (CDCl₃) δ: 2.17 (3H, s), 2.52 (3H, s), 2.57 (3H, s), 3.62 (3H, s), 5.12 (2H, s), 6.93 (1H, d, J=8.7 Hz), 6.98 (1H, d, J=5.1 Hz), 7.29 (1H, dd, J=6.8, 2.7 Hz), 7.40-7.45 (2H, m), 8.20-8.20 (1H, m), 8.24 (1H, dd, J=8.5, 2.2 Hz), 8.59 (1H, d, J=5.1 Hz).

Present Compound 92

¹H-NMR (CDCl₃) δ: 0.75-0.79 (2H, m), 0.97-1.02 (2H, m), 2.11-2.16 (4H, m), 2.56 (3H, s), 3.60 (3H, s), 5.34 (2H, s), 6.96-6.99 (2H, m), 7.28 (2H, d, J=7.8 Hz), 7.44 (1H, t, J=7.9 Hz), 8.19 (1H, dd, J=2.1, 0.9 Hz), 8.22-8.25 (1H, m), 8.59 (1H, d, J=4.9 Hz).

Present Compound 93

¹H-NMR (CDCl₃) δ: 1.29 (3H, t, J=7.6 Hz), 2.15 (3H, s), 2.56 (3H, s), 2.86 (2H, q, J=7.6 Hz), 3.58 (3H, s), 5.13 (2H, s), 6.94 (1H, d, J=8.8 Hz), 6.98 (1H, d, J=5.1 Hz), 7.29 (1H, dd, J=7.2, 2.1 Hz), 7.44-7.50 (2H, m), 8.19-8.20 (1H, m), 8.24 (1H, dd, J=8.5, 2.2 Hz), 8.59 (1H, d, J=4.9 Hz).

Present Compound 94

¹H-NMR (CDCl₃) δ: 1.46 (3H, t, J=7.0 Hz), 2.07 (3H, s), 2.55 (3H, s), 3.59 (3H, s), 4.16 (2H, q, J=6.9 Hz), 5.37 (2H, s), 6.96-7.00 (2H, m), 7.05 (1H, d, J=3.9 Hz), 7.07 (1H, d, J=4.3 Hz), 7.43 (1H, t, J=8.2 Hz), 8.15-8.15 (1H, m), 8.19 (1H, dd, J=8.6, 2.3 Hz), 8.57 (1H, d, J=5.1 Hz).

Present Compound 95

¹H-NMR (CDCl₃) δ: 2.27 (3H, s), 2.56 (3H, s), 3.68 (3H, s), 5.24 (2H, s), 6.89 (1H, d, J=9.2 Hz), 6.98 (1H, d, J=5.0 Hz), 7.49-7.56 (3H, m), 7.72 (1H, d, J=7.1 Hz), 8.20-8.22 (2H, m), 8.59 (1H, d, J=5.0 Hz).

Present Compound 96

¹H-NMR (CDCl₃) δ: 2.10 (3H, s), 2.56 (3H, s), 3.58 (3H, s), 5.40 (2H, s), 6.93 (1H, d, J=8.7 Hz), 6.98 (1H, d, J=5.0 Hz), 7.41 (1H, dd, J=8.0, 1.4 Hz), 7.47 (1H, t, J=8.0 Hz), 7.62 (1H, dd, J=8.0, 1.4 Hz), 8.18 (1H, dd, J=2.3, 0.7 Hz), 8.21-8.24 (1H, m), 8.58 (1H, d, J=5.0 Hz).

Present Compound 97

¹H-NMR (CDCl₃) δ: 2.14 (3H, s), 2.53 (3H, s), 2.56 (3H, s), 3.61 (3H, s), 5.31 (2H, s), 6.96 (1H, d, J=8.4 Hz), 6.97 (1H, d, J=5.0 Hz), 7.27 (1H, dd, J=6.4, 3.2 Hz), 7.46-7.53 (2H, m), 8.18 (1H, d, J=2.2 Hz), 8.22 (1H, dd, J=8.4, 2.2 Hz), 8.58 (1H, d, J=5.0 Hz).

Present Compound 98

¹H-NMR (CDCl₃) δ: 2.17 (3H, s), 2.52 (3H, s), 3.63 (3H, s), 5.12 (2H, s), 6.96 (1H, d, J=9.2 Hz), 7.29 (1H, dd, J=7.5, 1.6 Hz), 7.39-7.47 (2H, m), 7.61-7.68 (2H, m), 7.84 (2H, d, J=7.5 Hz).

Present Compound 99

¹H-NMR (CDCl₃) δ: 2.18 (3H, s), 2.52 (3H, s), 3.63 (3H, s), 5.12 (2H, s), 6.96 (1H, d, J=9.2 Hz), 7.29 (1H, dd, J=6.9, 2.4 Hz), 7.41-7.47 (2H, m), 7.78-7.83 (2H, m), 8.44 (1H, d, J=2.4 Hz), 8.58 (1H, dd, J=2.4, 1.5 Hz), 8.97 (1H, d, J=1.5 Hz).

Production Example 3

A mixture of 0.30 g of the present compound 61, 0.11 g of cyclopropylboronic acid, 0.05 g of [1,1'-bis(diphenylphosphino)ferrocene]palladium(II) dichloride dichloromethane adduct, 0.20 g of cesium fluoride, and 10 mL of 1,2-dimethoxyethane was stirred at 80° C. for 6.5 hours. After cooling, the reaction mixture was concentrated and the residue thus obtained was subjected to silica gel column chromatography to obtain 0.22 g of 1-{2-[2-cyclopropyl-4-(6-methylpyridin-2-yl)phenoxymethyl]-3-methylphenyl}-4-methyl-1,4-dihydrotetrazol-5-one (hereinafter referred to as the present compound 100).

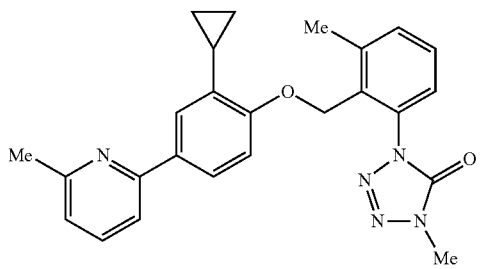 [SMILES: Cc1cccc(-c2ccc(OCc3c(C)cccc3-n3nnn(C)c3=O)c(C3CC3)c2)n1]

¹H-NMR (CDCl₃) δ:0.65-0.70 (2H, m), 0.83-0.90 (2H, m), 2.00-2.09 (1H, m), 2.53 (3H, s), 2.59 (3H, s), 3.64 (3H, s), 5.13 (2H, s), 6.92 (1H, d, J=8.6 Hz), 7.03 (1H, d, J=7.5 Hz), 7.29 (1H, dd, J=6.8, 2.3 Hz), 7.43-7.38 (4H, m), 7.58 (1H, t, J=7.7 Hz), 7.69 (1H, dd, J=8.6, 2.3 Hz).

Production Example 4

In the same manner as in Production Example 3, the following compounds were synthesized. Structural formulas and ¹H-NMR data of the thus obtained present compounds and ¹H-NMR data are shown below.

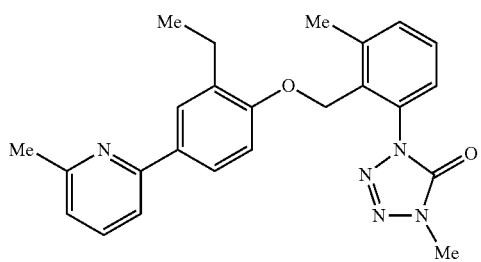 [SMILES: CCc1cc(-c2cccc(C)n2)ccc1OCc1c(C)cccc1-n1nnn(C)c1=O]

¹H-NMR (CDCl₃) δ: 1.14 (3H, t, J=7.6 Hz), 2.51 (3H, s), 2.57 (2H, t, J=7.6 Hz), 2.61 (3H, s), 3.64 (3H, s), 5.07 (2H, s), 6.94 (1H, d, J=8.5 Hz), 7.04 (1H, d, J=7.7 Hz), 7.29 (1H, d, J=2.5 Hz), 7.44 (3H, t, J=7.3 Hz), 7.59 (1H, t, J=7.7 Hz), 7.74-7.78 (2H, m).

Production Example 5

To a mixture of 0.25 g of the present compounds 98 and 10 mL of methanol, 0.35 mL of 28% sodium methoxide was added, followed by stirring with heating under reflux for 7 hours. The reaction mixture was concentrated and water was added, and then the mixture was extracted with ethyl acetate. The organic layer was washed with water and a saturated saline solution, dried over anhydrous sodium sulfate, and then concentrated under reduce pressure to obtain 0.25 g of 1-{3-methyl-2-[2-methyl-4-(6-methoxypyridazin-3-yl)-phenoxymethyl]-phenyl}-4-methyl-1,4-dihydrotetrazol-5-one (hereinafter referred to as the present compound 102).

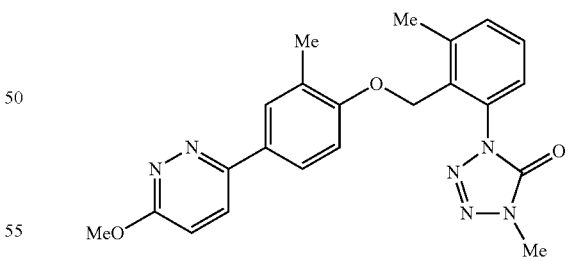

¹H-NMR (CDCl₃) δ: 2.16 (3H, s), 2.52 (3H, s), 3.62 (3H, s), 4.16 (3H, s), 5.10 (2H, s), 6.94 (1H, d, J=9.0 Hz), 6.99 (1H, dd, J=9.0, 1.1 Hz), 7.28 (1H, dd, J=6.0, 3.0 Hz), 7.38-7.47 (2H, m), 7.72 (1H, dd, J=9.0, 1.1 Hz), 7.78 (1H, dd, J=8.4, 2.2 Hz), 7.82 (1H, s).

Production Example 7

To a mixture of 0.20 g of the present compound 98 and 10 mL of ethanol, 0.63 mL of 20% sodium ethoxide was added, followed by stirring with heating under reflux for 5 hours. The reaction mixture was concentrated and water was added, and then the mixture was extracted with ethyl acetate. The organic layer was washed with water and a saturated saline solution, dried over anhydrous sodium sulfate, and then concentrated under reduced pressure to obtain 0.18 g of 1-{3-methyl-2-[2-methyl-4-(6-ethoxypyridazin-3-yl)-phenoxymethyl]-phenyl}-4-methyl-1,4-dihydrotetrazol-5-one (hereinafter referred to as the present compound 103).

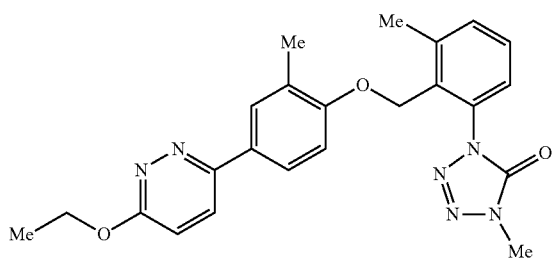 [SMILES: CCOc1ccc(-c2ccc(OCc3c(C)cccc3-n3nnn(C)c3=O)c(C)c2)nn1]

$^1$H-NMR (CDCl$_3$) δ: 1.46 (3H, t, J=7.1 Hz), 2.16 (3H, s), 2.51 (3H, s), 3.61 (3H, s), 4.61 (2H, q, J=7.1 Hz), 5.10 (2H, s), 6.94 (1H, d, J=8.6 Hz), 6.96 (1H, d, J=9.3 Hz), 7.28 (1H, dd, J=6.9, 2.3 Hz), 7.44-7.38 (2H, m), 7.71 (1H, d, J=9.3 Hz), 7.78 (1H, dd, J=8.6, 2.3 Hz), 7.83 (1H, d, J=1.6 Hz).

Production Example 8

To a mixture of 0.06 g of propargyl alcohol and 5 mL of N,N-dimethylformamide, 0.04 g of sodium hydride was added, followed by stirring at room temperature for 15 minutes. To the mixture, 0.20 g of the present compound 98 and 5 mL of an N,N-dimethylformamide solution were added, followed by stirring at 80° C. for 2.5 hours. After cooling, water was added to the reaction mixture and the mixture was extracted with ethyl acetate. The organic layer was washed with water and a saturated saline solution, and then dried over anhydrous sodium sulfate. The organic layer was concentrated under reduced pressure and then subjected to silica gel chromatography to obtain 0.04 g of 1-{3-methyl-2-[2-methyl-4-(6-propargyloxypyridazin-3-yl)-phenoxymethyl]-phenyl}-4-methyl-1,4-dihydrotetrazol-5-one (hereinafter referred to as the present compound 104).

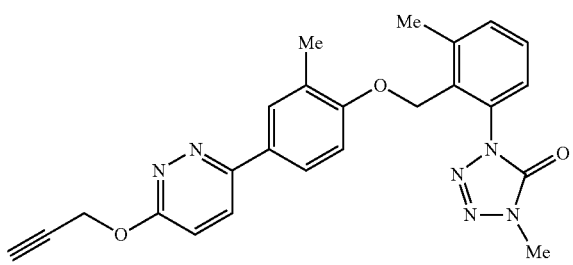 [SMILES: C#CCOc1ccc(-c2ccc(OCc3c(C)cccc3-n3nnn(C)c3=O)c(C)c2)nn1]

$^1$H-NMR (CDCl$_3$) δ: 2.17 (3H, s), 2.52 (3H, s), 2.56 (1H, t, J=2.5 Hz), 3.63 (3H, s), 5.10 (2H, s), 5.22 (2H, d, J=2.5 Hz), 6.95 (1H, d, J=8.5 Hz), 7.08 (1H, d, J=9.2 Hz), 7.29 (1H, dd, J=6.9, 2.3 Hz), 7.47-7.40 (2H, m), 7.77 (1H, d, J=9.2 Hz), 7.78 (1H, dd, J=8.5, 2.3 Hz), 7.83 (1H, d, J=1.8 Hz).

Production Example 9

A mixture of 0.76 g of the present compound B1 mentioned in Synthesis Example 5, 0.47 g of 2-chloro-5-pyridineboronic acid, 0.16 g of [1,1'-bis(diphenylphosphino)ferrocene]palladium(II) dichloride dichloromethane adduct, 1.27 g of tripotassium phosphate, 3 mL of 1,4-dioxane, and 0.2 mL of water was stirred at 100° C. for 5 hours. After cooling, the reaction mixture was filtered and the residue thus obtained was subjected to silica gel column chromatography to obtain 0.24 g of 1-{3-methyl-2-[2-methyl-4-(6-chloropyridin-3-yl)-phenoxymethyl]-phenyl}-4-methyl-1,4-dihydrotetrazol-5-one (hereinafter referred to as the present compound 105).

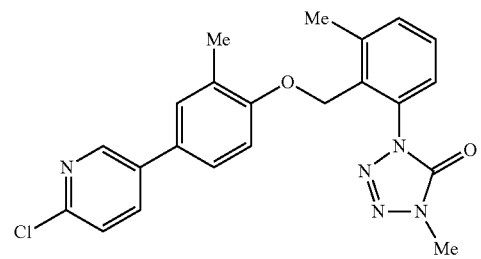 [SMILES: Cc1cc(-c2ccc(Cl)nc2)ccc1OCc1c(C)cccc1-n1nnn(C)c1=O]

$^1$H-NMR (CDCl$_3$) δ: 2.16 (3H, s), 2.52 (3H, s), 3.64 (3H, s), 5.08 (2H, s), 6.93 (1H, d, J=8.2 Hz), 7.28-7.36 (4H, m), 7.41-7.46 (2H, m), 7.78 (1H, dd, J=8.2, 2.7 Hz), 8.55 (1H, d, J=2.7 Hz).

Production Example 10

The same operation as in Production Example 9 was performed to synthesize the following present compounds. The structural formulas and $^1$H-NMR data of the thus obtained present compounds are shown below.

Present Compound 106

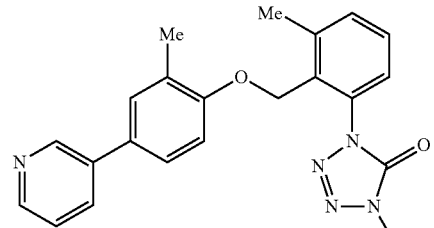

Present Compound 107

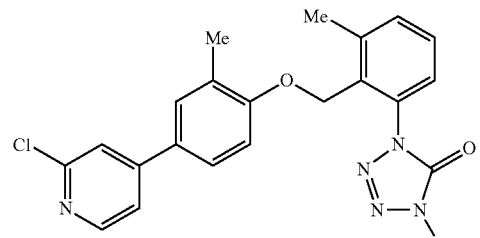

Present Compound 108

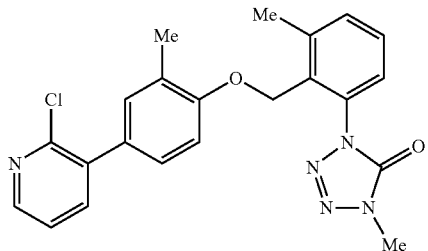

Present Compound 109

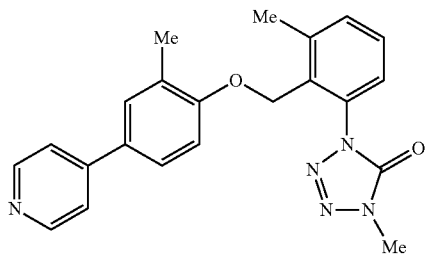

Present Compound 110

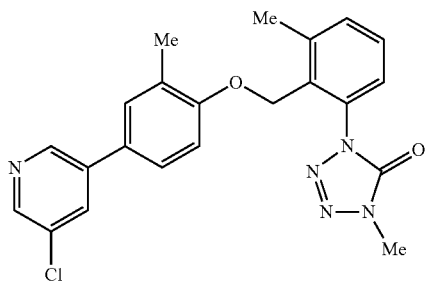

Present Compound 111

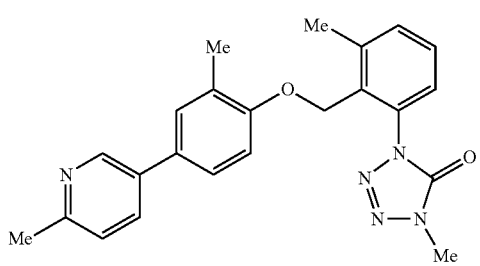

Present Compound 112

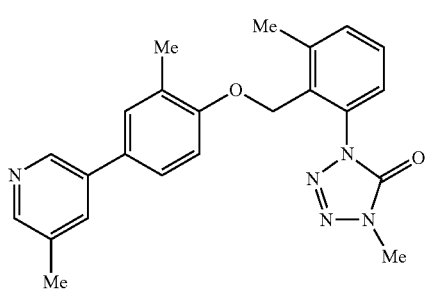

Present Compound 113

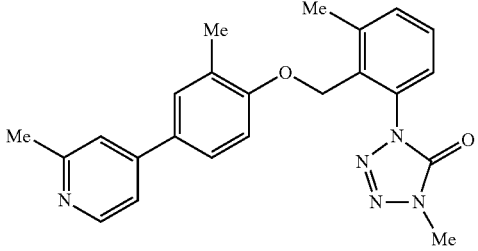

Present Compound 106

¹H-NMR (CDCl₃) δ: 2.17 (3H, s), 2.53 (3H, s), 3.64 (3H, s), 5.09 (2H, s), 6.94 (1H, d, J=8.2 Hz), 7.28-7.37 (4H, m), 7.41-7.46 (2H, m), 7.82 (1H, ddd, J=7.8, 2.3, 1.7 Hz), 8.54 (1H, dd, J=4.7, 1.6 Hz), 8.80 (1H, d, J=2.4 Hz).

Present Compound 107

¹H-NMR (CDCl₃) δ: 2.16 (3H, s), 2.52 (3H, s), 3.64 (3H, s), 5.10 (2H, s), 6.93 (1H, d, J=8.5 Hz), 7.29 (1H, dd, J=7.1, 2.3 Hz), 7.37-7.49 (6H, m), 8.37 (1H, d, J=5.1 Hz).

Present Compound 108

¹H-NMR (CDCl₃) δ: 2.15 (3H, s), 2.53 (3H, s), 3.65 (3H, s), 5.09 (2H, s), 6.93 (1H, d, J=8.5 Hz), 7.21 (1H, d, J=2.3 Hz), 7.24-7.30 (3H, m), 7.41-7.47 (2H, m), 7.64 (1H, dd, J=7.6, 2.1 Hz), 8.36 (1H, dd, J=4.7, 1.9 Hz).

Present Compound 109

¹H-NMR (CDCl₃) δ: 2.17 (3H, s), 2.52 (3H, s), 3.64 (3H, s), 5.10 (2H, s), 6.94 (1H, d, J=8.5 Hz), 7.29 (1H, dd, J=7.0, 2.2 Hz), 7.43-7.47 (6H, m), 8.61 (2H, d, J=5.7 Hz).

Present Compound 110

¹H-NMR (CDCl₃) δ: 2.17 (3H, s), 2.53 (3H, s), 3.64 (3H, s), 5.09 (2H, s), 6.94 (1H, d, J=8.2 Hz), 7.28-7.36 (3H, m), 7.41-7.47 (2H, m), 7.80 (1H, t, J=2.2 Hz), 8.49 (1H, d, J=2.2 Hz), 8.66 (1H, d, J=2.1 Hz).

Present Compound 111

¹H-NMR (CDCl₃) δ: 2.16 (3H, s), 2.52 (3H, s), 2.59 (3H, s), 3.64 (3H, s), 5.08 (2H, s), 6.93 (1H, d, J=8.2 Hz), 7.19 (1H, d, J=8.2 Hz), 7.29 (1H, dd, J=7.1, 2.3 Hz), 7.32-7.35 (2H, m), 7.41-7.46 (2H, m), 7.71 (1H, dd, J=8.0, 2.3 Hz), 8.67 (1H, d, J=2.3 Hz).

Present Compound 112

¹H-NMR (CDCl₃) δ: 2.16 (3H, s), 2.39 (3H, s), 2.53 (3H, s), 3.64 (3H, s), 5.08 (2H, s), 6.93 (1H, d, J=8.2 Hz), 7.29 (1H, dd, J=7.0, 2.4 Hz), 7.34-7.37 (2H, m), 7.41-7.46 (2H, m), 7.62 (1H, s), 8.37 (1H, d, J=1.4 Hz), 8.60 (1H, d, J=2.1 Hz).

Present Compound 113

¹H-NMR (CDCl₃) δ: 2.16 (3H, s), 2.52 (3H, s), 2.60 (3H, s), 3.63 (3H, s), 5.09 (2H, s), 6.93 (1H, d, J=8.2 Hz), 7.25-7.27 (1H, m), 7.29 (1H, dd, J=7.0, 2.2 Hz), 7.32 (1H, s), 7.41-7.46 (4H, m), 8.49 (1H, d, J=5.0 Hz).

Production Example 11

A mixture of 0.37 g of the present compound B15 mentioned in Synthesis Example 7, 0.11 g of 2-chloro-6-cyanopyridine, 0.03 g of [1,1'-bis(diphenylphosphino)ferrocene]palladium(II) dichloride dichloromethane adduct, 0.43 g of cesium fluoride, and 10 mL of 1,4-dioxane was stirred at 80° C. for 9 hours. After cooling, the reaction mixture was concentrated and the residue thus obtained was subjected to silica gel column chromatography to obtain 0.17 g of 1-{3-methyl-2-[2-methyl-4-(6-cyanopyridin-2-yl)-phenoxymethyl]-phenyl}-4-methyl-1,4-dihydrotetrazol-5-one (hereinafter referred to as the present compound 114).

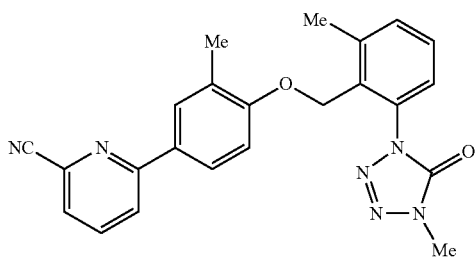 [SMILES: Cc1cc(-c2cccc(C#N)n2)ccc1OCc1c(C)cccc1-n1nnn(C)c1=O]

$^1$H-NMR (CDCl$_3$) δ: 2.17 (3H, s), 2.52 (3H, s), 3.64 (3H, s), 5.11 (2H, s), 6.94 (1H, d, J=9.2 Hz), 7.29 (1H, dd, J=6.8, 1.8 Hz), 7.47-7.40 (2H, m), 7.55 (1H, dd, J=7.2, 1.3 Hz), 7.80-7.84 (3H, m), 7.87 (1H, dd, J=8.2, 1.4 Hz).

Production Example 12

A mixture of 0.36 g of the present compound B19 mentioned in Synthesis Example 8, 0.11 g of 2-chloro-6-cyanopyridine, 0.07 g of [1,1'-bis(diphenylphosphino)ferrocene]palladium(II) dichloride dichloromethane adduct, 0.34 g of tripotassium phosphate, 6 mL of 1,2-dimethoxyethane, and 1 mL of water was stirred at 80° C. for 8 hours. After cooling, the reaction mixture was concentrated and the residue thus obtained was subjected to silica gel column chromatography to obtain 0.29 g of 1-{3-ethyl-2-[2-methyl-4-(6-cyanopyridin-3-yl)-phenoxymethyl]-phenyl}-4-methyl-1,4-dihydrotetrazol-5-one (hereinafter referred to as the present compound 115).

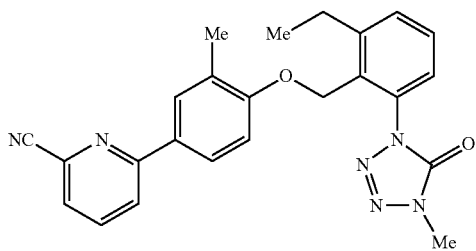 [SMILES: CCc1cccc(-n2nnn(C)c2=O)c1COc1ccc(-c2cccc(C#N)n2)cc1C]

$^1$H-NMR (CDCl$_3$) δ: 1.30 (3H, t, J=7.6 Hz), 2.16 (3H, s), 2.87 (2H, q, J=7.6 Hz), 3.60 (3H, s), 5.14 (2H, s), 6.95 (1H, d, J=8.1 Hz), 7.30 (1H, dd, J=7.3, 1.9 Hz), 7.45-7.52 (2H, m), 7.56 (1H, dd, J=7.3, 1.1 Hz), 7.81-7.84 (3H, m), 7.87 (1H, dd, J=8.1, 1.3 Hz).

Production Example 13

The reaction was performed in the same manner as in Production Example 12 to synthesize the following present compounds. The structural formula and $^1$H-NMR data of the thus obtained present compounds are shown below.

Present Compound 116

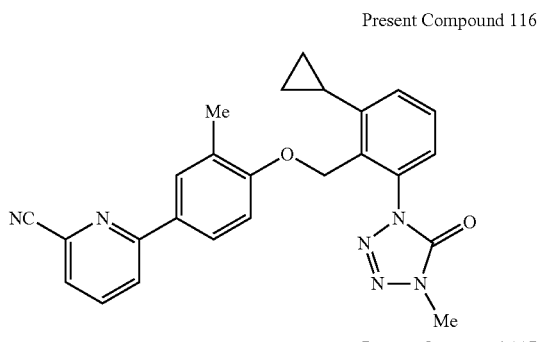

Present Compound 117

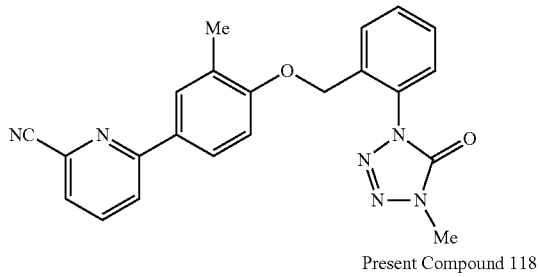

Present Compound 118

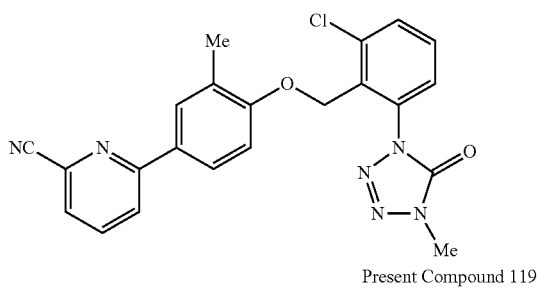

Present Compound 119

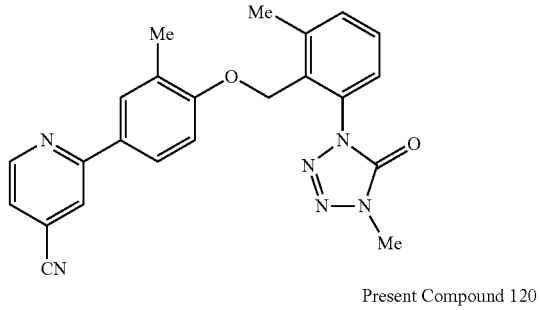

Present Compound 120

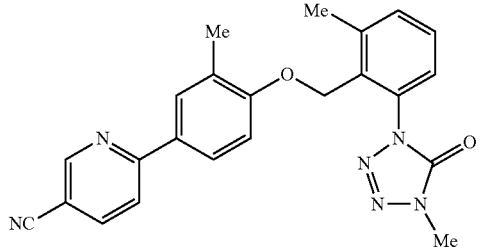

-continued

Present Compound 121

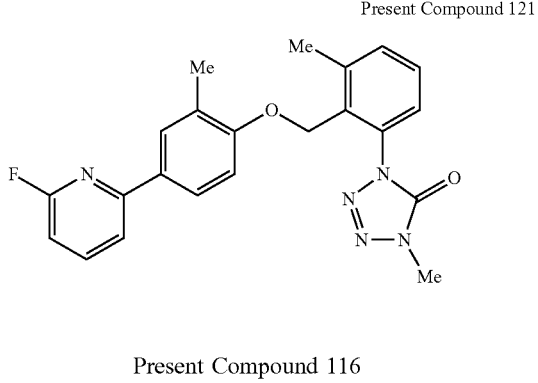

Present Compound 116

¹H-NMR (CDCl₃) δ:0.76-0.81 (2H, m), 0.98-1.04 (2H, m), 2.10-2.18 (4H, m), 3.62 (3H, s), 5.34 (2H, s), 6.99 (1H, d, J=7.8 Hz), 7.28 (1H, s), 7.30 (1H, s), 7.46 (1H, t, J=7.8 Hz), 7.56 (1H, dd, J=7.2, 1.3 Hz), 7.80-7.85 (3H, m), 7.88 (1H, dd, J=8.2, 1.3 Hz).

Present Compound 117

¹H-NMR (CDCl₃) δ: 2.28 (3H, s), 3.69 (3H, s), 5.25 (2H, s), 6.90 (1H, d, J=8.5 Hz), 7.49-7.58 (4H, m), 7.71 (1H, d, J=6.9 Hz), 7.78 (1H, dd, J=8.5, 2.5 Hz), 7.82 (1H, dd, J=8.1, 7.2 Hz), 7.85-7.87 (2H, m).

Present Compound 118

¹H-NMR (CDCl₃) δ: 2.11 (3H, s), 3.62 (3H, s), 5.39 (2H, s), 6.94 (1H, d, J=9.1 Hz), 7.42 (1H, dd, J=8.0, 1.4 Hz), 7.49 (1H, t, J=8.0 Hz), 7.55 (1H, dd, J=7.2, 1.4 Hz), 7.63 (1H, dd, J=8.0, 1.4 Hz), 7.79-7.81 (2H, m), 7.83 (1H, d, J=7.0 Hz), 7.86 (1H, dd, J=8.2, 1.1 Hz).

Present Compound 119

¹H-NMR (CDCl₃) δ: 2.18 (3H, s), 2.52 (3H, s), 3.64 (3H, s), 5.12 (2H, s), 6.95 (1H, d, J=8.2 Hz), 7.30 (1H, dd, J=7.0, 2.3 Hz), 7.37 (1H, dd, J=5.0, 1.4 Hz), 7.42-7.48 (2H, m), 7.77-7.82 (2H, m), 7.87 (1H, s), 8.80 (1H, dd, J=5.0, 0.9 Hz).

Present Compound 120

¹H-NMR (CDCl₃) δ: 2.17 (3H, s), 2.51 (3H, s), 3.63 (3H, s), 5.12 (2H, s), 6.95 (1H, d, J=9.3 Hz), 7.29 (1H, dd, J=7.1, 2.1 Hz), 7.40-7.47 (2H, m), 7.76 (1H, dd, J=8.4, 0.8 Hz), 7.82-7.86 (2H, m), 7.94 (1H, dd, J=8.4, 2.0 Hz), 8.88 (1H, dd, J=2.1, 0.8 Hz).

Present Compound 121

¹H-NMR (CDCl₃) δ: 2.16 (3H, s), 2.52 (3H, s), 3.63 (3H, s), 5.10 (2H, s), 6.79 (1H, dd, J=8.2, 2.9 Hz), 6.91 (1H, d, J=8.8 Hz), 7.29 (1H, dd, J=6.8, 2.4 Hz), 7.47-7.39 (2H, m), 7.54 (1H, dd, J=7.4, 2.4 Hz), 7.79 (3H, t, J=5.0 Hz).

Production Example 14

A mixture of 0.42 g of the present compound 37, 0.12 g of cyclopropylboronic acid, 0.04 g of [1,1'-bis(diphenylphosphino)ferrocene]palladium(II) dichloride dichloromethane adduct, 0.53 g of cesium fluoride, and 6 mL of 1,4-dioxane was stirred at 90° C. for 5.5 hours. After cooling, the reaction mixture was concentrated and the residue thus obtained was subjected to silica gel column chromatography to obtain 0.41 g of 1-{3-methyl-2-[2-methyl-4-(6-cyclopropylpyridin-3-yl)-phenoxymethyl]-phenyl}-4-methyl-1,4-dihydrotetrazol-5-one (hereinafter referred to as the present compound 122).

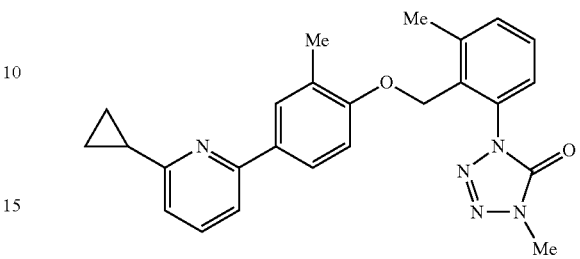

¹H-NMR (CDCl₃) δ:0.95-1.01 (2H, m), 1.09-1.14 (2H, m), 1.30-1.25 (1H, m), 2.15 (3H, s), 2.51 (3H, s), 3.62 (3H, s), 5.08 (2H, s), 6.90 (1H, d, J=8.0 Hz), 6.99 (1H, d, J=7.7 Hz), 7.28 (1H, dd, J=6.8, 2.4 Hz), 7.38-7.43 (3H, m), 7.53 (1H, t, J=7.7 Hz), 7.76 (1H, s), 7.78 (1H, d, J=9.2 Hz).

Production Example 15

To a mixture of 0.34 g of the present compound 37, 0.02 g of methanol, 0.02 g of sodium hydride, and 6 mL of toluene, 0.02 g of tris(dibenzylideneacetone)dipalladium(0) and 0.01 g of 2,2'-bis(diphenylphosphino)-1,1'-binaphthyl were added, followed by stirring at 70° C. for 6 hours. After cooling, the reaction mixture was concentrated and the residue thus obtained was subjected to silica gel column chromatography to obtain 0.19 g of 1-{3-methyl-2-[2-methyl-4-(6-methoxypyridin-3-yl)-phenoxymethyl]-phenyl}-4-methyl-1,4-dihydrotetrazol-5-one (hereinafter referred to as the present compound 123).

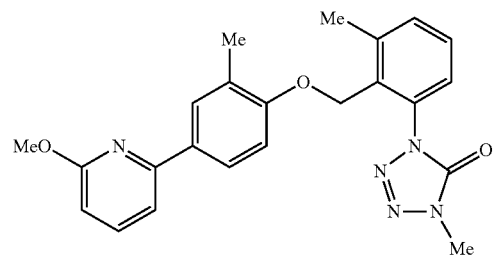 [SMILES: COc1cccc(-c2ccc(OCc3c(C)cccc3-n3nnn(C)c3=O)c(C)c2)n1]

¹H-NMR (CDCl₃) δ: 2.17 (3H, s), 2.51 (3H, s), 3.62 (3H, s), 4.02 (3H, s), 5.09 (2H, s), 6.62 (1H, dd, J=8.2, 0.5 Hz), 6.91 (1H, d, J=8.5 Hz), 7.25 (1H, dd, J=7.6, 0.5 Hz), 7.28 (1H, dd, J=7.0, 2.4 Hz), 7.39-7.45 (2H, m), 7.58 (1H, dd, J=8.0, 7.6 Hz), 7.85-7.79 (2H, m).

Production Example 16

A mixture of 0.10 g of the present compound 37, 0.04 g of propylboronic acid, 0.01 g of [1,1'-bis(diphenylphosphino)ferrocene]palladium(II) dichloride dichloromethane adduct, 0.13 g of cesium fluoride, and 6 mL of 1,4-dioxane was stirred at 80° C. for 6 hours. After cooling, the reaction mixture was concentrated and the residue thus obtained was subjected to silica gel column chromatography to obtain 0.06 g of 1-{3-methyl-2-[2-methyl-4-(6-propylpyridin-3- yl)-phenoxymethyl]-phenyl}-4-methyl-1,4-dihydrotetrazol-5-one (hereinafter referred to as the present compound 126).

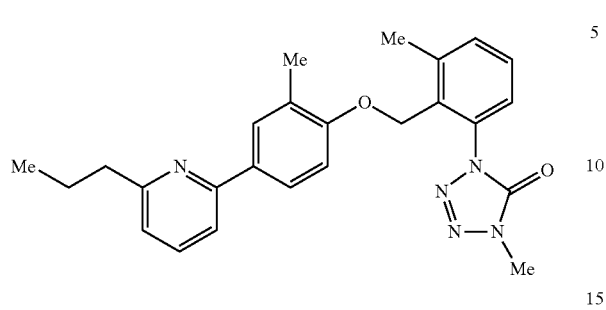

$^1$H-NMR (CDCl$_3$) δ: 1.01 (3H, t, J=7.4 Hz), 1.80-1.85 (2H, m), 2.17 (3H, s), 2.53 (3H, s), 2.82 (2H, t, J=7.7 Hz), 3.64 (3H, s), 5.10 (2H, s), 6.92 (1H, d, J=8.2 Hz), 7.03 (1H, d, J=7.7 Hz), 7.28-7.31 (1H, m), 7.41-7.47 (3H, m), 7.61 (1H, t, J=7.7 Hz), 7.74-7.79 (2H, m).

Production Example 17

Using the compounds mentioned in Reference Production Examples, the following present compounds were synthesized in the same manner as in Production Example 1. The structural formulas and $^1$H-NMR data of the thus obtained present compounds are shown below.

Present Compound 127

Present Compound 128

Present Compound 129

Present Compound 130

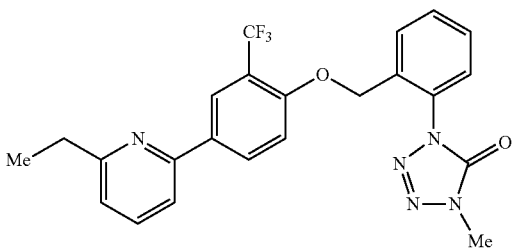

Present Compound 131

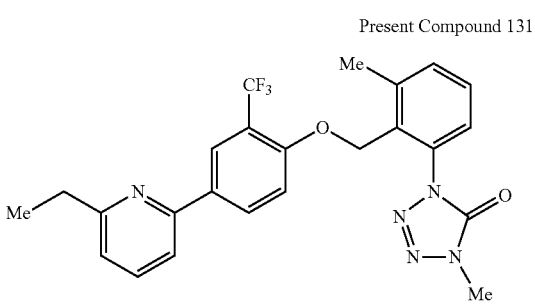

Present Compound 132

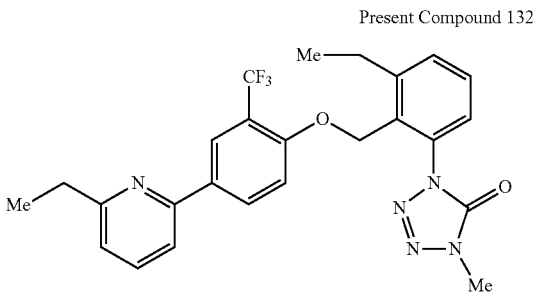

Present Compound 133

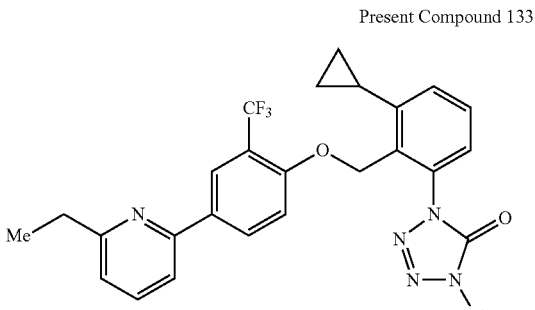

Present Compound 134

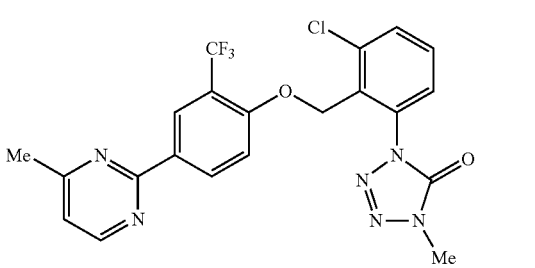

-continued
Present Compound 135
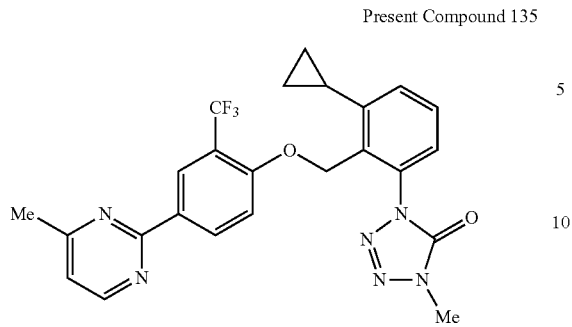
Present Compound 136
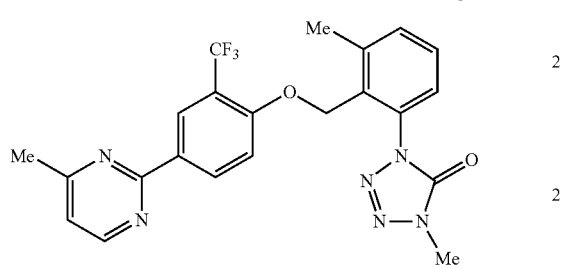
Present Compound 137
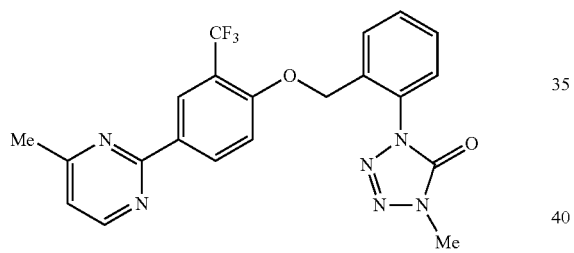
Present Compound 138
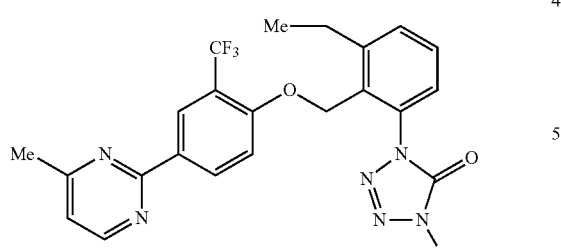
Present Compound 139
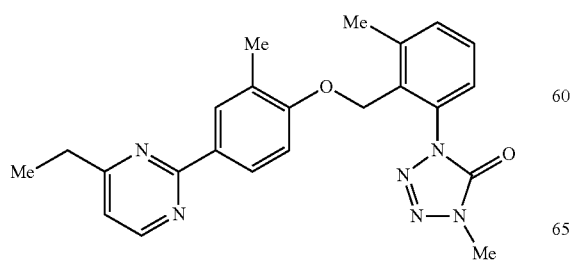
-continued
Present Compound 140
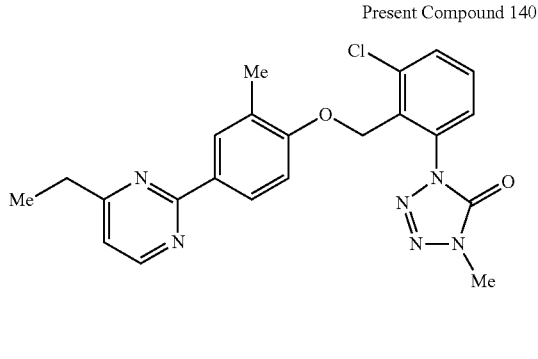
Present Compound 141
Present Compound 142
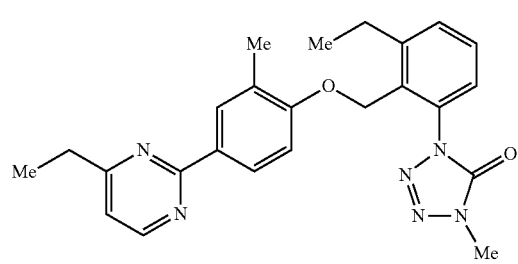
Present Compound 143
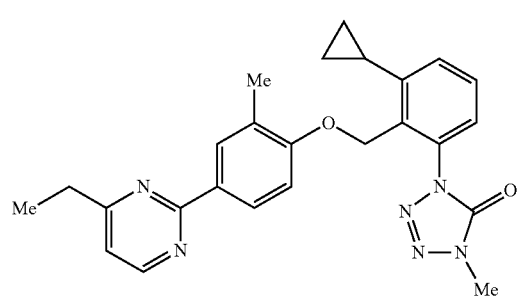
Present Compound 144
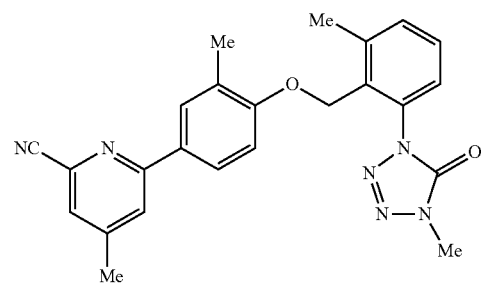

Present Compound 145

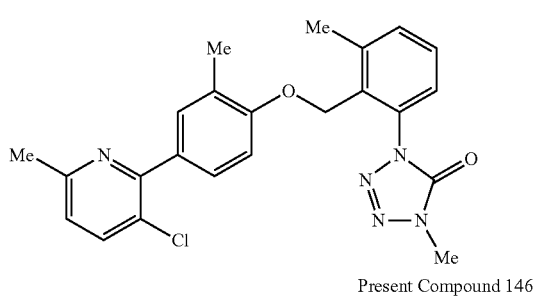

Present Compound 146

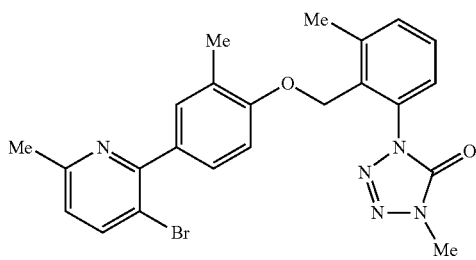 [SMILES: Cc1ccc(C)c(-c2ccc(OCc3c(C)cccc3-n3nnn(C)c3=O)c(C)c2)n1]

Present Compound 127

¹H-NMR (CDCl₃) δ: 2.61 (3H, s), 3.73 (3H, s), 5.34 (2H, s), 6.99-7.15 (2H, m), 7.44-7.57 (4H, m), 7.63 (1H, t, J=7.6 Hz), 7.76 (1H, d, J=7.6 Hz), 8.06 (1H, dd, J=8.6, 2.1 Hz), 8.24 (1H, d, J=2.1 Hz).

Present Compound 128

¹H-NMR (CDCl₃) δ: 1.28 (3H, t, J=7.6 Hz), 2.61 (3H, s), 2.88 (2H, q, J=7.6 Hz), 3.66 (3H, s), 5.25 (2H, s), 7.08 (2H, t, J=9.2 Hz), 7.32 (1H, dd, J=7.6, 1.8 Hz), 7.42-7.53 (3H, m), 7.63 (1H, t, J=7.6 Hz), 8.09 (1H, dd, J=8.6, 2.3 Hz), 8.18 (1H, d, J=2.3 Hz).

Present Compound 129

¹H-NMR (CDCl₃) δ: 0.74-0.79 (2H, m), 0.97-1.04 (2H, m), 2.12-2.21 (1H, m), 2.61 (3H, s), 3.67 (3H, s), 5.46 (2H, s), 7.09-7.11 (2H, m), 7.28-7.32 (2H, m), 7.43-7.45 (2H, m), 7.63 (1H, t, J=7.7 Hz), 8.09 (1H, dd, J=8.7, 2.3 Hz), 8.18 (1H, d, J=2.3 Hz).

Present Compound 130

¹H-NMR (CDCl₃) δ: 1.36 (3H, t, J=7.6 Hz), 2.88 (2H, q, J=7.6 Hz), 3.74 (3H, s), 5.35 (2H, s), 7.06 (1H, d, J=8.5 Hz), 7.10 (1H, d, J=7.0 Hz), 7.46-7.57 (4H, m), 7.65 (1H, t, J=7.8 Hz), 7.76 (1H, d, J=7.8 Hz), 8.10 (1H, dd, J=8.5, 2.3 Hz), 8.26 (1H, d, J=2.3 Hz).

Present Compound 131

¹H-NMR (CDCl₃) δ: 1.36 (3H, t, J=7.6 Hz), 2.53 (3H, s), 2.88 (2H, q, J=7.6 Hz), 3.69 (3H, s), 5.22 (2H, s), 7.05 (1H, d, J=8.7 Hz), 7.10 (1H, d, J=7.7 Hz), 7.30 (1H, dd, J=7.3, 1.6 Hz), 7.41-7.48 (3H, m), 7.65 (1H, t, J=7.7 Hz), 8.12 (1H, dd, J=8.7, 2.3 Hz), 8.21 (1H, d, J=2.3 Hz).

Present Compound 132

¹H-NMR (CDCl₃) δ: 1.28 (3H, t, J=7.5 Hz), 1.36 (3H, t, J=7.6 Hz), 2.85-2.90 (4H, m), 3.66 (3H, s), 5.25 (2H, s), 7.12-7.05 (2H, m), 7.31 (1H, d, J=7.7 Hz), 7.41-7.54 (3H, m), 7.65 (1H, t, J=9.5 Hz), 8.12 (1H, d, J=8.5 Hz), 8.19 (1H, s).

Present Compound 133

¹H-NMR (CDCl₃) δ: 0.76-0.78 (2H, m), 1.00-1.01 (2H, m), 1.36 (3H, t, J=7.6 Hz), 2.11-2.19 (1H, m), 2.88 (2H, q, J=7.6 Hz), 3.67 (3H, s), 5.46 (2H, s), 7.09 (1H, d, J=7.7 Hz), 7.11 (1H, d, J=8.8 Hz), 7.33-7.27 (2H, m), 7.42-7.48 (2H, m), 7.65 (1H, t, J=7.7 Hz), 8.12 (1H, dd, J=8.7, 2.1 Hz), 8.19 (1H, d, J=2.1 Hz).

Present Compound 134

¹H-NMR (CDCl₃) δ: 2.57 (3H, s), 3.66 (3H, s), 5.60 (2H, s), 7.03 (1H, d, J=5.1 Hz), 7.10 (1H, d, J=8.8 Hz), 7.47 (1H, s), 7.48 (1H, d, J=3.2 Hz), 7.61 (1H, dd, J=6.3, 3.2 Hz), 8.56 (1H, dd, J=8.8, 2.3 Hz), 8.60 (1H, d, J=5.1 Hz), 8.64 (1H, d, J=2.0 Hz).

Present Compound 135

¹H-NMR (CDCl₃) δ: 0.73-0.80 (2H, m), 0.97-1.04 (2H, m), 2.14-2.19 (1H, m), 2.58 (3H, s), 3.66 (3H, s), 5.49 (2H, s), 7.04 (1H, d, J=5.0 Hz), 7.12 (1H, d, J=8.7 Hz), 7.27-7.32 (2H, m), 7.45 (1H, t, J=7.9 Hz), 8.56 (1H, dd, J=8.7, 2.1 Hz), 8.61 (1H, d, J=5.0 Hz), 8.67 (1H, d, J=2.1 Hz).

Present Compound 136

¹H-NMR (CDCl₃) δ: 2.52 (3H, s), 2.58 (3H, s), 3.69 (3H, s), 5.23 (2H, s), 7.03-7.08 (2H, m), 7.30 (1H, dd, J=7.5, 1.8 Hz), 7.39-7.47 (2H, m), 8.56 (1H, dd, J=8.7, 2.2 Hz), 8.61 (1H, d, J=5.0 Hz), 8.68 (1H, d, J=2.2 Hz).

Present Compound 137

¹H-NMR (CDCl₃) δ: 2.58 (3H, s), 3.73 (3H, s), 5.36 (2H, s), 7.04-7.07 (2H, m), 7.50-7.57 (3H, m), 7.77 (1H, d, J=7.5 Hz), 8.54-8.57 (1H, m), 8.61 (1H, d, J=5.2 Hz), 8.71 (1H, d, J=2.0 Hz).

Present Compound 138

¹H-NMR (CDCl₃) δ: 1.28 (3H, t, J=7.2 Hz), 2.57 (3H, s), 2.88 (2H, q, J=7.6 Hz), 3.65 (3H, s), 5.27 (2H, s), 7.04 (1H, d, J=5.0 Hz), 7.08 (1H, d, J=9.0 Hz), 7.32 (1H, dd, J=7.6, 1.7 Hz), 7.45 (1H, dd, J=7.6, 1.7 Hz), 7.49 (1H, t, J=7.6 Hz), 8.56 (1H, dd, J=9.0, 2.2 Hz), 8.61 (1H, d, J=5.0 Hz), 8.67 (1H, d, J=2.2 Hz).

Present Compound 139

¹H-NMR (CDCl₃) δ: 1.36 (3H, t, J=7.6 Hz), 2.17 (3H, s), 2.52 (3H, s), 2.83 (2H, q, J=7.6 Hz), 3.62 (3H, s), 5.12 (2H, s), 6.93 (1H, d, J=8.6 Hz), 6.99 (1H, d, J=5.2 Hz), 7.29 (1H, dd, J=6.9, 2.4 Hz), 7.39-7.47 (2H, m), 8.21 (1H, s), 8.26 (1H, dd, J=8.6, 2.4 Hz), 8.62 (1H, d, J=5.2 Hz).

Present Compound 140

¹H-NMR (CDCl₃) δ: 1.36 (3H, t, J=7.6 Hz), 2.10 (3H, s), 2.83 (2H, q, J=7.6 Hz), 3.59 (3H, s), 5.40 (2H, s), 6.94 (1H, d, J=8.6 Hz), 6.99 (1H, d, J=5.2 Hz), 7.41 (1H, dd, J=8.0, 1.4

Hz), 7.48 (1H, t, J=8.0 Hz), 7.62 (1H, dd, J=8.0, 1.4 Hz), 8.19 (1H, dd, J=2.2, 0.7 Hz), 8.25 (1H, dd, J=8.6, 2.2 Hz), 8.61 (1H, d, J=5.2 Hz).

Present Compound 141

¹H-NMR (CDCl₃) δ: 1.36 (3H, t, J=7.6 Hz), 2.27 (3H, s), 2.83 (2H, q, J=7.6 Hz), 3.68 (3H, s), 5.24 (2H, s), 6.89 (1H, d, J=9.1 Hz), 6.99 (1H, d, J=5.2 Hz), 7.57-7.47 (3H, m), 7.73 (1H, d, J=7.0 Hz), 8.23-8.25 (2H, m), 8.61 (1H, d, J=5.0 Hz).

Present Compound 142

¹H-NMR (CDCl₃) δ: 1.29 (3H, t, J=7.6 Hz), 1.36 (3H, t, J=7.6 Hz), 2.15 (3H, s), 2.79-2.91 (4H, m), 3.59 (3H, s), 5.14 (2H, s), 6.94 (1H, d, J=8.6 Hz), 6.99 (1H, d, J=5.1 Hz), 7.29 (1H, d, J=7.2 Hz), 7.43-7.51 (2H, m), 8.21 (1H, s), 8.26 (1H, d, J=8.6 Hz), 8.63-8.60 (1H, m).

Present Compound 143

¹H-NMR (CDCl₃) δ: 0.76-0.79 (2H, m), 0.97-1.03 (2H, m), 1.36 (3H, t, J=7.6 Hz), 2.10-2.14 (1H, m), 2.16 (3H, s), 2.83 (2H, q, J=7.6 Hz), 3.61 (3H, s), 5.34 (2H, s), 6.98 (1H, d, J=8.5 Hz), 6.99 (1H, d, J=5.1 Hz), 7.27-7.29 (2H, m), 7.44 (1H, t, J=7.8 Hz), 8.21 (1H, dd, J=2.0, 0.8 Hz), 8.26 (1H, dd, J=8.5, 2.0 Hz), 8.62 (1H, d, J=5.1 Hz).

Present Compound 144

¹H-NMR (CDCl₃) δ: 2.14 (3H, s), 2.33 (3H, s), 2.51 (3H, s), 3.63 (3H, s), 5.07 (2H, s), 6.59-6.59 (2H, m), 6.89 (1H, d, J=9.1 Hz), 7.02 (1H, s), 7.27-7.29 (2H, m), 7.40-7.45 (2H, m).

Present Compound 145

¹H-NMR (CDCl₃) δ: 2.15 (3H, s), 2.51 (3H, s), 2.57 (3H, s), 3.66 (3H, s), 5.08 (2H, s), 6.92 (1H, d, J=8.4 Hz), 7.03 (1H, d, J=8.0 Hz), 7.29 (1H, dd, J=6.8, 2.3 Hz), 7.42-7.48 (3H, m), 7.52 (1H, dd, J=8.4, 2.3 Hz), 7.63 (1H, d, J=8.0 Hz).

Present Compound 146

¹H-NMR (CDCl₃) δ: 2.14 (3H, s), 2.51 (3H, s), 2.55 (3H, s), 3.66 (3H, s), 5.07 (2H, s), 6.91 (1H, d, J=8.5 Hz), 6.96 (1H, d, J=8.1 Hz), 7.28 (1H, t, J=4.7 Hz), 7.42-7.48 (4H, m), 7.81 (1H, d, J=8.1 Hz).

Production Example 18

In the same manner as in Production Example 16, except that the present compound 146 was used in place of the present compound 37, and that methylboronic acid was used in place of propylboronic acid, the present compound 147 was obtained. The structural formulas and ¹H-NMR data of the present compound 147 are shown below.

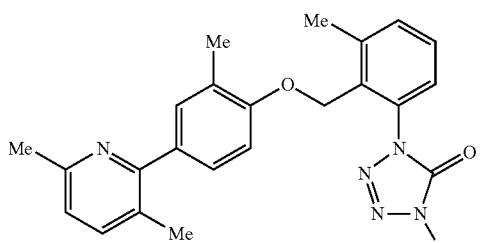

¹H-NMR (CDCl₃) δ: 2.13 (3H, s), 2.29 (3H, s), 2.51 (3H, s), 2.54 (3H, s), 3.66 (3H, s), 5.06 (2H, s), 6.89 (1H, d, J=9.1 Hz), 7.00 (1H, d, J=7.7 Hz), 7.25-7.29 (3H, m), 7.43 (3H, dd, J=7.2, 2.7 Hz).

Production Example 19

In the same manner as in Production Example 16, except that an isopropenylboronic acid pinacol ester was used in place of cyclopropylboronic acid, the present compound 148 was obtained. The structural formulas and ¹H-NMR data of the present compound 148 are shown below.

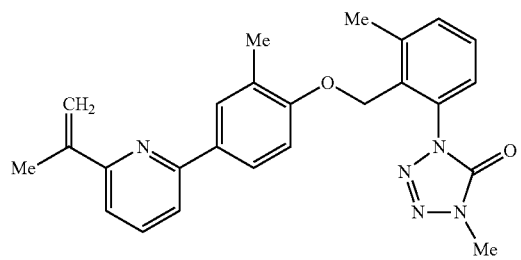 [SMILES: C=C(C)c1cccc(-c2ccc(OCc3c(C)cccc3-n3nnn(C)c3=O)c(C)c2)n1]

¹H-NMR (CDCl₃) δ: 2.17 (3H, s), 2.28 (3H, s), 2.52 (3H, s), 3.63 (3H, s), 5.10 (2H, s), 5.32-5.33 (1H, m), 5.34-5.32 (1H, m), 6.93 (1H, d, J=9.1 Hz), 7.29 (1H, dd, J=6.8, 2.5 Hz), 7.36 (1H, dd, J=7.8, 0.7 Hz), 7.40-7.46 (2H, m), 7.55 (1H, d, J=7.8 Hz), 7.67 (1H, t, J=7.8 Hz), 7.85-7.89 (2H, m).

Production Example 20

A mixture of 0.47 g of the present compound 148 mentioned in Production Example 19, 0.06 g of a palladium-fibroin complex, and 10 mL of methanol was stirred in a hydrogen atmosphere at room temperature for 5 hours. The reaction mixture was filtered and the filtrate was concentrated under reduced pressure. The residue thus obtained was subjected to a silica gel column chromatography to obtain 0.45 g of 1-{3-methyl-2-[2-methyl-4-(6-isopropylpyridin-3-yl)-phenoxymethyl]-phenyl}-4-methyl-1,4-dihydrotetrazol-5-one (hereinafter referred to as the present compound 149).

Present Compound 149

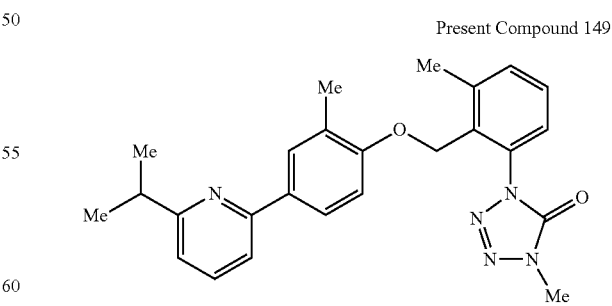

¹H-NMR (CDCl₃) δ: 1.34 (6H, d, J=7.0 Hz), 2.17 (3H, s), 2.52 (3H, s), 3.07-3.15 (1H, m), 3.63 (3H, s), 5.09 (2H, s), 6.91 (1H, d, J=9.1 Hz), 7.05 (1H, dd, J=7.7, 0.7 Hz), 7.28 (1H, dd, J=6.9, 2.4 Hz), 7.41-7.46 (3H, m), 7.61 (1H, t, J=7.7 Hz), 7.79-7.81 (2H, m).

Production Example 21

In the same manner as in Production Example 12, the reaction was performed to synthesize the following present compounds. The structural formulas and ¹H-NMR data of the thus obtained present compounds are shown below.

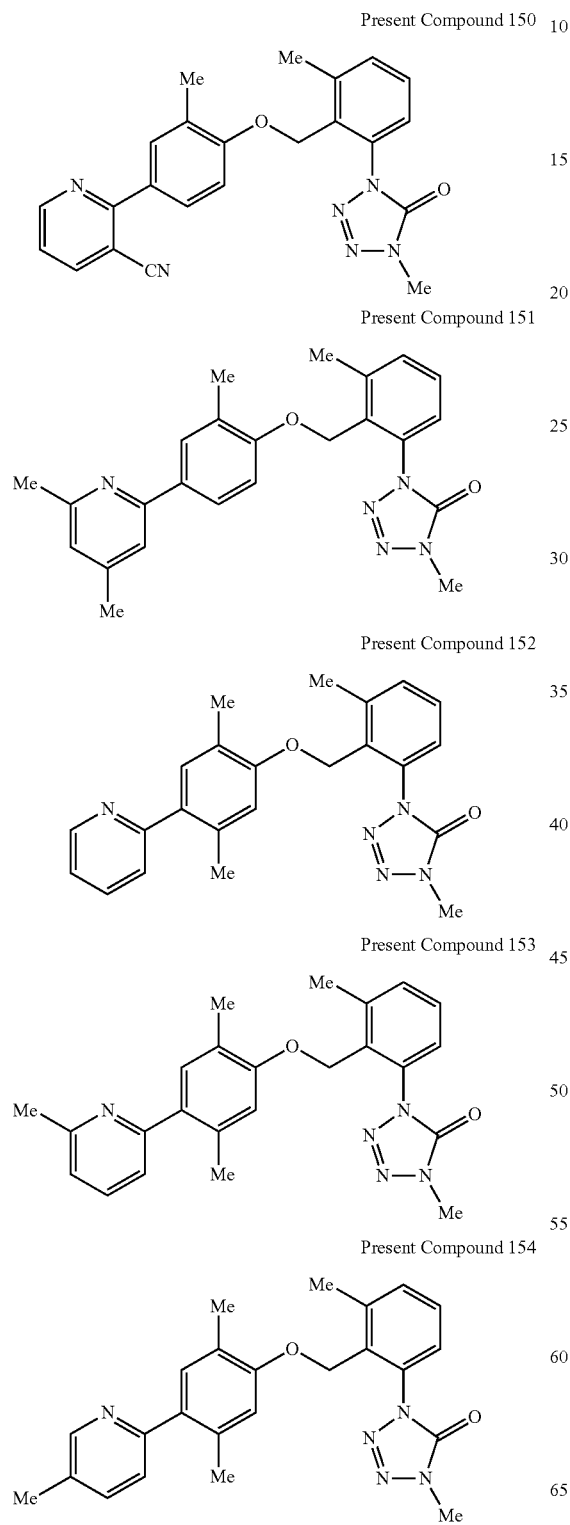

Present Compound 150

Present Compound 151

Present Compound 152

Present Compound 153

Present Compound 154

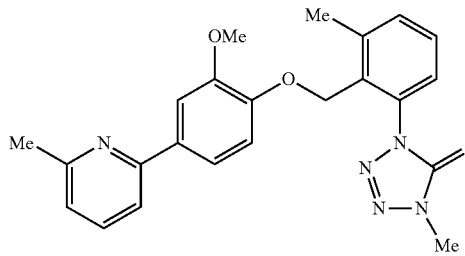

Present Compound 155

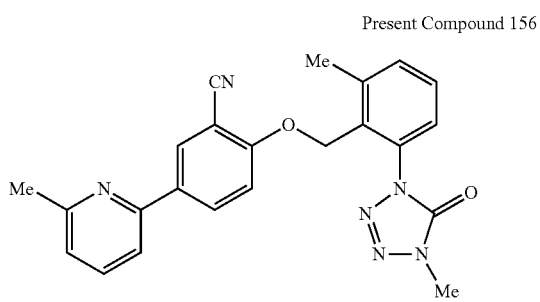

Present Compound 156

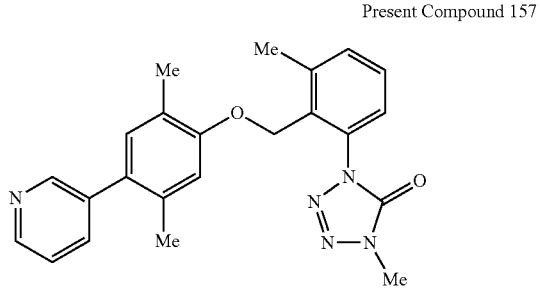

Present Compound 157

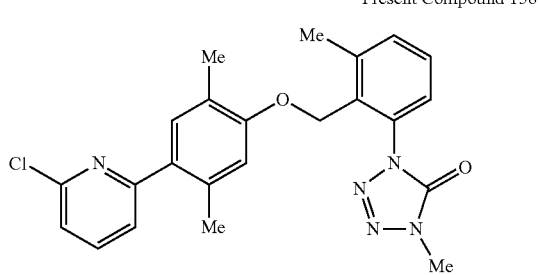

Present Compound 158

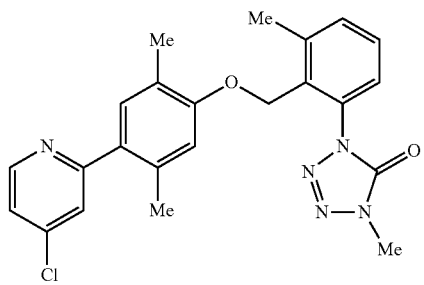

Present Compound 159

Present Compound 160
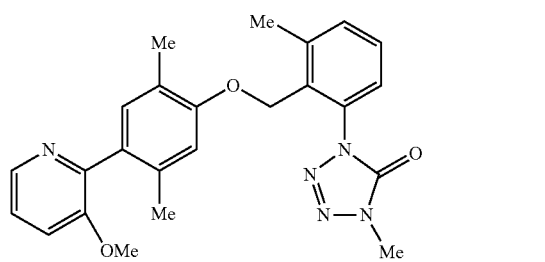
Present Compound 161
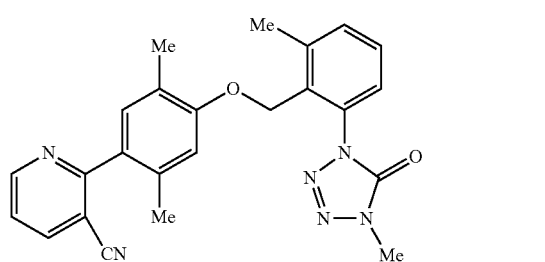
Present Compound 162
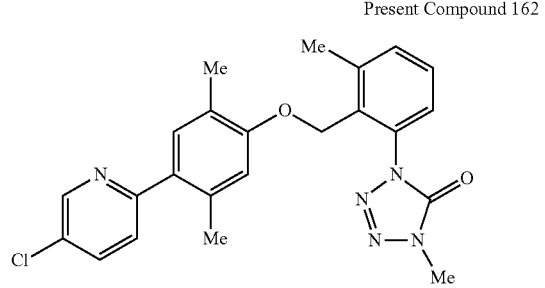
Present Compound 163
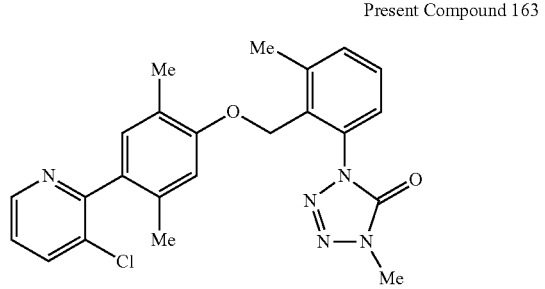
Present Compound 164
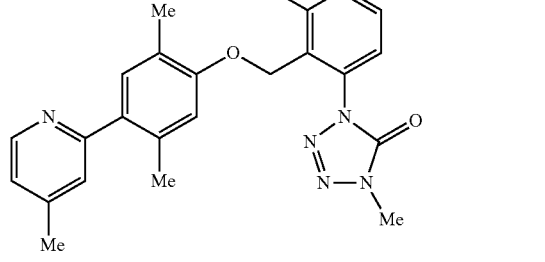
Present Compound 165
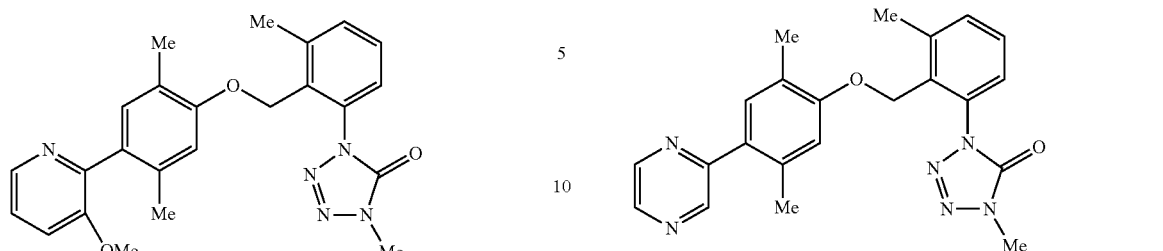
Present Compound 166
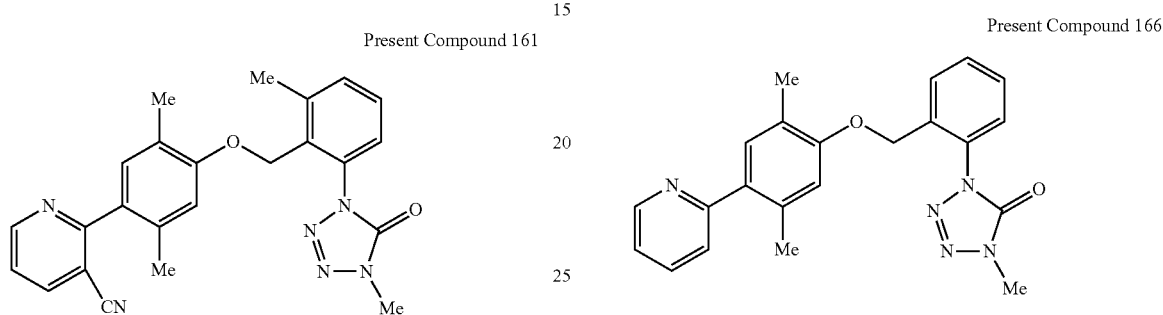
Present Compound 167
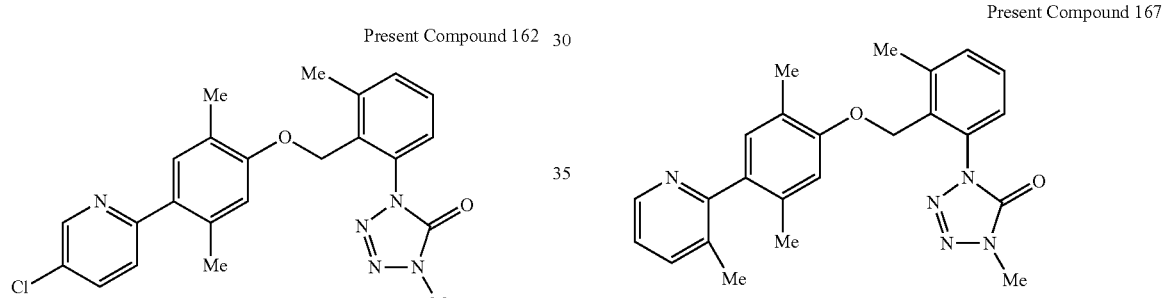
Present Compound 168
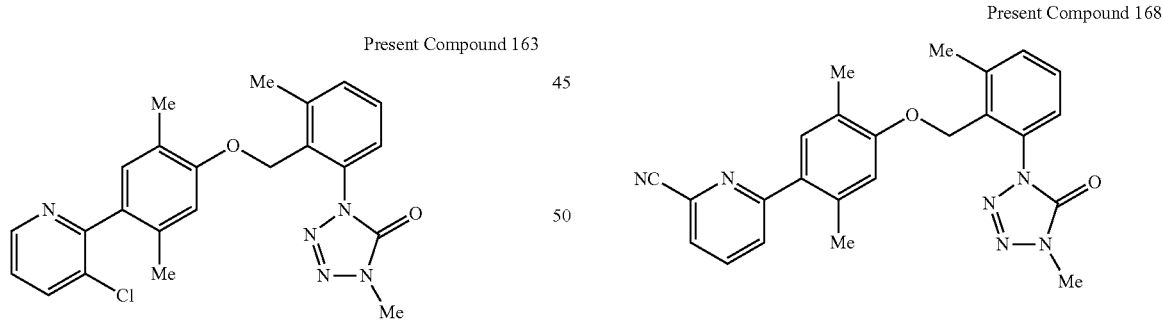
Present Compound 169
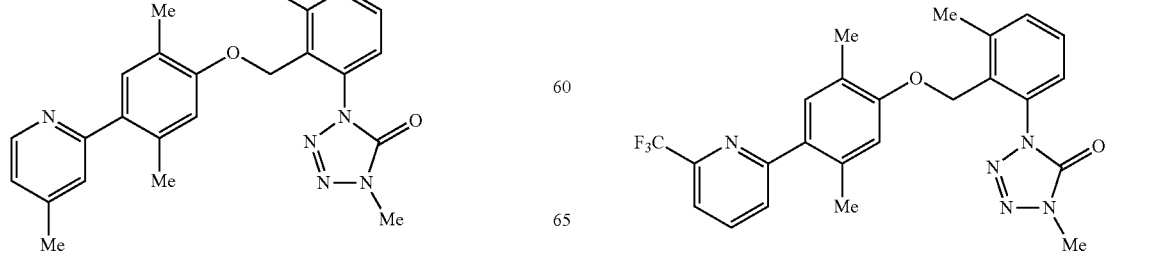

Present Compound 170
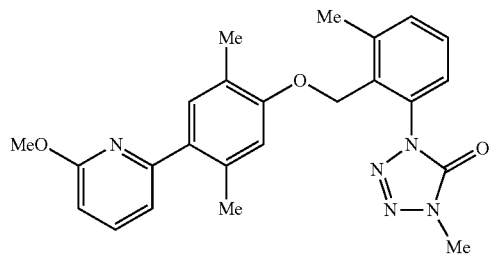
Present Compound 171
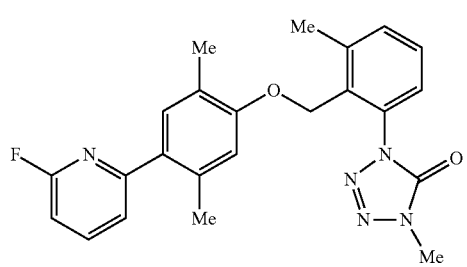
Present Compound 172
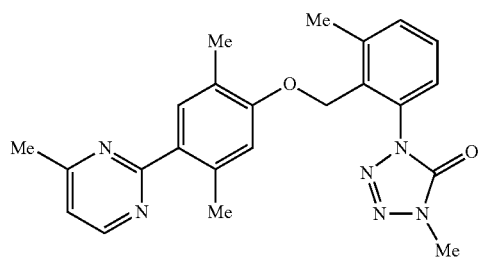
Present Compound 173
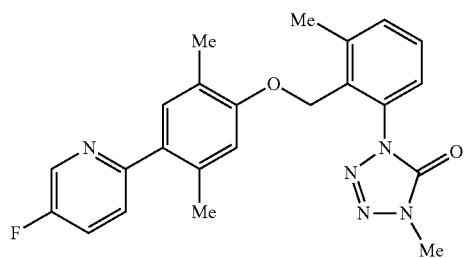
Present Compound 174
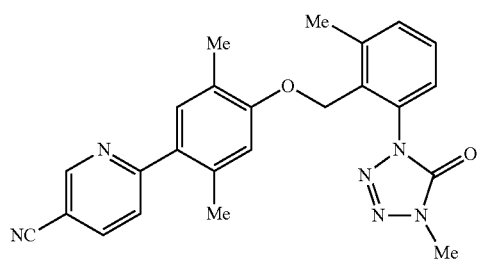
Present Compound 175
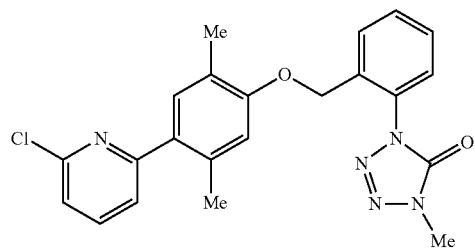
Present Compound 176
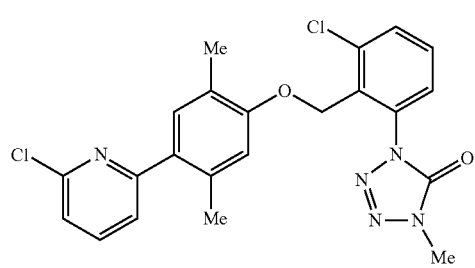
Present Compound 177
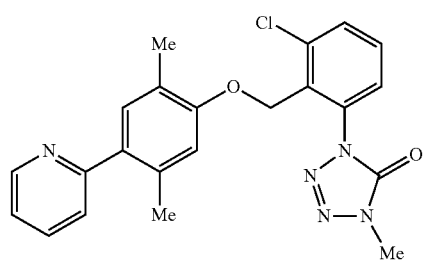
Present Compound 178
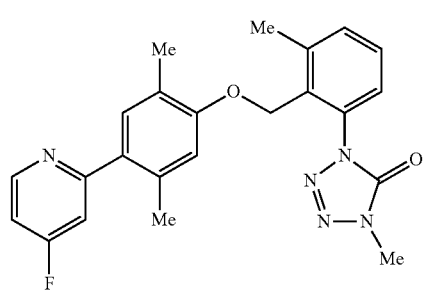
Present Compound 179
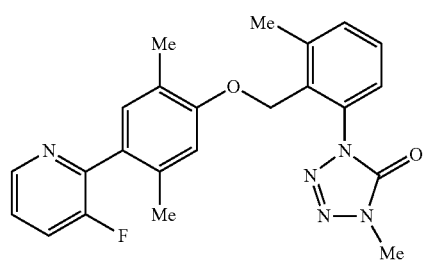

Present Compound 180
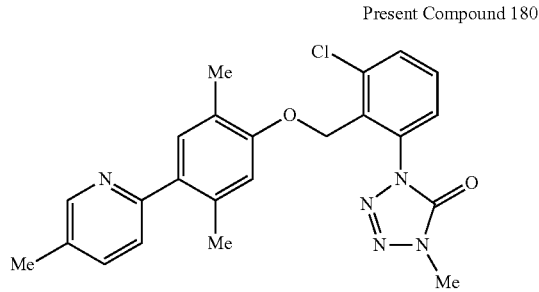
Present Compound 181
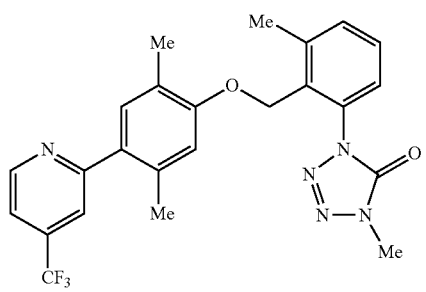
Present Compound 182
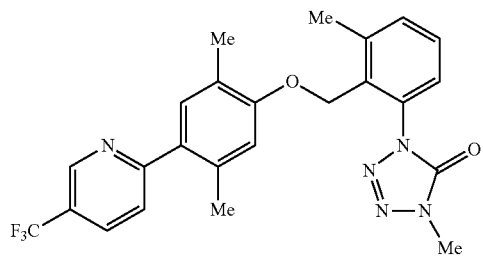
Present Compound 183
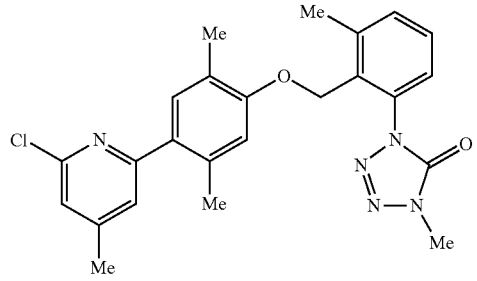
Present Compound 184
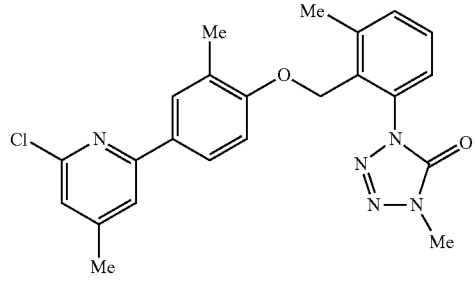
Present Compound 185
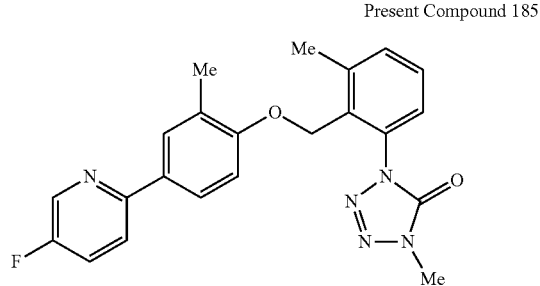
Present Compound 186
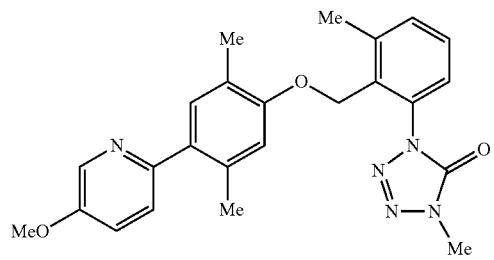
Present Compound 187
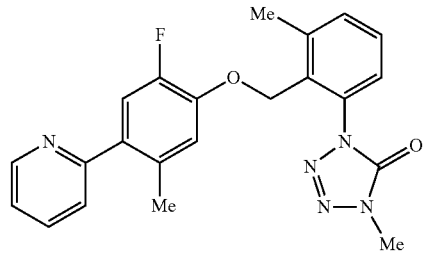
Present Compound 188
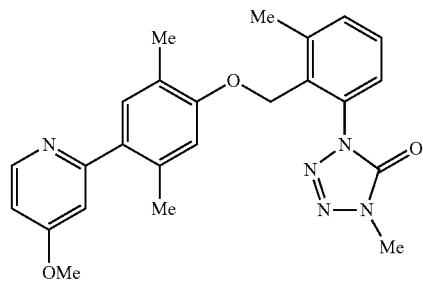
Present Compound 189
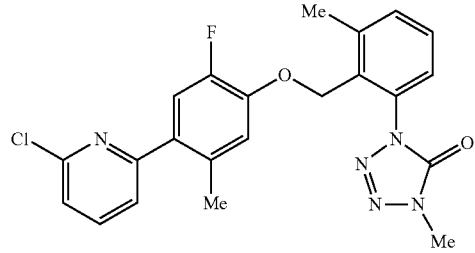

Present Compound 190
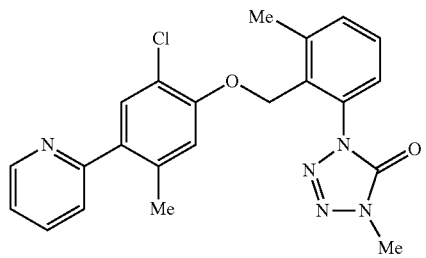
Present Compound 191
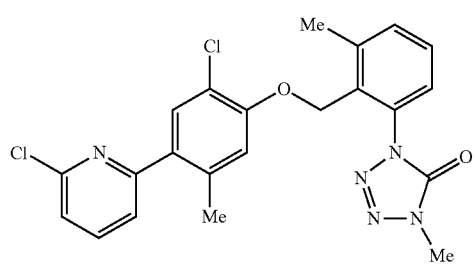
Present Compound 192
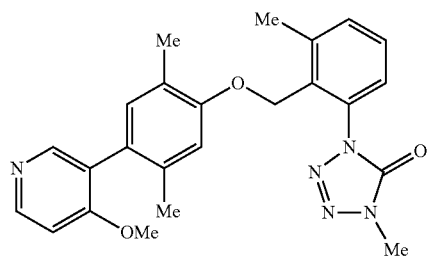
Present Compound 193
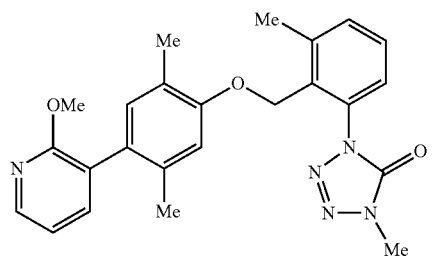
Present Compound 194
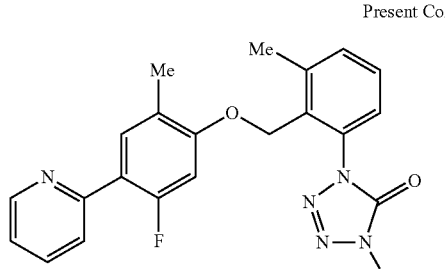
Present Compound 195
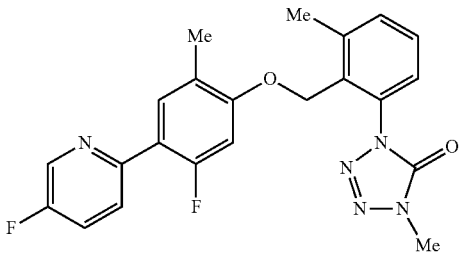
Present Compound 196
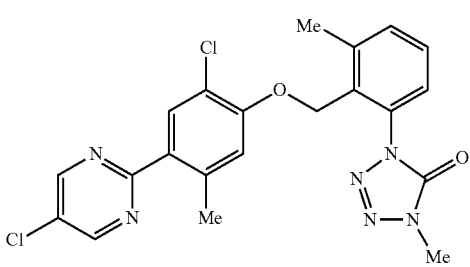
Present Compound 197
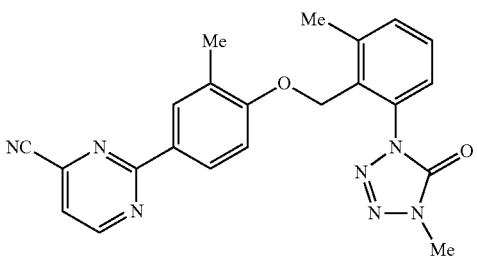
Present Compound 198
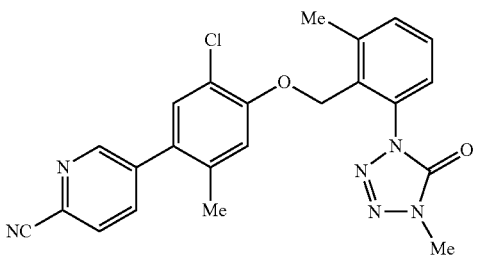
Present Compound 199
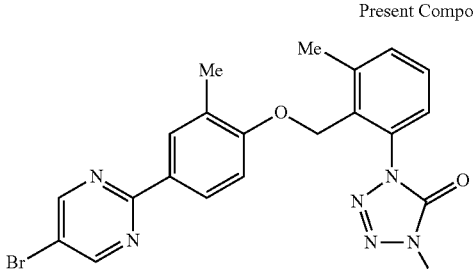

-continued

Present Compound 200

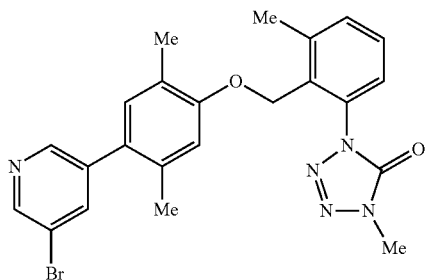

Present Compound 21

Present Compound 150

¹H-NMR (CDCl₃) δ: 2.17 (3H, s), 2.52 (3H, s), 3.64 (3H, s), 5.11 (2H, s), 6.98 (1H, d, J=8.6 Hz), 7.28-7.34 (2H, m), 7.40-7.47 (2H, m), 7.71 (1H, dd, J=2.5, 0.8 Hz), 7.77 (1H, dd, J=8.6, 2.5 Hz), 8.03 (1H, dd, J=7.8, 1.8 Hz), 8.83 (1H, dd, J=4.8, 1.8 Hz).

Present Compound 151

¹H-NMR (CDCl₃) δ: 2.15 (3H, s), 2.34 (3H, s), 2.51 (3H, s), 2.56 (3H, s), 3.62 (3H, s), 5.09 (2H, s), 6.87 (1H, s), 6.90 (1H, d, J=8.5 Hz), 7.26-7.30 (2H, m), 7.37-7.45 (2H, m), 7.72 (1H, dd, J=8.5, 2.3 Hz), 7.75 (1H, s).

Present Compound 152

¹H-NMR (CDCl₃) δ: 8.67-8.65 (1H, m), 7.70 (1H, tt, J=7.7, 1.6 Hz), 7.45-7.38 (2H, m), 7.38-7.33 (1H, m), 7.30-7.25 (1H, m), 7.21-7.17 (2H, m), 6.73 (1H, s), 5.07 (2H, s), 3.65 (3H, s), 2.52 (3H, s), 2.35 (3H, s), 2.09 (3H, s).

Present Compound 153

¹H-NMR (CDCl₃) δ: 2.08 (3H, s), 2.32 (3H, s), 2.51 (3H, s), 2.59 (3H, s), 3.67 (3H, s), 5.05 (2H, s), 6.72 (1H, s), 7.06 (1H, d, J=7.7 Hz), 7.14 (1H, d, J=7.7 Hz), 7.15 (1H, s), 7.28 (1H, dd, J=6.6, 2.7 Hz), 7.45-7.39 (2H, m), 7.59 (1H, t, J=7.7 Hz).

Present Compound 154

¹H-NMR (CDCl₃) δ: 2.08 (3H, s), 2.34 (3H, s), 2.37 (3H, s), 2.52 (3H, s), 3.66 (3H, s), 5.06 (2H, s), 6.72 (1H, s), 7.17 (1H, s), 7.24-7.29 (2H, m), 7.39-7.44 (2H, m), 7.51 (1H, ddd, J=7.9, 2.3, 0.7 Hz), 8.49 (1H, dd, J=1.4, 0.7 Hz).

Present Compound 155

¹H-NMR (CDCl₃) δ: 2.53 (3H, s), 2.61 (3H, s), 3.63 (3H, s), 3.90 (3H, s), 5.17 (2H, s), 6.90 (1H, d, J=8.4 Hz), 7.05 (1H, d, J=7.8 Hz), 7.25-7.27 (1H, m), 7.35-7.42 (3H, m), 7.44 (1H, d, J=7.8 Hz), 7.58 (1H, s), 7.60 (1H, t, J=6.8 Hz).

Present Compound 156

¹H-NMR (CDCl₃) δ: 2.57 (3H, s), 2.59 (3H, s), 3.72 (3H, s), 5.30 (2H, s), 6.93 (1H, d, J=8.8 Hz), 7.10 (1H, d, J=7.7 Hz), 7.29 (1H, dd, J=6.8, 1.8 Hz), 7.38-7.46 (3H, m), 7.63 (1H, t, J=7.7 Hz), 8.10 (1H, dt, J=8.8, 1.8 Hz), 8.18 (1H, d, J=2.3 Hz).

Present Compound 157

¹H-NMR (CDCl₃) δ: 2.09 (3H, s), 2.27 (3H, s), 2.53 (3H, s), 3.67 (3H, s), 5.07 (2H, s), 6.75 (1H, s), 6.98 (1H, s), 7.21-7.24 (2H, m), 7.28 (1H, dd, J=6.7, 2.6 Hz), 7.47-7.40 (2H, m), 8.61 (2H, dd, J=4.5, 1.6 Hz).

Present Compound 158

¹H-NMR (CDCl₃) δ: 2.08 (3H, s), 2.36 (3H, s), 2.51 (3H, s), 3.66 (3H, s), 5.06 (2H, s), 6.72 (1H, s), 7.19 (1H, s), 7.23 (1H, d, J=7.7 Hz), 7.27-7.30 (2H, m), 7.38-7.46 (2H, m), 7.66 (1H, t, J=7.7 Hz).

Present Compound 159

¹H-NMR (CDCl₃) δ: 2.09 (3H, s), 2.36 (3H, s), 2.52 (3H, s), 3.66 (3H, s), 5.07 (2H, s), 6.73 (1H, s), 7.17 (1H, s), 7.20-7.23 (1H, m), 7.28 (1H, d, J=8.5 Hz), 7.46-7.37 (3H, m), 8.56 (1H, d, J=5.5 Hz).

Present Compound 160

¹H-NMR (CDCl₃) δ: 2.07 (3H, s), 2.14 (3H, s), 2.51 (3H, s), 3.67 (3H, s), 3.80 (3H, s), 5.04 (2H, s), 6.73 (1H, s), 7.07 (1H, s), 7.24 (1H, s), 7.24 (1H, s), 7.27 (1H, dd, J=6.6, 1.8 Hz), 7.39-7.45 (2H, m), 8.26 (1H, t, J=3.1 Hz).

Present Compound 161

¹H-NMR (CDCl₃) δ: 2.09 (3H, s), 2.25 (3H, s), 2.52 (3H, s), 3.66 (3H, s), 5.08 (2H, s), 6.78 (1H, s), 7.11 (1H, s), 7.29 (1H, d, J=6.7 Hz), 7.34-7.39 (1H, br m), 7.39-7.46 (2H, m), 8.04 (1H, d, J=7.9 Hz), 8.84 (1H, s).

Present Compound 162

¹H-NMR (CDCl₃) δ: 2.08 (3H, s), 2.34 (3H, s), 2.51 (3H, s), 3.66 (3H, s), 5.06 (2H, s), 6.72 (1H, s), 7.16 (1H, s), 7.28 (1H, dd, J=7.1, 2.7 Hz), 7.31 (1H, dd, J=8.2, 0.7 Hz), 7.46-7.39 (2H, m), 7.68 (1H, dd, J=8.5, 2.5 Hz), 8.61 (1H, dd, J=2.5, 0.7 Hz).

Present Compound 163

¹H-NMR (CDCl₃) δ: 2.07 (3H, s), 2.13 (3H, s), 2.51 (3H, s), 3.66 (3H, s), 5.05 (2H, s), 6.74 (1H, s), 7.00 (1H, s), 7.19-7.31 (2H, m), 7.40-7.45 (2H, m), 7.77 (1H, dd, J=8.1, 1.5 Hz), 8.55 (1H, dd, J=4.7, 1.5 Hz).

Present Compound 164

¹H-NMR (CDCl₃) δ: 2.08 (3H, s), 2.33 (3H, s), 2.38 (3H, s), 2.51 (3H, s), 3.66 (3H, s), 5.06 (2H, s), 6.72 (1H, s), 7.02 (1H, d, J=5.0 Hz), 7.16 (2H, d, J=5.0 Hz), 7.28 (1H, t, J=1.0 Hz), 7.39-7.44 (2H, m), 8.51 (1H, d, J=5.0 Hz).

Present Compound 165

¹H-NMR (CDCl₃) δ: 2.10 (3H, s), 2.39 (3H, s), 2.52 (3H, s), 3.66 (3H, s), 5.08 (2H, s), 6.76 (1H, s), 7.21 (1H, s), 7.28 (1H, dd, J=6.9, 2.5 Hz), 7.40-7.45 (2H, m), 8.47 (1H, d, J=2.5 Hz), 8.62 (1H, dd, J=2.5, 1.6 Hz), 8.67 (1H, t, J=2.2 Hz).

Present Compound 166

¹H-NMR (CDCl₃) δ: 2.18 (3H, s), 2.32 (3H, s), 3.69 (3H, s), 5.19 (2H, s), 6.69 (1H, s), 7.17-7.22 (2H, m), 7.35 (1H, dt, J=7.8, 1.0 Hz), 7.47-7.57 (3H, m), 7.70-7.75 (2H, m), 8.66 (1H, dq, J=5.0, 1.0 Hz).

Present Compound 167

¹H-NMR (CDCl₃) δ: 2.04 (3H, s), 2.06 (3H, s), 2.12 (3H, s), 2.52 (3H, s), 3.67 (3H, s), 5.04 (2H, s), 6.72 (1H, s), 6.91 (1H, s), 7.16 (1H, dd, J=7.6, 4.8 Hz), 7.28 (1H, dd, J=6.6, 2.9 Hz), 7.39-7.43 (2H, m), 7.55 (1H, dq, J=7.6, 1.0 Hz), 8.47 (1H, dd, J=4.8, 1.0 Hz).

Present Compound 168

¹H-NMR (CDCl₃) δ: 2.10 (3H, s), 2.37 (3H, s), 2.52 (3H, s), 3.67 (3H, s), 5.08 (2H, s), 6.75 (1H, s), 7.19 (1H, s), 7.29 (1H, dd, J=6.9, 2.3 Hz), 7.40-7.45 (2H, m), 7.59 (1H, dd, J=5.4, 0.9 Hz), 7.62 (1H, dd, J=5.4, 0.9 Hz), 7.85 (1H, t, J=7.9 Hz).

Present Compound 169

¹H-NMR (CDCl₃) δ: 2.09 (3H, s), 2.39 (3H, s), 2.52 (3H, s), 3.67 (3H, s), 5.07 (2H, s), 6.75 (1H, s), 7.20 (1H, s), 7.28 (1H, dd, J=7.0, 2.7 Hz), 7.42-7.44 (2H, m), 7.57 (2H, t, J=8.0 Hz), 7.88 (1H, t, J=7.8 Hz).

Present Compound 170

¹H-NMR (CDCl₃) δ: 2.09 (3H, s), 2.43 (3H, s), 2.52 (3H, s), 3.67 (3H, s), 3.95 (3H, s), 5.06 (2H, s), 6.65 (1H, dd, J=8.2, 0.7 Hz), 6.74 (1H, s), 6.95 (1H, dd, J=7.3, 0.9 Hz), 7.21 (1H, s), 7.28 (1H, dd, J=6.9, 2.5 Hz), 7.40-7.44 (2H, m), 7.59 (1H, t, J=8.2 Hz).

Present Compound 171

¹H-NMR (CDCl₃) δ: 2.08 (3H, s), 2.39 (3H, s), 2.52 (3H, s), 3.66 (3H, s), 5.07 (2H, s), 6.72 (1H, s), 6.84 (1H, dd, J=8.2, 2.9 Hz), 7.21 (1H, s), 7.24-7.29 (2H, m), 7.39-7.46 (2H, m), 7.80 (1H, q, J=8.0 Hz).

Present Compound 172

¹H-NMR (CDCl₃) δ: 2.09 (3H, s), 2.51 (3H, s), 2.53 (3H, s), 2.57 (3H, s), 3.66 (3H, s), 5.08 (2H, s), 6.73 (1H, s), 7.02 (1H, d, J=5.0 Hz), 7.30-7.27 (1H, m), 7.42 (2H, dd, J=4.6, 3.1 Hz), 7.58 (1H, s), 8.64 (1H, d, J=5.0 Hz).

Present Compound 173

¹H-NMR (CDCl₃) δ: 2.09 (3H, s), 2.33 (3H, s), 2.52 (3H, s), 3.66 (3H, s), 5.07 (2H, s), 6.73 (1H, s), 7.15 (1H, s), 7.29-7.27 (1H, m), 7.35 (1H, dd, J=8.7, 4.4 Hz), 7.40-7.45 (3H, m), 8.52 (1H, d, J=2.7 Hz).

Present Compound 174

¹H-NMR (CDCl₃) δ: 2.10 (3H, s), 2.39 (3H, s), 2.52 (3H, s), 3.66 (3H, s), 5.08 (2H, s), 6.75 (1H, s), 7.23 (1H, s), 7.28 (1H, dd, J=7.3, 2.7 Hz), 7.39-7.47 (2H, m), 7.51 (1H, dd, J=8.2, 0.8 Hz), 7.96 (1H, dd, J=8.2, 2.3 Hz), 8.93 (1H, dd, J=2.3, 0.8 Hz).

Present Compound 175

¹H-NMR (CDCl₃) δ: 2.17 (3H, s), 2.34 (3H, s), 3.70 (3H, s), 5.19 (2H, s), 6.68 (1H, s), 7.22 (1H, s), 7.24 (1H, d, J=7.7 Hz), 7.28 (1H, d, J=7.7 Hz), 7.47-7.57 (3H, m), 7.66 (1H, t, J=7.7 Hz), 7.71 (1H, d, J=7.1 Hz).

Present Compound 176

¹H-NMR (CDCl₃) δ: 2.01 (3H, s), 2.36 (3H, s), 3.64 (3H, s), 5.34 (2H, s), 6.74 (1H, s), 7.17 (1H, s), 7.23 (1H, dd, J=7.9, 0.9 Hz), 7.27 (1H, dd, J=7.9, 0.9 Hz), 7.41 (1H, dd, J=8.0, 1.5 Hz), 7.47 (1H, t, J=8.0 Hz), 7.62 (1H, dd, J=8.0, 1.5 Hz), 7.66 (1H, t, J=7.9 Hz).

Present Compound 177

¹H-NMR (CDCl₃) δ: 2.02 (3H, s), 2.34 (3H, s), 3.63 (3H, s), 5.34 (2H, s), 6.75 (1H, s), 7.17-7.21 (2H, m), 7.35 (1H, d, J=7.9 Hz), 7.41 (1H, dd, J=7.9, 1.2 Hz), 7.47 (1H, t, J=8.0 Hz), 7.62 (1H, dd, J=7.9, 1.4 Hz), 7.70 (1H, td, J=7.6, 1.9 Hz), 8.66 (1H, d, J=4.8 Hz).

Present Compound 178

¹H-NMR (CDCl₃) δ: 2.01 (3H, s), 2.33 (3H, s), 2.36 (3H, s), 3.63 (3H, s), 5.34 (2H, s), 6.73 (1H, s), 7.15 (1H, s), 7.25 (1H, d, J=8.2 Hz), 7.40 (1H, dd, J=8.2, 2.0 Hz), 7.47 (1H, t, J=8.4 Hz), 7.51 (1H, dd, J=8.2, 2.3 Hz), 7.62 (1H, dd, J=7.9, 1.4 Hz), 8.48 (1H, dd, J=1.5, 0.8 Hz).

Present Compound 179

¹H-NMR (CDCl₃) δ: 2.08 (3H, s), 2.22 (3H, s), 2.52 (3H, s), 3.66 (3H, s), 5.07 (2H, s), 6.75 (1H, s), 7.13 (1H, s), 7.28-7.30 (1H, m), 7.48-7.37 (4H, m), 8.49 (1H, d, J=4.8 Hz).

Present Compound 180

¹H-NMR (CDCl₃) δ: 2.09 (3H, s), 2.36 (3H, s), 2.52 (3H, s), 3.66 (3H, s), 5.07 (2H, s), 6.73 (1H, s), 6.93-6.97 (1H, m), 7.09 (1H, dd, J=10.0, 2.0 Hz), 7.18 (1H, s), 7.28 (1H, t, J=3.3 Hz), 7.41-7.43 (2H, m), 8.62 (1H, dd, J=8.7, 5.8 Hz).

Present Compound 181

¹H-NMR (CDCl₃) δ: 2.10 (3H, s), 2.37 (3H, s), 2.52 (3H, s), 3.66 (3H, s), 5.08 (2H, s), 6.75 (1H, s), 6.99 (1H, s), 7.20 (1H, s), 7.28-7.31 (1H, m), 7.41-7.44 (2H, m), 7.58 (1H, s), 8.84 (1H, d, J=5.2 Hz).

Present Compound 182

¹H-NMR (CDCl₃) δ: 2.10 (3H, s), 2.37 (3H, s), 2.52 (3H, s), 3.66 (3H, s), 5.08 (2H, s), 6.75 (1H, s), 7.21 (1H, s), 7.27-7.30 (1H, m), 7.39-7.53 (3H, m), 7.62 (1H, d, J=0.9 Hz), 7.94 (1H, dd, J=8.4, 2.0 Hz).

Present Compound 183

¹H-NMR (CDCl₃) δ: 2.07 (3H, s), 2.35 (3H, s), 2.38 (3H, s), 2.51 (3H, s), 3.66 (3H, s), 5.06 (2H, s), 6.71 (1H, s), 7.08 (1H, s), 7.08 (1H, s), 7.15 (1H, s), 7.28 (1H, dd, J=6.9, 2.5 Hz), 7.38-7.46 (2H, m).

Present Compound 184

¹H-NMR (CDCl₃) δ: 2.14 (3H, s), 2.36 (3H, s), 2.50 (3H, s), 3.61 (3H, s), 5.08 (2H, s), 6.88 (1H, d, J=8.2 Hz), 7.01 (1H, s), 7.27 (1H, dd, J=7.0, 2.3 Hz), 7.36-7.45 (3H, m), 7.78-7.72 (2H, m).

Present Compound 185

¹H-NMR (CDCl₃) δ: 2.16 (3H, s), 2.52 (3H, s), 3.63 (3H, s), 5.09 (2H, s), 6.91 (1H, d, J=8.7 Hz), 7.28 (1H, d, J=6.9 Hz), 7.39-7.46 (3H, m), 7.74-7.61 (3H, m), 8.49 (1H, s).

Present Compound 186

¹H-NMR (CDCl₃) δ: 2.08 (3H, s), 2.33 (3H, s), 2.52 (3H, s), 3.66 (3H, s), 3.90 (3H, d, J=4.4 Hz), 5.06 (2H, s), 6.72 (1H, s), 7.16 (1H, s), 7.23 (1H, dd, J=8.6, 2.9 Hz), 7.27-7.30 (2H, m), 7.46-7.39 (2H, m), 8.37 (1H, dd, J=3.0, 0.7 Hz).

Present Compound 187

¹H-NMR (CDCl₃) δ: 2.31 (3H, s), 2.54 (3H, s), 3.68 (3H, s), 5.16 (2H, s), 6.83 (1H, d, J=8.2 Hz), 7.15 (1H, d, J=11.9 Hz), 7.23 (1H, t, J=5.6 Hz), 7.28 (1H, dd, J=7.8, 2.3 Hz), 7.34 (1H, d, J=7.8 Hz), 7.38-7.44 (2H, m), 7.72 (1H, t, J=7.8 Hz), 8.66 (1H, d, J=5.0 Hz).

Present Compound 188

¹H-NMR (CDCl₃) δ: 2.08 (3H, s), 2.34 (3H, s), 2.51 (3H, s), 3.65 (3H, s), 3.87 (3H, s), 5.05 (2H, s), 6.72 (1H, s), 6.74 (1H, dd, J=5.9, 2.5 Hz), 6.86 (1H, d, J=2.5 Hz), 7.17 (1H, s), 7.27 (1H, dd, J=6.8, 2.9 Hz), 7.45-7.38 (2H, m), 8.47 (1H, d, J=5.7 Hz).

Present Compound 189

¹H-NMR (CDCl₃) δ: 2.32 (3H, s), 2.54 (3H, s), 3.69 (3H, s), 5.16 (2H, s), 6.81 (1H, d, J=8.4 Hz), 7.15 (1H, d, J=11.8 Hz), 7.24-7.33 (3H, m), 7.37-7.46 (2H, m), 7.69 (1H, t, J=7.7 Hz).

Present Compound 190

¹H-NMR (CDCl₃) δ: 2.32 (3H, s), 2.55 (3H, s), 3.68 (3H, s), 5.19 (2H, s), 6.78 (1H, s), 7.23 (1H, ddd, J=7.6, 4.9, 1.1 Hz), 7.29 (1H, dd, J=7.2, 1.9 Hz), 7.34 (1H, dt, J=7.7, 1.0 Hz), 7.38-7.44 (3H, m), 7.72 (1H, td, J=7.7, 1.9 Hz), 8.66 (1H, dq, J=4.8, 0.9 Hz).

Present Compound 191

¹H-NMR (CDCl₃) δ: 2.34 (3H, s), 2.54 (3H, s), 3.68 (3H, s), 5.18 (2H, s), 6.76 (1H, s), 7.26 (1H, d, J=1.4 Hz), 7.28 (1H, s), 7.29 (1H, dd, J=7.9, 2.6 Hz), 7.37-7.45 (3H, m), 7.69 (1H, t, J=7.9 Hz).

Present Compound 192

¹H-NMR (CDCl₃) δ: 2.08 (3H, s), 2.10 (3H, s), 2.53 (3H, s), 3.68 (3H, s), 3.84 (3H, s), 5.05 (2H, s), 6.77 (1H, s), 6.87 (1H, d, J=5.7 Hz), 6.92 (1H, s), 7.27 (1H, dd, J=6.8, 2.9 Hz), 7.46-7.40 (2H, m), 8.25 (1H, s), 8.48 (1H, d, J=5.7 Hz).

Present Compound 193

¹H-NMR (CDCl₃) δ: 2.07 (3H, s), 2.12 (3H, s), 2.53 (3H, s), 3.68 (3H, s), 3.93 (3H, s), 5.05 (2H, s), 6.75 (1H, s), 6.91 (1H, s), 6.94 (1H, dd, J=7.0, 5.0 Hz), 7.27 (1H, dd, J=6.3, 2.5 Hz), 7.40-7.44 (3H, m), 8.17 (1H, dd, J=5.0, 1.8 Hz).

Present Compound 194

¹H-NMR (CDCl₃) δ: 2.10 (3H, s), 2.51 (3H, s), 3.65 (3H, d, J=5.9 Hz), 5.07 (2H, s), 6.67 (1H, d, J=13.1 Hz), 7.16-7.21 (1H, m), 7.30 (1H, dd, J=7.1, 2.2 Hz), 7.47-7.39 (2H, m), 7.70-7.77 (3H, m), 8.67-8.68 (1H, m).

Present Compound 195

¹H-NMR (CDCl₃) δ: 2.10 (3H, s), 2.51 (3H, s), 3.65 (3H, s), 5.06 (2H, s), 6.66 (1H, d, J=12.9 Hz), 7.30 (1H, dd, J=7.1, 1.7 Hz), 7.39-7.48 (3H, m), 7.77-7.69 (2H, m), 8.52 (1H, d, J=2.7 Hz).

Present Compound 196

¹H-NMR (CDCl₃) δ: 2.55 (3H, s), 2.56 (3H, s), 3.68 (3H, s), 5.22 (2H, s), 6.79 (1H, s), 7.31 (1H, dd, J=7.1, 1.7 Hz), 7.47-7.38 (2H, m), 7.96 (1H, s), 8.75 (2H, s).

Present Compound 197

¹H-NMR (CDCl₃) δ: 2.17 (3H, s), 2.52 (3H, s), 3.62 (3H, s), 5.13 (2H, s), 6.94 (1H, d, J=8.6 Hz), 7.29 (1H, dd, J=6.9, 2.2 Hz), 7.38 (1H, d, J=5.0 Hz), 7.40-7.46 (2H, m), 8.21 (1H, d, J=1.6 Hz), 8.26 (1H, dd, J=8.5, 1.9 Hz), 8.90 (1H, dd, J=3.3, 2.4 Hz).

Present Compound 198

¹H-NMR (CDCl₃) δ: 2.23 (3H, s), 2.57 (3H, s), 3.70 (3H, s), 5.21 (2H, s), 6.82 (1H, s), 7.18 (1H, s), 7.31 (1H, dd, J=7.2, 1.8 Hz), 7.40-7.46 (2H, m), 7.75 (2H, t, J=0.9 Hz), 8.65 (1H, t, J=1.6 Hz).

Present Compound 199

¹H-NMR (CDCl₃) δ: 2.16 (3H, s), 2.52 (3H, s), 3.63 (3H, s), 5.12 (2H, s), 6.93 (1H, d, J=8.6 Hz), 7.29 (1H, d, J=7.0 Hz), 7.40-7.47 (2H, m), 8.16 (1H, s), 8.21 (1H, d, J=8.6 Hz), 8.77 (2H, s).

Present Compound 200

¹H-NMR (CDCl₃) δ: 2.09 (3H, s), 2.25 (3H, s), 2.53 (3H, s), 3.66 (3H, s), 5.07 (2H, s), 6.75 (1H, s), 6.95 (1H, s), 7.28 (1H, dd, J=6.8, 2.5 Hz), 7.46-7.39 (2H, m), 7.76 (1H, t, J=2.2 Hz), 8.46 (1H, d, J=1.8 Hz), 8.61 (1H, d, J=2.3 Hz).

Present Compound 201

¹H-NMR (CDCl₃) δ: 2.30 (3H, s), 3.71 (3H, s), 3.87 (3H, s), 5.29 (2H, s), 6.77 (1H, dd, J=5.9, 2.5 Hz), 6.79 (1H, s), 6.84 (1H, d, J=2.5 Hz), 7.40 (1H, s), 7.56-7.48 (3H, m), 7.75 (1H, t, J=3.7 Hz), 8.47 (1H, d, J=5.9 Hz).

Production Example 22

To a mixture of 0.87 g of the present compound 97 mentioned in Production Example 2 and 15 mL of acetic acid, a 30% hydrogen peroxide solution was added, followed by stirring at room temperature for 4 hours. The mixture was further stirred at 50° C. for 3 hours. After cooling to room temperature, the mixture was neutralized by adding an aqueous magnesium sulfite solution and further adding a sodium bicarbonate solution. A liquid separating operation was performed by adding ethyl acetate, and then the organic layer was dried over anhydrous sodium sulfate. The organic layer was concentrated under reduced pressure and then subjected to silica gel chromatography to obtain 0.45 g of 1-{2-[2-methyl-4-(6-methylpyrimidin-2-yl)-phenoxymethyl]-3-methylsulfonyl phenyl}-4-methyl-1,4-dihydrotetrazol-5-one (hereinafter referred to as the present compound 124) and 0.32 g of 1-{2-[2-methyl-4-(6-methylpyrimidin-2-yl)-phenoxymethyl]-3-methylsulfinylphenyl}-4-methyl-1,4-dihydrotetrazol-5-one (hereinafter referred to as the present compound 125).

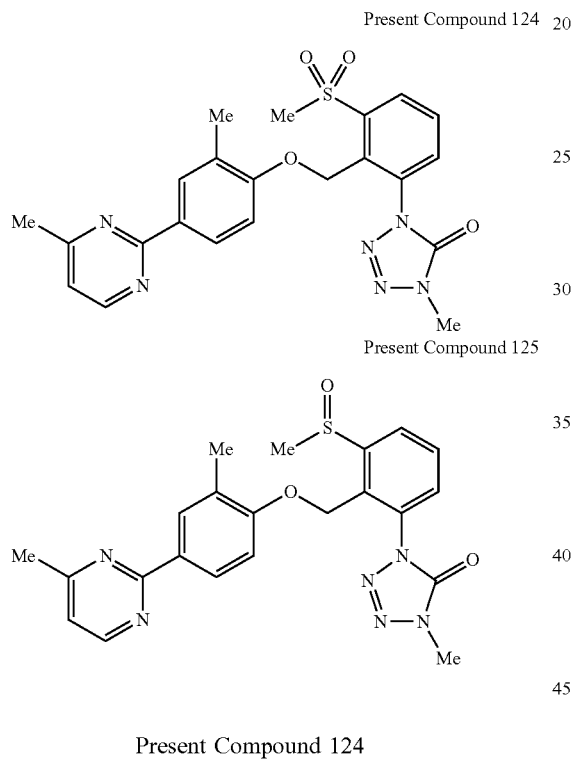

Present Compound 124

Present Compound 125

Present Compound 124

$^1$H-NMR (CDCl$_3$) δ: 2.12 (3H, s), 2.57 (3H, s), 3.20 (3H, s), 3.53 (3H, s), 5.69 (2H, s), 7.01 (1H, d, J=5.0 Hz), 7.02 (1H, d, J=8.5 Hz), 7.84-7.75 (2H, m), 8.20 (1H, s), 8.26 (1H, dd, J=8.7, 1.6 Hz), 8.39 (1H, dd, J=7.0, 2.4 Hz), 8.60 (1H, d, J=5.0 Hz).

Present Compound 125

$^1$H-NMR (CDCl$_3$) δ: 2.16 (3H, s), 2.57 (3H, s), 2.82 (3H, s), 3.62 (3H, s), 5.15 (1H, d, J=11.7 Hz), 5.31 (1H, d, J=11.7 Hz), 6.92 (1H, d, J=8.5 Hz), 7.01 (1H, d, J=5.0 Hz), 7.65 (1H, dd, J=8.0, 1.2 Hz), 7.84 (1H, t, J=8.0 Hz), 8.21 (1H, d, J=1.6 Hz), 8.25 (1H, dd, J=8.5, 2.3 Hz), 8.33 (1H, dd, J=8.0, 1.2 Hz), 8.60 (1H, d, J=5.0 Hz).

Production Example 23

Using the compounds mentioned in Reference Production Examples, the following present compounds were synthesized by the same reaction as in Production Example 1. Structural formulas and $^1$H-NMR data of the thus obtained present compounds are shown below.

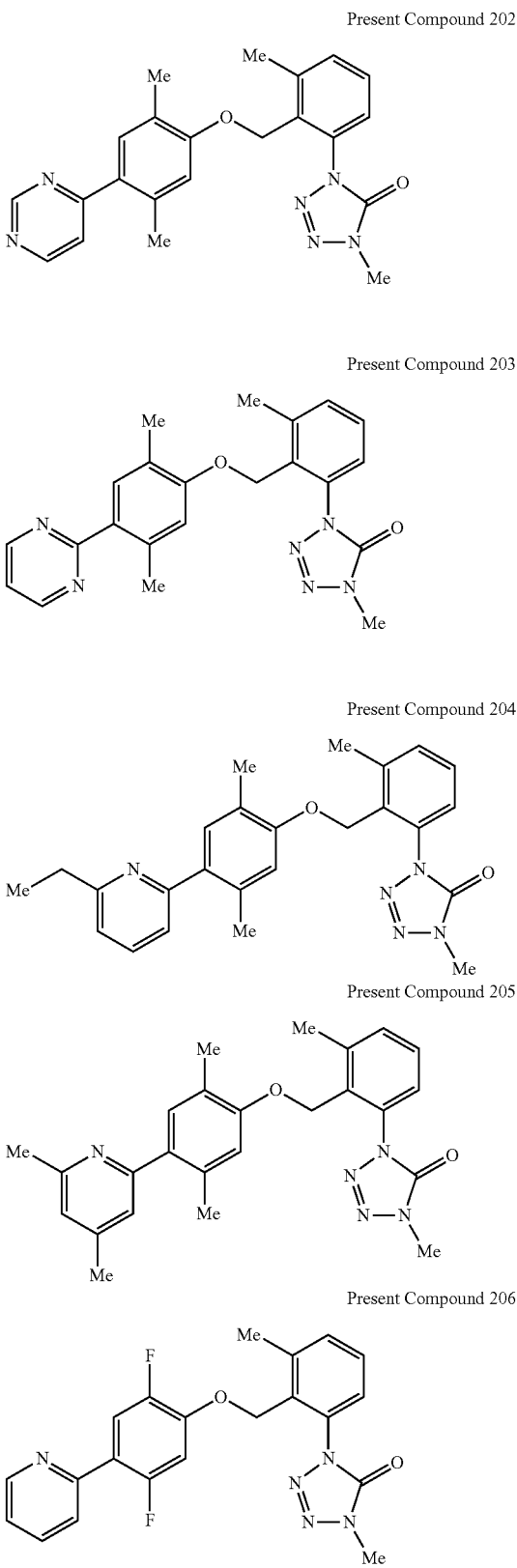

Present Compound 202

Present Compound 203

Present Compound 204

Present Compound 205

Present Compound 206

Present Compound 207
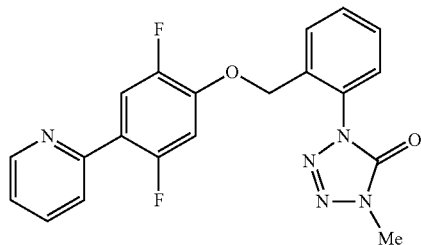
Present Compound 208
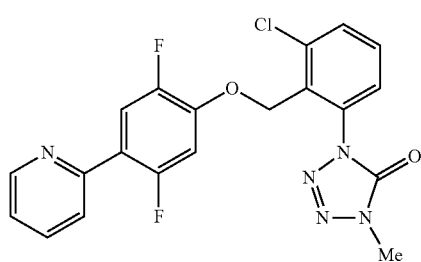
Present Compound 209
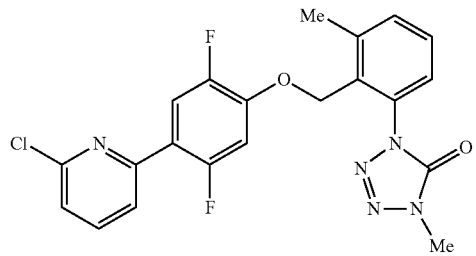
Present Compound 210
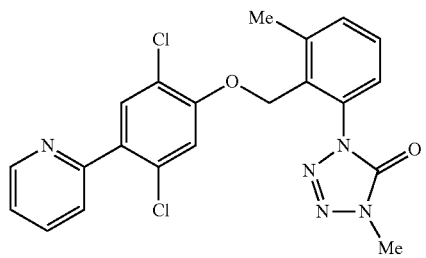
Present Compound 211
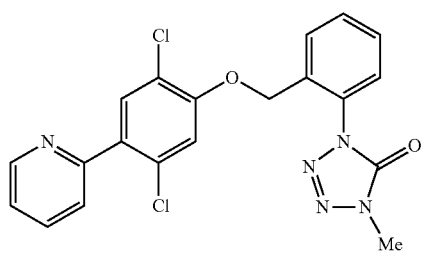
Present Compound 212
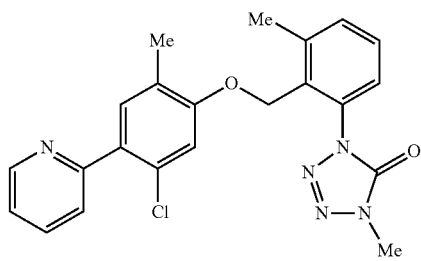
Present Compound 213
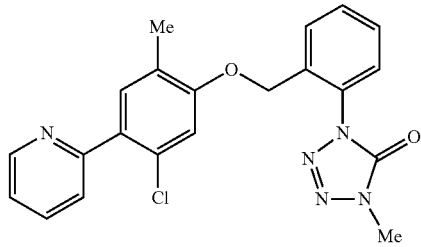
Present Compound 214
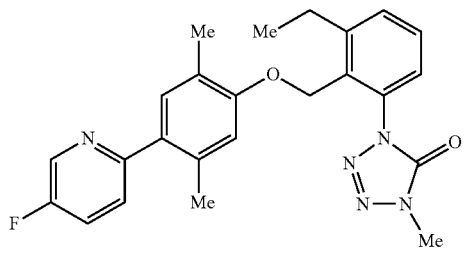
Present Compound 215
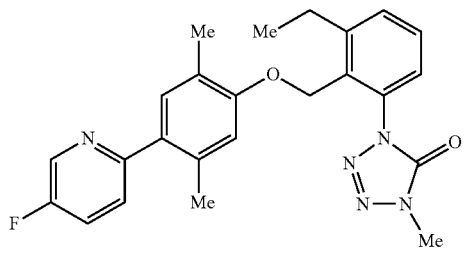
Present Compound 216
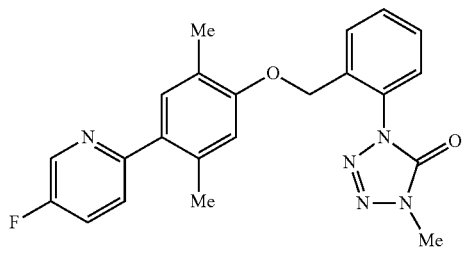

Present Compound 217
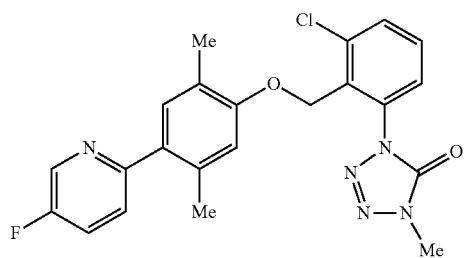
Present Compound 218
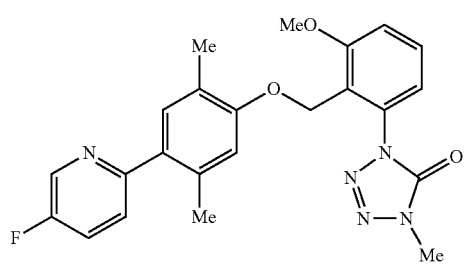
Present Compound 219
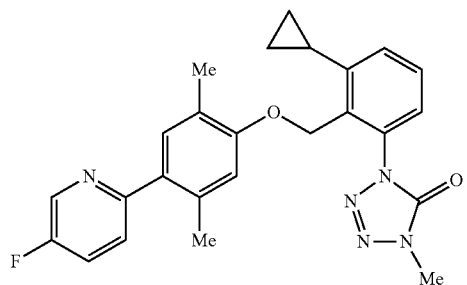
Present Compound 220
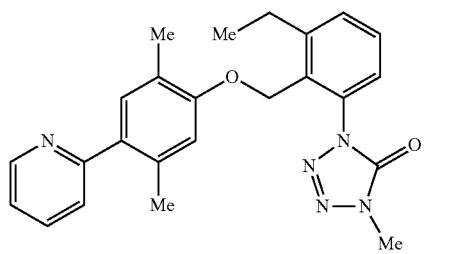
Present Compound 221
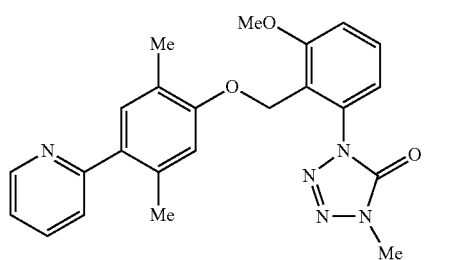
Present Compound 222
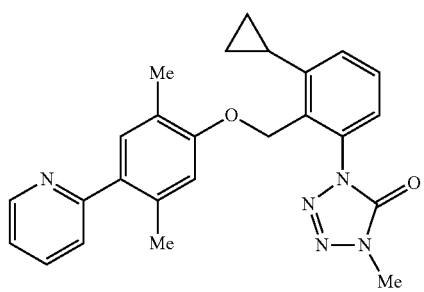
Present Compound 223
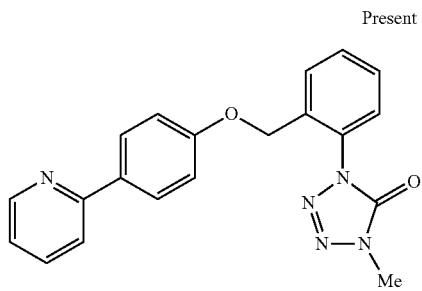
Present Compound 224
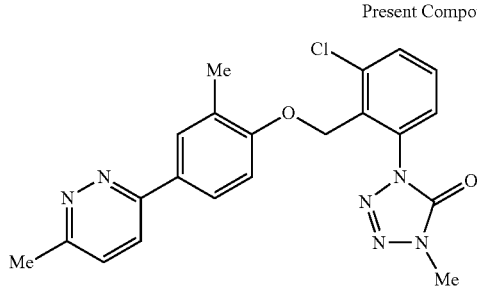
Present Compound 225
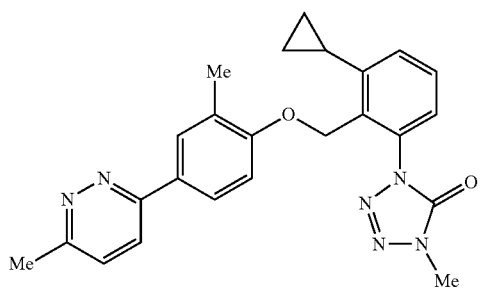
Present Compound 226
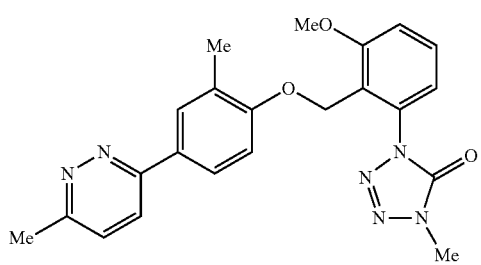

Present Compound 227

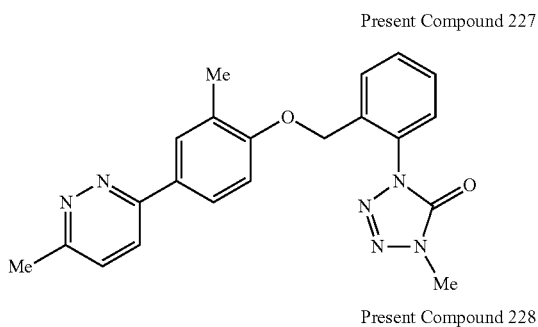

Present Compound 228

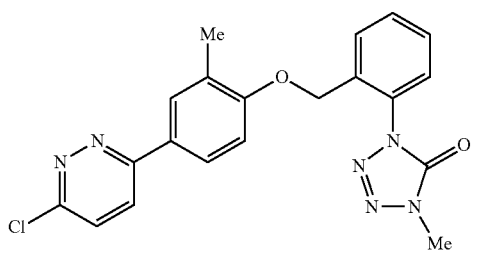

Present Compound 229

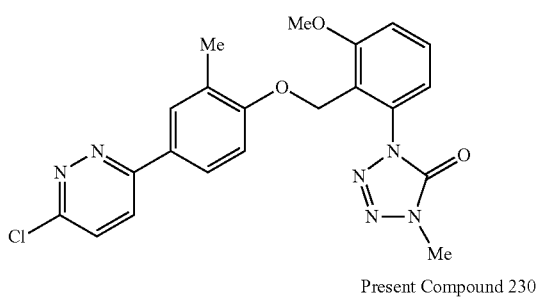

Present Compound 230

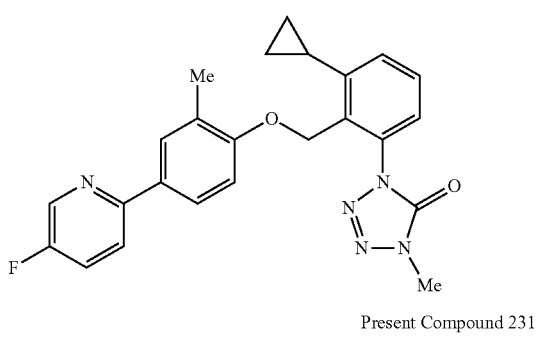

Present Compound 231

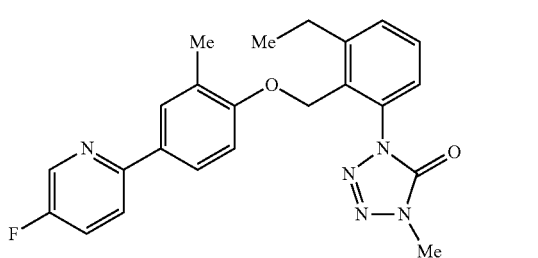

Present Compound 202

¹H-NMR (CDCl₃) δ: 2.04 (3H, s), 2.33 (3H, s), 2.51 (3H, s), 3.65 (3H, s), 5.00 (2H, s), 6.63 (1H, s), 7.00 (1H, s), 7.23-7.28 (3H, m), 7.44-7.38 (2H, m), 8.12 (1H, s).

Present Compound 203

¹H-NMR (CDCl₃) δ: 2.10 (3H, s), 2.51 (3H, s), 2.56 (3H, s), 3.65 (3H, s), 5.09 (2H, s), 6.74 (1H, s), 7.15 (1H, t, J=4.8 Hz), 7.26-7.29 (1H, m), 7.39-7.44 (2H, m), 7.64 (1H, s), 8.80 (2H, d, J=4.8 Hz).

Present Compound 204

¹H-NMR (CDCl₃) δ: 1.33 (3H, t, J=7.6 Hz), 2.08 (3H, s), 2.34 (3H, s), 2.51 (3H, s), 2.86 (2H, q, J=7.6 Hz), 3.67 (3H, s), 5.05 (2H, s), 6.73 (1H, s), 7.06 (1H, dd, J=7.7, 0.9 Hz), 7.15 (1H, dd, J=7.7, 0.9 Hz), 7.16 (1H, s), 7.27 (1H, dd, J=7.0, 2.7 Hz), 7.39-7.45 (2H, m), 7.61 (1H, t, J=7.7 Hz).

Present Compound 205

¹H-NMR (CDCl₃) δ: 2.07 (3H, s), 2.31 (3H, s), 2.33 (3H, s), 2.51 (3H, s), 2.54 (3H, s), 3.66 (3H, s), 5.05 (2H, s), 6.71 (1H, s), 6.90 (1H, s), 6.96 (1H, s), 7.13 (1H, s), 7.27 (1H, dd, J=6.9, 2.6 Hz), 7.37-7.45 (2H, m).

Present Compound 206

¹H-NMR (CDCl₃) δ: 2.54 (3H, s), 3.69 (3H, s), 5.17 (2H, s), 6.76 (1H, dd, J=12.0, 6.8 Hz), 7.23 (1H, ddd, J=7.2, 4.8, 1.5 Hz), 7.31 (1H, dd, J=7.4, 1.7 Hz), 7.46-7.39 (2H, m), 7.71-7.83 (3H, m), 8.68 (1H, dq, J=4.8, 0.9 Hz).

Present Compound 207

¹H-NMR (CDCl₃) δ: 3.72 (3H, s), 5.28 (2H, s), 6.77 (1H, dd, J=12.1, 6.9 Hz), 7.23 (1H, ddd, J=7.1, 4.8, 1.5 Hz), 7.51-7.57 (3H, m), 7.69-7.71 (1H, m), 7.73-7.78 (2H, m), 7.83 (1H, dd, J=12.0, 7.2 Hz), 8.68 (1H, dq, J=4.9, 0.9 Hz).

Present Compound 208

¹H-NMR (CDCl₃) δ: 3.67 (3H, s), 5.47 (2H, s), 6.78 (1H, dd, J=11.9, 6.9 Hz), 7.20-7.25 (1H, m), 7.41-7.51 (2H, m), 7.61 (1H, d, J=7.9 Hz), 7.82-7.70 (3H, m), 8.67 (1H, d, J=4.8 Hz).

Present Compound 209

¹H-NMR (CDCl₃) δ: 2.54 (3H, s), 3.70 (3H, s), 5.18 (2H, s), 6.75 (1H, dd, J=12.3, 6.8 Hz), 7.25-7.27 (1H, m), 7.31 (1H, dd, J=7.4, 1.5 Hz), 7.40-7.47 (2H, m), 7.66-7.75 (2H, m), 7.86 (1H, dd, J=12.1, 7.3 Hz).

Present Compound 210

¹H-NMR (CDCl₃) δ: 2.55 (3H, s), 3.69 (3H, s), 5.20 (2H, s), 7.01 (1H, s), 7.26-7.33 (2H, m), 7.47-7.39 (2H, m), 7.63-7.65 (2H, m), 7.73-7.77 (1H, m), 8.69-8.70 (1H, m).

Present Compound 211

¹H-NMR (CDCl₃) δ: 3.72 (3H, s), 5.31 (2H, s), 7.03 (1H, s), 7.26-7.30 (1H, m), 7.52-7.58 (3H, m), 7.64 (1H, d, J=7.9 Hz), 7.67 (1H, s), 7.72-7.78 (2H, m), 8.70 (1H, d, J=4.3 Hz).

Present Compound 212

¹H-NMR (CDCl₃) δ: 3.67 (3H, s), 5.54 (2H, s), 7.05 (1H, s), 7.28 (1H, ddd, J=7.5, 4.8, 0.9 Hz), 7.47-7.52 (2H, m), 7.59-7.66 (3H, m), 7.75 (1H, td, J=7.7, 1.8 Hz), 8.69 (1H, d, J=4.9 Hz).

Present Compound 213

¹H-NMR (CDCl₃) δ: 2.09 (3H, s), 2.52 (3H, s), 3.67 (3H, s), 5.07 (2H, s), 6.93 (1H, s), 7.23-7.30 (2H, m), 7.39-7.45 (3H, m), 7.64-7.73 (2H, m), 8.69 (1H, d, J=3.5 Hz).

Present Compound 214

¹H-NMR (CDCl₃) δ: 2.18 (3H, s), 3.70 (3H, s), 5.20 (2H, s), 6.91 (1H, s), 7.21-7.26 (1H, m), 7.42 (1H, s), 7.48-7.58 (3H, m), 7.62-7.76 (3H, m), 8.69 (1H, d, J=4.5 Hz).

Present Compound 215

¹H-NMR (CDCl₃) δ: 1.26 (3H, t, J=7.6 Hz), 2.05 (3H, s), 2.31 (3H, s), 2.83 (2H, q, J=7.6 Hz), 3.61 (3H, s), 5.05 (2H, s), 6.72 (1H, s), 7.12 (1H, s), 7.26 (1H, dd, J=7.0, 1.8 Hz), 7.33 (1H, ddd, J=8.6, 4.4, 0.6 Hz), 7.39-7.48 (3H, m), 8.49 (1H, d, J=2.7 Hz).

Present Compound 216

¹H-NMR (CDCl₃) δ: 2.15 (3H, s), 2.28 (3H, s), 3.68 (3H, s), 5.16 (2H, s), 6.67 (1H, s), 7.15 (1H, s), 7.33 (1H, ddd, J=8.7, 4.5, 0.6 Hz), 7.41 (1H, td, J=8.4, 2.9 Hz), 7.47-7.55 (3H, m), 7.70 (1H, d, J=7.2 Hz), 8.49 (1H, d, J=2.9 Hz).

Present Compound 217

¹H-NMR (CDCl₃) δ: 2.00 (3H, s), 2.30 (3H, s), 3.62 (3H, s), 5.32 (2H, s), 6.73 (1H, s), 7.11 (1H, s), 7.50-7.28 (4H, m), 7.59-7.61 (1H, m), 8.49 (1H, d, J=2.9 Hz).

Present Compound 218

¹H-NMR (CDCl₃) δ: 1.99 (3H, s), 2.31 (3H, s), 3.62 (3H, s), 3.94 (3H, s), 5.29 (2H, s), 6.78 (1H, s), 7.07-7.10 (3H, m), 7.33 (1H, dd, J=8.7, 4.6 Hz), 7.42 (1H, td, J=8.4, 2.8 Hz), 7.47 (1H, t, J=8.1 Hz), 8.50 (1H, d, J=3.0 Hz).

Present Compound 219

¹H-NMR (CDCl₃) δ: 0.75-0.80 (2H, m), 0.97-1.03 (2H, m), 2.07 (3H, s), 2.13-2.15 (1H, m), 2.34 (3H, s), 3.65 (3H, s), 5.28 (2H, s), 6.77 (1H, s), 7.15 (1H, s), 7.26 (1H, s), 7.28 (1H, s), 7.36 (1H, dd, J=8.6, 4.5 Hz), 7.41-7.46 (2H, m), 8.52 (1H, d, J=2.7 Hz).

Present Compound 220

¹H-NMR (CDCl₃) δ: 1.29 (3H, t, J=7.6 Hz), 2.07 (3H, s), 2.36 (3H, s), 2.86 (2H, q, J=7.6 Hz), 3.64 (3H, dd, J=4.5, 1.4 Hz), 5.08 (2H, s), 6.74 (1H, s), 7.18-7.21 (2H, m), 7.28 (1H, d, J=7.0 Hz), 7.36 (1H, dd, J=7.8, 1.0 Hz), 7.43-7.52 (2H, m), 7.69-7.73 (1H, m), 8.67 (1H, dd, J=4.9, 1.0 Hz).

Present Compound 221

¹H-NMR (CDCl₃) δ: 1.99 (3H, s), 2.33 (3H, s), 3.62 (3H, s), 3.94 (3H, s), 5.29 (2H, s), 6.78 (1H, s), 7.11-7.06 (2H, m), 7.15 (1H, s), 7.17-7.20 (1H, m), 7.35 (1H, d, J=7.9 Hz), 7.47 (1H, t, J=8.3 Hz), 7.69 (1H, t, J=8.3 Hz), 8.65 (1H, d, J=5.9 Hz).

Present Compound 222

¹H-NMR (CDCl₃) δ: 0.75-0.80 (2H, m), 0.98-1.03 (2H, m), 2.08 (3H, s), 2.12-2.17 (1H, m), 2.36 (3H, s), 3.65 (3H, d, J=3.9 Hz), 5.29 (2H, s), 6.78 (1H, s), 7.18-7.22 (2H, m), 7.29-7.26 (2H, m), 7.36 (1H, dt, J=7.7, 0.9 Hz), 7.44 (1H, t, J=7.7 Hz), 7.71 (1H, td, J=7.7, 1.8 Hz), 8.67 (1H, dd, J=4.8, 0.9 Hz).

Present Compound 223

¹H-NMR (CDCl₃) δ: 3.67 (3H, s), 5.21 (2H, s), 6.97 (2H, dd, J=6.8, 2.0 Hz), 7.18 (1H, ddd, J=7.4, 4.9, 1.2 Hz), 7.49-7.56 (3H, m), 7.64-7.74 (3H, m), 7.91 (2H, dd, J=6.8, 2.0 Hz), 8.65 (1H, dq, J=4.8, 0.9 Hz).

Present Compound 224

¹H-NMR (CDCl₃) δ: 2.11 (3H, s), 2.73 (3H, s), 3.60 (3H, s), 5.39 (2H, s), 6.96 (1H, d, J=8.4 Hz), 7.33 (1H, d, J=8.8 Hz), 7.41 (1H, dd, J=8.0, 1.3 Hz), 7.48 (1H, t, J=8.0 Hz), 7.63 (1H, dd, J=8.0, 1.3 Hz), 7.68 (1H, d, J=8.8 Hz), 7.82 (1H, dd, J=8.4, 2.3 Hz), 7.85 (1H, s).

Present Compound 225

¹H-NMR (CDCl₃) δ: 0.75-0.82 (2H, m), 0.98-1.05 (2H, m), 2.09-2.16 (1H, m), 2.17 (3H, s), 2.74 (3H, s), 3.61 (3H, s), 5.34 (2H, s), 7.01 (1H, d, J=8.9 Hz), 7.29 (1H, d, J=7.8 Hz), 7.30 (1H, s), 7.34 (1H, d, J=8.7 Hz), 7.45 (1H, t, J=7.8 Hz), 7.69 (1H, d, J=8.7 Hz), 7.88-7.84 (2H, m).

Present Compound 226

¹H-NMR (CDCl₃) δ: 2.08 (3H, s), 2.73 (3H, s), 3.60 (3H, s), 3.95 (3H, s), 5.34 (2H, s), 7.00 (1H, d, J=9.3 Hz), 7.07-7.11 (2H, m), 7.32 (1H, d, J=8.8 Hz), 7.48 (1H, t, J=8.2 Hz), 7.67 (1H, d, J=8.8 Hz), 7.81 (1H, dd, J=6.8, 2.0 Hz), 7.82 (1H, s).

Present Compound 227

¹H-NMR (CDCl₃) δ: 2.28 (3H, s), 2.73 (3H, s), 3.68 (3H, s), 5.24 (2H, s), 6.92 (1H, d, J=8.6 Hz), 7.33 (1H, d, J=8.8 Hz), 7.57-7.48 (3H, m), 7.68 (1H, d, J=8.8 Hz), 7.72 (1H, d, J=7.7 Hz), 7.80 (1H, dd, J=8.6, 2.3 Hz), 7.91 (1H, d, J=2.3 Hz).

Present Compound 228

¹H-NMR (CDCl₃) δ: 2.27 (3H, s), 3.68 (3H, s), 5.25 (2H, s), 6.92 (1H, d, J=8.4 Hz), 7.25-7.27 (1H, m), 7.49-7.57 (3H, m), 7.64 (1H, d, J=1.4 Hz), 7.71 (1H, d, J=7.0 Hz), 7.79 (1H, dd, J=8.6, 2.4 Hz), 7.89 (1H, d, J=2.4 Hz).

Present Compound 229

¹H-NMR (CDCl₃) δ: 2.08 (3H, s), 3.61 (3H, s), 3.95 (3H, s), 5.36 (2H, s), 7.00 (1H, d, J=8.9 Hz), 7.10 (2H, t, J=8.6 Hz), 7.49 (1H, t, J=8.1 Hz), 7.63 (2H, br s), 7.80-7.81 (2H, m).

Present Compound 230

¹H-NMR (CDCl₃) δ: 0.75-0.80 (2H, m), 0.98-1.01 (2H, m), 2.11-2.15 (4H, m), 3.60 (3H, s), 5.32 (2H, s), 6.96 (1H, d, J=8.4 Hz), 7.27 (2H, dd, J=8.4, 1.0 Hz), 7.39-7.46 (2H, m), 7.64 (1H, dd, J=8.8, 4.3 Hz), 7.74-7.68 (2H, m), 8.49 (1H, d, J=2.9 Hz).

Present Compound 231

¹H-NMR (CDCl₃) δ: 1.29 (3H, t, J=7.6 Hz), 2.15 (3H, s), 2.86 (2H, q, J=7.6 Hz), 3.59 (3H, s), 5.11 (2H, s), 6.93 (1H, d, J=8.4 Hz), 7.29 (1H, dd, J=7.1, 1.7 Hz), 7.51-7.39 (3H, m), 7.64 (H, dd, J=8.7, 4.2 Hz), 7.68-7.73 (2H, m), 8.49 (1H, d, J=2.9 Hz).

Production Example 24

The reaction was performed in the same manner as in Production Example 12 to synthesize the following present compounds. The structural formulas and ¹H-NMR data of the thus obtained present compounds are shown below.

Present Compound 232

Present Compound 233

Present Compound 234

Present Compound 235

Present Compound 236

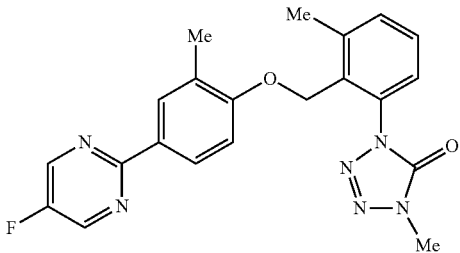

Present Compound 237

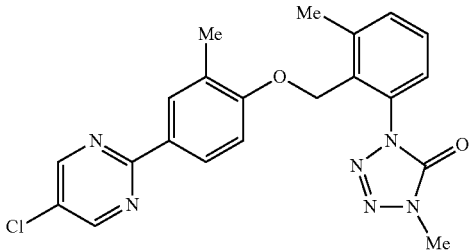

Present Compound 238

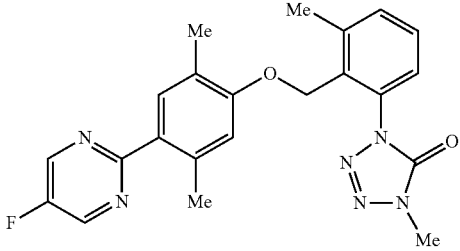

Present Compound 239

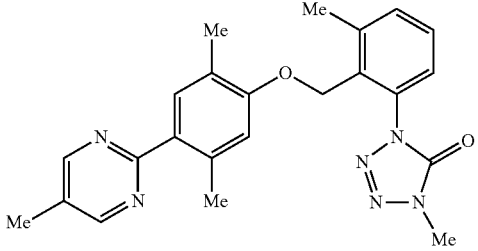

Present Compound 240

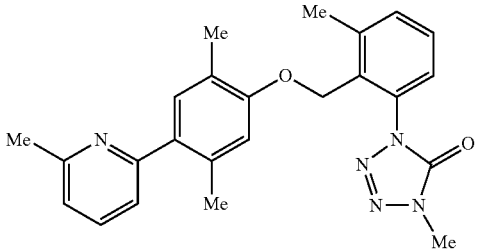

Present Compound 241

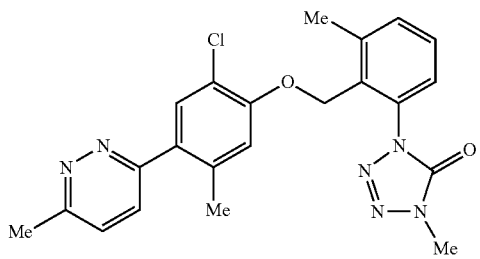

Present Compound 242

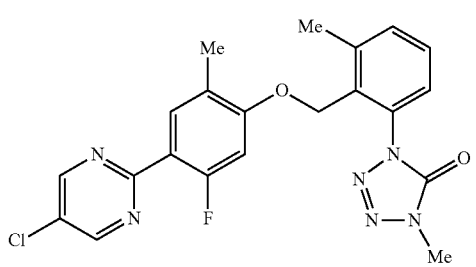

Present Compound 243

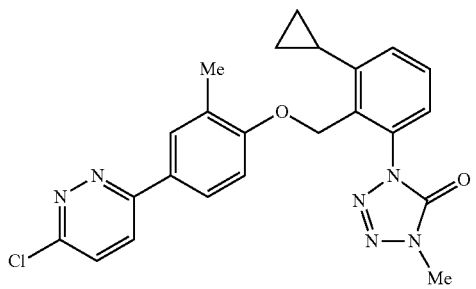

Present Compound 244

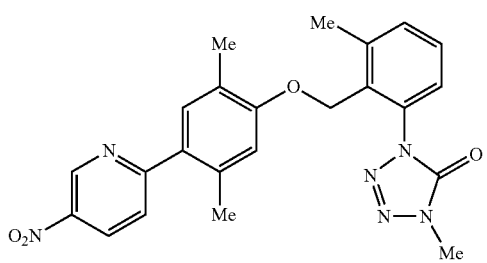

Present Compound 245

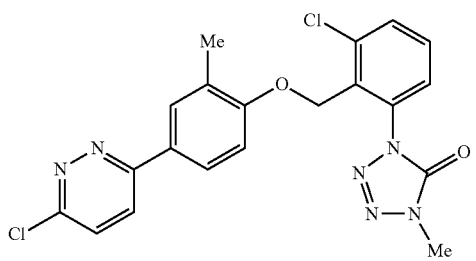

Present Compound 246

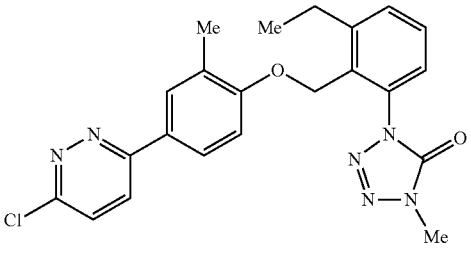

Present Compound 232

¹H-NMR (CDCl₃) δ: 2.10 (3H, s), 2.37 (3H, s), 2.52 (3H, s), 3.66 (3H, s), 5.09 (2H, s), 6.77 (1H, s), 7.20 (1H, s), 7.28 (1H, dd, J=6.8, 2.3 Hz), 7.39-7.45 (2H, m), 7.53-7.51 (2H, m).

Present Compound 233

¹H-NMR (CDCl₃) δ: 2.12 (3H, s), 2.52 (3H, s), 2.74 (3H, s), 3.66 (3H, s), 5.08 (2H, s), 6.67 (1H, d, J=13.3 Hz), 7.31 (1H, dd, J=7.2, 1.9 Hz), 7.34 (1H, d, J=8.9 Hz), 7.42-7.47 (2H, m), 7.80 (1H, dd, J=8.9, 1.9 Hz), 7.97 (1H, dd, J=8.9, 0.8 Hz).

Present Compound 234

¹H-NMR (CDCl₃) δ: 2.17 (3H, s), 2.52 (3H, s), 2.73 (3H, s), 3.62 (3H, s), 5.11 (2H, s), 6.96 (1H, d, J=8.2 Hz), 7.29 (1H, dd, J=6.9, 2.4 Hz), 7.33 (1H, d, J=8.8 Hz), 7.40-7.46 (2H, m), 7.68 (1H, d, J=8.6 Hz), 7.88-7.82 (2H, m).

Present Compound 235

¹H-NMR (CDCl₃) δ: 2.10 (3H, s), 2.37 (3H, s), 2.52 (3H, s), 2.75 (3H, s), 3.66 (3H, s), 5.09 (2H, s), 6.77 (1H, s), 7.20 (1H, s), 7.28 (1H, dd, J=6.6, 2.5 Hz), 7.34 (1H, d, J=8.6 Hz), 7.46-7.39 (3H, m).

Present Compound 236

¹H-NMR (CDCl₃) δ: 2.17 (3H, s), 2.52 (3H, s), 3.63 (3H, s), 5.12 (2H, s), 6.93 (1H, d, J=8.6 Hz), 7.29 (1H, dd, J=6.9, 2.4 Hz), 7.41-7.46 (2H, m), 8.14 (1H, d, J=2.0 Hz), 8.18 (1H, dd, J=8.6, 2.4 Hz), 8.60 (2H, s).

Present Compound 237

¹H-NMR (CDCl₃) δ: 2.16 (3H, s), 2.52 (3H, s), 3.63 (3H, s), 5.12 (2H, s), 6.93 (1H, d, J=8.6 Hz), 7.29 (1H, dd, J=7.1, 2.2 Hz), 7.39-7.47 (2H, m), 8.16 (1H, dd, J=2.2, 0.6 Hz), 8.21 (1H, ddd, J=8.6, 2.2, 0.6 Hz), 8.68 (2H, s).

Present Compound 238

¹H-NMR (CDCl₃) δ: 2.10 (3H, s), 2.52 (3H, s), 2.53 (3H, s), 3.65 (3H, s), 5.09 (2H, s), 6.73 (1H, s), 7.28 (1H, dd, J=7.0, 2.3 Hz), 7.46-7.39 (2H, m), 7.63 (1H, s), 8.65 (2H, s).

Present Compound 239

¹H-NMR (CDCl₃) δ: 2.09 (3H, s), 2.34 (3H, s), 2.51 (3H, s), 2.53 (3H, s), 3.65 (3H, s), 5.08 (2H, s), 6.73 (1H, s), 7.29 (1H, d, J=2.5 Hz), 7.41-7.45 (2H, m), 7.59 (1H, s), 8.63 (2H, d, J=0.7 Hz).

Present Compound 240

¹H-NMR (CDCl₃) δ: 2.10 (3H, s), 2.51 (3H, s), 2.61 (3H, s), 3.65 (3H, s), 5.06 (2H, s), 6.65 (1H, d, J=12.9 Hz), 7.06 (1H, dd, J=7.5, 0.5 Hz), 7.30 (1H, dd, J=7.2, 1.8 Hz), 7.40-7.46 (2H, m), 7.50-7.53 (1H, m), 7.60 (1H, t, J=7.7 Hz), 7.72 (1H, dd, J=9.1, 0.9).

Present Compound 241

¹H-NMR (CDCl₃) δ: 2.35 (3H, s), 2.56 (3H, s), 2.77 (3H, s), 3.69 (3H, s), 5.21 (2H, s), 6.82 (1H, s), 7.30 (1H, dd, J=7.1, 2.2 Hz), 7.46-7.35 (5H, m).

Present Compound 242

¹H-NMR (CDCl₃) δ: 2.10 (3H, s), 2.52 (3H, s), 3.65 (3H, s), 5.08 (2H, s), 6.70 (1H, d, J=12.9 Hz), 7.30 (1H, dd, J=7.2, 1.8 Hz), 7.41-7.47 (2H, m), 7.86 (1H, d, J=8.8 Hz), 8.76 (2H, s).

Present Compound 243

¹H-NMR (CDCl₃) δ: 0.77-0.81 (2H, m), 1.00-1.03 (2H, m), 2.11-2.16 (1H, m), 2.17 (3H, s), 3.62 (3H, s), 5.35 (2H, s), 7.02 (1H, d, J=9.4 Hz), 7.28 (1H, s), 7.30 (1H, s), 7.46 (1H, t, J=7.8 Hz), 7.51 (1H, d, J=8.9 Hz), 7.77 (1H, d, J=8.9 Hz), 7.84-7.87 (2H, m).

Present Compound 244

¹H-NMR (CDCl₃) δ: 2.11 (3H, s), 2.42 (3H, s), 2.52 (3H, s), 3.67 (3H, s), 5.09 (2H, s), 6.76 (1H, s), 7.25-7.31 (2H, m), 7.40-7.48 (2H, m), 7.57 (1H, dd, J=8.7, 0.8 Hz), 8.49 (1H, ddd, J=8.6, 2.7, 1.6 Hz), 9.48 (1H, d, J=2.7 Hz).

Present Compound 245

¹H-NMR (CDCl₃) δ: 2.11 (3H, s), 3.61 (3H, s), 5.40 (2H, s), 6.97 (1H, d, J=8.5 Hz), 7.42 (1H, dd, J=8.0, 1.4 Hz), 7.49 (1H, t, J=8.0 Hz), 7.50 (1H, d, J=8.9 Hz), 7.63 (1H, dd, J=8.0, 1.4 Hz), 7.75 (1H, d, J=8.9 Hz), 7.80-7.85 (2H, m).

Present Compound 246

¹H-NMR (CDCl₃) δ: 1.29 (3H, t, J=7.6 Hz), 2.16 (3H, s), 2.86 (2H, q, J=7.6 Hz), 3.60 (3H, s), 5.14 (2H, s), 6.98 (1H, d, J=9.2 Hz), 7.30 (1H, dd, J=7.1, 1.8 Hz), 7.44-7.53 (3H, m), 7.77 (1H, d, J=8.9 Hz), 7.87-7.82 (2H, m).

Production Example 25

In the same manner as in Production Example 16, except that cyclopropylboronic acid was used in place of propylboronic acid, and that the present compounds 199 and 200 were respectively used in place of the present compound 37, the present compound 247 and the present compound 248 were obtained. The structural formulas and ¹H-NMR data of the present compound 247 and the present compound 248 are shown below.

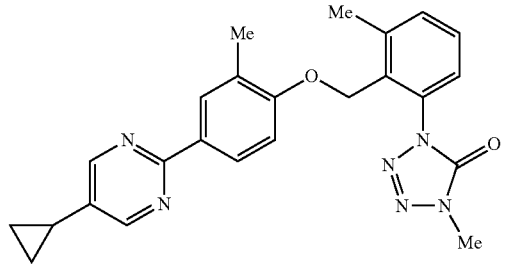

Present Compound 247

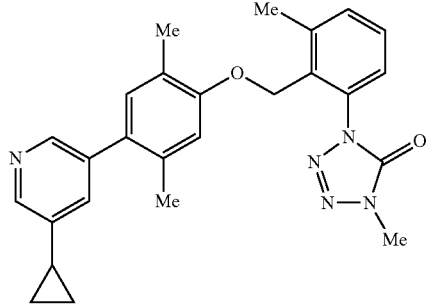

Present Compound 248

Present Compound 247

¹H-NMR (CDCl₃) δ: 0.77-0.83 (2H, m), 1.06-1.12 (2H, m), 1.86-1.90 (1H, m), 2.17 (3H, s), 2.52 (3H, s), 3.62 (3H, s), 5.11 (2H, s), 6.94 (1H, d, J=8.5 Hz), 7.29 (1H, d, J=6.9 Hz), 7.41-7.46 (2H, m), 8.19 (1H, d, J=8.9 Hz), 8.16 (1H, s), 8.49 (2H, s).

Present Compound 248

¹H-NMR (CDCl₃) δ: 0.74-0.76 (2H, m), 1.01-1.08 (2H, m), 1.88-1.98 (1H, m), 2.09 (3H, s), 2.23 (3H, s), 2.53 (3H, s), 3.67 (3H, s), 5.06 (2H, s), 6.75 (1H, s), 6.95 (1H, s), 7.19 (1H, t, J=2.2 Hz), 7.28 (1H, dd, J=6.6, 2.2 Hz), 7.40-7.46 (2H, m), 8.32 (1H, d, J=2.2 Hz), 8.36 (1H, d, J=2.2 Hz).

Production Example 26

A mixture of 0.40 g of the present compound 93, 1.2 g of Lawesson's reagent (2,4-Bis(4-methoxyphenyl)-1,3,2,4-dithiadiphosphetane 2,4-disulfide), and 20 mL of toluene was stirred with heating under reflux for 5 hours, and then concentrated under reduced pressure. The residue thus obtained was subjected to silica gel column chromatography to obtain 0.10 g of 1-{3-ethyl-2-[2-methyl-4-(6-methylpyrimidin-2-yl)-phenoxymethyl]-phenyl}-4-methyl-1,4-dihydrotetrazole-5-thione (hereinafter referred to as the present compound 249).

Present Compound 249

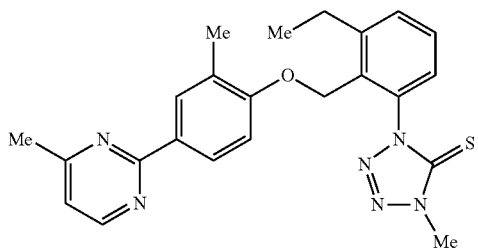

¹H-NMR (CDCl₃) δ: 1.30 (3H, t, J=7.6 Hz), 2.16 (3H, s), 2.56 (3H, s), 2.88 (2H, q, J=7.6 Hz), 3.87 (3H, s), 5.05 (2H, s), 6.89 (1H, d, J=8.5 Hz), 6.98 (1H, d, J=5.0 Hz), 7.30 (1H, t, J=4.5 Hz), 7.53 (1H, d, J=4.5 Hz), 7.53 (1H, d, J=4.5 Hz), 8.18 (1H, s), 8.22 (1H, d, J=8.5 Hz), 8.59 (1H, d, J=5.0 Hz).

Production Example 27

The following present compounds were synthesized by the same reaction as in Production Example 1. The structural formulas and ¹H-NMR data of the thus obtained present compounds are shown below.

Present Compound 250

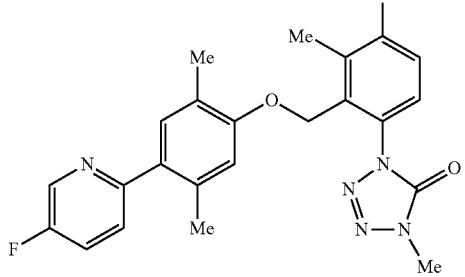

Present Compound 251

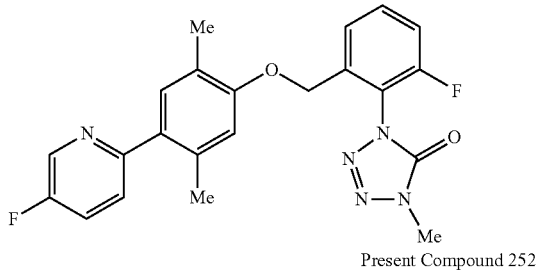

Present Compound 252

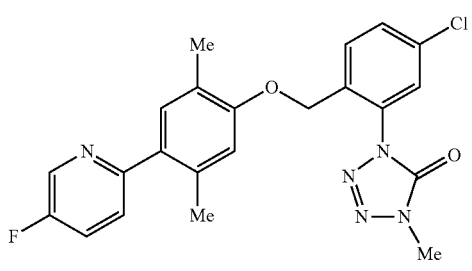

Present Compound 253

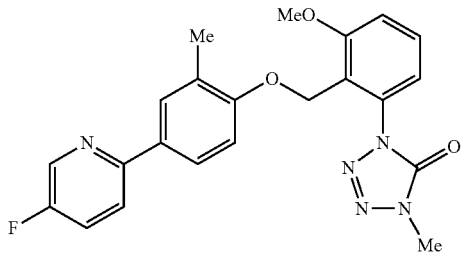

Present Compound 250

¹H-NMR (CDCl₃) δ: 2.09 (3H, s), 2.32 (3H, s), 2.41 (3H, s), 3.67 (3H, s), 5.03 (2H, s), 6.70 (1H, s), 7.16 (1H, s), 7.21 (1H, t, J=8.6 Hz), 7.35 (1H, dd, J=8.6, 4.5 Hz), 7.43 (1H, td, J=8.5, 2.9 Hz), 7.30-7.25 (1H, m), 8.52 (1H, d, J=2.3 Hz).

Present Compound 251

¹H-NMR (CDCl₃) δ: 2.20 (3H, s), 2.30 (3H, s), 3.70 (3H, s), 5.11 (2H, s), 6.67 (1H, s), 7.18 (1H, s), 7.27 (1H, t, J=8.9 Hz), 7.35 (1H, dd, J=8.9, 4.1 Hz), 7.40-7.46 (1H, m), 7.49 (1H, d, J=7.8 Hz), 7.52-7.59 (1H, m), 8.52 (1H, s).

Present Compound 252

¹H-NMR (CDCl₃) δ: 2.18 (3H, s), 2.30 (3H, s), 3.70 (3H, s), 5.16 (2H, s), 6.67 (1H, s), 7.18 (1H, s), 7.35 (1H, ddd, J=8.7, 4.5, 0.6 Hz), 7.44 (1H, td, J=8.2, 3.0 Hz), 7.49-7.56 (2H, m), 7.67 (1H, d, J=8.2 Hz), 8.52 (1H, d, J=3.0 Hz).

Present Compound 253

¹H-NMR (CDCl₃) δ: 2.06 (3H, s), 3.59 (3H, s), 3.93 (3H, s), 5.32 (2H, s), 6.95 (1H, d, J=8.2 Hz), 7.12-7.06 (2H, m), 7.41 (1H, td, J=8.5, 3.0 Hz), 7.47 (1H, t, J=8.2 Hz), 7.60-7.68 (3H, m), 8.47 (1H, d, J=2.7 Hz).

Production Example 28

It is also possible to produce the present compound 48 by the following process.

A mixture of 0.11 g of the present compound A4 mentioned in Synthesis Process 4, 0.12 g of potassium carbonate, 0.04 g of dimethylsulfuric acid, and 5 mL of N,N-dimethylformamide was stirred at room temperature for 12 hours. A saturated sodium bicarbonate solution was poured into the reaction mixture and the mixture was extracted with ethyl acetate. The organic layer was washed with a saturated sodium bicarbonate solution and then dried over anhydrous sodium sulfate. After concentration under reduced pressure, 0.10 g of the present compound 48 was obtained.

With respect to the present compound A, Synthesis Examples are shown below.

Synthesis Example 1

A mixture of 2.43 of the intermediate (HP30), 2.00 g of 2-methyl-6-nitrobenzylbromide, 0.20 g of potassium carbonate, and 20 mL of acetonitrile was stirred with heating under reflux for 6 hours. After cooling to room temperature, the reaction mixture was filtered and the filtrate was concentrated. The residue thus obtained was subjected to silica gel column chromatography to obtain 1.91 g of 1-methyl-6-[3-methyl-4-(2-methyl-6-nitrobenzyloxy)-phenyl]-pyridine (hereinafter referred to as the present compound A1).

Present Compound A1

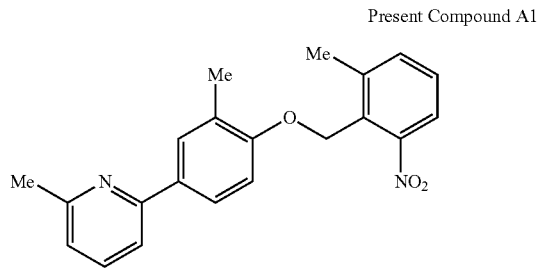 [SMILES: Cc1cccc(-c2ccc(OCc3c(C)cccc3N)c(C)c2)n1]

¹H-NMR (CDCl₃) δ: 2.22 (3H, s), 2.54 (3H, s), 2.62 (3H, s), 5.29 (2H, s), 6.99 (1H, d, J=8.2 Hz), 7.04 (1H, d, J=7.6 Hz), 7.40 (1H, t, J=7.9 Hz), 7.47 (2H, t, J=8.0 Hz), 7.60 (1H, t, J=7.8 Hz), 7.67 (1H, d, J=8.0 Hz), 7.77-7.80 (2H, m).

Synthesis Example 2

A mixture of 0.70 g of 1-methyl-6-[3-methyl-4-(2-methyl-6-nitrobenzyloxy)-phenyl]-pyridine, 0.26 g of copper(I) chloride, and 10 mL of methanol was stirred at 0° C. and 0.72 g of potassium borohydrate was added. The temperature of the reaction temperature was raised to room temperature, followed by stirring at the same temperature for 1 hour. The mixture was filtered and concentrated, and then a liquid separating operation was performed by adding ethyl acetate and water to the residue. The reaction mixture was concentrated and water was added, and then the mixture was extracted with ethyl acetate. The organic layer was washed with water and a saturated saline solution, dried over anhydrous sodium sulfate, and then concentrated under reduced pressure to obtain 0.57 g of 3-methyl-2-[2-methyl-4-(6-methylpyridin-2-yl)-phenoxymethyl]-phenylamine (hereinafter referred to as the present compound A2).

Present Compound A2

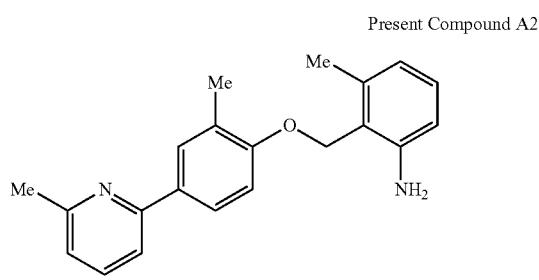

¹H-NMR (CDCl₃) δ: 2.27 (3H, s), 2.38 (3H, s), 2.62 (3H, s), 4.03 (2H, brs), 5.12 (2H, s), 6.63 (1H, d, J=7.9 Hz), 6.67 (1H, d, J=7.5 Hz), 7.02-7.12 (3H, m), 7.47 (1H, d, J=7.9 Hz), 7.60 (1H, t, J=7.7 Hz), 7.85-7.78 (2H, m).

Synthesis Example 3

A mixture of 0.81 g of 3-methyl-2-[2-methyl-4-(6-methylpyridin-2-yl)-phenoxymethyl]-phenylamine, 1.13 g of triphosgene, and 30 mL of toluene was stirred with heating under reflux for 5 hours. The reaction mixture allowed to cool was concentrated under reduced pressure to obtain 0.87 g of 1-[4-(2-isocyanato-6-methylbenzyloxy)-3-methylphenyl]-6-methyl-pyridine (hereinafter referred to as the present compound A3).

Present Compound A3

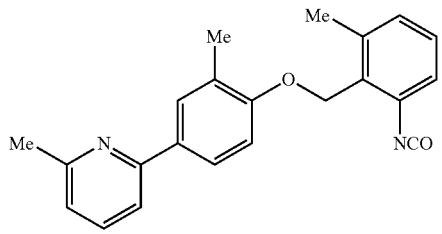

¹H-NMR (CDCl₃) δ: 2.25 (3H, s), 2.42 (3H, s), 2.62 (3H, s), 5.15 (2H, s), 7.02-7.07 (2H, m), 7.07-7.11 (2H, m), 7.23 (1H, d, J=7.7 Hz), 7.47 (1H, d, J=7.7 Hz), 7.60 (1H, t, J=7.7 Hz), 7.79-7.83 (2H, m).

Synthesis Example 4

Under ice cooling, 0.44 g of anhydrous aluminum trichloride was added to 10 mL of N,N-dimethylformamide, followed by stirring for 15 minutes. To this was added 0.20 g of sodium azide and the mixture was stirred for 15 minutes, followed by the addition of 0.80 g of the above-mentioned 1-[4-(2-isocyanato-6-methylbenzyloxy)-3-methylphenyl]-6-methyl-pyridine and further heating at 80° C. for 8 hours. After cooling, the reaction solution was added in a mixture of 0.30 g of sodium nitrite, 10 mL of water, and 10 g of ice while stirring. To the mixture, 10% hydrochloric acid was added. After stirring, the mixture was neutralized with a saturated sodium bicarbonate solution and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one (hereinafter referred to as the present compound A4).

Present Compound A4

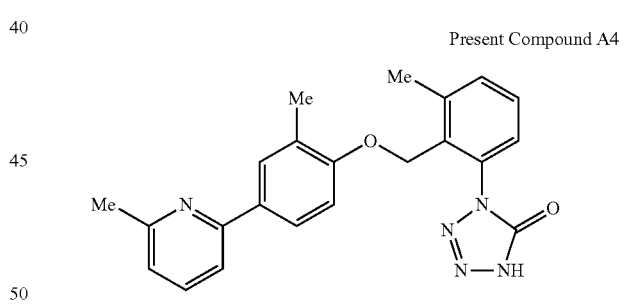

¹H-NMR (CDCl₃) δ: 2.13 (3H, s), 2.52 (3H, s), 2.61 (3H, s), 5.10 (2H, s), 6.89 (1H, d, J=8.2 Hz), 7.04 (1H, d, J=7.5 Hz), 7.28 (1H, dd, J=6.2, 3.1 Hz), 7.38-7.43 (3H, m), 7.59 (1H, t, J=7.7 Hz), 7.70-7.64 (2H, m).

With respect to the present compound B, Synthesis Examples are shown below.

Synthesis Example 5

A mixture of 23.5 g of CA14 mentioned in Reference Production Example 14, 15.5 g of 4-bromo-2-methylphenol, 22.9 g of potassium carbonate, and 330 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 30.1 g of 1-[2-(4-bromo-2-methylphenoxymethyl)-3-methylphenyl]-4-methyl-1,4-dihydrotetrazol-5-one (hereinafter referred to as the present compound B1).

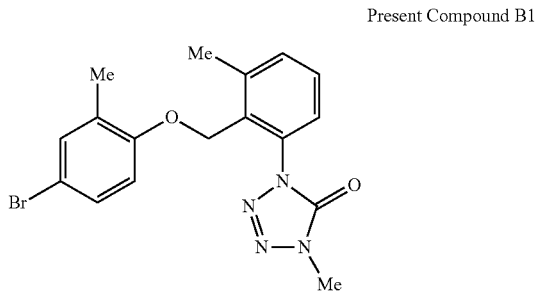 [SMILES: Cc1cc(Br)ccc1OCc1c(C)cccc1-n1nnn(C)c1=O]

Present Compound B1

¹H-NMR (CDCl₃) δ: 2.06 (3H, s), 2.49 (3H, s), 3.63 (3H, s), 5.00 (2H, s), 6.70 (1H, d, J=9.4 Hz), 7.21-7.25 (2H, m), 7.26-7.29 (1H, m), 7.39-7.46 (2H, m).

Synthesis Example 6

In accordance with the reaction mentioned in Synthesis Example 5, the following present compounds were obtained. The structural formulas and ¹H-NMR data of the thus obtained present compounds are shown below.

1-[2-(2-Methyl-4-bromophenoxymethyl)-phenyl]-4-methyl-1,4-dihydrotetrazol-5-one (Present Compound B2)

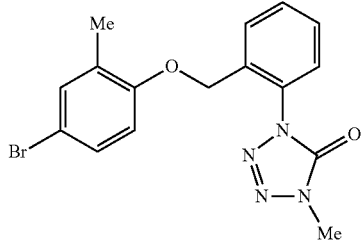 [SMILES: Cc1cc(Br)ccc1OCc1ccccc1-n1nnn(C)c1=O]

¹H-NMR (CDCl₃) δ: 2.16 (3H, s), 3.68 (3H, s), 5.13 (2H, s), 6.67 (1H, d, J=8.5 Hz), 7.20 (1H, dd, J=8.47, 2.5 Hz), 7.25 (1H, d, J=2.5 Hz), 7.47-7.56 (3H, m), 7.67 (1H, d, J=6.9 Hz).

1-[3-Methoxy-2-(2-methyl-4-bromophenoxymethyl)-phenyl]-4-methyl-1,4-dihydrotetrazol-5-one (Present Compound B3)

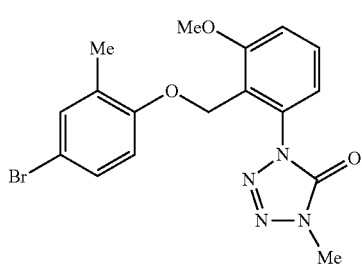 [SMILES: COc1cccc(-n2nnn(C)c2=O)c1COc1ccc(Br)cc1C]

¹H-NMR (CDCl₃) δ: 1.96 (3H, s), 3.59 (3H, s), 3.91 (3H, s), 5.22 (2H, s), 6.73 (1H, d, J=8.2 Hz), 7.04-7.10 (2H, m), 7.15-7.20 (2H, m), 7.46 (1H, t, J=8.2 Hz).

1-[3-Ethyl-2-(2-methyl-4-bromophenoxymethyl)-phenyl]-4-methyl-1,4-dihydrotetrazol-5-one (Present Compound B4)

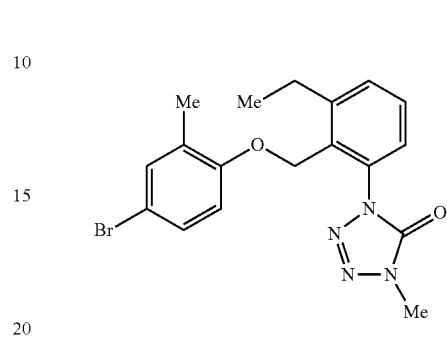

¹H-NMR (CDCl₃) δ: 1.27 (3H, t, J=7.56 Hz), 2.04 (3H, s), 2.83 (2H, q, J=7.6 Hz), 3.60 (3H, s), 5.02 (2H, s), 6.71 (1H, d, J=8.7 Hz), 7.21-7.25 (2H, m), 7.26-7.30 (1H, m), 7.43-7.50 (2H, m).

1-[3-Cyclopropyl-2-(2-methyl-4-bromophenoxymethyl)-phenyl]-4-methyl-1,4-dihydrotetrazol-5-one (Present Compound B5)

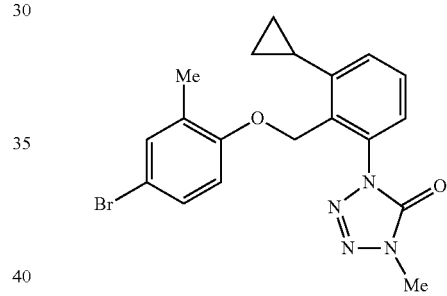

¹H-NMR (CDCl₃) δ:0.73-0.79 (2H, m), 0.96-1.02 (2H, m), 2.05 (3H, s), 2.07-2.12 (1H, m), 3.62 (3H, s), 5.23 (2H, s), 6.75 (1H, d, J=8.24 Hz), 7.24-7.26 (4H, m), 7.44 (1H, t, J=7.8 Hz).

1-[3-Chloro-2-(2-methyl-4-bromophenoxymethyl)-phenyl]-4-methyl-1,4-dihydrotetrazol-5-one (Present Compound B6)

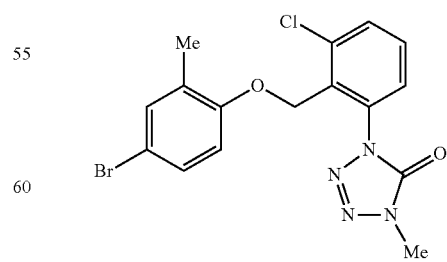

¹H-NMR (CDCl₃) δ: 2.03 (3H, s), 3.65 (3H, s), 5.31 (2H, s), 6.75 (1H, d, J=8.2 Hz), 7.24-7.30 (2H, m), 7.42-7.45 (1H, m), 7.51 (1H, t, J=8.0 Hz), 7.65 (1H, d, J=8 Hz).

211

1-[2-(4-Bromo-2-cyanophenoxymethyl)-3-methyl-phenyl]-4-methyl-1,4-dihydrotetrazol-5-one (Present Compound B7)

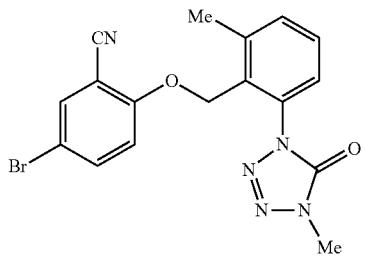 [SMILES: Cc1cccc(-n2nnn(C)c2=O)c1COc1ccc(Br)cc1C#N]

$^1$H-NMR (CDCl$_3$) δ: 2.54 (3H, s), 3.72 (3H, s), 5.22 (2H, s), 6.76 (1H, d, J=9.0 Hz), 7.29 (1H, d, J=7.9 Hz), 7.38-7.47 (2H, m), 7.55-7.57 (1H, m), 7.63 (1H, dd, J=2.5, 0.9 Hz).

1-[2-(4-Bromo-2-methoxyphenoxymethyl)-3-methyl-phenyl]-4-methyl-1,4-dihydrotetrazol-5-one (Present Compound B8)

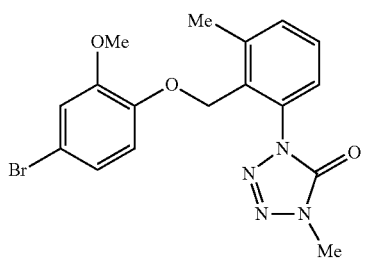 [SMILES: COc1cc(Br)ccc1OCc1c(C)cccc1-n1nnn(C)c1=O]

$^1$H-NMR (CDCl$_3$) δ: 2.50 (3H, s), 3.64 (3H, s), 3.78 (3H, s), 5.08 (2H, s), 6.70 (1H, d, J=8.2 Hz), 6.93-6.98 (2H, m), 7.25 (1H, dd, J=6.6, 1.8 Hz), 7.38-7.39 (2H, m).

1-[2-(4-Bromo-2,5-dimethylphenoxymethyl)-3-methyl-phenyl]-4-methyl-1,4-dihydrotetrazol-5-one (Present Compound B9)

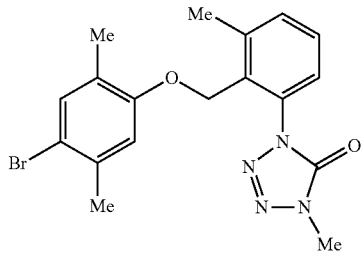

$^1$H-NMR (CDCl3) δ: 7.45-7.38 (2H, m), 7.29-7.25 (1H, m), 7.23 (1H, s), 6.69 (1H, s), 4.99 (2H, s), 3.64 (3H, s), 2.49 (3H, s), 2.34 (3H, s), 2.02 (3H, s).

212

1-[2-(4-Bromo-2,5-dimethylphenoxymethyl)-3-chlorophenyl]-4-methyl-1,4-dihydrotetrazol-5-one (Present Compound B10)

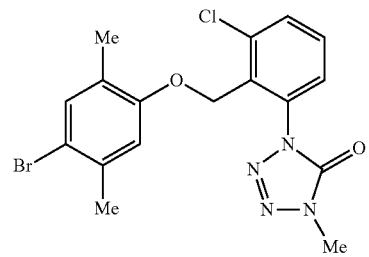 [SMILES: Cc1cc(OCc2c(Cl)cccc2-n2nnn(C)c2=O)c(C)cc1Br]

$^1$H-NMR (CDCl$_3$) δ: 1.96 (3H, s), 2.33 (3H, s), 3.62 (3H, s), 5.27 (2H, s), 6.71 (1H, s), 7.22 (1H, s), 7.40 (1H, d, J=8.8 Hz), 7.48 (1H, t, J=8.8 Hz), 7.61 (1H, d, J=8.8 Hz).

1-[2-(4-Bromo-2,5-dimethylphenoxymethyl)phenyl]-4-methyl-1,4-dihydrotetrazol-5-one (Present Compound B11)

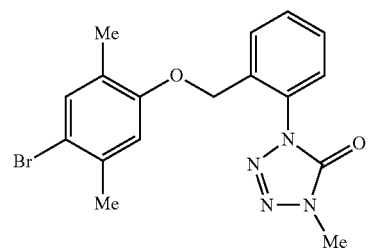 [SMILES: Cc1cc(OCc2ccccc2-n2nnn(C)c2=O)c(C)cc1Br]

$^1$H-NMR (CDCl$_3$) δ: 2.11 (3H, s), 2.31 (3H, s), 3.68 (3H, s), 5.12 (2H, s), 6.66 (1H, s), 7.26 (1H, s), 7.48-7.56 (3H, m), 7.68 (1H, dd, J=7.5, 0.9 Hz).

1-[2-(4-Bromo-2-fluoro-5-methylphenoxymethyl)-3-methyl-phenyl]-4-methyl-1,4-dihydrotetrazol-5-one (Present Compound

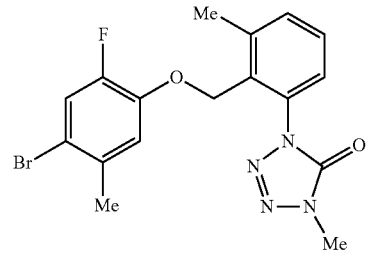 [SMILES: Cc1cc(OCc2c(C)cccc2-n2nnn(C)c2=O)c(F)cc1Br]

$^1$H-NMR (CDCl$_3$) δ: 2.30 (3H, s), 2.51 (3H, s), 3.67 (3H, s), 5.08 (2H, s), 6.79 (1H, d, J=8.6 Hz), 7.21 (1H, d, J=10.4 Hz), 7.27 (1H, dd, J=7.2, 2.0 Hz), 7.37-7.43 (2H, m).

1-[2-(4-Bromo-2-chloro-5-methylphenoxymethyl)-3-methylphenyl]-4-methyl-1,4-dihydrotetrazol-5-one (Present Compound B13)

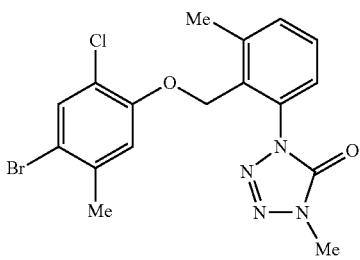

¹H-NMR (CDCl₃) δ: 2.33 (3H, s), 2.53 (3H, s), 3.68 (3H, s), 5.12 (2H, s), 6.75 (1H, s), 7.29 (1H, dd, J=7.3, 1.6 Hz), 7.45-7.37 (2H, m), 7.47 (1H, s).

1-[2-(4-Bromo-5-fluoro-2-methylphenoxymethyl)-3-methylphenyl]-4-methyl-1,4-dihydrotetrazol-5-one (Present Compound B14)

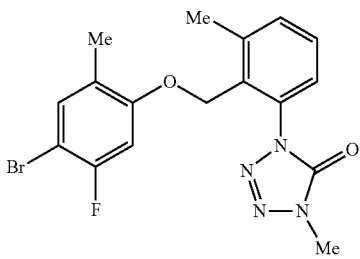

¹H-NMR (CDCl₃) δ: 2.02 (3H, s), 2.49 (3H, s), 3.65 (3H, s), 4.98 (2H, s), 6.65 (1H, d, J=10.2 Hz), 7.23 (1H, dd, J=7.9, 0.7 Hz), 7.29 (1H, dd, J=7.5, 1.7 Hz), 7.41 (1H, dd, J=8.4, 1.8 Hz), 7.41 (1H, t, J=7.5 Hz).

Synthesis Example 7

A mixture of 3.89 g of the present compound B1 mentioned in Synthesis Example 5, 2.79 g of bis(pinacolato)diboron, 0.25 g of [1,1'-bis(diphenylphosphino)ferrocene]palladium(II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool, and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.44 g of 1-[2-{4-(4,4,5,5-tetramethyl-1,3,2-dioxaborolan-2-yl)-2-methylphenoxymethyl}-3-methylphenyl]-4-methyl-1,4-dihydrotetrazol-5-one (Present Compound B15).

Present Compound B15

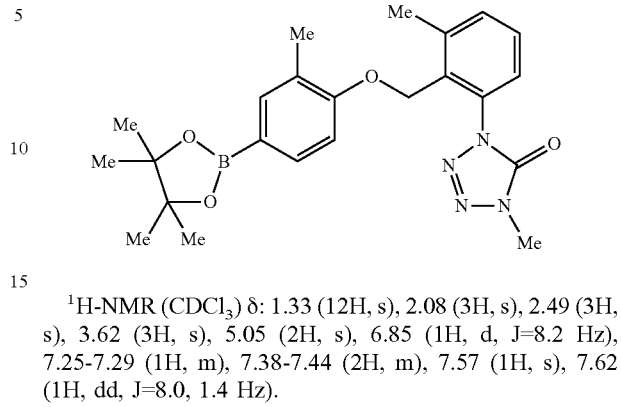

¹H-NMR (CDCl₃) δ: 1.33 (12H, s), 2.08 (3H, s), 2.49 (3H, s), 3.62 (3H, s), 5.05 (2H, s), 6.85 (1H, d, J=8.2 Hz), 7.25-7.29 (1H, m), 7.38-7.44 (2H, m), 7.57 (1H, s), 7.62 (1H, dd, J=8.0, 1.4 Hz).

Synthesis Example 8

In accordance with the reaction mentioned in Synthesis Example 7, the following present compounds were obtained. The structural formulas and ¹H-NMR data of the present compound are shown below.

1-{3-Methoxy-2-[2-methyl-4-(4,4,5,5-tetramethyl-1,3,2-dioxaborolan-2-yl)-phenoxymethyl]-phenyl}-4-methyl-1,4-dihydrotetrazol-5-one (Present Compound B16)

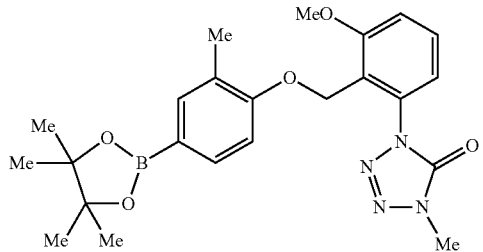 [SMILES: COc1cccc(-n2nnn(C)c2=O)c1COc1ccc(B2OC(C)(C)C(C)(C)O2)cc1C]

¹H-NMR (CDCl₃) δ: 1.31 (12H, s), 1.97 (3H, s), 3.57 (3H, s), 3.91 (3H, s), 5.28 (2H, s), 6.87 (1H, d, J=8.2 Hz), 7.04-7.08 (2H, m), 7.45 (1H, t, J=8.3 Hz), 7.51 (1H, s), 7.58 (1H, dd, J=8.2, 1.4 Hz).

1-{[2-Methyl-4-(4,4,5,5-tetramethyl-1,3,2-dioxaborolan-2-yl)-phenoxymethyl]-phenyl}-4-methyl-1,4-dihydrotetrazol-5-one (Present Compound B17)

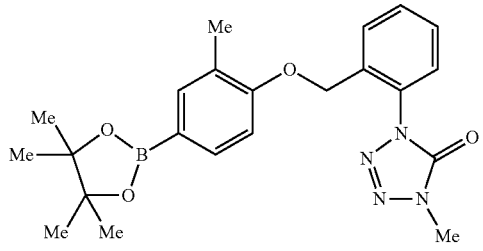 [SMILES: Cc1cc(B2OC(C)(C)C(C)(C)O2)ccc1OCc1ccccc1-n1nnn(C)c1=O]

¹H-NMR (CDCl₃) δ: 1.33 (12H, s), 2.18 (3H, s), 3.67 (3H, s), 5.19 (2H, s), 6.80 (1H, d, J=8.7 Hz), 7.47-7.55 (3H, m), 7.58-7.61 (2H, m), 7.70 (1H, d, J=6.9 Hz).

1-{3-Chloro-2-[2-methyl-4-(4,4,5,5-tetramethyl-1,3,2-dioxaborolan-2-yl)-phenoxymethyl]-phenyl}-4-methyl-1,4-dihydrotetrazol-5-one (Present Compound B18)

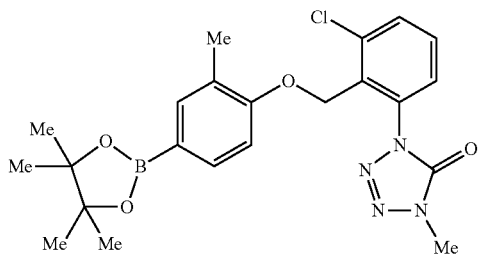 [SMILES: Cc1cc(B2OC(C)(C)C(C)(C)O2)ccc1OCc1c(Cl)cccc1-n1nnn(C)c1=O]

¹H-NMR (CDCl₃) δ: 1.33 (12H, s), 2.02 (3H, s), 3.59 (3H, s), 5.34 (2H, s), 6.85 (1H, d, J=8.2 Hz), 7.39 (1H, dd, J=8.0, 0.9 Hz), 7.46 (1H, t, J=7.9 Hz), 7.55 (1H, s), 7.59-7.63 (2H, m).

1-{3-Ethyl-2-[2-methyl-4-(4,4,5,5-tetramethyl-1,3,2-dioxaborolan-2-yl)-phenoxymethyl]-phenyl}-4-methyl-1,4-dihydrotetrazol-5-one (Present Compound B19)

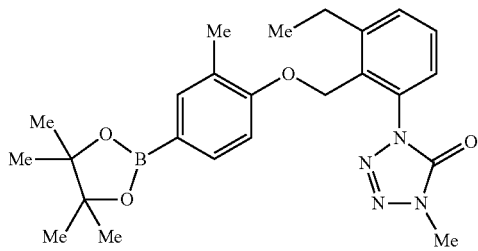 [SMILES: CCc1cccc(-n2nnn(C)c2=O)c1COc1ccc(B2OC(C)(C)C(C)(C)O2)cc1C]

¹H-NMR (CDCl₃) δ: 1.26 (3H, t, J=7.6 Hz), 1.33 (12H, s), 2.07 (3H, s), 2.83 (2H, q, J=7.6 Hz), 3.59 (3H, s), 5.07 (2H, s), 6.86 (1H, d, J=8.2 Hz), 7.25-7.29 (1H, m), 7.43-7.49 (2H, m), 7.56 (1H, s), 7.63 (1H, dd, J=8.1, 1.3 Hz).

1-{3-Cyclopropyl-2-[2-methyl-4-(4,4,5,5-tetramethyl-1,3,2-dioxaborolan-2-yl)-phenoxymethyl]-phenyl}-4-methyl-1,4-dihydrotetrazol-5-one (Present Compound B20)

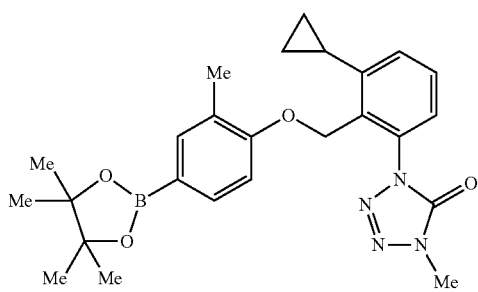 [SMILES: Cc1cc(B2OC(C)(C)C(C)(C)O2)ccc1OCc1c(C2CC2)cccc1-n1nnn(C)c1=O]

¹H-NMR (CDCl₃) δ: 0.72-0.78 (2H, m), 0.94-1.00 (2H, m), 1.33 (12H, s), 2.06-2.11 (4H, m), 3.60 (3H, s), 5.28 (2H, s), 6.89 (1H, d, J=8.2 Hz), 7.24-7.28 (2H, m), 7.43 (1H, t, J=7.9 Hz), 7.56 (1H, s), 7.63 (1H, d, J=8.0 Hz).

1-[2-{4-(4,4,5,5-Tetramethyl-1,3,2-dioxaborolan-2-yl)-2-cyanophenoxymethyl}-3-methylphenyl]-4-methyl-1,4-dihydrotetrazol-5-one (Present Compound B21)

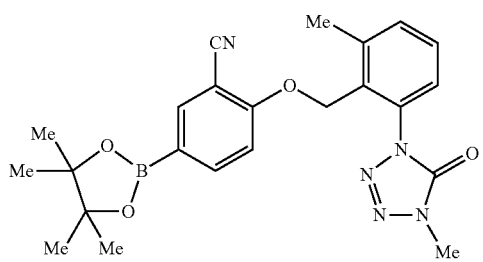 [SMILES: Cc1cccc(-n2nnn(C)c2=O)c1COc1ccc(B2OC(C)(C)C(C)(C)O2)cc1C#N]

¹H-NMR (CDCl₃) δ: 1.32 (12H, s), 2.55 (3H, s), 3.71 (3H, s), 5.26 (2H, s), 6.84 (1H, d, J=8.7 Hz), 7.28 (1H, dd, J=7.3, 1.5 Hz), 7.37-7.44 (2H, m), 7.87-7.89 (1H, m), 7.97 (1H, d, J=1.5 Hz).

1-[2-{4-(4,4,5,5-Tetramethyl-1,3,2-dioxaborolan-2-yl)-2-methoxyphenoxymethyl}-3-methylphenyl]-4-methyl-1,4-dihydrotetrazol-5-one (Present Compound B22)

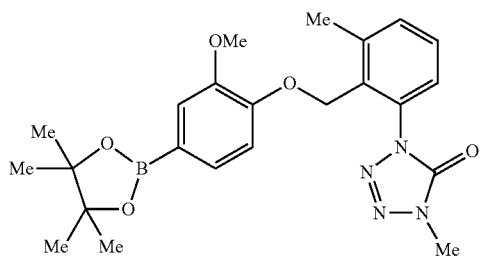 [SMILES: COc1cc(B2OC(C)(C)C(C)(C)O2)ccc1OCc1c(C)cccc1-n1nnn(C)c1=O]

¹H-NMR (CDCl₃) δ: 1.33 (12H, s), 2.50 (3H, s), 3.62 (3H, s), 3.83 (3H, s), 5.14 (2H, s), 6.85 (1H, d, J=8.0 Hz), 7.27-7.24 (2H, m), 7.34-7.38 (3H, m).

1-[2-{4-(4,4,5,5-Tetramethyl-1,3,2-dioxaborolan-2-yl)-2,5-dimethylphenoxymethyl}-3-methylphenyl]-4-methyl-1,4-dihydrotetrazol-5-one (Present Compound B23)

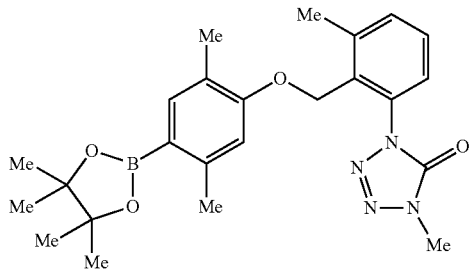 [SMILES: Cc1cc(B2OC(C)(C)C(C)(C)O2)c(C)cc1OCc1c(C)cccc1-n1nnn(C)c1=O]

$^1$H-NMR (CDCl$_3$) δ: 7.50 (1H, s), 7.44-7.38 (2H, m), 7.28-7.25 (1H, m), 6.65 (1H, s), 5.04 (2H, s), 3.64 (3H, s), 2.51 (3H, s), 2.49 (3H, s), 2.03 (3H, s), 1.32 (12H, s).

1-[3-Chloro-2-{4-(4,4,5,5-tetramethyl-1,3,2-dioxaborolan-2-yl)-2,5-dimethylphenoxymethyl}phenyl]-4-methyl-1,4-dihydrotetrazol-5-one (Present Compound B24)

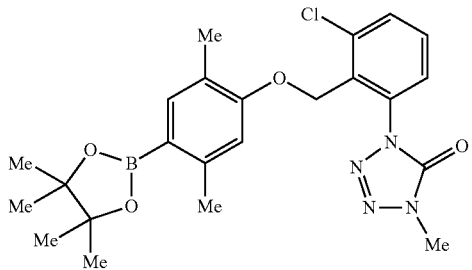 [SMILES: Cc1cc(B2OC(C)(C)C(C)(C)O2)c(C)cc1OCc1c(Cl)cccc1-n1nnn(C)c1=O]

$^1$H-NMR (CDCl$_3$) δ: 1.32 (12H, s), 1.97 (3H, s), 2.50 (3H, s), 3.61 (3H, s), 5.32 (2H, s), 6.65 (1H, s), 7.39 (1H, d, J=7.8 Hz), 7.46 (1H, t, J=7.8 Hz), 7.48 (1H, s), 7.61 (1H, d, J=7.8 Hz).

1-[2-{4-(4,4,5,5-Tetramethyl-1,3,2-dioxaborolan-2-yl)-2,5-dimethylphenoxymethyl}phenyl]-4-methyl-1,4-dihydrotetrazol-5-one (Present Compound B25)

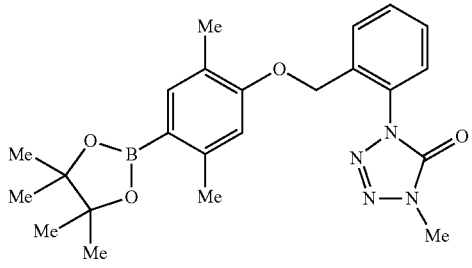 [SMILES: Cc1cc(B2OC(C)(C)C(C)(C)O2)c(C)cc1OCc1ccccc1-n1nnn(C)c1=O]

$^1$H-NMR (CDCl$_3$) δ: 1.32 (12H, s), 2.14 (3H, s), 2.48 (3H, s), 3.68 (3H, s), 5.16 (2H, s), 6.60 (1H, s), 7.47-7.54 (4H, m), 7.70 (1H, d, J=7.5 Hz).

1-[2-{2-Fluoro-4-(4,4,5,5-tetramethyl-1,3,2-dioxaborolan-2-yl)-5-methylphenoxymethyl}-3-methylphenyl]-4-methyl-1,4-dihydrotetrazol-5-one (Present Compound B26)

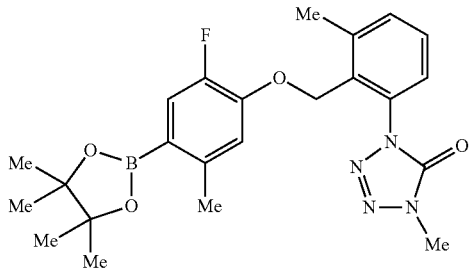 [SMILES: Cc1cc(OCc2c(C)cccc2-n2nnn(C)c2=O)c(F)cc1B1OC(C)(C)C(C)(C)O1]

$^1$H-NMR (CDCl$_3$) δ: 1.33 (12H, s), 2.48 (3H, s), 2.52 (3H, s), 3.68 (3H, s), 5.14 (2H, s), 6.72 (1H, d, J=7.7 Hz), 7.28-7.31 (1H, m), 7.36-7.46 (3H, m).

1-[2-{2-Chloro-4-(4,4,5,5-tetramethyl-1,3,2-dioxaborolan-2-yl)-5-methylphenoxymethyl}-3-methylphenyl]-4-methyl-1,4-dihydrotetrazol-5-one (Present Compound B27)

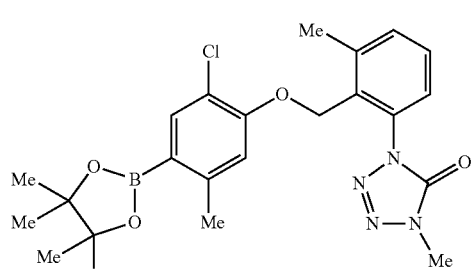

$^1$H-NMR (CDCl$_3$) δ: 1.32 (12H, s), 2.48 (3H, s), 2.52 (3H, s), 3.66 (3H, s), 5.16 (2H, s), 6.67 (1H, s), 7.29 (1H, dd, J=7.2, 2.3 Hz), 7.43-7.37 (2H, m), 7.70 (1H, s).

1-[2-{5-Fluoro-4-(4,4,5,5-tetramethyl-1,3,2-dioxaborolan-2-yl)-2-methylphenoxymethyl}-3-methylphenyl]-4-methyl-1,4-dihydrotetrazol-5-one (Present Compound B28)

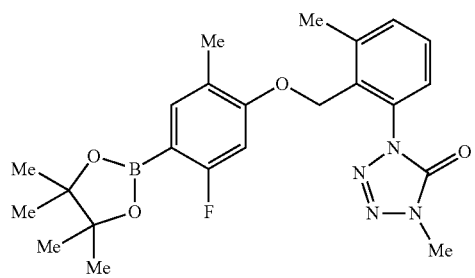 [SMILES: Cc1cc(B2OC(C)(C)C(C)(C)O2)c(F)cc1OCc1c(C)cccc1-n1nnn(C)c1=O]

$^1$H-NMR (CDCl$_3$) δ: 1.34 (12H, s), 2.01 (3H, s), 2.49 (3H, s), 3.64 (3H, d, J=2.9 Hz), 5.01 (2H, s), 6.55 (1H, d, J=11.3 Hz), 7.28 (1H, dd, J=7.6, 2.0 Hz), 7.46-7.40 (3H, m).

With respect to the intermediates for the production of the present compounds, Reference Production Example are shown below.

Reference Production Example 1

Under ice cooling, 21.9 g of anhydrous aluminum chloride was added to 250 mL of N,N-dimethylformamide, followed by stirring for 15 minutes. To this was added 10.7 g of sodium azide and the mixture was stirred for 15 minutes, followed by the addition of 25.0 g of 1-chloro-3-isocyanato-2-methylbenzene and further heating at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one (referred to as CA1).

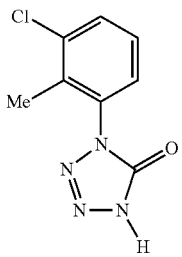

$^1$H-NMR (CDCl$_3$) δ (ppm): 2.32 (3H, s), 7.28-7.36 (2H, m), 7.57 (1H, dd, J=6.8, 2.2 Hz), 13.08 (1H, s).

Reference Production Example 2

To a mixture of 10.00 g of CA1 mentioned in Reference Production Example 1 and 100 mL of N,N-dimethylformamide, 2.30 g of 60% sodium hydride was added under ice cooling. The temperature of the mixture was raised to room temperature, followed by stirring for 1 hour. Under ice cooling, 3.2 mL of methyl iodide was added to the reaction mixture. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one (referred to as CA2).

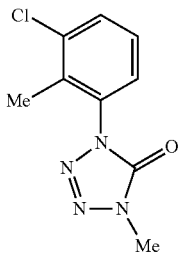

$^1$H-NMR (CDCl$_3$) δ (ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Reference Production Example 3

A mixture of 1.56 g of CA2 mentioned in Reference Production Example 2, 0.34 g of 1,1'-azobis(cyclohexane-1-carbonitrile), 1.42 g of N-bromosuccinimide, and 30 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-(2-bromomethyl-3-chlorophenyl)-4-methyl-1,4-dihydrotetrazol-5-one.

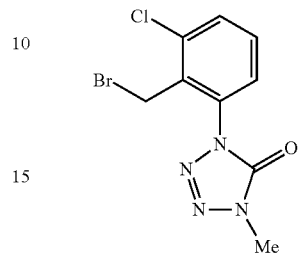

$^1$H-NMR (CDCl$_3$) δ (ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Production Example 4

A mixture of 15.0 g of 3-amino-1-methoxy-2-methylbenzene, 48.7 g of triphosgene, and 350 ml of toluene was stirred with heating under reflux for 3 hours. The reaction mixture allowed to cool was concentrated under reduced pressure to obtain 17.0 g of 1-methoxy-3-isocyanato-2-methylbenzene (referred to as CA4).

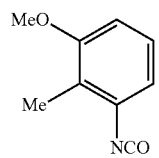

$^1$H-NMR (CDCl$_3$) δ (ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Reference Production Example 5

Under ice cooling, 16.0 g of anhydrous aluminum chloride was added to 180 mL of N,N-dimethylformamide, followed by stirring for 15 minutes. To this was added 7.8 g of sodium azide and the mixture was stirred for 15 minutes, followed by the addition of CA4 (17.0 g) mentioned in Reference Production Example 4 and further heating at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one (referred to as CA5).

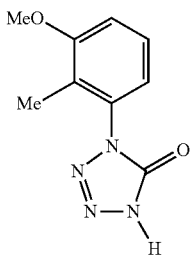 [SMILES: COc1cccc(-n2nn[nH]c2=O)c1C]

¹H-NMR (DMSO-D₆) δ (ppm): 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

Reference Production Example 6

To a mixture of 10.00 g of CA5 mentioned in Reference Production Example 5 and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one

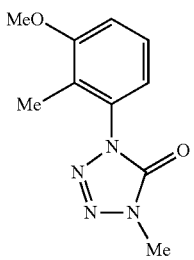

¹H-NMR (CDCl₃) δ (ppm): 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

Reference Production Example 7

A mixture of 2.19 g of CA6 mentioned in Reference Production Example 6, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.36 g of 1-(2-bromomethyl-3-methoxyphenyl)-4-methyl-1,4-dihydrotetrazol-5-one.

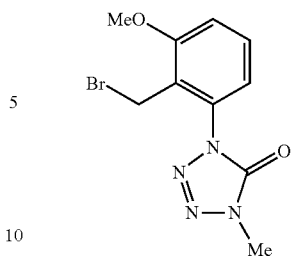

¹H-NMR (CDCl₃) δ (ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 8

A mixture of 25.0 g of 1-bromo-2-methyl-3-aminobenzene, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanato-2-methylbenzene (referred to as CA8).

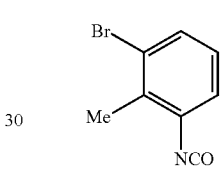

¹H-NMR (CDCl₃) δ (ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Production Example 9

Under ice cooling, 19.7 g of anhydrous aluminum chloride was added to 220 mL of N,N-dimethylformamide, followed by stirring for 15 minutes. To this was added 9.6 g of sodium azide and the mixture was stirred for 15 minutes, followed by the addition of CA8 (30.3 g) mentioned in Reference Production Example 8 and further heating at 80° C. for hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one (referred to as CA9).

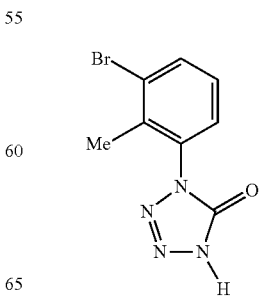

¹H-NMR (DMSO-d₆) δ (ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Production Example 10

To a mixture of 31.4 g of CA9 mentioned in Reference Production Example 9 and 250 mL of N,N-dimethylformamide, 5.90 g of 60% sodium hydride was added under ice cooling. The temperature of the mixture was raised to room temperature, followed by stirring for 1 hour. Under ice cooling, 8.4 mL of methyl iodide was added to the reaction mixture. The temperature of the mixture was raised to room temperature, stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one (referred to as CA10).

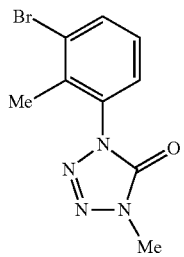 [SMILES: Cc1c(Br)cccc1-n1nnn(C)c1=O]

¹H-NMR (CDCl₃) δ (ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Production Example 11

A mixture of 8.47 g of CA10 mentioned in Reference Production Example 10, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-(2-bromomethyl-3-bromophenyl)-4-methyl-1,4-dihydrotetrazol-5-one (referred to as CA11).

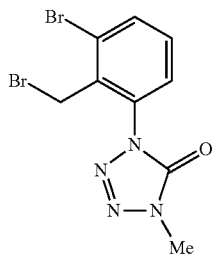 [SMILES: Cn1nnn(-c2cccc(Br)c2CBr)c1=O]

¹H-NMR (CDCl₃) δ (ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 12

A mixture of 45.0 g of CA11 mentioned in Reference Production Example 11, 37.4 g of sodium methoxide, and 600 mL of tetrahydrofuran was stirred at room temperature for 3 hours. A saturated sodium bicarbonate solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 36.2 g of 1-(2-methoxymethyl-3-bromophenyl)-4-methyl-1,4-dihydrotetrazol-5-one (referred to as CA12).

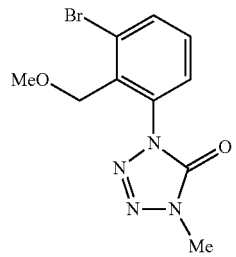 [SMILES: COCc1c(Br)cccc1-n1nnn(C)c1=O]

¹H-NMR (CDCl₃) δ (ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Production Example 13

A mixture of 36.2 g of CA12 mentioned in Reference Production Example 12, 23.2 g of methylboronic acid, 66.7 g of cesium fluoride, 10.6 g of [1,1'-bis(diphenylphosphino)ferrocene]palladium(II) dichloride dichloromethane adduct, and 500 ml of 1,4-dioxane was stirred at 90° C. for 5.5 hours. After cooling, the reaction mixture was filtered and the filtrate was concentrated under reduced pressure. The residue thus obtained was subjected to silica gel column chromatography to obtain 25.6 g of 1-(2-methoxymethyl-3-methylphenyl)-4-methyl-1,4-dihydrotetrazol-5-one (referred to as CA13).

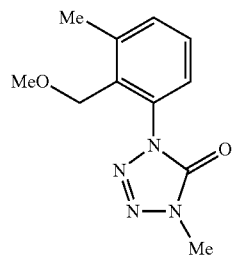 [SMILES: COCc1c(C)cccc1-n1nnn(C)c1=O]

¹H-NMR (CDCl₃) δ (ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Production Example 14

A mixture of 25.6 g of CA13 mentioned in Reference Production Example 13, acetic acid 50 mL, and 50 mL of a 25% hydrogen bromide-acetic acid solution was stirred at 65° C. for 1 hour. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 27.9 g of 1-(2-bromomethyl-3-methylphenyl)-4-methyl-1,4-dihydrotetrazol-5-one (referred to as CA14).

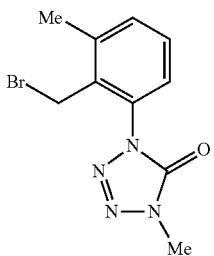 [SMILES: Cc1cccc(-n2nnn(C)c2=O)c1CBr]

$^1$H-NMR (CDCl$_3$) δ (ppm): 2.51 (3H, s), 3.75 (3H, s), 4.51 (2H, s), 7.22-7.24 (1H, m), 7.36-7.39 (2H, m).

Reference Production Example 15

A mixture of 30.1 g of CA12 mentioned in Reference Production Example 12, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 ml of 1,4-dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-(2-methoxymethyl-3-cyclopropylphenyl)-4-methyl-1,4-dihydrotetrazol-5-one (referred to as CA15).

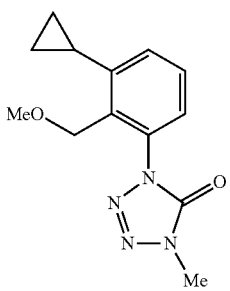 [SMILES: COCc1c(C2CC2)cccc1-n1nnn(C)c1=O]

$^1$H-NMR (CDCl$_3$) δ (ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 16

A mixture of 26.0 g of CA15 mentioned in Reference Production Example 15, 40 mL of acetic acid, and 40 mL of a 25% hydrogen bromide-acetic acid solution was stirred at 65° C. for 2 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 30.8 g of 1-(2-bromomethyl-3-cyclopropylphenyl)-4-methyl-1,4-dihydrotetrazol-5-one.

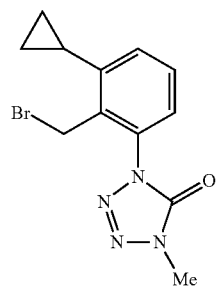 [SMILES: Cn1nnn(-c2cccc(C3CC3)c2CBr)c1=O]

$^1$H-NMR (CDCl$_3$) δ (ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 17

A mixture of 29.8 g of CA12 mentioned in Reference Production Example 12, 35.2 g of tributylvinyltin, 11.6 g of tetrakistriphenylphosphinepalladium, and 500 mL of toluene was stirred with heating under reflux for 14 hours. After cooling, an aqueous saturated ammonium chloride solution was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 19.7 g of 1-(2-methoxymethyl-3-ethenylphenyl)-4-methyl-1,4-dihydrotetrazol-5-one (referred to as CA17).

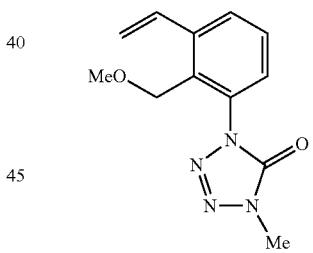

$^1$H-NMR (CDCl$_3$) δ (ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Reference Production Example 18

A mixture of 19.7 g of CA17 mentioned in Reference Production Example 17, 3.02 g of a palladium-fibroin complex, and 1 L of methanol was stirred in a hydrogen atmosphere at room temperature for 11 hours. The reaction mixture was filtered and the filtrate was concentrated under reduced pressure. The residue thus obtained was subjected to silica gel column chromatography to obtain 19.3 g of 1-(2-methoxymethyl-3-ethylphenyl)-4-methyl-1,4-dihydrotetrazol-5-one (referred to as CA18).

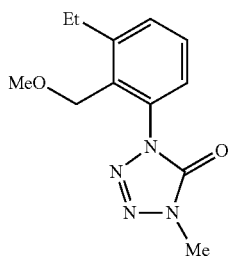 [SMILES: CCc1cccc(-n2nnn(C)c2=O)c1COC]

¹H-NMR (CDCl₃) δ (ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Reference Production Example 19

A mixture of 19.3 g of CA18 mentioned in Reference Production Example 18, 40 mL of acetic acid, and 40 mL of a 25% hydrogen bromide-acetic acid solution was stirred at 65° C. for 1.5 hours. A saturated saline solution was poured into the reaction mixture and the mixture was extracted with ethyl acetate. The organic layer was washed with a saturated sodium bicarbonate solution, dried over anhydrous sodium sulfate, and then concentrated to obtain 23.3 g of 1-(2-bromomethyl-3-ethylphenyl)-4-methyl-1,4-dihydrotetrazol-5-one.

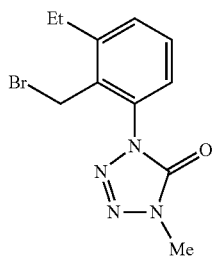 [SMILES: CCc1cccc(-n2nnn(C)c2=O)c1CBr]

¹H-NMR (CDCl₃) δ (ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 20

A mixture of 3.92 g of 4-methoxy-3-methylphenylboronic acid, 3.50 g of 2,3-dichloropyridine, 0.39 g of [1,1'-bis(diphenylphosphino)ferrocene]palladium(II) dichloride dichloromethane adduct, 20.1 g of tripotassium phosphate, 50 mL of 1,4-dioxane, and 50 mL of water was stirred at 80° C. for 8 hours. After cooling, the reaction mixture was filtered and the filtrate was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 5.41 g of 3-chloro-2-(4-methoxy-3-methylphenyl)pyridine (hereinafter referred to as the intermediate (PME1)).

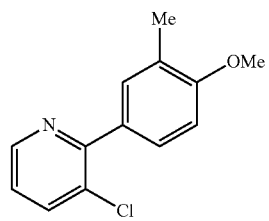

¹H-NMR (CDCl₃) δ: 2.28 (3H, s), 3.89 (3H, s), 6.90 (1H, d, J=8.5 Hz), 7.17 (1H, dd, J=8.1, 4.7 Hz), 7.55 (1H, s), 7.60 (1H, dd, J=8.5, 1.8 Hz), 7.77 (1H, dd, J=8.1, 1.8 Hz), 8.56 (1H, dd, J=4.6, 1.4 Hz).

Reference Production Example 21

In accordance with the reaction mentioned in Reference Production Example 20, the following compound was obtained. The structural formulas and ¹H-NMR data of the thus obtained compounds are shown below.

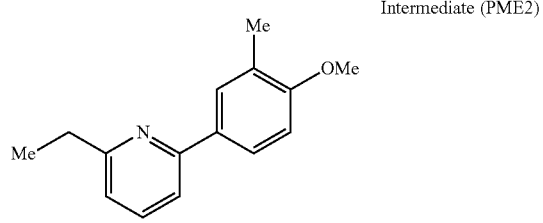

Intermediate (PME2)

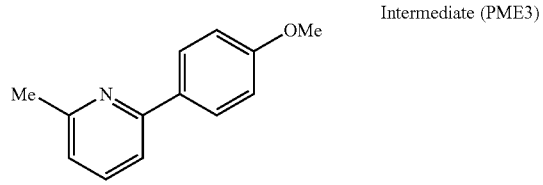

Intermediate (PME3)

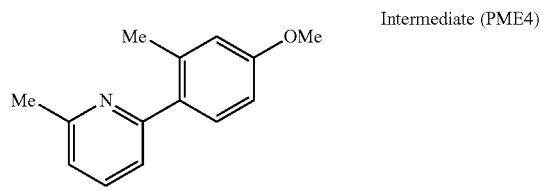

Intermediate (PME4)

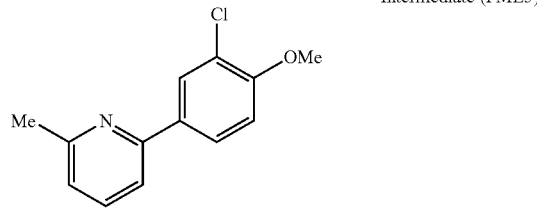

Intermediate (PME5)

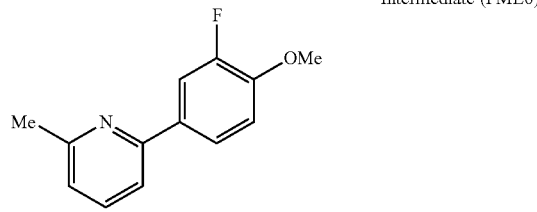

Intermediate (PME6)

229
-continued

Intermediate (PME7)

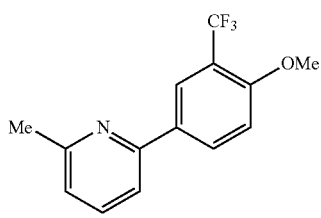

Intermediate (PME8)

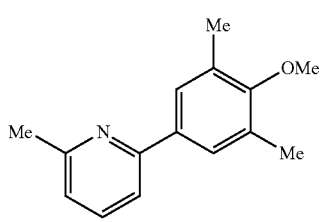

Intermediate (PME9)

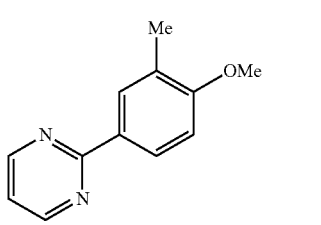

Intermediate (PME10)

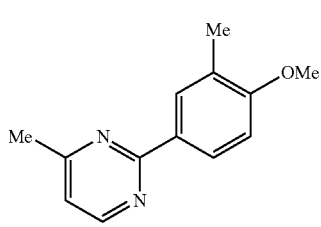

Intermediate (PME11)

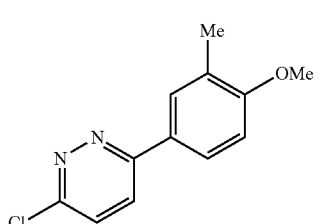

Intermediate (PME12)

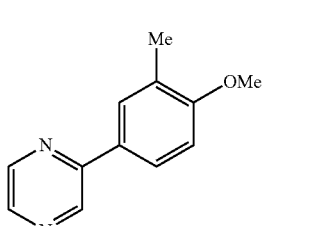

Intermediate (PME13)

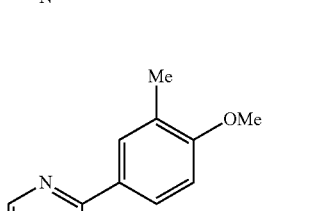
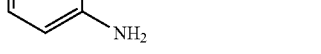

230

Intermediate (PME2)

$^1$H-NMR (CDCl$_3$) δ: 1.36 (3H, t, J=7.6 Hz), 2.30 (3H, s), 2.88 (2H, q, J=7.6 Hz), 3.87 (3H, s), 6.90 (1H, d, J=8.2 Hz), 7.03 (1H, d, J=7.6 Hz), 7.46 (1H, d, J=7.8 Hz), 7.61 (1H, t, J=7.8 Hz), 7.80 (1H, dd, J=8.2, 2.1 Hz), 7.81 (1H, s).

Intermediate (PME3)

$^1$H-NMR (CDCl$_3$) δ: 2.61 (3H, s), 3.86 (3H, s), 6.98 (2H, dt, J=8.9, 2.3 Hz), 7.04 (1H, d, J=7.7 Hz), 7.46 (1H, d, J=7.7 Hz), 7.59 (1H, t, J=7.7 Hz), 7.94 (2H, dt, J=8.9, 2.3 Hz).

Intermediate (PME4)

$^1$H-NMR (CDCl$_3$) δ: 2.36 (3H, s), 2.61 (3H, s), 3.83 (3H, s), 6.78-6.83 (2H, m), 7.08 (1H, d, J=7.7 Hz), 7.16 (1H, d, J=7.7 Hz), 7.34 (1H, d, J=8.5 Hz), 7.61 (1H, t, J=7.7 Hz).

Intermediate (PME5)

$^1$H-NMR (CDCl$_3$) δ: 2.61 (3H, s), 3.95 (3H, s), 7.00 (1H, d, J=8.6 Hz), 7.07 (1H, d, J=7.6 Hz), 7.45 (1H, d, J=7.8 Hz), 7.61 (1H, t, J=7.8 Hz), 7.87 (1H, dd, J=8.6, 2.2 Hz), 8.06 (1H, d, J=2.2 Hz).

Intermediate (PME6)

$^1$H-NMR (CDCl$_3$) δ: 2.61 (3H, s), 3.95 (3H, s), 7.03 (1H, t, J=8.6 Hz), 7.07 (1H, d, J=7.7 Hz), 7.45 (1H, d, J=7.7 Hz), 7.62 (1H, t, J=7.7 Hz), 7.73 (1H, ddd, J=8.6, 2.0, 1.1 Hz), 7.80 (1H, dd, J=12.7, 2.0 Hz).

Intermediate (PME7)

$^1$H-NMR (CDCl$_3$) δ: 2.62 (3H, s), 3.96 (3H, s), 7.08 (1H, s), 7.10 (1H, s), 7.48 (1H, d, J=7.7 Hz), 7.63 (1H, t, J=7.7 Hz), 8.14 (1H, dd, J=7.7, 2.4 Hz), 8.23 (1H, d, J=2.3 Hz).

Intermediate (PME8)

$^1$H-NMR (CDCl$_3$) δ: 2.36 (6H, s), 2.62 (3H, s), 3.74 (3H, s), 7.05 (1H, d, J=7.7 Hz), 7.45 (1H, d, J=7.7 Hz), 7.60 (1H, t, J=7.7 Hz), 7.61 (2H, s).

Intermediate (PME9)

$^1$H-NMR (CDCl$_3$) δ: 2.30 (3H, s), 3.90 (3H, s), 6.92 (1H, d, J=8.6 Hz), 7.11 (1H, t, J=5.0 Hz), 8.23 (1H, brs), 8.27 (1H, dd, J=8.6, 2.3 Hz), 8.75 (2H, d, J=5.0 Hz).

Intermediate (PME10)

$^1$H-NMR (CDCl$_3$) δ: 2.30 (3H, s), 2.56 (3H, s), 3.89 (3H, s), 6.91 (1H, d, J=8.6 Hz), 6.97 (1H, d, J=4.8 Hz), 8.23 (1H, d, J=1.8 Hz), 8.27 (1H, dd, J=8.6, 1.8 Hz), 8.59 (1H, d, J=4.8 Hz).

Intermediate (PME11)

$^1$H-NMR (CDCl$_3$) δ: 2.30 (3H, s), 3.91 (3H, s), 6.95 (1H, d, J=9.0 Hz), 7.50 (1H, d, J=9.2 Hz), 7.77 (1H, d, J=8.9 Hz), 7.87-7.88 (2H, m).

Intermediate (PME12)

¹H-NMR (CDCl₃) δ: 2.31 (3H, s), 3.90 (3H, s), 6.97-6.92 (1H, m), 7.81-7.86 (2H, m), 8.43 (1H, d, J=2.5 Hz), 8.57-8.58 (1H, m), 8.98 (1H, d, J=1.4 Hz).

Intermediate (PME13)

¹H-NMR (CDCl₃) δ: 2.27 (3H, s), 3.86 (2H, brs), 3.88 (3H, s), 6.91 (1H, d, J=8.2 Hz), 7.03-7.06 (2H, m), 7.47 (1H, s), 7.49 (1H, d, J=8.9 Hz), 8.11 (1H, dd, J=4.2, 1.7 Hz).

Reference Production Example 22

Using 4-methoxy-3-methylphenylboronic acid, 2-bromopyridine, [1,1'-bis(diphenylphosphino)ferrocene]palladium(II) dichloride dichloromethane adduct, potassium carbonate, 1,4-dioxane, and water, the same reaction as in Reference Production Example 20 was performed to obtain 2-(4-methoxy-3-methylphenyl)pyridine (hereinafter referred to as the intermediate (PME14)).

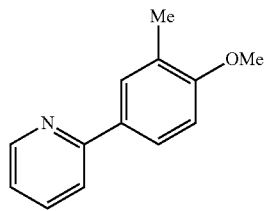 [SMILES: COc1ccc(-c2ccccn2)cc1C]

¹H-NMR (CDCl₃) δ: 2.30 (3H, s), 3.89 (3H, s), 6.91 (1H, d, J=8.3 Hz), 7.14-7.18 (1H, m), 7.65-7.73 (2H, m), 7.78-7.84 (2H, m), 8.66-8.63 (1H, m).

Reference Production Example 23

In accordance with the reaction mentioned in Reference Production Example 22, the following compounds were obtained. The structural formulas and ¹H-NMR data of the thus obtained compounds are shown below.

Intermediate (PME15)

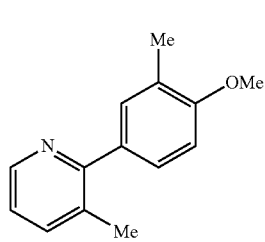

Intermediate (PME16)

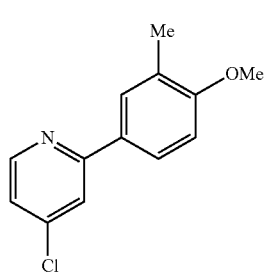

Intermediate (PME17)

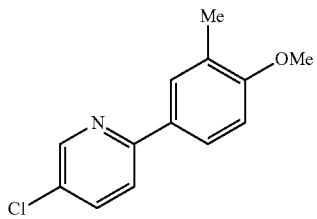

Intermediate (PME18)

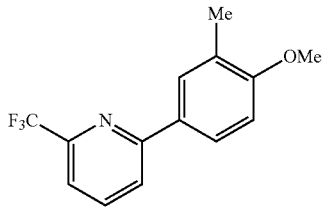

Intermediate (PME19)

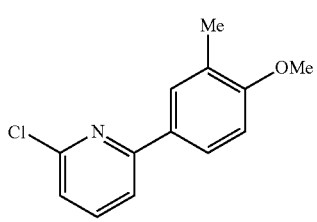

Intermediate (PME20)

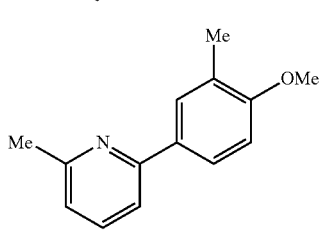

Intermediate (PME15)

¹H-NMR (CDCl₃) δ: 2.27 (3H, s), 2.37 (3H, s), 3.88 (3H, s), 6.89 (1H, d, J=8.0 Hz), 7.13 (1H, dd, J=7.6, 4.6 Hz), 7.31-7.37 (2H, m), 7.55 (1H, d, J=7.6 Hz), 8.50 (1H, d, J=4.6 Hz).

Intermediate (PME16)

¹H-NMR (CDCl₃) δ: 2.29 (3H, s), 3.88 (3H, s), 6.90 (1H, d, J=8.3 Hz), 7.16 (1H, dd, J=5.5, 2.0 Hz), 7.66 (1H, d, J=1.7 Hz), 7.78 (1H, dd, J=8.3, 2.0 Hz), 7.79 (1H, s), 8.52 (1H, d, J=5.5 Hz).

Intermediate (PME17)

¹H-NMR (CDCl₃) δ: 2.29 (3H, s), 3.88 (3H, s), 6.90 (1H, d, J=8.4 Hz), 7.61 (1H, d, J=8.4 Hz), 7.66 (1H, dd, J=8.8, 2.7 Hz), 7.79-7.74 (2H, m), 8.58 (1H, dd, J=2.4, 0.7 Hz).

Intermediate (PME18)

¹H-NMR (CDCl₃) δ: 2.30 (3H, s), 3.89 (3H, s), 6.92 (1H, d, J=8.0 Hz), 7.52 (1H, dd, J=6.1, 2.4 Hz), 7.90-7.81 (4H, m).

Intermediate (PME19)

$^1$H-NMR (CDCl$_3$) δ: 2.29 (3H, s), 3.88 (3H, s), 6.89 (1H, dd, J=6.8, 2.2 Hz), 7.18 (1H, dd, J=7.7, 0.8 Hz), 7.58 (1H, dd, J=7.7, 0.8 Hz), 7.65 (1H, t, J=7.7 Hz), 7.81 (1H, dd, J=6.8, 2.2 Hz), 7.82 (1H, s).

Intermediate (PME20)

$^1$H-NMR (CDCl$_3$) δ: 2.29 (3H, s), 2.61 (3H, s), 3.87 (3H, s), 6.89 (1H, d, J=8.3 Hz), 7.02 (1H, d, J=7.7 Hz), 7.45 (1H, d, J=7.7 Hz), 7.58 (1H, t, J=7.7 Hz), 7.77 (1H, dd, J=8.3, 2.7 Hz), 7.80 (1H, s).

Reference Production Example 24

Using 4-methoxy-3-methylphenylboronic acid, 2-bromo-4-methylpyridine, [1,1′-bis(diphenylphosphino)ferrocene]palladium(II) dichloride dichloromethane adduct, tripotassium phosphate, 1,4-dioxane, and water, the same reaction as in Reference Production Example 20 was performed to obtain 4-methyl-2-(4-methoxy-3-methylphenyl)pyridine (hereinafter referred to as the intermediate (PME21)).

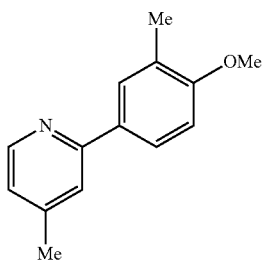 [SMILES: COc1ccc(-c2cc(C)ccn2)cc1C]

$^1$H-NMR (CDCl$_3$) δ: 2.29 (3H, s), 2.40 (3H, s), 3.88 (3H, s), 6.90 (1H, d, J=8.5 Hz), 6.99 (1H, d, J=4.8 Hz), 7.49 (1H, s), 7.78 (1H, dd, J=8.5, 2.7 Hz), 7.80 (1H, s), 8.50 (1H, d, J=4.8 Hz).

Reference Production Example 25

In accordance with the reaction mentioned in Reference Production Example 24, the following compounds were obtained. The structural formulas and $^1$H-NMR data of the thus obtained compounds are shown below.

Intermediate (PME22)

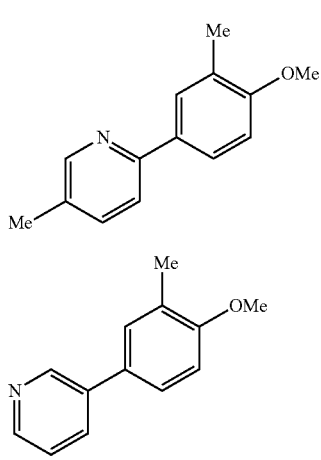

Intermediate (PME23)

Intermediate (PME24)

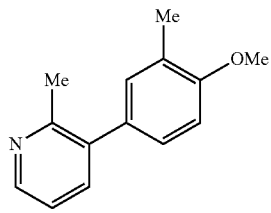

Intermediate (PME25)

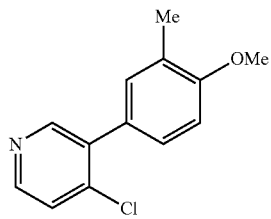

Intermediate (PME26)

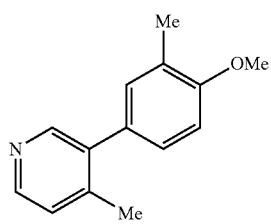

Intermediate (PME27)

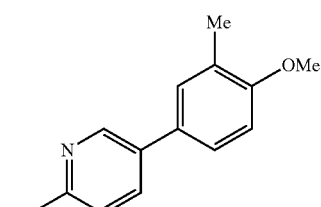

Intermediate (PME28)

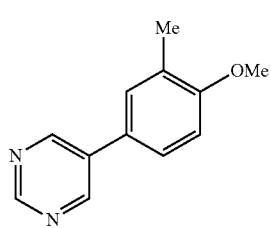

Intermediate (PME22)

$^1$H-NMR (CDCl$_3$) δ: 2.29 (3H, s), 2.35 (3H, s), 3.88 (3H, s), 6.90 (1H, d, J=8.5 Hz), 7.49-7.52 (1H, m), 7.57 (1H, d, J=8.2 Hz), 7.76 (1H, dd, J=8.2, 2.7 Hz), 7.79 (1H, s), 8.47 (1H, brs).

Intermediate (PME23)

$^1$H-NMR (CDCl$_3$) δ: 2.29 (3H, s), 3.88 (3H, s), 6.92 (1H, d, J=8.1 Hz), 7.31 (1H, dd, J=8.1, 4.8 Hz), 7.37-7.40 (2H, m), 7.82 (1H, dt, J=8.0, 2.0 Hz), 8.53 (1H, dd, J=4.8, 1.4 Hz), 8.81 (1H, d, J=2.0 Hz).

Intermediate (PME24)

$^1$H-NMR (CDCl$_3$) δ: 2.27 (3H, s), 2.52 (3H, s), 3.88 (3H, d, J=1.0 Hz), 6.89 (1H, d, J=8.2 Hz), 7.08-7.18 (3H, m), 7.49 (1H, d, J=7.5 Hz), 8.46 (1H, dd, J=4.8, 1.7 Hz).

Intermediate (PME25)

¹H-NMR (CDCl₃) δ: 2.28 (3H, s), 3.89 (3H, s), 6.92 (1H, d, J=8.5 Hz), 7.24-7.29 (2H, m), 7.40 (1H, d, J=5.3 Hz), 8.43 (1H, d, J=5.3 Hz), 8.54 (1H, s).

Intermediate (PME26)

¹H-NMR (CDCl₃) δ: 2.27 (3H, s), 2.30 (3H, s), 3.88 (3H, s), 6.90 (1H, d, J=8.0 Hz), 7.10 (1H, s), 7.12 (1H, dd, J=8.0, 2.1 Hz), 7.16 (1H, d, J=5.0 Hz), 8.40 (1H, s), 8.41 (1H, s).

Intermediate (PME27)

¹H-NMR (CDCl₃) δ: 2.29 (3H, s), 2.59 (3H, s), 3.88 (3H, s), 6.91 (1H, d, J=8.2 Hz), 7.18 (1H, d, J=8.0 Hz), 7.33-7.39 (2H, m), 7.72 (1H, dd, J=8.0, 2.2 Hz), 8.69 (1H, d, J=2.2 Hz).

Intermediate (PME28)

¹H-NMR (CDCl₃) δ: 2.30 (3H, s), 3.90 (3H, s), 6.96 (1H, d, J=8.2 Hz), 7.37-7.41 (2H, m), 8.91 (2H, s), 9.15 (1H, s).

Reference Production Example 26

A mixture of 0.57 g of the intermediate (PME13) mentioned in Reference Production Example 21 and an aqueous 48% tetrafluoroboric acid solution was cooled to 0° C., and 2 ml of an aqueous solution of 0.20 g of sodium nitrite was added dropwise. After stirring at the same temperature for 30 minutes, stirring was performed at room temperature for 3 hours. After adding a sodium bicarbonate solution, the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 5.41 g of 3-fluoro-2-(4-methoxy-3-methylphenyl)pyridine (hereinafter referred to as the intermediate (PME29)).

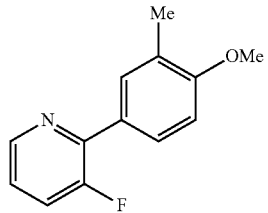

¹H-NMR (CDCl₃) δ: 2.30 (3H, s), 3.90 (3H, s), 6.93 (1H, d, J=9.1 Hz), 7.18-7.23 (1H, m), 7.43-7.48 (1H, m), 7.81 (1H, s), 7.82 (1H, d, J=9.1 Hz), 8.48 (1H, dd, J=2.9, 1.6 Hz).

Reference Production Example 27

A mixture of 0.46 g of 2-chloro-6-methylpyridine, 1.00 g of a 4-methoxy-3-nitro-phenylboronic acid pinacol ester, 0.29 g of [1,1'-bis(diphenylphosphino)ferrocene]palladium (II) dichloride dichloromethane adduct, 1.52 g of tripotassium phosphate, 40 mL of 1,2-dimethoxyethane, and 5 mL of water was stirred at 80° C. for 6.5 hours. After cooling, water was added and the reaction mixture was filtered, and then the filtrate was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.38 g of 2-(4-methoxy-3-nitrophenyl)-6-methylpyridine (referred to as CA27).

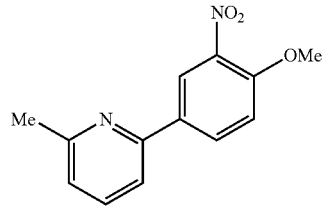 [SMILES: COc1ccc(-c2cccc(C)n2)cc1[N+](=O)[O-]]

¹H-NMR (CDCl₃) δ: 2.62 (3H, s), 4.01 (3H, s), 7.12 (1H, d, J=7.8 Hz), 7.17 (1H, d, J=8.8 Hz), 7.50 (1H, d, J=7.8 Hz), 7.66 (1H, t, J=7.8 Hz), 8.21 (1H, dd, J=8.8, 2.3 Hz), 8.52 (1H, d, J=2.3 Hz).

Reference Production Example 28

A mixture of 1.00 g of CA27 mentioned in Reference Production Example 27, 1.14 g of an iron powder, 20 mL of acetic acid, and 20 mL of water was stirred at 80° C. for 9 hours. After concentration of the mixture under reduced pressure, a saturated sodium bicarbonate solution and ethyl acetate were added, followed by filtration and further extraction of the filtrate with ethyl acetate. The organic layer was washed with water and a saturated saline solution, dried over anhydrous sodium sulfate, and then concentrated under reduced pressure. The residue thus obtained was subjected to silica gel column chromatography to obtain 0.79 g of 2-(3-amino-4-methoxyphenyl)-6-methylpyridine (referred to as CA28).

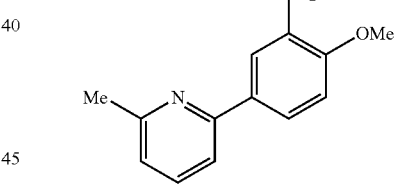

¹H-NMR (CDCl₃) δ: 2.61 (3H, s), 3.88 (2H, brs), 3.90 (3H, s), 6.86 (1H, d, J=8.3 Hz), 7.03 (1H, d, J=7.5 Hz), 7.33 (1H, dd, J=8.3, 2.2 Hz), 7.43 (1H, d, J=2.2 Hz), 7.44 (1H, d, J=7.5 Hz), 7.58 (1H, t, J=7.5 Hz).

Reference Production Example 29

A mixture of 2.42 g of CA28 mentioned in Reference Production Example 28, 15 mL of 48% hydrobromic acid, and 10 mL of water was cooled to 0° C., and 5 mL of an aqueous solution of 0.20 g of sodium nitrite was added dropwise. A mixture of 1.69 g of copper(I) bromide and 5 ml of 48% hydrobromic acid was added dropwise, followed by stirring at 60° C. for 3 hours. After cooling, a sodium bicarbonate solution and ethyl acetate was added, followed by filtration and further extraction of the filtrate with ethyl acetate. The organic layer was washed with water and a saturated saline solution, dried over anhydrous sodium sulfate, and then concentrated under reduced pressure. The residue thus obtained was subjected to silica gel column chromatography to obtain 2.16 g of 4-(6-methylpyridin-2-yl)-2-bromoanisole (hereinafter referred to as the intermediate (PME30)).

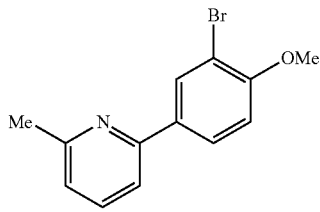 [SMILES: COc1ccc(-c2cccc(C)n2)cc1Br]

$^1$H-NMR (CDCl$_3$) δ: 2.61 (3H, s), 3.95 (3H, s), 6.98 (1H, d, J=8.6 Hz), 7.07 (1H, d, J=7.7 Hz), 7.45 (1H, d, J=7.7 Hz), 7.61 (1H, t, J=7.7 Hz), 7.91 (1H, dt, J=8.6, 1.1 Hz), 8.23 (1H, t, J=1.1 Hz).

Reference Production Example 30

A mixture of 5.0 g of 1-(4-hydroxy-3-methyl)-ethanone, 5.70 g of methyl iodide, 20.0 g of potassium carbonate, and 200 ml of acetone was stirred with heating under reflux for 6 hours. The reaction mixture was filtered and extracted with ethyl acetate. The organic layer was washed with water, dried over anhydrous magnesium sulfate, and then concentrated under reduced pressure to obtain 5.3 g of 1-(4-hydroxy-3-methylphenyl)ethan-1-one (referred to as CA30).

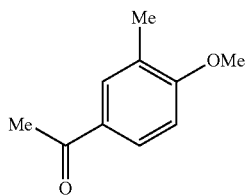 [SMILES: COc1ccc(C(C)=O)cc1C]

$^1$H-NMR (CDCl$_3$) δ:7.82 (1H, dd, J=8.5, 1.7 Hz), 7.79-7.76 (1H, m), 6.85 (1H, d, J=8.5 Hz), 3.90 (3H, s), 2.55 (3H, s), 2.25 (3H, s).

Reference Production Example 31

A mixture of 5.76 g of CA30 mentioned in Reference Production Example 30 and 7.46 ml of N,N-dimethylformamide diethyl acetal was stirred with heating under reflux for 24 hours, and then concentrated under reduced pressure to obtain 4.78 g of 2-(dimethylamino)vinyl(4-methoxy-3-methylphenyl) ketone (referred to as CA31).

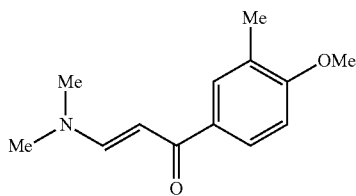 [SMILES: COc1ccc(C(=O)/C=C/N(C)C)cc1C]

$^1$H-NMR (DMSO-D$_6$) δ:7.76 (1H, dd, J=8.5, 2.2 Hz), 7.72 (1H, s), 7.64 (1H, d, J=12.4 Hz), 6.95 (1H, d, J=8.5 Hz), 5.80 (1H, d, J=12.4 Hz), 3.83 (3H, s), 3.11 (3H, brs), 2.90 (3H, brs), 2.18 (3H, s).

Reference Production Example 32

To 50 mL of ethanol, 0.85 g of sodium hydride was added. Next, 3.20 g of acetamidine hydrochloride and CA31 (7.06 g) mentioned in Reference Production Example 31 were added, followed by heating under reflux for 7 hours. After concentration of the mixture under reduced pressure, water was added and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 4.20 g of 2-chloro-4-(4-methoxy-3-methylphenyl)pyrimidine (hereinafter referred to as the intermediate (PME31)).

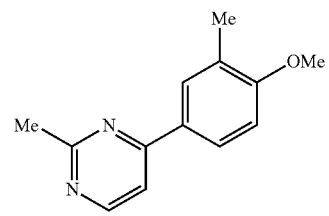 [SMILES: COc1ccc(-c2ccnc(C)n2)cc1C]

$^1$H-NMR (CDCl$_3$) δ: 2.30 (3H, s), 2.78 (3H, s), 3.90 (3H, s), 6.92 (1H, dd, J=6.3, 2.2 Hz), 7.44 (1H, d, J=5.3 Hz), 7.90 (1H, s), 7.92 (1H, dd, J=6.3, 2.2 Hz), 8.59 (1H, d, J=5.3 Hz).

Reference Production Example 33

A mixture of 5.41 g of the intermediate (PME1) mentioned in Reference Production Example 20, 50 mL of 48% hydrobromic acid, and 50 mL of acetic acid 50 mL was stirred at 110° C. for 20 hours. The reaction solution was concentrated and a saturated sodium bicarbonate solution was added, and then the mixture was extracted with ethyl acetate. The organic layer was washed with water and a saturated saline solution, dried over anhydrous sodium sulfate, and then concentrated under reduced pressure to obtain 4.32 g of 3-chloro-2-(4-hydroxy-3-methylphenyl)pyridine (hereinafter referred to as the intermediate (HP1)).

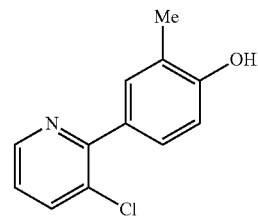 [SMILES: Cc1cc(-c2ncccc2Cl)ccc1O]

$^1$H-NMR (CDCl$_3$) δ: 2.26 (3H, s), 6.43-6.58 (1H, brm), 6.69 (1H, d, J=8.3 Hz), 7.19 (1H, dd, J=8.0, 4.7 Hz), 7.39 (1H, dd, J=8.3, 2.0 Hz), 7.48 (1H, d, J=2.0 Hz), 7.79 (1H, dd, J=8.0, 1.4 Hz), 8.56 (1H, dd, J=4.7, 1.4 Hz).

Reference Production Example 34

The same reaction as in Reference Production Example 33 was performed to obtain the following compounds. The structural formulas and $^1$H-NMR data of the thus obtained compounds are shown below.

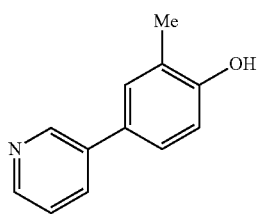

Intermediate (HP2)

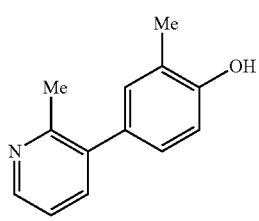

Intermediate (HP3)

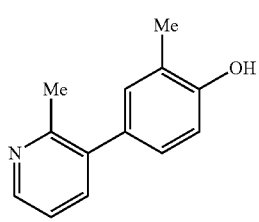

Intermediate (HP4)

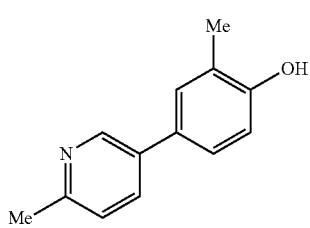

Intermediate (HP5)

Intermediate (HP2)

$^1$H-NMR (CDCl$_3$) δ: 2.34 (3H, s), 5.88 (1H, s), 6.90 (1H, d, J=8.2 Hz), 7.29-7.32 (1H, m), 7.33-7.36 (2H, m), 7.84 (1H, dt, J=7.8, 2.0 Hz), 8.54 (1H, dd, J=4.6, 2.0 Hz), 8.80 (1H, dd, J=2.4, 1.0 Hz).

Intermediate (HP3)

$^1$H-NMR (CDCl$_3$) δ: 2.31 (3H, s), 2.52 (3H, s), 5.15 (1H, s), 6.85 (1H, d, J=8.0 Hz), 7.04 (1H, d, J=7.7 Hz), 7.09 (1H, s), 7.14-7.20 (1H, m), 7.50 (1H, d, J=8.0 Hz), 8.47 (1H, d, J=4.8 Hz).

Intermediate (HP4)

$^1$H-NMR (CDCl$_3$) δ: 2.32 (3H, s), 5.14 (1H, s), 6.88 (1H, d, J=8.2 Hz), 7.19 (1H, d, J=8.2 Hz), 7.23 (1H, s), 7.40 (1H, d, J=5.3 Hz), 8.43 (1H, d, J=5.3 Hz), 8.53 (1H, s).

Intermediate (HP5)

$^1$H-NMR (CDCl$_3$) δ: 2.34 (3H, s), 2.60 (3H, s), 6.49 (1H, s), 6.88 (1H, d, J=8.2 Hz), 7.21 (1H, d, J=7.9 Hz), 7.27 (1H, dd, J=7.9, 1.5 Hz), 7.34 (1H, s), 7.75 (1H, dd, J=51.3, 2.2 Hz), 8.68 (1H, d, J=2.2 Hz).

Reference Production Example 35

A mixture of 3.82 g of the intermediate (PME2) mentioned in Reference Production Example 21, 35 mL of 48% hydrobromic acid, and 35 mL of acetic acid was stirred at 110° C. for 20 hours. The reaction solution was concentrated and were made basic by adding tert-butyl methyl ether and an aqueous sodium hydroxide solution, and then a liquid separating operation was performed. The aqueous layer was taken out, neutralized by adding concentrated hydrochloric acid, and then extracted with ethyl acetate. The organic layer was washed with water and a saturated saline solution, and then dried over anhydrous sodium sulfate. The organic layer was concentrated under reduced pressure, washed with water, dried, and then concentrated under reduced pressure to obtain 2.86 g of 6-ethyl-2-(4-hydroxy-3-methylphenyl)pyridine (hereinafter referred to as the intermediate (HP6)).

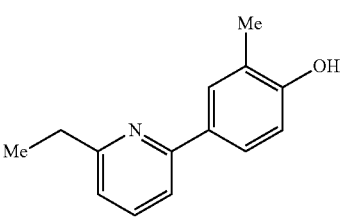

$^1$H-NMR (CDCl$_3$) δ: 1.36 (3H, t, J=7.6 Hz), 2.32 (3H, s), 2.88 (2H, q, J=7.6 Hz), 5.33 (1H, brs), 6.81 (1H, dd, J=8.2, 1.7 Hz), 7.05 (1H, dd, J=7.8, 0.5 Hz), 7.44 (1H, d, J=7.8 Hz), 7.62 (1H, t, J=7.8 Hz), 7.69 (1H, dd, J=6.4, 1.7 Hz), 7.79 (1H, s).

Reference Production Example 36

In accordance with the reaction mentioned in Reference Production Example 35, the following compounds were synthesized. The structural formulas and $^1$H-NMR data of the thus obtained compounds are shown below.

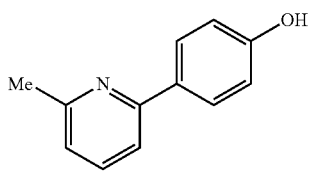

Intermediate (HP7)

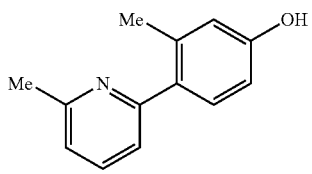

Intermediate (HP8)

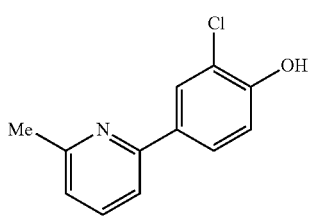

Intermediate (HP9)

Intermediate (HP10)
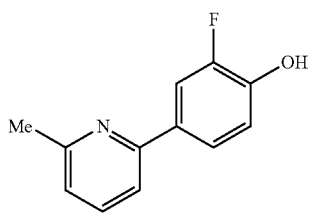

Intermediate (HP11)
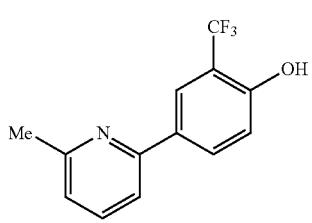

Intermediate (HP12)
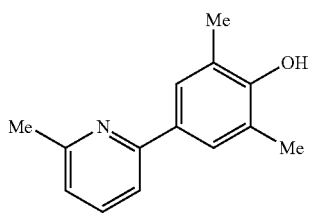

Intermediate (HP13)
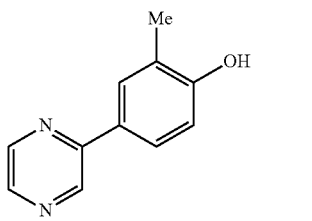

Intermediate (HP14)
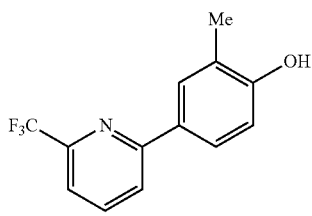

Intermediate (HP15)
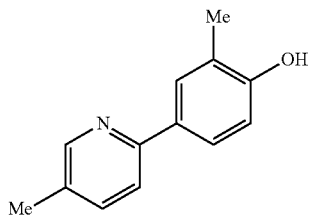

Intermediate (HP16)
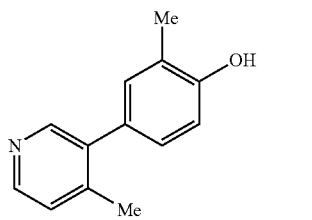

Intermediate (HP17)
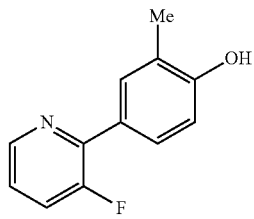

Intermediate (HP18)
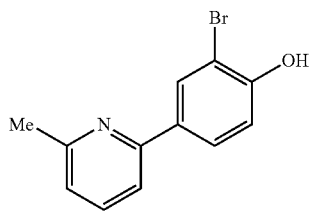

Intermediate (HP19)
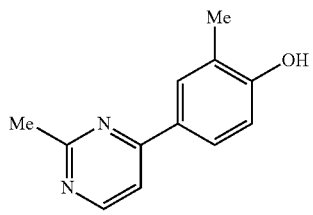

Intermediate (HP7)

$^1$H-NMR (CDCl$_3$) δ: 2.61 (3H, s), 6.27 (1H, s), 6.83 (2H, dt, J=8.9, 2.5 Hz), 7.05 (1H, d, J=7.8 Hz), 7.43 (1H, d, J=7.8 Hz), 7.61 (1H, t, J=7.8 Hz), 7.81 (2H, dt, J=8.9, 2.5 Hz).

Intermediate (HP8)

$^1$H-NMR (CDCl$_3$) δ: 2.24 (3H, s), 2.64 (3H, s), 6.57-6.61 (2H, m), 7.01 (1H, brs), 7.11 (1H, d, J=7.7 Hz), 7.17 (2H, dd, J=8.2, 2.0 Hz), 7.64 (1H, t, J=7.7 Hz).

Intermediate (HP9)

$^1$H-NMR (CDCl$_3$) δ: 2.62 (3H, s), 5.70 (1H, s), 7.09 (1H, d, J=7.7 Hz), 7.10 (1H, d, J=8.4 Hz), 7.45 (1H, d, J=7.7 Hz), 7.63 (1H, t, J=7.7 Hz), 7.81 (1H, dd, J=8.4, 2.2 Hz), 8.06 (1H, d, J=2.2 Hz).

Intermediate (HP10)

$^1$H-NMR (CDCl$_3$) δ: 2.62 (3H, s), 5.65 (1H, brs), 7.05 (1H, t, J=8.6 Hz), 7.08 (1H, d, J=7.8 Hz), 7.44 (1H, d, J=7.8 Hz), 7.60-7.66 (2H, m), 7.79 (1H, dd, J=11.9, 2.0 Hz).

Intermediate (HP11)

$^1$H-NMR (CDCl$_3$) δ: 2.63 (3H, s), 6.90 (1H, d, J=8.6 Hz), 7.11 (1H, d, J=7.8 Hz), 7.45 (1H, d, J=7.8 Hz), 7.65 (1H, t, J=7.8 Hz), 7.95 (1H, dd, J=8.6, 2.0 Hz), 8.11 (1H, d, J=2.0 Hz).

Intermediate (HP12)

$^1$H-NMR (CDCl$_3$) δ: 2.32 (6H, s), 2.61 (3H, s), 4.86 (1H, s), 7.03 (1H, d, J=7.7 Hz), 7.43 (1H, d, J=7.7 Hz), 7.58 (1H, t, J=7.7 Hz), 7.61 (2H, s).

Intermediate (HP13)

¹H-NMR (CDCl₃) δ: 2.33 (3H, s), 5.68 (1H, s), 6.88 (1H, d, J=8.2 Hz), 7.73 (1H, dd, J=8.2, 2.2 Hz), 7.82 (1H, d, J=1.6 Hz), 8.43 (1H, d, J=2.5 Hz), 8.57 (1H, dd, J=2.5, 1.6 Hz), 8.95 (1H, d, J=1.6 Hz).

Intermediate (HP14)

¹H-NMR (DMSO-D₆) δ: 2.21 (3H, s), 6.91 (1H, d, J=8.2 Hz), 7.71 (1H, d, J=7.7 Hz), 7.81 (1H, dd, J=8.2, 2.1 Hz), 7.88 (1H, s), 8.07 (1H, t, J=7.7 Hz), 8.14 (1H, d, J=8.2 Hz), 9.82 (1H, s).

Intermediate (HP15)

¹H-NMR (CDCl₃) δ: 2.32 (3H, s), 2.35 (3H, s), 5.05 (1H, brs), 6.84 (1H, d, J=8.2 Hz), 7.52 (1H, dd, J=8.2, 2.2 Hz), 7.56 (1H, d, J=8.2 Hz), 7.66 (1H, dd, J=8.2, 2.2 Hz), 7.78 (1H, d, J=2.2 Hz), 8.47 (1H, s).

Intermediate (HP16)

¹H-NMR (CDCl₃) δ: 2.30 (3H, s), 2.32 (3H, s), 5.62 (1H, s), 6.86 (1H, d, J=8.0 Hz), 7.03 (1H, dd, J=8.5, 2.1 Hz), 7.09 (1H, d, J=2.1 Hz), 7.18 (1H, d, J=5.0 Hz), 8.41 (1H, d, J=5.0 Hz), 8.41 (1H, s).

Intermediate (HP17)

¹H-NMR (CDCl₃) δ: 2.33 (3H, s), 5.08 (1H, s), 6.86 (1H, d, J=8.5 Hz), 7.19-7.23 (1H, m), 7.46 (1H, ddd, J=11.2, 8.2, 1.5 Hz), 7.72 (1H, d, J=8.5 Hz), 7.80 (1H, s), 8.48 (1H, dt, J=4.6, 1.5 Hz).

Intermediate (HP18)

¹H-NMR (CDCl₃) δ: 2.61 (3H, s), 5.72 (1H, s), 7.07 (1H, d, J=7.7 Hz), 7.09 (1H, d, J=8.5 Hz), 7.43 (1H, d, J=7.7 Hz), 7.62 (1H, t, J=7.7 Hz), 7.83 (1H, dd, J=8.5, 2.1 Hz), 8.18 (1H, d, J=2.1 Hz).

Intermediate (HP19)

¹H-NMR (DMSO-D₆) δ: 2.20 (3H, s), 2.62 (3H, s), 6.90 (1H, d, J=8.4 Hz), 7.71 (1H, d, J=5.5 Hz), 7.88 (1H, dd, J=8.4, 1.9 Hz), 7.96 (1H, d, J=1.9 Hz), 8.61 (1H, d, J=5.5 Hz), 9.96 (1H, s).

Reference Production Example 37

A mixture of 2.00 g of the intermediate (PME9) mentioned in Reference Production Example 21, 30 mL of 48% hydrobromic acid, and 30 mL of acetic acid was stirred at 110° C. for 8 hours. The reaction solution was concentrated and were made basic by adding tert-butyl methyl ether and an aqueous sodium hydroxide solution, and then a liquid separating operation was performed. The aqueous layer was taken out and then neutralized by adding concentrated hydrochloric acid. The precipitated solid was collected by filtration, washed with water, dried, and then concentrated under reduced pressure to obtain 0.71 g of 2-(4-hydroxy-3-methylphenyl)pyrimidine (hereinafter referred to as the intermediate (HP20)).

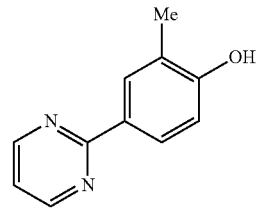

¹H-NMR (CDCl₃) δ: 1.60 (1H, brs), 2.34 (3H, s), 6.87 (1H, d, J=8.3 Hz), 7.12 (1H, t, J=4.8 Hz), 8.18 (1H, dd, J=8.3, 1.9 Hz), 8.24 (1H, s), 8.76 (2H, d, J=4.8 Hz).

Reference Production Example 38

In accordance with the reaction mentioned in Reference Production Example 37, the following compounds were synthesized. The structural formulas and ¹H-NMR data of the thus obtained compounds are shown below.

Intermediate (HP21)

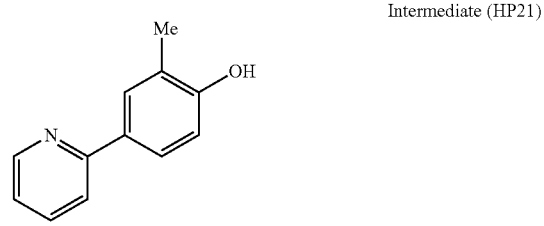

Intermediate (HP22)

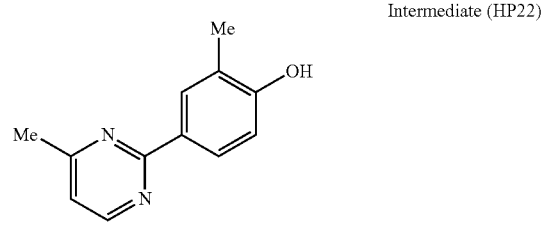 [SMILES: Cc1nccc(-c2ccc(O)c(C)c2)n1]

Intermediate (HP23)

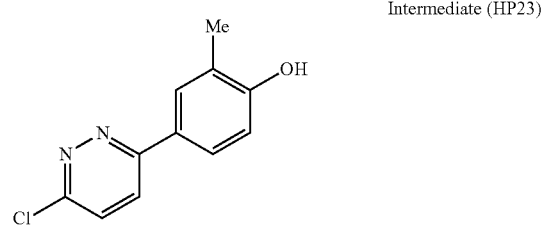

Intermediate (HP24)

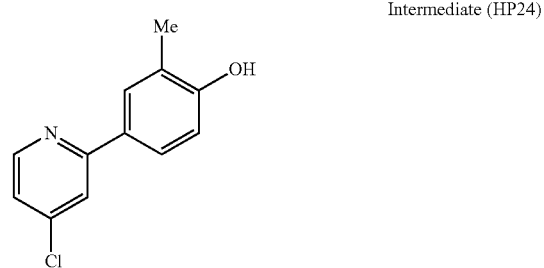

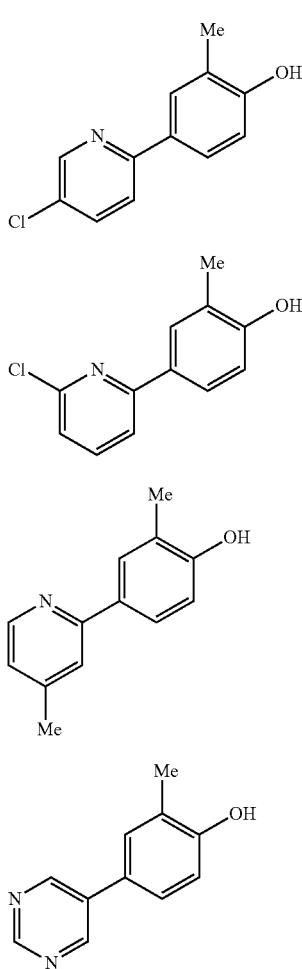

Intermediate (HP21)

¹H-NMR (DMSO-D₆) δ: 2.20 (3H, s), 6.86 (1H, d, J=8.5 Hz), 7.21-7.24 (1H, m), 7.73-7.84 (4H, m), 8.56-8.58 (1H, m), 9.62 (1H, d, J=1.0 Hz).

Intermediate (HP22)

¹H-NMR (DMSO-D₆) δ: 2.19 (3H, s), 2.49 (3H, s), 6.87 (1H, d, J=8.4 Hz), 7.17 (1H, d, J=5.1 Hz), 8.06 (1H, dd, J=8.4, 2.1 Hz), 8.13 (1H, s), 8.63 (1H, d, J=5.1 Hz), 9.82 (1H, s).

Intermediate (HP23)

¹H-NMR (CDCl₃) δ: 2.34 (3H, s), 6.91 (1H, d, J=8.3 Hz), 7.65 (2H, d, J=1.7 Hz), 7.77 (1H, dd, J=8.3, 1.7 Hz), 7.88 (1H, s).

Intermediate (HP24)

¹H-NMR (DMSO-D₆) δ: 2.20 (3H, s), 6.95 (1H, d, J=8.5 Hz), 7.57 (1H, d, J=5.6 Hz), 7.84 (1H, d, J=8.5 Hz), 7.93 (1H, s), 8.16 (1H, s), 8.60 (1H, d, J=5.6 Hz), 10.11 (1H, s).

Intermediate (HP25)

¹H-NMR (DMSO-D₆) δ: 2.19 (3H, s), 6.87 (1H, d, J=8.5 Hz), 7.74 (1H, dd, J=8.3, 2.1 Hz), 7.83-7.92 (3H, m), 8.59 (1H, t, J=1.2 Hz), 9.72 (1H, s).

Intermediate (HP26)

¹H-NMR (DMSO-D₆) δ: 2.20 (3H, s), 6.88 (1H, d, J=8.5 Hz), 7.35-7.30 (1H, m), 7.74 (1H, dd, J=8.5, 2.4 Hz), 7.80-7.87 (3H, m), 9.80 (1H, s).

Intermediate (HP27)

¹H-NMR (DMSO-D₆) δ: 2.22 (3H, s), 2.58 (3H, s), 7.01 (1H, d, J=8.2 Hz), 7.62 (1H, d, J=5.7 Hz), 7.78 (1H, d, J=8.2 Hz), 7.87 (1H, s), 8.15 (1H, s), 8.59 (1H, d, J=5.7 Hz), 10.37 (1H, brs).

Intermediate (HP28)

¹H-NMR (CDCl₃) δ: 2.35 (3H, s), 6.92 (1H, d, J=8.2 Hz), 7.32 (1H, dd, J=8.2, 2.0 Hz), 7.36 (1H, d, J=2.0 Hz), 8.91 (2H, s), 9.16 (1H, s).

Reference Production Example 39

A mixture of 1.60 g of the intermediate (PME15) of Reference Production Example 23, 12 mL of 48% hydrobromic acid, and 12 mL of acetic acid was stirred with heating under reflux for 8 hours. The reaction solution was concentrated and then dried to obtain 2.10 g of 2-(4-hydroxy-3-methylphenyl)pyridine hydrobromide (hereinafter referred to as the intermediate (HP29)).

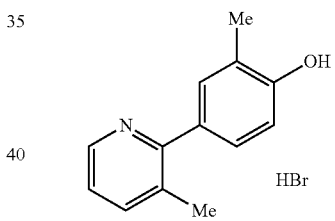

¹H-NMR (DMSO-D₆) δ: 2.22 (3H, s), 2.46 (3H, s), 3.90 (1H, brs), 7.01 (1H, d, J=8.2 Hz), 7.38 (1H, dd, J=8.3, 2.0 Hz), 7.44 (1H, d, J=2.0 Hz), 7.90 (1H, dd, J=8.0, 6.0 Hz), 8.50 (1H, d, J=7.2 Hz), 8.70 (1H, d, J=6.0 Hz), 10.17 (1H, s).

Reference Production Example 40

In accordance with the reaction mentioned in Reference Production Example 39, the following compounds were synthesized. The structural formulas and ¹H-NMR data of the thus obtained compounds are shown below.

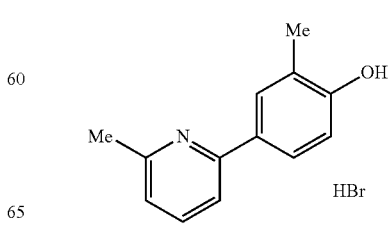

Intermediate (HP30)

¹H-NMR (CDCl₃) δ: 2.30 (3H, s), 3.89 (3H, s), 6.92 (1H, d, J=8.0 Hz), 7.52 (1H, dd, J=6.1, 2.4 Hz), 7.90-7.81 (4H, m), 10.27 (1H, brs).

Reference Production Example 41

A mixture of 1.00 g of 4-acetyl-2-methylphenol, 1.93 g of N,N',N'-methylidynetrisformamide, 0.06 g of p-toluenesulfonic acid monohydrate, and 3 g of formamide was heated at 160° C. for 8.5 hours. After cooling, the reaction solution was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 4.20 g of 4-(4-hydroxy-3-methylphenyl)pyrimidine (hereinafter referred to as the intermediate (HP31))

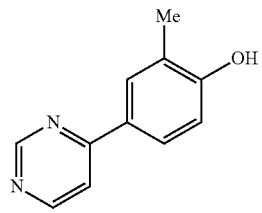 [SMILES: Cc1cc(-c2ccncn2)ccc1O]

¹H-NMR (CDCl₃) δ: 2.35 (3H, s), 6.27 (1H, s), 6.90 (1H, d, J=8.5 Hz), 7.66 (1H, dd, J=5.5, 1.4 Hz), 7.84 (1H, dd, J=8.5, 2.1 Hz), 7.94 (1H, s), 8.70 (1H, d, J=5.5 Hz), 9.21 (1H, s).

Reference Production Example 46

A mixture of 33.5 g of 2-methyl-3-nitrophenol, 41 g of iodoethane, 90 g of potassium carbonate, and 400 ml of acetone was stirred with heating under reflux for 10 hours. The mixture was cooled to room temperature and filtered, and the filtrate was concentrated and extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 39.9 g of 1-ethoxy-2-methyl-3-nitrobenzene (referred to as CA46).

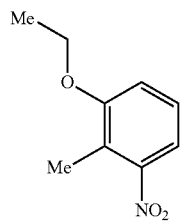

¹H-NMR (CDCl₃) δ (ppm): 7.39 (1H, dd, J=8.2, 1.0 Hz), 7.24 (1H, t, J=8.3 Hz), 7.02 (1H, d, J=8.2 Hz), 4.08 (2H, q, J=7.0 Hz), 2.37 (3H, s), 1.50-1.42 (3H, m).

Reference Production Example 47

A mixture of 39.9 g of CA46 mentioned in Reference Production Example 46, 4 g of palladium-carbon (palladium of 5%), and 200 ml of ethanol was stirred in a hydrogen atmosphere at room temperature for 18 hours. The mixture was filtered and the filtrate was concentrated to obtain 33.0 g of 3-ethoxy-2-methylaniline (referred to as CA47).

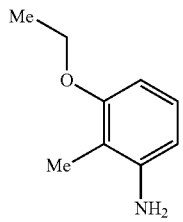 [SMILES: CCOc1cccc(N)c1C]

¹H-NMR (CDCl₃) δ (ppm): 6.95 (1H, t, J=8.1 Hz), 6.35 (1H, d, J=2.9 Hz), 6.33 (1H, d, J=3.1 Hz), 4.02-3.97 (2H, m), 3.61 (2H, brs), 2.05 (3H, s), 1.40 (3H, t, J=7.1 Hz).

Reference Production Example 48

At room temperature, 25 g of triphosgene was added to a mixture of 33.0 g of CA47 mentioned in Reference Production Example 47 and 400 ml of toluene, followed by stirring with heating under reflux for 4 hours. The mixture was concentrated under reduced pressure to obtain 37.2 g of 1-ethoxy-3-isocyanato-2-methylbenzene (referred to as CA48).

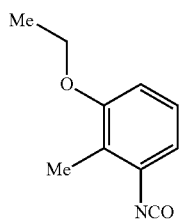

¹H-NMR (CDCl₃) δ (ppm): 7.07 (1H, t, J=8.2 Hz), 6.70 (1H, d, J=7.7 Hz), 6.68 (1H, d, J=8.2 Hz), 4.02 (2H, q, J=7.0 Hz), 2.20 (3H, s), 1.42 (3H, t, J=7.0 Hz).

Reference Production Example 49

Under ice cooling, 15 g of sodium azide was added to a mixture of 350 ml of N,N-dimethylformamide and 33.6 g of anhydrous aluminum chloride, followed by stirring for 1 hour. Then, CA48 (37.2 g) mentioned in Reference Production Example 48 was added and the temperature of the reaction mixture was raised to 75° C., followed by stirring for 5 hours. After cooling the mixture, 100 ml of ice water was added to the reaction mixture under ice cooling. A mixture of 23 g of sodium nitrite and 150 ml of water was added, and then concentrated hydrochloric acid was added to adjust the pH of the mixture to about pH 4. After extraction with ethyl acetate, the organic layer was washed with water and a saturated saline solution, dried over anhydrous magnesium sulfate, and then concentrated under reduced pressure. The residue thus obtained was subjected to silica gel column chromatography to obtain 39.0 g of 1-(2-methyl-3-ethoxyphenyl)-1,4-dihydrotetrazol-5-one (referred to as CA49).

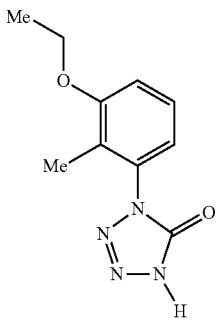 [SMILES: CCOc1cccc(-n2nn[nH]c2=O)c1C]

¹H-NMR (CDCl₃) δ (ppm): 7.30 (1H, t, J=8.1 Hz), 6.99 (1H, d, J=8.5 Hz), 6.96 (1H, d, J=8.0 Hz), 4.10 (2H, q, J=6.9 Hz), 2.13 (3H, s), 1.46 (3H, t, J=7.0 Hz).

Reference Production Example 50

Under ice cooling, 44.7 g of dimethyl sulfate was added to a mixture of 39.0 g of CA49 mentioned in Reference Production Example 49, 36.7 g of potassium carbonate, and 400 ml of N,N-dimethylformamide, and the temperature was raised to room temperature, followed by stirring for 7 hours. After the addition of 100 ml of water, the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 38.2 g of 1-(2-methyl-3-ethoxyphenyl)-4-methyl-1,4-dihydrotetrazol-5-one (referred to as CA50).

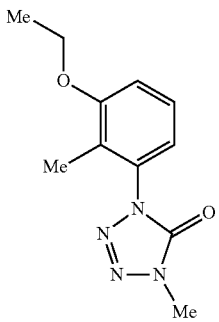 [SMILES: CCOc1cccc(-n2nnn(C)c2=O)c1C]

¹H-NMR (CDCl₃) δ (ppm): 7.29-7.23 (1H, m), 6.96 (1H, d, J=8.2 Hz), 6.93 (1H, d, J=8.2 Hz), 4.08 (2H, q, J=6.9 Hz), 3.72 (3H, s), 2.11 (3H, s), 1.45 (3H, t, J=7.1 Hz).

Reference Production Example 51

A mixture of 38.2 g of CA50 mentioned in Reference Production Example 50, 7.95 g of 1,1'-azobis(cyclohexane-1-carbonitrile), 33.4 g of N-bromosuccinimide, and 380 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 38.2 g of 1-(2-bromomethyl-3-ethoxyphenyl)-4-methyl-1,4-dihydrotetrazol-5-one.

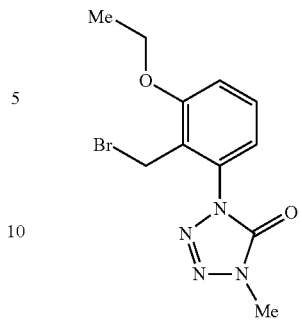

¹H-NMR (CDCl₃) δ (ppm): 7.40 (1H, t, J=8.2 Hz), 7.01 (2H, t, J=8.3 Hz), 4.64 (2H, s), 4.17 (2H, q, J=7.0 Hz), 3.74 (3H, s), 1.49 (3H, t, J=6.9 Hz).

Reference Production Example 52

To a mixture of 4.99 g of triisopropylsilanethiol and 30 mL of toluene, 0.63 g of 60% sodium hydride was added under ice cooling, followed by stirring for 30 minutes. To the reaction mixture, 2.82 g of CA10 mentioned in Reference Production Example 10 and 0.856 g of [1,1'-bis(diphenylphosphino)ferrocene]palladium(II) dichloride dichloromethane adduct were added. The temperature of the reaction mixture was raised to 90° C., followed by stirring for 4 hours. After cooling, water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 3.64 g of 1-(2-methyl-3-triisopropylsilanylthiophenyl)-4-methyl-1,4-dihydrotetrazol-5-one (referred to as CA52).

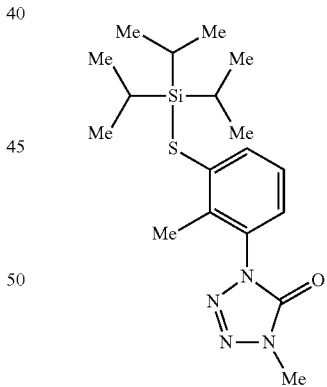

¹H-NMR (CDCl₃) δ (ppm): 1.09 (18H, d, J=6.6 Hz), 1.31 (3H, q, J=6.6 Hz), 2.45 (3H, s), 3.71 (3H, s), 7.16-7.21 (2H, m), 7.64 (1H, dd, J=6.6, 2.7 Hz).

Reference Production Example 53

A mixture of 3.63 g of CA52 mentioned in Reference Production Example 52, 2.91 g of cesium fluoride, and 10 mL of N,N-dimethylformamide was stirred at room temperature for 30 minutes. To the mixture, 2.72 g of methyl iodide was added, followed by stirring at room temperature for 3 hours. Water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.65 g of 1-(2-methyl-3-methylthiophenyl)-4-methyl-1,4-dihydrotetrazol-5-one (referred to as CA53).

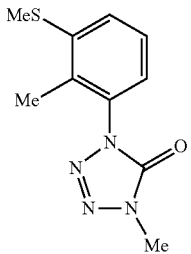 [SMILES: CSc1cccc(-n2nnn(C)c2=O)c1C]

$^1$H-NMR (CDCl$_3$) δ (ppm): 2.22 (3H, s), 2.51 (3H, s), 3.72 (3H, s), 7.10-7.16 (1H, m), 7.36-7.29 (2H, m).

Reference Production Example 54

A mixture of 1.50 g of CA53 mentioned in Reference Production Example 53, 0.620 g of 1,1'-azobis(cyclohexane-1-carbonitrile), 1.30 g of N-bromosuccinimide, and 15 mL of chlorobenzene was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.400 g of 1-(2-bromomethyl-3-methyl-thiophenyl)-4-methyl-1,4-dihydrotetrazol-5-one.

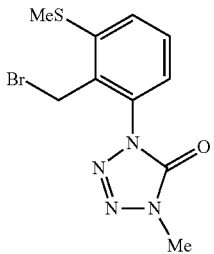 [SMILES: CSc1cccc(-n2nnn(C)c2=O)c1CBr]

$^1$H-NMR (CDCl$_3$) δ (ppm): 2.57 (3H, s), 3.75 (3H, s), 4.69 (2H, s), 7.20 (1H, t, J=4.5 Hz), 7.44 (2H, d, J=4.5 Hz).

Reference Production Example 55

1-(2-Bromomethyl-phenyl)-4-methyl-1,4-dihydrotetrazol-5-one (referred to as CA55) was produced in accordance with the steps (1) to (3).

Step (1)

Under ice cooling, 55.1 g of anhydrous aluminum chloride was added to 500 mL of N,N-dimethylformamide, followed by stirring for 15 minutes. To this was added 26.9 g of sodium azide, the mixture was stirred for 15 minutes, followed by the addition of 50.6 g of 1-isocyanato-2-methylbenzene and further heating at 70° C. for 4 hours. After cooling, the reaction solution was added in a mixture of 51.8 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 69.8 g of 1-(2-methylphenyl)-1,4-dihydrotetrazol-5-one.

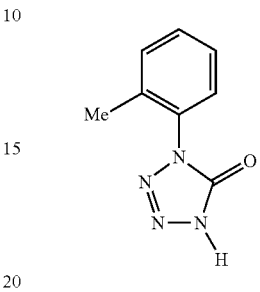

$^1$H-NMR (CDCl$_3$) δ: 2.32 (3H, s), 7.37-7.47 (4H, m), 13.55 (1H, s).

Step (2)

To a mixture of 69.8 g of the 1-(2-methylphenyl)-1,4-dihydrotetrazol-5-one and 380 mL of N,N-dimethylformamide, 18.2 g of 55% sodium hydride was added under ice cooling, followed by stirring for 20 minutes and further the addition of 59.4 g of methyl iodide. The temperature of the mixture was raised to room temperature, followed by stirring for 2.5 hours. Water was poured into the reaction mixture and the mixture was extracted with methyl tert-butyl ether. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 52.5 g of 1-(2-methylphenyl)-4-methyl-1,4-dihydrotetrazol-5-one.

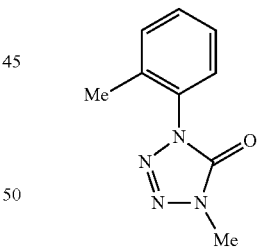

$^1$H-NMR (CDCl$_3$) δ: 2.29 (3H, s), 3.72 (3H, s), 7.32-7.44 (4H, m).

Step (3)

A mixture of 1.5 g of the 1-(2-methylphenyl)-4-methyl-1,4-dihydrotetrazol-5-one, 1.5 g of N-bromosuccinimide, 20 mL of carbon tetrachloride, and 0.01 g of azoisobutyronitrile was stirred with heating under reflux for 8 hours. After cooling to room temperature, the mixture was filtered and the filtrate was concentrated under reduced pressure. The residue thus obtained was subjected to silica gel chromatography to obtain 2.1 g of CA55.

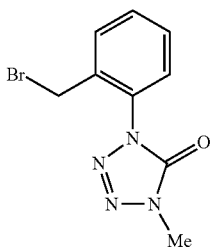 [SMILES: Cn1nnn(-c2ccccc2CBr)c1=O]

¹H-NMR (CDCl₃) δ:3.75 (3H, s), 4.59 (2H, s), 7.43-7.51 (3H, m), 7.53-7.56 (1H, m).

Reference Production Example 56

In accordance with the reaction mentioned in Reference Production Example 27, the following compounds were obtained. The structural formulas and ¹H-NMR data of the thus obtained compounds are shown below.

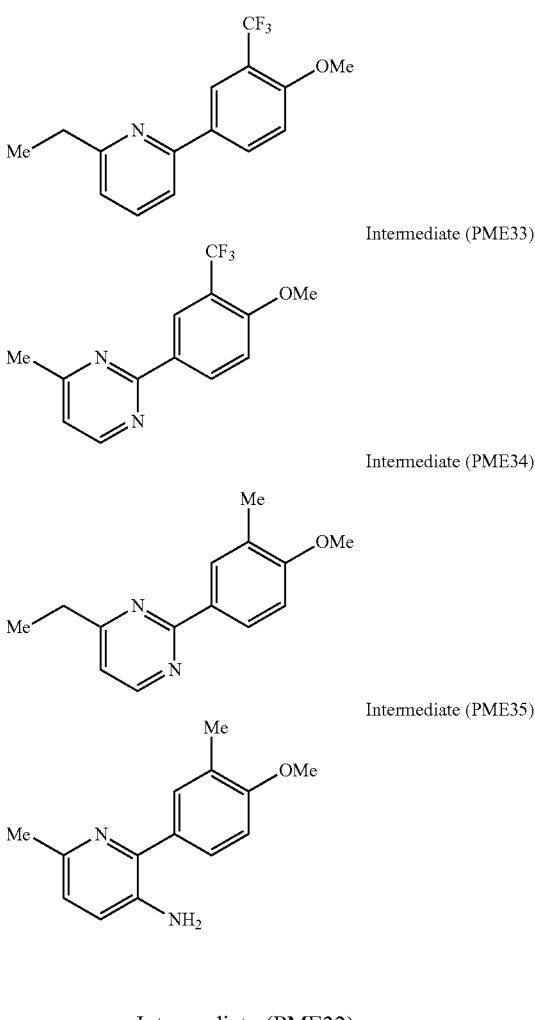

Intermediate (PME32)

¹H-NMR (CDCl₃) δ: 1.37 (3H, t, J=7.6 Hz), 2.89 (2H, q, J=7.6 Hz), 3.96 (3H, s), 7.09 (1H, d, J=8.6 Hz), 7.10 (1H, d, J=7.7 Hz), 7.49 (1H, d, J=7.7 Hz), 7.66 (1H, t, J=7.7 Hz), 8.18 (1H, dd, J=8.6, 2.3 Hz), 8.25 (1H, d, J=2.3 Hz).

Intermediate (PME33)

¹H-NMR (CDCl₃) δ: 2.58 (3H, s), 3.98 (3H, s), 7.04 (1H, d, J=5.2 Hz), 7.09 (1H, d, J=8.8 Hz), 8.59-8.62 (2H, m), 8.72 (1H, d, J=2.3 Hz).

Intermediate (PME34)

¹H-NMR (CDCl₃) δ: 1.37 (3H, t, J=7.6 Hz), 2.30 (3H, s), 2.83 (2H, q, J=7.6 Hz), 3.90 (3H, s), 6.91 (1H, d, J=8.5 Hz), 6.98 (1H, d, J=5.0 Hz), 8.24 (1H, s), 8.29 (1H, d, J=8.5 Hz), 8.62 (1H, dd, J=5.0, 0.7 Hz).

Intermediate (PME35)

¹H-NMR (CDCl₃) δ: 2.26 (3H, s), 2.48 (3H, s), 3.67 (2H, s), 3.87 (3H, s), 6.90 (1H, d, J=8.2 Hz), 6.91 (1H, s), 6.97 (1H, d, J=8.2 Hz), 7.42-7.47 (2H, m).

Reference Production Example 57

A mixture of 2.50 g of the intermediate (PME35) mentioned in Reference Production Example 56, 5 ml of an aqueous 48% hydrobromic acid solution, and 1.04 g of copper(I) bromide was cooled to 0° C., and then 5 ml of an aqueous solution of 0.79 g of sodium nitrite was added dropwise. After stirring at the same temperature for 30 minutes, stirring was performed at room temperature for 3 hours. A sodium bicarbonate solution was added and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.50 g of 3-bromo-2-(4-methoxy-3-methylphenyl)6-methylpyridine (hereinafter referred to as the intermediate (PME36)).

¹H-NMR (CDCl₃) δ: 2.27 (3H, s), 2.56 (3H, s), 3.88 (3H, s), 6.89 (1H, d, J=8.5 Hz), 6.96 (1H, d, J=8.1 Hz), 7.45 (1H, d, J=2.2 Hz), 7.51 (1H, dd, J=8.5, 2.2 Hz), 7.82 (1H, t, J=8.1 Hz).

Reference Production Example 58

A mixture of 2.00 g of the intermediate (PME35) mentioned in Reference Production Example 56, 5 ml of concentrated hydrochloric acid, and 0.57 g of copper(I) chloride was cooled to 0° C., 10 ml of an aqueous solution of 0.64 g of sodium nitrite was added dropwise. After stirring at the same temperature for 30 minutes, stirring was performed at room temperature for 3 hours. A sodium bicarbonate solution was added and then the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 0.51 g of 3-chloro-2-(4-methoxy-3-methylphenyl)6-methylpyridine (hereinafter referred to as the intermediate (PME37)).

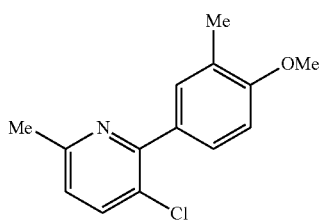 [SMILES: COc1ccc(-c2nc(C)ccc2Cl)cc1C]

$^1$H-NMR (CDCl$_3$) δ: 2.28 (3H, s), 2.58 (3H, s), 3.88 (3H, s), 6.90 (1H, d, J=8.5 Hz), 7.03 (1H, d, J=8.0 Hz), 7.51 (1H, dd, J=2.2, 0.5 Hz), 7.56 (1H, ddd, J=8.5, 2.2, 0.5 Hz), 7.63 (1H, d, J=8.0 Hz).

Reference Production Example 59

In accordance with the reaction mentioned in Reference Production Example 35, the following compounds were synthesized. The structural formulas and $^1$H-NMR data of the thus obtained compounds are shown below.

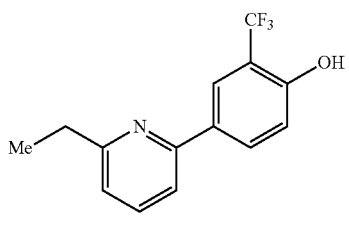

Intermediate (HP32)

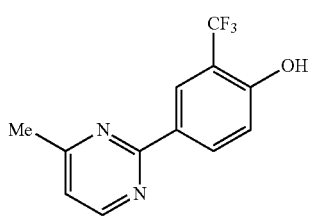

Intermediate (HP33)

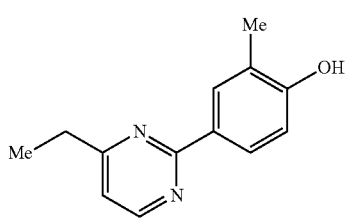

Intermediate (HP34)

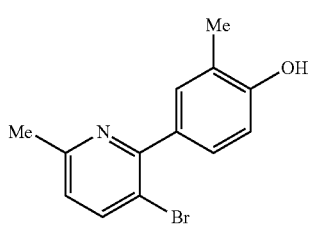

Intermediate (HP35)

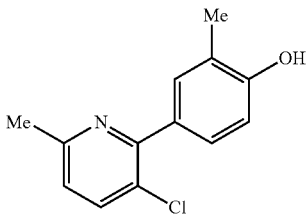

Intermediate (HP36)

Intermediate (HP32)

$^1$H-NMR (CDCl$_3$) δ: 1.37 (3H, t, J=7.6 Hz), 2.90 (2H, q, J=7.6 Hz), 6.93 (1H, d, J=8.6 Hz), 7.12 (1H, d, J=7.8 Hz), 7.47 (1H, d, J=7.8 Hz), 7.68 (1H, t, J=7.8 Hz), 8.01 (1H, d, J=8.6 Hz), 8.15 (1H, s).

Intermediate (HP33)

$^1$H-NMR (CDCl$_3$) δ: 2.59 (3H, s), 5.92 (1H, s), 7.04 (1H, d, J=3.9 Hz), 7.06 (1H, s), 8.52-8.55 (1H, m), 8.62 (1H, d, J=5.2 Hz), 8.68 (1H, d, J=2.0 Hz).

Intermediate (HP34)

$^1$H-NMR (CDCl$_3$) δ: 1.36 (3H, t, J=7.6 Hz), 2.34 (3H, s), 2.84 (2H, q, J=7.6 Hz), 5.27 (1H, br s), 6.85 (1H, d, J=8.2 Hz), 6.99 (1H, d, J=5.2 Hz), 8.20 (1H, d, J=8.2 Hz), 8.25 (1H, br s), 8.62 (1H, d, J=5.2 Hz).

Intermediate (HP35)

$^1$H-NMR (CDCl$_3$) δ: 2.28 (3H, s), 2.56 (3H, s), 5.32 (1H, s), 6.77 (1H, d, J=8.0 Hz), 6.96 (1H, d, J=8.5 Hz), 7.37 (1H, d, J=8.5 Hz), 7.41 (1H, s), 7.82 (1H, d, J=8.0 Hz).

Intermediate (HP36)

$^1$H-NMR (CDCl$_3$) δ: 2.27 (3H, s), 2.59 (3H, s), 5.75 (1H, br s), 6.73 (1H, d, J=8.2 Hz), 7.04 (1H, d, J=8.2 Hz), 7.38 (1H, dd, J=8.2, 2.0 Hz), 7.44 (1H, d, J=2.0 Hz), 7.65 (1H, d, J=8.2 Hz).

Reference Production Example 70

A mixture of 5.00 g of 4-bromo-2-methylphenol, 5.03 g of benzyl bromide, 4.20 g of potassium carbonate, and 50 mL of acetonitrile was stirred with heating under reflux for 5 hours. After cooling to room temperature, the reaction mixture was filtered and the filtrate was concentrated. The residue thus obtained was subjected to silica gel column chromatography to obtain 7.40 g of 2-benzyloxy-5-bromo-toluene (referred to as CA70).

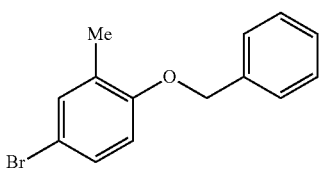 [SMILES: Cc1cc(Br)ccc1OCc1ccccc1]

¹H-NMR (CDCl₃) δ: 2.26 (3H, s), 5.06 (2H, s), 6.74 (1H, d, J=8.6 Hz), 7.23 (1H, dd, J=8.6, 2.3 Hz), 7.28-7.28 (1H, m), 7.36-7.41 (5H, m).

Reference Production Example 71

A mixture of 7.40 g of CA70 mentioned in Reference Production Example 70, 8.14 g of bis(pinacolato)diboron, 1.33 g of [1,1'-bis(diphenylphosphino)ferrocene]palladium(II) dichloride dichloromethane adduct, 7.86 g of potassium acetate, and 50 mL of dimethyl sulfoxide was stirred in a nitrogen atmosphere at 80° C. for 6 hours while heating. Water was poured into the reaction mixture allowed to cool and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 5.16 g of 4-benzyloxy-3-methyl-phenylboronic acid pinacol ester (referred to as CA71).

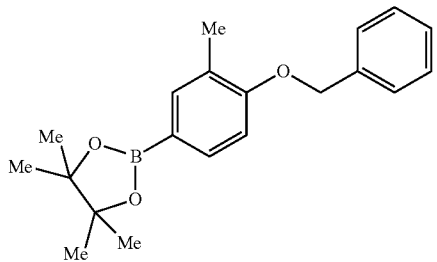 [SMILES: Cc1cc(B2OC(C)(C)C(C)(C)O2)ccc1OCc1ccccc1]

¹H-NMR (CDCl₃) δ: 1.34 (12H, s), 2.29 (3H, s), 5.12 (2H, s), 6.89 (1H, d, J=8.7 Hz), 7.33 (1H, d, J=7.1 Hz), 7.38 (2H, t, J=7.5 Hz), 7.46-7.43 (2H, m), 7.61-7.65 (2H, m).

Production Example 72

A mixture of 2.74 g of CA71 mentioned in Reference Production Example 71, 0.26 g of [1,1'-bis(diphenylphosphino)ferrocene]palladium(II) dichloride dichloromethane adduct, 8.44 g of tripotassium phosphate, 100 mL of 1,2-dimethoxyethane, and 5 mL of water was stirred at 80° C. for 10 hours. After cooling, water was added and the reaction mixture was filtered and the filtrate was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 3.34 g of 2-benzyloxy-5-(4-methylpyridin-2-yl)-toluene (referred to as CA72).

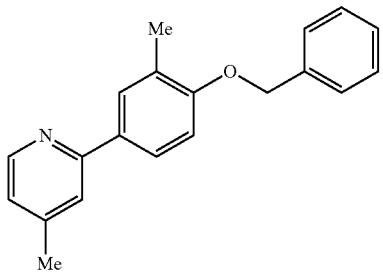 [SMILES: Cc1ccnc(-c2ccc(OCc3ccccc3)c(C)c2)c1]

¹H-NMR (CDCl₃) δ: 2.36 (3H, s), 2.40 (3H, s), 5.15 (2H, s), 6.96 (1H, d, J=8.5 Hz), 6.99-7.00 (1H, m), 7.31-7.42 (3H, m), 7.50-7.45 (3H, m), 7.76 (1H, dd, J=8.5, 2.3 Hz), 7.83 (1H, dd, J=2.3, 0.7 Hz), 8.50 (1H, d, J=5.0 Hz).

Production Example 73

A mixture of 3.34 g of CA72 of Reference Production Example 72, 2.09 g of m-chloroperbenzoic acid, 20 mL of chloroform, and 5 mL of water was stirred at room temperature for 9 hours. A sodium bicarbonate solution was slowly added to the reaction solution and the mixture was extracted with ethyl acetate. The organic layer was washed with a sodium bicarbonate solution, water, and a saturated saline solution, dried over anhydrous sodium sulfate, and then concentrated under reduced pressure. A mixture of the residue thus obtained and 0.84 g of dimethyl sulfate was stirred at 85° C. for 5 hours. After cooling to room temperature, 10 ml of 1,2-dimethoxyethane was added and 10 mL of an aqueous solution of 0.85 g of sodium cyanate was subsequently stirred for 2 hours. Water and ethyl acetate were added to the reaction solution and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 1.52 g of 2-benzyloxy-5-(6-cyano-4-methylpyridin-2-yl)-toluene (referred to as CA73).

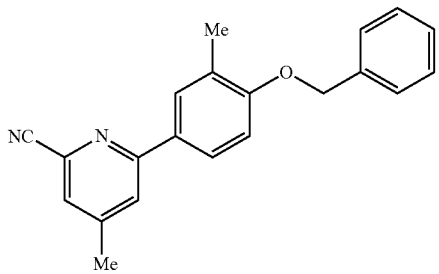 [SMILES: Cc1cc(C#N)nc(-c2ccc(OCc3ccccc3)c(C)c2)c1]

¹H-NMR (CDCl₃) δ: 2.37 (3H, s), 2.46 (3H, s), 5.16 (2H, s), 6.97 (1H, d, J=8.6 Hz), 7.34-7.48 (6H, m), 7.68

Production Example 74

A mixture of 1.52 g of CA73 mentioned in Reference Production Example 73, 0.08 g palladium-carbon (palladium of 10%), and 10 mL of ethyl acetate was stirred in a hydrogen atmosphere at room temperature for 9 hours. The reaction mixture was filtered and the filtrate was concentrated under reduced pressure. The residue thus obtained was recrystallized with methanol and ethyl acetate to obtain 0.19 g of (6-cyano-4-methylpyridin-2-yl)-2-methylphenol.

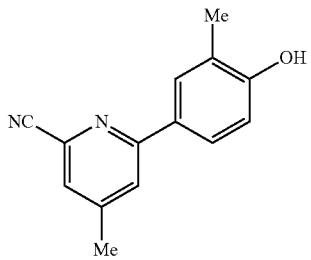 [SMILES: Cc1cc(C#N)nc(-c2ccc(O)c(C)c2)c1]

¹H-NMR (DMSO-D₆) δ: 2.08 (3H, s), 2.35 (3H, s), 6.78-6.81 (1H, m), 7.13 (1H, s), 7.69 (1H, s), 7.85-7.88 (1H, m), 7.91 (1H, d, J=0.5 Hz), 9.68-9.70 (1H, m).

Reference Production Example 75

In accordance with the reaction mentioned in Reference Production Example 27, the following compounds were obtained. The structural formulas and ¹H-NMR data of the thus obtained compounds are shown below.

Intermediate (PME38)
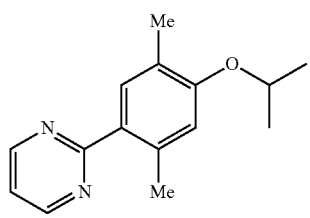

Intermediate (PME39)
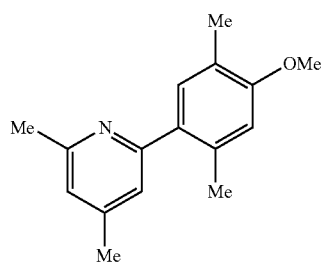

Intermediate (PME40)
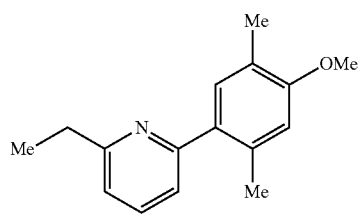

Intermediate (PME41)
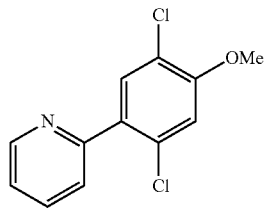

Intermediate (PME42)
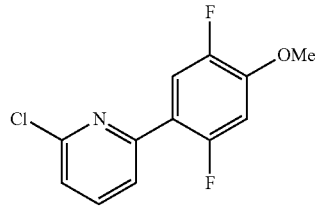

Intermediate (PME43)
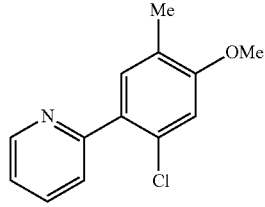

Intermediate (PME44)
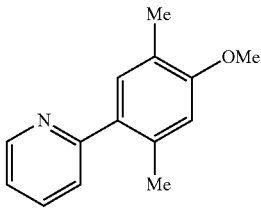

Intermediate (PME45)
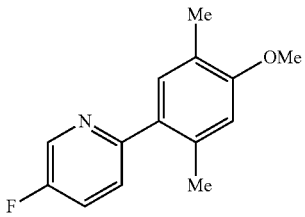

Intermediate (PME38)

¹H-NMR (CDCl₃) δ: 1.36 (6H, d, J=6.1 Hz), 2.22 (3H, s), 2.55 (3H, s), 4.65-4.53 (1H, m), 6.74 (1H, s), 7.14 (1H, t, J=4.9 Hz), 7.68 (1H, s), 8.80 (2H, d, J=4.8 Hz).

Intermediate (PME39)

¹H-NMR (CDCl₃) δ: 2.20 (3H, s), 2.33 (6H, s), 2.55 (3H, s), 3.84 (3H, s), 6.70 (1H, s), 6.90 (1H, s), 6.97 (1H, s), 7.16 (1H, s).

Intermediate (PME40)

¹H-NMR (CDCl₃) δ: 1.34 (3H, t, J=7.6 Hz), 2.21 (3H, s), 2.36 (3H, s), 2.87 (2H, q, J=7.6 Hz), 3.85 (3H, s), 6.72 (1H, s), 7.06 (1H, d, J=7.8 Hz), 7.16 (1H, d, J=7.8 Hz), 7.19 (1H, s), 7.61 (1H, t, J=7.8 Hz).

Intermediate (PME41)

¹H-NMR (CDCl₃) δ: 3.95 (3H, s), 7.02 (1H, s), 7.27-7.30 (1H, m), 7.65 (1H, dt, J=7.9, 1.1 Hz), 7.68 (1H, s), 7.73-7.78 (1H, m), 8.70 (1H, d, J=4.9 Hz).

Intermediate (PME42)

¹H-NMR (CDCl₃) δ: 3.93 (3H, t, J=5.4 Hz), 6.76 (1H, dd, J=12.4, 6.9 Hz), 7.25 (1H, dd, J=7.8, 0.9 Hz), 7.69 (1H, t, J=7.8 Hz), 7.75 (1H, dt, J=7.9, 1.2 Hz), 7.89 (1H, dd, J=12.2, 7.3 Hz).

Intermediate (PME43)

¹H-NMR (CDCl₃) δ: 2.22 (3H, s), 3.88 (3H, s), 6.90 (1H, s), 7.22-7.28 (1H, m), 7.42 (1H, d, J=1.0 Hz), 7.66 (1H, dt, J=7.8, 1.0 Hz), 7.72 (1H, td, J=7.8, 1.8 Hz), 8.68-8.70 (1H, m).

Intermediate (PME44)

¹H-NMR (CDCl₃) δ: 2.22 (3H, s), 2.38 (3H, s), 3.87 (3H, s), 6.73 (1H, s), 7.20 (1H, ddd, J=7.7, 5.0, 1.0 Hz), 7.23 (1H, s), 7.38 (1H, dt, J=7.7, 1.0 Hz), 7.71 (1H, td, J=7.7, 1.9 Hz), 8.67 (1H, ddd, J=4.8, 1.9, 1.0 Hz).

Intermediate (PME45)

$^1$H-NMR (CDCl$_3$) δ: 2.22 (3H, s), 2.35 (3H, s), 3.86 (3H, s), 6.72 (1H, s), 7.18 (1H, s), 7.36 (1H, dd, J=8.6, 4.6 Hz), 7.43 (1H, td, J=8.6, 3.0 Hz), 8.52 (1H, d, J=3.0 Hz).

Reference Production Example 76

In accordance with the reaction mentioned in Reference Production Example 35, the following compounds were synthesized. The structural formulas and $^1$H-NMR data of the thus obtained compounds are shown below.

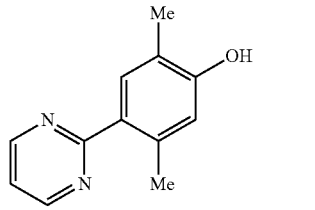

Intermediate (HP38)

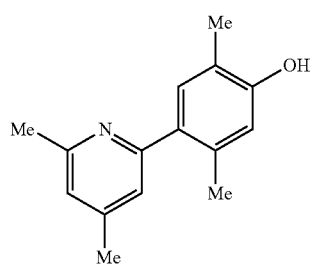

Intermediate (HP39)

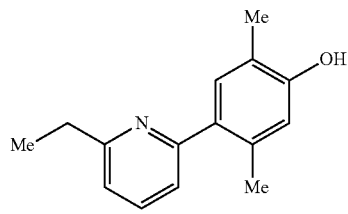

Intermediate (HP40)

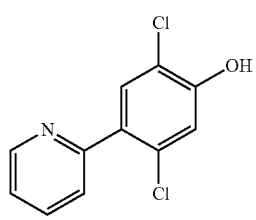

Intermediate (HP41)

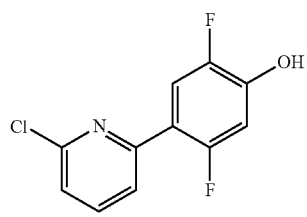

Intermediate (HP42)

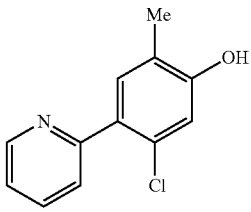

Intermediate (HP43)

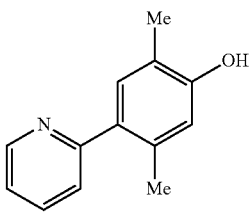 [SMILES: Oc1cc(F)c(-c2ccccn2)cc1F]

Intermediate (HP44)

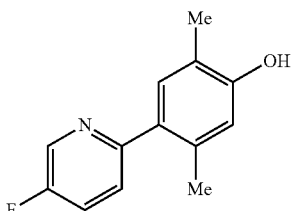

Intermediate (HP45)

Intermediate (HP38)

$^1$H-NMR (CDCl$_3$) δ: 2.27 (3H, s), 2.51 (3H, s), 4.98 (1H, s), 6.68 (1H, s), 7.16 (1H, t, J=4.9 Hz), 7.68 (1H, s), 8.80 (2H, d, J=4.8 Hz).

Intermediate (HP39)

$^1$H-NMR (CDCl$_3$) δ: 2.18 (6H, s), 2.34 (3H, s), 2.58 (3H, s), 6.11 (1H, br s), 6.51 (1H, s), 6.92 (1H, d, J=0.7 Hz), 6.96 (1H, d, J=0.7 Hz), 7.04 (1H, s).

Intermediate (HP40)

$^1$H-NMR (CDCl$_3$) δ: 1.35 (3H, t, J=7.7 Hz), 2.20 (3H, s), 2.22 (3H, s), 2.90 (2H, q, J=7.7 Hz), 6.02 (1H, s), 6.54 (1H, s), 7.08 (1H, s), 7.09 (1H, d, J=7.5 Hz), 7.16 (1H, d, J=7.5 Hz), 7.64 (1H, t, J=7.5 Hz).

Intermediate (HP41)

$^1$H-NMR (CDCl$_3$) δ: 6.17 (1H, br s), 7.13 (1H, s), 7.28-7.32 (1H, m), 7.62 (1H, s), 7.65 (1H, d, J=7.9 Hz), 7.77 (1H, td, J=7.7, 1.7 Hz), 8.70 (1H, d, J=5.9 Hz).

Intermediate (HP42)

$^1$H-NMR (CDCl$_3$) δ: 6.63-6.88 (1H, m), 7.15 (1H, t, J=1.6 Hz), 7.31-7.49 (1H, m), 7.75-7.58 (2H, m).

Intermediate (HP43)

$^1$H-NMR (CDCl$_3$) δ: 2.19 (3H, s), 6.50 (1H, br s), 6.80 (1H, s), 7.27-7.31 (2H, m), 7.61 (1H, dt, J=7.8, 1.0 Hz), 7.77 (1H, td, J=7.8, 1.8 Hz), 8.69 (1H, dq, J=5.0, 1.0 Hz).

Intermediate (HP44)

$^1$H-NMR (CDCl$_3$) δ: 2.24 (3H, s), 2.27 (3H, s), 5.40 (1H, br s), 6.63 (1H, s), 7.18 (1H, s), 7.22 (1H, ddd, J=7.7, 4.9, 1.1 Hz), 7.37 (1H, dt, J=7.7, 1.0 Hz), 7.72 (1H, td, J=7.7, 1.9 Hz), 8.67 (1H, dq, J=4.9, 1.0 Hz).

Intermediate (HP45)

¹H-NMR (CDCl₃) δ: 2.24 (3H, s), 2.26 (3H, s), 5.07 (1H, s), 6.64 (1H, s), 7.15 (1H, s), 7.36 (1H, dd, J=8.6, 4.6 Hz), 7.44 (1H, td, J=8.6, 2.9 Hz), 8.52 (1H, d, J=2.9 Hz).

Reference Production Example 77

A mixture of 1.35 g of 2-bromopyridine, 0.80 g of 2,5-difluoro-4-methoxyphenylboronic acid, 0.09 g of [1,1'-bis(diphenylphosphino)ferrocene]palladium(II) dichloride dichloromethane adduct, 2.26 g of tripotassium phosphate, 5 mL of 1,2-dimethoxyethane, and 1 mL of water was stirred at 80° C. for 5 hours. After cooling, water was added and the reaction mixture was filtered, and then the filtrate was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 1.21 g of an oily substance. A mixture of 1.21 g of the oily substance thus obtained, 10 mL of 48% hydrobromic acid, and 10 mL of acetic acid mixture was stirred at 110° C. for 10 hours. The reaction solution was concentrated and a saturated sodium bicarbonate solution was added, and then aqueous sodium hydroxide solution was added and a liquid separating operation was performed. The aqueous layer was taken out and neutralized by adding concentrated hydrochloric acid. The aqueous layer was extracted with ethyl acetate, and the organic layer was washed with water and a saturated saline solution and then dried over anhydrous sodium sulfate. The organic layer was concentrated under reduced pressure to obtain 0.54 g of 2-(4-hydroxy-2,5-difluorophenyl)pyridine (hereinafter referred to as the intermediate (HP46)).

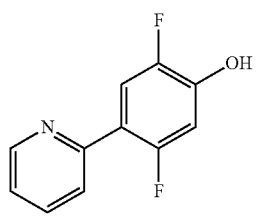

¹H-NMR (CDCl₃) δ: 6.09 (1H, br s), 6.81 (1H, dd, J=11.6, 7.0 Hz), 7.22-7.26 (1H, m), 7.73-7.81 (3H, m), 8.68 (1H, d, J=5.2 Hz).

Reference Production Example 78

In the same manner as in Reference Production Example 41, except that 4-acetyl-2,5-dimethylphenol was used in place of 4-acetyl-2-methylphenol, 4-(4-hydroxy-2,5-dimethylphenyl)pyrimidine (hereinafter referred to as the intermediate (HP47)) was obtained. The structural formulas and ¹H-NMR data of the thus obtained compound are shown below.

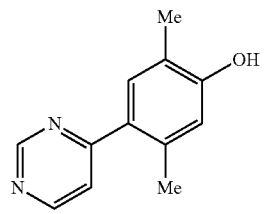 [SMILES: Cc1cc(-c2ccncn2)c(C)cc1O]

¹H-NMR (DMSO-D₆) δ: 2.07 (3H, s), 2.17 (3H, s), 5.02 (1H, t, J=7.4 Hz), 6.53 (1H, s), 6.99 (1H, s), 7.92 (1H, s), 8.37 (1H, d, J=7.9 Hz), 9.11 (1H, s).

Reference Production Example 79

A mixture of 6.85 g of 3-methoxy-4-methylaniline and 150 mL of chloroform was cooled to 0° C. and 26.5 g of tetrabutylammonium tribromide was added, followed by stirring at the same temperature for 20 minutes. To the reaction mixture, chloroform was added. The organic layer was washed with a sodium bicarbonate solution, an aqueous sodium sulfite solution, water, and a saturated saline solution, dried over anhydrous sodium sulfate, and then concentrated under reduced pressure.

The residue thus obtained was subjected to silica gel column chromatography to obtain 7.85 g of 2-bromo-5-methoxy-3-methylalanine.

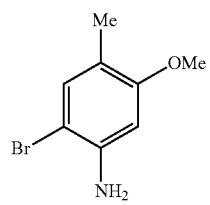

¹H-NMR (CDCl₃) δ: 2.08 (3H, s), 3.76 (3H, s), 3.93 (2H, br s), 6.28 (1H, s), 7.12 (1H, s).

Reference Production Example 80

A mixture of 3.24 g of 2-bromo-5-methoxy-3-methylaniline and 50 mL of concentrated hydrochloric acid was cooled to 0° C., and 10 ml of an aqueous solution of 1.14 g of sodium nitrite was added dropwise. Then, 1.78 g of copper(I) bromide was added, followed by stirring at 70° C. for 1 hour. After cooling, water was added and the mixture was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 2.00 g of 1-bromo-2-chloro-4-methoxy-5-methylbenzene.

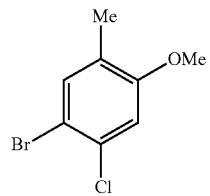

$^1$H-NMR (CDCl$_3$) δ: 2.15 (3H, s), 3.80 (3H, s), 6.88 (1H, s), 7.33 (1H, s).

Reference Production Example 81

In accordance with the reaction mentioned in Reference Production Example 71, the following compounds were obtained. The structural formulas and $^1$H-NMR data of the thus obtained compound are shown below.

2-(2-Chloro-4-methoxy-5-methylphenyl)-4,4,5,5-tetramethyl-1,3,2-dioxaborolane

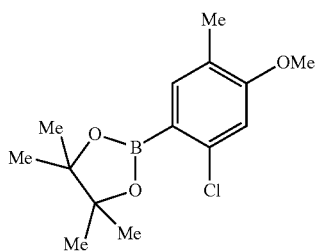 [SMILES: COc1cc(Cl)c(B2OC(C)(C)C(C)(C)O2)cc1C]

$^1$H-NMR (CDCl$_3$) δ: 1.36 (12H, s), 2.15 (3H, s), 3.83 (3H, s), 6.81 (1H, s), 7.47 (1H, s).

Reference Production Example 82

A mixture of 5.00 g of 4-bromo-2,5-dimethylphenol, 4.23 g of isopropyl iodide, 6.87 g of potassium carbonate, and 30 mL of acetonitrile was stirred at 80° C. for 7 hours. After cooling, ethyl acetate was added. The mixture was filtered and the filtrate was concentrated. The residue thus obtained was subjected to silica gel column chromatography to obtain 2.88 g of 1-bromo-4-isopropoxy-2,5-dimethylbenzene.

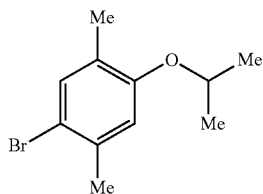

$^1$H-NMR (CDCl$_3$) δ: 1.32 (6H, d, J=6.0 Hz), 2.14 (3H, s), 2.34 (3H, s), 4.53-4.41 (1H, m), 6.71 (1H, s), 7.27 (1H, d, J=1.8 Hz).

Reference Production Example 83

In a nitrogen atmosphere, a mixture of 1.50 g of 1-bromo-4-isopropoxy-2,5-dimethylbenzene and 20 mL of tetrahydrofuran was added dropwise to 0.16 g of magnesium. The reaction mixture was stirred at 50° C. for 30 minutes. After the reaction mixture was cooled −78° C., 0.67 g of trimethoxyborane was added dropwise. The temperature was slowly raised to room temperature, followed by stirring at the same temperature for 1 hour. Water and chloroform were added to the reaction mixture, and a liquid separating operation was performed. The organic layer was washed with water and a saturated saline solution, dried over anhydrous sodium sulfate, and then concentrated under reduced pressure. The residue thus obtained was collected by filtration by adding hexane to obtain 0.82 g of 4-isopropoxy-2,5-dimethylphenylboronic acid.

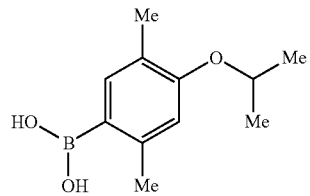 [SMILES: Cc1cc(B(O)O)c(C)cc1OC(C)C]

$^1$H-NMR (CDCl$_3$) δ: 1.38 (6H, d, J=6.1 Hz), 2.23 (3H, s), 2.78 (3H, s), 4.62-4.68 (1H, m), 6.72 (1H, s), 7.97 (1H, s).

Reference Production Example 84

At room temperature, 50 g of 2-methyl-6-nitrobenzoic acid was added to a mixture of 15.6 g of sodium borohydride and 200 ml of tetrahydrofuran. At 0° C., 34 ml of dimethylsulfuric acid was added to the reaction mixture, followed by stirring at room temperature for 20 hours. At 0° C., 300 ml of an aqueous 5% hydrochloric acid solution was added, followed by stirring for 1 hour. After extraction with ethyl acetate, the organic layer was washed with water, dried over anhydrous magnesium sulfate, and then concentrated under reduced pressure to obtain 30.5 g of 2-methyl-6-nitrobenzyl alcohol.

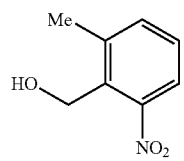 [SMILES: Cc1cccc([N+](=O)[O-])c1CO]

$^1$H-NMR (CDCl$_3$) δ (ppm): 7.71 (1H, d, J=7.7 Hz), 7.49 (1H, d, J=7.5 Hz), 7.36 (1H, t, J=7.9 Hz), 4.71 (2H, d, J=7.2 Hz), 2.62 (1H, t, J=7.4 Hz), 2.56 (3H, s).

Reference Production Example 85

At room temperature, 74.1 g of phosphorus tribromide was added to a mixture of 30.5 g of 2-methyl-6-nitrobenzyl alcohol mentioned in Reference Production Example 84 and 100 ml of chloroform, followed by stirring for 10 hours. After the addition of 200 ml of ice water and extraction with chloroform, the organic layer was washed with water, dried over anhydrous magnesium sulfate, and then concentrated under reduced pressure to obtain 35 g of 2-methyl-6-nitrobenzylbromide.

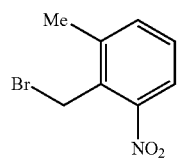

$^1$H-NMR (CDCl$_3$) δ (ppm): 7.75 (1H, d, J=8.2 Hz), 7.46 (1H, d, J=7.7 Hz), 7.36 (1H, t, J=7.8 Hz), 4.72 (2H, s), 2.54 (3H, s).

In accordance with the process mentioned above, it is possible to obtain compounds TSHA1-1 to TSHH10-1798.

The compounds TSHA1-1 to TSHH10-1798 are tetrazolinone compounds represented by formulas:
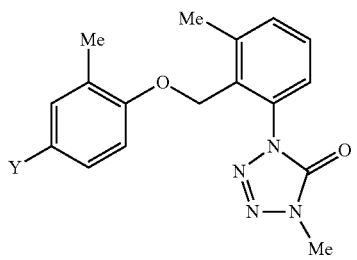
(TSHA1)
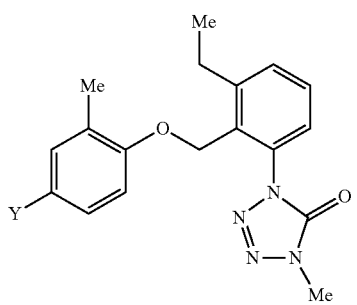
(TSHB1)
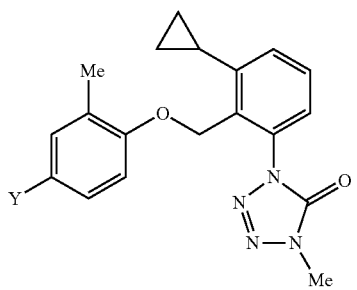
(TSHC1)
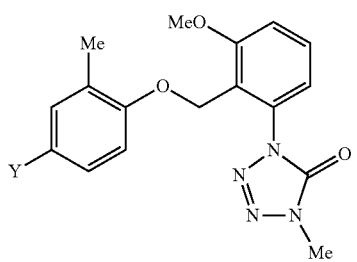
(TSHD1)
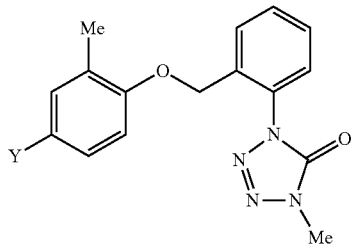
(TSHE1)
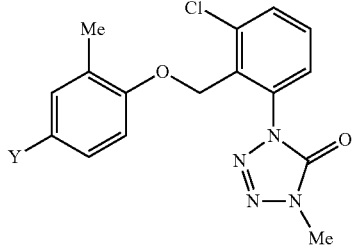
(TSHF1)
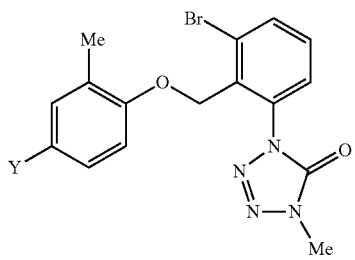
(TSHG1)
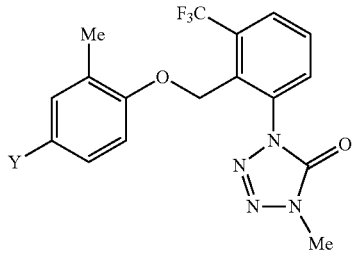
(TSHH1)
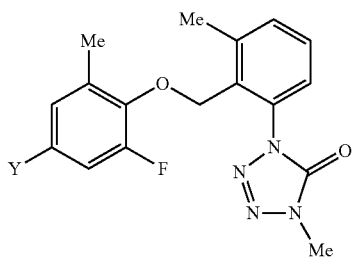
(TSHA2)
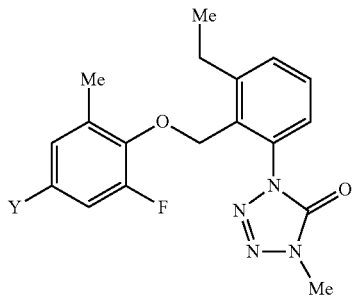
(TSHB2)
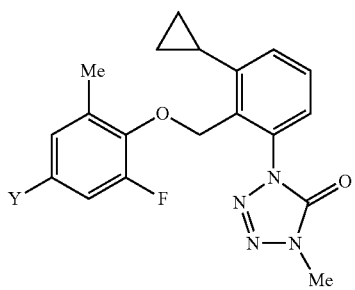
(TSHC2)

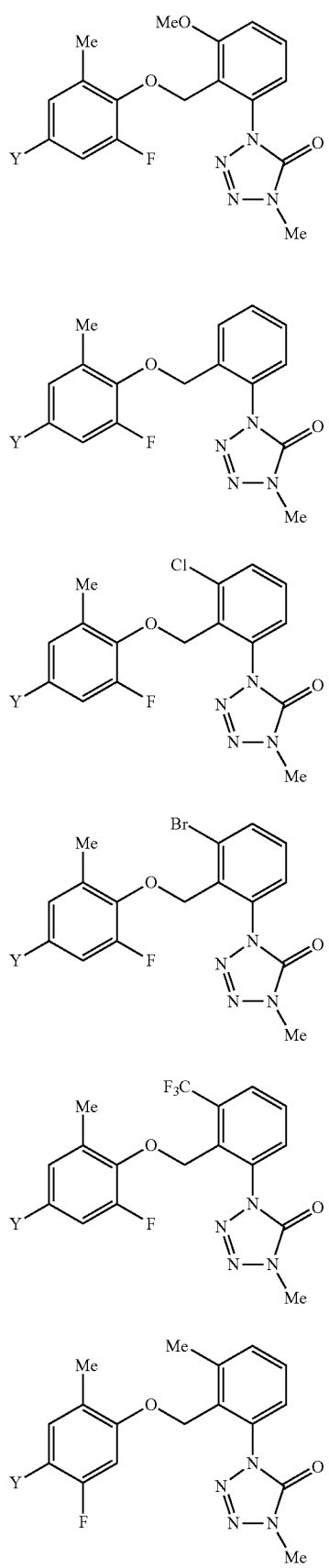
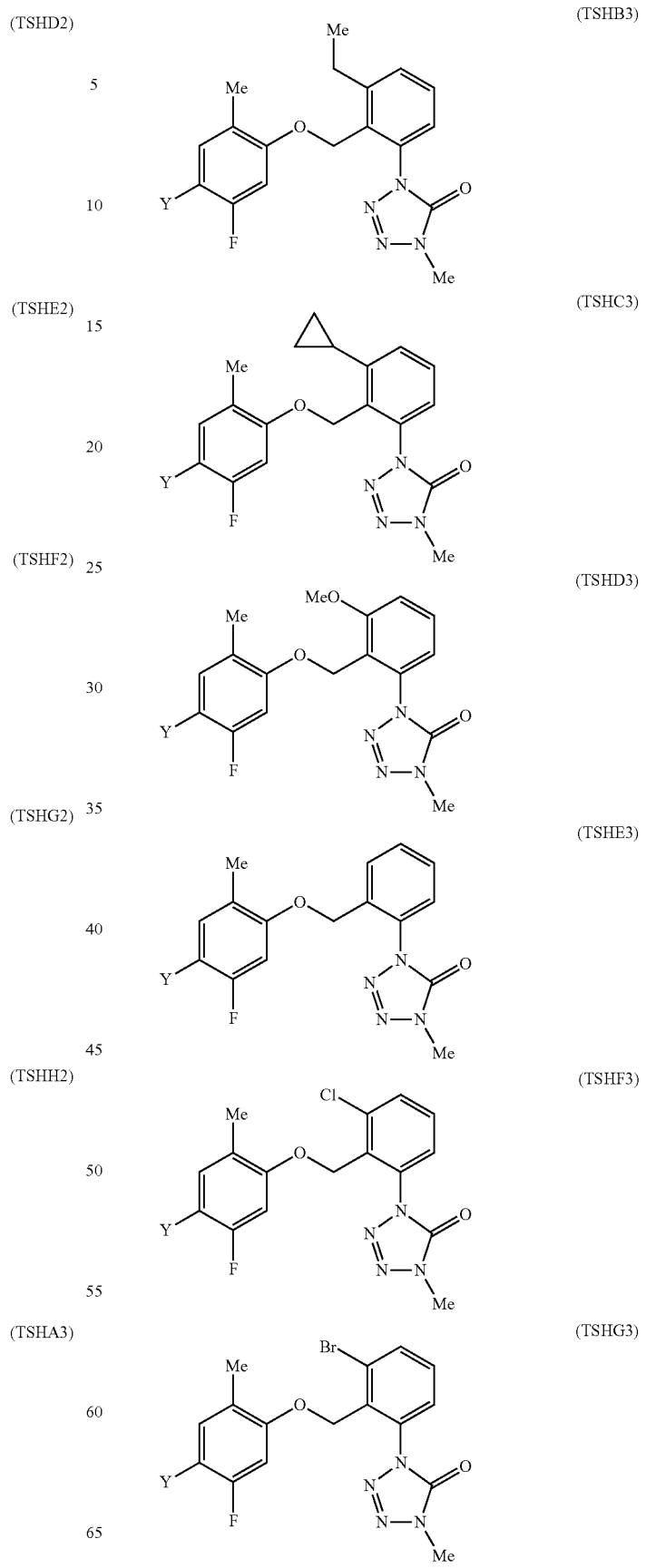

271
-continued
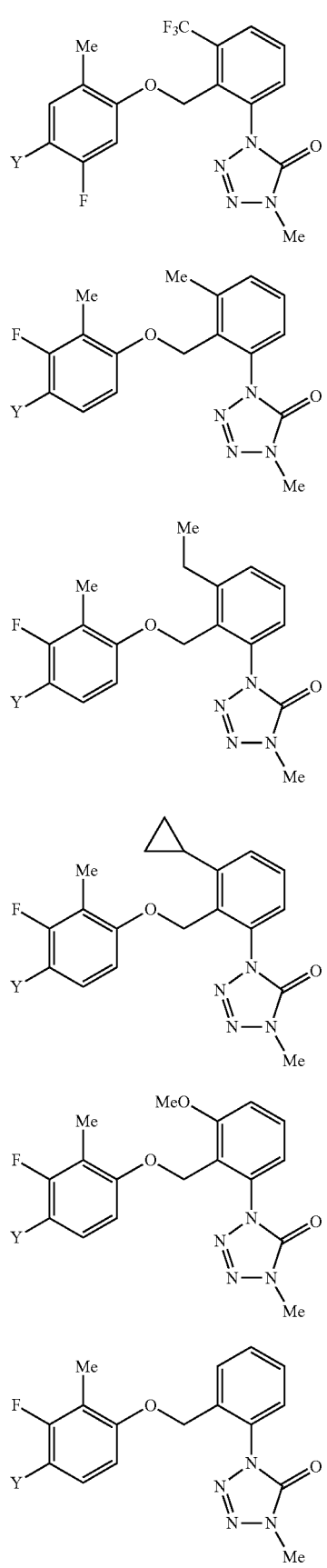
272
-continued
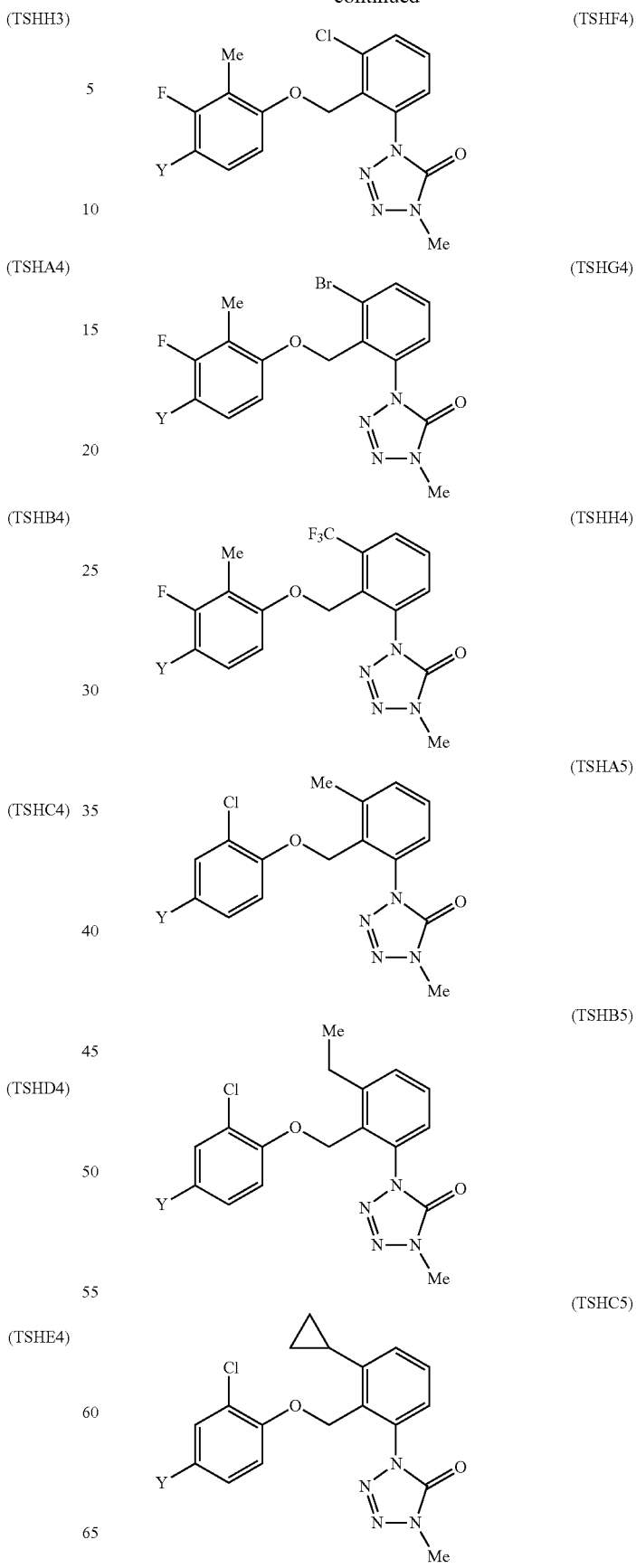

| 273 -continued | 274 -continued |
|---|---|
| 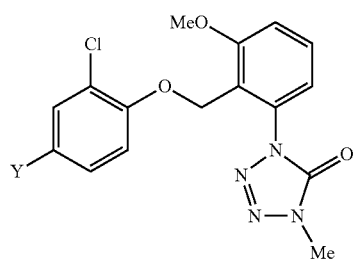 (TSHD5) | 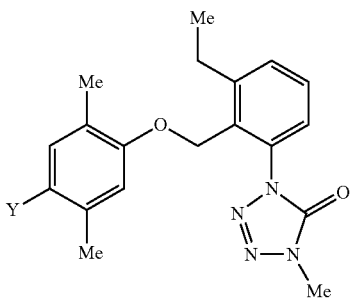 (TSHB6) |
| 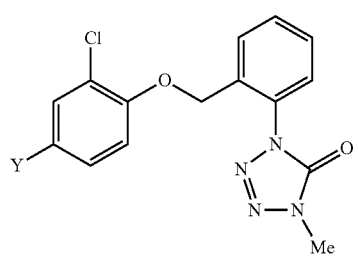 (TSHE5) | 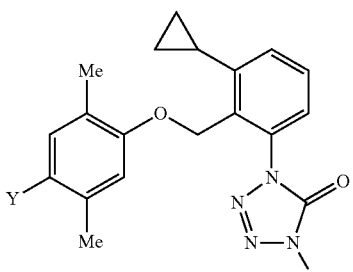 (TSHC6) |
| 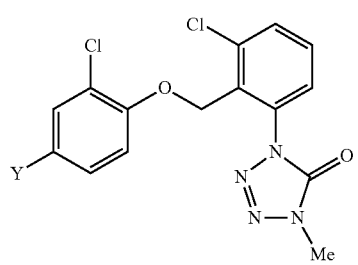 (TSHF5) | 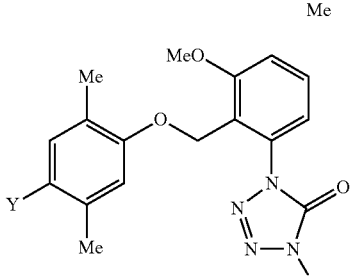 (TSHD6) |
| 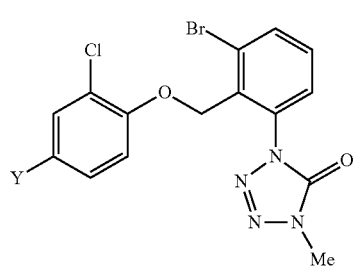 (TSHG5) | 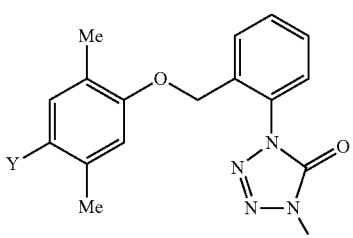 (TSHE6) |
| 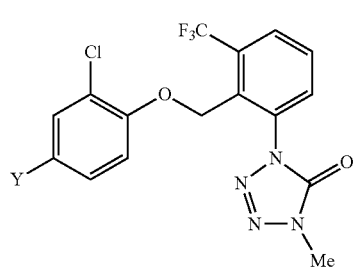 (TSHH5) | 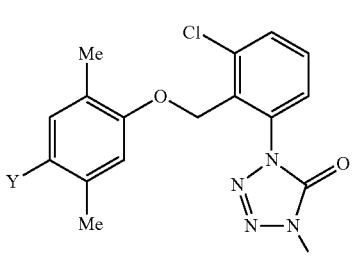 (TSHF6) |
| 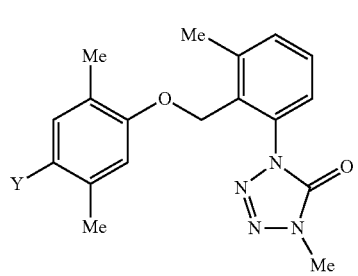 (TSHA6) | 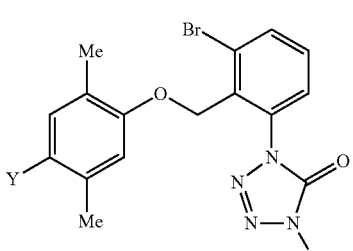 (TSHG6) |

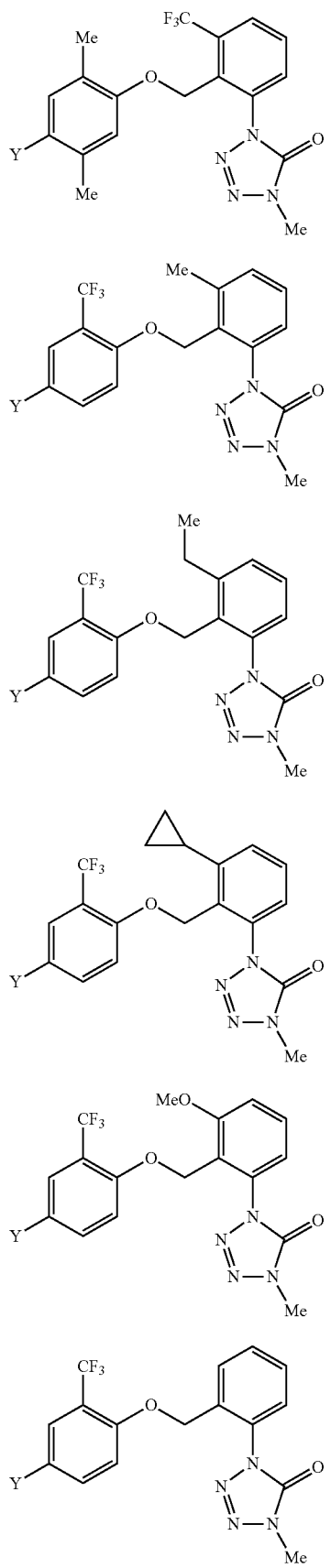
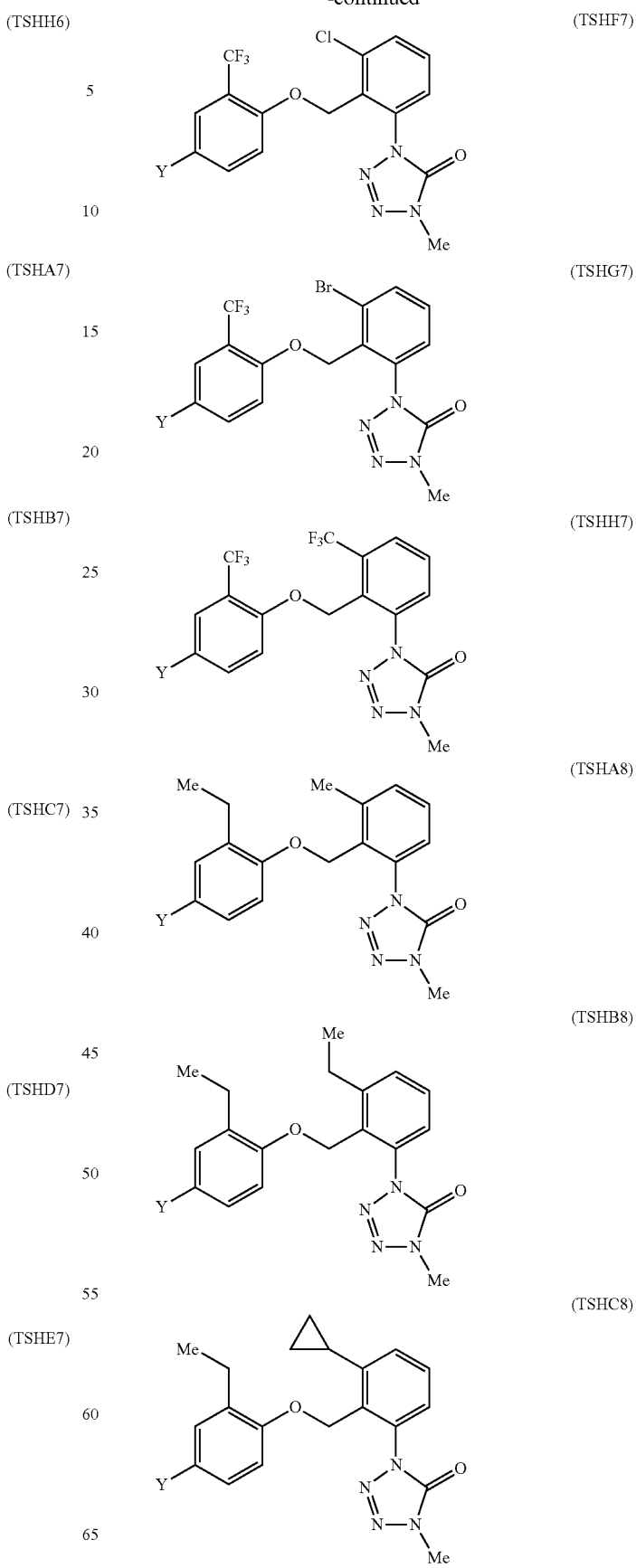

| 277 -continued | 278 -continued |
|---|---|
| 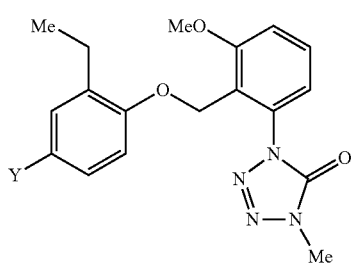 (TSHD8) | 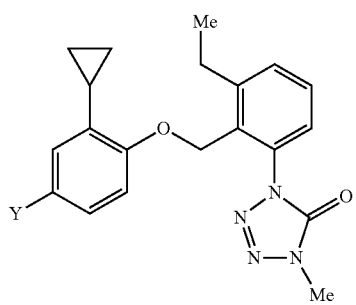 (TSHB9) |
| 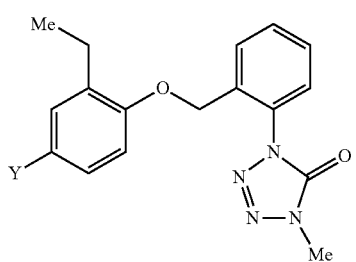 (TSHE8) | 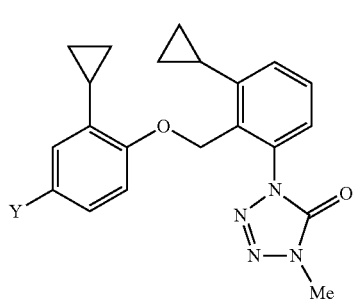 (TSHC9) |
| 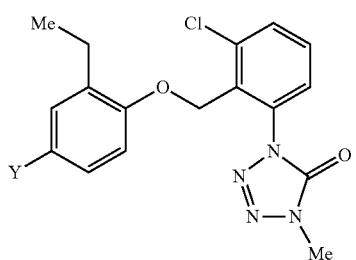 (TSHF8) | 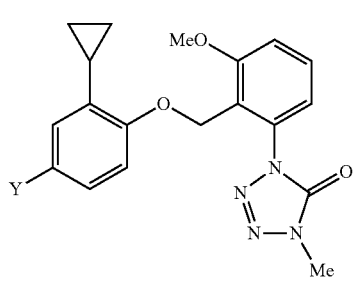 (TSHD9) |
| 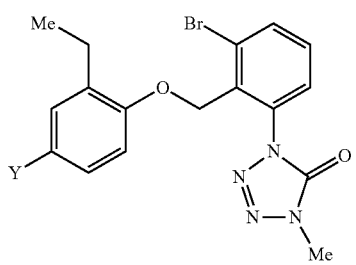 (TSHG8) | 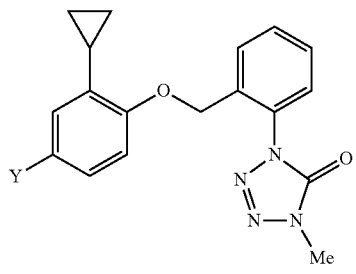 (TSHE9) |
| 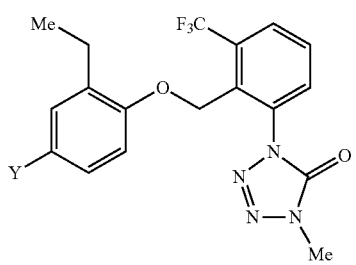 (TSHH8) | 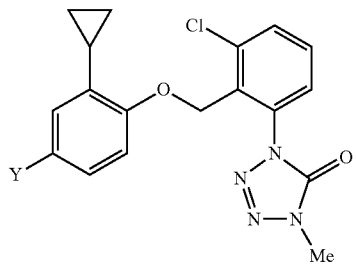 (TSHF9) |
| 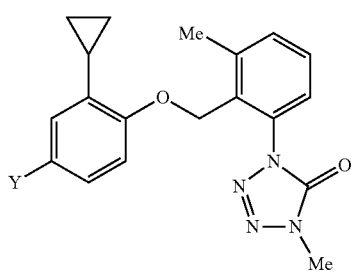 (TSHA9) | |

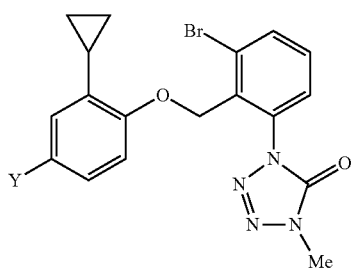
(TSHG9)
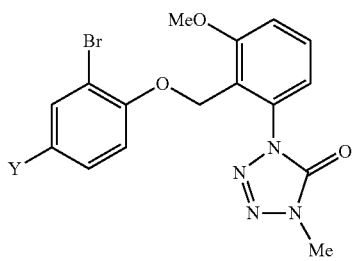
(TSHD10)
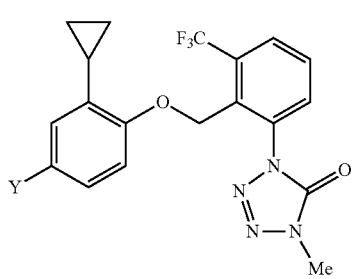
(TSHH9)
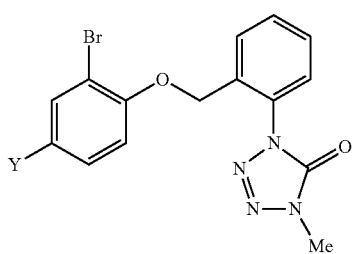
(TSHE10)
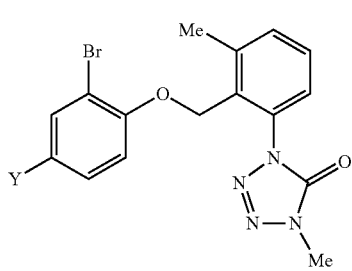
(TSHA10)
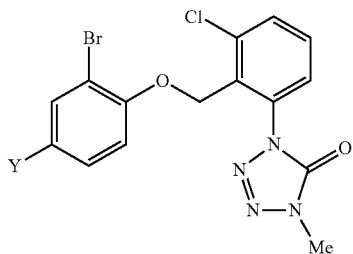
(TSHF10)
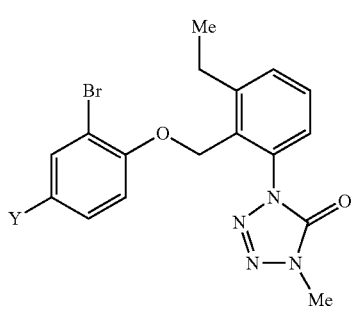
(TSHB10)
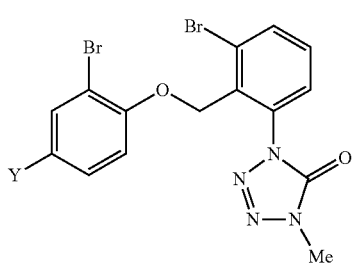
(TSHG10)
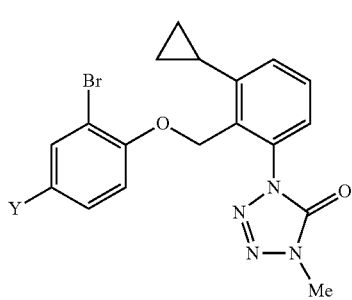
(TSHC10)
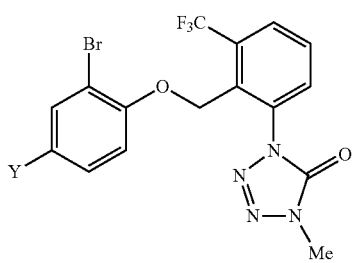
(TSHH10)
wherein Y is a substituent corresponding to each of the following substituent numbers 1 to 1798.
For example, TSHA1-001 represents a compound represented by formula (TSHA1) in which Y is substituent number 1, and is represented by the following formula:

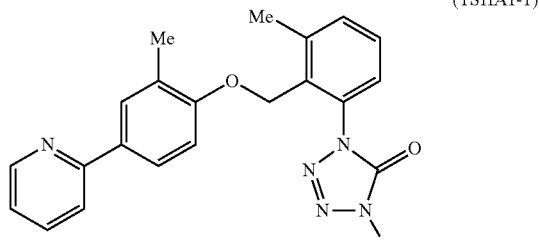

(TSHA1-1)

substituent number; Y

[1; Y=Q1, $R^{13}$=H, $R^{14}$=H, $R^{15}$=H, $R^{16}$=H], [2; Y=Q1, $R^{13}$=Me, $R^{14}$=H, $R^{15}$=H, $R^{16}$=H], [3; Y=Q1, $R^{13}$=H, $R^{14}$=Me, $R^{15}$=H, $R^{16}$=H], [4; Y=Q1, $R^{13}$=H, $R^{14}$=H, $R^{15}$=Me, $R^{16}$=H], [5; Y=Q1, $R^{13}$=H, $R^{14}$=H, $R^{15}$=H, $R^{16}$=Me], [6; Y=Q1, $R^{13}$=Me, $R^{14}$=Me, $R^{15}$=H, $R^{16}$=H], [7; Y=Q1, $R^{13}$=Me, $R^{14}$=H, $R^{15}$=Me, $R^{16}$=H], [8; Y=Q1, $R^{13}$=Me, $R^{14}$=H, $R^{15}$=H, $R^{16}$=Me], [9; Y=Q1, $R^{13}$=H, $R^{14}$=Me, $R^{15}$=Me, $R^{16}$=H], [10; Y=Q1, $R^{13}$=H, $R^{14}$=Me, $R^{15}$=H, $R^{16}$=Me], [11; Y=Q1, $R^{13}$=H, $R^{14}$=H, $R^{15}$=Me, $R^{16}$=Me], [12; Y=Q1, $R^{13}$=H, $R^{14}$=Me, $R^{15}$=H, $R^{16}$=Me], [13; Y=Q1, $R^{13}$=Me, $R^{14}$=Me, $R^{15}$=Me, $R^{16}$=H], [14; Y=Q1, $R^{13}$=Me, $R^{14}$=Me, $R^{15}$=H, $R^{16}$=Me], [15; Y=Q1, $R^{13}$=Me, $R^{14}$=H, $R^{15}$=Me, $R^{16}$=Me], [16; Y=Q1, $R^{13}$=H, $R^{14}$=Me, $R^{15}$=Me, $R^{16}$=Me], [17; Y=Q1, $R^{13}$=Me, $R^{14}$=Me, $R^{15}$=Me, $R^{16}$=Me], [18; Y=Q1, $R^{13}$=Me, $R^{14}$=F, $R^{15}$=H, $R^{16}$=H], [19; Y=Q1, $R^{13}$=Me, $R^{14}$=H, $R^{15}$=F, $R^{16}$=H], [20; Y=Q1, $R^{13}$=Me, $R^{14}$=H, $R^{15}$=H, $R^{16}$=F], [21; Y=Q1, $R^{13}$=Me, $R^{14}$=F, $R^{15}$=F, $R^{16}$=H], [22; Y=Q1, $R^{13}$=Me, $R^{14}$=F, $R^{15}$=H, $R^{16}$=F], [23; Y=Q1, $R^{13}$=Me, $R^{14}$=H, $R^{15}$=F, $R^{16}$=F], [24; Y=Q1, $R^{13}$=Me, $R^{14}$=F, $R^{15}$=F, $R^{16}$=F], [25; Y=Q1, $R^{13}$=F, $R^{14}$=Me, $R^{15}$=H, $R^{16}$=H], [26; Y=Q1, $R^{13}$=H, $R^{14}$=Me, $R^{15}$=F, $R^{16}$=H], [27; Y=Q1, $R^{13}$=H, $R^{14}$=Me, $R^{15}$=H, $R^{16}$=F], [28; Y=Q1, $R^{13}$=F, $R^{14}$=Me, $R^{15}$=F, $R^{16}$=H], [29; Y=Q1, $R^{13}$=F, $R^{14}$=Me, $R^{15}$=H, $R^{16}$=F], [30; Y=Q1, $R^{13}$=H, $R^{14}$=Me, $R^{15}$=F, $R^{16}$=F], [31; Y=Q1, $R^{13}$=F, $R^{14}$=Me, $R^{15}$=F, $R^{16}$=F], [32; Y=Q1, $R^{13}$=F, $R^{14}$=H, $R^{15}$=Me, $R^{16}$=H], [33; Y=Q1, $R^{13}$=H, $R^{14}$=F, $R^{15}$=Me, $R^{16}$=H], [34; Y=Q1, $R^{13}$=H, $R^{14}$=H, $R^{15}$=Me, $R^{16}$=F], [35; Y=Q1, $R^{13}$=F, $R^{14}$=F, $R^{15}$=Me, $R^{16}$=H], [36; Y=Q1, $R^{13}$=F, $R^{14}$=H, $R^{15}$=Me, $R^{16}$=F], [37; Y=Q1, $R^{13}$=H, $R^{14}$=F, $R^{15}$=Me, $R^{16}$=F], [38; Y=Q1, $R^{13}$=F, $R^{14}$=F, $R^{15}$=Me, $R^{16}$=F], [39; Y=Q1, $R^{13}$=F, $R^{14}$=H, $R^{15}$=H, $R^{16}$=Me], [40; Y=Q1, $R^{13}$=H, $R^{14}$=F, $R^{15}$=H, $R^{16}$=Me], [41; Y=Q1, $R^{13}$=H, $R^{14}$=H, $R^{15}$=F, $R^{16}$=Me], [42; Y=Q1, $R^{13}$=F, $R^{14}$=F, $R^{15}$=H, $R^{16}$=Me], [43; Y=Q1, $R^{13}$=F, $R^{14}$=H, $R^{15}$=F, $R^{16}$=Me], [44; Y=Q1, $R^{13}$=H, $R^{14}$=F, $R^{15}$=F, $R^{16}$=Me], [45; Y=Q1, $R^{13}$=F, $R^{14}$=F, $R^{15}$=F, $R^{16}$=Me], [46; Y=Q1, $R^{13}$=Me, $R^{14}$=Me, $R^{15}$=F, $R^{16}$=H], [47; Y=Q1, $R^{13}$=Me, $R^{14}$=Me, $R^{15}$=H, $R^{16}$=F], [48; Y=Q1, $R^{13}$=Me, $R^{14}$=F, $R^{15}$=Me, $R^{16}$=H], [49; Y=Q1, $R^{13}$=Me, $R^{14}$=H, $R^{15}$=Me, $R^{16}$=F], [50; Y=Q1, $R^{13}$=Me, $R^{14}$=F, $R^{15}$=H, $R^{16}$=Me], [51; Y=Q1, $R^{13}$=Me, $R^{14}$=H, $R^{15}$=F, $R^{16}$=Me], [52; Y=Q1, $R^{13}$=Me, $R^{14}$=Me, $R^{15}$=Cl, $R^{16}$=H], [53; Y=Q1, $R^{13}$=Me, $R^{14}$=Me, $R^{15}$=H, $R^{16}$=Cl], [54; Y=Q1, $R^{13}$=Me, $R^{14}$=Cl, $R^{15}$=Me, $R^{16}$=H], [55; Y=Q1, $R^{13}$=Me, $R^{14}$=H, $R^{15}$=Me, $R^{16}$=Cl], [56; Y=Q1, $R^{13}$=Me, $R^{14}$=Cl, $R^{15}$=H, $R^{16}$=Me], [57; Y=Q1, $R^{13}$=Me, $R^{14}$=H, $R^{15}$=Cl, $R^{16}$=Me], [58; Y=Q1, $R^{13}$=Me, $R^{14}$=Cl, $R^{15}$=H, $R^{16}$=H], [59; Y=Q1, $R^{13}$=Me, $R^{14}$=H, $R^{15}$=Cl, $R^{16}$=H], [60; Y=Q1, $R^{13}$=Me, $R^{14}$=H, $R^{15}$=H, $R^{16}$=Cl], [61; Y=Q1, $R^{13}$=Me, $R^{14}$=Cl, $R^{15}$=Cl, $R^{16}$=H], [62; Y=Q1, $R^{13}$=Me, $R^{14}$=Cl, $R^{15}$=H, $R^{16}$=Cl], [63; Y=Q1, $R^{13}$=Me, $R^{14}$=H, $R^{15}$=Cl, $R^{16}$=Cl], [64; Y=Q1, $R^{13}$=Cl, $R^{14}$=Me, $R^{15}$=H, $R^{16}$=H], [65; Y=Q1, $R^{13}$=H, $R^{14}$=Me, $R^{15}$=Cl, $R^{16}$=H], [66; Y=Q1, $R^{13}$=H, $R^{14}$=Me, $R^{15}$=H, $R^{16}$=Cl], [67; Y=Q1, $R^{13}$=Cl, $R^{14}$=Me, $R^{15}$=Cl, $R^{16}$=H], [68; Y=Q1, $R^{13}$=Cl, $R^{14}$=Me, $R^{15}$=H, $R^{16}$=Cl], [69; Y=Q1, $R^{13}$=H, $R^{14}$=Me, $R^{15}$=Cl, $R^{16}$=Cl], [70; Y=Q1, $R^{13}$=Cl, $R^{14}$=H, $R^{15}$=Me, $R^{16}$=H], [71; Y=Q1, $R^{13}$=H, $R^{14}$=Cl, $R^{15}$=Me, $R^{16}$=H], [72; Y=Q1, $R^{13}$=H, $R^{14}$=H, $R^{15}$=Me, $R^{16}$=Cl], [73; Y=Q1, $R^{13}$=Cl, $R^{14}$=Cl, $R^{15}$=Me, $R^{16}$=H], [74; Y=Q1, $R^{13}$=Cl, $R^{14}$=H, $R^{15}$=Me, $R^{16}$=Cl], [75; Y=Q1, $R^{13}$=H, $R^{14}$=Cl, $R^{15}$=Me, $R^{16}$=Cl], [76; Y=Q1, $R^{13}$=Cl, $R^{14}$=H, $R^{15}$=H, $R^{16}$=Me], [77; Y=Q1, $R^{13}$=H, $R^{14}$=Cl, $R^{15}$=H, $R^{16}$=Me], [78; Y=Q1, $R^{13}$=H, $R^{14}$=H, $R^{15}$=Cl, $R^{16}$=Me], [79; Y=Q1, $R^{13}$=Cl, $R^{14}$=Cl, $R^{15}$=H, $R^{16}$=Me], [80; Y=Q1, $R^{13}$=Cl, $R^{14}$=H, $R^{15}$=Cl, $R^{16}$=Me], [81; Y=Q1, $R^{13}$=H, $R^{14}$=Cl, $R^{15}$=Cl, $R^{16}$=Me], [82; Y=Q1, $R^{13}$=Me, $R^{14}$=Br, $R^{15}$=H, $R^{16}$=H], [83; Y=Q1, $R^{13}$=Me, $R^{14}$=H, $R^{15}$=Br, $R^{16}$=H], [84; Y=Q1, $R^{13}$=Me, $R^{14}$=H, $R^{15}$=H, $R^{16}$=Br], [85; Y=Q1, $R^{13}$=Br, $R^{14}$=Me, $R^{15}$=H, $R^{16}$=H], [86; Y=Q1, $R^{13}$=H, $R^{14}$=Me, $R^{15}$=Br, $R^{16}$=H], [87; Y=Q1, $R^{13}$=H, $R^{14}$=Me, $R^{15}$=H, $R^{16}$=Br], [88; Y=Q1, $R^{13}$=Br, $R^{14}$=H, $R^{15}$=Me, $R^{16}$=H], [89; Y=Q1, $R^{13}$=H, $R^{14}$=Br, $R^{15}$=Me, $R^{16}$=H], [90; Y=Q1, $R^{13}$=H, $R^{14}$=H, $R^{15}$=Me, $R^{16}$=Br], [91; Y=Q1, $R^{13}$=Br, $R^{14}$=H, $R^{15}$=H, $R^{16}$=Me], [92; Y=Q1, $R^{13}$=H, $R^{14}$=Br, $R^{15}$=H, $R^{16}$=Me], [93; Y=Q1, $R^{13}$=H, $R^{14}$=H, $R^{15}$=Br, $R^{16}$=Me], [94; Y=Q1, $R^{13}$=Me, $R^{14}$=Me, $R^{15}$=Br, $R^{16}$=H], [95; Y=Q1, $R^{13}$=Me, $R^{14}$=Me, $R^{15}$=H, $R^{16}$=Br], [96; Y=Q1, $R^{13}$=Me, $R^{14}$=Br, $R^{15}$=Me, $R^{16}$=H], [97; Y=Q1, $R^{13}$=Me, $R^{14}$=H, $R^{15}$=Me, $R^{16}$=Br], [98; Y=Q1, $R^{13}$=Me, $R^{14}$=Br, $R^{15}$=H, $R^{16}$=Me], [99; Y=Q1, $R^{13}$=Me, $R^{14}$=H, $R^{15}$=Br, $R^{16}$=Me], [100; Y=Q1, $R^{13}$=Me, $R^{14}$=CN, $R^{15}$=H, $R^{16}$=H],

[101; Y=Q1, $R^{13}$=Me, $R^{14}$=H, $R^{15}$=CN, $R^{16}$=H], [102; Y=Q1, $R^{13}$=Me, $R^{14}$=H, $R^{15}$=H, $R^{16}$=CN], [103; Y=Q1, $R^{13}$=CN, $R^{14}$=Me, $R^{15}$=H, $R^{16}$=H], [104; Y=Q1, $R^{13}$=H, $R^{14}$=Me, $R^{15}$=CN, $R^{16}$=H], [105; Y=Q1, $R^{13}$=H, $R^{14}$=Me, $R^{15}$=H, $R^{16}$=CN], [106; Y=Q1, $R^{13}$=CN, $R^{14}$=H, $R^{15}$=Me, $R^{16}$=H], [107; Y=Q1, $R^{13}$=H, $R^{14}$=CN, $R^{15}$=Me, $R^{16}$=H], [108; Y=Q1, $R^{13}$=H, $R^{14}$=H, $R^{15}$=Me, $R^{16}$=CN], [109; Y=Q1, $R^{13}$=CN, $R^{14}$=H, $R^{15}$=H, $R^{16}$=Me], [110; Y=Q1, $R^{13}$=H, $R^{14}$=CN, $R^{15}$=H, $R^{16}$=Me], [111; Y=Q1, $R^{13}$=H, $R^{14}$=H, $R^{15}$=CN, $R^{16}$=Me], [112; Y=Q1, $R^{13}$=Me, $R^{14}$=Me, $R^{15}$=CN, $R^{16}$=H], [113; Y=Q1, $R^{13}$=Me, $R^{14}$=Me, $R^{15}$=H, $R^{16}$=CN], [114; Y=Q1, $R^{13}$=Me, $R^{14}$=CN, $R^{15}$=Me, $R^{16}$=H], [115; Y=Q1, $R^{13}$=Me, $R^{14}$=H, $R^{15}$=Me, $R^{16}$=CN], [116; Y=Q1, $R^{13}$=Me, $R^{14}$=CN, $R^{15}$=H, $R^{16}$=Me], [117; Y=Q1, $R^{13}$=Me, $R^{14}$=H, $R^{15}$=CN, $R^{16}$=Me], [118; Y=Q1, $R^{13}$=Me, $R^{14}$=OMe, $R^{15}$=H, $R^{16}$=H], [119; Y=Q1, $R^{13}$=Me, $R^{14}$=H, $R^{15}$=OMe, $R^{16}$=H], [120; Y=Q1, $R^{13}$=Me, $R^{14}$=H, $R^{15}$=H, $R^{16}$=OMe], [121; Y=Q1, $R^{13}$=OMe, $R^{14}$=Me, $R^{15}$=H, $R^{16}$=H], [122; Y=Q1, $R^{13}$=H, $R^{14}$=Me, $R^{15}$=OMe, $R^{16}$=H], [123; Y=Q1, $R^{13}$=H, $R^{14}$=Me, $R^{15}$=H, $R^{16}$=OMe], [124; Y=Q1, $R^{13}$=OMe, $R^{14}$=H, $R^{15}$=Me, $R^{16}$=H], [125; Y=Q1, $R^{13}$=H, $R^{14}$=OMe, $R^{15}$=Me, $R^{16}$=H], [126; Y=Q1, $R^{13}$=H, $R^{14}$=H, $R^{15}$=Me, $R^{16}$=OMe], [127; Y=Q1, $R^{13}$=OMe, $R^{14}$=H, $R^{15}$=H, $R^{16}$=Me], [128; Y=Q1, $R^{13}$=H, $R^{14}$=OMe, $R^{15}$=H, $R^{16}$=Me], [129; Y=Q1, $R^{13}$=H, $R^{14}$=H, $R^{15}$=OMe, $R^{16}$=Me], [130; Y=Q1, $R^{13}$=Me, $R^{14}$=Me, $R^{15}$=OMe, $R^{16}$=H], [131; Y=Q1, $R^{13}$=Me, $R^{14}$=Me, $R^{15}$=H, $R^{16}$=OMe], [132; Y=Q1, $R^{13}$=Me, $R^{14}$=OMe, $R^{15}$=Me, $R^{16}$=H], [133; Y=Q1, $R^{13}$=Me, $R^{14}$=H, $R^{15}$=Me, $R^{16}$=OMe], [134; Y=Q1, $R^{13}$=Me, $R^{14}$=OMe, $R^{15}$=H, $R^{16}$=Me], [135; Y=Q1,

R$^{13}$=Me, R$^{14}$=H, R$^{15}$=OMe, R$^{16}$=Me], [136; Y=Q1, R$^{13}$=Me, R$^{14}$=OEt, R$^{15}$=H, R$^{16}$=H], [137; R$^{13}$=Me, R$^{14}$=H, R$^{15}$=OEt, R$^{16}$=H], [138; Y=Q1, R$^{13}$=Me, R$^{14}$=H, R$^{15}$=H, R$^{16}$=OEt], [139; Y=Q1, R$^{13}$=OEt, R$^{14}$=Me, R$^{15}$=H, R$^{16}$=H], [140; Y=Q1, R$^{13}$=H, R$^{14}$=Me, R$^{15}$=OEt, R$^{16}$=H], [141; Y=Q1, R$^{13}$=H, R$^{14}$=Me, R$^{15}$=H, R$^{16}$=OEt], [142; Y=Q1, R$^{13}$=OEt, R$^{14}$=H, R$^{15}$=Me, R$^{16}$=H], [143; Y=Q1, R$^{13}$=H, R$^{14}$=OEt, R$^{15}$=Me, R$^{16}$=H], [144; Y=Q1, R$^{13}$=H, R$^{14}$=H, R$^{15}$=Me, R$^{16}$=OEt], [145; Y=Q1, R$^{13}$=OEt, R$^{14}$=H, R$^{15}$=H, R$^{16}$=Me], [146; Y=Q1, R$^{13}$=H, R$^{14}$=OEt, R$^{15}$=H, R$^{16}$=Me], [147; Y=Q1, R$^{13}$=H, R$^{14}$=H, R$^{15}$=OEt, R$^{16}$=Me], [148; Y=Q1, R$^{13}$=Me, R$^{14}$=Me, R$^{15}$=OEt, R$^{16}$=H], [149; Y=Q1, R$^{13}$=Me, R$^{14}$=Me, R$^{15}$=H, R$^{16}$=OEt], [150; Y=Q1, R$^{13}$=Me, R$^{14}$=OEt, R$^{15}$=Me, R$^{16}$=H], [151; Y=Q1, R$^{13}$=Me, R$^{14}$=H, R$^{15}$=Me, R$^{16}$=OEt], [152; Y=Q1, R$^{13}$=Me, R$^{14}$=OEt, R$^{15}$=H, R$^{16}$=Me], [153; Y=Q1, R$^{13}$=Me, R$^{14}$=H, R$^{15}$=OEt, R$^{16}$=Me], [154; Y=Q1, R$^{13}$=Me, R$^{14}$=Et, R$^{15}$=H, R$^{16}$=H], [155; Y=Q1, R$^{13}$=Me, R$^{14}$=H, R$^{15}$=Et, R$^{16}$=H], [156; Y=Q1, R$^{13}$=Me, R$^{14}$=H, R$^{15}$=H, R$^{16}$=Et], [157; Y=Q1, R$^{13}$=Et, R$^{14}$=Me, R$^{15}$=H, R$^{16}$=H], [158; Y=Q1, R$^{13}$=H, R$^{14}$=Me, R$^{15}$=Et, R$^{16}$=H], [159; Y=Q1, R$^{13}$=H, R$^{14}$=Me, R$^{15}$=H, R$^{16}$=Et], [160; Y=Q1, R$^{13}$=Et, R$^{14}$=H, R$^{15}$=Me, R$^{16}$=H], [161; Y=Q1, R$^{13}$=H, R$^{14}$=Et, R$^{15}$=Me, R$^{16}$=H], [162; Y=Q1, R$^{13}$=H, R$^{14}$=H, R$^{15}$=Me, R$^{16}$=Et], [163; Y=Q1, R$^{13}$=Et, R$^{14}$=H, R$^{15}$=H, R$^{16}$=Me], [164; Y=Q1, R$^{13}$=H, R$^{14}$=Et, R$^{15}$=H, R$^{16}$=Me], [165; Y=Q1, R$^{13}$=H, R$^{14}$=H, R$^{15}$=Et, R$^{16}$=Me], [166; Y=Q1, R$^{13}$=Me, R$^{14}$=Me, R$^{15}$=Et, R$^{16}$=H], [167; Y=Q1, R$^{13}$=Me, R$^{14}$=Me, R$^{15}$=H, R$^{16}$=Et], [168; Y=Q1, R$^{13}$=Me, R$^{14}$=Et, R$^{15}$=Me, R$^{16}$=H], [169; Y=Q1, R$^{13}$=Me, R$^{14}$=H, R$^{15}$=Me, R$^{16}$=Et], [170; Y=Q1, R$^{13}$=Me, R$^{14}$=Et, R$^{15}$=H, R$^{16}$=Me], [171; Y=Q1, R$^{13}$=Me, R$^{14}$=H, R$^{15}$=Et, R$^{16}$=Me], [172; Y=Q1, R$^{13}$=Me, R$^{14}$=CF$_3$, R$^{15}$=H, R$^{16}$=H], [173; Y=Q1, R$^{13}$=Me, R$^{14}$=H, R$^{15}$=CF$_3$, R$^{16}$=H], [174; Y=Q1, R$^{13}$=Me, R$^{14}$=H, R$^{15}$=H, R$^{16}$=CF$_3$], [175; Y=Q1, R$^{13}$=CF$_3$, R$^{14}$=Me, R$^{15}$=H, R$^{16}$=H], [176; Y=Q1, R$^{13}$=H, R$^{14}$=Me, R$^{15}$=CF$_3$, R$^{16}$=H], [177; Y=Q1, R$^{13}$=H, R$^{14}$=Me, R$^{15}$=H, R$^{16}$=CF$_3$], [178; Y=Q1, R$^{13}$=CF$_3$, R$^{14}$=H, R$^{15}$=Me, R$^{16}$=H], [179; Y=Q1, R$^{13}$=H, R$^{14}$=CF$_3$, R$^{15}$=Me, R$^{16}$=H], [180; Y=Q1, R$^{13}$=H, R$^{14}$=H, R$^{15}$=Me, R$^{16}$=CF$_3$], [181; Y=Q1, R$^{13}$=CF$_3$, R$^{14}$=H, R$^{15}$=H, R$^{16}$=Me], [182; Y=Q1, R$^{13}$=H, R$^{14}$=CF$_3$, R$^{15}$=H, R$^{16}$=Me], [183; Y=Q1, R$^{13}$=H, R$^{14}$=H, R$^{15}$=CF$_3$, R$^{16}$=Me], [184; Y=Q1, R$^{13}$=Me, R$^{14}$=cyclopropyl, R$^{15}$=H, R$^{16}$=H], [185; Y=Q1, R$^{13}$=Me, R$^{14}$=H, R$^{15}$=cyclopropyl, R$^{16}$=H], [186; Y=Q1, R$^{13}$=Me, R$^{14}$=H, R$^{15}$=H, R$^{16}$=cyclopropyl], [187; Y=Q1, R$^{13}$=cyclopropyl, R$^{14}$=Me, R$^{15}$=H, R$^{16}$=H], [188; Y=Q1, R$^{13}$=H, R$^{14}$=Me, R$^{15}$=cyclopropyl, R$^{16}$=H], [189; Y=Q1, R$^{13}$=H, R$^{14}$=Me, R$^{15}$=H, R$^{16}$=cyclopropyl], [190; Y=Q1, R$^{13}$=cyclopropyl, R$^{14}$=H, R$^{15}$=Me, R$^{16}$=H], [191; Y=Q1, R$^{13}$=H, R$^{14}$=cyclopropyl, R$^{15}$=Me, R$^{16}$=H], [192; Y=Q1, R$^{13}$=H, R$^{14}$=H, R$^{15}$=Me, R$^{16}$=cyclopropyl], [193; Y=Q1, R$^{13}$=cyclopropyl, R$^{14}$=H, R$^{15}$=H, R$^{16}$=Me], [194; Y=Q1, R$^{13}$=H, R$^{14}$=cyclopropyl, R$^{15}$=H, R$^{16}$=Me], [195; Y=Q1, R$^{13}$=H, R$^{14}$=H, R$^{15}$=cyclopropyl, R$^{16}$=Me], [196; Y=Q1, R$^{13}$=Et, R$^{14}$=H, R$^{15}$=H, R$^{16}$=H], [197; Y=Q1, R$^{13}$=H, R$^{14}$=Et, R$^{15}$=H, R$^{16}$=H], [198; Y=Q1, R$^{13}$=H, R$^{14}$=H, R$^{15}$=Et, R$^{16}$=H], [199; Y=Q1, R$^{13}$=H, R$^{14}$=H, R$^{15}$=H, R$^{16}$=Et], [200; Y=Q1, R$^{13}$=Et, R$^{14}$=Et, R$^{15}$=H, R$^{16}$=H], [201; Y=Q1, R$^{13}$=Et, R$^{14}$=H, R$^{15}$=Et, R$^{16}$=H], [202; Y=Q1, R$^{13}$=Et, R$^{14}$=H, R$^{15}$=H, R$^{16}$=Et], [203; Y=Q1, R$^{13}$=H, R$^{14}$=Et, R$^{15}$=Et, R$^{16}$=H], [204; Y=Q1, R$^{13}$=H, R$^{14}$=Et, R$^{15}$=H, R$^{16}$=Et], [205; Y=Q1, R$^{13}$=H, R$^{14}$=H, R$^{15}$=Et, R$^{16}$=Et], [206; Y=Q1, R$^{13}$=Et, R$^{14}$=Et, R$^{15}$=Et, R$^{16}$=H], [207; Y=Q1, R$^{13}$=Et, R$^{14}$=Et, R$^{15}$=H, R$^{16}$=Et], [208; Y=Q1, R$^{13}$=Et, R$^{14}$=F, R$^{15}$=H, R$^{16}$=H], [209; Y=Q1, R$^{13}$=Et, R$^{14}$=H, R$^{15}$=F, R$^{16}$=H], [210; Y=Q1, R$^{13}$=Et, R$^{14}$=H, R$^{15}$=H, R$^{16}$=F], [211; Y=Q1, R$^{13}$=Et, R$^{14}$=F, R$^{15}$=F, R$^{16}$=H], [212; Y=Q1, R$^{13}$=Et, R$^{14}$=F, R$^{15}$=H, R$^{16}$=F], [213; Y=Q1, R$^{13}$=Et, R$^{14}$=H, R$^{15}$=F, R$^{16}$=F], [214; Y=Q1, R$^{13}$=F, R$^{14}$=Et, R$^{15}$=H, R$^{16}$=H], [215; Y=Q1, R$^{13}$=H, R$^{14}$=Et, R$^{15}$=F, R$^{16}$=H], [216; Y=Q1, R$^{13}$=H, R$^{14}$=Et, R$^{15}$=H, R$^{16}$=F], [217; Y=Q1, R$^{13}$=F, R$^{14}$=Et, R$^{15}$=F, R$^{16}$=H], [218; Y=Q1, R$^{13}$=F, R$^{14}$=Et, R$^{15}$=H, R$^{16}$=F], [219; Y=Q1, R$^{13}$=H, R$^{14}$=Et, R$^{15}$=F, R$^{16}$=F], [220; Y=Q1, R$^{13}$=F, R$^{14}$=H, R$^{15}$=Et, R$^{16}$=H], [221; Y=Q1, R$^{13}$=H, R$^{14}$=F, R$^{15}$=Et, R$^{16}$=H], [222; Y=Q1, R$^{13}$=H, R$^{14}$=H, R$^{15}$=Et, R$^{16}$=F], [223; Y=Q1, R$^{13}$=F, R$^{14}$=F, R$^{15}$=Et, R$^{16}$=H], [224; Y=Q1, R$^{13}$=F, R$^{14}$=H, R$^{15}$=Et, R$^{16}$=F], [225; Y=Q1, R$^{13}$=H, R$^{14}$=F, R$^{15}$=Et, R$^{16}$=F], [226; Y=Q1, R$^{13}$=F, R$^{14}$=H, R$^{15}$=H, R$^{16}$=Et], [227; Y=Q1, R$^{13}$=H, R$^{14}$=F, R$^{15}$=H, R$^{16}$=Et], [228; Y=Q1, R$^{13}$=H, R$^{14}$=H, R$^{15}$=F, R$^{16}$=Et], [229; Y=Q1, R$^{13}$=F, R$^{14}$=F, R$^{15}$=H, R$^{16}$=Et], [230; Y=Q1, R$^{13}$=F, R$^{14}$=H, R$^{15}$=F, R$^{16}$=Et], [231; Y=Q1, R$^{13}$=H, R$^{14}$=F, R$^{15}$=F, R$^{16}$=Et], [232; Y=Q1, R$^{13}$=Et, R$^{14}$=Et, R$^{15}$=F, R$^{16}$=H], [233; Y=Q1, R$^{13}$=Et, R$^{14}$=Et, R$^{15}$=H, R$^{16}$=F], [234; Y=Q1, R$^{13}$=Et, R$^{14}$=Et, R$^{15}$=Et, R$^{16}$=H], [235; Y=Q1, R$^{13}$=Et, R$^{14}$=Et, R$^{15}$=Et, R$^{16}$=F], [236; Y=Q1, R$^{13}$=Et, R$^{14}$=F, R$^{15}$=H, R$^{16}$=Et], [237; Y=Q1, R$^{13}$=Et, R$^{14}$=Et, R$^{15}$=Cl, R$^{16}$=H], [238; Y=Q1, R$^{13}$=Et, R$^{14}$=Et, R$^{15}$=H, R$^{16}$=Cl], [239; Y=Q1, R$^{13}$=Et, R$^{14}$=Cl, R$^{15}$=Et, R$^{16}$=H], [240; Y=Q1, R$^{13}$=Et, R$^{14}$=H, R$^{15}$=Et, R$^{16}$=Cl], [241; Y=Q1, R$^{13}$=Et, R$^{14}$=Cl, R$^{15}$=H, R$^{16}$=Et], [242; Y=Q1, R$^{13}$=Et, R$^{14}$=H, R$^{15}$=Cl, R$^{16}$=Et], [243; Y=Q1, R$^{13}$=Et, R$^{14}$=Cl, R$^{15}$=H, R$^{16}$=H], [244; Y=Q1, R$^{13}$=Et, R$^{14}$=H, R$^{15}$=Cl, R$^{16}$=H], [245; Y=Q1, R$^{13}$=Et, R$^{14}$=H, R$^{15}$=H, R$^{16}$=Cl], [246; Y=Q1, R$^{13}$=Et, R$^{14}$=Cl, R$^{15}$=Cl, R$^{16}$=H], [247; Y=Q1, R$^{13}$=Et, R$^{14}$=Cl, R$^{15}$=H, R$^{16}$=Cl], [248; Y=Q1, R$^{13}$=Et, R$^{14}$=H, R$^{15}$=Cl, R$^{16}$=Cl], [249; Y=Q1, R$^{13}$=Cl, R$^{14}$=Et, R$^{15}$=H, R$^{16}$=H], [250; Y=Q1, R$^{13}$=H, R$^{14}$=Et, R$^{15}$=Cl, R$^{16}$=H], [251; Y=Q1, R$^{13}$=H, R$^{14}$=Et, R$^{15}$=H, R$^{16}$=Cl], [252; Y=Q1, R$^{13}$=Cl, R$^{14}$=Et, R$^{15}$=Cl, R$^{16}$=H], [253; Y=Q1, R$^{13}$=Cl, R$^{14}$=Et, R$^{15}$=H, R$^{16}$=Cl], [254; Y=Q1, R$^{13}$=H, R$^{14}$=Et, R$^{15}$=Cl, R$^{16}$=Cl], [255; Y=Q1, R$^{13}$=Cl, R$^{14}$=H, R$^{15}$=Et, R$^{16}$=H], [256; Y=Q1, R$^{13}$=H, R$^{14}$=Cl, R$^{15}$=Et, R$^{16}$=H], [257; Y=Q1, R$^{13}$=H, R$^{14}$=H, R$^{15}$=Et, R$^{16}$=Cl], [258; Y=Q1, R$^{13}$=Cl, R$^{14}$=Cl, R$^{15}$=Et, R$^{16}$=H], [259; Y=Q1, R$^{13}$=Cl, R$^{14}$=H, R$^{15}$=Et, R$^{16}$=Cl], [260; Y=Q1, R$^{13}$=H, R$^{14}$=Cl, R$^{15}$=Et, R$^{16}$=Cl], [261; Y=Q1, R$^{13}$=Cl, R$^{14}$=H, R$^{15}$=H, R$^{16}$=Et], [262; Y=Q1, R$^{13}$=H, R$^{14}$=Cl, R$^{15}$=H, R$^{16}$=Et], [263; Y=Q1, R$^{13}$=H, R$^{14}$=H, R$^{15}$=Cl, R$^{16}$=Et], [264; Y=Q1, R$^{13}$=Cl, R$^{14}$=Cl, R$^{15}$=H, R$^{16}$=Et], [265; Y=Q1, R$^{13}$=Cl, R$^{14}$=H, R$^{15}$=Cl, R$^{16}$=Et], [266; Y=Q1, R$^{13}$=H, R$^{14}$=Cl, R$^{15}$=Cl, R$^{16}$=Et], [267; Y=Q1, R$^{13}$=Et, R$^{14}$=CN, R$^{15}$=H, R$^{16}$=H], [268; Y=Q1, R$^{13}$=Et, R$^{14}$=H, R$^{15}$=CN, R$^{16}$=H], [269; Y=Q1, R$^{13}$=Et, R$^{14}$=H, R$^{15}$=H, R$^{16}$=CN], [270; Y=Q1, R$^{13}$=CN, R$^{14}$=Et, R$^{15}$=H, R$^{16}$=H], [271; Y=Q1, R$^{13}$=H, R$^{14}$=Et, R$^{15}$=CN, R$^{16}$=H], [272; Y=Q1, R$^{13}$=H, R$^{14}$=Et, R$^{15}$=H, R$^{16}$=CN], [273; Y=Q1, R$^{13}$=CN, R$^{14}$=H, R$^{15}$=Et, R$^{16}$=H], [274; Y=Q1, R$^{13}$=H, R$^{14}$=CN, R$^{15}$=Et, R$^{16}$=H], [275; Y=Q1, R$^{13}$=H, R$^{14}$=H, R$^{15}$=Et, R$^{16}$=CN], [276; Y=Q1, R$^{13}$=CN, R$^{14}$=H, R$^{15}$=H, R$^{16}$=Et], [277; Y=Q1, R$^{13}$=H, R$^{14}$=CN, R$^{15}$=H, R$^{16}$=Et], [278; Y=Q1, R$^{13}$=H, R$^{14}$=H, R$^{15}$=CN, R$^{16}$=Et], [279; Y=Q1, R$^{13}$=Et, R$^{14}$=CF$_3$, R$^{15}$=H, R$^{16}$=H], [280; Y=Q1, R$^{13}$=Et, R$^{14}$=H, R$^{15}$=CF$_3$, R$^{16}$=H], [281; Y=Q1, R$^{13}$=Et, R$^{14}$=H, R$^{15}$=H, R$^{16}$=CF$_3$], [282; Y=Q1, R$^{13}$=CF$_3$, R$^{14}$=Et, R$^{15}$=H, R$^{16}$=H], [283; Y=Q1, R$^{13}$=H, R$^{14}$=Et, $R^{15}$=CF$_3$, $R^{16}$=H], [284; Y=Q1, $R^{13}$=H, $R^{14}$=Et, $R^{15}$=H, $R^{16}$=CF$_3$], [285; Y=Q1, $R^{13}$=CF$_3$, $R^{14}$=H, $R^{15}$=Et, $R^{16}$=H], [286; Y=Q1, $R^{13}$=H, $R^{14}$=CF$_3$, $R^{15}$=Et, $R^{16}$=H], [287; Y=Q1, $R^{13}$=H, $R^{14}$=H, $R^{15}$=Et, $R^{16}$=CF$_3$], [288; Y=Q1, $R^{13}$=CF$_3$, $R^{14}$=H, $R^{15}$=H, $R^{16}$=Et], [289; Y=Q1, $R^{13}$=H, $R^{14}$=CF$_3$, $R^{15}$=H, $R^{16}$=Et], [290; Y=Q1, $R^{13}$=H, $R^{14}$=H, $R^{15}$=CF$_3$, $R^{16}$=Et], [291; Y=Q1, $R^{13}$=Et, $R^{14}$=OMe, $R^{15}$=H, $R^{16}$=H], [292; Y=Q1, $R^{13}$=Et, $R^{14}$=H, $R^{15}$=OMe, $R^{16}$=H], [293; Y=Q1, $R^{13}$=Et, $R^{14}$=H, $R^{15}$=H, $R^{16}$=OMe], [294; Y=Q1, $R^{13}$=OMe, $R^{14}$=Et, $R^{15}$=H, $R^{16}$=H], [295; Y=Q1, $R^{13}$=H, $R^{14}$=Et, $R^{15}$=OMe, $R^{16}$=H], [296; Y=Q1, $R^{13}$=H, $R^{14}$=Et, $R^{15}$=H, $R^{16}$=OMe], [297; Y=Q1, $R^{13}$=OMe, $R^{14}$=H, $R^{15}$=Et, $R^{16}$=H], [298; Y=Q1, $R^{13}$=H, $R^{14}$=OMe, $R^{15}$=Et, $R^{16}$=H], [299; Y=Q1, $R^{13}$=H, $R^{14}$=H, $R^{15}$=Et, $R^{16}$=OMe], [300; Y=Q1, $R^{13}$=OMe, $R^{14}$=H, $R^{15}$=H, $R^{16}$=Et],

[301; Y=Q1, $R^{13}$=H, $R^{14}$=OMe, $R^{15}$=H, $R^{16}$=Et], [302; Y=Q1, $R^{13}$=H, $R^{14}$=H, $R^{15}$=OMe, $R^{16}$=Et], [303; Y=Q1, $R^{13}$=F, $R^{14}$=H, $R^{15}$=H, $R^{16}$=H], [304; Y=Q1, $R^{13}$=H, $R^{14}$=F, $R^{15}$=H, $R^{16}$=H], [305; Y=Q1, $R^{13}$=H, $R^{14}$=H, $R^{15}$=F, $R^{16}$=H], [306; Y=Q1, $R^{13}$=H, $R^{14}$=H, $R^{15}$=H, $R^{16}$=F], [307; Y=Q1, $R^{13}$=F, $R^{14}$=F, $R^{15}$=H, $R^{16}$=H], [308; Y=Q1, $R^{13}$=F, $R^{14}$=H, $R^{15}$=F, $R^{16}$=H], [309; Y=Q1, $R^{13}$=F, $R^{14}$=H, $R^{15}$=H, $R^{16}$=F], [310; Y=Q1, $R^{13}$=H, $R^{14}$=F, $R^{15}$=F, $R^{16}$=H], [311; Y=Q1, $R^{13}$=H, $R^{14}$=F, $R^{15}$=H, $R^{16}$=F], [312; Y=Q1, $R^{13}$=H, $R^{14}$=H, $R^{15}$=F, $R^{16}$=F], [313; Y=Q1, $R^{13}$=F, $R^{14}$=F, $R^{15}$=F, $R^{16}$=H], [314; Y=Q1, $R^{13}$=F, $R^{14}$=F, $R^{15}$=F, $R^{16}$=F], [315; Y=Q1, $R^{13}$=F, $R^{14}$=F, $R^{15}$=H, $R^{16}$=F], [316; Y=Q1, $R^{13}$=Cl, $R^{14}$=H, $R^{15}$=H, $R^{16}$=H], [317; Y=Q1, $R^{13}$=H, $R^{14}$=Cl, $R^{15}$=H, $R^{16}$=H], [318; Y=Q1, $R^{13}$=H, $R^{14}$=H, $R^{15}$=Cl, $R^{16}$=H], [319; Y=Q1, $R^{13}$=H, $R^{14}$=H, $R^{15}$=H, $R^{16}$=Cl], [320; Y=Q1, $R^{13}$=Cl, $R^{14}$=Cl, $R^{15}$=H, $R^{16}$=H], [321; Y=Q1, $R^{13}$=Cl, $R^{14}$=H, $R^{15}$=Cl, $R^{16}$=H], [322; Y=Q1, $R^{13}$=Cl, $R^{14}$=H, $R^{15}$=H, $R^{16}$=Cl], [323; Y=Q1, $R^{13}$=H, $R^{14}$=Cl, $R^{15}$=Cl, $R^{16}$=H], [324; Y=Q1, $R^{13}$=H, $R^{14}$=Cl, $R^{15}$=H, $R^{16}$=Cl], [325; Y=Q1, $R^{13}$=H, $R^{14}$=H, $R^{15}$=Cl, $R^{16}$=Cl], [326; Y=Q1, $R^{13}$=Cl, $R^{14}$=H, $R^{15}$=Cl, $R^{16}$=Cl], [327; Y=Q1, $R^{13}$=Cl, $R^{14}$=Cl, $R^{15}$=H, $R^{16}$=Cl], [328; Y=Q1, $R^{13}$=Cl, $R^{14}$=Cl, $R^{15}$=Cl, $R^{16}$=H], [329; Y=Q1, $R^{13}$=F, $R^{14}$=Cl, $R^{15}$=H, $R^{16}$=H], [330; Y=Q1, $R^{13}$=F, $R^{14}$=H, $R^{15}$=Cl, $R^{16}$=H], [331; Y=Q1, $R^{13}$=F, $R^{14}$=H, $R^{15}$=H, $R^{16}$=Cl], [332; Y=Q1, $R^{13}$=Cl, $R^{14}$=F, $R^{15}$=H, $R^{16}$=H], [333; Y=Q1, $R^{13}$=H, $R^{14}$=F, $R^{15}$=Cl, $R^{16}$=H], [334; Y=Q1, $R^{13}$=H, $R^{14}$=F, $R^{15}$=H, $R^{16}$=Cl], [335; Y=Q1, $R^{13}$=Cl, $R^{14}$=H, $R^{15}$=F, $R^{16}$=H], [336; Y=Q1, $R^{13}$=H, $R^{14}$=Cl, $R^{15}$=F, $R^{16}$=H], [337; Y=Q1, $R^{13}$=H, $R^{14}$=H, $R^{15}$=F, $R^{16}$=Cl], [338; Y=Q1, $R^{13}$=Cl, $R^{14}$=H, $R^{15}$=H, $R^{16}$=F], [339; Y=Q1, $R^{13}$=H, $R^{14}$=Cl, $R^{15}$=H, $R^{16}$=F], [340; Y=Q1, $R^{13}$=H, $R^{14}$=H, $R^{15}$=Cl, $R^{16}$=F], [341; Y=Q1, $R^{13}$=n-propyl, $R^{14}$=H, $R^{15}$=H, $R^{16}$=H], [342; Y=Q1, $R^{13}$=H, $R^{14}$=n-propyl, $R^{15}$=H, $R^{16}$=H], [343; Y=Q1, $R^{13}$=H, $R^{14}$=H, $R^{15}$=n-propyl, $R^{16}$=H], [344; Y=Q1, $R^{13}$=H, $R^{14}$=H, $R^{15}$=H, $R^{16}$=n-propyl], [345; Y=Q1, $R^{13}$=isopropyl, $R^{14}$=H, $R^{15}$=H, $R^{16}$=H], [346; Y=Q1, $R^{13}$=H, $R^{14}$=isopropyl, $R^{15}$=H, $R^{16}$=H], [347; Y=Q1, $R^{13}$=H, $R^{14}$=H, $R^{15}$=isopropyl, $R^{16}$=H], [348; Y=Q1, $R^{13}$=H, $R^{14}$=H, $R^{15}$=H, $R^{16}$=isopropyl], [349; Y=Q1, $R^{13}$=cyclopropyl, $R^{14}$=H, $R^{15}$=H, $R^{16}$=H], [350; Y=Q1, $R^{13}$=H, $R^{14}$=cyclopropyl, $R^{15}$=H, $R^{16}$=H], [351; Y=Q1, $R^{13}$=H, $R^{14}$=H, $R^{15}$=cyclopropyl, $R^{16}$=H], [352; Y=Q1, $R^{13}$=H, $R^{14}$=H, $R^{15}$=H, $R^{16}$=cyclopropyl], [353; Y=Q1, $R^{13}$=cyclopropyl, $R^{14}$=F, $R^{15}$=H, $R^{16}$=H], [354; Y=Q1, $R^{13}$=cyclopropyl, $R^{14}$=H, $R^{15}$=F, $R^{16}$=H], [355; Y=Q1, $R^{13}$=cyclopropyl, $R^{14}$=H, $R^{15}$=H, $R^{16}$=F], [356; Y=Q1, $R^{13}$=F, $R^{14}$=cyclopropyl, $R^{15}$=H, $R^{16}$=H], [357; Y=Q1, $R^{13}$=H, $R^{14}$=cyclopropyl, $R^{15}$=F, $R^{16}$=H], [358; Y=Q1, $R^{13}$=H, $R^{14}$=cyclopropyl, $R^{15}$=H, $R^{16}$=F], [359; Y=Q1, $R^{13}$=F, $R^{14}$=H, $R^{15}$=cyclopropyl, $R^{16}$=H], [360; Y=Q1, $R^{13}$=H, $R^{14}$=F, $R^{15}$=cyclopropyl, $R^{16}$=H], [361; Y=Q1, $R^{13}$=H, $R^{14}$=H, $R^{15}$=cyclopropyl, $R^{16}$=F], [362; Y=Q1, $R^{13}$=F, $R^{14}$=H, $R^{15}$=H, $R^{16}$=cyclopropyl], [363; Y=Q1, $R^{13}$=H, $R^{14}$=F, $R^{15}$=H, $R^{16}$=cyclopropyl], [364; Y=Q1, $R^{13}$=H, $R^{14}$=H, $R^{15}$=F, $R^{16}$=cyclopropyl], [365; Y=Q1, $R^{13}$=cyclopropyl, $R^{14}$=Cl, $R^{15}$=H, $R^{16}$=H], [366; Y=Q1, $R^{13}$=cyclopropyl, $R^{14}$=H, $R^{15}$=Cl, $R^{16}$=H], [367; Y=Q1, $R^{13}$=cyclopropyl, $R^{14}$=H, $R^{15}$=H, $R^{16}$=Cl], [368; Y=Q1, $R^{13}$=Cl, $R^{14}$=cyclopropyl, $R^{15}$=H, $R^{16}$=H], [369; Y=Q1, $R^{13}$=H, $R^{14}$=cyclopropyl, $R^{15}$=Cl, $R^{16}$=H], [370; Y=Q1, $R^{13}$=H, $R^{14}$=cyclopropyl, $R^{15}$=H, $R^{16}$=Cl], [371; Y=Q1, $R^{13}$=Cl, $R^{14}$=H, $R^{15}$=cyclopropyl, $R^{16}$=H], [372; Y=Q1, $R^{13}$=H, $R^{14}$=Cl, $R^{15}$=cyclopropyl, $R^{16}$=H], [373; Y=Q1, $R^{13}$=H, $R^{14}$=H, $R^{15}$=cyclopropyl, $R^{16}$=Cl], [374; Y=Q1, $R^{13}$=Cl, $R^{14}$=H, $R^{15}$=H, $R^{16}$=cyclopropyl], [375; Y=Q1, $R^{13}$=H, $R^{14}$=Cl, $R^{15}$=H, $R^{16}$=cyclopropyl], [376; Y=Q1, $R^{13}$=H, $R^{14}$=H, $R^{15}$=Cl, $R^{16}$=cyclopropyl], [377; Y=Q1, $R^{13}$=OMe, $R^{14}$=H, $R^{15}$=H, $R^{16}$=H], [378; Y=Q1, $R^{13}$=H, $R^{14}$=H, $R^{15}$=H, $R^{16}$=OMe], [379; Y=Q1, $R^{13}$=OMe, $R^{14}$=H, $R^{15}$=H, $R^{16}$=H], [380; Y=Q1, $R^{13}$=OMe, $R^{14}$=H, $R^{15}$=H, $R^{16}$=H], [381; Y=Q1, $R^{13}$=H, $R^{14}$=OMe, $R^{15}$=H, $R^{16}$=H], [382; Y=Q1, $R^{13}$=H, $R^{14}$=H, $R^{15}$=OMe, $R^{16}$=H], [383; Y=Q1, $R^{13}$=H, $R^{14}$=H, $R^{15}$=H, $R^{16}$=OMe], [384; Y=Q1, $R^{13}$=OMe, $R^{14}$=F, $R^{15}$=H, $R^{16}$=H], [385; Y=Q1, $R^{13}$=OMe, $R^{14}$=H, $R^{15}$=F, $R^{16}$=H], [386; Y=Q1, $R^{13}$=OMe, $R^{14}$=H, $R^{15}$=H, $R^{16}$=F], [387; Y=Q1, $R^{13}$=F, $R^{14}$=OMe, $R^{15}$=H, $R^{16}$=H], [388; Y=Q1, $R^{13}$=H, $R^{14}$=OMe, $R^{15}$=F, $R^{16}$=H], [389; Y=Q1, $R^{13}$=H, $R^{14}$=OMe, $R^{15}$=H, $R^{16}$=F], [390; Y=Q1, $R^{13}$=F, $R^{14}$=H, $R^{15}$=OMe, $R^{16}$=H], [391; Y=Q1, $R^{13}$=H, $R^{14}$=F, $R^{15}$=OMe, $R^{16}$=H], [392; Y=Q1, $R^{13}$=H, $R^{14}$=H, $R^{15}$=OMe, $R^{16}$=F], [393; Y=Q1, $R^{13}$=F, $R^{14}$=H, $R^{15}$=H, $R^{16}$=OMe], [394; Y=Q1, $R^{13}$=H, $R^{14}$=F, $R^{15}$=H, $R^{16}$=OMe], [395; Y=Q1, $R^{13}$=H, $R^{14}$=H, $R^{15}$=F, $R^{16}$=OMe], [396; Y=Q1, $R^{13}$=OMe, $R^{14}$=Cl, $R^{15}$=H, $R^{16}$=H], [397; Y=Q1, $R^{13}$=OMe, $R^{14}$=H, $R^{15}$=Cl, $R^{16}$=H], [398; Y=Q1, $R^{13}$=OMe, $R^{14}$=H, $R^{15}$=H, $R^{16}$=Cl], [399; Y=Q1, $R^{13}$=Cl, $R^{14}$=OMe, $R^{15}$=H, $R^{16}$=H], [400; Y=Q1, $R^{13}$=H, $R^{14}$=OMe, $R^{15}$=Cl, $R^{16}$=H],

[401; Y=Q1, $R^{13}$=H, $R^{14}$=OMe, $R^{15}$=H, $R^{16}$=Cl], [402; Y=Q1, $R^{13}$=Cl, $R^{14}$=H, $R^{15}$=OMe, $R^{16}$=H], [403; Y=Q1, $R^{13}$=H, $R^{14}$=Cl, $R^{15}$=OMe, $R^{16}$=H], [404; Y=Q1, $R^{13}$=H, $R^{14}$=H, $R^{15}$=OMe, $R^{16}$=Cl], [405; Y=Q1, $R^{13}$=Cl, $R^{14}$=H, $R^{15}$=H, $R^{16}$=OMe], [406; Y=Q1, $R^{13}$=H, $R^{14}$=Cl, $R^{15}$=H, $R^{16}$=OMe], [407; Y=Q1, $R^{13}$=H, $R^{14}$=H, $R^{15}$=Cl, $R^{16}$=OMe], [408; Y=Q1, $R^{13}$=CN, $R^{14}$=H, $R^{15}$=H, $R^{16}$=H], [409; Y=Q1, $R^{13}$=H, $R^{14}$=CN, $R^{15}$=H, $R^{16}$=H], [410; Y=Q1, $R^{13}$=H, $R^{14}$=H, $R^{15}$=CN, $R^{16}$=H], [411; Y=Q1, $R^{13}$=H, $R^{14}$=H, $R^{15}$=H, $R^{16}$=CN], [412; Y=Q1, $R^{13}$=CN, $R^{14}$=F, $R^{15}$=H, $R^{16}$=H], [413; Y=Q1, $R^{13}$=CN, $R^{14}$=H, $R^{15}$=F, $R^{16}$=H], [414; Y=Q1, $R^{13}$=CN, $R^{14}$=H, $R^{15}$=H, $R^{16}$=F], [415; Y=Q1, $R^{13}$=F, $R^{14}$=CN, $R^{15}$=H, $R^{16}$=H], [416; Y=Q1, $R^{13}$=H, $R^{14}$=CN, $R^{15}$=F, $R^{16}$=H], [417; Y=Q1, $R^{13}$=H, $R^{14}$=CN, $R^{15}$=H, $R^{16}$=F], [418; Y=Q1, $R^{13}$=F, $R^{14}$=H, $R^{15}$=CN, $R^{16}$=H], [419; Y=Q1, $R^{13}$=H, $R^{14}$=F, $R^{15}$=CN, $R^{16}$=H], [420; Y=Q1, $R^{13}$=H, $R^{14}$=H, $R^{15}$=CN, $R^{16}$=F], [421; Y=Q1, $R^{13}$=F, $R^{14}$=H, $R^{15}$=H, $R^{16}$=CN], [422; Y=Q1, $R^{13}$=H, $R^{14}$=F, $R^{15}$=H, $R^{16}$=CN], [423; Y=Q1, $R^{13}$=H, $R^{14}$=H, $R^{15}$=F, $R^{16}$=CN], [424; Y=Q1, $R^{13}$=CN, $R^{14}$=Cl, $R^{15}$=H, $R^{16}$=H], [425; Y=Q1, $R^{13}$=CN, $R^{14}$=H, $R^{15}$=Cl, $R^{16}$=H], [426; Y=Q1, $R^{13}$=CN, $R^{14}$=H, $R^{15}$=H, $R^{16}$=Cl], [427; Y=Q1, $R^{13}$=Cl, $R^{14}$=CN, $R^{15}$=H, $R^{16}$=H], [428; Y=Q1, $R^{13}$=H, $R^{14}$=CN, $R^{15}$=Cl, $R^{16}$=H], [429; Y=Q1, $R^{13}$=H, $R^{14}$=CN, $R^{15}$=H, $R^{16}$=Cl], [430; Y=Q1, $R^{13}$=Cl, $R^{14}$=H, $R^{15}$=CN, $R^{16}$=H], [431; Y=Q1, $R^{13}$=H, $R^{14}$=Cl, $R^{15}$=CN, $R^{16}$=H], [432; Y=Q1, $R^{13}$=H, $R^{14}$=H, $R^{15}$=CN, $R^{16}$=Cl], [433; Y=Q1, $R^{13}$=Cl, $R^{14}$=H, $R^{15}$=H, $R^{16}$=CN], [434; Y=Q1, $R^{13}$=H, $R^{14}$=Cl, $R^{15}$=H, $R^{16}$=CN], [435; Y=Q1, $R^{13}$=H, $R^{14}$=H, $R^{15}$=Cl, $R^{16}$=CN], [436; Y=Q1, $R^{13}$=NH$_2$, $R^{14}$=H, $R^{15}$=H, $R^{16}$=H], [437; Y=Q1, $R^{13}$=H, $R^{14}$=NH$_2$, $R^{15}$=H, $R^{16}$=H], [438; Y=Q1, $R^{13}$=H, $R^{14}$=H, $R^{15}$=NH$_2$, $R^{16}$=H], [439; Y=Q1, $R^{13}$=H, $R^{14}$=H, $R^{15}$=H, $R^{16}$=NH$_2$], [440; Y=Q1, $R^{13}$=NH$_2$, $R^{14}$=F, $R^{15}$=H, $R^{16}$=H], [441; Y=Q1, $R^{13}$=NH$_2$, $R^{14}$=H, $R^{15}$=F, $R^{16}$=H], [442; Y=Q1, $R^{13}$=NH$_2$, $R^{14}$=H, $R^{15}$=H, $R^{16}$=F], [443; Y=Q1, $R^{13}$=F, $R^{14}$=NH$_2$, $R^{15}$=H, $R^{16}$=H], [444; Y=Q1, $R^{13}$=H, $R^{14}$=NH$_2$, $R^{15}$=F, $R^{16}$=H], [445; Y=Q1, $R^{13}$=H, $R^{14}$=NH$_2$, $R^{15}$=H, $R^{16}$=F], [446; Y=Q1, $R^{13}$=F, $R^{14}$=H, $R^{15}$=NH$_2$, $R^{16}$=H], [447; Y=Q1, $R^{13}$=H, $R^{14}$=F, $R^{15}$=NH$_2$, $R^{16}$=H], [448; Y=Q1, $R^{13}$=H, $R^{14}$=H, $R^{15}$=NH$_2$, $R^{16}$=F], [449; Y=Q1, $R^{13}$=F, $R^{14}$=H, $R^{15}$=H, $R^{16}$=NH$_2$], [450; Y=Q1, $R^{13}$=H, $R^{14}$=F, $R^{15}$=H, $R^{16}$=NH$_2$], [451; Y=Q1, $R^{13}$=H, $R^{14}$=H, $R^{15}$=F, $R^{16}$=NH$_2$], [452; Y=Q1, $R^{13}$=NH$_2$, $R^{14}$=Cl, $R^{15}$=H, $R^{16}$=H], [453; Y=Q1, $R^{13}$=NH$_2$, $R^{14}$=H, $R^{15}$=Cl, $R^{16}$=H], [454; Y=Q1, $R^{13}$=NH$_2$, $R^{14}$=H, $R^{15}$=H, $R^{16}$=Cl], [455; Y=Q1, $R^{13}$=Cl, $R^{14}$=NH$_2$, $R^{15}$=H, $R^{16}$=H], [456; Y=Q1, $R^{13}$=H, $R^{14}$=NH$_2$, $R^{15}$=Cl, $R^{16}$=H], [457; Y=Q1, $R^{13}$=H, $R^{14}$=NH$_2$, $R^{15}$=H, $R^{16}$=Cl], [458; Y=Q1, $R^{13}$=Cl, $R^{14}$=H, $R^{15}$=NH$_2$, $R^{16}$=H], [459; Y=Q1, $R^{13}$=H, $R^{14}$=Cl, $R^{15}$=NH$_2$, $R^{16}$=H], [460; Y=Q1, $R^{13}$=H, $R^{14}$=H, $R^{15}$=NH$_2$, $R^{16}$=Cl], [461; Y=Q1, $R^{13}$=Cl, $R^{14}$=H, $R^{15}$=H, $R^{16}$=NH$_2$], [462; Y=Q1, $R^{13}$=H, $R^{14}$=Cl, $R^{15}$=H, $R^{16}$=NH$_2$], [463; Y=Q1, $R^{13}$=H, $R^{14}$=H, $R^{15}$=Cl, $R^{16}$=NH$_2$], [464; Y=Q1, $R^{13}$=NHMe, $R^{14}$=H, $R^{15}$=H, $R^{16}$=H], [465; Y=Q1, $R^{13}$=H, $R^{14}$=NHMe, $R^{15}$=H, $R^{16}$=H], [466; Y=Q1, $R^{13}$=H, $R^{14}$=H, $R^{15}$=NHMe, $R^{16}$=H], [467; Y=Q1, $R^{13}$=H, $R^{14}$=H, $R^{15}$=H, $R^{16}$=NHMe], [468; Y=Q1, $R^{13}$=NHMe, $R^{14}$=F, $R^{15}$=H, $R^{16}$=H], [469; Y=Q1, $R^{13}$=NHMe, $R^{14}$=H, $R^{15}$=F, $R^{16}$=H], [470; Y=Q1, $R^{13}$=NHMe, $R^{14}$=H, $R^{15}$=H, $R^{16}$=F], [471; Y=Q1, $R^{13}$=F, $R^{14}$=NHMe, $R^{15}$=H, $R^{16}$=H], [472; Y=Q1, $R^{13}$=H, $R^{14}$=NHMe, $R^{15}$=F, $R^{16}$=H], [473; Y=Q1, $R^{13}$=H, $R^{14}$=NHMe, $R^{15}$=H, $R^{16}$=F], [474; Y=Q1, $R^{13}$=F, $R^{14}$=H, $R^{15}$=NHMe, $R^{16}$=H], [475; Y=Q1, $R^{13}$=H, $R^{14}$=F, $R^{15}$=NHMe, $R^{16}$=H], [476; Y=Q1, $R^{13}$=H, $R^{14}$=H, $R^{15}$=NHMe, $R^{16}$=F], [477; Y=Q1, $R^{13}$=F, $R^{14}$=H, $R^{15}$=H, $R^{16}$=NHMe], [478; Y=Q1, $R^{13}$=H, $R^{14}$=F, $R^{15}$=H, $R^{16}$=NHMe], [479; Y=Q1, $R^{13}$=H, $R^{14}$=H, $R^{15}$=F, $R^{16}$=NHMe], [480; Y=Q1, $R^{13}$=NHMe, $R^{14}$=Cl, $R^{15}$=H, $R^{16}$=H], [481; Y=Q1, $R^{13}$=NHMe, $R^{14}$=H, $R^{15}$=Cl, $R^{16}$=H], [482; Y=Q1, $R^{13}$=NHMe, $R^{14}$=H, $R^{15}$=H, $R^{16}$=Cl], [483; Y=Q1, $R^{13}$=Cl, $R^{14}$=NHMe, $R^{15}$=H, $R^{16}$=H], [484; Y=Q1, $R^{13}$=H, $R^{14}$=NHMe, $R^{15}$=Cl, $R^{16}$=H], [485; Y=Q1, $R^{13}$=H, $R^{14}$=NHMe, $R^{15}$=H, $R^{16}$=Cl], [486; Y=Q1, $R^{13}$=Cl, $R^{14}$=H, $R^{15}$=NHMe, $R^{16}$=H], [487; Y=Q1, $R^{13}$=H, $R^{14}$=Cl, $R^{15}$=NHMe, $R^{16}$=H], [488; Y=Q1, $R^{13}$=H, $R^{14}$=H, $R^{15}$=NHMe, $R^{16}$=Cl], [489; Y=Q1, $R^{13}$=Cl, $R^{14}$=H, $R^{15}$=H, $R^{16}$=NHMe], [490; Y=Q1, $R^{13}$=H, $R^{14}$=Cl, $R^{15}$=H, $R^{16}$=NHMe], [491; Y=Q1, $R^{13}$=H, $R^{14}$=H, $R^{15}$=Cl, $R^{16}$=NHMe], [492; Y=Q1, $R^{13}$=NMe$_2$, $R^{14}$=H, $R^{15}$=H, $R^{16}$=H], [493; Y=Q1, $R^{13}$=H, $R^{14}$=NMe$_2$, $R^{15}$=NMe$_2$, $R^{16}$=H], [494; Y=Q1, $R^{13}$=H, $R^{14}$=H, $R^{15}$=NMe$_2$, $R^{16}$=H], [495; Y=Q1, $R^{13}$=H, $R^{14}$=H, $R^{15}$=H, $R^{16}$=NMe$_2$], [496; Y=Q1, $R^{13}$=NMe$_2$, $R^{14}$=F, $R^{15}$=H, $R^{16}$=H], [497; Y=Q1, $R^{13}$=NMe$_2$, $R^{14}$=H, $R^{15}$=F, $R^{16}$=H], [498; Y=Q1, $R^{13}$=NMe$_2$, $R^{14}$=H, $R^{15}$=H, $R^{16}$=F], [499; Y=Q1, $R^{13}$=F, $R^{14}$=NMe$_2$, $R^{15}$=H, $R^{16}$=H], [500; Y=Q1, $R^{13}$=H, $R^{14}$=NMe$_2$, $R^{15}$=F, $R^{16}$=H],

[501; Y=Q1, $R^{13}$=H, $R^{14}$=NMe$_2$, $R^{15}$=H, $R^{16}$=F], [502; Y=Q1, $R^{13}$=F, $R^{14}$=H, $R^{15}$=NMe$_2$, $R^{16}$=H], [503; Y=Q1, $R^{13}$=H, $R^{14}$=F, $R^{15}$=NMe$_2$, $R^{16}$=H], [504; Y=Q1, $R^{13}$=H, $R^{14}$=H, $R^{15}$=NMe$_2$, $R^{16}$=F], [505; Y=Q1, $R^{13}$=F, $R^{14}$=H, $R^{15}$=H, $R^{16}$=NMe$_2$], [506; Y=Q1, $R^{13}$=H, $R^{14}$=F, $R^{15}$=H, $R^{16}$=NMe$_2$], [507; Y=Q1, $R^{13}$=H, $R^{14}$=H, $R^{15}$=F, $R^{16}$=NMe$_2$], [508; Y=Q1, $R^{13}$=NMe$_2$, $R^{14}$=Cl, $R^{15}$=H, $R^{16}$=H], [509; Y=Q1, $R^{13}$=NMe$_2$, $R^{14}$=H, $R^{15}$=Cl, $R^{16}$=H], [510; Y=Q1, $R^{13}$=NMe$_2$, $R^{14}$=H, $R^{15}$=H, $R^{16}$=Cl], [511; Y=Q1, $R^{13}$=Cl, $R^{14}$=NMe$_2$, $R^{15}$=H, $R^{16}$=H], [512; Y=Q1, $R^{13}$=H, $R^{14}$=NMe$_2$, $R^{15}$=Cl, $R^{16}$=H], [513; Y=Q1, $R^{13}$=H, $R^{14}$=NMe$_2$, $R^{15}$=H, $R^{16}$=Cl], [514; Y=Q1, $R^{13}$=Cl, $R^{14}$=H, $R^{15}$=NMe$_2$, $R^{16}$=H], [515; Y=Q1, $R^{13}$=H, $R^{14}$=Cl, $R^{15}$=NMe$_2$, $R^{16}$=H], [516; Y=Q1, $R^{13}$=H, $R^{14}$=H, $R^{15}$=NMe$_2$, $R^{16}$=Cl], [517; Y=Q1, $R^{13}$=Cl, $R^{14}$=H, $R^{15}$=H, $R^{16}$=NMe$_2$], [518; Y=Q1, $R^{13}$=H, $R^{14}$=Cl, $R^{15}$=H, $R^{16}$=NMe$_2$], [519; Y=Q1, $R^{13}$=H, $R^{14}$=H, $R^{15}$=Cl, $R^{16}$=NMe$_2$], [520; Y=Q1, $R^{13}$=SMe, $R^{14}$=H, $R^{15}$=H, $R^{16}$=H], [521; Y=Q1, $R^{13}$=H, $R^{14}$=SMe, $R^{15}$=H, $R^{16}$=H], [522; Y=Q1, $R^{13}$=H, $R^{14}$=H, $R^{15}$=SMe, $R^{16}$=H], [523; Y=Q1, $R^{13}$=H, $R^{14}$=H, $R^{15}$=H, $R^{16}$=SMe], [524; Y=Q1, $R^{13}$=SMe, $R^{14}$=F, $R^{15}$=H, $R^{16}$=H], [525; Y=Q1, $R^{13}$=SMe, $R^{14}$=H, $R^{15}$=F, $R^{16}$=H], [526; Y=Q1, $R^{13}$=SMe, $R^{14}$=H, $R^{15}$=H, $R^{16}$=F], [527; Y=Q1, $R^{13}$=F, $R^{14}$=SMe, $R^{15}$=H, $R^{16}$=H], [528; Y=Q1, $R^{13}$=H, $R^{14}$=SMe, $R^{15}$=F, $R^{16}$=H], [529; Y=Q1, $R^{13}$=H, $R^{14}$=SMe, $R^{15}$=H, $R^{16}$=F], [530; Y=Q1, $R^{13}$=F, $R^{14}$=H, $R^{15}$=SMe, $R^{16}$=H], [531; Y=Q1, $R^{13}$=H, $R^{14}$=F, $R^{15}$=SMe, $R^{16}$=H], [532; Y=Q1, $R^{13}$=H, $R^{14}$=H, $R^{15}$=SMe, $R^{16}$=F], [533; Y=Q1, $R^{13}$=F, $R^{14}$=H, $R^{15}$=H, $R^{16}$=SMe], [534; Y=Q1, $R^{13}$=H, $R^{14}$=F, $R^{15}$=H, $R^{16}$=SMe], [535; Y=Q1, $R^{13}$=H, $R^{14}$=H, $R^{15}$=F, $R^{16}$=SMe], [536; Y=Q1, $R^{13}$=SMe, $R^{14}$=Cl, $R^{15}$=H, $R^{16}$=H], [537; Y=Q1, $R^{13}$=SMe, $R^{14}$=H, $R^{15}$=Cl, $R^{16}$=H], [538; Y=Q1, $R^{13}$=SMe, $R^{14}$=H, $R^{15}$=H, $R^{16}$=Cl], [539; Y=Q1, $R^{13}$=Cl, $R^{14}$=SMe, $R^{15}$=H, $R^{16}$=H], [540; Y=Q1, $R^{13}$=H, $R^{14}$=SMe, $R^{15}$=Cl, $R^{16}$=H], [541; Y=Q1, $R^{13}$=H, $R^{14}$=SMe, $R^{15}$=H, $R^{16}$=Cl], [542; Y=Q1, $R^{13}$=Cl, $R^{14}$=H, $R^{15}$=SMe, $R^{16}$=H], [543; Y=Q1, $R^{13}$=H, $R^{14}$=Cl, $R^{15}$=SMe, $R^{16}$=H], [544; Y=Q1, $R^{13}$=H, $R^{14}$=H, $R^{15}$=SMe, $R^{16}$=Cl], [545; Y=Q1, $R^{13}$=Cl, $R^{14}$=H, $R^{15}$=H, $R^{16}$=SMe], [546; Y=Q1, $R^{13}$=H, $R^{14}$=Cl, $R^{15}$=H, $R^{16}$=SMe], [547; Y=Q1, $R^{13}$=H, $R^{14}$=H, $R^{15}$=Cl, $R^{16}$=SMe], [548; Y=Q1, $R^{13}$=NO$_2$, $R^{14}$=H, $R^{15}$=H, $R^{16}$=H], [549; Y=Q1, $R^{13}$=H, $R^{14}$=NO$_2$, $R^{15}$=H, $R^{16}$=H], [550; Y=Q1, $R^{13}$=H, $R^{14}$=H, $R^{15}$=NO$_2$, $R^{16}$=H], [551; Y=Q1, $R^{13}$=H, $R^{14}$=H, $R^{15}$=H, $R^{16}$=NO$_2$], [552; Y=Q1, $R^{13}$=NO$_2$, $R^{14}$=F, $R^{15}$=H, $R^{16}$=H], [553; Y=Q1, $R^{13}$=NO$_2$, $R^{14}$=H, $R^{15}$=F, $R^{16}$=H], [554; Y=Q1, $R^{13}$=NO$_2$, $R^{14}$=H, $R^{15}$=H, $R^{16}$=F], [555; Y=Q1, $R^{13}$=F, $R^{14}$=NO$_2$, $R^{15}$=H, $R^{16}$=H], [556; Y=Q1, $R^{13}$=H, $R^{14}$=NO$_2$, $R^{15}$=F, $R^{16}$=H], [557; Y=Q1, $R^{13}$=H, $R^{14}$=NO$_2$, $R^{15}$=H, $R^{16}$=F], [558; Y=Q1, $R^{13}$=F, $R^{14}$=H, $R^{15}$=NO$_2$, $R^{16}$=H], [559; Y=Q1, $R^{13}$=H, $R^{14}$=F, $R^{15}$=NO$_2$, $R^{16}$=H], [560; Y=Q1, $R^{13}$=H, $R^{14}$=H, $R^{15}$=NO$_2$, $R^{16}$=F], [561; Y=Q1, $R^{13}$=F, $R^{14}$=H, $R^{15}$=H, $R^{16}$=NO$_2$], [562; Y=Q1, $R^{13}$=H, $R^{14}$=F, $R^{15}$=H, $R^{16}$=NO$_2$], [563; Y=Q1, $R^{13}$=H, $R^{14}$=H, $R^{15}$=F, $R^{16}$=NO$_2$], [564; Y=Q1, $R^{13}$=NO$_2$, $R^{14}$=Cl, $R^{15}$=H, $R^{16}$=H], [565; Y=Q1, $R^{13}$=NO$_2$, $R^{14}$=H, $R^{15}$=Cl, $R^{16}$=H], [566; Y=Q1, $R^{13}$=NO$_2$, $R^{14}$=H, $R^{15}$=H, $R^{16}$=Cl], [567; Y=Q1, $R^{13}$=Cl, $R^{14}$=NO$_2$, $R^{15}$=H, $R^{16}$=H], [568; Y=Q1, $R^{13}$=H, $R^{14}$=NO$_2$, $R^{15}$=Cl, $R^{16}$=H], [569; Y=Q1, $R^{13}$=H, $R^{14}$=NO$_2$, $R^{15}$=H, $R^{16}$=Cl], [570; Y=Q1, $R^{13}$=Cl, $R^{14}$=H, $R^{15}$=NO$_2$, $R^{16}$=H], [571; Y=Q1, $R^{13}$=H, $R^{14}$=Cl, $R^{15}$=NO$_2$, $R^{16}$=H], [572; Y=Q1, $R^{13}$=H, $R^{14}$=H, $R^{15}$=NO$_2$, $R^{16}$=Cl], [573; Y=Q1, $R^{13}$=Cl, $R^{14}$=H, $R^{15}$=H, $R^{16}$=NO$_2$], [574; Y=Q1, $R^{13}$=H, $R^{14}$=Cl, $R^{15}$=H, $R^{16}$=NO$_2$], [575; Y=Q1, $R^{13}$=H, $R^{14}$=H, $R^{15}$=Cl, $R^{16}$=NO$_2$], [576; Y=Q2, $R^{12}$=H, $R^{14}$=H, $R^{15}$=H, $R^{16}$=H], [577; Y=Q2, $R^{12}$=Me, $R^{14}$=H, $R^{15}$=H, $R^{16}$=H], [578; Y=Q2, $R^{12}$=H, $R^{14}$=Me, $R^{15}$=H, $R^{16}$=H], [579; Y=Q2, $R^{12}$=H, $R^{14}$=H, $R^{15}$=Me, $R^{16}$=H], [580; Y=Q2, $R^{12}$=H, $R^{14}$=H, $R^{15}$=H, $R^{16}$=Me], [581; Y=Q2, $R^{12}$=Me, $R^{14}$=Me, $R^{15}$=H, $R^{16}$=H], [582; Y=Q2, $R^{12}$=Me, $R^{14}$=H, $R^{15}$=Me, $R^{16}$=H], [583; Y=Q2, $R^{12}$=Me, $R^{14}$=H, $R^{15}$=H, $R^{16}$=Me], [584; Y=Q2, $R^{12}$=H, $R^{14}$=Me, $R^{15}$=Me, $R^{16}$=H], [585; Y=Q2, $R^{12}$=H, $R^{14}$=Me, $R^{15}$=H, $R^{16}$=Me], [586; Y=Q2, $R^{12}$=H, $R^{14}$=H, $R^{15}$=Me, $R^{16}$=Me], [587; Y=Q2, $R^{12}$=H, $R^{14}$=Me, $R^{15}$=H, $R^{16}$=H], [588; Y=Q2, $R^{12}$=Me, $R^{14}$=Me, $R^{15}$=Me, $R^{16}$=H], [589; Y=Q2, $R^{12}$=Me, $R^{14}$=Me, $R^{15}$=H, $R^{16}$=Me], [590; Y=Q2, $R^{12}$=Me, $R^{14}$=H, $R^{15}$=Me, $R^{16}$=Me], [591; Y=Q2, $R^{12}$=H, $R^{14}$=Me, $R^{15}$=Me, $R^{16}$=Me], [592; Y=Q2, $R^{12}$=Me, $R^{14}$=Me, $R^{15}$=Me, $R^{16}$=Me], [593; Y=Q2, $R^{12}$=Me, $R^{14}$=F, $R^{15}$=H, $R^{16}$=H], [594; Y=Q2, $R^{12}$=Me, $R^{14}$=H, $R^{15}$=F, $R^{16}$=H], [595; Y=Q2, $R^{12}$=Me, $R^{14}$=H, $R^{15}$=H, $R^{16}$=F], [596; Y=Q2, $R^{12}$=Me, $R^{14}$=F, $R^{15}$=F, $R^{16}$=H], [597; Y=Q2, $R^{12}$=Me, $R^{14}$=F, $R^{15}$=H, $R^{16}$=F], [598; Y=Q2, $R^{12}$=Me, $R^{14}$=H, $R^{15}$=F, $R^{16}$=F], [599; Y=Q2, $R^{12}$=Me, $R^{14}$=F, $R^{15}$=F, $R^{16}$=F], [600; Y=Q2, $R^{12}$=F, $R^{14}$=Me, $R^{15}$=H, $R^{16}$=H], [601; Y=Q2, $R^{12}$=H, $R^{14}$=Me, $R^{15}$=F, $R^{16}$=H], [602; Y=Q2, $R^{12}$=H, $R^{14}$=Me, $R^{15}$=H, $R^{16}$=F], [603; Y=Q2, $R^{12}$=F, $R^{14}$=Me, $R^{15}$=F, $R^{16}$=H], [604; Y=Q2, $R^{12}$=F, $R^{14}$=Me, $R^{15}$=H, $R^{16}$=F], [605; Y=Q2, $R^{12}$=H, $R^{14}$=Me, $R^{15}$=F, $R^{16}$=F], [606; Y=Q2, $R^{12}$=F, $R^{14}$=Me, $R^{15}$=F, $R^{16}$=F], [607; Y=Q2, $R^{12}$=F, $R^{14}$=H, $R^{15}$=Me, $R^{16}$=H], [608; Y=Q2, $R^{12}$=H, $R^{14}$=F, $R^{15}$=Me, $R^{16}$=H], [609; Y=Q2, $R^{12}$=H, $R^{14}$=H, $R^{15}$=Me, $R^{16}$=F], [610; Y=Q2, $R^{12}$=F, $R^{14}$=F, $R^{15}$=Me, $R^{16}$=H], [611; Y=Q2, $R^{12}$=F, $R^{14}$=H, $R^{15}$=Me, $R^{16}$=F], [612; Y=Q2, $R^{12}$=H, $R^{14}$=F, $R^{15}$=Me, $R^{16}$=F], [613; Y=Q2, $R^{12}$=F, $R^{14}$=F, $R^{15}$=Me, $R^{16}$=F], [614; Y=Q2, $R^{12}$=F, $R^{14}$=H, $R^{15}$=H, $R^{16}$=Me], [615; Y=Q2, $R^{12}$=H, $R^{14}$=F, $R^{15}$=H, $R^{16}$=Me], [616; Y=Q2, $R^{12}$=H, $R^{14}$=H, $R^{15}$=F, $R^{16}$=Me], [617; Y=Q2, $R^{12}$=F, $R^{14}$=F, $R^{15}$=H, $R^{16}$=Me], [618; Y=Q2, $R^{12}$=F, $R^{14}$=H, $R^{15}$=F, $R^{16}$=Me], [619; Y=Q2, $R^{12}$=H, $R^{14}$=F, $R^{15}$=F, $R^{16}$=Me], [620; Y=Q2, $R^{12}$=F, $R^{14}$=F, $R^{15}$=F, $R^{16}$=Me], [621; Y=Q2, $R^{12}$=Me, $R^{14}$=Me, $R^{15}$=F, $R^{16}$=H], [622; Y=Q2, $R^{12}$=Me, $R^{14}$=Me, $R^{15}$=H, $R^{16}$=F], [623; Y=Q2, $R^{12}$=Me, $R^{14}$=F, $R^{15}$=Me, $R^{16}$=H], [624; Y=Q2, $R^{12}$=Me, $R^{14}$=H, $R^{15}$=Me, $R^{16}$=F], [625; Y=Q2, $R^{12}$=Me, $R^{14}$=F, $R^{15}$=H, $R^{16}$=Me], [626; Y=Q2, $R^{12}$=Me, $R^{14}$=H, $R^{15}$=F, $R^{16}$=Me], [627; Y=Q2, $R^{12}$=Me, $R^{14}$=M, $R^{15}$=Cl, $R^{16}$=H], [628; Y=Q2, $R^{12}$=Me, $R^{14}$=Me, $R^{15}$=H, $R^{16}$=Cl], [629; Y=Q2, $R^{12}$=Me, $R^{14}$=Cl, $R^{15}$=Me, $R^{15}$=H], [630; Y=Q2, $R^{12}$=Me, $R^{14}$=H, $R^{15}$=Me, $R^{16}$=Cl], [631; Y=Q2, $R^{12}$=Me, $R^{14}$=Cl, $R^{15}$=H, $R^{16}$=Me], [632; Y=Q2, $R^{12}$=Me, $R^{14}$=H, $R^{15}$=Cl, $R^{16}$=Me], [633; Y=Q2, $R^{12}$=Me, $R^{14}$=Cl, $R^{15}$=Cl, $R^{16}$=H], [634; Y=Q2, $R^{12}$=Me, $R^{14}$=H, $R^{15}$=Cl, $R^{16}$=Cl], [635; Y=Q2, $R^{12}$=Me, $R^{14}$=H, $R^{15}$=H, $R^{16}$=Cl], [636; Y=Q2, $R^{12}$=Me, $R^{14}$=Cl, $R^{15}$=Cl, $R^{16}$=H], [637; Y=Q2, $R^{12}$=Me, $R^{14}$=Cl, $R^{15}$=H, $R^{16}$=Cl], [638; Y=Q2, $R^{12}$=Me, $R^{14}$=H, $R^{15}$=Cl, $R^{16}$=Cl], [639; Y=Q2, $R^{12}$=Cl, $R^{14}$=Me, $R^{15}$=H, $R^{16}$=H], [640; Y=Q2, $R^{12}$=H, $R^{14}$=Me, $R^{15}$=Me, $R^{15}$=Cl, $R^{16}$=H], [641; Y=Q2, $R^{12}$=H, $R^{14}$=Me, $R^{15}$=H, $R^{16}$=C], [642; Y=Q2, $R^{12}$=Cl, $R^{14}$=Me, $R^{15}$=Cl, $R^{16}$=H], [643; Y=Q2, $R^{12}$=Cl, $R^{14}$=Me, $R^{15}$=H, $R^{16}$=Cl], [644; Y=Q2, $R^{12}$=H, $R^{14}$=Me, $R^{15}$=Cl, $R^{16}$=Cl], [645; Y=Q2, $R^{12}$=Cl, $R^{14}$=H, $R^{15}$=Me, $R^{16}$=H], [646; Y=Q2, $R^{12}$=H, $R^{14}$=Cl, $R^{15}$=Me, $R^{16}$=H], [647; Y=Q2, $R^{12}$=H, $R^{14}$=H, $R^{15}$=Me, $R^{16}$=Cl], [648; Y=Q2, $R^{12}$=Cl, $R^{14}$=Cl, $R^{15}$=Me, $R^{16}$=H], [649; Y=Q2, $R^{12}$=Cl, $R^{14}$=H, $R^{15}$=Me, $R^{16}$=Cl], [650; Y=Q2, $R^{12}$=H, $R^{14}$=Cl, $R^{15}$=Me, $R^{16}$=Cl], [651; Y=Q2, $R^{12}$=Cl, $R^{14}$=H, $R^{15}$=H, $R^{16}$=Me], [652; Y=Q2, $R^{12}$=H, $R^{14}$=Cl, $R^{15}$=H, $R^{16}$=Me], [653; Y=Q2, $R^{12}$=H, $R^{14}$=H, $R^{15}$=Cl, $R^{16}$=Me], [654; Y=Q2, $R^{12}$=Cl, $R^{14}$=Cl, $R^{15}$=H, $R^{16}$=Me], [655; Y=Q2, $R^{12}$=Cl, $R^{14}$=H, $R^{15}$=Cl, $R^{16}$=Me], [656; Y=Q2, $R^{12}$=H, $R^{14}$=Cl, $R^{15}$=Cl, $R^{16}$=Me], [657; Y=Q2, $R^{12}$=Me, $R^{14}$=Br, $R^{15}$=H, $R^{16}$=H], [658; Y=Q2, $R^{12}$=Me, $R^{14}$=H, $R^{15}$=Br, $R^{16}$=H], [659; Y=Q2, $R^{12}$=Me, $R^{14}$=H, $R^{15}$=H, $R^{16}$=Br], [660; Y=Q2, $R^{12}$=Br, $R^{14}$=Me, $R^{15}$=H, $R^{16}$=H], [661; Y=Q2, $R^{12}$=H, $R^{14}$=Me, $R^{15}$=Br, $R^{16}$=H], [662; Y=Q2, $R^{12}$=H, $R^{14}$=Me, $R^{15}$=H, $R^{16}$=Br], [663; Y=Q2, $R^{12}$=Br, $R^{14}$=H, $R^{15}$=Me, $R^{16}$=H], [664; Y=Q2, $R^{12}$=H, $R^{14}$=Br, $R^{15}$=Me, $R^{16}$=H], [665; Y=Q2, $R^{12}$=H, $R^{14}$=H, $R^{15}$=Me, $R^{16}$=Br], [666; Y=Q2, $R^{12}$=Br, $R^{14}$=H, $R^{15}$=H, $R^{16}$=Me], [667; Y=Q2, $R^{12}$=H, $R^{14}$=Br, $R^{15}$=H, $R^{16}$=Me], [668; Y=Q2, $R^{12}$=H, $R^{14}$=H, $R^{15}$=Br, $R^{16}$=Me], [669; Y=Q2, $R^{12}$=Me, $R^{14}$=Me, $R^{15}$=Br, $R^{16}$=H], [670; Y=Q2, $R^{12}$=Me, $R^{14}$=Me, $R^{15}$=H, $R^{16}$=Br], [671; Y=Q2, $R^{12}$=Me, $R^{14}$=Br, $R^{15}$=Me, $R^{16}$=H], [672; Y=Q2, $R^{12}$=Me, $R^{14}$=H, $R^{15}$=Me, $R^{16}$=Br], [673; Y=Q2, $R^{12}$=Me, $R^{14}$=Br, $R^{15}$=H, $R^{16}$=Me], [674; Y=Q2, $R^{12}$=Me, $R^{14}$=H, $R^{15}$=Br, $R^{16}$=Me], [675; Y=Q2, $R^{12}$=Me, $R^{14}$=CN, $R^{15}$=H, $R^{16}$=H], [676; Y=Q2, $R^{12}$=Me, $R^{14}$=H, $R^{15}$=CN, $R^{16}$=H], [677; Y=Q2, $R^{12}$=Me, $R^{14}$=H, $R^{15}$=H, $R^{16}$=CN], [678; Y=Q2, $R^{12}$=CN, $R^{14}$=Me, $R^{15}$=H, $R^{16}$=H], [679; Y=Q2, $R^{12}$=H, $R^{14}$=Me, $R^{15}$=CN, $R^{16}$=H], [680; Y=Q2, $R^{12}$=H, $R^{14}$=Me, $R^{15}$=H, $R^{16}$=CN], [681; Y=Q2, $R^{12}$=CN, $R^{14}$=H, $R^{15}$=Me, $R^{16}$=H], [682; Y=Q2, $R^{12}$=H, $R^{14}$=CN, $R^{15}$=Me, $R^{16}$=H], [683; Y=Q2, $R^{12}$=H, $R^{14}$=H, $R^{15}$=Me, $R^{16}$=CN], [684; Y=Q2, $R^{12}$=CN, $R^{14}$=H, $R^{15}$=H, $R^{16}$=Me], [685; Y=Q2, $R^{12}$=H, $R^{14}$=CN, $R^{15}$=H, $R^{16}$=Me], [686; Y=Q2, $R^{12}$=H, $R^{14}$=H, $R^{15}$=CN, $R^{16}$=Me], [687; Y=Q2, $R^{12}$=Me, $R^{14}$=Me, $R^{15}$=CN, $R^{16}$=H], [688; Y=Q2, $R^{12}$=Me, $R^{14}$=Me, $R^{15}$=H, $R^{16}$=CN], [689; Y=Q2, $R^{12}$=Me, $R^{14}$=CN, $R^{15}$=Me, $R^{16}$=H], [690; Y=Q2, $R^{12}$=Me, $R^{14}$=H, $R^{15}$=Me, $R^{16}$=CN], [691; Y=Q2, $R^{12}$=Me, $R^{14}$=CN, $R^{15}$=H, $R^{16}$=Me], [692; Y=Q2, $R^{12}$=Me, $R^{14}$=H, $R^{15}$=CN, $R^{16}$=Me], [693; Y=Q2, $R^{12}$=Me, $R^{14}$=OMe, $R^{15}$=H, $R^{16}$=H], [694; Y=Q2, $R^{12}$=Me, $R^{14}$=H, $R^{15}$=OMe, $R^{16}$=H], [695; Y=Q2, $R^{12}$=Me, $R^{14}$=H, $R^{15}$=H, $R^{16}$=OMe], [696; Y=Q2, $R^{12}$=OMe, $R^{14}$=Me, $R^{15}$=H,

R¹⁶=H], [697; Y=Q2, R¹²=H, R¹⁴=Me, R¹⁵=OMe, R¹⁶=H], [698; Y=Q2, R¹²=H, R¹⁴=Me, R¹⁵=H, R¹⁶=OMe], [699; Y=Q2, R¹²=OMe, R¹⁴=H, R¹⁵=Me, R¹⁶=H], [700; Y=Q2, R¹²=H, R¹⁴=OMe, R¹⁵=Me, R¹⁶=H], [701; Y=Q2, R¹²=H, R¹⁴=H, R¹⁵=Me, R¹⁶=OMe], [702; Y=Q2, R¹²=OMe, R¹⁴=H, R¹⁵=H, R¹⁶=Me], [703; Y=Q2, R¹²=H, R¹⁴=OMe, R¹⁵=H, R¹⁶=Me], [704; Y=Q2, R¹²=H, R¹⁴=H, R¹⁵=OMe, R¹⁶=Me], [705; Y=Q2, R¹²=Me, R¹⁴=Me, R¹⁵=OMe, R¹⁶=H], [706; Y=Q2, R¹²=Me, R¹⁴=Me, R¹⁵=H, R¹⁶=OMe], [707; Y=Q2, R¹²=Me, R¹⁴=OMe, R¹⁵=Me, R¹⁶=H], [708; Y=Q2, R¹²=Me, R¹⁴=H, R¹⁵=Me, R¹⁶=OMe], [709; Y=Q2, R¹²=Me, R¹⁴=OMe, R¹⁵=H, R¹⁶=Me], [710; Y=Q2, R¹²=Me, R¹⁴=H, R¹⁵=OMe, R¹⁶=Me], [711; Y=Q2, R¹²=Me, R¹⁴=OEt, R¹⁵=H, R¹⁶=H], [712; Y=Q2, R¹²=Me, R¹⁴=H, R¹⁵=OEt, R¹⁶=H], [713; Y=Q2, R¹²=Me, R¹⁴=H, R¹⁵=H, R¹⁶=OEt], [714; Y=Q2, R¹²=OEt, R¹⁴=Me, R¹⁵=H, R¹⁶=H], [715; Y=Q2, R¹²=H, R¹⁴=Me, R¹⁵=OEt, R¹⁶=H], [716; Y=Q2, R¹²=H, R¹⁴=Me, R¹⁵=H, R¹⁶=OEt], [717; Y=Q2, R¹²=OEt, R¹⁴=H, R¹⁵=Me, R¹⁶=H], [718; Y=Q2, R¹²=H, R¹⁴=OEt, R¹⁵=Me, R¹⁶=H], [719; Y=Q2, R¹²=H, R¹⁴=H, R¹⁵=Me, R¹⁶=OEt], [720; Y=Q2, R¹²=OEt, R¹⁴=H, R¹⁵=H, R¹⁶=Me], [721; Y=Q2, R¹²=H, R¹⁴=OEt, R¹⁵=H, R¹⁶=Me], [722; Y=Q2, R¹²=H, R¹⁴=H, R¹⁵=OEt, R¹⁶=Me], [723; Y=Q2, R¹²=Me, R¹⁴=Me, R¹⁵=OEt, R¹⁶=H], [724; Y=Q2, R¹²=Me, R¹⁴=Me, R¹⁵=H, R¹⁶=OEt], [725; Y=Q2, R¹²=Me, R¹⁴=OEt, R¹⁵=Me, R¹⁶=H], [726; Y=Q2, R¹²=Me, R¹⁴=H, R¹⁵=Me, R¹⁶=OEt], [727; Y=Q2, R¹²=Me, R¹⁴=OEt, R¹⁵=H, R¹⁶=Me], [728; Y=Q2, R¹²=Me, R¹⁴=H, R¹⁵=OEt, R¹⁶=Me], [729; Y=Q2, R¹²=Me, R¹⁴=Et, R¹⁵=H, R¹⁶=H], [730; Y=Q2, R¹²=Me, R¹⁴=H, R¹⁵=Et, R¹⁶=H], [731; Y=Q2, R¹²=Me, R¹⁴=H, R¹⁵=H, R¹⁶=Et], [732; Y=Q2, R¹²=Et, R¹⁴=Me, R¹⁵=H, R¹⁶=H], [733; Y=Q2, R¹²=H, R¹⁴=Me, R¹⁵=Et, R¹⁶=H], [734; Y=Q2, R¹²=H, R¹⁴=Me, R¹⁵=H, R¹⁶=Et], [735; Y=Q2, R¹²=Et, R¹⁴=H, R¹⁵=Me, R¹⁶=H], [736; Y=Q2, R¹²=H, R¹⁴=Et, R¹⁵=Me, R¹⁶=H], [737; Y=Q2, R¹²=H, R¹⁴=H, R¹⁵=Me, R¹⁶=Et], [738; Y=Q2, R¹²=Et, R¹⁴=H, R¹⁵=H, R¹⁶=Me], [739; Y=Q2, R¹²=H, R¹⁴=Et, R¹⁵=H, R¹⁶=Me], [740; Y=Q2, R¹²=H, R¹⁴=H, R¹⁵=Et, R¹⁶=Me], [741; Y=Q2, R¹²=Me, R¹⁴=Me, R¹⁵=Et, R¹⁶=H], [742; Y=Q2, R¹²=Me, R¹⁴=Me, R¹⁵=H, R¹⁶=Et], [743; Y=Q2, R¹²=Me, R¹⁴=Et, R¹⁵=Me, R¹⁶=H], [744; Y=Q2, R¹²=Me, R¹⁴=H, R¹⁵=Me, R¹⁶=Et], [745; Y=Q2, R¹²=Me, R¹⁴=Et, R¹⁵=H, R¹⁶=Me], [746; Y=Q2, R¹²=Me, R¹⁴=H, R¹⁵=Et, R¹⁶=Me], [747; Y=Q2, R¹²=Me, R¹⁴=CF₃, R¹⁵=H, R¹⁶=H], [748; Y=Q2, R¹²=Me, R¹⁴=H, R¹⁵=CF₃, R¹⁶=H], [749; Y=Q2, R¹²=Me, R¹⁴=H, R¹⁵=H, R¹⁶=CF₃], [750; Y=Q2, R¹²=CF₃, R¹⁴=Me, R¹⁵=H, R¹⁶=H], [751; Y=Q2, R¹²=H, R¹⁴=Me, R¹⁵=CF₃, R¹⁶=H], [752; Y=Q2, R¹²=H, R¹⁴=Me, R¹⁵=H, R¹⁶=CF₃], [753; Y=Q2, R¹²=CF₃, R¹⁴=H, R¹⁵=Me, R¹⁶=H], [754; Y=Q2, R¹²=H, R¹⁴=CF₃, R¹⁵=Me, R¹⁶=H], [755; Y=Q2, R¹²=H, R¹⁴=H, R¹⁵=Me, R¹⁶=CF₃], [756; Y=Q2, R¹²=CF₃, R¹⁴=H, R¹⁵=H, R¹⁶=Me], [757; Y=Q2, R¹²=H, R¹⁴=CF₃, R¹⁵=H, R¹⁶=Me], [758; Y=Q2, R¹²=H, R¹⁴=H, R¹⁵=CF₃, R¹⁶=Me], [759; Y=Q2, R¹²=Me, R¹⁴=cyclopropyl, R¹⁵=H, R¹⁶=H], [760; Y=Q2, R¹²=Me, R¹⁴=H, R¹⁵=cyclopropyl, R¹⁶=H], [761; Y=Q2, R¹²=Me, R¹⁴=H, R¹⁵=H, R¹⁶=cyclopropyl], [762; Y=Q2, R¹²=cyclopropyl, R¹⁴=Me, R¹⁵=H, R¹⁶=H], [763; Y=Q2, R¹²=H, R¹⁴=Me, R¹⁵=cyclopropyl, R¹⁶=H], [764; Y=Q2, R¹²=H, R¹⁴=Me, R¹⁵=H, R¹⁶=cyclopropyl], [765; Y=Q2, R¹²=cyclopropyl, R¹⁴=H, R¹⁵=Me, R¹⁶=H], [766; Y=Q2, R¹²=H, R¹⁴=cyclopropyl, R¹⁵=Me, R¹⁶=H], [767; Y=Q2, R¹²=H, R¹⁴=H, R¹⁵=Me, R¹⁶=cyclopropyl], [768; Y=Q2, R¹²=cyclopropyl, R¹⁴=H, R¹⁵=H, R¹⁶=Me], [769; Y=Q2, R¹²=H, R¹⁴=cyclopropyl, R¹⁵=H, R¹⁶=Me], [770; Y=Q2, R¹²=H, R¹⁴=H, R¹⁵=cyclopropyl, R¹⁶=Me], [771; Y=Q2, R¹²=Et, R¹⁴=H, R¹⁵=H, R¹⁶=H], [772; Y=Q2, R¹²=H, R¹⁴=Et, R¹⁵=H, R¹⁶=H], [773; Y=Q2, R¹²=H, R¹⁴=H, R¹⁵=Et, R¹⁶=H], [774; Y=Q2, R¹²=H, R¹⁴=H, R¹⁵=H, R¹⁶=Et], [775; Y=Q2, R¹²=Et, R¹⁴=Et, R¹⁵=H, R¹⁶=H], [776; Y=Q2, R¹²=Et, R¹⁴=H, R¹⁵=Et, R¹⁶=H], [777; Y=Q2, R¹²=Et, R¹⁴=H, R¹⁵=H, R¹⁶=Et], [778; Y=Q2, R¹²=H, R¹⁴=Et, R¹⁵=Et, R¹⁶=H], [779; Y=Q2, R¹²=H, R¹⁴=Et, R¹⁵=H, R¹⁶=Et], [780; Y=Q2, R¹²=H, R¹⁴=H, R¹⁵=Et, R¹⁶=Et], [781; Y=Q2, R¹²=Et, R¹⁴=Et, R¹⁵=Et, R¹⁶=H], [782; Y=Q2, R¹²=Et, R¹⁴=Et, R¹⁵=H, R¹⁶=Et], [783; Y=Q2, R¹²=Et, R¹⁴=F, R¹⁵=H, R¹⁶=H], [784; Y=Q2, R¹²=Et, R¹⁴=H, R¹⁵=F, R¹⁶=H], [785; Y=Q2, R¹²=Et, R¹⁴=H, R¹⁵=H, R¹⁶=F], [786; Y=Q2, R¹²=Et, R¹⁴=F, R¹⁵=F, R¹⁶=H], [787; Y=Q2, R¹²=Et, R¹⁴=F, R¹⁵=H, R¹⁶=F], [788; Y=Q2, R¹²=Et, R¹⁴=H, R¹⁵=F, R¹⁶=F], [789; Y=Q2, R¹²=F, R¹⁴=Et, R¹⁵=H, R¹⁶=H], [790; Y=Q2, R¹²=H, R¹⁴=Et, R¹⁵=F, R¹⁶=H], [791; Y=Q2, R¹²=H, R¹⁴=Et, R¹⁵=H, R¹⁶=F], [792; Y=Q2, R¹²=F, R¹⁴=Et, R¹⁵=F, R¹⁶=H], [793; Y=Q2, R¹²=F, R¹⁴=Et, R¹⁵=H, R¹⁶=F], [794; Y=Q2, R¹²=H, R¹⁴=Et, R¹⁵=F, R¹⁶=F], [795; Y=Q2, R¹²=F, R¹⁴=H, R¹⁵=Et, R¹⁶=H], [796; Y=Q2, R¹²=H, R¹⁴=F, R¹⁵=Et, R¹⁶=H], [797; Y=Q2, R¹²=H, R¹⁴=H, R¹⁵=Et, R¹⁶=F], [798; Y=Q2, R¹²=F, R¹⁴=F, R¹⁵=Et, R¹⁶=H], [799; Y=Q2, R¹²=F, R¹⁴=H, R¹⁵=Et, R¹⁶=F], [800; Y=Q2, R¹²=H, R¹⁴=F, R¹⁵=Et, R¹⁶=F], [801; Y=Q2, R¹²=F, R¹⁴=H, R¹⁵=H, R¹⁶=Et], [802; Y=Q2, R¹²=H, R¹⁴=F, R¹⁵=H, R¹⁶=Et], [803; Y=Q2, R¹²=H, R¹⁴=H, R¹⁵=F, R¹⁶=Et], [804; Y=Q2, R¹²=F, R¹⁴=F, R¹⁵=H, R¹⁶=Et], [805; Y=Q2, R¹²=F, R¹⁴=H, R¹⁵=F, R¹⁶=Et], [806; Y=Q2, R¹²=H, R¹⁴=F, R¹⁵=F, R¹⁶=Et], [807; Y=Q2, R¹²=Et, R¹⁴=Et, R¹⁵=F, R¹⁶=H], [808; Y=Q2, R¹²=Et, R¹⁴=Et, R¹⁵=H, R¹⁶=F], [809; Y=Q2, R¹²=Et, R¹⁴=F, R¹⁵=Et, R¹⁶=H], [810; Y=Q2, R¹²=Et, R¹⁴=H, R¹⁵=Et, R¹⁶=F], [811; Y=Q2, R¹²=Et, R¹⁴=F, R¹⁵=H, R¹⁶=Et], [812; Y=Q2, R¹²=Et, R¹⁴=Et, R¹⁵=Cl, R¹⁶=H], [813; Y=Q2, R¹²=Et, R¹⁴=Et, R¹⁵=H, R¹⁶=Cl], [814; Y=Q2, R¹²=Et, R¹⁴=Cl, R¹⁵=Et, R¹⁶=H], [815; Y=Q2, R¹²=Et, R¹⁴=H, R¹⁵=Et, R¹⁶=Cl], [816; Y=Q2, R¹²=Et, R¹⁴=Cl, R¹⁵=H, R¹⁶=Et], [817; Y=Q2, R¹²=Et, R¹⁴=HCl, R¹⁵=Cl, R¹⁶=Et], [818; Y=Q2, R¹²=Et, R¹⁴=Cl, R¹⁵=H, R¹⁶=H], [819; Y=Q2, R¹²=Et, R¹⁴=H, R¹⁵=Cl, R¹⁶=H], [820; Y=Q2, R¹²=Et, R¹⁴=H, R¹⁵=H, R¹⁶=C], [821; Y=Q2, R¹²=Et, R¹⁴=Cl, R¹⁵=Cl, R¹⁶=H], [822; Y=Q2, R¹²=Et, R¹⁴=Cl, R¹⁵=H, R¹⁶=Cl], [823; Y=Q2, R¹²=Et, R¹⁴=H, R¹⁵=Cl, R¹⁶=Cl], [824; Y=Q2, R¹²=Cl, R¹⁴=Et, R¹⁵=H, R¹⁶=H], [825; Y=Q2, R¹²=H, R¹⁴=Et, R¹⁵=Cl, R¹⁶=H], [826; Y=Q2, R¹²=H, R¹⁴=Et, R¹⁵=H, R¹⁶=Cl], [827; Y=Q2, R¹²=Cl, R¹⁴=Et, R¹⁵=Cl, R¹⁶=H], [828; Y=Q2, R¹²=Cl, R¹⁴=Et, R¹⁵=H, R¹⁶=Cl], [829; Y=Q2, R¹²=H, R¹⁴=Et, R¹⁵=Cl, R¹⁶=Cl], [830; Y=Q2, R¹²=Cl, R¹⁴=H, R¹⁵=Et, R¹⁶=H], [831; Y=Q2, R¹²=H, R¹⁴=Cl, R¹⁵=Et, R¹⁶=H], [832; Y=Q2, R¹²=H, R¹⁴=H, R¹⁵=Et, R¹⁶=Cl], [833; Y=Q2, R¹²=Cl, R¹⁴=Cl, R¹⁵=Et, R¹⁶=H], [834; Y=Q2, R¹²=Cl, R¹⁴=H, R¹⁵=Et, R¹⁶=Cl], [835; Y=Q2, R¹²=H, R¹⁴=Cl, R¹⁵=Et, R¹⁶=Cl], [836; Y=Q2, R¹²=Cl, R¹⁴=H, R¹⁵=H, R¹⁶=Et], [837; Y=Q2, R¹²=H, R¹⁴=Cl, R¹⁵=H, R¹⁶=Et], [838; Y=Q2, R¹²=H, R¹⁴=H, R¹⁵=Cl, R¹⁶=Et], [839; Y=Q2, R¹²=Cl, R¹⁴=Cl, R¹⁵=H, R¹⁶=Et], [840; Y=Q2, R¹²=Cl, R¹⁴=H, R¹⁵=Cl, R¹⁶=Et], [841; Y=Q2, R¹²=H, R¹⁴=Cl, $R^{15}$=Cl, $R^{16}$=Et], [842; Y=Q2, $R^{12}$=Et, $R^{14}$=CN, $R^{15}$=H, $R^{16}$=H], [843; Y=Q2, $R^{12}$=Et, $R^{14}$=H, $R^{15}$=CN, $R^{16}$=H], [844; Y=Q2, $R^{12}$=Et, $R^{14}$=H, $R^{15}$=H, $R^{16}$=CN], [845; Y=Q2, $R^{12}$=CN, $R^{14}$=Et, $R^{15}$=H, $R^{16}$=H], [846; Y=Q2, $R^{12}$=H, $R^{14}$=Et, $R^{15}$=CN, $R^{16}$=H], [847; Y=Q2, $R^{12}$=H, $R^{14}$=Et, $R^{15}$=H, $R^{16}$=CN], [848; Y=Q2, $R^{12}$=CN, $R^{14}$=H, $R^{15}$=Et, $R^{16}$=H], [849; Y=Q2, $R^{12}$=H, $R^{14}$=CN, $R^{15}$=Et, $R^{16}$=H], [850; Y=Q2, $R^{12}$=H, $R^{14}$=H, $R^{15}$=Et, $R^{16}$=CN], [851; Y=Q2, $R^{12}$=CN, $R^{14}$=H, $R^{15}$=H, $R^{16}$=Et], [852; Y=Q2, $R^{12}$=H, $R^{14}$=CN, $R^{15}$=H, $R^{16}$=Et], [853; Y=Q2, $R^{12}$=H, $R^{14}$=H, $R^{15}$=CN, $R^{16}$=Et], [854; Y=Q2, $R^{12}$=Et, $R^{14}$=CF$_3$, $R^{15}$=H, $R^{16}$=H], [855; Y=Q2, $R^{12}$=Et, $R^{14}$=H, $R^{15}$=CF$_3$, $R^{16}$=H], [856; Y=Q2, $R^{12}$=Et, $R^{14}$=H, $R^{15}$=H, $R^{16}$=CF$_3$], [857; Y=Q2, $R^{12}$=CF$_3$, $R^{14}$=Et, $R^{15}$=H, $R^{16}$=H], [858; Y=Q2, $R^{12}$=H, $R^{14}$=Et, $R^{15}$=CF$_3$, $R^{16}$=H], [859; Y=Q2, $R^{12}$=H, $R^{14}$=Et, $R^{15}$=H, $R^{16}$=CF$_3$], [860; Y=Q2, $R^{12}$=CF$_3$, $R^{14}$=H, $R^{15}$=Et, $R^{16}$=H], [861; Y=Q2, $R^{12}$=H, $R^{14}$=CF$_3$, $R^{15}$=Et, $R^{16}$=H], [862; Y=Q2, $R^{12}$=H, $R^{14}$=H, $R^{15}$=Et, $R^{16}$=CF$_3$], [863; Y=Q2, $R^{12}$=CF$_3$, $R^{14}$=H, $R^{15}$=H, $R^{16}$=Et], [864; Y=Q2, $R^{12}$=H, $R^{14}$=CF$_3$, $R^{15}$=H, $R^{16}$=Et], [865; Y=Q2, $R^{12}$=H, $R^{14}$=H, $R^{15}$=CF$_3$, $R^{16}$=Et], [866; Y=Q2, $R^{12}$=Et, $R^{14}$=OMe, $R^{15}$=H, $R^{16}$=H], [867; Y=Q2, $R^{12}$=Et, $R^{14}$=H, $R^{15}$=OMe, $R^{16}$=H], [868; Y=Q2, $R^{12}$=Et, $R^{14}$=H, $R^{15}$=H, $R^{16}$=OMe], [869; Y=Q2, $R^{12}$=OMe, $R^{14}$=Et, $R^{15}$=H, $R^{16}$=H], [870; Y=Q2, $R^{12}$=H, $R^{14}$=Et, $R^{15}$=OMe, $R^{16}$=H], [871; Y=Q2, $R^{12}$=H, $R^{14}$=Et, $R^{15}$=H, $R^{16}$=OMe], [872; Y=Q2, $R^{12}$=OMe, $R^{14}$=H, $R^{15}$=Et, $R^{16}$=H], [873; Y=Q2, $R^{12}$=H, $R^{14}$=OMe, $R^{15}$=Et, $R^{16}$=H], [874; Y=Q2, $R^{12}$=H, $R^{14}$=H, $R^{15}$=Et, $R^{16}$=OMe], [875; Y=Q2, $R^{12}$=OMe, $R^{14}$=H, $R^{15}$=H, $R^{16}$=Et], [876; Y=Q2, $R^{12}$=H, $R^{14}$=OMe, $R^{15}$=H, $R^{16}$=Et], [877; Y=Q2, $R^{12}$=H, $R^{14}$=H, $R^{15}$=OMe, $R^{16}$=Et], [878; Y=Q2, $R^{12}$=F, $R^{14}$=H, $R^{15}$=H, $R^{16}$=H], [879; Y=Q2, $R^{12}$=H, $R^{14}$=F, $R^{15}$=H, $R^{16}$=H], [880; Y=Q2, $R^{12}$=H, $R^{14}$=H, $R^{15}$=F, $R^{16}$=H], [881; Y=Q2, $R^{12}$=H, $R^{14}$=H, $R^{15}$=H, $R^{16}$=F], [882; Y=Q2, $R^{12}$=F, $R^{14}$=F, $R^{15}$=H, $R^{16}$=H], [883; Y=Q2, $R^{12}$=F, $R^{14}$=H, $R^{15}$=F, $R^{16}$=H], [884; Y=Q2, $R^{12}$=F, $R^{14}$=H, $R^{15}$=H, $R^{16}$=F], [885; Y=Q2, $R^{12}$=H, $R^{14}$=F, $R^{15}$=F, $R^{16}$=H], [886; Y=Q2, $R^{12}$=H, $R^{14}$=F, $R^{15}$=H, $R^{16}$=F], [887; Y=Q2, $R^{12}$=F, $R^{14}$=F, $R^{15}$=F, $R^{16}$=H], [888; Y=Q2, $R^{12}$=F, $R^{14}$=H, $R^{15}$=F, $R^{16}$=F], [889; Y=Q2, $R^{12}$=F, $R^{14}$=F, $R^{15}$=H, $R^{16}$=F], [890; Y=Q2, $R^{12}$=F, $R^{14}$=F, $R^{15}$=F, $R^{16}$=F], [891; Y=Q2, $R^{12}$=Cl, $R^{14}$=H, $R^{15}$=H, $R^{16}$=H], [892; Y=Q2, $R^{12}$=H, $R^{14}$=Cl, $R^{15}$=H, $R^{16}$=H], [893; Y=Q2, $R^{12}$=H, $R^{14}$=H, $R^{15}$=Cl, $R^{16}$=H], [894; Y=Q2, $R^{12}$=H, $R^{14}$=H, $R^{15}$=H, $R^{16}$=Cl], [895; Y=Q2, $R^{12}$=Cl, $R^{14}$=Cl, $R^{15}$=H, $R^{16}$=H], [896; Y=Q2, $R^{12}$=Cl, $R^{14}$=H, $R^{15}$=Cl, $R^{16}$=H], [897; Y=Q2, $R^{12}$=Cl, $R^{14}$=H, $R^{15}$=H, $R^{16}$=Cl], [898; Y=Q2, $R^{12}$=H, $R^{14}$=Cl, $R^{15}$=Cl, $R^{16}$=H], [899; Y=Q2, $R^{12}$=H, $R^{14}$=Cl, $R^{15}$=H, $R^{16}$=Cl], [900; Y=Q2, $R^{12}$=H, $R^{14}$=H, $R^{15}$=Cl, $R^{16}$=Cl],
[901; Y=Q2, $R^{12}$=Cl, $R^{14}$=H, $R^{15}$=Cl, $R^{16}$=Cl], [902; Y=Q2, $R^{12}$=Cl, $R^{14}$=Cl, $R^{15}$=H, $R^{16}$=Cl], [903; Y=Q2, $R^{12}$=Cl, $R^{14}$=Cl, $R^{15}$=Cl, $R^{16}$=H], [904; Y=Q2, $R^{12}$=F, $R^{14}$=Cl, $R^{15}$=H, $R^{16}$=H], [905; Y=Q2, $R^{12}$=F, $R^{14}$=H, $R^{15}$=Cl, $R^{16}$=H], [906; Y=Q2, $R^{12}$=F, $R^{14}$=H, $R^{15}$=H, $R^{16}$=Cl], [907; Y=Q2, $R^{12}$=Cl, $R^{14}$=F, $R^{15}$=H, $R^{16}$=H], [908; Y=Q2, $R^{12}$=H, $R^{14}$=F, $R^{15}$=Cl, $R^{16}$=H], [909; Y=Q2, $R^{12}$=H, $R^{14}$=F, $R^{15}$=H, $R^{16}$=Cl], [910; Y=Q2, $R^{12}$=Cl, $R^{14}$=H, $R^{15}$=F, $R^{16}$=H], [911; Y=Q2, $R^{12}$=H, $R^{14}$=Cl, $R^{15}$=F, $R^{16}$=H], [912; Y=Q2, $R^{12}$=H, $R^{14}$=H, $R^{15}$=F, $R^{16}$=Cl], [913; Y=Q2, $R^{12}$=Cl, $R^{14}$=H, $R^{15}$=H, $R^{16}$=F], [914; Y=Q2, $R^{12}$=H, $R^{14}$=Cl, $R^{15}$=H, $R^{16}$=F], [915; Y=Q2, $R^{12}$=H, $R^{14}$=H, $R^{15}$=Cl, $R^{16}$=F], [916; Y=Q2, $R^{12}$=n-propyl, $R^{14}$=H, $R^{15}$=H, $R^{16}$=H], [917; Y=Q2, $R^{12}$=H, $R^{14}$=n-propyl, $R^{15}$=H, $R^{16}$=H], [918; Y=Q2, $R^{12}$=H, $R^{14}$=H, $R^{15}$=n-propyl, $R^{16}$=H], [919; Y=Q2, $R^{12}$=H, $R^{14}$=H, $R^{15}$=H, $R^{16}$=n-propyl], [920; Y=Q2, $R^{12}$=isopropyl, $R^{14}$=H, $R^{15}$=H, $R^{16}$=H], [921; Y=Q2, $R^{12}$=H, $R^{14}$=isopropyl, $R^{15}$=H, $R^{16}$=H], [922; Y=Q2, $R^{12}$=H, $R^{14}$=H, $R^{15}$=isopropyl, $R^{16}$=H], [923; Y=Q2, $R^{12}$=H, $R^{14}$=H, $R^{15}$=H, $R^{16}$=isopropyl], [924; Y=Q2, $R^{12}$=cyclopropyl, $R^{14}$=H, $R^{15}$=H, $R^{16}$=H], [925; Y=Q2, $R^{12}$=H, $R^{14}$=cyclopropyl, $R^{15}$=H, $R^{16}$=H], [926; Y=Q2, $R^{12}$=H, $R^{14}$=H, $R^{15}$=cyclopropyl, $R^{16}$=H], [927; Y=Q2, $R^{12}$=H, $R^{14}$=H, $R^{15}$=H, $R^{16}$=cyclopropyl], [928; Y=Q2, $R^{12}$=cyclopropyl, $R^{14}$=F, $R^{15}$=H, $R^{16}$=H], [929; Y=Q2, $R^{12}$=cyclopropyl, $R^{14}$=H, $R^{15}$=F, $R^{16}$=H], [930; Y=Q2, $R^{12}$=cyclopropyl, $R^{14}$=H, $R^{15}$=H, $R^{16}$=F], [931; Y=Q2, $R^{12}$=F, $R^{14}$=cyclopropyl, $R^{15}$=H, $R^{16}$=H], [932; Y=Q2, $R^{12}$=H, $R^{14}$=cyclopropyl, $R^{15}$=F, $R^{16}$=H], [933; Y=Q2, $R^{12}$=H, $R^{14}$=cyclopropyl, $R^{15}$=H, $R^{16}$=F], [934; Y=Q2, $R^{12}$=F, $R^{14}$=H, $R^{15}$=cyclopropyl, $R^{16}$=H], [935; Y=Q2, $R^{12}$=H, $R^{14}$=F, $R^{15}$=cyclopropyl, $R^{16}$=H], [936; Y=Q2, $R^{12}$=H, $R^{14}$=H, $R^{15}$=cyclopropyl, $R^{16}$=F], [937; Y=Q2, $R^{12}$=F, $R^{14}$=H, $R^{15}$=H, $R^{16}$=cyclopropyl], [938; Y=Q2, $R^{12}$=H, $R^{14}$=F, $R^{15}$=H, $R^{16}$=cyclopropyl], [939; Y=Q2, $R^{12}$=H, $R^{14}$=H, $R^{15}$=F, $R^{16}$=cyclopropyl], [940; Y=Q2, $R^{12}$=cyclopropyl, $R^{14}$=Cl, $R^{15}$=H, $R^{16}$=H], [941; Y=Q2, $R^{12}$=cyclopropyl, $R^{14}$=H, $R^{15}$=Cl, $R^{16}$=H], [942; Y=Q2, $R^{12}$=cyclopropyl, $R^{14}$=H, $R^{15}$=H, $R^{16}$=Cl], [943; Y=Q2, $R^{12}$=Cl, $R^{14}$=cyclopropyl, $R^{15}$=H, $R^{16}$=H], [944; Y=Q2, $R^{12}$=H, $R^{14}$=cyclopropyl, $R^{15}$=Cl, $R^{16}$=H], [945; Y=Q2, $R^{12}$=H, $R^{14}$=cyclopropyl, $R^{15}$=H, $R^{16}$=Cl], [946; Y=Q2, $R^{12}$=Cl, $R^{14}$=H, $R^{15}$=cyclopropyl, $R^{16}$=H], [947; Y=Q2, $R^{12}$=H, $R^{14}$=Cl, $R^{15}$=cyclopropyl, $R^{16}$=H], [948; Y=Q2, $R^{12}$=H, $R^{14}$=H, $R^{15}$=cyclopropyl, $R^{16}$=Cl], [949; Y=Q2, $R^{12}$=Cl, $R^{14}$=H, $R^{15}$=H, $R^{16}$=cyclopropyl], [950; Y=Q2, $R^{12}$=H, $R^{14}$=Cl, $R^{15}$=H, $R^{16}$=cyclopropyl], [951; Y=Q2, $R^{12}$=H, $R^{14}$=H, $R^{15}$=Cl, $R^{16}$=cyclopropyl], [952; Y=Q2, $R^{12}$=OMe, $R^{14}$=H, $R^{15}$=H, $R^{16}$=H], [953; Y=Q2, $R^{12}$=H, $R^{14}$=H, $R^{15}$=H, $R^{16}$=OMe], [954; Y=Q2, $R^{12}$=OMe, $R^{14}$=H, $R^{15}$=H, $R^{16}$=H], [955; Y=Q2, $R^{12}$=OMe, $R^{14}$=H, $R^{15}$=OMe, $R^{16}$=H], [956; Y=Q2, $R^{12}$=H, $R^{14}$=OMe, $R^{15}$=OMe, $R^{16}$=H], [957; Y=Q2, $R^{12}$=H, $R^{14}$=H, $R^{15}$=OMe, $R^{16}$=H], [958; Y=Q2, $R^{12}$=H, $R^{14}$=H, $R^{15}$=H, $R^{16}$=OMe], [959; Y=Q2, $R^{12}$=OMe, $R^{14}$=F, $R^{15}$=H, $R^{16}$=H], [960; Y=Q2, $R^{12}$=OMe, $R^{14}$=H, $R^{15}$=F, $R^{16}$=H], [961; Y=Q2, $R^{12}$=OMe, $R^{14}$=H, $R^{15}$=H, $R^{16}$=F], [962; Y=Q2, $R^{12}$=F, $R^{14}$=OMe, $R^{15}$=H, $R^{16}$=H], [963; Y=Q2, $R^{12}$=H, $R^{14}$=OMe, $R^{15}$=F, $R^{16}$=H], [964; Y=Q2, $R^{12}$=H, $R^{14}$=OMe, $R^{15}$=H, $R^{16}$=F], [965; Y=Q2, $R^{12}$=F, $R^{14}$=H, $R^{15}$=OMe, $R^{16}$=H], [966; Y=Q2, $R^{12}$=H, $R^{14}$=F, $R^{15}$=OMe, $R^{16}$=H], [967; Y=Q2, $R^{12}$=H, $R^{14}$=H, $R^{15}$=OMe, $R^{16}$=F], [968; Y=Q2, $R^{12}$=F, $R^{14}$=H, $R^{15}$=H, $R^{16}$=OMe], [969; Y=Q2, $R^{12}$=H, $R^{14}$=F, $R^{15}$=H, $R^{16}$=OMe], [970; Y=Q2, $R^{12}$=H, $R^{14}$=H, $R^{15}$=F, $R^{16}$=OMe], [971; Y=Q2, $R^{12}$=OMe, $R^{14}$=Cl, $R^{15}$=H, $R^{16}$=H], [972; Y=Q2, $R^{12}$=OMe, $R^{14}$=H, $R^{15}$=Cl, $R^{16}$=H], [973; Y=Q2, $R^{12}$=OMe, $R^{14}$=H, $R^{15}$=H, $R^{16}$=Cl], [974; Y=Q2, $R^{12}$=Cl, $R^{14}$=OMe, $R^{15}$=H, $R^{16}$=H], [975; Y=Q2, $R^{12}$=H, $R^{14}$=OMe, $R^{15}$=Cl, $R^{16}$=H], [976; Y=Q2, $R^{12}$=H, $R^{14}$=OMe, $R^{15}$=H, $R^{16}$=Cl], [977; Y=Q2, $R^{12}$=Cl, $R^{14}$=H, $R^{15}$=OMe, $R^{16}$=H], [978; Y=Q2, $R^{12}$=H, $R^{14}$=Cl, $R^{15}$=OMe, $R^{16}$=H], [979; Y=Q2, $R^{12}$=H, $R^{14}$=H, $R^{15}$=OMe, $R^{16}$=Cl], [980; Y=Q2, $R^{12}$=Cl, $R^{14}$=H, $R^{15}$=H, $R^{16}$=OMe], [981; Y=Q2, R$^{12}$=H, R$^{14}$=Cl, R$^{15}$=H, R$^{16}$=OMe], [982; Y=Q2, R$^{12}$=H, R$^{14}$=H, R$^{15}$=Cl, R$^{16}$=OMe], [983; Y=Q2, R$^{12}$=CN, R$^{14}$=H, R$^{15}$=H, R$^{16}$=H], [984; Y=Q2, R$^{12}$=H, R$^{14}$=CN, R$^{15}$=H, R$^{16}$=H], [985; Y=Q2, R$^{12}$=H, R$^{14}$=H, R$^{15}$=CN, R$^{16}$=H], [986; Y=Q2, R$^{12}$=H, R$^{14}$=H, R$^{15}$=H, R$^{16}$=CN], [987; Y=Q2, R$^{12}$=CN, R$^{14}$=F, R$^{15}$=H, R$^{16}$=H], [988; Y=Q2, R$^{12}$=CN, R$^{14}$=H, R$^{15}$=F, R$^{16}$=H], [989; Y=Q2, R$^{12}$=CN, R$^{14}$=H, R$^{15}$=H, R$^{16}$=F], [990; Y=Q2, R$^{12}$=F, R$^{14}$=CN, R$^{15}$=H, R$^{16}$=H], [991; Y=Q2, R$^{12}$=H, R$^{14}$=CN, R$^{15}$=F, R$^{16}$=H], [992; Y=Q2, R$^{12}$=H, R$^{14}$=CN, R$^{15}$=H, R$^{16}$=F], [993; Y=Q2, R$^{12}$=F, R$^{14}$=H, R$^{15}$=CN, R$^{16}$=H], [994; Y=Q2, R$^{12}$=H, R$^{14}$=F, R$^{15}$=CN, R$^{16}$=H], [995; Y=Q2, R$^{12}$=H, R$^{14}$=H, R$^{15}$=CN, R$^{16}$=F], [996; Y=Q2, R$^{12}$=F, R$^{14}$=H, R$^{15}$=H, R$^{16}$=CN], [997; Y=Q2, R$^{12}$=H, R$^{14}$=F, R$^{15}$=H, R$^{16}$=CN], [998; Y=Q2, R$^{12}$=H, R$^{14}$=H, R$^{15}$=F, R$^{16}$=CN], [999; Y=Q2, R$^{12}$=CN, R$^{14}$=Cl, R$^{15}$=H, R$^{16}$=H], [1000; Y=Q2, R$^{12}$=CN, R$^{14}$=H, R$^{15}$=Cl, R$^{16}$=H],

[1001; Y=Q2, R$^{12}$=CN, R$^{14}$=H, R$^{15}$=H, R$^{16}$=Cl], [1002; Y=Q2, R$^{12}$=Cl, R$^{14}$=CN, R$^{15}$=H, R$^{16}$=H], [1003; Y=Q2, R$^{12}$=H, R$^{14}$=CN, R$^{15}$=Cl, R$^{16}$=H], [1004; Y=Q2, R$^{12}$=H, R$^{14}$=CN, R$^{15}$=H, R$^{16}$=Cl], [1005; Y=Q2, R$^{12}$=Cl, R$^{14}$=H, R$^{15}$=CN, R$^{16}$=H], [1006; Y=Q2, R$^{12}$=H, R$^{14}$=Cl, R$^{15}$=CN, R$^{16}$=H], [1007; Y=Q2, R$^{12}$=H, R$^{14}$=H, R$^{15}$=CN, R$^{16}$=Cl], [1008; Y=Q2, R$^{12}$=Cl, R$^{14}$=H, R$^{15}$=H, R$^{16}$=CN], [1009; Y=Q2, R$^{12}$=H, R$^{14}$=Cl, R$^{15}$=H, R$^{16}$=CN], [1010; Y=Q2, R$^{12}$=H, R$^{14}$=H, R$^{15}$=Cl, R$^{16}$=CN], [1011; Y=Q2, R$^{12}$=NH$_2$, R$^{14}$=H, R$^{15}$=H, R$^{16}$=H], [1012; Y=Q2, R$^{12}$=H, R$^{14}$=NH$_2$, R$^{15}$=H, R$^{16}$=H], [1013; Y=Q2, R$^{12}$=H, R$^{14}$=H, R$^{15}$=NH$_2$, R$^{16}$=H], [1014; Y=Q2, R$^{12}$=H, R$^{14}$=H, R$^{15}$=H, R$^{16}$=NH$_2$], [1015; Y=Q2, R$^{12}$=NH$_2$, R$^{14}$=F, R$^{15}$=H, R$^{16}$=H], [1016; Y=Q2, R$^{12}$=NH$_2$, R$^{14}$=H, R$^{15}$=F, R$^{16}$=H], [1017; Y=Q2, R$^{12}$=NH$_2$, R$^{14}$=H, R$^{15}$=H, R$^{16}$=F], [1018; Y=Q2, R$^{12}$=F, R$^{14}$=NH$_2$, R$^{15}$=H, R$^{16}$=H], [1019; Y=Q2, R$^{12}$=H, R$^{14}$=NH$_2$, R$^{15}$=F, R$^{16}$=H], [1020; Y=Q2, R$^{12}$=H, R$^{14}$=NH$_2$, R$^{15}$=H, R$^{16}$=F], [1021; Y=Q2, R$^{12}$=F, R$^{14}$=H, R$^{15}$=NH$_2$, R$^{16}$=H], [1022; Y=Q2, R$^{12}$=H, R$^{14}$=F, R$^{15}$=NH$_2$, R$^{16}$=H], [1023; Y=Q2, R$^{12}$=H, R$^{14}$=H, R$^{15}$=NH$_2$, R$^{16}$=F], [1024; Y=Q2, R$^{12}$=F, R$^{14}$=H, R$^{15}$=H, R$^{16}$=NH$_2$][1025; Y=Q2, R$^{12}$=H, R$^{14}$=F, R$^{15}$=H, R$^{16}$=NH$_2$], [1026; Y=Q2, R$^{12}$=H, R$^{14}$=H, R$^{15}$=F, R$^{16}$=NH$_2$], [1027; Y=Q2, R$^{12}$=NH$_2$, R$^{14}$=Cl, R$^{15}$=H, R$^{16}$=H], [1028; Y=Q2, R$^{12}$=NH$_2$, R$^{14}$=H, R$^{15}$=Cl, R$^{16}$=H], [1029; Y=Q2, R$^{12}$=NH$_2$, R$^{14}$=H, R$^{15}$=H, R$^{16}$=Cl], [1030; Y=Q2, R$^{12}$=Cl, R$^{14}$=NH$_2$, R$^{15}$=H, R$^{16}$=H], [1031; Y=Q2, R$^{12}$=H, R$^{14}$=NH$_2$, R$^{15}$=Cl, R$^{16}$=H], [1032; Y=Q2, R$^{12}$=H, R$^{14}$=NH$_2$, R$^{15}$=H, R$^{16}$=Cl], [1033; Y=Q2, R$^{12}$=Cl, R$^{14}$=H, R$^{15}$=NH$_2$, R$^{16}$=H], [1034; Y=Q2, R$^{12}$=H, R$^{14}$=Cl, R$^{15}$=NH$_2$, R$^{16}$=H], [1035; Y=Q2, R$^{12}$=H, R$^{14}$=H, R$^{15}$=NH$_2$, R$^{16}$=Cl], [1036; Y=Q2, R$^{12}$=Cl, R$^{14}$=H, R$^{15}$=H, R$^{16}$=NH$_2$], [1037; Y=Q2, R$^{12}$=H, R$^{14}$=Cl, R$^{15}$=H, R$^{16}$=NH$_2$], [1038; Y=Q2, R$^{12}$=H, R$^{14}$=H, R$^{15}$=Cl, R$^{16}$=NH$_2$], [1039; Y=Q2, R$^{12}$=NHMe, R$^{14}$=H, R$^{15}$=H, R$^{16}$=H], [1040; Y=Q2, R$^{12}$=H, R$^{14}$=NHMe, R$^{15}$=H, R$^{16}$=H], [1041; Y=Q2, R$^{12}$=H, R$^{14}$=H, R$^{15}$=NHMe, R$^{16}$=H], [1042; Y=Q2, R$^{12}$=H, R$^{14}$=H, R$^{15}$=H, R$^{16}$=NHMe], [1043; Y=Q2, R$^{12}$=NHMe, R$^{14}$=F, R$^{15}$=H, R$^{16}$=H], [1044; Y=Q2, R$^{12}$=NHMe, R$^{14}$=H, R$^{15}$=F, R$^{16}$=H], [1045; Y=Q2, R$^{12}$=NHMe, R$^{14}$=H, R$^{15}$=H, R$^{16}$=F], [1046; Y=Q2, R$^{12}$=F, R$^{14}$=NHMe, R$^{15}$=H, R$^{16}$=H], [1047; Y=Q2, R$^{12}$=H, R$^{14}$=NHMe, R$^{15}$=F, R$^{16}$=H], [1048; Y=Q2, R$^{12}$=H, R$^{14}$=NHMe, R$^{15}$=H, R$^{16}$=F], [1049; Y=Q2, R$^{12}$=F, R$^{14}$=H, R$^{15}$=NHMe, R$^{16}$=H], [1050; Y=Q2, R$^{12}$=H, R$^{14}$=F, R$^{15}$=NHMe, R$^{16}$=H], [1051; Y=Q2, R$^{12}$=H, R$^{14}$=H, R$^{15}$=NHMe, R$^{16}$=F], [1052; Y=Q2, R$^{12}$=F, R$^{14}$=H, R$^{15}$=H, R$^{16}$=NHMe], [1053; Y=Q2, R$^{12}$=H, R$^{14}$=F, R$^{15}$=H, R$^{16}$=NHMe], [1054; Y=Q2, R$^{12}$=H, R$^{14}$=H, R$^{15}$=F, R$^{16}$=NHMe], [1055; Y=Q2, R$^{12}$=NHMe, R$^{14}$=Cl, R$^{15}$=H, R$^{16}$=H], [1056; Y=Q2, R$^{12}$=NHMe, R$^{14}$=H, R$^{15}$=Cl, R$^{16}$=H], [1057; Y=Q2, R$^{12}$=NHMe, R$^{14}$=H, R$^{15}$=H, R$^{16}$=Cl], [1058; Y=Q2, R$^{12}$=Cl, R$^{14}$=NHMe, R$^{15}$=H, R$^{16}$=H], [1059; Y=Q2, R$^{12}$=H, R$^{14}$=NHMe, R$^{15}$=Cl, R$^{16}$=H], [1060; Y=Q2, R$^{12}$=H, R$^{14}$=NHMe, R$^{15}$=H, R$^{16}$=Cl], [1061; Y=Q2, R$^{12}$=Cl, R$^{14}$=H, R$^{15}$=NHMe, R$^{16}$=H], [1062; Y=Q2, R$^{12}$=H, R$^{14}$=Cl, R$^{15}$=NHMe, R$^{16}$=H], [1063; Y=Q2, R$^{12}$=H, R$^{14}$=H, R$^{15}$=NHMe, R$^{16}$=Cl], [1064; Y=Q2, R$^{12}$=Cl, R$^{14}$=H, R$^{15}$=H, R$^{16}$=NHMe], [1065; Y=Q2, R$^{12}$=H, R$^{14}$=Cl, R$^{15}$=H, R$^{16}$=NHMe], [1066; Y=Q2, R$^{12}$=H, R$^{14}$=H, R$^{15}$=Cl, R$^{16}$=NHMe], [1067; Y=Q2, R$^{12}$=NMe$_2$, R$^{14}$=H, R$^{15}$=H, R$^{16}$=H], [1068; Y=Q2, R$^{12}$=H, R$^{14}$=NMe$_2$, R$^{15}$=H, R$^{16}$=H], [1069; Y=Q2, R$^{12}$=H, R$^{14}$=H, R$^{15}$=NMe$_2$, R$^{16}$=H], [1070; Y=Q2, R$^{12}$=H, R$^{14}$=H, R$^{15}$=H, R$^{16}$=NMe$_2$], [1071; Y=Q2, R$^{12}$=NMe$_2$, R$^{14}$=F, R$^{15}$=H, R$^{16}$=H], [1072; Y=Q2, R$^{12}$=NMe$_2$, R$^{14}$=H, R$^{15}$=F, R$^{16}$=H], [1073; Y=Q2, R$^{12}$=NMe$_2$, R$^{14}$=H, R$^{15}$=H, R$^{16}$=F], [1074; Y=Q2, R$^{12}$=F, R$^{14}$=NMe$_2$, R$^{15}$=H, R$^{16}$=H], [1075; Y=Q2, R$^{12}$=H, R$^{14}$=NMe$_2$, R$^{15}$=F, R$^{16}$=H], [1076; Y=Q2, R$^{12}$=H, R$^{14}$=NMe$_2$, R$^{15}$=H, R$^{16}$=F], [1077; Y=Q2, R$^{12}$=F, R$^{14}$=H, R$^{15}$=NMe$_2$, R$^{16}$=H], [1078; Y=Q2, R$^{12}$=H, R$^{14}$=F, R$^{15}$=NMe$_2$, R$^{16}$=H], [1079; Y=Q2, R$^{12}$=H, R$^{14}$=H, R$^{15}$=NMe$_2$, R$^{16}$=F], [1080; Y=Q2, R$^{12}$=F, R$^{14}$=H, R$^{15}$=H, R$^{16}$=NMe$_2$], [1081; Y=Q2, R$^{12}$=H, R$^{14}$=F, R$^{15}$=H, R$^{16}$=NMe$_2$], [1082; Y=Q2, R$^{12}$=H, R$^{14}$=H, R$^{15}$=F, R$^{16}$=NMe$_2$], [1083; Y=Q2, R$^{12}$=NMe$_2$, R$^{14}$=Cl, R$^{15}$=H, R$^{16}$=H], [1084; Y=Q2, R$^{12}$=NMe$_2$, R$^{14}$=H, R$^{15}$=Cl, R$^{16}$=H], [1085; Y=Q2, R$^{12}$=NMe$_2$, R$^{14}$=H, R$^{15}$=H, R$^{16}$=Cl], [1086; Y=Q2, R$^{12}$=Cl, R$^{14}$=NMe$_2$, R$^{15}$=H, R$^{16}$=H], [1087; Y=Q2, R$^{12}$=H, R$^{14}$=NMe$_2$, R$^{15}$=Cl, R$^{16}$=H], [1088; Y=Q2, R$^{12}$=H, R$^{14}$=NMe$_2$, R$^{15}$=H, R$^{16}$=Cl], [1089; Y=Q2, R$^{12}$=Cl, R$^{14}$=H, R$^{15}$=NMe$_2$, R$^{16}$=H], [1090; Y=Q2, R$^{12}$=H, R$^{14}$=Cl, R$^{15}$=NMe$_2$, R$^{16}$=H], [1091; Y=Q2, R$^{12}$=H, R$^{14}$=H, R$^{15}$=NMe$_2$, R$^{16}$=Cl], [1092; Y=Q2, R$^{12}$=Cl, R$^{14}$=H, R$^{15}$=H, R$^{16}$=NMe$_2$], [1093; Y=Q2, R$^{12}$=H, R$^{14}$=Cl, R$^{15}$=H, R$^{16}$=NMe$_2$], [1094; Y=Q2, R$^{12}$=H, R$^{14}$=H, R$^{15}$=Cl, R$^{16}$=NMe$_2$], [1095; Y=Q2, R$^{12}$=SMe, R$^{14}$=H, R$^{15}$=H, R$^{16}$=H], [1096; Y=Q2, R$^{12}$=H, R$^{14}$=SMe, R$^{15}$=H, R$^{16}$=H], [1097; Y=Q2, R$^{12}$=H, R$^{14}$=H, R$^{15}$=SMe, R$^{16}$=H], [1098; Y=Q2, R$^{12}$=H, R$^{14}$=H, R$^{15}$=H, R$^{16}$=SMe], [1099; Y=Q2, R$^{12}$=SMe, R$^{14}$=F, R$^{15}$=H, R$^{16}$=H], [1100; Y=Q2, R$^{12}$=SMe, R$^{14}$=H, R$^{15}$=F, R$^{16}$=H],

[1101; Y=Q2, R$^{12}$=SMe, R$^{14}$=H, R$^{15}$=H, R$^{16}$=F], [1102; Y=Q2, R$^{12}$=F, R$^{14}$=SMe, R$^{15}$=H, R$^{16}$=H], [1103; Y=Q2, R$^{12}$=H, R$^{14}$=SMe, R$^{15}$=F, R$^{16}$=H], [1104; Y=Q2, R$^{12}$=H, R$^{14}$=SMe, R$^{15}$=H, R$^{16}$=F], [1105; Y=Q2, R$^{12}$=F, R$^{14}$=H, R$^{15}$=SMe, R$^{16}$=H], [1106; Y=Q2, R$^{12}$=H, R$^{14}$=F, R$^{15}$=SMe, R$^{16}$=H], [1107; Y=Q2, R$^{12}$=H, R$^{14}$=H, R$^{15}$=SMe, R$^{16}$=F], [1108; Y=Q2, R$^{12}$=F, R$^{14}$=H, R$^{15}$=H, R$^{16}$=SMe], [1109; Y=Q2, R$^{12}$=H, R$^{14}$=F, R$^{15}$=H, R$^{16}$=SMe], [1110; Y=Q2, R$^{12}$=H, R$^{14}$=H, R$^{15}$=F, R$^{16}$=SMe], [1111; Y=Q2, R$^{12}$=SMe, R$^{14}$=Cl, R$^{15}$=H, R$^{16}$=H], [1112; Y=Q2, R$^{12}$=SMe, R$^{14}$=H, R$^{15}$=Cl, R$^{16}$=H], [1113; Y=Q2, R$^{12}$=SMe, R$^{14}$=H, R$^{15}$=H, R$^{16}$=Cl], [1114; Y=Q2, R$^{12}$=Cl, R$^{14}$=SMe, R$^{15}$=H, R$^{16}$=H], [1115;

Y=Q2, $R^{12}$=H, $R^{14}$=SMe, $R^{15}$=Cl, $R^{16}$=H], [1116; Y=Q2, $R^{12}$=H, $R^{14}$=SMe, $R^{15}$=H, $R^{16}$=Cl], [1117; Y=Q2, $R^{12}$=Cl, $R^{14}$=H, $R^{15}$=SMe, $R^{16}$=H], [1118; Y=Q2, $R^{12}$=H, $R^{14}$=Cl, $R^{15}$=SMe, $R^{16}$=H], [1119; Y=Q2, $R^{12}$=H, $R^{14}$=H, $R^{15}$=SMe, $R^{16}$=Cl], [1120; Y=Q2, $R^{12}$=Cl, $R^{14}$=H, $R^{15}$=H, $R^{16}$=SMe], [1121; Y=Q2, $R^{12}$=H, $R^{14}$=Cl, $R^{15}$=H, $R^{16}$=SMe], [1122; Y=Q2, $R^{12}$=H, $R^{14}$=H, $R^{15}$=Cl, $R^{16}$=SMe], [1123; Y=Q2, $R^{12}$=$NO_2$, $R^{14}$=H, $R^{15}$=H, $R^{16}$=H], [1124; Y=Q2, $R^{12}$=H, $R^{14}$=$NO_2$, $R^{15}$=H, $R^{16}$=H], [1125; Y=Q2, $R^{12}$=H, $R^{14}$=H, $R^{15}$=$NO_2$, $R^{16}$=H], [1126; Y=Q2, $R^{12}$=H, $R^{14}$=H, $R^{15}$=H, $R^{16}$=$NO_2$], [1127; Y=Q2, $R^{12}$=$NO_2$, $R^{14}$=F, $R^{15}$=H, $R^{16}$=H], [1128; Y=Q2, $R^{12}$=$NO_2$, $R^{14}$=H, $R^{15}$=F, $R^{16}$=H], [1129; Y=Q2, $R^{12}$=$NO_2$, $R^{14}$=H, $R^{15}$=H, $R^{16}$=F], [1130; Y=Q2, $R^{12}$=F, $R^{14}$=$NO_2$, $R^{15}$=H, $R^{16}$=H], [1131; Y=Q2, $R^{12}$=H, $R^{14}$=$NO_2$, $R^{15}$=F, $R^{16}$=H], [1132; Y=Q2, $R^{12}$=H, $R^{14}$=$NO_2$, $R^{15}$=H, $R^{16}$=F], [1133; Y=Q2, $R^{12}$=F, $R^{14}$=H, $R^{15}$=$NO_2$, $R^{16}$=H], [1134; Y=Q2, $R^{12}$=H, $R^{14}$=F, $R^{15}$=$NO_2$, $R^{16}$=H], [1135; Y=Q2, $R^{12}$=H, $R^{14}$=H, $R^{15}$=$NO_2$, $R^{16}$=F], [1136; Y=Q2, $R^{12}$=F, $R^{14}$=H, $R^{15}$=H, $R^{16}$=$NO_2$], [1137; Y=Q2, $R^{12}$=H, $R^{14}$=F, $R^{15}$=H, $R^{16}$=$NO_2$], [1138; Y=Q2, $R^{12}$=H, $R^{14}$=H, $R^{15}$=F, $R^{16}$=$NO_2$], [1139; Y=Q2, $R^{12}$=$NO_2$, $R^{14}$=Cl, $R^{15}$=H, $R^{16}$=H], [1140; Y=Q2, $R^{12}$=$NO_2$, $R^{14}$=H, $R^{15}$=Cl, $R^{16}$=H], [1141; Y=Q2, $R^{12}$=$NO_2$, $R^{14}$=H, $R^{15}$=H, $R^{16}$=Cl], [1142; Y=Q2, $R^{12}$=Cl, $R^{14}$=$NO_2$, $R^{15}$=H, $R^{16}$=H], [1143; Y=Q2, $R^{12}$=H, $R^{14}$=$NO_2$, $R^{15}$=Cl, $R^{16}$=H], [1144; Y=Q2, $R^{12}$=H, $R^{14}$=$NO_2$, $R^{15}$=H, $R^{16}$=Cl], [1145; Y=Q2, $R^{12}$=Cl, $R^{14}$=H, $R^{15}$=$NO_2$, $R^{16}$=H], [1146; Y=Q2, $R^{12}$=H, $R^{14}$=Cl, $R^{15}$=$NO_2$, $R^{16}$=H], [1147; Y=Q2, $R^{12}$=H, $R^{14}$=H, $R^{15}$=$NO_2$, $R^{16}$=Cl], [1148; Y=Q2, $R^{12}$=Cl, $R^{14}$=H, $R^{15}$=H, $R^{16}$=$NO_2$], [1149; Y=Q2, $R^{12}$=H, $R^{14}$=Cl, $R^{15}$=H, $R^{16}$=$NO_2$], [1150; Y=Q2, $R^{12}$=H, $R^{14}$=H, $R^{15}$=Cl, $R^{16}$=$NO_2$]

[1151; Y=Q4, $R^{13}$=Me, $R^{14}$=H, $R^{15}$=H], [1152; Y=Q4, $R^{13}$=H, $R^{14}$=Me, $R^{16}$=H], [1153; Y=Q4, $R^{13}$=Me, $R^{14}$=Me, $R^{16}$=H], [1154; Y=Q4, $R^{13}$=Me, $R^{14}$=H, $R^{15}$=Me], [1155; Y=Q4, $R^{13}$=Me, $R^{14}$=Me, $R^{15}$=Me], [1156; Y=Q4, $R^{13}$=Me, $R^{14}$=F, $R^{15}$=H], [1157; Y=Q4, $R^{13}$=Me, $R^{14}$=H, $R^{15}$=F], [1158; Y=Q4, $R^{13}$=F, $R^{14}$=Me, $R^{15}$=H], [1159; Y=Q4, $R^{13}$=Me, $R^{14}$=F, $R^{15}$=F], [1160; Y=Q4, $R^{13}$=F, $R^{14}$=Me, $R^{15}$=F], [1161; Y=Q4, $R^{13}$=F, $R^{14}$=Me, $R^{15}$=F], [1162; Y=Q4, $R^{13}$=Me, $R^{14}$=F, $R^{15}$=Me], [1163; Y=Q4, $R^{13}$=Me, $R^{14}$=Cl, $R^{15}$=H], [1164; Y=Q4, $R^{13}$=Me, $R^{14}$=H, $R^{15}$=Cl], [1165; Y=Q4, $R^{13}$=Cl, $R^{14}$=Me, $R^{15}$=H], [1166; Y=Q4, $R^{13}$=Me, $R^{14}$=Cl, $R^{15}$=Cl], [1167; Y=Q4, $R^{13}$=Cl, $R^{14}$=Me, $R^{15}$=Cl], [1168; Y=Q4, $R^{13}$=Me, $R^{14}$=Me, $R^{15}$=Cl], [1169; Y=Q4, $R^{13}$=Me, $R^{14}$=Cl, $R^{15}$=Me], [1170; Y=Q4, $R^{13}$=Me, $R^{14}$=Br, $R^{15}$=H], [1171; Y=Q4, $R^{13}$=Me, $R^{14}$=H, $R^{15}$=Br], [1172; Y=Q4, $R^{13}$=Br, $R^{14}$=Me, $R^{15}$=H], [1173; Y=Q4, $R^{13}$=Me, $R^{14}$=Br, $R^{15}$=Br], [1174; Y=Q4, $R^{13}$=Br, $R^{14}$=Me, $R^{15}$=Br], [1175; Y=Q4, $R^{13}$=Me, $R^{14}$=Me, $R^{15}$=Br], [1176; Y=Q4, $R^{13}$=Me, $R^{14}$=Br, $R^{15}$=Me], [1177; Y=Q4, $R^{13}$=F, $R^{14}$=H, $R^{15}$=H], [1178; Y=Q4, $R^{13}$=H, $R^{14}$=F, $R^{15}$=H], [1179; Y=Q4, $R^{13}$=F, $R^{14}$=F, $R^{15}$=H], [1180; Y=Q4, $R^{13}$=F, $R^{14}$=H, $R^{15}$=F], [1181; Y=Q4, $R^{13}$=F, $R^{14}$=F, $R^{15}$=F], [1182; Y=Q4, $R^{13}$=F, $R^{14}$=Cl, $R^{15}$=H], [1183; Y=Q4, $R^{13}$=F, $R^{14}$=H, $R^{15}$=Cl], [1184; Y=Q4, $R^{13}$=Cl, $R^{14}$=F, $R^{15}$=H], [1185; Y=Q4, $R^{13}$=F, $R^{14}$=Cl, $R^{15}$=Cl], [1186; Y=Q4, $R^{13}$=Cl, $R^{14}$=F, $R^{15}$=Cl], [1187; Y=Q4, $R^{13}$=F, $R^{14}$=F, $R^{15}$=Cl], [1188; Y=Q4, $R^{13}$=F, $R^{14}$=Cl, $R^{15}$=F], [1189; Y=Q4, $R^{13}$=Et, $R^{14}$=H, $R^{15}$=H], [1190; Y=Q4, $R^{13}$=H, $R^{14}$=Et, $R^{15}$=H], [1191; Y=Q4, $R^{13}$=Et, $R^{14}$=Et, $R^{15}$=H], [1192; Y=Q4, $R^{13}$=Et, $R^{14}$=H, $R^{15}$=Et], [1193; Y=Q4, $R^{13}$=Et, $R^{14}$=Et, $R^{15}$=Et], [1194; Y=Q4, $R^{13}$=Et, $R^{14}$=F, $R^{15}$=H], [1195; Y=Q4, $R^{13}$=Et, $R^{14}$=H, $R^{15}$=F], [1196; Y=Q4, $R^{13}$=F, $R^{14}$=Et, $R^{15}$=H], [1197; Y=Q4, $R^{13}$=Et, $R^{14}$=F, $R^{15}$=F], [1198; Y=Q4, $R^{13}$=F, $R^{14}$=Et, $R^{15}$=F], [1199; Y=Q4, $R^{13}$=Et, $R^{14}$=Et, $R^{15}$=F], [1200; Y=Q4, $R^{13}$=Et, $R^{14}$=F, $R^{15}$=Et],

[1201; Y=Q4, $R^{13}$=Et, $R^{14}$=Cl, $R^{15}$=H], [1202; Y=Q4, $R^{13}$=Et, $R^{14}$=H, $R^{15}$=Cl], [1203; Y=Q4, $R^{13}$=Cl, $R^{14}$=Et, $R^{15}$=H], [1204; Y=Q4, $R^{13}$=Et, $R^{14}$=Cl, $R^{15}$=Cl], [1205; Y=Q4, $R^{13}$=Cl, $R^{14}$=Et, $R^{15}$=Cl], [1206; Y=Q4, $R^{13}$=Et, $R^{14}$=Et, $R^{15}$=Cl], [1207; Y=Q4, $R^{13}$=Et, $R^{14}$=Cl, $R^{15}$=Et], [1208; Y=Q4, $R^{13}$=OMe, $R^{14}$=H, $R^{15}$=H], [1209; Y=Q4, $R^{13}$=H, $R^{14}$=OMe, $R^{15}$=H], [1210; Y=Q4, $R^{13}$=OMe, $R^{14}$=OMe, $R^{15}$=H], [1211; Y=Q4, $R^{13}$=OMe, $R^{14}$=H, $R^{15}$=OMe], [1213; Y=Q4, $R^{13}$=OMe, $R^{14}$=F, $R^{15}$=H], [1214; Y=Q4, $R^{13}$=OMe, $R^{14}$=H, $R^{15}$=F], [1215; Y=Q4, $R^{13}$=F, $R^{14}$=OMe, $R^{15}$=H], [1216; Y=Q4, $R^{13}$=OMe, $R^{14}$=F, $R^{15}$=F], [1217; Y=Q4, $R^{13}$=F, $R^{14}$=OMe, $R^{15}$=F], [1218; Y=Q4, $R^{13}$=OMe, $R^{14}$=OMe, $R^{15}$=F], [1219; Y=Q4, $R^{13}$=OMe, $R^{14}$=F, $R^{15}$=OMe], [1220; Y=Q4, $R^{13}$=OMe, $R^{14}$=Cl, $R^{15}$=H], [1221; Y=Q4, $R^{13}$=OMe, $R^{14}$=H, $R^{15}$=Cl], [1222; Y=Q4, $R^{13}$=Cl, $R^{14}$=OMe, $R^{15}$=H], [1223; Y=Q4, $R^{13}$=OMe, $R^{14}$=OMe, $R^{15}$=Cl], [1224; Y=Q4, $R^{13}$=Cl, $R^{14}$=OMe, $R^{15}$=Cl], [1225; Y=Q4, $R^{13}$=OMe, $R^{14}$=OMe, $R^{15}$=Cl], [1226; Y=Q4, $R^{13}$=OMe, $R^{14}$=Cl, $R^{15}$=OMe], [1227; Y=Q4, $R^{13}$=n-propyl, $R^{14}$=H, $R^{15}$=H], [1228; Y=Q4, $R^{13}$=H, $R^{14}$=n-propyl, $R^{15}$=H], [1229; Y=Q4, $R^{13}$=n-propyl, $R^{14}$=H, $R^{15}$=F], [1230; Y=Q4, $R^{13}$=F, $R^{14}$=n-propyl, $R^{15}$=H], [1231; Y=Q4, $R^{13}$=n-propyl, $R^{14}$=F, $R^{15}$=F], [1232; Y=Q4, $R^{13}$=F, $R^{14}$=n-propyl, $R^{15}$=F], [1235; Y=Q4, $R^{13}$=n-propyl, $R^{14}$=Cl, $R^{15}$=H], [1236; Y=Q4, $R^{13}$=n-propyl, $R^{14}$=H, $R^{15}$=Cl], [1237; Y=Q4, $R^{13}$=Cl, $R^{14}$=n-propyl, $R^{15}$=H], [1238; Y=Q4, $R^{13}$=n-propyl, $R^{14}$=Cl, $R^{15}$=Cl], [1239; Y=Q4, $R^{13}$=Cl, $R^{14}$=n-propyl, $R^{15}$=Cl], [1242; Y=Q4, $R^{13}$=SMe, $R^{14}$=H, $R^{15}$=H], [1243; Y=Q4, $R^{13}$=H, $R^{14}$=SMe, $R^{15}$=H], [1244; Y=Q4, $R^{13}$=SMe, $R^{14}$=H, $R^{15}$=F], [1245; Y=Q4, $R^{13}$=F, $R^{14}$=SMe, $R^{15}$=H], [1246; Y=Q4, $R^{13}$=SMe, $R^{14}$=F, $R^{15}$=F], [1247; Y=Q4, $R^{13}$=F, $R^{14}$=SMe, $R^{15}$=F], [1248; Y=Q4, $R^{13}$=SMe, $R^{14}$=Cl, $R^{15}$=H], [1249; Y=Q4, $R^{13}$=SMe, $R^{14}$=H, $R^{15}$=Cl], [1250; Y=Q4, $R^{13}$=Cl, $R^{14}$=SMe, $R^{15}$=H], [1251; Y=Q4, $R^{13}$=SMe, $R^{14}$=Cl, $R^{15}$=Cl], [1252; Y=Q4, $R^{13}$=Cl, $R^{14}$=SMe, $R^{15}$=Cl], [1253; Y=Q4, $R^{13}$=$CF_3$, $R^{14}$=H, $R^{15}$=H], [1254; Y=Q4, $R^{13}$=H, $R^{14}$=$CF_3$, $R^{15}$=H], [1255; Y=Q4, $R^{13}$=$CF_3$, $R^{14}$=H, $R^{15}$=F], [1256; Y=Q4, $R^{13}$=F, $R^{14}$=$CF_3$, $R^{15}$=H], [1257; Y=Q4, $R^{13}$=$CF_3$, $R^{14}$=F, $R^{15}$=F], [1258; Y=Q4, $R^{13}$=F, $R^{14}$=$CF_3$, $R^{15}$=F], [1259; Y=Q4, $R^{13}$=$CF_3$, $R^{14}$=Cl, $R^{15}$=H], [1260; Y=Q4, $R^{13}$=$CF_3$, $R^{14}$=H, $R^{15}$=Cl], [1261; Y=Q4, $R^{13}$=Cl, $R^{14}$=$CF_3$, $R^{15}$=H], [1262; Y=Q4, $R^{13}$=$CF_3$, $R^{14}$=Cl, $R^{15}$=Cl], [1263; Y=Q4, $R^{13}$=H, $R^{14}$=H, $R^{15}$=H], [1264; Y=Q1, $R^{13}$=n-Bu, $R^{14}$=H, $R^{15}$=H, $R^{16}$=H], [1265; Y=Q1, $R^{13}$=H, $R^{14}$=cyclobutyl, $R^{15}$=H, $R^{16}$=H], [1266; Y=Q1, $R^{13}$=H, $R^{14}$=H, $R^{15}$=Ph, $R^{16}$=H], [1267; Y=Q1, $R^{13}$=H, $R^{14}$=H, $R^{15}$=H, $R^{16}$=OPh], [1268; Y=Q1, $R^{14}$=cyclopropyloxy, $R^{14}$=H, $R^{15}$=H, $R^{16}$=H], [1269; Y=Q1, $R^{13}$=H, $R^{14}$=$CF_2H$, $R^{15}$=H, $R^{16}$=H], [1270; Y=Q1, $R^{13}$=H, $R^{14}$=H, $R^{15}$=SOMe, $R^{16}$=H], [1271; Y=Q1, $R^{13}$=$SO_2Me$, $R^{14}$=H, $R^{15}$=H, $R^{16}$=H], [1272; Y=Q1, $R^{13}$=H, $R^{14}$=$SO_2Et$, $R^{15}$=H, $R^{16}$=H], [1273; Y=Q1, $R^{13}$=H, $R^{14}$=H, $R^{15}$=Bn, $R^{16}$=Me], [1274; Y=Q1, $R^{13}$=Bn, $R^{14}$=Me, $R^{15}$=H, $R^{16}$=H], [1275; Y=Q2, $R^{12}$=CHO, $R^{14}$=H, $R^{15}$=H, $R^{16}$=H], [1276; Y=Q2, $R^{12}$=H, $R^{14}$=CHO, $R^{15}$=H, $R^{16}$=H], [1277; Y=Q2, $R^{12}$=H, $R^{14}$=H, $R^{15}$=acetyl, $R^{16}$=H], [1278; Y=Q2, $R^{12}$=H, $R^{14}$=H, $R^{15}$=H, $R^{16}$=SPh], [1279; Y=Q2, $R^{12}$=SH, $R^{14}$=Me, $R^{15}$=H, $R^{16}$=H], [1280; Y=Q3, $R^{12}$=H, $R^{15}$=H, $R^{15}$=H, $R^{16}$=H], [1281; Y=Q3, $R^{12}$=Me, $R^{14}$=H, $R^{15}$=H, $R^{16}$=H], [1282; Y=Q3, $R^{12}$=H, $R^{13}$=Me, $R^{15}$=H, $R^{16}$=H], [1283; Y=Q3, $R^{12}$=H, $R^{13}$=H, $R^{15}$=Me, $R^{16}$=H], [1284; Y=Q3, $R^{12}$=H, $R^{13}$=H, $R^{15}$=H, $R^{16}$=Me], [1285; Y=Q3, $R^{12}$=Me, $R^{13}$=Me, $R^{15}$=H, $R^{16}$=H], [1286; Y=Q3, $R^{12}$=Me, $R^{13}$=H, $R^{15}$=Me, $R^{16}$=H], [1287; Y=Q3, $R^{12}$=Me, $R^{13}$=H, $R^{15}$=H, $R^{16}$=Me], [1288; Y=Q3, $R^{12}$=H, $R^{13}$=Me, $R^{15}$=Me, $R^{16}$=H], [1289; Y=Q3, $R^{12}$=H, $R^{13}$=Me, $R^{15}$=H, $R^{16}$=Me], [1290; Y=Q3, $R^{12}$=H, $R^{13}$=H, $R^{15}$=Me, $R^{16}$=Me], [1291; Y=Q3, $R^{12}$=H, $R^{13}$=Me, $R^{15}$=H, $R^{16}$=H], [1292; Y=Q3, $R^{12}$=Me, $R^{13}$=Me, $R^{15}$=Me, $R^{16}$=H], [1293; Y=Q3, $R^{12}$=Me, $R^{14}$=Me, $R^{15}$=H, $R^{16}$=Me], [1294; Y=Q3, $R^{12}$=Me, $R^{13}$=H, $R^{15}$=Me, $R^{16}$=Me], [1295; Y=Q3, $R^{12}$=H, $R^{14}$=Me, $R^{15}$=Me, $R^{16}$=Me], [1296; Y=Q3, $R^{12}$=Me, $R^{13}$=Me, $R^{15}$=Me, $R^{16}$=Me], [1297; Y=Q3, $R^{12}$=Me, $R^{13}$=F, $R^{15}$=H, $R^{16}$=H], [1298; Y=Q3, $R^{12}$=Me, $R^{13}$=H, $R^{15}$=F, $R^{16}$=H], [1299; Y=Q3, $R^{12}$=Me, $R^{13}$=H, $R^{15}$=H, $R^{16}$=F], [1300; Y=Q3, $R^{12}$=Me, $R^{13}$=F, $R^{15}$=F, $R^{16}$=H], [1301; Y=Q3, $R^{12}$=Me, $R^{13}$=F, $R^{15}$=H, $R^{16}$=F], [1302; Y=Q3, $R^{12}$=Me, $R^{13}$=H, $R^{15}$=F, $R^{16}$=F], [1303; Y=Q3, $R^{12}$=Me, $R^{13}$=F, $R^{15}$=F, $R^{16}$=F], [1304; Y=Q3, $R^{12}$=F, $R^{13}$=Me, $R^{15}$=H, $R^{16}$=H], [1305; Y=Q3, $R^{12}$=H, $R^{13}$=Me, $R^{15}$=F, $R^{16}$=H], [1306; Y=Q3, $R^{12}$=H, $R^{13}$=Me, $R^{15}$=H, $R^{16}$=F], [1307; Y=Q3, $R^{12}$=F, $R^{13}$=Me, $R^{15}$=F, $R^{16}$=H], [1308; Y=Q3, $R^{12}$=F, $R^{13}$=Me, $R^{15}$=H, $R^{16}$=F], [1309; Y=Q3, $R^{12}$=H, $R^{13}$=Me, $R^{15}$=F, $R^{16}$=F], [1310; Y=Q3, $R^{12}$=F, $R^{13}$=Me, $R^{15}$=F, $R^{16}$=F], [1311; Y=Q3, $R^{12}$=F, $R^{14}$=H, $R^{15}$=Me, $R^{16}$=H], [1312; Y=Q3, $R^{12}$=H, $R^{13}$=F, $R^{15}$=Me, $R^{16}$=H], [1313; Y=Q3, $R^{12}$=H, $R^{13}$=H, $R^{15}$=Me, $R^{16}$=F], [1314; Y=Q3, $R^{12}$=F, $R^{13}$=F, $R^{15}$=Me, $R^{16}$=H], [1315; Y=Q3, $R^{12}$=F, $R^{13}$=H, $R^{15}$=Me, $R^{16}$=F], [1316; Y=Q3, $R^{12}$=H, $R^{13}$=F, $R^{15}$=Me, $R^{16}$=F], [1317; Y=Q3, $R^{12}$=F, $R^{13}$=F, $R^{15}$=Me, $R^{16}$=F], [1318; Y=Q3, $R^{12}$=F, $R^{13}$=H, $R^{15}$=H, $R^{16}$=Me], [1319; Y=Q3, $R^{12}$=H, $R^{13}$=F, $R^{15}$=H, $R^{16}$=Me], [1320; Y=Q3, $R^{12}$=H, $R^{13}$=H, $R^{15}$=F, $R^{16}$=Me], [1321; Y=Q3, $R^{12}$=F, $R^{13}$=F, $R^{15}$=H, $R^{16}$=Me], [1322; Y=Q3, $R^{12}$=F, $R^{13}$=H, $R^{15}$=F, $R^{16}$=Me], [1323; Y=Q3, $R^{12}$=H, $R^{13}$=F, $R^{15}$=F, $R^{16}$=Me], [1324; Y=Q3, $R^{12}$=F, $R^{13}$=F, $R^{15}$=F, $R^{16}$=Me], [1325; Y=Q3, $R^{12}$=Me, $R^{13}$=Me, $R^{15}$=F, $R^{16}$=H], [1326; Y=Q3, $R^{12}$=Me, $R^{13}$=Me, $R^{15}$=H, $R^{16}$=F], [1327; Y=Q3, $R^{12}$=Me, $R^{13}$=F, $R^{15}$=Me, $R^{16}$=H], [1328; Y=Q3, $R^{12}$=Me, $R^{13}$=H, $R^{15}$=Me, $R^{16}$=F], [1329; Y=Q3, $R^{12}$=Me, $R^{13}$=F, $R^{15}$=H, $R^{16}$=Me], [1330; Y=Q3, $R^{12}$=Me, $R^{13}$=H, $R^{15}$=F, $R^{16}$=Me], [1331; Y=Q3, $R^{12}$=Me, $R^{13}$=Me, $R^{15}$=Cl, $R^{16}$=H], [1332; Y=Q3, $R^{12}$=Me, $R^{13}$=Me, $R^{15}$=H, $R^{16}$=Cl], [1333; Y=Q3, $R^{12}$=Me, $R^{13}$=Cl, $R^{15}$=Me, $R^{16}$=H], [1334; Y=Q3, $R^{12}$=Me, $R^{13}$=H, $R^{15}$=Me, $R^{16}$=Cl], [1335; Y=Q3, $R^{12}$=Me, $R^{13}$=Cl, $R^{15}$=H, $R^{16}$=Me], [1336; Y=Q3, $R^{12}$=Me, $R^{14}$=H, $R^{15}$=Cl, $R^{16}$=Me], [1337; Y=Q3, $R^{12}$=Me, $R^{13}$=Cl, $R^{15}$=H, $R^{16}$=H], [1338; Y=Q3, $R^{12}$=Me, $R^{14}$=H, $R^{15}$=Cl, $R^{16}$=H], [1339; Y=Q3, $R^{12}$=Me, $R^{13}$=H, $R^{15}$=H, $R^{16}$=Cl], [1340; Y=Q3, $R^{12}$=Me, $R^{13}$=Cl, $R^{15}$=Cl, $R^{16}$=H], [1341; Y=Q3, $R^{12}$=Me, $R^{13}$=Cl, $R^{15}$=H, $R^{16}$=Cl], [1342; Y=Q3, $R^{12}$=Me, $R^{14}$=H, $R^{15}$=Cl, $R^{16}$=Cl], [1343; Y=Q3, $R^{12}$=Cl, $R^{13}$=Me, $R^{15}$=H, $R^{16}$=H], [1344; Y=Q3, $R^{12}$=H, $R^{13}$=Me, $R^{15}$=Cl, $R^{16}$=H], [1345; Y=Q3, $R^{12}$=H, $R^{13}$=Me, $R^{15}$=H, $R^{16}$=Cl], [1346; Y=Q3, $R^{12}$=Cl, $R^{13}$=Me, $R^{15}$=Cl, $R^{16}$=H], [1347; Y=Q3, $R^{12}$=Cl, $R^{13}$=Me, $R^{15}$=H, $R^{16}$=Cl], [1348; Y=Q3, $R^{12}$=H, $R^{13}$=Me, $R^{15}$=Cl, $R^{16}$=Cl], [1349; Y=Q3, $R^{12}$=Cl, $R^{13}$=Cl, $R^{15}$=Me, $R^{16}$=H], [1350; Y=Q3, $R^{12}$=H, $R^{13}$=Cl, $R^{14}$=Me, $R^{16}$=H], [1351; Y=Q3, $R^{12}$=H, $R^{13}$=H, $R^{15}$=Me, $R^{16}$=Cl], [1352; Y=Q3, $R^{12}$=Cl, $R^{13}$=Cl, $R^{15}$=Me, $R^{16}$=H], [1353; Y=Q3, $R^{12}$=Cl, $R^{13}$=H, $R^{15}$=Me, $R^{16}$=Cl], [1354; Y=Q3, $R^{12}$=H, $R^{13}$=Cl, $R^{15}$=Me, $R^{16}$=Cl], [1355; Y=Q3, $R^{12}$=Bn, $R^{13}$=H, $R^{15}$=H, $R^{16}$=H], [1356; Y=Q3, $R^{12}$=Bn, $R^{13}$=Me, $R^{15}$=H, $R^{16}$=H], [1357; Y=Q3, $R^{12}$=n-Bu, $R^{13}$=H, $R^{15}$=H, $R^{16}$=H], [1358; Y=Q3, $R^{12}$=H, $R^{13}$=cyclobutyl, $R^{15}$=H, $R^{16}$=H], [1359; Y=Q3, $R^{12}$=H, $R^{13}$=H, $R^{15}$=Ph, $R^{16}$=H], [1360; Y=Q3, $R^{12}$=H, $R^{13}$=H, $R^{15}$=H, $R^{16}$=OPh], [1361; Y=Q3, $R^{12}$=cyclopropyloxy, $R^{13}$=H, $R^{15}$=H, $R^{16}$=H], [1362; Y=Q3, $R^{12}$=H, $R^{13}$=CF$_2$H, $R^{15}$=H, $R^{16}$=H], [1363; Y=Q3, $R^{12}$=H, $R^{13}$=H, $R^{15}$=SOMe, $R^{16}$=H], [1364; Y=Q3, $R^{12}$=SO$_2$Me, $R^{13}$=H, $R^{15}$=H, $R^{16}$=H], [1365; Y=Q3, $R^{12}$=H, $R^{13}$=SO$_2$Et, $R^{15}$=H, $R^{16}$=H], [1366; Y=Q3, $R^{12}$=H, $R^{13}$=H, $R^{15}$=Bn, $R^{16}$=Me], [1367; Y=Q5, $R^{13}$=H, $R^{15}$=H, $R^{16}$=H], [1368; Y=Q5, $R^{13}$=Me, $R^{15}$=H, $R^{16}$=H], [1369; Y=Q5, $R^{14}$=H, $R^{15}$=H, $R^{16}$=H], [1370; Y=Q5, $R^{13}$=H, $R^{15}$=H, $R^{16}$=Me], [1371; Y=Q5, $R^{13}$=Me, $R^{15}$=Me, $R^{16}$=H], [1372; Y=Q5, $R^{13}$=Me, $R^{15}$=H, $R^{16}$=Me], [1373; Y=Q5, $R^{13}$=Me, $R^{15}$=Me, $R^{16}$=Me], [1374; Y=Q5, $R^{13}$=Me, $R^{15}$=F, $R^{16}$=H], [1375; Y=Q5, $R^{13}$=Me, $R^{15}$=H, $R^{16}$=F], [1376; Y=Q5, $R^{13}$=F, $R^{15}$=Me, $R^{16}$=H], [1377; Y=Q5, $R^{13}$=Me, $R^{15}$=F, $R^{16}$=F], [1378; Y=Q5, $R^{14}$=F, $R^{15}$=Me, $R^{16}$=F], [1379; Y=Q5, $R^{13}$=Me, $R^{15}$=Me, $R^{16}$=F], [1380; Y=Q5, $R^{13}$=Me, $R^{15}$=F, $R^{16}$=Me], [1381; Y=Q5, $R^{13}$=Me, $R^{15}$=Cl, $R^{16}$=H], [1382; Y=Q5, $R^{13}$=Me, $R^{15}$=H, $R^{16}$=Cl], [1383; Y=Q5, $R^{13}$=Cl, $R^{65}$=Me, $R^{16}$=H], [1384; Y=Q5, $R^{13}$=Me, $R^{15}$=Cl, $R^{16}$=Cl], [1385; Y=Q5, $R^{13}$=Cl, $R^{15}$=Me, $R^{16}$=Cl], [1386; Y=Q5, $R^{13}$=Me, $R^{15}$=Me, $R^{16}$=Cl], [1387; Y=Q5, $R^{13}$=Me, $R^{15}$=Cl, $R^{16}$=Me], [1388; Y=Q5, $R^{13}$=Me, $R^{15}$=Br, $R^{16}$=H], [1389; Y=Q5, $R^{13}$=Me, $R^{15}$=H, $R^{16}$=Br], [1390; Y=Q5, $R^{13}$=Br, $R^{15}$=Me, $R^{16}$=H], [1391; Y=Q5, $R^{13}$=Me, $R^{15}$=Br, $R^{16}$=Br], [1392; Y=Q5, $R^{13}$=Br, $R^{15}$=Me, $R^{16}$=Br], [1393; Y=Q5, $R^{13}$=Me, $R^{15}$=Me, $R^{16}$=Br], [1394; Y=Q5, $R^{13}$=Me, $R^{15}$=Br, $R^{16}$=Me], [1395; Y=Q5, $R^{13}$=Et, $R^{15}$=H, $R^{16}$=H], [1396; Y=Q5, $R^{13}$=H, $R^{15}$=Et, $R^{16}$=H], [1397; Y=Q5, $R^{13}$=Et, $R^{15}$=Et, $R^{16}$=H], [1398; Y=Q5, $R^{13}$=Et, $R^{15}$=Et, $R^{16}$=Et], [139; Y=Q5, $R^{13}$=Et, $R^{15}$=F, $R^{16}$=H], [1400; Y=Q5, $R^{13}$=Et, $R^{15}$=H, $R^{16}$=F], [1401; Y=Q5, $R^{13}$=F, $R^{15}$=Et, $R^{16}$=H], [1402; Y=Q5, $R^{13}$=Et, $R^{15}$=F, $R^{16}$=F], [1403; Y=Q5, $R^{13}$=F, $R^{15}$=Et, $R^{16}$=F], [1404; Y=Q5, $R^{13}$=Et, $R^{15}$=Et, $R^{16}$=F], [1405; Y=Q5, $R^{13}$=Et, $R^{15}$=F, $R^{16}$=Et], [1406; Y=Q5, $R^{13}$=Et, $R^{15}$=Cl, $R^{16}$=H], [1407; Y=Q5, $R^{13}$=Et, $R^{15}$=H, $R^{16}$=Cl], [1408; Y=Q5, $R^{13}$=Cl, $R^{15}$=Et, $R^{16}$=H], [1409; Y=Q5, $R^{13}$=Et, $R^{15}$=Cl, $R^{16}$=Cl], [1410; Y=Q5, $R^{13}$=Cl, $R^{15}$=Et, $R^{16}$=Cl], [1411; Y=Q5, $R^{13}$=Et, $R^{15}$=Et, $R^{16}$=Cl], [1412; Y=Q5, $R^{13}$=Et, $R^{15}$=Cl, $R^{16}$=Et], [1413; Y=Q5, $R^{13}$=OMe, $R^{15}$=H, $R^{16}$=H], [1414; Y=Q5, $R^{13}$=H, $R^{15}$=OMe, $R^{16}$=H], [1415; Y=Q5, $R^{13}$=OMe, $R^{15}$=OMe, $R^{16}$=H], [1416; Y=Q5, $R^{13}$=OMe, $R^{15}$=H, $R^{16}$=OMe], [1417; Y=Q5, $R^{13}$=OMe, $R^{15}$=F, $R^{16}$=H], [1418; Y=Q5, $R^{13}$=OMe, $R^{15}$=H, $R^{16}$=F], [1419; Y=Q5, $R^{13}$=F, $R^{15}$=OMe, $R^{16}$=H], [1420; Y=Q5, $R^{13}$=OMe, $R^{15}$=F, $R^{16}$=F], [1421; Y=Q5, $R^{13}$=F, $R^{15}$=OMe, $R^{16}$=F], [1422; Y=Q5, $R^{13}$=OMe, $R^{15}$=OMe, $R^{16}$=F], [1423; Y=Q5, $R^{13}$=OMe, $R^{15}$=F, $R^{16}$=OMe], [1424; Y=Q5, $R^{13}$=OMe, $R^{15}$=Cl, $R^{16}$=H], [1425; Y=Q5, $R^{13}$=OMe, $R^{15}$=H, $R^{16}$=Cl], [1426; Y=Q5, $R^{13}$=Cl, $R^{15}$=OMe, R$^{16}$=H], [1428; Y=Q5, R$^{13}$=OMe, R$^{15}$=Cl, R$^{16}$=Cl], [1429; Y=Q5, R$^{13}$=Cl, R$^{15}$=OMe, R$^{16}$=Cl], [1430; Y=Q5, R$^{13}$=OMe, R$^{15}$=OMe, R$^{16}$=Cl], [1431; Y=Q5, R$^{13}$=OMe, R$^{15}$=Cl, R$^{16}$=OMe], [1432; Y=Q5, R$^{13}$=n-propyl, R$^{15}$=H, R$^{16}$=H], [1433; Y=Q5, R$^{13}$=H, R$^{15}$=n-propyl, R$^{16}$=H], [1434; Y=Q5, R$^{13}$=n-propyl, R$^{15}$=H, R$^{16}$=F], [1435; Y=Q5, R$^{13}$=F, R$^{15}$=n-propyl, R$^{16}$=H], [1436; Y=Q5, R$^{13}$=n-propyl, R$^{15}$=F, R$^{16}$=F], [1437; Y=Q5, R$^{13}$=F, R$^{15}$=n-propyl, R$^{16}$=F], [1438; Y=Q5, R$^{13}$=n-propyl, R$^{15}$=Cl, R$^{16}$=H], [1439; Y=Q5, R$^{13}$=n-propyl, R$^{15}$=H, R$^{16}$=Cl], [1440; Y=Q5, R$^{13}$=Cl, R$^{15}$=n-propyl, R$^{16}$=H], [1441; Y=Q5, R$^{13}$=n-propyl, R$^{15}$=Cl, R$^{16}$=Cl], [1442; Y=Q5, R$^{13}$=Cl, R$^{15}$=n-propyl, R$^{16}$=Cl], [1443; Y=Q5, R$^{13}$=SMe, R$^{15}$=H, R$^{16}$=H], [1444; Y=Q5, R$^{13}$=H, R$^{15}$=SMe, R$^{16}$=H], [1445; Y=Q5, R$^{13}$=SMe, R$^{15}$=H, R$^{16}$=F], [1446; Y=Q5, R$^{13}$=F, R$^{15}$=SMe, R$^{16}$=H], [1447; Y=Q5, R$^{13}$=SMe, R$^{15}$=F, R$^{16}$=F], [1448; Y=Q5, R$^{13}$=F, R$^{15}$=SMe, R$^{16}$=F], [1449; Y=Q5, R$^{13}$=SMe, R$^{15}$=Cl, R$^{16}$=H], [1450; Y=Q5, R$^{13}$=SMe, R$^{15}$=H, R$^{16}$=Cl], [1451; Y=Q5, R$^{13}$=Cl, R$^{15}$=SMe, R$^{16}$=H], [1452; Y=Q5, R$^{13}$=SMe, R$^{15}$=Cl, R$^{16}$=Cl], [1453; Y=Q5, R$^{13}$=Cl, R$^{15}$=SMe, R$^{16}$=Cl], [1454; Y=Q6, R$^{12}$=H, R$^{14}$=H, R$^{16}$=H], [1455; Y=Q6, R$^{12}$=Me, R$^{14}$=H, R$^{16}$=H], [1456; Y=Q6, R$^{12}$=H, R$^{14}$=Me, R$^{16}$=H], [1457; Y=Q6, R$^{12}$=Me, R$^{14}$=Me, R$^{16}$=H], [1458; Y=Q6, R$^{12}$=Me, R$^{14}$=H, R$^{16}$=Me], [1459; Y=Q6, R$^{12}$=Me, R$^{14}$=Me, R$^{16}$=Me], [1460; Y=Q6, R$^{12}$=Me, R$^{14}$=F, R$^{16}$=H], [1461; Y=Q6, R$^{12}$=Me, R$^{14}$=H, R$^{16}$=F], [1462; Y=Q6, R$^{12}$=F, R$^{14}$=Me, R$^{15}$=H], [1463; Y=Q6, R$^{12}$=Me, R$^{14}$=F, R$^{16}$=F], [1464; Y=Q6, R$^{12}$=F, R$^{14}$=Me, R$^{16}$=F], [1465; Y=Q6, R$^{12}$=Me, R$^{14}$=Me, R$^{16}$=F], [1466; Y=Q6, R$^{12}$=Me, R$^{14}$=F, R$^{16}$=Me], [1467; Y=Q6, R$^{12}$=Me, R$^{14}$=Cl, R$^{16}$=H], [1468; Y=Q6, R$^{12}$=Me, R$^{14}$=H, R$^{16}$=Cl], [1469; Y=Q6, R$^{12}$=Cl, R$^{14}$=Me, R$^{16}$=H], [1470; Y=Q6, R$^{12}$=Me, R$^{14}$=Cl, R$^{16}$=Cl], [1471; Y=Q6, R$^{12}$=Cl, R$^{14}$=Me, R$^{16}$=Cl], [1472; Y=Q6, R$^{12}$=Me, R$^{14}$=Me, R$^{16}$=Cl], [1473; Y=Q6, R$^{12}$=Me, R$^{14}$=Cl, R$^{16}$=Me], [1474; Y=Q6, R$^{12}$=Me, R$^{14}$=Br, R$^{16}$=H], [1475; Y=Q6, R$^{12}$=Me, R$^{14}$=H, R$^{16}$=Br], [1476; Y=Q6, R$^{12}$=Br, R$^{14}$=Me, R$^{16}$=H], [1477; Y=Q6, R$^{12}$=Me, R$^{14}$=Br, R$^{16}$=Br], [1478; Y=Q6, R$^{12}$=Br, R$^{14}$=Me, R$^{16}$=Br], [1479; Y=Q6, R$^{12}$=Me, R$^{14}$=Me, R$^{16}$=Br], [1480; Y=Q6, R$^{12}$=Me, R$^{14}$=Br, R$^{16}$=Me], [1481; Y=Q6, R$^{12}$=F, R$^{14}$=H, R$^{16}$=H], [1482; Y=Q6, R$^{12}$=H, R$^{14}$=F, R$^{16}$=H], [1483; Y=Q6, R$^{12}$=F, R$^{14}$=F, R$^{16}$=H], [1484; Y=Q6, R$^{12}$=F, R$^{14}$=H, R$^{16}$=F], [1485; Y=Q6, R$^{12}$=F, R$^{14}$=F, R$^{16}$=F], [1486; Y=Q6, R$^{12}$=F, R$^{14}$=Cl, R$^{16}$=H], [1487; Y=Q6, R$^{12}$=F, R$^{14}$=H, R$^{16}$=Cl], [1488; Y=Q6, R$^{12}$=Cl, R$^{14}$=F, R$^{16}$=H], [1489; Y=Q6, R$^{12}$=F, R$^{14}$=Cl, R$^{16}$=Cl], [1490; Y=Q6, R$^{12}$=Cl, R$^{14}$=F, R$^{16}$=Cl], [1491; Y=Q6, R$^{12}$=F, R$^{14}$=F, R$^{16}$=Cl], [1492; Y=Q6, R$^{12}$=F, R$^{14}$=Cl, R$^{16}$=F], [1493; Y=Q6, R$^{12}$=Et, R$^{14}$=H, R$^{16}$=H], [1494; Y=Q6, R$^{12}$=H, R$^{14}$=Et, R$^{16}$=H], [1495; Y=Q6, R$^{12}$=Et, R$^{14}$=Et, R$^{16}$=H], [1496; Y=Q6, R$^{12}$=Et, R$^{14}$=H, R$^{16}$=Et], [1497; Y=Q6, R$^{12}$=Et, R$^{14}$=Et, R$^{16}$=Et], [1498; Y=Q6, R$^{12}$=Et, R$^{14}$=F, R$^{16}$=H], [1499; Y=Q6, R$^{12}$=Et, R$^{14}$=H, R$^{16}$=F], [1500; Y=Q6, R$^{12}$=F, R$^{14}$=Et, R$^{16}$=H],
[1501; Y=Q6, R$^{12}$=Et, R$^{14}$=F, R$^{16}$=F], [1502; Y=Q6, R$^{12}$=F, R$^{14}$=Et, R$^{16}$=F], [1503; Y=Q6, R$^{12}$=Et, R$^{14}$=Et, R$^{16}$=F], [1504; Y=Q6, R$^{12}$=Et, R$^{14}$=F, R$^{16}$=Et], [1505; Y=Q6, R$^{12}$=Et, R$^{14}$=Cl, R$^{16}$=H], [1506; Y=Q6, R$^{12}$=Et, R$^{14}$=H, R$^{16}$=Cl], [1507; Y=Q6, R$^{12}$=Cl, R$^{14}$=Et, R$^{16}$=H], [1508; Y=Q6, R$^{12}$=Et, R$^{14}$=Cl, R$^{16}$=Cl], [1509; Y=Q6, R$^{12}$=Cl, R$^{14}$=Et, R$^{16}$=Cl], [1510; Y=Q6, R$^{12}$=Et, R$^{14}$=Et, R$^{16}$=Cl], [1511; Y=Q6, R$^{12}$=Et, R$^{14}$=Cl, R$^{16}$=Et], [1512; Y=Q6, R$^{12}$=OMe, R$^{14}$=H, R$^{16}$=H], [1513; Y=Q6, R$^{12}$=H, R$^{14}$=OMe, R$^{16}$=H], [1514; Y=Q6, R$^{12}$=OMe, R$^{14}$=OMe, R$^{16}$=H], [1515; Y=Q6, R$^{12}$=OMe, R$^{14}$=H, R$^{16}$=OMe], [1516; Y=Q6, R$^{12}$=OMe, R$^{14}$=F, R$^{16}$=H], [1517; Y=Q6, R$^{12}$=OMe, R$^{14}$=H, R$^{16}$=F], [1518; Y=Q6, R$^{12}$=F, R$^{14}$=OMe, R$^{15}$=H], [1519; Y=Q6, R$^{12}$=OMe, R$^{14}$=F, R$^{16}$=F], [1520; Y=Q6, R$^{12}$=F, R$^{14}$=OMe, R$^{16}$=F], [1521; Y=Q6, R$^{12}$=OMe, R$^{14}$=OMe, R$^{16}$=F], [1522; Y=Q6, R$^{12}$=OMe, R$^{14}$=F, R$^{16}$=OMe], [1523; Y=Q6, R$^{12}$=OMe, R$^{14}$=Cl, R$^{16}$=H], [1524; Y=Q6, R$^{12}$=OMe, R$^{14}$=H, R$^{16}$=Cl], [1525; Y=Q6, R$^{12}$=Cl, R$^{14}$=OMe, R$^{16}$=H], [1526; Y=Q6, R$^{12}$=OMe, R$^{14}$=Cl, R$^{16}$=Cl], [1527; Y=Q6, R$^{12}$=Cl, R$^{14}$=OMe, R$^{15}$=Cl], [1528; Y=Q6, R$^{12}$=OMe, R$^{14}$=OMe, R$^{16}$=Cl], [1529; Y=Q6, R$^{12}$=OMe, R$^{15}$=Cl, R$^{16}$=OMe], [1530; Y=Q6, R$^{12}$=n-propyl, R$^{16}$=H, R$^{16}$=H], [1531; Y=Q6, R$^{12}$=H, R$^{14}$=n-propyl, R$^{16}$=H], [1532; Y=Q6, R$^{12}$=n-propyl, R$^{14}$=H, R$^{16}$=F], [1533; Y=Q6, R$^{12}$=F, R$^{14}$=n-propyl, R$^{16}$=H], [1534; Y=Q6, R$^{12}$=n-propyl, R$^{14}$=F, R$^{16}$=F], [1535; Y=Q6, R$^{12}$=F, R$^{14}$=n-propyl, R$^{16}$=F], [1536; Y=Q6, R$^{12}$=n-propyl, R$^{14}$=Cl, R$^{16}$=H], [1537; Y=Q6, R$^{12}$=n-propyl, R$^{14}$=H, R$^{16}$=Cl], [1538; Y=Q6, R$^{12}$=Cl, R$^{14}$=n-propyl, R$^{16}$=H], [1539; Y=Q6, R$^{12}$=n-propyl, R$^{14}$=Cl, R$^{16}$=Cl], [1540; Y=Q6, R$^{12}$=Cl, R$^{14}$=n-propyl, R$^{16}$=Cl], [1541; Y=Q6, R$^{12}$=SMe, R$^{14}$=H, R$^{16}$=H], [1542; Y=Q6, R$^{12}$=H, R$^{14}$=SMe, R$^{16}$=H], [1543; Y=Q6, R$^{12}$=SMe, R$^{14}$=H, R$^{16}$=F], [1544; Y=Q6, R$^{12}$=F, R$^{14}$=SMe, R$^{16}$=H], [1545; Y=Q6, R$^{12}$=SMe, R$^{14}$=F, R$^{16}$=F], [1546; Y=Q6, R$^{12}$=F, R$^{14}$=SMe, R$^{16}$=F], [1547; Y=Q6, R$^{12}$=SMe, R$^{14}$=Cl, R$^{16}$=H], [1548; Y=Q6, R$^{12}$=SMe, R$^{15}$=H, R$^{16}$=Cl], [1549; Y=Q6, R$^{12}$=Cl, R$^{14}$=SMe, R$^{16}$=H], [1550; Y=Q6, R$^{12}$=SMe, R$^{14}$=Cl, R$^{16}$=Cl], [1551; Y=Q6, R$^{12}$=Cl, R$^{14}$=SMe, R$^{16}$=Cl], [1552; Y=Q7, R$^{14}$=H, R$^{15}$=H, R$^{16}$=H], [1553; Y=Q7, R$^{14}$=Me, R$^{15}$=H, R$^{16}$=H], [1554; Y=Q7, R$^{14}$=H, R$^{15}$=Me, R$^{16}$=H], [1555; Y=Q7, R$^{14}$=Me, R$^{16}$=Me, R$^{16}$=H], [1556; Y=Q7, R$^{14}$=Me, R$^{15}$=H, R$^{16}$=Me], [1557; Y=Q7, R$^{14}$=Me, R$^{15}$=Me, R$^{16}$=Me], [1558; Y=Q7, R$^{14}$=Me, R$^{15}$=F, R$^{16}$=H], [1559; Y=Q7, R$^{14}$=Me, R$^{15}$=H, R$^{16}$=F], [1560; Y=Q7, R$^{14}$=F, R$^{14}$=Me, R$^{16}$=H], [1561; Y=Q7, R$^{14}$=Me, R$^{15}$=F, R$^{16}$=F], [1562; Y=Q7, R$^{14}$=F, R$^{15}$=Me, R$^{16}$=F], [1563; Y=Q7, R$^{14}$=Me, R$^{15}$=Me, R$^{16}$=F], [1564; Y=Q7, R$^{14}$=Me, R$^{15}$=F, R$^{16}$=Me], [1565; Y=Q7, R$^{14}$=Me, R$^{15}$=Cl, R$^{16}$=H], [1566; Y=Q7, R$^{14}$=Me, R$^{15}$=H, R$^{16}$=Cl], [1567; Y=Q7, R$^{14}$=Cl, R$^{15}$=Me, R$^{16}$=H], [1568; Y=Q7, R$^{14}$=Me, R$^{15}$=Cl, R$^{16}$=Cl], [1569; Y=Q7, R$^{14}$=Cl, R$^{15}$=Me, R$^{16}$=Cl], [1570; Y=Q7, R$^{14}$=Me, R$^{15}$=Me, R$^{16}$=Cl], [1571; Y=Q7, R$^{14}$=Me, R$^{15}$=Cl, R$^{16}$=Me], [1572; Y=Q7, R$^{14}$=Me, R$^{15}$=Br, R$^{16}$=H], [1573; Y=Q7, R$^{14}$=Me, R$^{15}$=H, R$^{16}$=Br], [1574; Y=Q7, R$^{14}$=Br, R$^{15}$=Me, R$^{16}$=H], [1575; Y=Q7, R$^{14}$=Me, R$^{15}$=Br, R$^{16}$=Br], [1576; Y=Q7, R$^{14}$=Br, R$^{15}$=Me, R$^{16}$=Br], [1577; Y=Q7, R$^{14}$=Me, R$^{15}$=Me, R$^{15}$=Br], [1578; Y=Q7, R$^{14}$=Me, R$^{15}$=Br, R$^{16}$=Me], [1579; Y=Q7, R$^{14}$=F, R$^{15}$=H, R$^{16}$=H], [1580; Y=Q7, R$^{14}$=H, R$^{15}$=F, R$^{16}$=H], [1581; Y=Q7, R$^{14}$=F, R$^{15}$=F, R$^{16}$=H], [1582; Y=Q7, R$^{14}$=F, R$^{15}$=H, R$^{16}$=F], [1583; Y=Q7, R$^{14}$=F, R$^{15}$=F, R$^{16}$=F], [1584; Y=Q7, R$^{14}$=F, R$^{15}$=Cl, R$^{16}$=H], [1585; Y=Q7, R$^{14}$=F, R$^{15}$=H, R$^{16}$=Cl], [1586; Y=Q7, R$^{14}$=Cl, R$^{15}$=F, R$^{16}$=H], [1587; Y=Q7, R$^{14}$=F, R$^{15}$=Cl, R$^{16}$=Cl], [1588; Y=Q7, R$^{14}$=Cl, R$^{15}$=F, R$^{16}$=Cl], [1589; Y=Q7, R$^{14}$=F, R$^{15}$=F, R$^{16}$=Cl], [1590; Y=Q7, R$^{14}$=F, R$^{15}$=Cl, R$^{16}$=F], [1591; Y=Q7, R$^{14}$=Et, R$^{15}$=H, R$^{16}$=H], [1592; Y=Q7, R$^{14}$=H, R$^{15}$=Et, R$^{16}$=H], [1593; Y=Q7, R$^{14}$=Et, R$^{15}$=Et, R$^{16}$=H], [1594; Y=Q7, R$^{14}$=Et, R$^{15}$=H, R$^{16}$=Et], [1595; Y=Q7, R$^{14}$=Et, R$^{15}$=Et, R$^{16}$=Et], [1596; Y=Q7, R$^{14}$=Et, R$^{15}$=F, R$^{16}$=H], [1597; Y=Q7, R$^{14}$=Et, R$^{15}$=H, R$^{16}$=F], [1598; Y=Q7, R$^{14}$=F, R$^{15}$=Et, $R^{16}$=H], [1599; Y=Q7, $R^{14}$=Et, $R^{15}$=F, $R^{16}$=F], [1600; Y=Q7, $R^{14}$=F, $R^{15}$=Et, $R^{16}$=F],
[1601; Y=Q7, $R^{14}$=Et, $R^{15}$=Et, $R^{16}$=F], [1602; Y=Q7, $R^{14}$=Et, $R^{15}$=F, $R^{16}$=Et], [1603; Y=Q7, $R^{14}$=Et, $R^{15}$=Cl, $R^{16}$=H], [1604; Y=Q7, $R^{14}$=Et, $R^{15}$=H, $R^{16}$=Cl], [1605; Y=Q7, $R^{14}$=Cl, $R^{15}$=Et, $R^{16}$=H], [1606; Y=Q7, $R^{14}$=Et, $R^{15}$=Cl, $R^{16}$=Cl], [1607; Y=Q7, $R^{14}$=Cl, $R^{15}$=Et, $R^{16}$=Cl], [1608; Y=Q7, $R^{14}$=Et, $R^{15}$=Et, $R^{16}$=Cl], [1609; Y=Q7, $R^{14}$=Et, $R^{15}$=Cl, $R^{16}$=Et], [1610; Y=Q7, $R^{14}$=OMe, $R^{15}$=H, $R^{16}$=H], [1611; Y=Q7, $R^{14}$=H, $R^{15}$=OMe, $R^{16}$=H], [1612; Y=Q7, $R^{14}$=OMe, $R^{15}$=OMe, $R^{16}$=H], [1613; Y=Q7, $R^{14}$=OMe, $R^{15}$=H, $R^{16}$=OMe], [1614; Y=Q7, $R^{14}$=OMe, $R^{15}$=F, $R^{16}$=H], [1615; Y=Q7, $R^{14}$=OMe, $R^{15}$=H, $R^{16}$=F], [1616; Y=Q7, $R^{14}$=F, $R^{15}$=OMe, $R^{16}$=H], [1617; Y=Q7, $R^{14}$=OMe, $R^{15}$=F, $R^{16}$=F], [1618; Y=Q7, $R^{14}$=F, $R^{15}$=OMe, $R^{16}$=F], [1619; Y=Q7, $R^{14}$=OMe, $R^{15}$=OMe, $R^{16}$=F], [1620; Y=Q7, $R^{14}$=OMe, $R^{15}$=F, $R^{16}$=OMe], [1621; Y=Q7, $R^{14}$=OMe, $R^{15}$=Cl, $R^{16}$=H], [1622; Y=Q7, $R^{14}$=OMe, $R^{15}$=H, $R^{15}$=Cl], [1623; Y=Q7, $R^{14}$=Cl, $R^{15}$=OMe, $R^{16}$=H], [1624; Y=Q7, $R^{14}$=OMe, $R^{15}$=Cl, $R^{16}$=Cl], [1625; Y=Q7, $R^{14}$=Cl, $R^{15}$=OMe, $R^{16}$=Cl], [1626; Y=Q7, $R^{14}$=OMe, $R^{15}$=OMe, $R^{16}$=Cl], [1627; Y=Q7, $R^{14}$=OMe, $R^{15}$=Cl, $R^{16}$=OMe], [1628; Y=Q7, $R^{14}$=n-propyl, $R^{15}$=H, $R^{16}$=H], [1629; Y=Q7, $R^{14}$=n-propyl, $R^{16}$=H], [1630; Y=Q7, $R^{14}$=n-propyl, $R^{15}$=H, $R^{16}$=F], [1631; Y=Q7, $R^{14}$=F, $R^{15}$=n-propyl, $R^{16}$=H], [1632; Y=Q7, $R^{14}$=n-propyl, $R^{15}$=F, $R^{16}$=F], [1633; Y=Q7, $R^{14}$=F, $R^{15}$=n-propyl, $R^{16}$=F], [1634; Y=Q7, $R^{14}$=n-propyl, $R^{15}$=Cl, $R^{16}$=H], [1635; Y=Q7, $R^{14}$=n-propyl, $R^{15}$=H, $R^{16}$=Cl], [1636; Y=Q7, $R^{14}$=Cl, $R^{15}$=n-propyl, $R^{16}$=H], [1637; Y=Q7, $R^{14}$=n-propyl, $R^{15}$=Cl, $R^{16}$=Cl], [1638; Y=Q7, $R^{14}$=Cl, $R^{15}$=n-propyl, $R^{16}$=Cl], [1639; Y=Q7, $R^{14}$=SMe, $R^{15}$=H, $R^{16}$=H], [1640; Y=Q7, $R^{14}$=H, $R^{15}$=SMe, $R^{16}$=H], [1641; Y=Q7, $R^{14}$=SMe, $R^{15}$=H, $R^{16}$=F], [1642; Y=Q7, $R^{14}$=F, $R^{15}$=SMe, $R^{16}$=H], [1643; Y=Q7, $R^{14}$=SMe, $R^{15}$=F, $R^{16}$=F], [1644; Y=Q7, $R^{14}$=F, $R^{15}$=SMe, $R^{16}$=F], [1645; Y=Q7, $R^{14}$=SMe, $R^{15}$=Cl, $R^{16}$=H], [1646; Y=Q7, $R^{14}$=SMe, $R^{15}$=H, $R^{16}$=Cl], [1647; Y=Q7, $R^{14}$=Cl, $R^{15}$=SMe, $R^{16}$=H], [1648; Y=Q7, $R^{14}$=SMe, $R^{15}$=Cl, $R^{16}$=Cl], [1649; Y=Q7, $R^{14}$=Cl, $R^{15}$=SMe, $R^{16}$=Cl], [1650; Y=Q7, $R^{14}$=OEt, $R^{15}$=H, $R^{16}$=H], [1651; Y=Q7, $R^{14}$=propargyloxy, $R^{15}$=H, $R^{16}$=H], [1652; Y=Q8, $R^{12}$=H, $R^{15}$=H, $R^{16}$=H], [1653; Y=Q8, $R^{12}$=Me, $R^{15}$=H, $R^{16}$=H], [1654; Y=Q8, $R^{12}$=H, $R^{15}$=Me, $R^{16}$=H], [1655; Y=Q8, $R^{12}$=H, $R^{15}$=H, $R^{16}$=Me], [1656; Y=Q8, $R^{12}$=Cl, $R^{15}$=H, $R^{16}$=H], [1657; Y=Q8, $R^{12}$=H, $R^{15}$=Cl, $R^{16}$=H], [1658; Y=Q8, $R^{12}$=H, $R^{15}$=H, $R^{16}$=Cl], [1659; Y=Q8, $R^{12}$=F, $R^{15}$=H, $R^{16}$=H], [1660; Y=Q8, $R^{12}$=H, $R^{15}$=F, $R^{16}$=H], [1661; Y=Q8, $R^{12}$=H, $R^{15}$=H, $R^{16}$=F], [1662; Y=Q8, $R^{12}$=OMe, $R^{15}$=H, $R^{16}$=H], [1663; Y=Q8, $R^{12}$=H, $R^{15}$=OMe, $R^{16}$=H], [1664; Y=Q8, $R^{12}$=H, $R^{15}$=H, $R^{16}$=OMe], [1665; Y=Q8, $R^{12}$=Et, $R^{15}$=H, $R^{16}$=H], [1666; Y=Q8, $R^{12}$=H, $R^{15}$=Et, $R^{16}$=H], [1667; Y=Q8, $R^{12}$=H, $R^{15}$=H, $R^{16}$=Et], [1668; Y=Q8, $R^{12}$=Ph, $R^{15}$=H, $R^{16}$=H], [1669; Y=Q8, $R^{12}$=H, $R^{15}$=Ph, $R^{16}$=H], [1670; Y=Q8, $R^{12}$=H, $R^{15}$=H, $R^{16}$=Ph], [1671; Y=Q8, $R^{12}$=NHCOCH$_3$, $R^{15}$=H, $R^{16}$=H], [1672; Y=Q8, $R^{12}$=H, $R^{15}$=NHCOCH$_3$, $R^{16}$=H], [1673; Y=Q8, $R^{12}$=H, $R^{15}$=H, $R^{16}$=NHCOCH$_3$], [1674; Y=Q9, $R^{12}$=H, $R^{13}$=H, $R^{16}$=H], [1675; Y=Q9, $R^{12}$=Me, $R^{15}$=H, $R^{16}$=H], [1676; Y=Q9, $R^{12}$=H, $R^{13}$=Me, $R^{16}$=H], [1677; Y=Q9, $R^{13}$=H, $R^{16}$=Me], [1678; Y=Q9, $R^{12}$=Cl, $R^{13}$=H, $R^{16}$=H], [1679; Y=Q9, $R^{12}$=H, $R^{13}$=Cl, $R^{16}$=H], [1680; Y=Q9, $R^{12}$=H, $R^{13}$=H, $R^{16}$=Cl], [1681; Y=Q9, $R^{12}$=F, $R^{13}$=H, $R^{16}$=H], [1682; Y=Q9, $R^{12}$=H, $R^{13}$=F, $R^{16}$=H], [1683; Y=Q9, $R^{12}$=H, $R^{13}$=H, $R^{16}$=F], [1684; Y=Q9, $R^{12}$=OMe, $R^{13}$=H, $R^{16}$=H], [1685; Y=Q9, $R^{12}$=H, $R^{15}$=OMe, $R^{16}$=H], [1686; Y=Q9, $R^{12}$=H, $R^{15}$=H, $R^{16}$=OMe], [1687; Y=Q9, $R^{12}$=Et, $R^{13}$=H, $R^{16}$=H], [1688; Y=Q9, $R^{12}$=H, $R^{13}$=Et, $R^{16}$=H], [1689; Y=Q9, $R^{12}$=H, $R^{13}$=H, $R^{16}$=Et], [1690; Y=Q9, $R^{12}$=Ph, $R^{15}$=H, $R^{16}$=H], [1691; Y=Q9, $R^{12}$=H, $R^{13}$=Ph, $R^{16}$=H], [1692; Y=Q9, $R^{12}$=H, $R^{13}$=H, $R^{16}$=Ph], [1693; Y=Q9, $R^{12}$=SPh, $R^{13}$=H, $R^{16}$=H], [1694; Y=Q9, $R^{12}$=H, $R^{13}$=SPh, $R^{16}$=H], [1695; Y=Q9, $R^{12}$=H, $R^{13}$=H, $R^{16}$=SPh], [1696; Y=Q10, $R^{13}$=H, $R^{14}$=H, $R^{16}$=H], [1697; Y=Q10, $R^{13}$=Me, $R^{14}$=H, $R^{16}$=H], [1698; Y=Q10, $R^{13}$=H, $R^{14}$=Me, $R^{16}$=H], [1699; Y=Q10, $R^{13}$=H, $R^{14}$=H, $R^{16}$=Me], [1700; Y=Q10, $R^{13}$=Cl, $R^{14}$=H, $R^{16}$=H],
[1701; Y=Q10, $R^{13}$=H, $R^{14}$=Cl, $R^{16}$=H], [1702; Y=Q10, $R^{13}$=H, $R^{14}$=H, $R^{16}$=Cl], [1703; Y=Q10, $R^{13}$=F, $R^{14}$=H, $R^{16}$=H], [1704; Y=Q10, $R^{13}$=H, $R^{14}$=F, $R^{16}$=H], [1705; Y=Q10, $R^{13}$=H, $R^{14}$=H, $R^{16}$=F], [1706; Y=Q10, $R^{12}$=OMe, $R^{14}$=H, $R^{16}$=H], [1707; Y=Q10, $R^{13}$=H, $R^{14}$=OMe, $R^{16}$=H], [1708; Y=Q10, $R^{13}$=H, $R^{14}$=H, $R^{16}$=OMe], [1709; Y=Q10, $R^{13}$=Et, $R^{14}$=H, $R^{16}$=H], [1710; Y=Q10, $R^{13}$=H, $R^{14}$=Et, $R^{16}$=H], [1711; Y=Q10, $R^{13}$=H, $R^{14}$=H, $R^{16}$=Et], [1712; Y=Q10, $R^{13}$=Ph, $R^{14}$=H, $R^{16}$=H], [1713; Y=Q10, $R^{13}$=H, $R^{15}$=Ph, $R^{16}$=H], [1714; Y=Q10, $R^{13}$=H, $R^{14}$=H, $R^{16}$=Ph], [1715; Y=Q10, $R^{13}$=benzyl, $R^{14}$=H, $R^{16}$=H], [1716; Y=Q10, $R^{13}$=H, $R^{14}$=benzyl, $R^{16}$=H], [1717; Y=Q10, $R^{13}$=H, $R^{14}$=H, $R^{16}$=benzyl], [1718; Y=Q11, $R^{13}$=H, $R^{15}$=H], [1719; Y=Q11, $R^{13}$=Me, $R^{15}$=H], [1720; Y=Q11, $R^{13}$=H, $R^{16}$=Me], [1721; Y=Q11, $R^{13}$=Cl, $R^{15}$=H], [1722; Y=Q11, $R^{13}$=H, $R^{15}$=Cl], [1723; Y=Q11, $R^{13}$=F, $R^{15}$=H], [1724; Y=Q11, $R^{13}$=H, $R^{15}$=F], [1725; Y=Q11, $R^{13}$=OMe, $R^{15}$=H], [1726; Y=Q11, $R^{13}$=H, $R^{15}$=OMe], [1727; Y=Q11, $R^{14}$=Et, $R^{15}$=H], [1728; Y=Q11, $R^{13}$=H, $R^{15}$=Et], [1729; Y=Q11, $R^{13}$=Ph, $R^{15}$=H], [1730; Y=Q11, $R^{13}$=H, $R^{15}$=Ph], [1731; Y=Q12, $R^{12}$=H, $R^{13}$=H], [1732; Y=Q12, $R^{12}$=Me, $R^{13}$=H], [1733; Y=Q12, $R^{12}$=H, $R^{13}$=Me], [1734; Y=Q12, $R^{12}$=Cl, $R^{13}$=H], [1735; Y=Q12, $R^{12}$=H, $R^{13}$=Cl], [1736; Y=Q12, $R^{12}$=F, $R^{16}$=H], [1737; Y=Q12, $R^{15}$=H, $R^{16}$=F], [1738; Y=Q12, $R^{12}$=OMe, $R^{16}$=H], [1739; Y=Q12, $R^{12}$=H, $R^{16}$=OMe], [1740; Y=Q12, $R^{12}$=Et, $R^{16}$=H], [1741; Y=Q12, $R^{12}$=H, $R^{13}$=Et], [1742; Y=Q12, $R^{12}$=Ph, $R^{16}$=H], [1743; Y=Q12, $R^{12}$=H, $R^{16}$=Ph], [1744; Y=Q13, $R^{12}$=H, $R^{16}$=H], [1745; Y=Q13, $R^{12}$=Me, $R^{16}$=H], [1746; Y=Q13, $R^{12}$=H, $R^{16}$=Me], [1747; Y=Q13, $R^{12}$=Cl, $R^{16}$=H], [1748; Y=Q13, $R^{12}$=H, $R^{16}$=Cl], [1749; Y=Q13, $R^{12}$=F, $R^{16}$=H], [1750; Y=Q13, $R^{15}$=H, $R^{16}$=F], [1751; Y=Q13, $R^{12}$=OMe, $R^{16}$=H], [1752; Y=Q13, $R^{12}$=H, $R^{16}$=OMe], [1753; Y=Q13, $R^{12}$=Et, $R^{16}$=H], [1754; Y=Q13, $R^{12}$=H, $R^{16}$=Et], [1755; Y=Q13, $R^{12}$=Ph, $R^{16}$=H], [1756; Y=Q13, $R^{12}$=H, $R^{16}$=Ph], [1757; Y=Q14, $R^{13}$=H, $R^{14}$=H], [1758; Y=Q14, $R^{12}$=Me, $R^{14}$=H], [1759; Y=Q14, $R^{12}$=H, $R^{14}$=Me], [1760; Y=Q14, $R^{12}$=Cl, $R^{14}$=H], [1761; Y=Q14, $R^{12}$=H, $R^{14}$=Cl], [1762; Y=Q14, $R^{12}$=F, $R^{14}$=H], [1763; Y=Q14, $R^{12}$=H, $R^{14}$=F], [1764; Y=Q14, $R^{12}$=OMe, $R^{16}$=H], [1765; Y=Q14, $R^{12}$=H, $R^{16}$=OMe], [1766; Y=Q14, $R^{12}$=Et, $R^{16}$=H], [1767; Y=Q14, $R^{15}$=H, $R^{16}$=Et], [1768; Y=Q14, $R^{12}$=Ph, $R^{14}$=H], [1769; Y=Q14, $R^{13}$=H, $R^{14}$=Ph], [1770; Y=Q15, $R^{13}$=H, $R^{16}$=H], [1771; Y=Q15, $R^{13}$=Me, $R^{16}$=H], [1772; Y=Q15, $R^{13}$=H, $R^{16}$=Me], [1773; Y=Q15, $R^{13}$=Cl, $R^{16}$=H], [1774; Y=Q15, $R^{13}$=H, $R^{16}$=Cl], [1775; Y=Q15, $R^{13}$=F, $R^{16}$=H], [1776; Y=Q15, $R^{13}$=H, $R^{16}$=F], [1777; Y=Q15, $R^{13}$=OMe, $R^{16}$=H], [1778; Y=Q15, $R^{13}$=H, $R^{14}$=OMe],

[1779; Y=Q15, R$^{13}$=Et, R$^{16}$=H], [1780; Y=Q15, R$^{13}$=H, R$^{16}$=Et], [1781; Y=Q15, R$^{13}$=Ph, R$^{16}$=H], [1782; Y=Q15, R$^{13}$=H, R$^{16}$=Ph], [1783; Y=Q16, R$^{13}$=H, R$^{14}$=H], [1784; Y=Q16, R$^{13}$=Me, R$^{14}$=H], [1785; Y=Q16, R$^{13}$=H, R$^{14}$=Me], [1786; Y=Q16, R$^{13}$=Cl, R$^{14}$=H], [1787; Y=Q16, R$^{13}$=H, R$^{14}$=Cl], [1788; Y=Q16, R$^{13}$=F, R$^{14}$=H], [1789; Y=Q16, R$^{15}$=H, R$^{16}$=F], [1790; Y=Q16, R$^{12}$=OMe, R$^{16}$=H], [1791; Y=Q16, R$^{13}$=H, R$^{16}$=OMe], [1792; Y=Q16, R$^{13}$=Et, R$^{14}$=H], [1793; Y=Q16, R$^{13}$=H, R$^{16}$=Et], [1794; Y=Q16, R$^{13}$=Ph, R$^{14}$=H], [1795; Y=Q16, R$^{13}$=H, R$^{16}$=Ph], [1796; Y=Q7, R$^{14}$=Cl, R$^{15}$=H, R$^{16}$=H], [1797; Y=Q7, R$^{14}$=H, R$^{15}$=Cl, R$^{16}$=H], and [1798; Y=Q7, R$^{14}$=H, R$^{15}$=H, R$^{16}$=Cl].

In accordance with the process mentioned above, it is possible to obtain the present compounds RAAA1-1 to RAAF5-126.

The present compounds RAAA1-1 to RAAF5-126 are the present compounds represented by formulas:

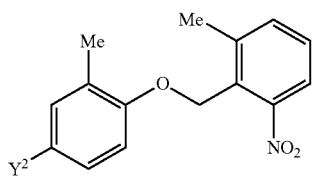
(RAAA1)

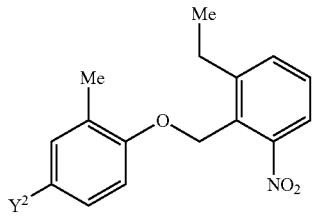
(RAAB1)

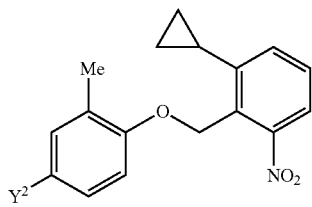
(RAAC1)

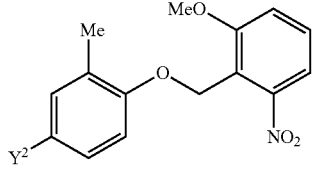
(RAAD1)

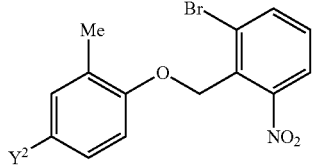
(RAAE1)

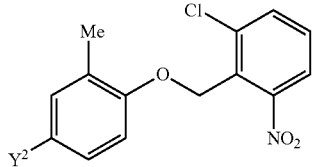
(RAAF1)

-continued

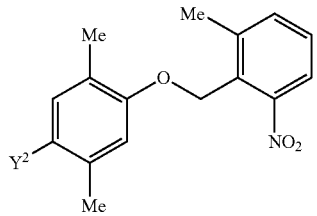
(RAAA2)

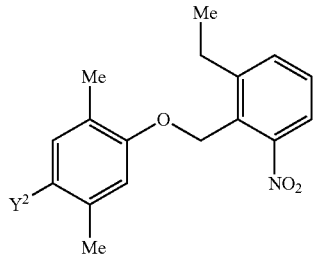
(RAAB2)

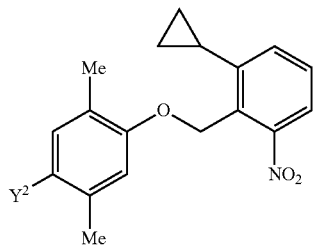
(RAAC2)

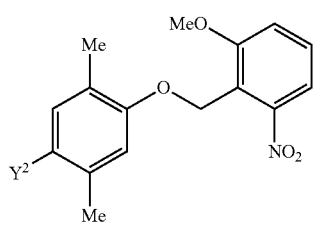
(RAAD2)

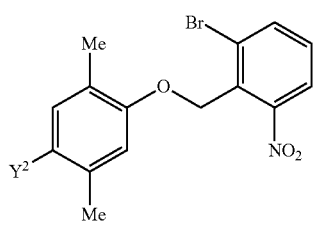
(RAAE2)

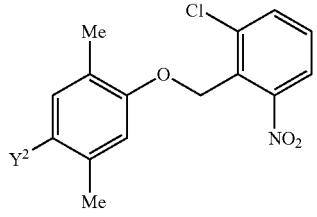
(RAAF2)

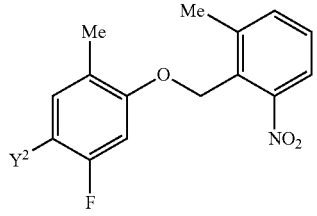
(RAAA3)

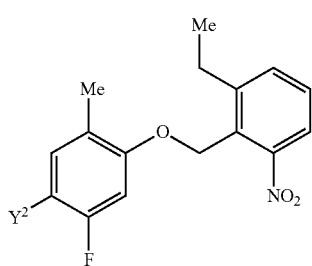 (RAAB3)
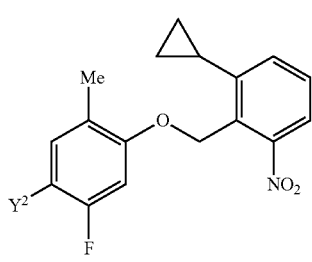 (RAAC3)
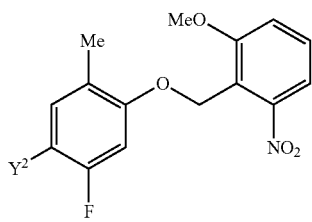 (RAAD3)
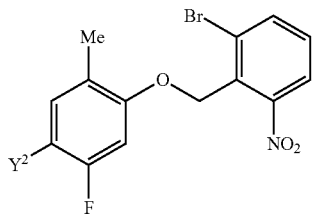 (RAAE3)
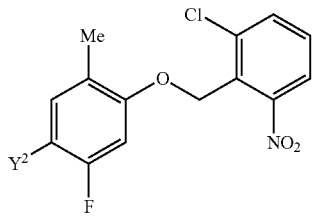 (RAAF3)
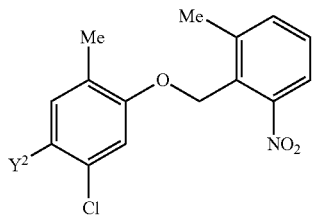 (RAAA4)
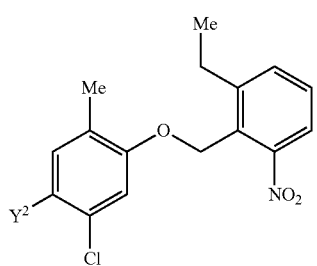 (RAAB4)
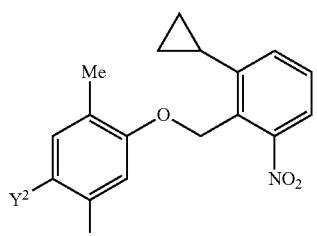 (RAAC4)
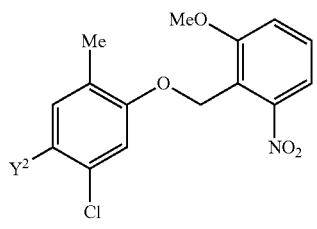 (RAAD4)
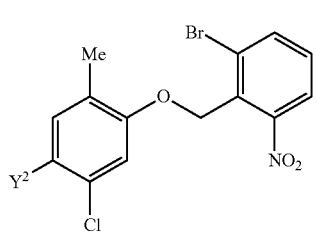 (RAAE4)
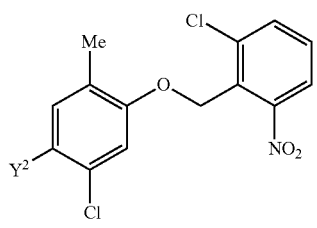 (RAAF4)
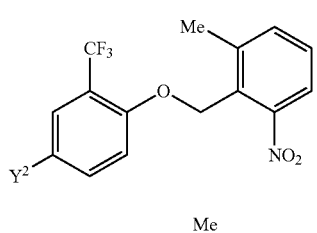 (RAAA5)
(RAAB5)

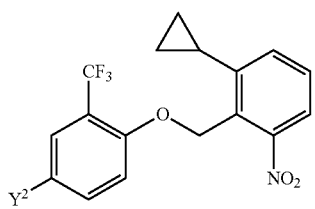
(RAAC5)

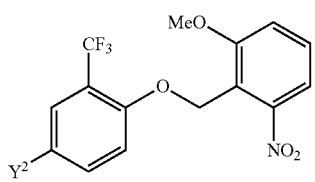
(RAAD5)

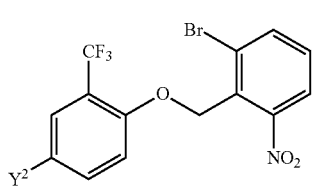
(RAAE5)

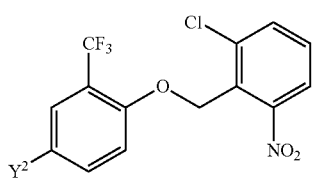
(RAAF5)

wherein $Y^2$ is a substituent corresponding to each of the above substituent numbers 1 to 126.

For example, the present compound RAAA1-1 represents the present compound represented by formula (RAAA1) in which $Y^2$ is substituent number 1, and is represented by the following formula:

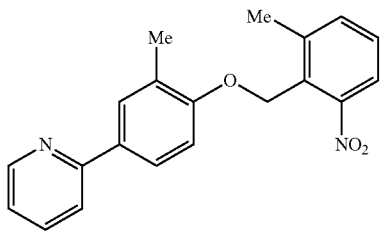
(RAAA1-1)

substituent number; $Y^2$

[1; $Y^2=Q^1$, $R^{13}$=H, $R^{14}$=H, $R^{15}$=H, $R^{16}$=H], [2; $Y^2=Q^1$, $R^{13}$=Me, $R^{14}$=H, $R^{15}$=H, $R^{16}$=H], [3; $Y^2=Q^1$, $R^{13}$=H, $R^{14}$=Me, $R^{15}$=H, $R^{16}$=H], [4; $Y^2=Q^1$, $R^{13}$=H, $R^{14}$=H, $R^{15}$=Me, $R^{16}$=H], [5; $Y^2=Q^1$, $R^{13}$=H, $R^{14}$=H, $R^{15}$=H, $R^{16}$=Me], [6; $Y^2=Q^1$, $R^{13}$=Et, $R^{14}$=H, $R^{15}$=H, $R^{16}$=H], [7; $Y^2=Q^1$, $R^{13}$=H, $R^{14}$=Et, $R^{15}$=H, $R^{16}$=H], [8; $Y^2=Q^1$, $R^{13}$=H, $R^{14}$=H, $R^{15}$=Et, $R^{16}$=H], [9; $Y^2=Q^1$, $R^{13}$=H, $R^{14}$=H, $R^{15}$=H, $R^{16}$=Et], [10; $Y^2=Q^1$, $R^{13}$=cPr, $R^{14}$=H, $R^{15}$=H, $R^{16}$=H], [11; $Y^2=Q^1$, $R^{13}$=H, $R^{14}$=cPr, $R^{15}$=H, $R^{16}$=H], [12; $Y^2=Q^1$, $R^{13}$=H, $R^{14}$=H, $R^{15}$=cPr, $R^{16}$=H], [13; $Y^2=Q^1$, $R^{13}$=H, $R^{14}$=H, $R^{15}$=H, $R^{16}$=cPr], [14; $Y^2=Q^1$, $R^{13}$=CN, $R^{14}$=H, $R^{15}$=H, $R^{16}$=H], [15; $Y^2=Q^1$, $R^{13}$=H, $R^{14}$=CN, $R^{15}$=H, $R^{16}$=H], [16; $Y^2=Q^1$, $R^{13}$=H, $R^{14}$=H, $R^{15}$=CN, $R^{16}$=H], [17; $Y^2=Q^1$, $R^{13}$=H, $R^{14}$=H, $R^{15}$=H, $R^{16}$=CN], [18; $Y^2=Q^1$, $R^{13}$=OMe, $R^{14}$=H, $R^{15}$=H, $R^{16}$=H], [19; $Y^2=Q1$, $R^{13}$=H, $R^{14}$=OMe, $R^{15}$=H, $R^{16}$=H], [20; $Y^2=Q^1$, $R^{13}$=H, $R^{14}$=H, $R^{15}$H, $R^{16}$=OMe, $R^{16}$=H], [21; $Y^2=Q^1$, $R^{13}$=H, $R^{14}$=H, $R^{15}$=H, $R^{16}$=OMe], [22; $Y^2=Q^1$, $R^{13}$=F, $R^{14}$=H, $R^{15}$=H, $R^{16}$=H], [23; $Y^2=Q^1$, $R^{13}$=H, $R^{14}$=F, $R^{15}$=H, $R^{16}$=H], [24; $Y^2=Q^1$, $R^{13}$=H, $R^{14}$=H, $R^{15}$=F, $R^{16}$=H], [25; $Y^2=Q^1$, $R^{13}$=H, $R^{14}$=H, $R^{15}$=H, $R^{16}$=F], [26; $Y^2=Q^1$, $R^{13}$=Cl, $R^{14}$=H, $R^{15}$=H, $R^{16}$=H], [27; $Y^2=Q^1$, $R^{13}$=H, $R^{14}$=Cl, $R^{15}$=H, $R^{16}$=H], [28; $Y^2=Q^1$, $R^{13}$=H, $R^{14}$=H, $R^{15}$=Cl, $R^{16}$=H], [29; $Y^2=Q^1$, $R^{13}$=H, $R^{14}$=H, $R^{15}$=H, $R^{16}$=Cl], [30; $Y^2=Q^1$, $R^{13}$=Me, $R^{14}$=Me, $R^{15}$=H, $R^{16}$=H], [31; $Y^2=Q^1$, $R^{13}$=Me, $R^{14}$=H, $R^{15}$=Me, $R^{16}$=H], [32; $Y^2=Q^1$, $R^{13}$=Me, $R^{14}$=H, $R^{15}$=H, $R^{16}$=Me], [33; $Y^2=Q^1$, $R^{13}$=Me, $R^{14}$=F, $R^{15}$=H, $R^{16}$=H], [34; $Y^2=Q^1$, $R^{13}$=Me, $R^{14}$=H, $R^{15}$=F, $R^{16}$=H], [35; $Y^2=Q^1$, $R^{13}$=Me, $R^{14}$=H, $R^{15}$=H, $R^{16}$=F], [36; $Y^2=Q^1$, $R^{13}$=Me, $R^{14}$=Cl, $R^{15}$=H, $R^{16}$=H], [37; $Y^2=Q^1$, $R^{13}$=Me, $R^{14}$=H, $R^{15}$=Cl, $R^{16}$=H], [38; $Y^2=Q^1$, $R^{13}$=Me, $R^{14}$=H, $R^{15}$=H, $R^{16}$=Cl], [39; $Y^2=Q^1$, $R^{13}$=H, $R^{14}$=Me, $R^{15}$=F, $R^{16}$=H], [40; $Y^2=Q^1$, $R^{13}$=H, $R^{14}$=Me, $R^{15}$=H, $R^{16}$=F], [41; $Y^2=Q^1$, $R^{13}$=H, $R^{14}$=Me, $R^{15}$=Cl, $R^{16}$=H], [42; $Y^2=Q^1$, $R^{13}$=H, $R^{14}$=Me, $R^{15}$=H, $R^{16}$=Cl], [43; $Y^2=Q^1$, $R^{13}$=Et, $R^{14}$=F, $R^{15}$=H, $R^{16}$=H], [44; $Y^2=Q^1$, $R^{13}$=Et, $R^{14}$=H, $R^{15}$=F, $R^{16}$=H], [45; $Y^2=Q^1$, $R^{13}$=Et, $R^{14}$=H, $R^{15}$=H, $R^{16}$=F], [46; $Y^2=Q^1$, $R^{13}$=H, $R^{14}$=Et, $R^{15}$=F, $R^{16}$=H], [47; $Y^2=Q^1$, $R^{13}$=H, $R^{14}$=Et, $R^{15}$=H, $R^{16}$=F], [48; $Y^2=Q^1$, $R^{13}$=F, $R^{14}$=Me, $R^{15}$=H, $R^{16}$=H], [49; $Y^2=Q^1$, $R^{13}$=F, $R^{14}$=H, $R^{15}$=Me, $R^{16}$=H], [50; $Y^2=Q^1$, $R^{13}$=F, $R^{14}$=H, $R^{15}$=H, $R^{16}$=Me], [51; $Y^2=Q^1$, $R^{13}$=F, $R^{14}$=Et, $R^{15}$=H, $R^{16}$=H], [52; $Y^2=Q^1$, $R^{13}$=F, $R^{14}$=H, $R^{15}$=Et, $R^{16}$=H], [53; $Y^2=Q^1$, $R^{13}$=F, $R^{14}$=H, $R^{15}$=H, $R^{16}$=Et], [54; $Y^2=Q^1$, $R^{13}$=F, $R^{14}$=Cl, $R^{15}$=H, $R^{16}$=H], [55; $Y^2=Q^1$, $R^{13}$=F, $R^{14}$=H, $R^{15}$=Cl, $R^{16}$=H], [56; $Y^2=Q^1$, $R^{13}$=F, $R^{14}$=H, $R^{15}$=H, $R^{16}$=Cl], [57; $Y^2=Q^1$, $R^{13}$=H, $R^{14}$=F, $R^{15}$=F, $R^{16}$=H], [58; $Y^2=Q^1$, $R^{13}$=H, $R^{14}$=F, $R^{15}$=H, $R^{16}$=F], [59; $Y^2=Q^1$, $R^{13}$=H, $R^{14}$=F, $R^{15}$=Cl, $R^{16}$=H], [60; $Y^2=Q^1$, $R^{13}$=H, $R^{14}$=F, $R^{15}$=H, $R^{16}$=Cl], [61; $Y^2=Q^1$, $R^{13}$=H, $R^{14}$=F, $R^{15}$=Me, $R^{16}$=H], [62; $Y^2=Q^1$, $R^{13}$=H, $R^{14}$=F, $R^{15}$=H, $R^{16}$=Me], [63; $Y^2=Q^1$, $R^{13}$=Cl, $R^{14}$=Me, $R^{15}$=H, $R^{16}$=H], [64; $Y^2=Q^1$, $R^{13}$=Cl, $R^{14}$=H, $R^{15}$=Me, $R^{16}$=H], [65; $Y^2=Q^1$, $R^{13}$=Cl, $R^{14}$=H, $R^{15}$=H, $R^{16}$=Me], [66; $Y^2=Q^1$, $R^{13}$=Cl, $R^{14}$=Et, $R^{15}$=H, $R^{16}$=H], [67; $Y^2=Q^1$, $R^{13}$=Cl, $R^{14}$=H, $R^{15}$=Et, $R^{16}$=H], [68; $Y^2=Q^1$, $R^{13}$=Cl, $R^{14}$=H, $R^{15}$=H, $R^{16}$=Et], [69; $Y^2=Q^1$, $R^{13}$=Cl, $R^{14}$=Cl, $R^{15}$=H, $R^{16}$=H], [70; $Y^2=Q^1$, $R^{13}$=Cl, $R^{14}$=H, $R^{15}$=Cl, $R^{16}$=H], [71; $Y^2=Q^1$, $R^{13}$=Cl, $R^{14}$=H, $R^{15}$=H, $R^{16}$=Cl], [72; $Y^2=Q^1$, $R^{13}$=H, $R^{14}$=Cl, $R^{15}$=F, $R^{16}$=H], [73; $Y^2=Q^1$, $R^{13}$=H, $R^{14}$=Cl, $R^{15}$=H, $R^{16}$=F], [74; $Y^2=Q^1$, $R^{13}$=H, $R^{14}$=Cl, $R^{15}$=Cl, $R^{16}$=H], [75; $Y^2=Q^1$, $R^{13}$=H, $R^{14}$=Cl, $R^{15}$=H, $R^{16}$=Cl], [76; $Y^2=Q^1$, $R^{13}$=H, $R^{14}$=Cl, $R^{15}$=Me, $R^{16}$=H], [77; $Y^2=Q^1$, $R^{13}$=H, $R^{14}$=Cl, $R^{15}$=H, $R^{16}$=Me], [78; $Y^2=Q^1$, $R^{13}$=CN, $R^{14}$=Me, $R^{15}$=H, $R^{16}$=H], [79; $Y^2=Q^1$, $R^{13}$=CN, $R^{14}$=H, $R^{15}$=Me, $R^{16}$=H], [80; $Y^2=Q^1$, $R^{13}$=CN, $R^{14}$=H, $R^{15}$=H, $R^{16}$=Me], [81; $Y^2=Q^1$, $R^{13}$=CN, $R^{14}$=Et, $R^{15}$=H, $R^{16}$=H], [82; $Y^2=Q^1$, $R^{13}$=CN, $R^{14}$=H, $R^{15}$=Et, $R^{16}$=H], [83; $Y^2=Q^1$, $R^{13}$=CN, $R^{14}$=H, $R^{15}$=H, $R^{16}$=Et], [84; $Y^2=Q^1$, $R^{13}$=CN, $R^{14}$=Cl, $R^{15}$=H, $R^{16}$=H], [85; $Y^2=Q^1$, $R^{13}$=CN, $R^{14}$=H, $R^{15}$=Cl, $R^{16}$=H], [86; $Y^2=Q^1$, $R^{13}$=CN, $R^{14}$=H, $R^{15}$=H, $R^{16}$=Cl], [87; $Y^2=Q^1$, $R^{13}$=H, $R^{14}$=CN, $R^{15}$=F, $R^{16}$=H], [88; $Y^2=Q^1$, $R^{13}$=H, $R^{14}$=CN, $R^{15}$=H, $R^{16}$=F], [89; $Y^2=Q^1$, $R^{13}$=H, $R^{14}$=CN, $R^{15}$=Cl, $R^{16}$=H], [90; $Y^2=Q^1$, $R^{13}$=H, $R^{14}$=CN, $R^{15}$=H, $R^{16}$=Cl], [91; $Y^2=Q^1$, $R^{13}$=H, $R^{14}$=CN, $R^{15}$=Me, $R^{16}$=H], [92; $Y^2=Q^1$, $R^{13}$=H, $R^{14}$=CN, $R^{15}$=H, $R^{16}$=Me], [93; $Y^2=Q^1$, $R^{13}$=CF$_3$, $R^{14}$=H, $R^{15}$=H, $R^{16}$=H], [94; $Y^2$=$Q^1$, $R^{13}$=H, $R^{14}$=CF$_3$, $R^{15}$=H, $R^{16}$=H], [95; $Y^2$=$Q^1$, $R^{13}$=H, $R^{14}$=H, $R^{15}$=CF$_3$, $R^{16}$=H], [96; $Y^2$=$Q^1$, $R^{13}$=H, $R^{14}$=H, $R^{15}$=H, $R^{16}$=CF$_3$], [97; $Y^2$=$Q^1$, $R^{13}$=CF$_3$, $R^{14}$=Me, $R^{15}$=H, $R^{16}$=H], [98; $Y^2$=$Q^1$, $R^{13}$=CF$_3$, $R^{14}$=H, $R^{15}$=Me, $R^{16}$=H], [99; $Y^2$=$Q^1$, $R^{13}$=CF$_3$, $R^{14}$=H, $R^{15}$=H, $R^{16}$=Me], [100; $Y^2$=$Q^1$, $R^{13}$=CF$_3$, $R^{14}$=Et, $R^{15}$=H, $R^{16}$=H],
[101; $Y^2$=$Q^1$, $R^{13}$=CF$_3$, $R^{14}$=H, $R^{15}$=Et, $R^{16}$=H], [102; $Y^2$=$Q^1$, $R^{13}$=CF$_3$, $R^{14}$=H, $R^{15}$=H, $R^{16}$=Et], [103; $Y^2$=$Q^1$, $R^{13}$=CF$_3$, $R^{14}$=Cl, $R^{15}$=H, $R^{16}$=H], [104; $Y^2$=$Q^1$, $R^{13}$=CF$_3$, $R^{14}$=H, $R^{15}$=Cl, $R^{16}$=H], [105; $Y^2$=$Q^1$, $R^{13}$=CF$_3$, $R^{14}$=H, $R^{15}$=H, $R^{16}$=Cl], [106; $Y^2$=$Q^1$, $R^{13}$=H, $R^{14}$=CF$_3$, $R^{15}$=F, $R^{16}$=H], [107; $Y^2$=$Q^1$, $R^{13}$=H, $R^{14}$=CF$_3$, $R^{15}$=H, $R^{16}$=F], [108; $Y^2$=$Q^1$, $R^{13}$=H, $R^{14}$=CF$_3$, $R^{15}$=Cl, $R^{16}$=H], [109; $Y^2$=$Q^1$, $R^{13}$=H, $R^{14}$=CF$_3$, $R^{15}$=H, $R^{16}$=Cl], [110; $Y^2$=$Q^1$, $R^{13}$=H, $R^{14}$=CF$_3$, $R^{15}$=Me, $R^{16}$=H], [111; $Y^2$=$Q^1$, $R^{13}$=H, $R^{14}$=CF$_3$, $R^{15}$=H, $R^{16}$=Me], [112; $Y^2$=$Q^1$, $R^{13}$=OMe, $R^{14}$=Me, $R^{15}$=H, $R^{16}$=H], [113; $Y^2$=$Q^1$, $R^{13}$=OMe, $R^{14}$=H, $R^{15}$=Me, $R^{16}$=H], [114; $Y^2$=$Q^1$, $R^{13}$=OMe, $R^{14}$=H, $R^{15}$=H, $R^{16}$=Me], [115; $Y^2$=$Q^1$, $R^{13}$=OMe, $R^{14}$=Et, $R^{15}$=H, $R^{16}$=H], [116; $Y^2$=$Q^1$, $R^{13}$=OMe, $R^{14}$=H, $R^{15}$=Et, $R^{16}$=H], [117; $Y^2$=$Q^1$, $R^{13}$=OMe, $R^{14}$=H, $R^{15}$=H, $R^{16}$=Et], [118; $Y^2$=$Q^1$, $R^{13}$=OMe, $R^{14}$=Cl, $R^{15}$=H, $R^{16}$=H], [119; $Y^2$=$Q^1$, $R^{13}$=OMe, $R^{14}$=H, $R^{15}$=Cl, $R^{16}$=H], [120; $Y^2$=$Q^1$, $R^{13}$=OMe, $R^{14}$=H, $R^{15}$=H, $R^{16}$=Cl], [121; $Y^2$=$Q^1$, $R^{13}$=H, $R^{14}$=OMe, $R^{15}$=F, $R^{16}$=H], [122; $Y^2$=$Q^1$, $R^{13}$=H, $R^{14}$=OMe, $R^{15}$=H, $R^{16}$=F], [123; $Y^2$=$Q^1$, $R^{13}$=H, $R^{14}$=OMe, $R^{15}$=Cl, $R^{16}$=H], [124; $Y^2$=$Q^1$, $R^{13}$=H, $R^{14}$=OMe, $R^{15}$=H, $R^{16}$=Cl], [125; $Y^2$=$Q^1$, $R^{13}$=H, $R^{14}$=OMe, $R^{15}$=Me, $R^{16}$=H], [126; $Y^2$=$Q^1$, $R^{13}$=H, $R^{14}$=OMe, $R^{15}$=H, $R^{16}$=Me].

In accordance with the process mentioned above, it is possible to obtain the present compounds RABA1-1 to RABF5-126.

The present compounds RABA1-1 to RABF5-126 are present compounds represented by the following formulas:

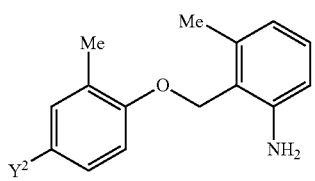
(RABA1)

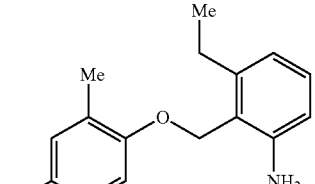
(RABB1)

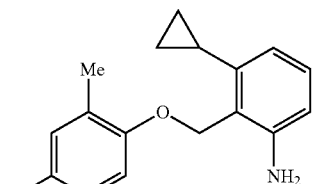
(RABC1)

-continued

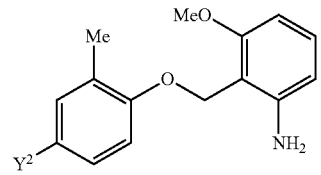
(RABD1)

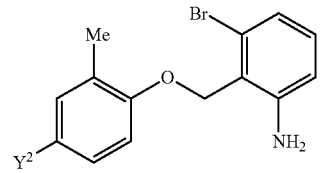
(RABE1)

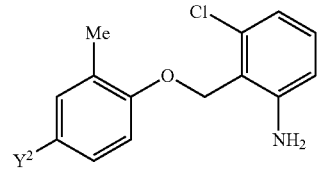
(RABF1)

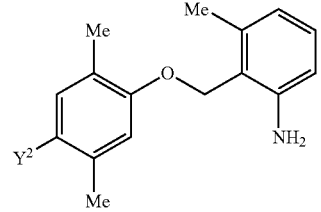
(RABA2)

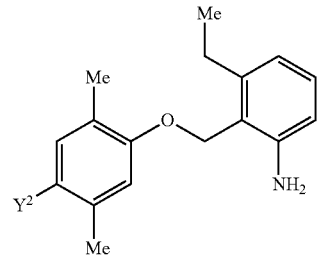
(RABB2)

(RABC2)

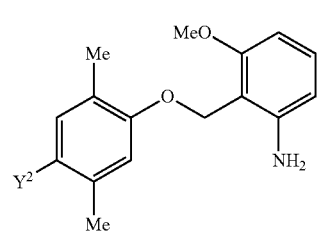
(RABD2)

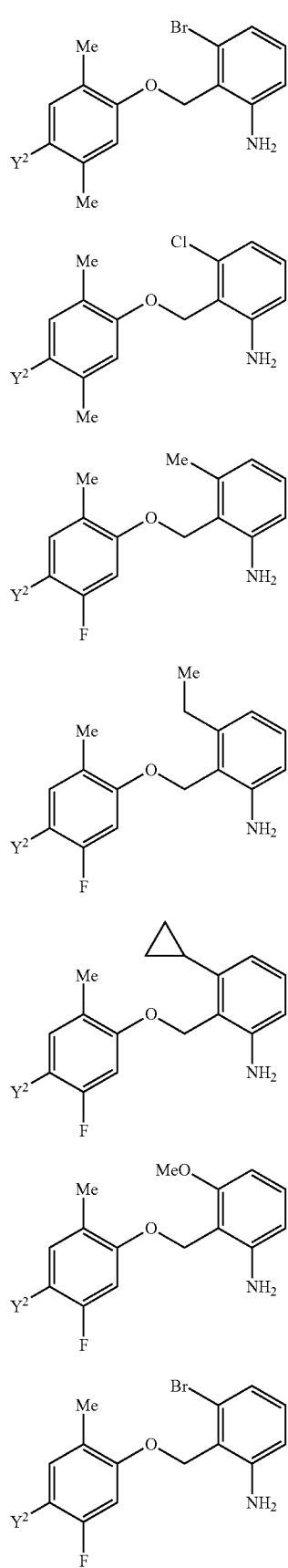
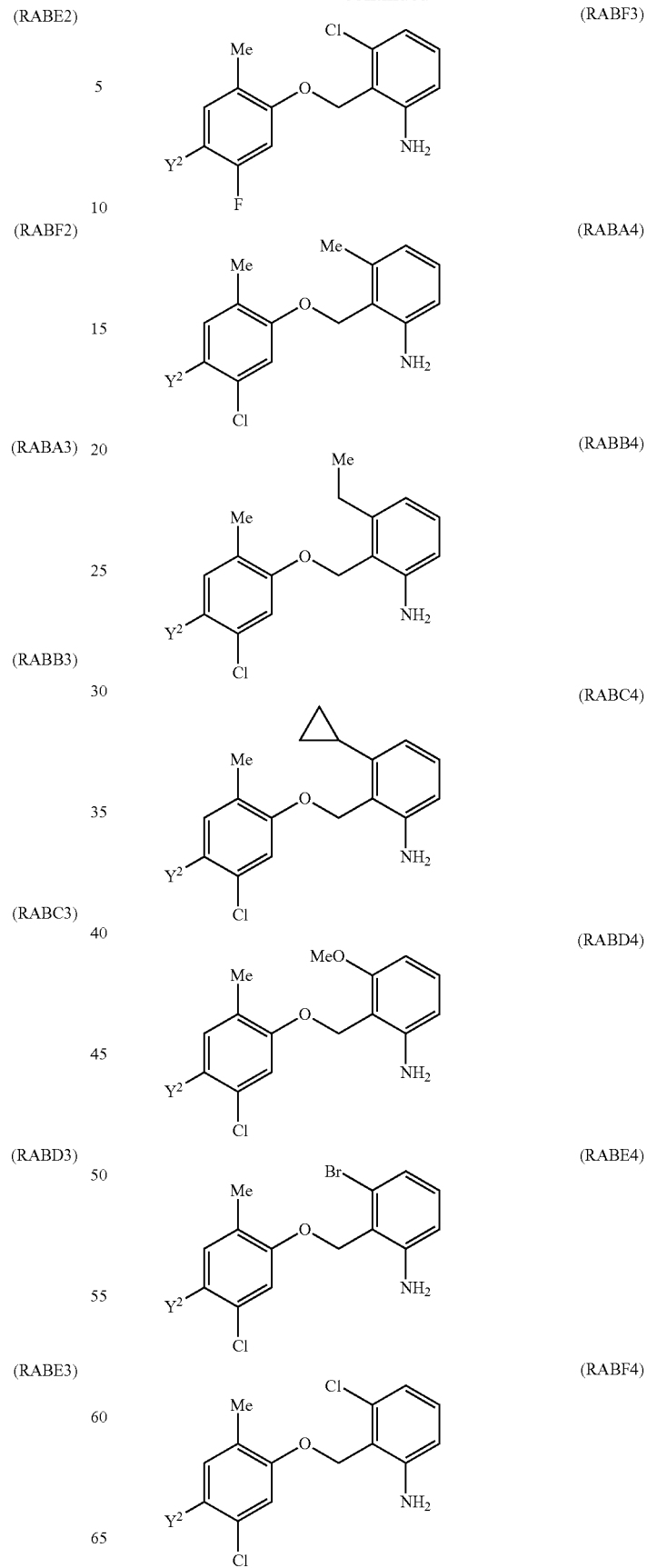

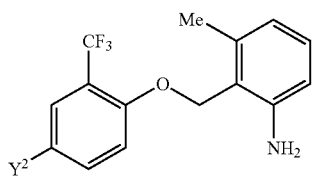
(RABA5)

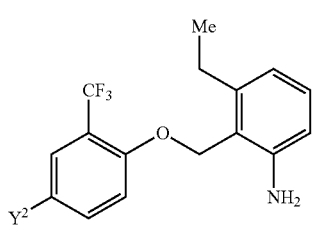
(RABB5)

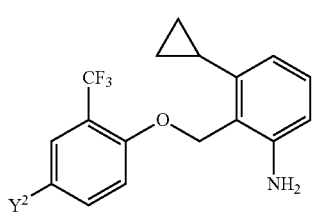
(RABC5)

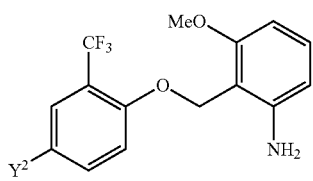
(RABD5)

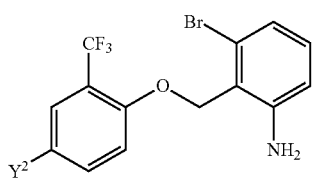
(RABE5)

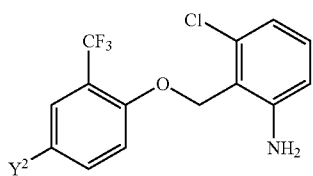
(RABF5)

wherein $Y^2$ is a substituent corresponding to each of the above substituent numbers 1 to 126.

For example, the present compound RABA1-1 represents the present compound represented by formula (RABA1) in which $Y^2$ is substituent number 1, and is represented by the following formula.

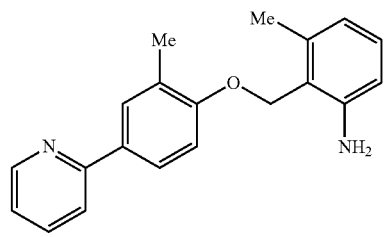
(RABA1-1)

In accordance with the process mentioned above, it is possible to obtain the present compounds RACA1-1 to RACF5-126.

The present compounds RACA1-1 to RACF5-126 are the present compounds represented by formulas:

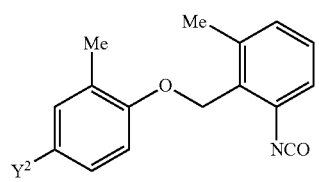
(RACA1)

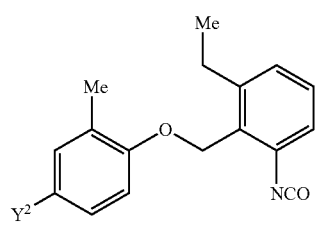
(RACB1)

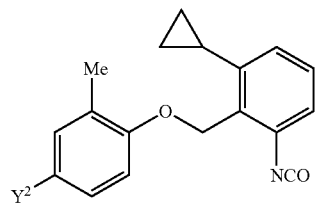
(RACC1)

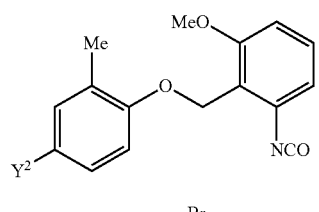
(RACD1)

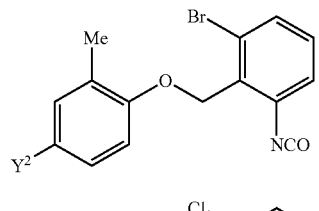
(RACE1)

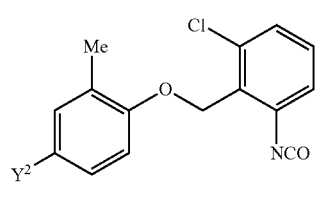
(RACF1)

317
-continued
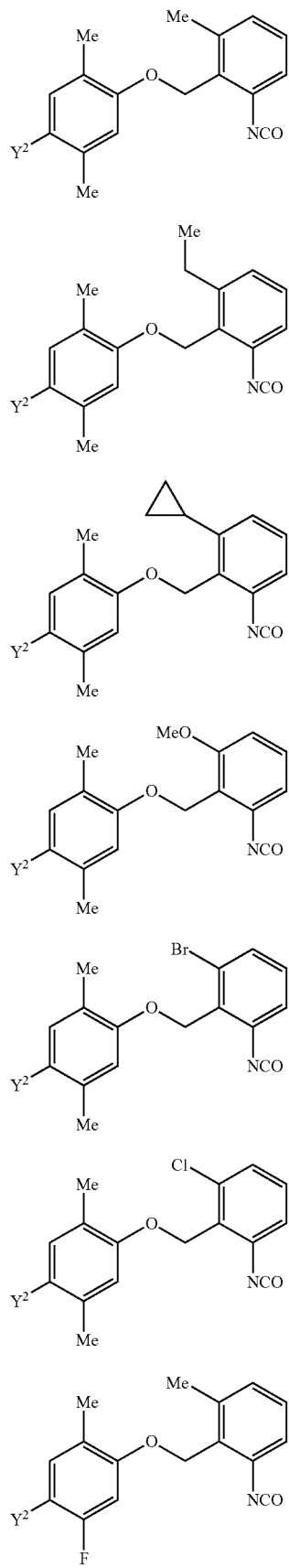
(RACA2)
(RACB2)
(RACC2)
(RACD2)
(RACE2)
(RACF2)
(RACA3)
318
-continued
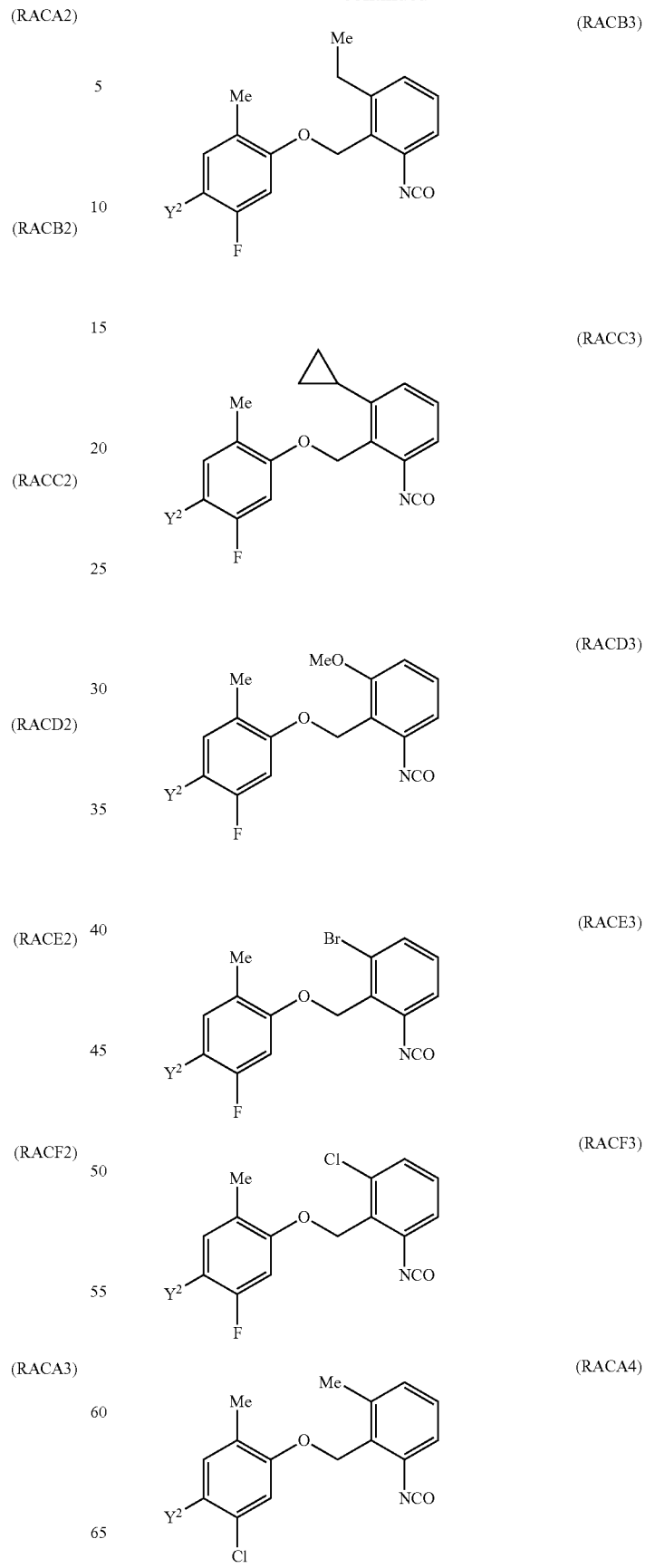
(RACB3)
(RACC3)
(RACD3)
(RACE3)
(RACF3)
(RACA4)

(RACB4)
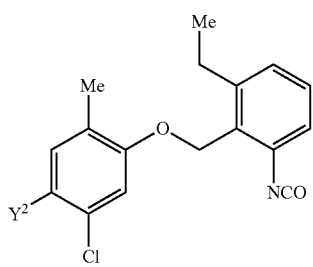

(RACC4)
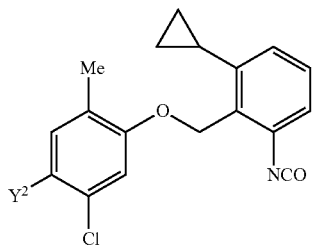

(RACD4)
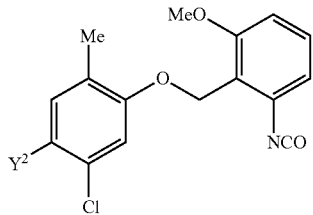

(RACE4)
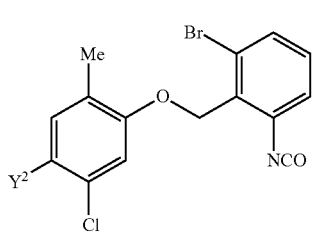

(RACF4)
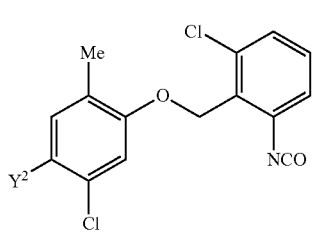

(RACA5)
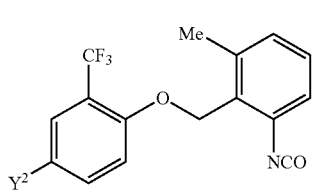

(RACB5)
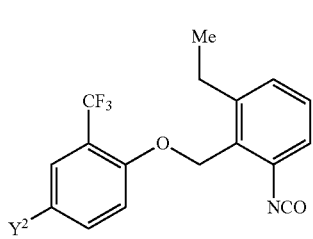

-continued (RACC5)
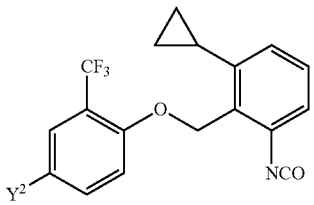

(RACD5)
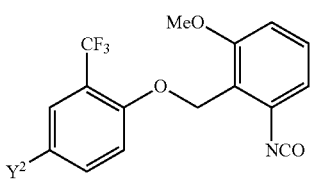

(RACE5)
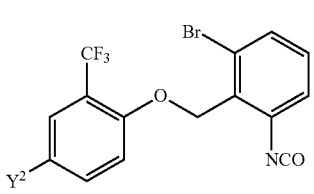

(RACF5)
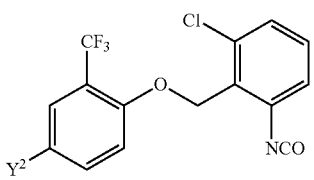

wherein $Y^2$ is a substituent corresponding to each of the above substituent numbers 1 to 126.

For example, the present compound RACA1-1 represents the present compound represented by formula (RACA1) in which $Y^2$ is substituent number 1, and is represented by the following formula.

(RACA1-1)
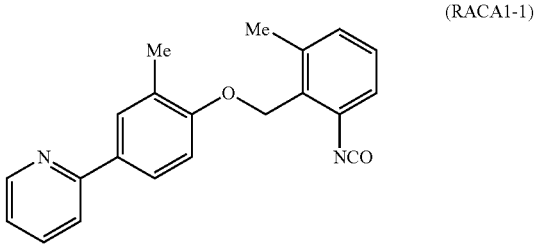 [SMILES: Cc1cc(-c2ccccn2)ccc1OCc1c(C)cccc1C(=O)Cl]

In accordance with the process mentioned above, it is possible to obtain the present compounds RADA1-1 to RADF5-126.

The present compounds RADA1-1 to RADF5-126 are the present compounds represented by formulas:

(RADA1)
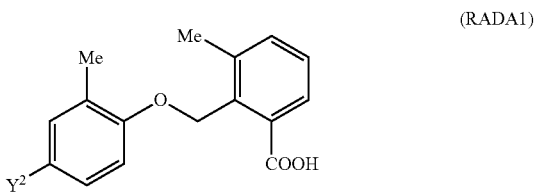

-continued
(RADB1)
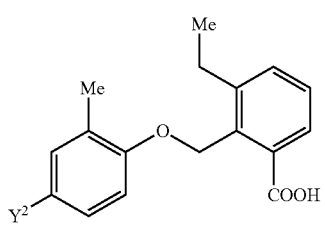
(RADC1)
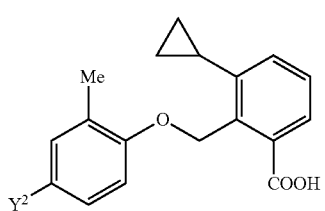
(RADD1)
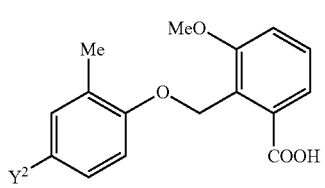
(RADE1)
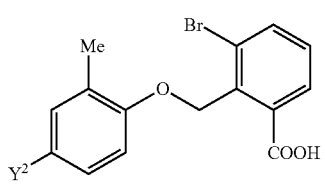
(RADF1)
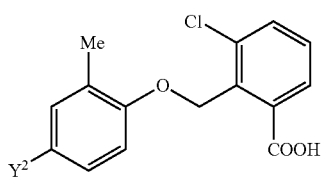
(RADA2)
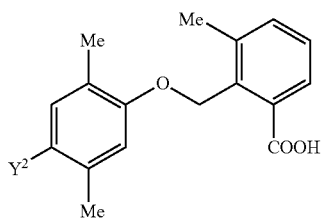
(RADB2)
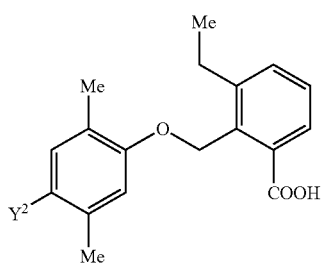
-continued
(RADC2)
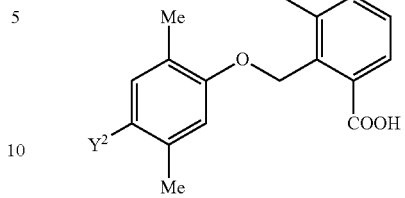
(RADD2)
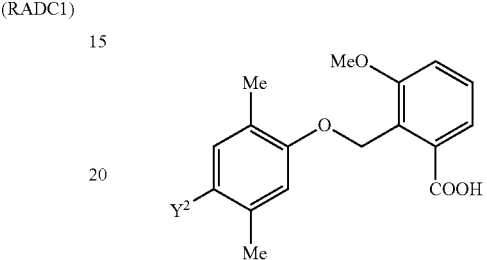
(RADE2)
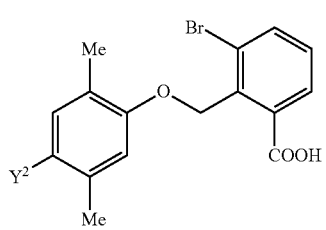
(RADF2)
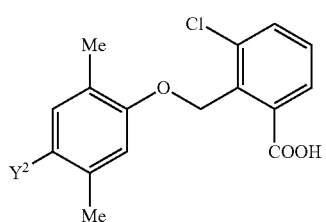
(RADA3)
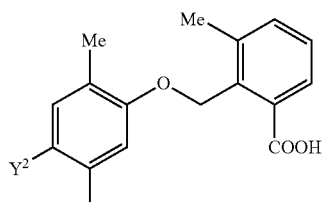
(RADB3)
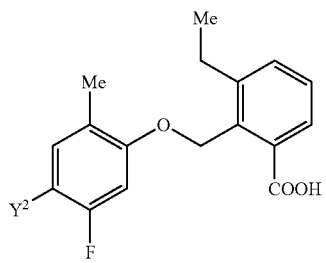

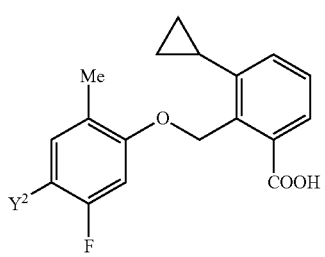
(RADC3)
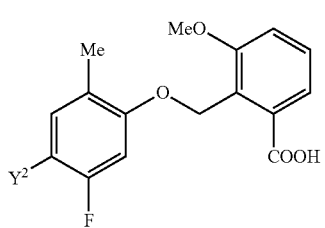
(RADD3)
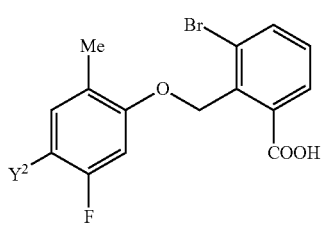
(RADE3)
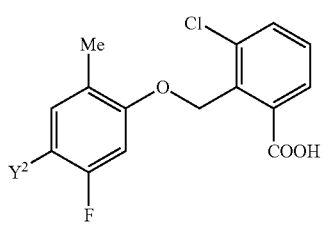
(RADF3)
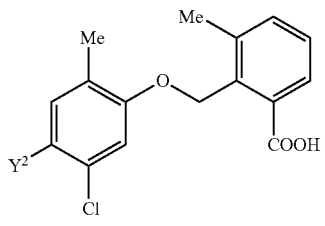
(RADA4)
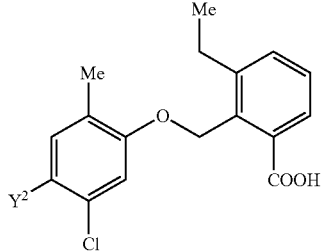
(RADB4)
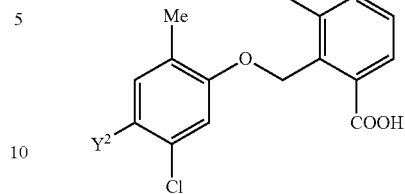
(RADC4)
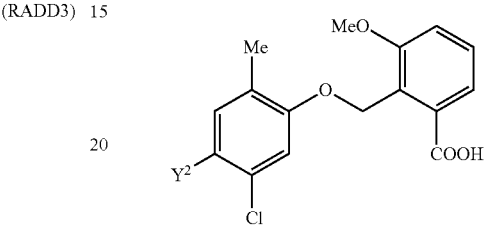
(RADD4)
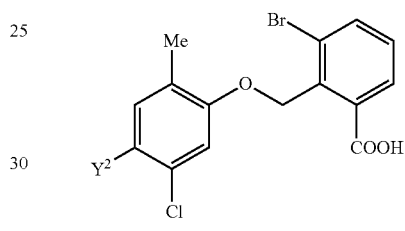
(RADE4)
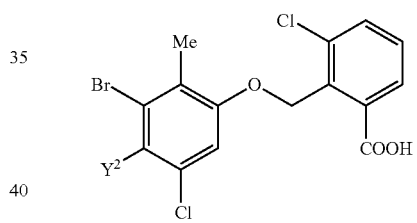
(RADF4)
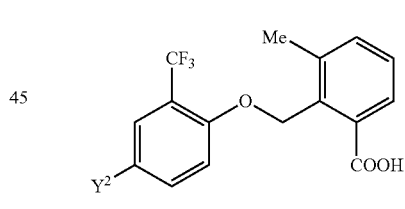
(RADA5)
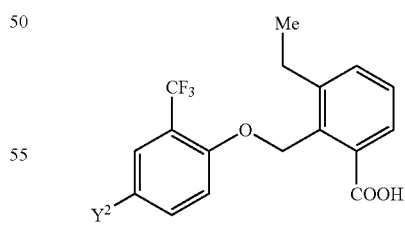
(RADB5)
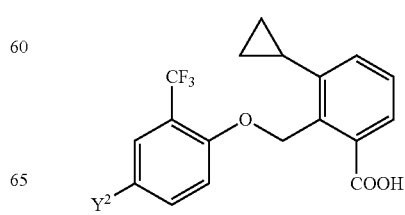
(RADC5)

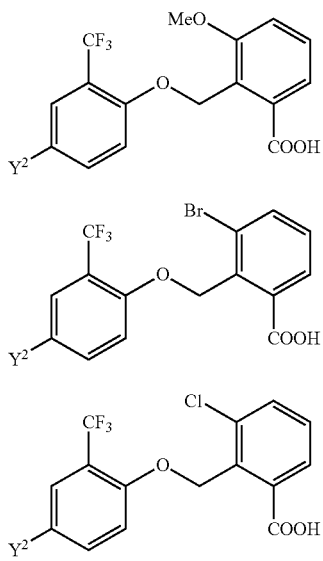

(RADD5)

(RADE5)

(RADF5)

wherein Y² is a substituent corresponding to each of the above substituent numbers 1 to 126.

For example, the present compound RADA1-1 represents the present compound represented by formula (RADA1) in which Y² is substituent number 1, and is represented by the following formula.

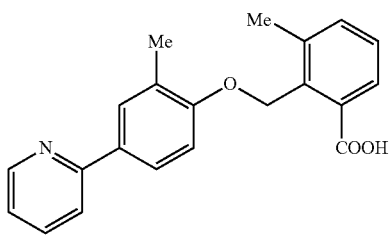

(RADA1-1)

In accordance with the process mentioned above, it is possible to obtain the present compounds RAEA1-1 to RAEF5-126.

The present compounds RAEA1-1 to RAEF5-126 are the present compounds represented by formulas:

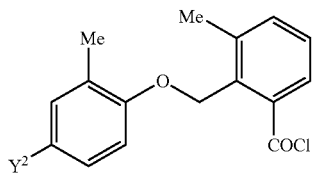

(RAEA1)

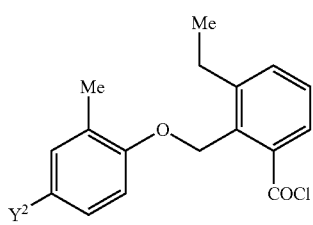

(RAEB1)

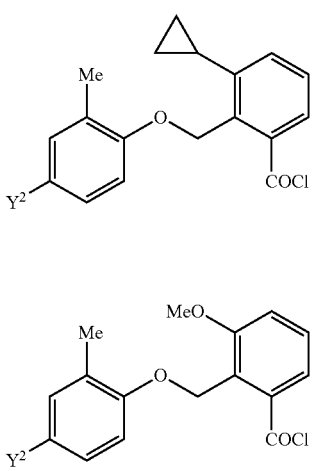

(RAEC1)

(RAED1)

(RAEE1)

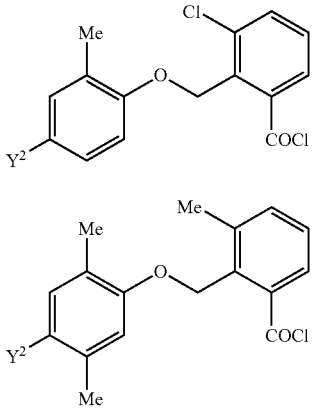

(RAEF1)

(RAEA2)

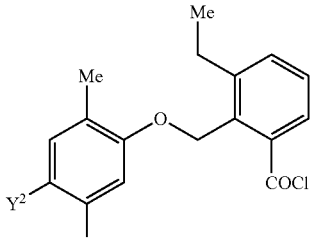

(RAEB2)

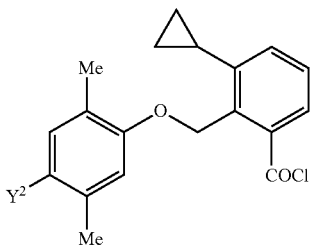

(RAEC2)

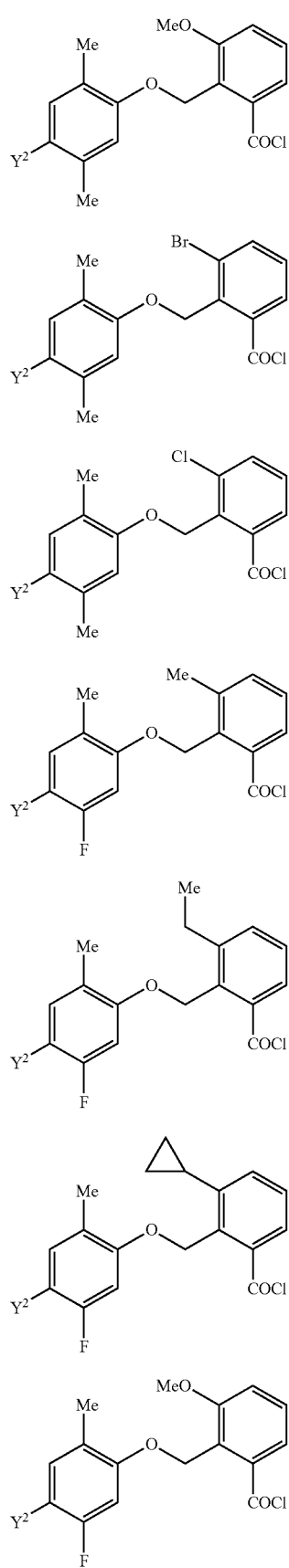
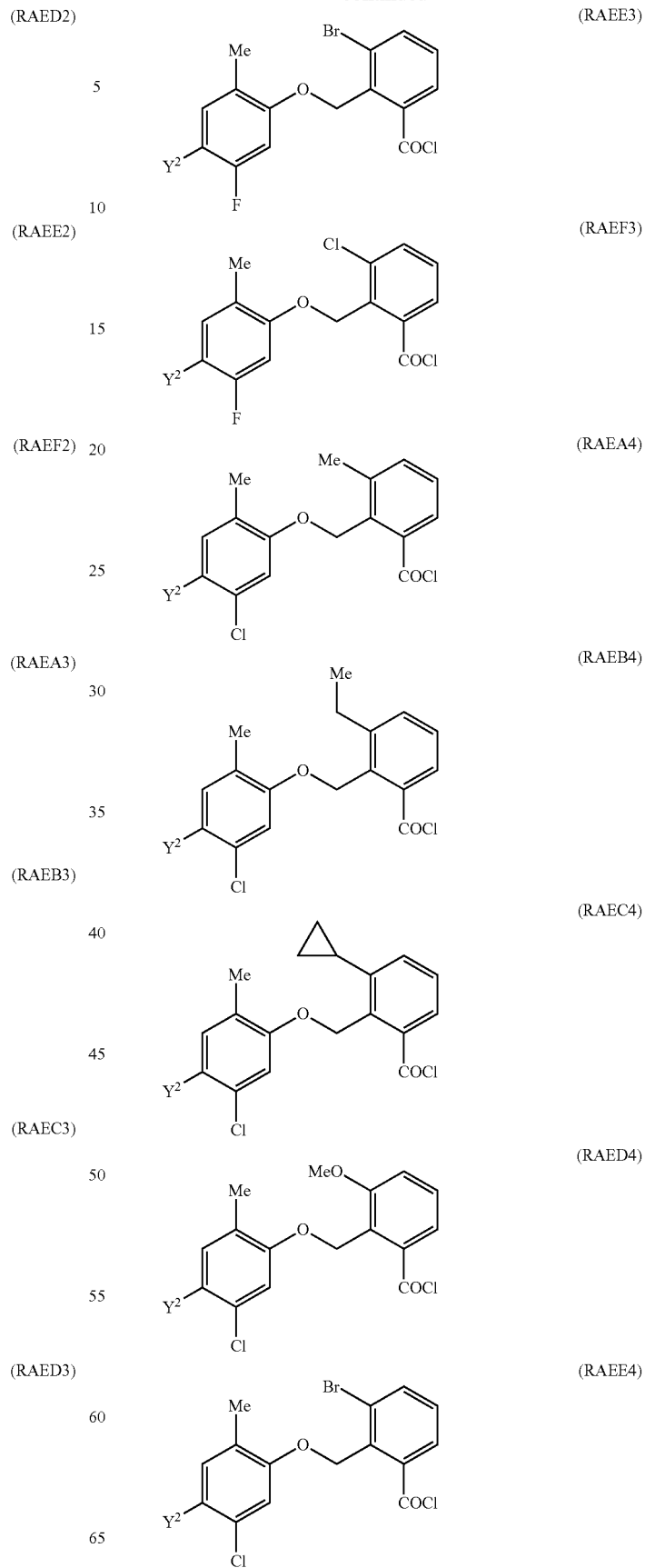

(RAEF4) 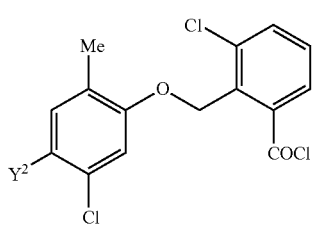

(RAEA5) 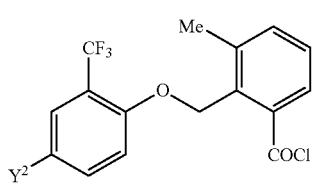

(RAEB5) 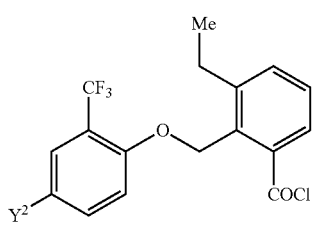

(RAEC5) 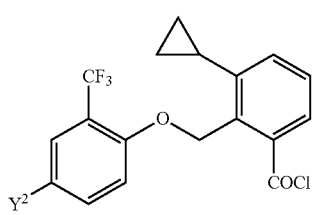

(RAED5) 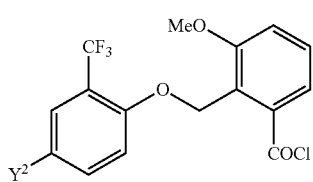

(RAEE5) 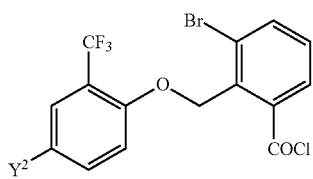

(RAEF5) 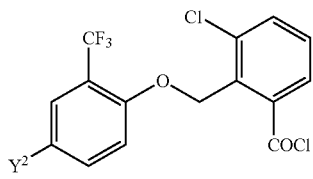

wherein $Y^2$ is a substituent corresponding to each of the above substituent numbers 1 to 126.

For example, the present compound RAEA1-1 represents the present compound represented by formula (RAEA1) in which $Y^2$ is substituent number 1, and is represented by the following formula.

(RAEA1-1) 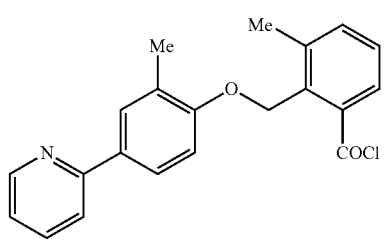

In accordance with the process mentioned above, it is possible to obtain the present compounds RAFA1-1 to RAFF5-126.

The present compounds RAFA1-1 to RAFF5-126 are the present compounds represented by formulas:

(RAFA1) 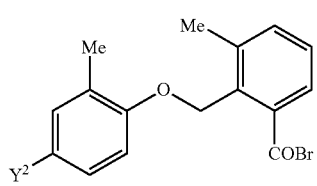

(RAFB1) 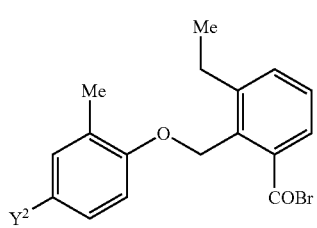

(RAFC1) 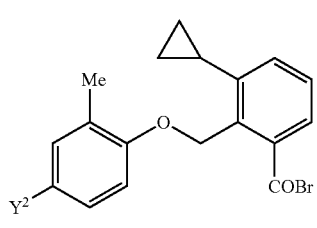

(RAFD1) 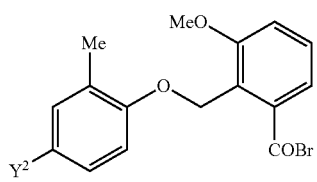

(RAFE1) 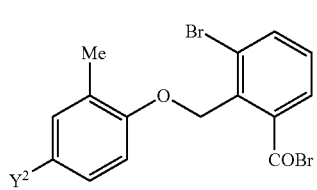

(RAFF1) 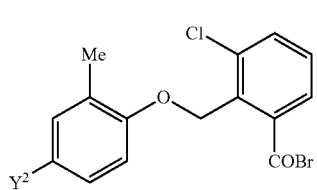

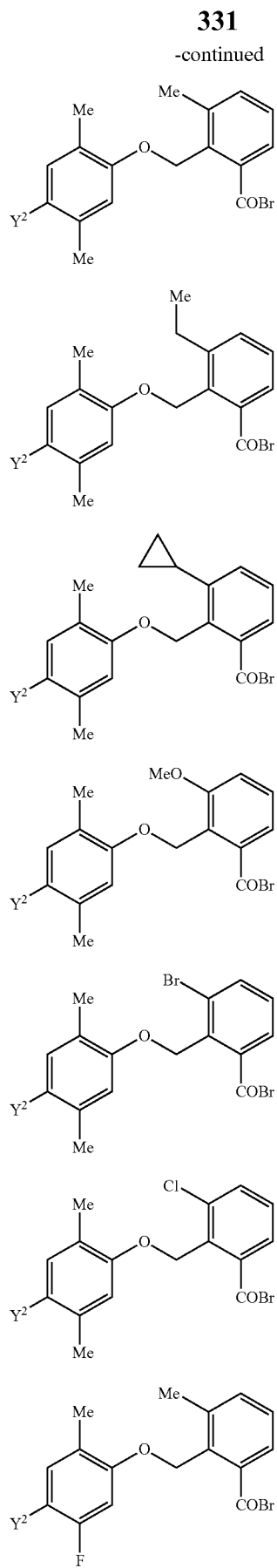
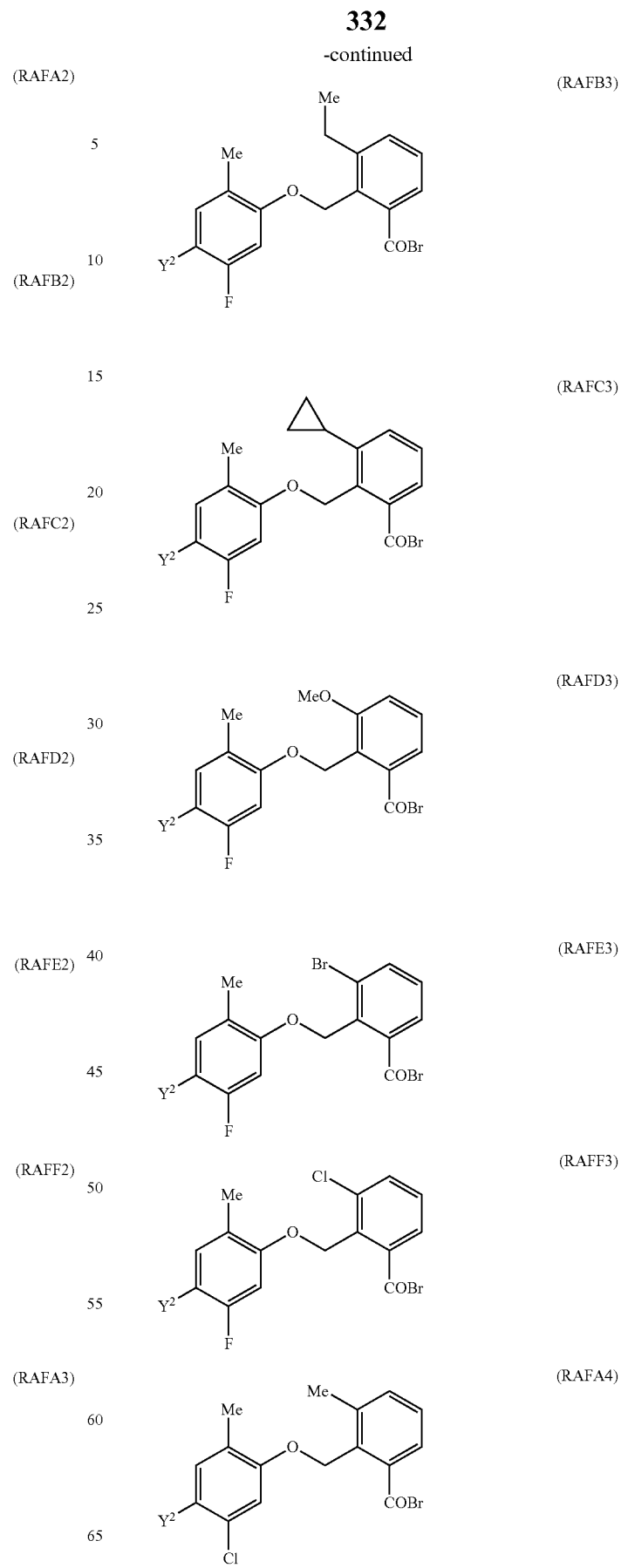

(RAFB4)
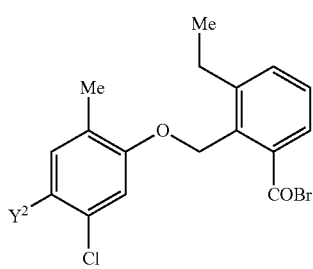

(RAFC4)
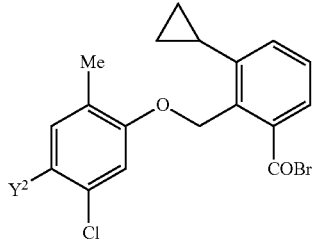

(RAFD4)
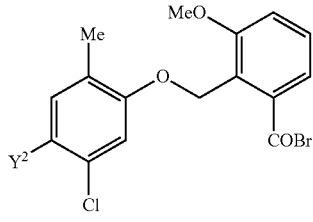

(RAFE4)
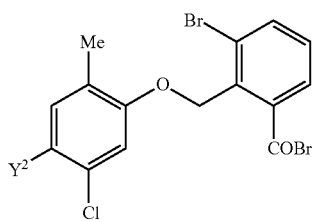

(RAFF4)
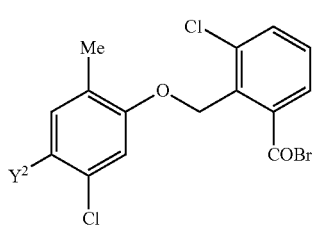

(RAFA5)
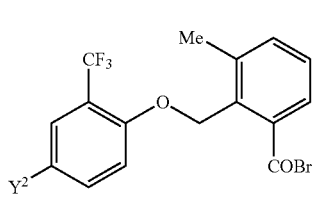

(RAFB5)
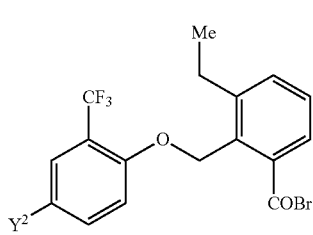

(RAFC5)
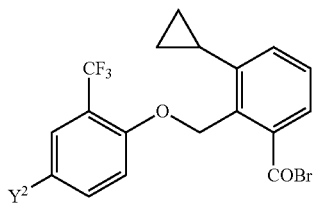

(RAFD5)
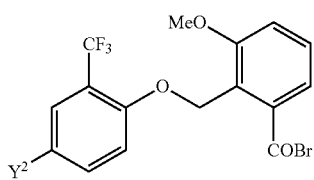

(RAFE5)
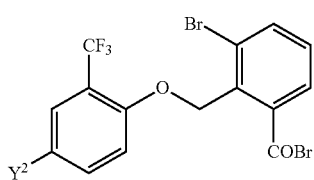

(RAFF5)
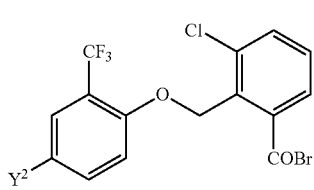

wherein $Y^2$ is a substituent corresponding to each of the above substituent numbers 1 to 126.

For example, the present compound RAFA1-1 represents the present compound represented by formula (RAFA1) in which $Y^2$ is substituent number 1, and is represented by the following formula.

(RAFA1-1)
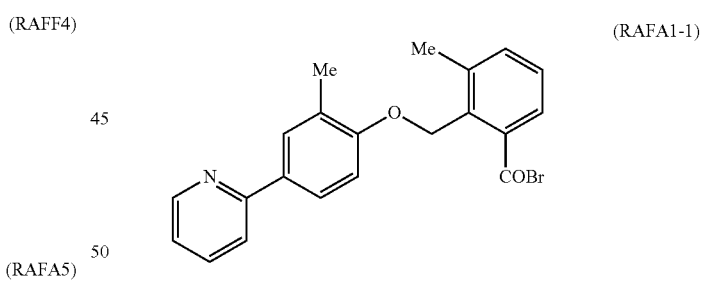

In accordance with the process mentioned above, it is possible to obtain the present compounds RAGA1-1 to RAGF5-126.

The present compounds RAGA1-1 to RAGF5-126 are the present compounds represented by formulas:

(RAGA1)
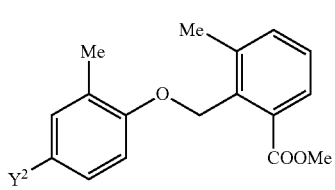

(RAGB1)
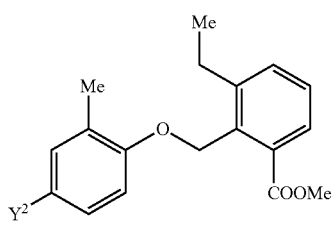
(RAGC1)
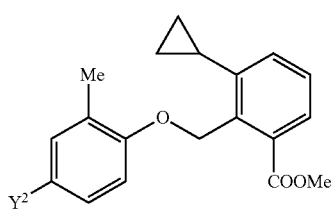
(RAGD1)
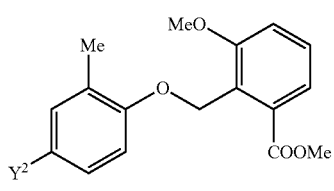
(RAGE1)
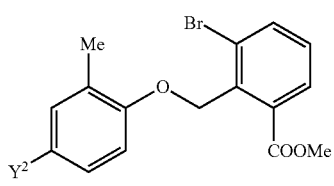
(RAGF1)
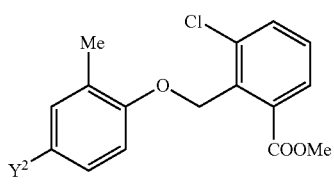
(RAGA2)
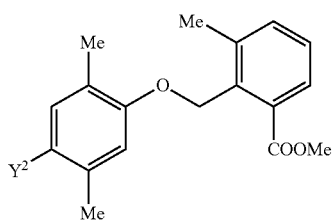
(RAGB2)
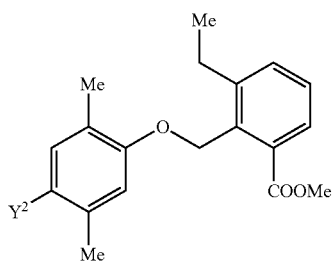
(RAGC2)
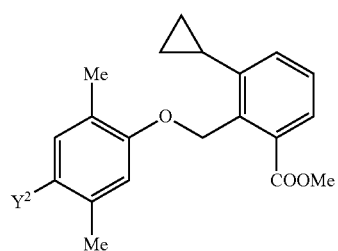
(RAGD2)
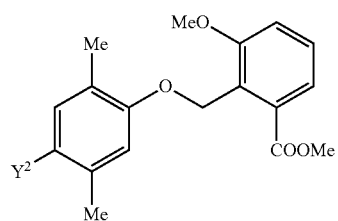
(RAGE2)
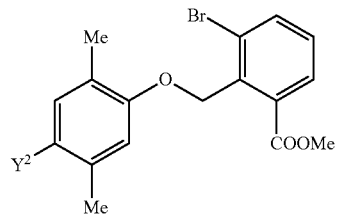
(RAGF2)
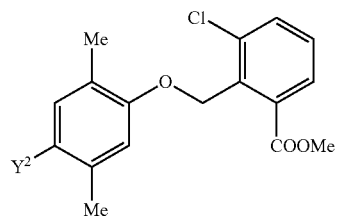
(RAGA3)
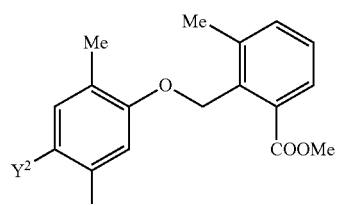
(RAGB3)
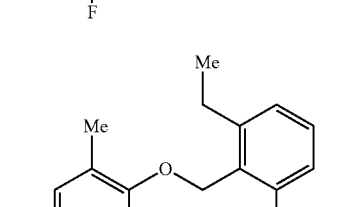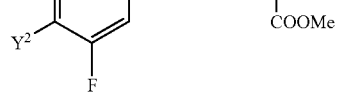

(RAGC3)
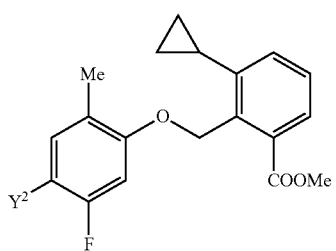
(RAGC4)
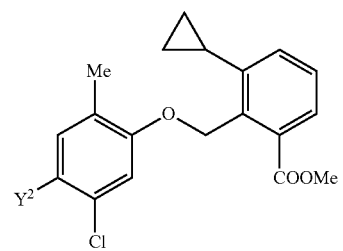
(RAGD3)
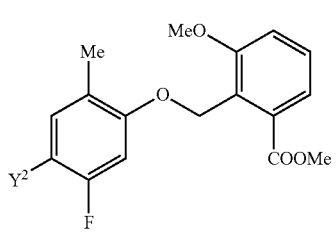
(RAGD4)
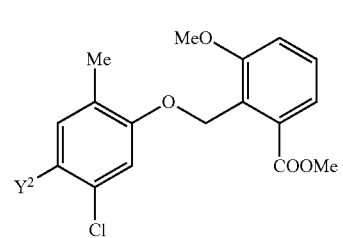
(RAGE3)
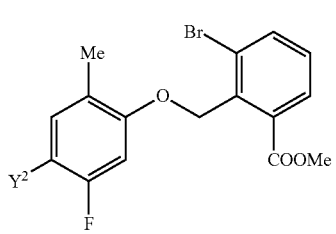
(RAGE4)
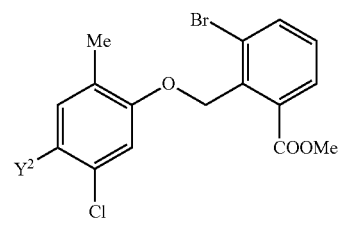
(RAGF3)
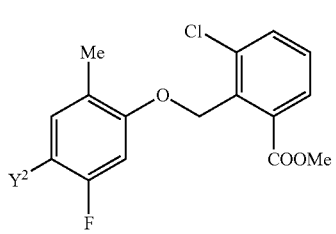
(RAGF4)
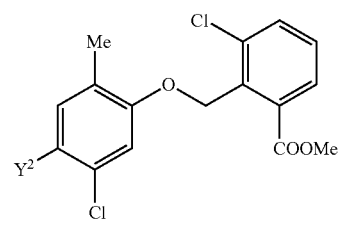
(RAGA4)
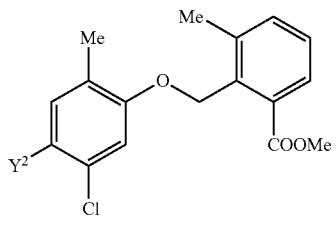
(RAGA5)
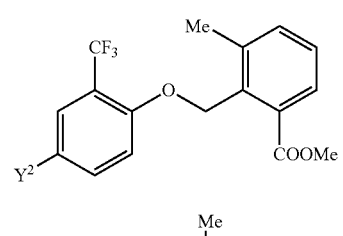
(RAGB4)
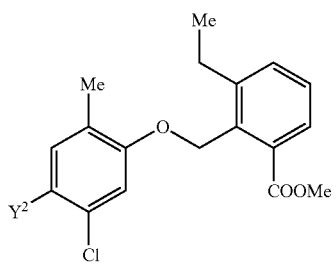
(RAGB5)
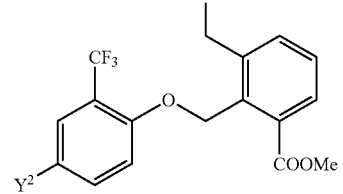
(RAGC5)
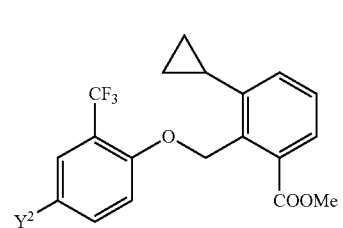

-continued

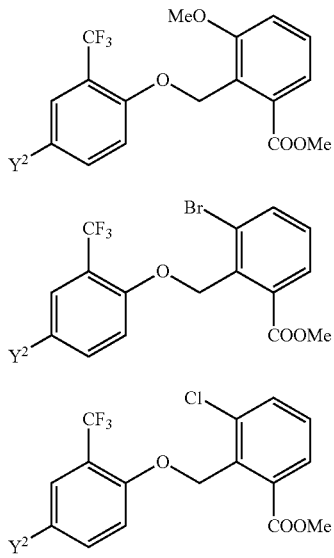

(RAGD5)

(RAGE5)

(RAGF5)

wherein Y² is a substituent corresponding to each of the above substituent numbers 1 to 126.

For example, the present compound RAGA1-1 represents the present compound represented by formula (RAGA1) in which Y² is substituent number 1, and is represented by the following formula.

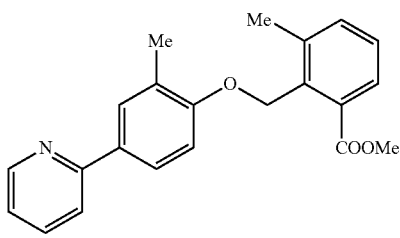

(RAGA1-1)

In accordance with the process mentioned above, it is possible to obtain the present compounds RAHA1-1 to RAHF5-126.

The present compounds RAHA1-1 to RAHF5-126 are the present compounds represented by formulas:

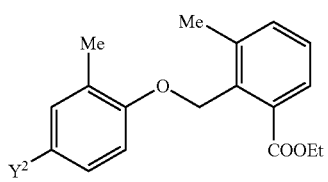

(RAHA1)

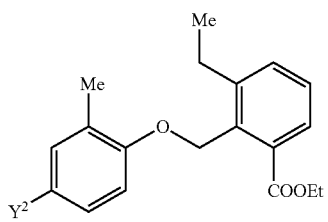

(RAHB1)

-continued

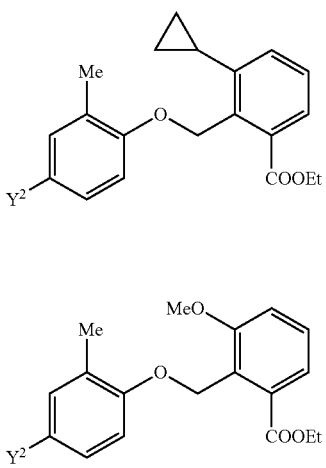

(RAHC1)

(RAHD1)

(RAHE1)

(RAHF1)

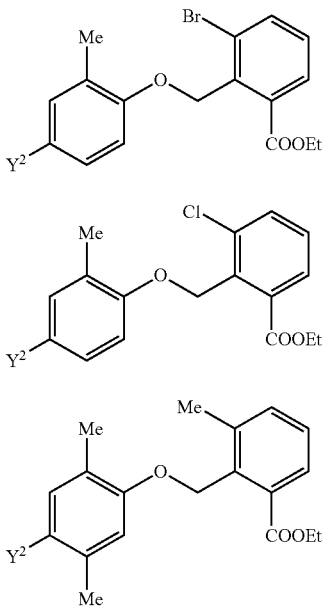

(RAHA2)

(RAHB2)

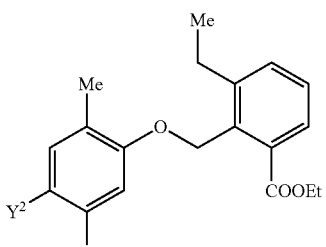

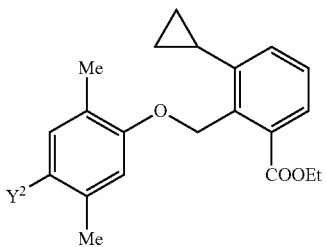

(RAHC2)

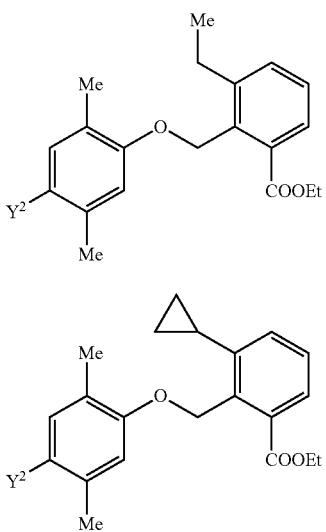

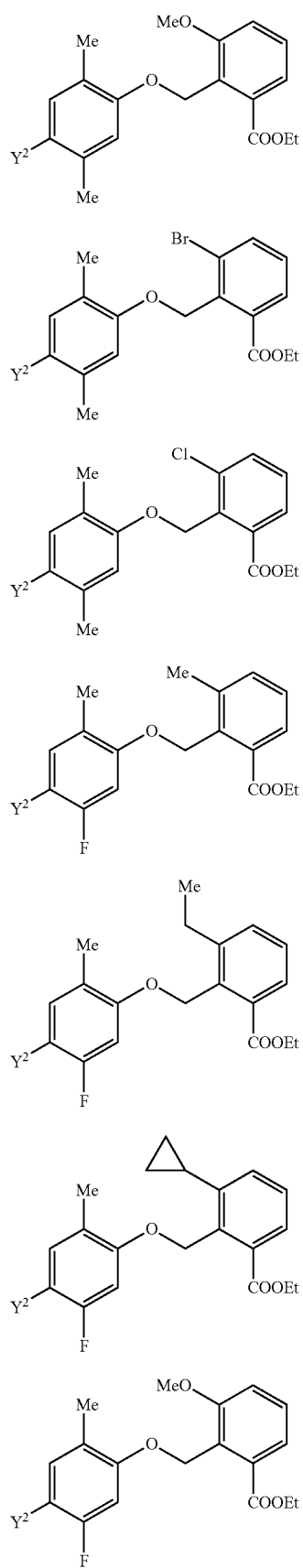
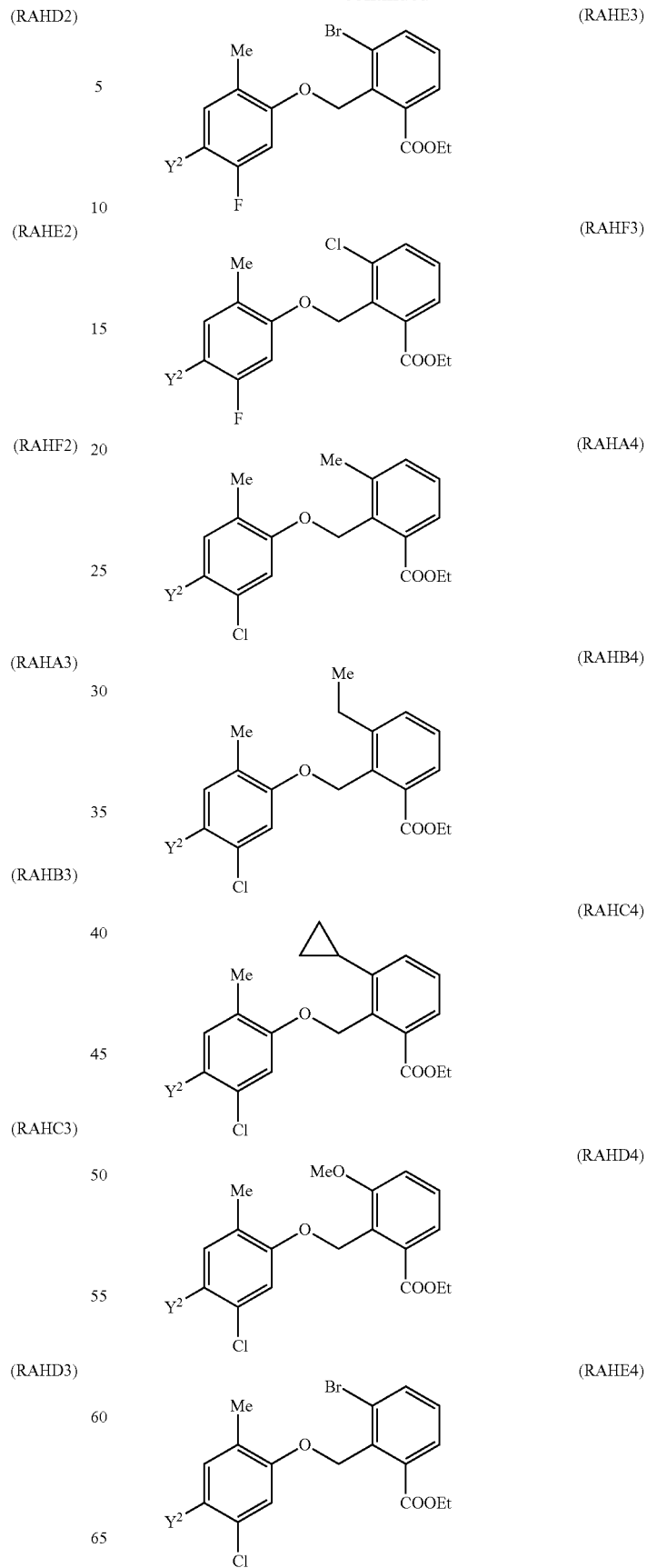

(RAHF4) 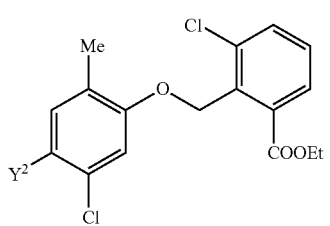

(RAHA5) 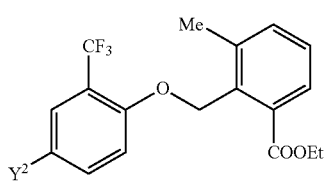

(RAHB5) 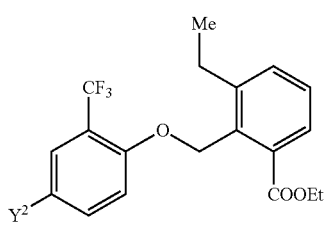

(RAHC5) 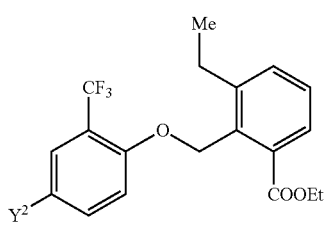

(RAHD5) 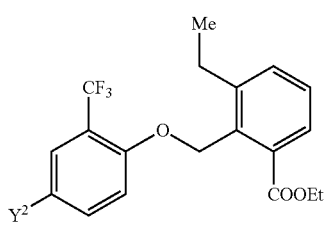

(RAHE5) 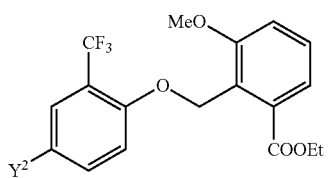

(RAHF5) 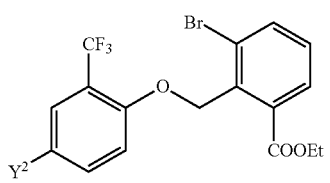

wherein $Y^2$ is a substituent corresponding to each of the above substituent numbers 1 to 126.

For example, the present compound RAHA1-1 represents the present compound represented by formula (RAHA1-1) in which $Y^2$ is substituent number 1, and is represented by the following formula.

(RAHA1-1) 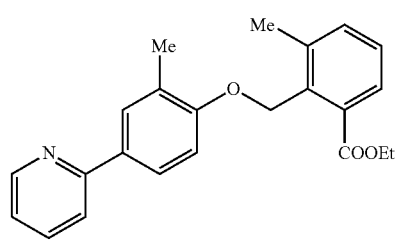

In accordance with the process mentioned above, it is possible to obtain the present compounds RAIA1-1 to RAIF5-126.

The present compounds RAIA1-1 to RAIF5-126 are the present compounds represented by formulas:

(RAIA1) 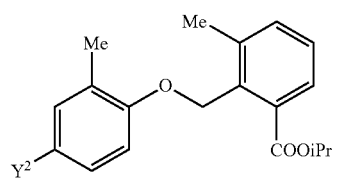

(RAIB1) 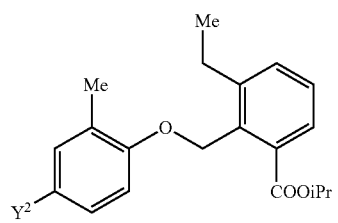

(RAIC1) 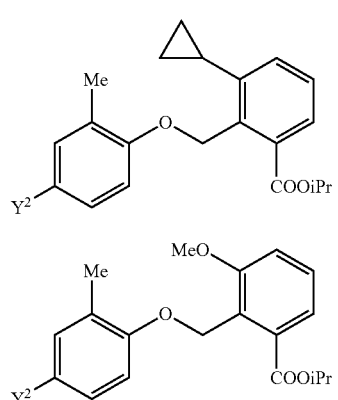

(RAID1) 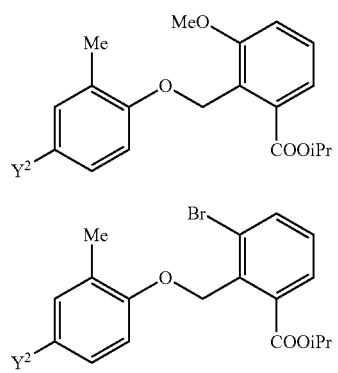

(RAIE1) 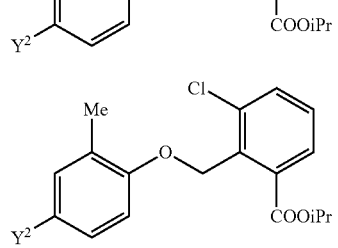

(RAIF1) 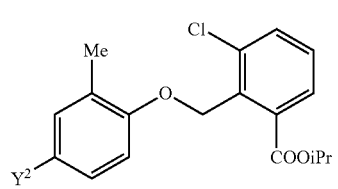

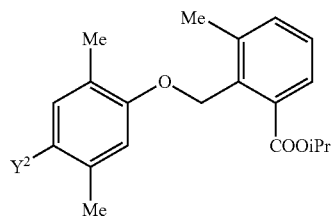 (RAIA2)
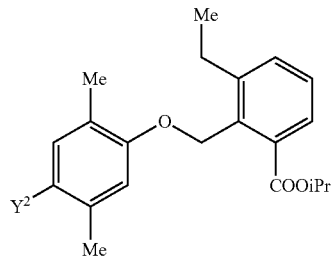 (RAIB2)
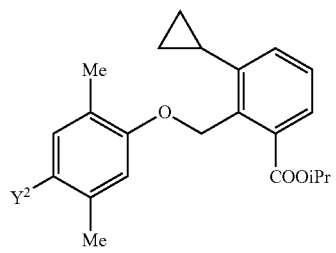 (RAIC2)
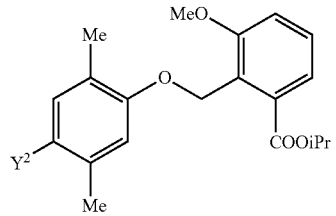 (RAID2)
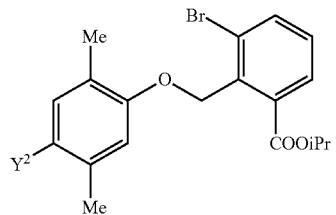 (RAIE2)
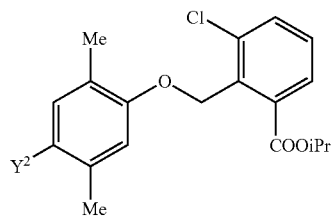 (RAIF2)
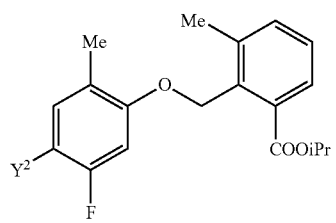 (RAIA3)
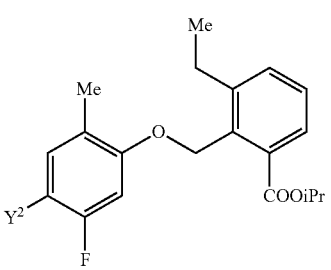 (RAIB3)
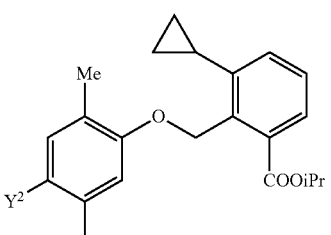 (RAIC3)
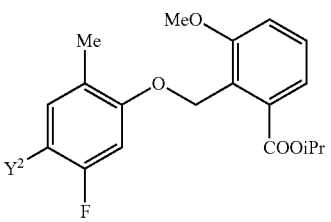 (RAID3)
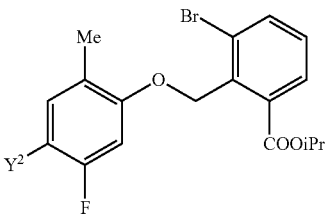 (RAIE3)
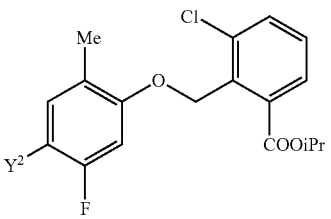 (RAIF3)
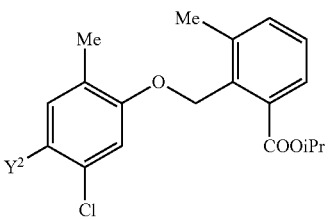 (RAIA4)

(RAIB4)
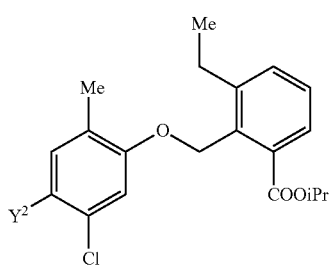

(RAIC4)
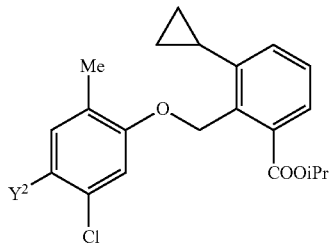

(RAID4)
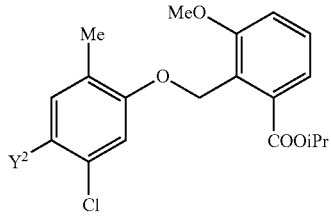

(RAIE4)
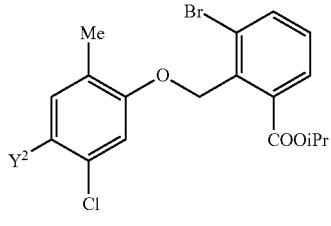

(RAIF4)
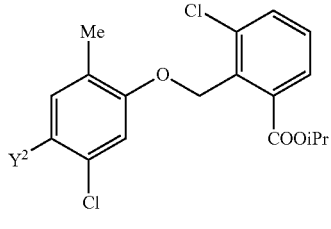

(RAIA5)
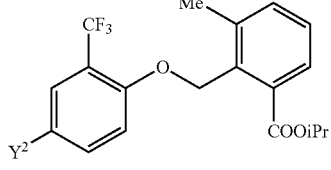

(RAIB5)
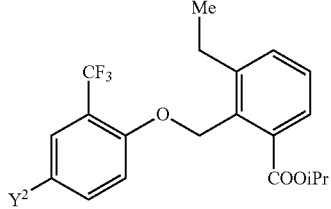

(RAIC5)
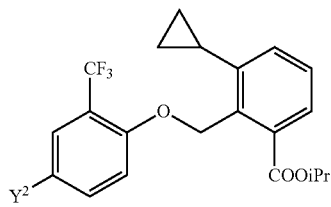

(RAID5)
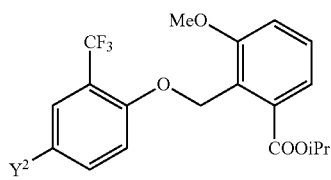

(RAIE5)
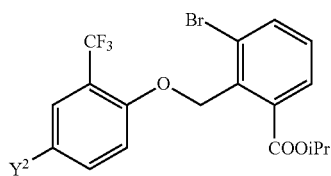

(RAIF5)
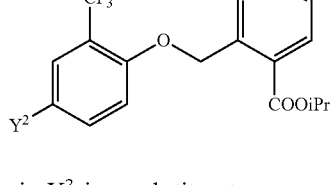

wherein $Y^2$ is a substituent corresponding to each of the above substituent numbers 1 to 126.

For example, the present compound RAIA1-1 represents the present compound represented by formula (RAIA1-1) in which $Y^2$ is substituent number 1, and is represented by the following formula.

(RAIA1-1)
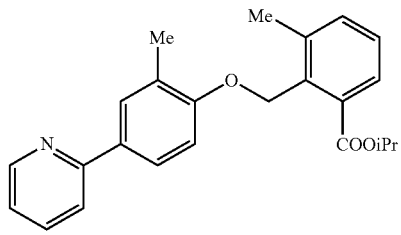

In accordance with the process mentioned above, it is possible to obtain the present compounds RAJA1-1 to RAJF5-126.

The present compounds RAJA1-1 to RAJF5-126 are the present compounds represented by formulas:

(RAJA1)
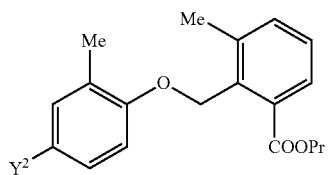

-continued
(RAJB1)
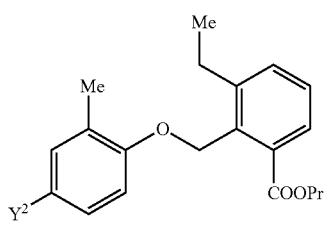
(RAJC1)
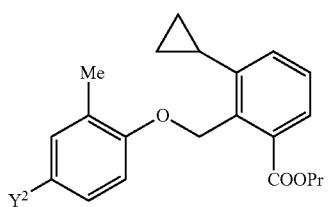
(RAJD1)
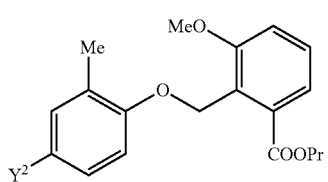
(RAJE1)
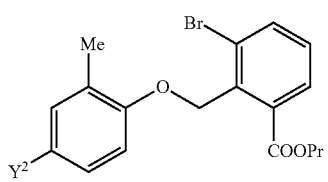
(RAJF1)
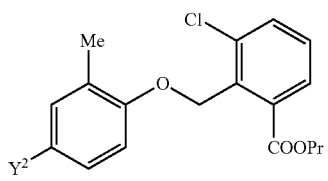
(RAJA2)
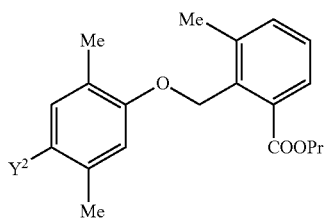
(RAJB2)
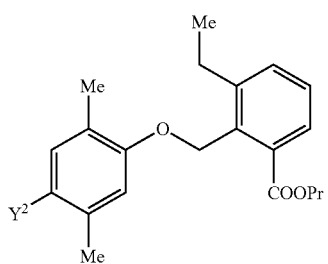
-continued
(RAJC2)
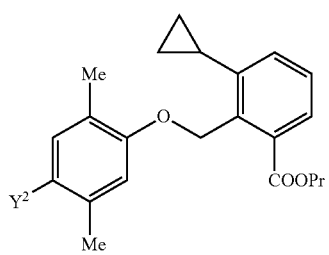
(RAJD2)
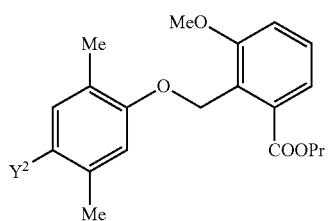
(RAJE2)
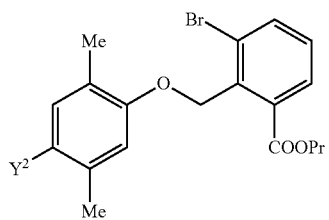
(RAJF2)
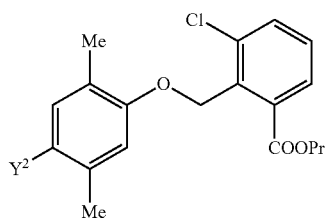
(RAJA3)
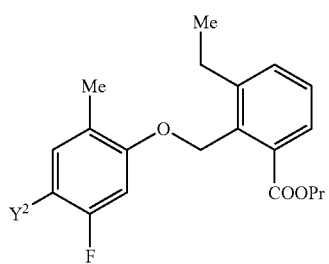
(RAJB3)

-continued
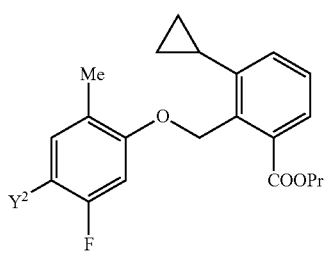
(RAJC3)
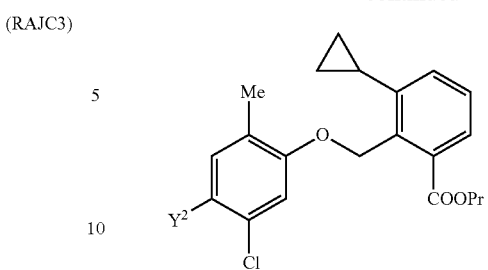
(RAJC4)
(RAJD3)
(RAJD4)
(RAJE4)
(RAJE3)
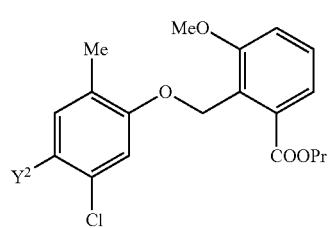
(RAJF4)
(RAJF3)
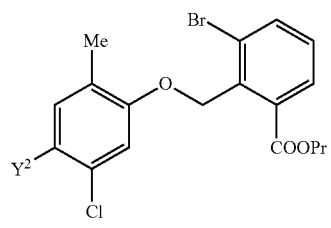
(RAJA5)
(RAJA4)
(RAJB5)
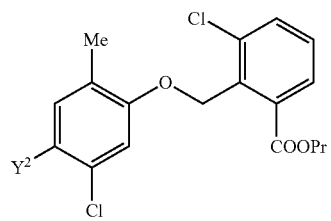
(RAJB4)
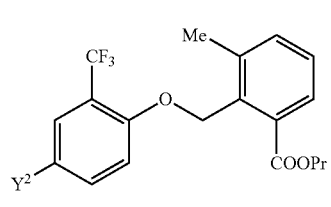
(RAJC5)
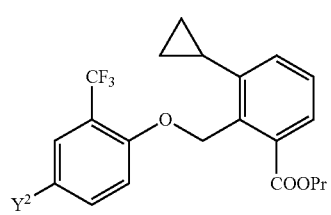

wherein $Y^2$ is a substituent corresponding to each of the above substituent numbers 1 to 126.

For example, the present compound RAJA1-1 represents the present compound represented by formula (RAJA1-1) in which $Y^2$ is substituent number 1, and is represented by the following formula.

In accordance with the process mentioned above, it is possible to obtain the present compounds RAKA1-1 to RAKF5-126.

The present compounds RAKA1-1 to RAKF5-126 are the present compounds represented by formulas:

355
-continued
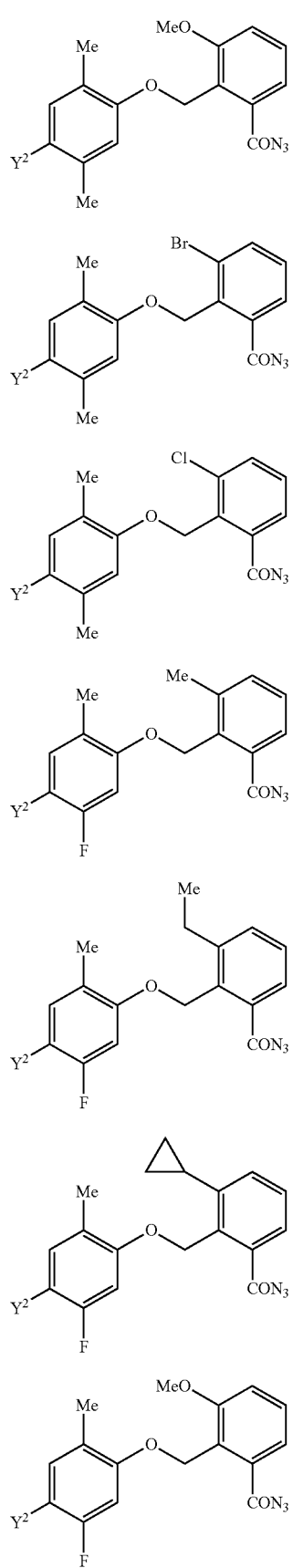
356
-continued
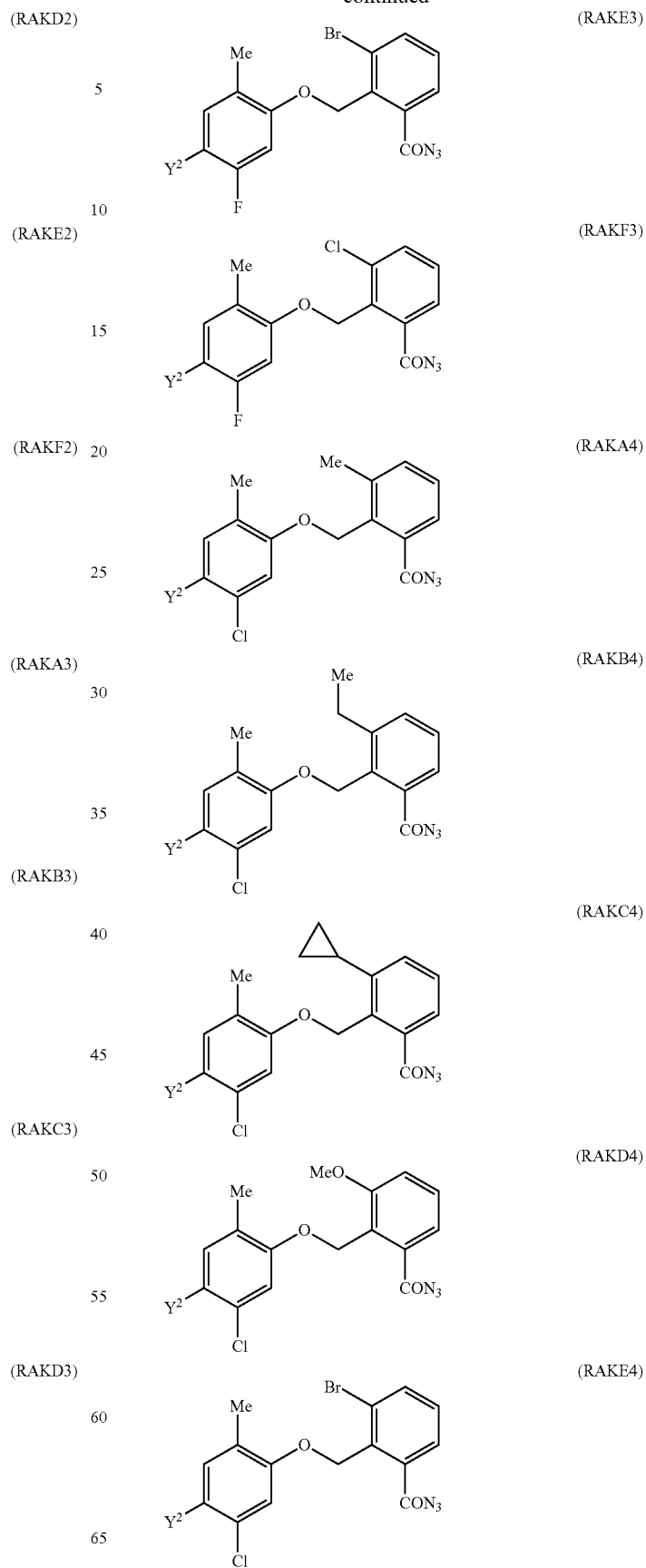

(RAKF4) 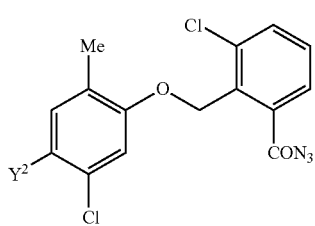

(RAKA5) 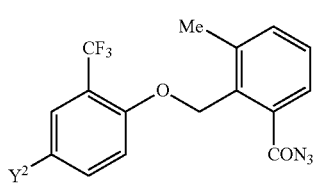

(RAKB5) 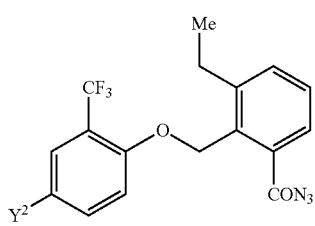

(RAKC5) 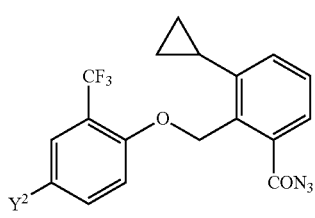

(RAKD5) 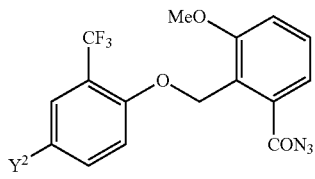

(RAKE5) 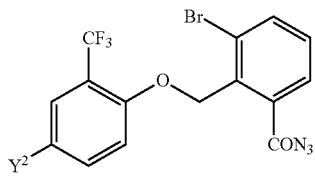

(RAKF5) 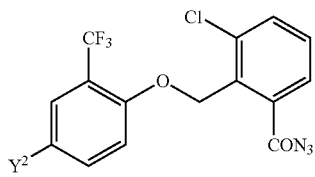

wherein $Y^2$ is a substituent corresponding to each of the above substituent numbers 1 to 126.

For example, the present compound RAKA1-1 represents the present compound represented by formula (RAKA1-1) in which $Y^2$ is substituent number 1, and is represented by the following formula.

(RAKA1-1) 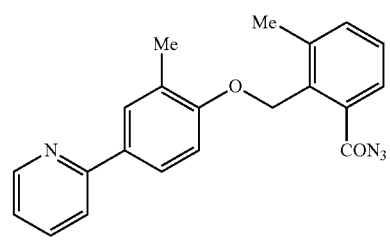

In accordance with the process mentioned above, it is possible to obtain the present compounds RALA1-1 to RALF5-126.

The present compounds RALA1-1 to RALF5-126 are the present compounds represented by formulas:

(RALA1) 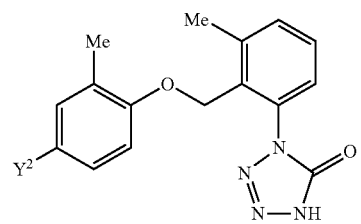

(RALB1) 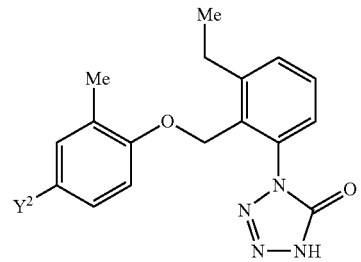

(RALC1) 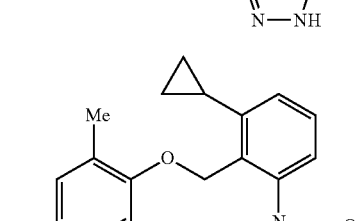

(RALD1) 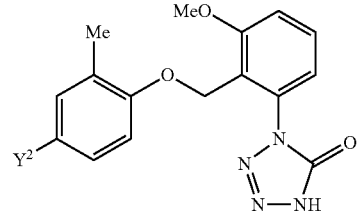

(RALE1) 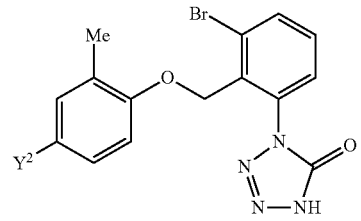

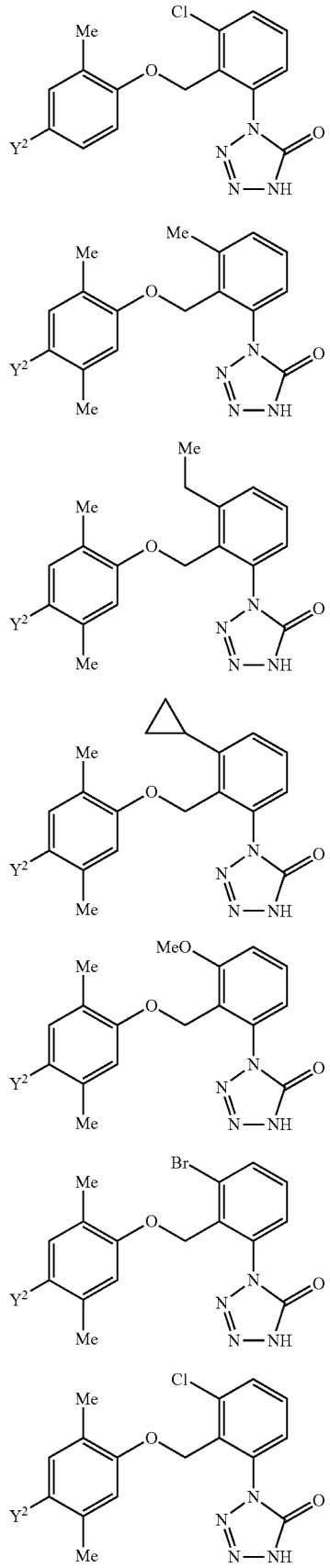
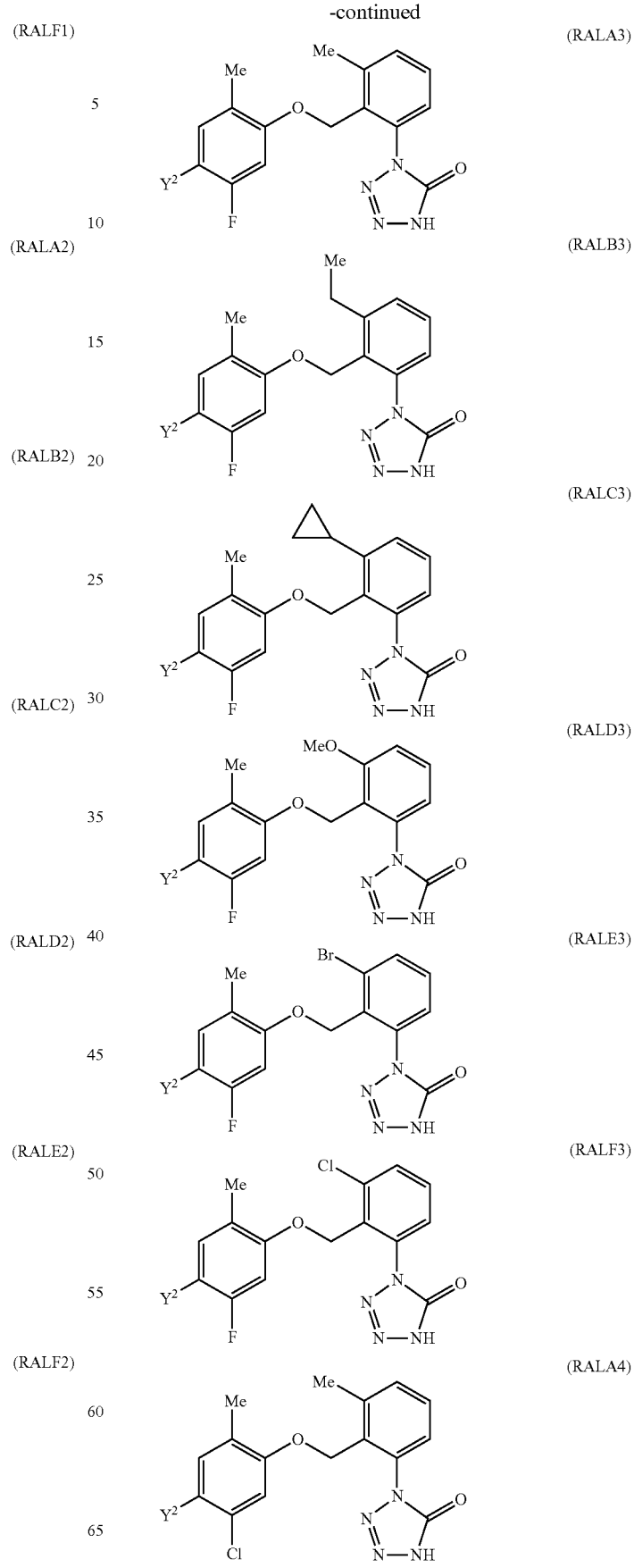

(RALB4)
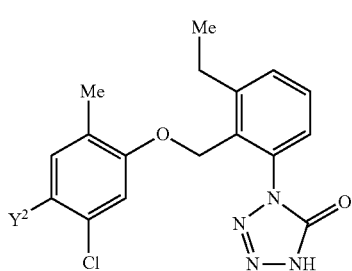
(RALB5)
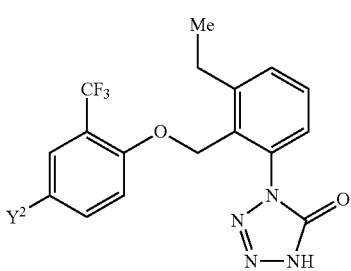
(RALC4)
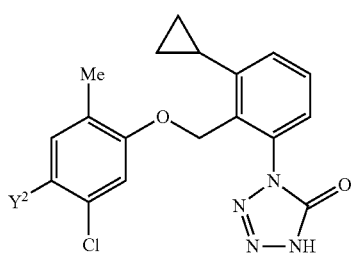
(RALC5)
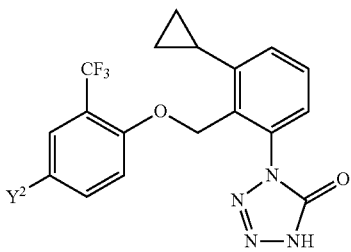
(RALD4)
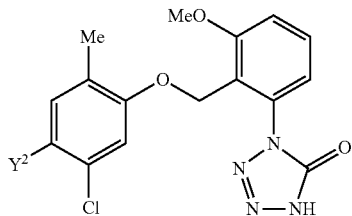
(RALD5)
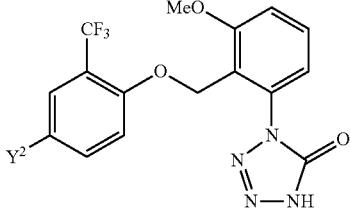
(RALE4)
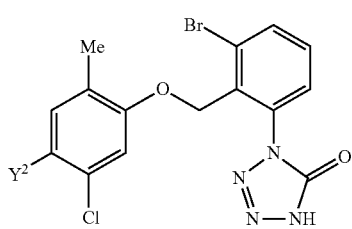
(RALE5)
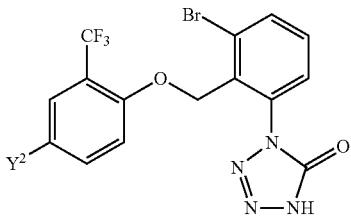
(RALF4)
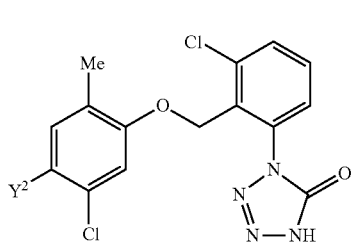
(RALF5)
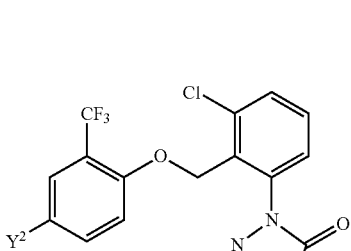
(RALA5)
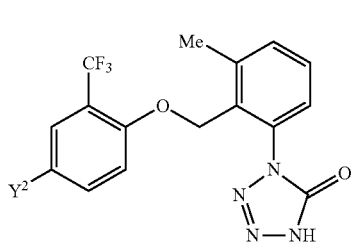
wherein $Y^2$ is a substituent corresponding to each of the above substituent numbers 1 to 126.
For example, the present compound RALA1-1 represents the present compound represented by formula (RALA1-1) in which $Y^2$ is substituent number 1, and is represented by the following formula.

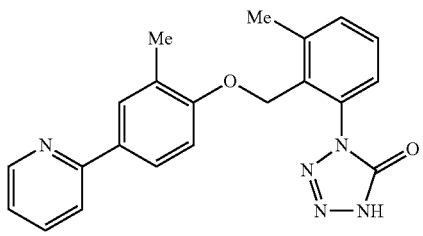
(RALA1-1)

In accordance with the process mentioned above, it is possible to obtain the present compounds LAMA-1 to LAMA-299, which are represented by formula:

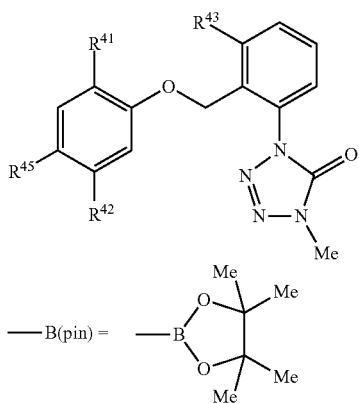
(LAMA)

wherein $R^{41}$, $R^{42}$, $R^{43}$, and $R^{45}$ are substituents corresponding to each of the above substituent numbers 1 to 299.

[substituent numbers; $R^{41}$, $R^{42}$, $R^{43}$, $R^{45}$], [1; $R^{41}$=Me, $R^{42}$=H, $R^{43}$=Me, $R^{45}$=B(OH)$_2$], [2; $R^{41}$=Me, $R^{42}$=H, $R^{43}$=Me, $R^{45}$=B(pin)], [3; $R^{41}$=Me, $R^{42}$=H, $R^{43}$=Me, $R^{45}$=I], [4; $R^{41}$=Me, $R^{42}$=H, $R^{43}$=Me, $R^{45}$=Br], [5; $R^{41}$=Me, $R^{42}$=H, $R^{43}$=Me, $R^{45}$=Cl], [6; $R^{41}$=Me, $R^{42}$=H, $R^{43}$=Et, $R^{45}$=B(OH)$_2$], [7; $R^{41}$=Me, $R^{42}$=H, $R^{43}$=Et, $R^{45}$=B(pin)], [8; $R^{41}$=Me, $R^{42}$=H, $R^{43}$=Et, $R^{45}$=I], [9; $R^{41}$=Me, $R^{42}$=H, $R^{43}$=Et, $R^{45}$=Br], [10; $R^{41}$=Me, $R^{42}$=H, $R^{43}$=Et, $R^{45}$=Cl], [11; $R^{41}$=Me, $R^{42}$=H, $R^{43}$=cPr, $R^{45}$=B(OH)$_2$], [12; $R^{41}$=Me, $R^{42}$=H, $R^{43}$=cPr, $R^{45}$=B(pin)], [13; $R^{41}$=Me, $R^{42}$=H, $R^{43}$=cPr, $R^{45}$=I], [14; $R^{41}$=Me, $R^{42}$=H, $R^{43}$=cPr, $R^{45}$=Br], [15; $R^{41}$=Me, $R^{42}$=H, $R^{43}$=cPr, $R^{45}$=Cl], [16; $R^{41}$=Me, $R^{42}$=H, $R^{43}$=MeO, $R^{45}$=B(OH)$_2$], [17; $R^{41}$=Me, $R^{42}$=H, $R^{43}$=MeO, $R^{45}$=B(pin)], [18; $R^{41}$=Me, $R^{42}$=H, $R^{43}$=MeO, $R^{45}$=I], [19; $R^{41}$=Me, $R^{42}$=H, $R^{43}$=MeO, $R^{45}$=Br], [20; $R^{41}$=Me, $R^{42}$=H, $R^{43}$=MeO, $R^{45}$=Cl], [21; $R^{41}$=Me, $R^{42}$=H, $R^{43}$=Cl, $R^{45}$=B(OH)$_2$], [22; $R^{41}$=Me, $R^{42}$=H, $R^{43}$=Cl, $R^{45}$=B(pin)], [23; $R^{41}$=Me, $R^{42}$=H, $R^{43}$=Cl, $R^{45}$=I], [24; $R^{41}$=Me, $R^{42}$=H, $R^{43}$=Cl, $R^{45}$=Br], [25; $R^{41}$=Me, $R^{42}$=H, $R^{43}$=Cl, $R^{45}$=Cl], [26; $R^{41}$=Me, $R^{42}$=Me, $R^{43}$=Me, $R^{45}$=B(OH)$_2$], [27; $R^{41}$=Me, $R^{42}$=Me, $R^{43}$=Me, $R^{45}$=B(pin)], [28; $R^{41}$=Me, $R^{42}$=Me, $R^{43}$=Me, $R^{45}$=I], [29; $R^{41}$=Me, $R^{42}$=Me, $R^{43}$=Me, $R^{45}$=Br], [30; $R^{41}$=Me, $R^{42}$=Me, $R^{43}$=Me, $R^{45}$=Cl], [31; $R^{41}$=Me, $R^{42}$=Me, $R^{43}$=Et, $R^{45}$=B(OH)$_2$], [32; $R^{41}$=Me, $R^{42}$=Me, $R^{43}$=Et, $R^{45}$=B(pin)], [33; $R^{41}$=Me, $R^{42}$=Me, $R^{43}$=Et, $R^{45}$=I], [34; $R^{41}$=Me, $R^{42}$=Me, $R^{43}$=Et, $R^{45}$=Br], [35; $R^{41}$=Me, $R^{42}$=Me, $R^{43}$=Et, $R^{45}$=Cl], [36; $R^{41}$=Me, $R^{42}$=Me, $R^{43}$=cPr, $R^{45}$=B(OH)$_2$], [37; $R^{41}$=Me, $R^{42}$=Me, $R^{43}$=cPr, $R^{45}$=B(pin)], [38; $R^{41}$=Me, $R^{42}$=Me, $R^{43}$=cPr, $R^{45}$=I], [39; $R^{41}$=Me, $R^{42}$=Me, $R^{43}$=cPr, $R^{45}$=Br], [40; $R^{41}$=Me, $R^{42}$=Me, $R^{43}$=cPr, $R^{45}$=Cl], [41; $R^{41}$=Me, $R^{42}$=Me, $R^{43}$=MeO, $R^{45}$=B(OH)$_2$], [42; $R^{41}$=Me, $R^{42}$=Me, $R^{43}$=MeO, $R^{45}$=B(pin)], [43; $R^{41}$=Me, $R^{42}$=Me, $R^{43}$=MeO, $R^{45}$=I], [44; $R^{41}$=Me, $R^{42}$=Me, $R^{43}$=MeO, $R^{45}$=Br], [45; $R^{41}$=Me, $R^{42}$=Me, $R^{43}$=MeO, $R^{45}$=Cl], [46; $R^{41}$=Me, $R^{42}$=Me, $R^{43}$=Cl, $R^{45}$=B(OH)$_2$], [47; $R^{41}$=Me, $R^{42}$=Me, $R^{43}$=Cl, $R^{45}$=B(pin)], [48; $R^{41}$=Me, $R^{42}$=Me, $R^{43}$=Cl, $R^{45}$=I], [49; $R^{41}$=Me, $R^{42}$=Me, $R^{43}$=Cl, $R^{45}$=Br], [50; $R^{41}$=Me, $R^{42}$=Me, $R^{43}$=Cl, $R^{45}$=Cl], [51; $R^{41}$=Me, $R^{42}$=F, $R^{43}$=Me, $R^{45}$=B(OH)$_2$], [52; $R^{41}$=Me, $R^{42}$=F, $R^{43}$=Me, $R^{45}$=B(pin)], [53; $R^{41}$=Me, $R^{42}$=F, $R^{43}$=Me, $R^{45}$=I], [54; $R^{41}$=Me, $R^{42}$=F, $R^{43}$=Me, $R^{45}$=Br], [55; $R^{41}$=Me, $R^{42}$=F, $R^{43}$=Me, $R^{45}$=Cl], [56; $R^{41}$=Me, $R^{42}$=F, $R^{43}$=Et, $R^{45}$=B(OH)$_2$], [57; $R^{41}$=Me, $R^{42}$=F, $R^{43}$=Et, $R^{45}$=B(pin)], [58; $R^{41}$=Me, $R^{42}$=F, $R^{43}$=Et, $R^{45}$=I], [59; $R^{41}$=Me, $R^{42}$=F, $R^{43}$=Et, $R^{45}$=Br], [60; $R^{41}$=Me, $R^{42}$=F, $R^{43}$=Et, $R^{45}$=Cl], [61; $R^{41}$=Me, $R^{42}$=F, $R^{43}$=cPr, $R^{45}$=B(OH)$_2$], [62; $R^{41}$=Me, $R^{42}$=F, $R^{43}$=cPr, $R^{45}$=B(pin)], [63; $R^{41}$=Me, $R^{42}$=F, $R^{43}$=cPr, $R^{45}$=I], [64; $R^{41}$=Me, $R^{42}$=F, $R^{43}$=cPr, $R^{45}$=Br], [65; $R^{41}$=Me, $R^{42}$=F, $R^{43}$=cPr, $R^{45}$=Cl], [66; $R^{41}$=Me, $R^{42}$=F, $R^{43}$=MeO, $R^{45}$=B(OH)$_2$], [67; $R^{41}$=Me, $R^{42}$=F, $R^{43}$=MeO, $R^{45}$=B(pin)], [68; $R^{41}$=Me, $R^{42}$=F, $R^{43}$=MeO, $R^{45}$=I], [69; $R^{41}$=Me, $R^{42}$=F, $R^{43}$=MeO, $R^{45}$=Br], [70; $R^{41}$=Me, $R^{42}$=F, $R^{43}$=MeO, $R^{45}$=Cl], [71; $R^{41}$=Me, $R^{42}$=F, $R^{43}$=Cl, $R^{45}$=B(OH)$_2$], [72; $R^{41}$=Me, $R^{42}$=F, $R^{43}$=Cl, $R^{45}$=B(pin)], [73; $R^{41}$=Me, $R^{42}$=F, $R^{43}$=Cl, $R^{45}$=I], [74; $R^{41}$=Me, $R^{42}$=F, $R^{43}$=Cl, $R^{45}$=Br], [75; $R^{41}$=Me, $R^{42}$=F, $R^{43}$=Cl, $R^{45}$=Cl], [76; $R^{41}$=Me, $R^{42}$=Cl, $R^{43}$=Me, $R^{45}$=B(OH)$_2$], [77; $R^{41}$=Me, $R^{42}$=Cl, $R^{43}$=Me, $R^{45}$=B(pin)], [78; $R^{41}$=Me, $R^{42}$=Cl, $R^{43}$=Me, $R^{45}$=I], [79; $R^{41}$=Me, $R^{42}$=Cl, $R^{43}$=Me, $R^{45}$=Br], [80; $R^{41}$=Me, $R^{42}$=Cl, $R^{43}$=Me, $R^{45}$=Cl], [81; $R^{41}$=Me, $R^{42}$=Cl, $R^{43}$=Et, $R^{45}$=B(OH)$_2$], [82; $R^{41}$=Me, $R^{42}$=Cl, $R^{43}$=Et, $R^{45}$=B(pin)], [83; $R^{41}$=Me, $R^{42}$=Cl, $R^{43}$=Et, $R^{45}$=I], [84; $R^{41}$=Me, $R^{42}$=Cl, $R^{43}$=Et, $R^{45}$=Br], [85; $R^{41}$=Me, $R^{42}$=Cl, $R^{43}$=Et, $R^{45}$=Cl], [86; $R^{41}$=Me, $R^{42}$=Cl, $R^{43}$=cPr, $R^{45}$=B(OH)$_2$], [87; $R^{41}$=Me, $R^{42}$=Cl, $R^{43}$=cPr, $R^{45}$=B(pin)], [88; $R^{41}$=Me, $R^{42}$=Cl, $R^{43}$=cPr, $R^{45}$=I], [89; $R^{41}$=Me, $R^{42}$=Cl, $R^{43}$=cPr, $R^{45}$=Br], [90; $R^{41}$=Me, $R^{42}$=Cl, $R^{43}$=cPr, $R^{45}$=Cl], [91; $R^{41}$=Me, $R^{42}$=Cl, $R^{43}$=MeO, $R^{45}$=B(OH)$_2$], [92; $R^{41}$=Me, $R^{42}$=Cl, $R^{43}$=MeO, $R^{45}$=B(pin)], [93; $R^{41}$=Me, $R^{42}$=Cl, $R^{43}$=MeO, $R^{45}$=I], [94; $R^{41}$=Me, $R^{42}$=Cl, $R^{43}$=MeO, $R^{45}$=Br], [95; $R^{41}$=Me, $R^{42}$=Cl, $R^{43}$=MeO, $R^{45}$=Cl], [96; $R^{41}$=Me, $R^{42}$=Cl, $R^{43}$=Cl, $R^{45}$=B(OH)$_2$], [97; $R^{41}$=Me, $R^{42}$=Cl, $R^{43}$=Cl, $R^{45}$=B(pin)], [98; $R^{41}$=Me, $R^{42}$=Cl, $R^{43}$=Cl, $R^{45}$=I], [99; $R^{41}$=Me, $R^{42}$=Cl, $R^{43}$=Cl, $R^{45}$=Br], [100; $R^{41}$=Me, $R^{42}$=Cl, $R^{43}$=Cl, $R^{45}$=Cl], [101; $R^{41}$=Et, $R^{42}$=H, $R^{43}$=Me, $R^{45}$=B(OH)$_2$], [102; $R^{41}$=Et, $R^{42}$=H, $R^{43}$=Me, $R^{45}$=B(pin)], [103; $R^{41}$=Et, $R^{42}$=H, $R^{43}$=Me, $R^{45}$=I], [104; $R^{41}$=Et, $R^{42}$=H, $R^{43}$=Me, $R^{45}$=Br], [105; $R^{41}$=Et, $R^{42}$=H, $R^{43}$=Me, $R^{45}$=Cl], [106; $R^{41}$=Et, $R^{42}$=H, $R^{43}$=Et, $R^{45}$=B(OH)$_2$], [107; $R^{41}$=Et, $R^{42}$=H, $R^{43}$=Et, $R^{45}$=B(pin)], [108; $R^{41}$=Et, $R^{42}$=H, $R^{43}$=Et, $R^{45}$=I], [109; $R^{41}$=Et, $R^{42}$=H, $R^{43}$=Et, $R^{45}$=Br], [110; $R^{41}$=Et, $R^{42}$=H, $R^{43}$=Et, $R^{45}$=Cl], [111; $R^{41}$=Et, $R^{42}$=H, $R^{43}$=cPr, $R^{45}$=B(OH)$_2$], [112; $R^{41}$=Et, $R^{42}$=H, $R^{43}$=cPr, $R^{45}$=B(pin)], [113; $R^{41}$=Et, $R^{42}$=H, $R^{43}$=cPr, $R^{45}$=I], [114; $R^{41}$=Et, $R^{42}$=H, $R^{43}$=cPr, $R^{45}$=Br], [115; $R^{41}$=Et, $R^{42}$=H, $R^{43}$=cPr, $R^{45}$=Cl], [116; $R^{41}$=Et, $R^{42}$=H, $R^{43}$=MeO, $R^{45}$=B(OH)$_2$], [117; $R^{41}$=Et, $R^{42}$=H, $R^{43}$=MeO, $R^{45}$=B(pin)], [118; $R^{41}$=Et, $R^{42}$=H, $R^{43}$=MeO, $R^{45}$=I], [119; $R^{41}$=Et, $R^{42}$=H, $R^{43}$=MeO, $R^{45}$=Br], [120; $R^{41}$=Et, $R^{42}$=H, $R^{43}$=MeO, $R^{45}$=Cl], [121; $R^{41}$=Et, $R^{42}$=H, $R^{43}$=Cl, $R^{45}$=B(OH)$_2$], [122; $R^{41}$=Et, $R^{42}$=H, $R^{43}$=Cl, $R^{45}$=B(pin)], [123; $R^{41}$=Et, $R^{42}$=H, $R^{43}$=Cl, $R^{45}$=I], [124; $R^{41}$=Et, $R^{42}$=H, $R^{43}$=Cl, $R^{45}$=Br], [125; $R^{41}$=Et, $R^{42}$=H, $R^{43}$=Cl, $R^{45}$=Cl], [126; $R^{41}$=Et, $R^{42}$=Me, $R^{43}$=Me, $R^{45}$=B(OH)$_2$], [127; $R^{41}$=Et, $R^{42}$=Me, $R^{43}$=Me, $R^{45}$=B(pin)], [128; $R^{41}$=Et, $R^{42}$=Me, $R^{43}$=Me, $R^{45}$=I], [129; $R^{41}$=Et, $R^{42}$=Me, $R^{43}$=Me, $R^{45}$=Br], [130; $R^{41}$=Et, $R^{42}$=Me, $R^{43}$=Me, $R^{45}$=Cl], [131; $R^{41}$=Et, $R^{42}$=Me, $R^{43}$=Et, $R^{45}$=B(OH)$_2$], [132; $R^{41}$=Et, $R^{42}$=Me, $R^{43}$=Et, $R^{45}$=B(pin)], [133; $R^{41}$=Et, $R^{42}$=Me, $R^{43}$=Et, $R^{45}$=I], [134; $R^{41}$=Et, $R^{42}$=Me, $R^{43}$=Et, $R^{45}$=Br], [135; $R^{41}$=Et, $R^{42}$=Me, $R^{43}$=Et, $R^{45}$=Cl], [136; $R^{41}$=Et, $R^{42}$=Me, $R^{43}$=cPr, $R^{45}$=B(OH)$_2$], [137; $R^{41}$=Et, $R^{42}$=Me, $R^{43}$=cPr, $R^{45}$=B(pin)], [138; $R^{41}$=Et, $R^{42}$=Me, $R^{43}$=cPr, $R^{45}$=I], [139; $R^{41}$=Et, $R^{42}$=Me, $R^{43}$=cPr, $R^{41}$=Br], [140; $R^{41}$=Et, $R^{42}$=Me, $R^{43}$=cPr, $R^{45}$=Cl], [141; $R^{41}$=Et, $R^{42}$=Me, $R^{43}$=MeO, $R^{45}$=B(OH)$_2$], [142; $R^{41}$=Et, $R^{42}$=Me, $R^{43}$=MeO, $R^{45}$=B(pin)], [143; $R^{41}$=Et, $R^{42}$=Me, $R^{43}$=MeO, $R^{45}$=I], [144; $R^{41}$=Et, $R^{42}$=Me, $R^{43}$=MeO, $R^{45}$=Br], [145; $R^{41}$=Et, $R^{42}$=Me, $R^{43}$=MeO, $R^{45}$=Cl], [146; $R^{41}$=Et, $R^{42}$=Me, $R^{43}$=Cl, $R^{45}$=B(OH)$_2$], [147; $R^{41}$=Et, $R^{42}$=Me, $R^{43}$=Cl, $R^{45}$=B (pin)], [148; $R^{41}$=Et, $R^{42}$=Me, $R^{43}$=Cl, $R^{45}$=I], [149; $R^{41}$=Et, $R^{42}$=Me, $R^{43}$=Cl, $R^{45}$=Br], [150; $R^{41}$=Et, $R^{42}$=Me, $R^{43}$=Cl, $R^{45}$=Cl], [151; $R^{41}$=Et, $R^{42}$=F, $R^{43}$=Me, $R^{45}$=B(OH)$_2$], [152; $R^{41}$=Et, $R^{42}$=F, $R^{43}$=Me, $R^{45}$=B(pin)], [153; $R^{41}$=Et, $R^{42}$=F, $R^{43}$=Me, $R^{45}$=I], [154; $R^{41}$=Et, $R^{42}$=F, $R^{43}$=Me, $R^{45}$=Br], [155; $R^{41}$=Et, $R^{42}$=F, $R^{43}$=Me, $R^{45}$=Cl], [156; $R^{41}$=Et, $R^{42}$=F, $R^{43}$=Et, $R^{45}$=B(OH)$_2$], [157; $R^{41}$=Et, $R^{42}$=F, $R^{43}$=Et, $R^{45}$=B(pin)], [158; $R^{41}$=Et, $R^{42}$=F, $R^{43}$=Et, $R^{45}$=I], [159; $R^{41}$=Et, $R^{42}$=F, $R^{43}$=Et, $R^{45}$=Br], [160; $R^{41}$=Et, $R^{42}$=F, $R^{43}$=Et, $R^{45}$=Cl], [161; $R^{41}$=Et, $R^{42}$=F, $R^{43}$=cPr, $R^{45}$=B(OH)$_2$], [162; $R^{41}$=Et, $R^{42}$=F, $R^{43}$=cPr, $R^{45}$=B(pin)], [163; $R^{41}$=Et, $R^{42}$=F, $R^{43}$=cPr, $R^{45}$=I], [164; $R^{41}$=Et, $R^{42}$=F, $R^{43}$=cPr, $R^{45}$=Br], [165; $R^{41}$=Et, $R^{42}$=F, $R^{43}$=cPr, $R^{45}$=Cl], [166; $R^{41}$=Et, $R^{42}$=F, $R^{43}$=MeO, $R^{45}$=B(OH)$_2$], [167; $R^{41}$=Et, $R^{42}$=F, $R^{43}$=MeO, $R^{45}$=B (pin)], [168; $R^{41}$=Et, $R^{42}$=F, $R^{43}$=MeO, $R^{45}$=I], [169; $R^{41}$=Et, $R^{42}$=F, $R^{43}$=MeO, $R^{45}$=Br], [170; $R^{41}$=Et, $R^{42}$=F, $R^{43}$=MeO, $R^{45}$=Cl], [171; $R^{41}$=Et, $R^{42}$=F, $R^{43}$=Cl, $R^{45}$=B(OH)$_2$], [172; $R^{41}$=Et, $R^{42}$=F, $R^{43}$=Cl, $R^{45}$=B(pin)], [173; $R^{41}$=Et, $R^{42}$=F, $R^{43}$=Cl, $R^{45}$=I], [174; $R^{41}$=Et, $R^{42}$=F, $R^{43}$=Cl, $R^{45}$=Br], [175; $R^{41}$=Et, $R^{42}$=F, $R^{43}$=Cl, $R^{45}$=Cl], [176; $R^{41}$=Et, $R^{42}$=Cl, $R^{43}$=Me, $R^{45}$=B(OH)$_2$], [177; $R^{41}$=Et, $R^{42}$=Cl, $R^{43}$=Me, $R^{45}$=B(pin)], [178; $R^{41}$=Et, $R^{42}$=Cl, $R^{43}$=Me, $R^{45}$=I], [179; $R^{41}$=Et, $R^{42}$=Cl, $R^{43}$=Me, $R^{45}$=Br], [180; $R^{41}$=Et, $R^{42}$=Cl, $R^{43}$=Me, $R^{45}$=Cl], [181; $R^{41}$=Et, $R^{42}$=Cl, $R^{43}$=Et, $R^{45}$=B(OH)$_2$], [182; $R^{41}$=Et, $R^{42}$=Cl, $R^{43}$=Et, $R^{45}$=B(pin)], [183; $R^{41}$=Et, $R^{42}$=Cl, $R^{43}$=Et, $R^{45}$=I], [184; $R^{41}$=Et, $R^{42}$=Cl, $R^{43}$=Et, $R^{45}$=Br], [185; $R^{41}$=Et, $R^{42}$=Cl, $R^{43}$=Et, $R^{45}$=Cl], [186; $R^{41}$=Et, $R^{42}$=Cl, $R^{43}$=cPr, $R^{45}$=B(OH)$_2$], [187; $R^{41}$=Et, $R^{42}$=Cl, $R^{43}$=cPr, $R^{45}$=B(pin)], [188; $R^{41}$=Et, $R^{42}$=Cl, $R^{43}$=cPr, $R^{45}$=I], [189; $R^{41}$=Et, $R^{42}$=Cl, $R^{43}$=cPr, $R^{45}$=Br], [190; $R^{41}$=Et, $R^{42}$=Cl, $R^{43}$=cPr, $R^{45}$=Cl], [191; $R^{41}$=Et, $R^{42}$=Cl, $R^{43}$=MeO, $R^{45}$=B(OH)$_2$], [192; $R^{41}$=Et, $R^{42}$=Cl, $R^{43}$=MeO, $R^{45}$=B(pin)], [193; $R^{41}$=Et, $R^{42}$=Cl, $R^{43}$=MeO, $R^{45}$=I], [194; $R^{41}$=Et, $R^{42}$=Cl, $R^{43}$=MeO, $R^{45}$=Br], [195; $R^{41}$=Et, $R^{42}$=Cl, $R^{43}$=MeO, $R^{45}$=Cl], [196; $R^{41}$=Et, $R^{42}$=Cl, $R^{43}$=Cl, $R^{45}$=B(OH)$_2$], [197; $R^{41}$=Et, $R^{42}$=Cl, $R^{43}$=Cl, $R^{45}$=B (pin)], [198; $R^{41}$=Et, $R^{42}$=Cl, $R^{43}$=Cl, $R^{45}$=I], [199; $R^{41}$=Et, $R^{42}$=Cl, $R^{43}$=Cl, $R^{45}$=Br], [200; $R^{41}$=Et, $R^{42}$=Cl, $R^{43}$=Cl, $R^{45}$=Cl], [201; $R^{41}$=CF$_3$, $R^{42}$=H, $R^{43}$=Me, $R^{45}$=B(pin)], [202; $R^{41}$=CF$_3$, $R^{42}$=H, $R^{43}$=Me, $R^{45}$=I], [203; $R^{41}$=CF$_3$, $R^{42}$=H, $R^{43}$=Me, $R^{45}$=Br], [204; $R^{41}$=CF$_3$, $R^{42}$=H, $R^{43}$=Me, $R^{45}$=Cl], [205; $R^{41}$=CF$_3$, $R^{42}$=H, $R^{43}$=Et, $R^{45}$=B(OH)$_2$], [206; $R^{41}$=CF$_3$, $R^{42}$=H, $R^{43}$=Et, $R^{45}$=B(pin)], [207; $R^{41}$=CF$_3$, $R^{42}$=H, $R^{43}$=Et, $R^{45}$=I], [208; $R^{41}$=CF$_3$, $R^{42}$=H, $R^{43}$=Et, $R^{45}$=Br], [209; $R^{41}$=CF$_3$, $R^{42}$=H, $R^{43}$=Et, $R^{45}$=Cl], [210; $R^{41}$=CF$_3$, $R^{42}$=H, $R^{43}$=cPr, $R^{45}$=B(OH)$_2$], [211; $R^{41}$=CF$_3$, $R^{42}$=H, $R^{43}$=cPr, $R^{45}$=B(pin)], [212; $R^{41}$=CF$_3$, $R^{42}$=H, $R^{43}$=cPr, $R^{45}$=I], [213; $R^{41}$=CF$_3$, $R^{42}$=H, $R^{43}$=cPr, $R^{45}$=Br], [214; $R^{41}$=CF$_3$, $R^{42}$=H, $R^{43}$=cPr, $R^{45}$=Cl], [215; $R^{41}$=CF$_3$, $R^{42}$=H, $R^{43}$=MeO, $R^{45}$=B(OH)$_2$], [216; $R^{41}$=CF$_3$, $R^{42}$=H, $R^{43}$=MeO, $R^{45}$=B(pin)], [217; $R^{41}$=CF$_3$, $R^{42}$=H, $R^{43}$=MeO, $R^{45}$=I], [218; $R^{41}$=CF$_3$, $R^{42}$=H, $R^{43}$=MeO, $R^{45}$=Br], [219; $R^{41}$=CF$_3$, $R^{42}$=H, $R^{43}$=MeO, $R^{45}$=Cl], [220; $R^{41}$=CF$_3$, $R^{42}$=H, $R^{43}$=Cl, $R^{45}$=B(OH)$_2$], [221; $R^{41}$=CF$_3$, $R^{42}$=H, $R^{43}$=Cl, $R^{45}$=B (pin)], [222; $R^{41}$=CF$_3$, $R^{42}$=H, $R^{43}$=Cl, $R^{45}$=I], [223; $R^{41}$=CF$_3$, $R^{42}$=H, $R^{43}$=Cl, $R^{45}$=Br], [224; $R^{41}$=CF$_3$, $R^{42}$=H, $R^{43}$=Cl, $R^{45}$=Cl], [225; $R^{41}$=CF$_3$, $R^{42}$=Me, $R^{43}$=Me, $R^{45}$=B(OH)$_2$], [226; $R^{41}$=CF$_3$, $R^{42}$=Me, $R^{43}$=Me, $R^{45}$=B(pin)], [227; $R^{41}$=CF$_3$, $R^{42}$=Me, $R^{43}$=Me, $R^{45}$=I], [228; $R^{41}$=CF$_3$, $R^{42}$=Me, $R^{43}$=Me, $R^{45}$=Br], [229; $R^{41}$=CF$_3$, $R^{42}$=Me, $R^{43}$=Me, $R^{45}$=Cl], [230; $R^{41}$=CF$_3$, $R^{42}$=Me, $R^{43}$=Et, $R^{45}$=B(OH)$_2$], [231; $R^{41}$=CF$_3$, $R^{42}$=Me, $R^{43}$=Et, $R^{45}$=B(pin)], [232; $R^{41}$=CF$_3$, $R^{42}$=Me, $R^{43}$=Et, $R^{45}$=I], [233; $R^{41}$=CF$_3$, $R^{42}$=Me, $R^{43}$=Et, $R^{45}$=Br], [234; $R^{41}$=CF$_3$, $R^{42}$=Me, $R^{43}$=Et, $R^{45}$=Cl], [235; $R^{41}$=CF$_3$, $R^{42}$=Me, $R^{43}$=cPr, $R^{45}$=B(OH)$_2$], [236; $R^{41}$=CF$_3$, $R^{42}$=Me, $R^{43}$=cPr, $R^{45}$=B (pin)], [237; $R^{41}$=CF$_3$, $R^{42}$=Me, $R^{43}$=cPr, $R^{45}$=I], [238; $R^{41}$=CF$_3$, $R^{42}$=Me, $R^{43}$=cPr, $R^{45}$=Br], [239; $R^{41}$=CF$_3$, $R^{42}$=Me, $R^{43}$=cPr, $R^{45}$=Cl], [240; $R^{41}$=CF$_3$, $R^{42}$=Me, $R^{43}$=MeO, $R^{45}$=B(OH)$_2$], [241; $R^{41}$=CF$_3$, $R^{42}$=Me, $R^{43}$=MeO, $R^{45}$=B(pin)], [242; $R^{41}$=CF$_3$, $R^{42}$=Me, $R^{43}$=MeO, $R^{45}$=I], [243; $R^{41}$=CF$_3$, $R^{42}$=Me, $R^{43}$=MeO, $R^{45}$=Br], [244; $R^{41}$=CF$_3$, $R^{42}$=Me, $R^{43}$=MeO, $R^{45}$=Cl], [245; $R^{41}$=CF$_3$, $R^{42}$=Me, $R^{43}$=Cl, $R^{45}$=B(OH)$_2$], [246; $R^{41}$=CF$_3$, $R^{42}$=Me, $R^{43}$=Cl, $R^{45}$=B (pin)], [247; $R^{41}$=CF$_3$, $R^{42}$=Me, $R^{43}$=Cl, $R^{45}$=I], [248; $R^{41}$=CF$_3$, $R^{42}$=Me, $R^{43}$=Cl, $R^{45}$=Br], [249; $R^{41}$=CF$_3$, $R^{42}$=Me, $R^{43}$=Cl, $R^{45}$=Cl], [250; $R^{41}$=CF$_3$, $R^{42}$=F, $R^{43}$=Me, $R^{45}$=B(OH)$_2$], [251; $R^{41}$=CF$_3$, $R^{42}$=F, $R^{43}$=Me, $R^{45}$=B(pin)], [252; $R^{41}$=CF$_3$, $R^{42}$=F, $R^{43}$=Me, $R^{45}$=I], [253; $R^{41}$=CF$_3$, $R^{42}$=F, $R^{43}$=Me, $R^{45}$=Br], [254; $R^{41}$=CF$_3$, $R^{42}$=F, $R^{43}$=Me, $R^{45}$=Cl], [255; $R^{41}$=CF$_3$, $R^{42}$=F, $R^{43}$=Et, $R^{45}$=B(OH)$_2$], [256; $R^{41}$=CF$_3$, $R^{42}$=F, $R^{43}$=Et, $R^{45}$=B(pin)], [257; $R^{41}$=CF$_3$, $R^{42}$=F, $R^{43}$=Et, $R^{45}$=I], [258; $R^{41}$=CF$_3$, $R^{42}$=F, $R^{43}$=Et, $R^{45}$=Br], [259; $R^{41}$=CF$_3$, $R^{42}$=F, $R^{43}$=Et, $R^{45}$=Cl], [260; $R^{41}$=CF$_3$, $R^{42}$=F, $R^{43}$=cPr, $R^{45}$=B(OH)$_2$], [261; $R^{41}$=CF$_3$, $R^{42}$=F, $R^{43}$=cPr, $R^{45}$=B(pin)], [262; $R^{41}$=CF$_3$, $R^{42}$=F, $R^{43}$=cPr, $R^{45}$=I], [263; $R^{41}$=CF$_3$, $R^{42}$=F, $R^{43}$=cPr, $R^{45}$=Br], [264; $R^{41}$=CF$_3$, $R^{42}$=F, $R^{43}$=cPr, $R^{45}$=Cl], [265; $R^{41}$=CF$_3$, $R^{42}$=F, $R^{43}$=MeO, $R^{45}$=B(OH)$_2$], [266; $R^{41}$=CF$_3$, $R^{42}$=F, $R^{43}$=MeO, $R^{45}$=B(pin)], [267; $R^{41}$=CF$_3$, $R^{42}$=F, $R^{43}$=MeO, $R^{45}$=I], [268; $R^{41}$=CF$_3$, $R^{42}$=F, $R^{43}$=MeO, $R^{45}$=Br], [269; $R^{41}$=CF$_3$, $R^{42}$=F, $R^{43}$=MeO, $R^{45}$=Cl], [270; $R^{41}$=CF$_3$, $R^{42}$=F, $R^{43}$=Cl, $R^{45}$=B(OH)$_2$][271; $R^{41}$=CF$_3$, $R^{42}$=F, $R^{43}$=Cl, $R^{45}$=B(pin)], [272; $R^{41}$=CF$_3$, $R^{42}$=F, $R^{43}$=Cl, $R^{45}$=I], [273; $R^{41}$=CF$_3$, $R^{42}$=F, $R^{43}$=Cl, $R^{45}$=Br], [274; $R^{41}$=CF$_3$, $R^{42}$=F, $R^{43}$=Cl, $R^{45}$=Cl], [275; $R^{41}$=CF$_3$, $R^{42}$=Cl, $R^{43}$=Me, $R^{45}$=B(OH)$_2$], [276; $R^{41}$=CF$_3$, $R^{42}$=Cl, $R^{43}$=Me, $R^{45}$=B (pin)], [277; $R^{41}$=CF$_3$, $R^{42}$=Cl, $R^{43}$=Me, $R^{45}$=I], [278; $R^{41}$=CF$_3$, $R^{42}$=Cl, $R^{43}$=Me, $R^{45}$=Br], [279; $R^{41}$=CF$_3$, $R^{42}$=Cl, $R^{43}$=Me, $R^{45}$=Cl], [280; $R^{41}$=CF$_3$, $R^{42}$=Cl, $R^{43}$=Et, $R^{45}$=B(OH)$_2$], [281; $R^{41}$=CF$_3$, $R^{42}$=Cl, $R^{43}$=Et, $R^{41}$=B(pin)], [282; $R^{41}$=CF$_3$, $R^{42}$=Cl, $R^{43}$=Et, $R^{45}$=I], [283; $R^{41}$=CF$_3$, $R^{42}$=Cl, $R^{43}$=Et, $R^{45}$=Br], [284; $R^{41}$=CF$_3$, $R^{42}$=Cl, $R^{43}$=Et, $R^{45}$=Cl], [285; $R^{41}$=CF$_3$, $R^{42}$=Cl, $R^{43}$=cPr, $R^{45}$=B(OH)$_2$], [286; $R^{41}$=CF$_3$, $R^{42}$=Cl, $R^{43}$=cPr, $R^{45}$=B (pin)], [287; $R^{41}$=CF$_3$, $R^{42}$=Cl, $R^{43}$=cPr, $R^{45}$=I], [288; $R^{41}$=CF$_3$, $R^{42}$=Cl, $R^{43}$=cPr, $R^{45}$=Br], [289; $R^{41}$=CF$_3$, $R^{42}$=Cl, $R^{43}$=cPr, $R^{45}$=Cl], [290; $R^{41}$=CF$_3$, $R^{42}$=Cl, $R^{43}$=MeO, $R^{45}$=B (OH)$_2$], [291; $R^{41}$=CF$_3$, $R^{42}$=Cl, $R^{43}$=MeO, $R^{45}$=B (pin)], [292; $R^{41}$=CF$_3$, $R^{42}$=Cl, $R^{43}$=MeO, $R^{45}$=I], [293; $R^{41}$=CF$_3$, $R^{42}$=Cl, $R^{43}$=MeO, $R^{45}$=Br], [294; $R^{41}$=CF$_3$, $R^{42}$=Cl, $R^{43}$=MeO, $R^{45}$=Cl], [295; $R^{41}$=CF$_3$, $R^{42}$=Cl, $R^{43}$=Cl, $R^{45}$=B(OH)$_2$], [296; $R^{41}$=CF$_3$, $R^{42}$=Cl, $R^{43}$=Cl, $R^{45}$=B(pin)], [297; $R^{41}$=CF$_3$, $R^{42}$=Cl, $R^{43}$=Cl, $R^{45}$=I], [298; $R^{41}$=CF$_3$, $R^{42}$=Cl, $R^{43}$=Cl, $R^{45}$=Br], [299; $R^{41}$=CF$_3$, $R^{42}$=Cl, $R^{43}$=Cl, $R^{45}$=Cl]

For example, the present compound LAMA-1 is represented by the following formula, which has substituent number 1 in formula (LAMA).

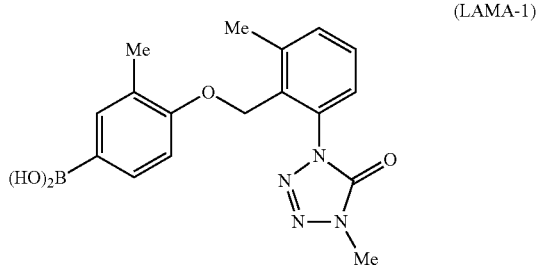 [SMILES: Cc1cc(B(O)O)ccc1OCc1c(C)cccc1-n1nnn(C)c1=O]

(LAMA-1)

Examples of the present control agent include the followings:
a pest control composition comprising any one of the present compounds 1 to 253 and prothioconazole at a ratio of 0.1:1; a pest control composition comprising any one of the present compounds 1 to 253 and prothioconazole at a ratio of 1:1; a pest control composition comprising any one of the present compounds 1 to 253 and prothioconazole at a ratio of 10:1; a pest control composition comprising any one of the present compounds 1 to 253 and bromuconazole at a ratio of 0.1:1; a pest control composition comprising any one of the present compounds 1 to 253 and bromuconazole at a ratio of 1:1; a pest control composition comprising any one of the present compounds 1 to 253 and bromuconazole at a ratio of 10:1; a pest control composition comprising any one of the present compounds 1 to 253 and metconazole at a ratio of 0.1:1; a pest control composition comprising any one of the present compounds 1 to 253 and metconazole at a ratio of 1:1; a pest control composition comprising any one of the present compounds 1 to 253 and metconazole at a ratio of 10:1; a pest control composition comprising any one of the present compounds 1 to 253 and tebuconazole at a ratio of 0.1:1; a pest control composition comprising any one of the present compounds 1 to 253 and tebuconazole at a ratio of 1:1; a pest control composition comprising any one of the present compounds 1 to 253 and tebuconazole at a ratio of 10:1; a pest control composition comprising any one of the present compounds 1 to 253 and tetraconazole at a ratio of 0.1:1; a pest control composition comprising any one of the present compounds 1 to 253 and tetraconazole at a ratio of 1:1; a pest control composition comprising any one of the present compounds 1 to 253 and tetraconazole at a ratio of 10:1; a compounds 1 to 253 and cyproconazole at a ratio of 0.1:1; a pest control composition comprising any one of the present compounds 1 to 253 and cyproconazole at a ratio of 1:1; a pest control composition comprising any one of the present compounds 1 to 253 and cyproconazole at a ratio of 10:1; a pest control composition comprising any one of the present compounds 1 to 253 and flusilazol at a ratio of 0.1:1; a pest control composition comprising any one of the present compounds 1 to 253 and flusilazol at a ratio of 1:1; a pest control composition comprising any one of the present compounds 1 to 253 and flusilazol at a ratio of 10:1;
a pest control composition comprising any one of the present compounds 1 to 253 and prochloraz at a ratio of 0.1:1; a pest control composition comprising any one of the present compounds 1 to 253 and prochloraz at a ratio of 1:1; a pest control composition comprising any one of the present compounds 1 to 253 and prochloraz at a ratio of 10:1; a pest control composition comprising any one of the present compounds 1 to 253 and imazalil at a ratio of 0.1:1; a pest control composition comprising any one of the present compounds 1 to 253 and imazalil at a ratio of 1:1; a pest control composition comprising any one of the present compounds 1 to 253 and imazalil at a ratio of 10:1; a pest control composition comprising any one of the present compounds 1 to 253 and epoxiconazol at a ratio of 0.1:1; a pest control composition comprising any one of the present compounds 1 to 253 and epoxiconazol at a ratio of 1:1; a pest control composition comprising any one of the present compounds 1 to 253 and epoxiconazol at a ratio of 10:1; a pest control composition comprising any one of the present compounds 1 to 253 and propiconazole at a ratio of 0.1:1; a pest control composition comprising any one of the present compounds 1 to 253 and propiconazole at a ratio of 1:1; a pest control composition comprising any one of the present compounds 1 to 253 and propiconazole at a ratio of 10:1; a pest control composition comprising any one of the present compounds 1 to 253 and difenoconazole at a ratio of 0.1:1; a pest control composition comprising any one of the present compounds 1 to 253 and difenoconazole at a ratio of 1:1; a pest control composition comprising any one of the present compounds 1 to 253 and difenoconazole at a ratio of 10:1; a pest control composition comprising any one of the present compounds 1 to 253 and myclobutanil at a ratio of 0.1:1; a pest control composition comprising any one of the present compounds 1 to 253 and myclobutanil at a ratio of 1:1; a pest control composition comprising any one of the present compounds 1 to 253 and myclobutanil at a ratio of 10:1; a pest control composition comprising any one of the present compounds 1 to 253 and triadimenol at a ratio of 0.1:1; a pest control composition comprising any one of the present compounds 1 to 253 and triadimenol at a ratio of 1:1; a pest control composition comprising any one of the present compounds 1 to 253 and triadimenol at a ratio of 10:1;
a pest control composition comprising any one of the present compounds 1 to 253 and triadimefon at a ratio of 0.1:1; a pest control composition comprising any one of the present compounds 1 to 253 and triadimefon at a ratio of 1:1; a pest compounds 1 to 253 and triadimefon at a ratio of 10:1; a pest control composition comprising any one of the present compounds 1 to 253 and fluquinconazole at a ratio of 0.1:1; a pest control composition comprising any one of the present compounds 1 to 253 and fluquinconazole at a ratio of 1:1; a pest control composition comprising any one of the present compounds 1 to 253 and fluquinconazole at a ratio of 10:1; a pest control composition comprising any one of the present compounds 1 to 253 and triticonazole at a ratio of 0.1:1; a pest control composition comprising any one of the present compounds 1 to 253 and triticonazole at a ratio of 1:1; a pest control composition comprising any one of the present compounds 1 to 253 and triticonazole at a ratio of 10:1; a pest control composition comprising any one of the present compounds 1 to 253 and ipconazole at a ratio of 0.1:1; a pest control composition comprising any one of the present compounds 1 to 253 and ipconazole at a ratio of 1:1; a pest control composition comprising any one of the present compounds 1 to 253 and ipconazole at a ratio of 10:1; a pest control composition comprising any one of the present compounds 1 to 253 and triflumizol at a ratio of 0.1:1; a pest control composition comprising any one of the present compounds 1 to 253 and triflumizol at a ratio of 1:1; a pest control composition comprising any one of the present compounds 1 to 253 and triflumizol at a ratio of 10:1; a pest control composition comprising any one of the present compounds 1 to 253 and fenbuconazole at a ratio of 0.1:1; a pest control composition comprising any one of the present compounds 1 to 253 and fenbuconazole at a ratio of 1:1; a pest compounds 1 to 253 and fenbuconazole at a ratio of 10:1; a pest control composition comprising any one of the present compounds 1 to 253 and hexaconazole at a ratio of 0.1:1;

a pest control composition comprising any one of the present compounds 1 to 253 and hexaconazole at a ratio of 1:1; a pest control composition comprising any one of the present compounds 1 to 253 and hexaconazole at a ratio of 10:1; a pest control composition comprising any one of the present compounds 1 to 253 and bitertanol at a ratio of 0.1:1; a pest control composition comprising any one of the present compounds 1 to 253 and bitertanol at a ratio of 1:1; a pest control composition comprising any one of the present compounds 1 to 253 and bitertanol at a ratio of 10:1; a pest control composition comprising any one of the present compounds 1 to 253 and flutriafol at a ratio of 0.1:1; a pest control composition comprising any one of the present compounds 1 to 253 and flutriafol at a ratio of 1:1; a pest control composition comprising any one of the present compounds 1 to 253 and flutriafol at a ratio of 10:1; a pest control composition comprising any one of the present compounds 1 to 253 and simeconazole at a ratio of 0.1:1; a pest control composition comprising any one of the present compounds 1 to 253 and simeconazole at a ratio of 1:1; a pest control composition comprising any one of the present compounds 1 to 253 and simeconazole at a ratio of 10:1; a pest control composition comprising any one of the present compounds 1 to 253 and imibenconazole at a ratio of 0.1:1; a pest control composition comprising any one of the present compounds 1 to 253 and imibenconazole at a ratio of 1:1; a pest control composition comprising any one of the present compounds 1 to 253 and imibenconazole at a ratio of 10:1; a pest control composition comprising any one of the present compounds 1 to 253 and oxpoconazole at a ratio of 0.1:1; a pest control composition comprising any one of the present compounds 1 to 253 and oxpoconazole at a ratio of 1:1; a pest control composition comprising any one of the present compounds 1 to 253 and oxpoconazole at a ratio of 10:1; a pest control composition comprising any one of the present compounds 1 to 253 and azoxystrobin at a ratio of 0.1:1; a pest control composition comprising any one of the present compounds 1 to 253 and azoxystrobin at a ratio of 1:1; a pest control composition comprising any one of the present compounds 1 to 253 and azoxystrobin at a ratio of 10:1; a pest control composition comprising any one of the present compounds 1 to 253 and pyraclostrobin at a ratio of 0.1:1; a pest control composition comprising any one of the present compounds 1 to 253 and pyraclostrobin at a ratio of 1:1; a pest control composition comprising any one of the present compounds 1 to 253 and pyraclostrobin at a ratio of 10:1; a pest control composition comprising any one of the present compounds 1 to 253 and picoxystrobin at a ratio of 0.1:1; a pest control composition comprising any one of the present compounds 1 to 253 and picoxystrobin at a ratio of 1:1; a pest control composition comprising any one of the present compounds 1 to 253 and picoxystrobin at a ratio of 10:1; a pest control composition comprising any one of the present compounds 1 to 253 and fluoxastrobin at a ratio of 0.1:1; a compounds 1 to 253 and fluoxastrobin at a ratio of 1:1; a pest control composition comprising any one of the present compounds 1 to 253 and fluoxastrobin at a ratio of 10:1; a pest control composition comprising any one of the present compounds 1 to 253 and trifloxystrobin at a ratio of 0.1:1; a pest control composition comprising any one of the present compounds 1 to 253 and trifloxystrobin at a ratio of 1:1; a pest control composition comprising any one of the present compounds 1 to 253 and trifloxystrobin at a ratio of 10:1; a pest control composition comprising any one of the present compounds 1 to 253 and mandestrobin at a ratio of 0.1:1; a pest control composition comprising any one of the present compounds 1 to 253 and mandestrobin at a ratio of 1:1; a pest control composition comprising any one of the present compounds 1 to 253 and mandestrobin at a ratio of 10:1; a pest control composition comprising any one of the present compounds 1 to 253 and kresoxim-methyl at a ratio of 0.1:1; a pest control composition comprising any one of the present compounds 1 to 253 and kresoxim-methyl at a ratio of 1:1; a pest control composition comprising any one of the present compounds 1 to 253 and kresoxim-methyl at a ratio of 10:1; a pest control composition comprising any one of the present compounds 1 to 253 and dimoxystrobin at a ratio of 0.1:1; a pest control composition comprising any one of the present compounds 1 to 253 and dimoxystrobin at a ratio of 1:1; a pest control composition comprising any one of the present compounds 1 to 253 and dimoxystrobin at a ratio of 10:1; a pest control composition comprising any one of the present compounds 1 to 253 and pyribencarb at a ratio of 0.1:1; a pest control composition comprising any one of the present compounds 1 to 253 and pyribencarb at a ratio of 1:1; a pest control composition comprising any one of the present compounds 1 to 253 and pyribencarb at a ratio of 10:1; a pest control composition comprising any one of the present compounds 1 to 253 and famoxadon at a ratio of 0.1:1; a pest control composition comprising any one of the present compounds 1 to 253 and famoxadon at a ratio of 1:1; a pest control composition comprising any one of the present compounds 1 to 253 and famoxadon at a ratio of 10:1; a pest control composition comprising any one of the present compounds 1 to 253 and fenamidone at a ratio of 0.1:1; a pest control composition comprising any one of the present compounds 1 to 253 and fenamidone at a ratio of 1:1; a pest control composition comprising any one of the present compounds 1 to 253 and fenamidone at a ratio of 10:1; a pest control composition comprising any one of the present compounds 1 to 253 and metominostrobin at a ratio of 0.1:1; a pest control composition comprising any one of the present compounds 1 to 253 and metominostrobin at a ratio of 1:1; a pest control composition comprising any one of the present compounds 1 to 253 and metominostrobin at a ratio of 10:1; a pest control composition comprising any one of the present compounds 1 to 253 and orysastrobin at a ratio of 0.1:1; a pest control composition comprising any one of the present compounds 1 to 253 and orysastrobin at a ratio of 1:1; a pest control composition comprising any one of the present compounds 1 to 253 and orysastrobin at a ratio of 10:1; a pest control composition comprising any one of the present compounds 1 to 253 and enestrobin at a ratio of 0.1:1; a pest control composition comprising any one of the present compounds 1 to 253 and enestrobin at a ratio of 1:1; a pest control composition comprising any one of the present compounds 1 to 253 and enestrobin at a ratio of 10:1; a pest control composition comprising any one of the present compounds 1 to 253 and pyraoxystrobin at a ratio of 0.1:1; a pest control composition comprising any one of the present compounds 1 to 253 and pyraoxystrobin at a ratio of 1:1; a pest control composition comprising any one of the present compounds 1 to 253 and pyraoxystrobin at a ratio of 10:1; a pest control composition comprising any one of the present compounds 1 to 253 and pyrametostrobin at a ratio of 0.1:1; a pest control composition comprising any one of the present compounds 1 to 253 and pyrametostrobin at a ratio of 1:1; a pest control composition comprising any one of the present compounds 1 to 253 and pyrametostrobin at a ratio of 10:1; a pest control composition comprising any one of the present compounds 1 to 253 and fenaminstrobin at a ratio of 0.1:1; a pest control composition comprising any one of the present compounds 1 to 253 and fenaminstrobin at a ratio of 1:1; a pest control composition comprising any one of the present compounds 1 to 253 and fenaminstrobin at a ratio of 10:1; a pest control composition comprising any one of the present compounds 1 to 253 and enoxastrobin at a ratio of 0.1:1; a pest control composition comprising any one of the present compounds 1 to 253 and enoxastrobin at a ratio of 1:1; a pest control composition comprising any one of the present compounds 1 to 253 and enoxastrobin at a ratio of 10:1; a pest compounds 1 to 253 and coumoxystrobin at a ratio of 0.1:1; a pest control composition comprising any one of the present compounds 1 to 253 and coumoxystrobin at a ratio of 1:1; a pest control composition comprising any one of the present compounds 1 to 253 and coumoxystrobin at a ratio of 10:1; a pest control composition comprising any one of the present compounds 1 to 253 and triclopyricarb at a ratio of 0.1:1; a pest control composition comprising any one of the present compounds 1 to 253 and triclopyricarb at a ratio of 1:1;

a pest control composition comprising any one of the present compounds 1 to 253 and triclopyricarb at a ratio of 10:1; a pest control composition comprising any one of the present compounds 1 to 253 and bixafen at a ratio of 0.1:1; a pest control composition comprising any one of the present compounds 1 to 253 and bixafen at a ratio of 1:1; a pest control composition comprising any one of the present compounds 1 to 253 and bixafen at a ratio of 10:1; a pest control composition comprising any one of the present compounds 1 to 253 and isopyrazam at a ratio of 0.1:1; a pest control composition comprising any one of the present compounds 1 to 253 and isopyrazam at a ratio of 1:1; a pest control composition comprising any one of the present compounds 1 to 253 and isopyrazam at a ratio of 10:1; a pest control composition comprising any one of the present compounds 1 to 253 and fluopyram at a ratio of 0.1:1; a pest control composition comprising any one of the present compounds 1 to 253 and fluopyram at a ratio of 1:1; a pest control composition comprising any one of the present compounds 1 to 253 and fluopyram at a ratio of 10:1; a pest control composition comprising any one of the present compounds 1 to 253 and penthiopyrad at a ratio of 0.1:1; a pest control composition comprising any one of the present compounds 1 to 253 and penthiopyrad at a ratio of 1:1; a pest control composition comprising any one of the present compounds 1 to 253 and penthiopyrad at a ratio of 10:1; a pest control composition comprising any one of the present compounds 1 to 253 and benzovindiflupyr at a ratio of 0.1:1; a pest control composition comprising any one of the present compounds 1 to 253 and benzovindiflupyr at a ratio of 1:1; a pest control composition comprising any one of the present compounds 1 to 253 and benzovindiflupyr at a ratio of 10:1; a pest control composition comprising any one of the present compounds 1 to 253 and fluxapyroxad at a ratio of 0.1:1; a pest control composition comprising any one of the present compounds 1 to 253 and fluxapyroxad at a ratio of 1:1; a pest control composition comprising any one of the present compounds 1 to 253 and fluxapyroxad at a ratio of 10:1; a pest control composition comprising any one of the present compounds 1 to 253 and boscalid at a ratio of 0.1:1; a pest control composition comprising any one of the present compounds 1 to 253 and boscalid at a ratio of 1:1; a pest control composition comprising any one of the present compounds 1 to 253 and boscalid at a ratio of 10:1; a pest control composition comprising any one of the present compounds 1 to 253 and sedaxane at a ratio of 0.1:1; a pest control composition comprising any one of the present compounds 1 to 253 and sedaxane at a ratio of 1:1; a pest compounds 1 to 253 and sedaxane at a ratio of 10:1; a pest control composition comprising any one of the present compounds 1 to 253 and penflufen at a ratio of 0.1:1; a pest control composition comprising any one of the present compounds 1 to 253 and penflufen at a ratio of 1:1; a pest control composition comprising any one of the present compounds 1 to 253 and penflufen at a ratio of 10:1; a pest control composition comprising any one of the present compounds 1 to 253 and carboxin at a ratio of 0.1:1; a pest control composition comprising any one of the present compounds 1 to 253 and carboxin at a ratio of 1:1; a pest control composition comprising any one of the present compounds 1 to 253 and carboxin at a ratio of 10:1; a pest control composition comprising any one of the present compounds 1 to 253 and mepronil at a ratio of 0.1:1; a pest control composition comprising any one of the present compounds 1 to 253 and mepronil at a ratio of 1:1; a pest control composition comprising any one of the present compounds 1 to 253 and mepronil at a ratio of 10:1; a pest control composition comprising any one of the present compounds 1 to 253 and flutolanil at a ratio of 0.1:1; a pest control composition comprising any one of the present compounds 1 to 253 and flutolanil at a ratio of 1:1; a pest control composition comprising any one of the present compounds 1 to 253 and flutolanil at a ratio of 10:1; a pest control composition comprising any one of the present compounds 1 to 253 and thifluzamide at a ratio of 0.1:1; a pest control composition comprising any one of the present compounds 1 to 253 and thifluzamide at a ratio of 1:1; a pest compounds 1 to 253 and thifluzamide at a ratio of 10:1; a pest control composition comprising any one of the present compounds 1 to 253 and furametpyr at a ratio of 0.1:1; a pest control composition comprising any one of the present compounds 1 to 253 and furametpyr at a ratio of 1:1; a pest control composition comprising any one of the present compounds 1 to 253 and furametpyr at a ratio of 10:1; a pest control composition comprising any one of the present compounds 1 to 253 and isofetamid at a ratio of 0.1:1; a pest control composition comprising any one of the present compounds 1 to 253 and isofetamid at a ratio of 1:1; a pest control composition comprising any one of the present compounds 1 to 253 and isofetamid at a ratio of 10:1; a pest control composition comprising any one of the present compounds 1 to 253 and N-[2-(3,4-difluorophenyl)phenyl]-3-trifluoromethylpyrazine-2-carboxylic acid amide at a ratio of 0.1:1; a pest control composition comprising any one of the present compounds 1 to 253 and N-[2-(3,4-difluorophenyl)phenyl]-3-trifluoromethylpyrazine-2-carboxylic acid amide at a ratio of 1:1; a pest control composition comprising any one of the present compounds 1 to 253 and N-[2-(3,4-difluorophenyl)phenyl]-3-trifluoromethylpyrazine-2-carboxylic acid amide at a ratio of 10:1; a pest control composition comprising any one of the present compounds 1 to 253 and (R)-(−)-N-(1,1,3-trimethylindan-4-yl)-1-methyl-3-difluoromethylpyrazole-4-carboxylic acid amide at a ratio of 0.1:1; a pest control composition comprising any one of the present compounds 1 to 253 and (R)-(−)-N-(1,1,3-trimethylindan-4-yl)-1-methyl-3-difluoromethylpyrazole-4-carboxylic acid amide at a ratio of 1:1; a pest control composition comprising any one of the present compounds 1 to 253 and (R)-(−)-N-(1,1,3-trimethylindan-4-yl)-1-methyl-3-difluoromethylpyrazole-4-carboxylic acid amide at a ratio of 10:1; a pest control composition comprising any one of the present compounds 1 to 253 and 3-chloro-4-(2,6-difluorophenyl)-6-methyl-5-phenylpyridazine at a ratio of 0.1:1;

a pest control composition comprising any one of the present compounds 1 to 253 and 3-chloro-4-(2,6-difluorophenyl)-6-methyl-5-phenylpyridazine at a ratio of 1:1; a pest control composition comprising any one of the present compounds 1 to 253 and 3-chloro-4-(2,6-difluorophenyl)-6-methyl-5-phenylpyridazine at a ratio of 10:1; a pest control composition comprising any one of the present compounds 1 to 253 and 3-cyano-4-(2,6-difluorophenyl)-6-methyl-5-phenylpyridazine at a ratio of 0.1:1; a pest control composition comprising any one of the present compounds 1 to 253 and 3-cyano-4-(2,6-difluorophenyl)-6-methyl-5-phenylpyridazine at a ratio of 1:1; a pest control composition comprising any one of the present compounds 1 to 253 and 3-cyano-4-(2,6-difluorophenyl)-6-methyl-5-phenylpyridazine at a ratio of 10:1; a pest control composition comprising any one of the present compounds 1 to 253 and fenpropimorph at a ratio of 0.1:1; a pest control composition comprising any one of the present compounds 1 to 253 and fenpropimorph at a ratio of 1:1; a pest control composition comprising any one of the present compounds 1 to 253 and fenpropimorph at a ratio of 10:1; a pest control composition comprising any one of the present compounds 1 to 253 and fenpropidin at a ratio of 0.1:1; a pest control composition comprising any one of the present compounds 1 to 253 and fenpropidin at a ratio of 1:1; a pest control composition comprising any one of the present compounds 1 to 253 and fenpropidin at a ratio of 10:1; a pest control composition comprising any one of the present compounds 1 to 253 and spiroxamine at a ratio of 0.1:1; a pest control composition comprising any one of the present compounds 1 to 253 and spiroxamine at a ratio of 1:1; a pest control composition comprising any one of the present compounds 1 to 253 and spiroxamine at a ratio of 10:1; a pest control composition comprising any one of the present compounds 1 to 253 and tridemorph at a ratio of 0.1:1; a pest control composition comprising any one of the present compounds 1 to 253 and tridemorph at a ratio of 1:1; a pest control composition comprising any one of the present compounds 1 to 253 and tridemorph at a ratio of 10:1;

a pest control composition comprising any one of the present compounds 1 to 253 and cyprodinil at a ratio of 0.1:1; a pest control composition comprising any one of the present compounds 1 to 253 and cyprodinil at a ratio of 1:1; a pest control composition comprising any one of the present compounds 1 to 253 and cyprodinil at a ratio of 10:1; a pest control composition comprising any one of the present compounds 1 to 253 and pyrimethanil at a ratio of 0.1:1; a pest control composition comprising any one of the present compounds 1 to 253 and pyrimethanil at a ratio of 1:1; a pest control composition comprising any one of the present compounds 1 to 253 and pyrimethanil at a ratio of 10:1; a pest control composition comprising any one of the present compounds 1 to 253 and mepanipyrim at a ratio of 0.1:1; a pest control composition comprising any one of the present compounds 1 to 253 and mepanipyrim at a ratio of 1:1; a pest control composition comprising any one of the present compounds 1 to 253 and mepanipyrim at a ratio of 10:1; a pest control composition comprising any one of the present compounds 1 to 253 and fenpiclonil at a ratio of 0.1:1; a pest control composition comprising any one of the present compounds 1 to 253 and fenpiclonil at a ratio of 1:1; a pest control composition comprising any one of the present compounds 1 to 253 and fenpiclonil at a ratio of 10:1; a pest control composition comprising any one of the present compounds 1 to 253 and fludioxonil at a ratio of 0.1:1; a pest control composition comprising any one of the present compounds 1 to 253 and fludioxonil at a ratio of 1:1; a pest control composition comprising any one of the present compounds 1 to 253 and fludioxonil at a ratio of 10:1; a pest control composition comprising any one of the present compounds 1 to 253 and procymidone at a ratio of 0.1:1; a pest control composition comprising any one of the present compounds 1 to 253 and procymidone at a ratio of 1:1; a pest control composition comprising any one of the present compounds 1 to 253 and procymidone at a ratio of 10:1; a pest control composition comprising any one of the present compounds 1 to 253 and iprodione at a ratio of 0.1:1;

a pest control composition comprising any one of the present compounds 1 to 253 and iprodione at a ratio of 1:1; a pest compounds 1 to 253 and iprodione at a ratio of 10:1; a pest control composition comprising any one of the present compounds 1 to 253 and vinclozolin at a ratio of 0.1:1; a pest control composition comprising any one of the present compounds 1 to 253 and vinclozolin at a ratio of 1:1; a pest control composition comprising any one of the present compounds 1 to 253 and vinclozolin at a ratio of 10:1; a pest control composition comprising any one of the present compounds 1 to 253 and benomyl at a ratio of 0.1:1; a pest control composition comprising any one of the present compounds 1 to 253 and benomyl at a ratio of 1:1; a pest control composition comprising any one of the present compounds 1 to 253 and benomyl at a ratio of 10:1; a pest control composition comprising any one of the present compounds 1 to 253 and thiophanate-methyl at a ratio of 0.1:1; a pest control composition comprising any one of the present compounds 1 to 253 and thiophanate-methyl at a ratio of 1:1; a pest control composition comprising any one of the present compounds 1 to 253 and thiophanate-methyl at a ratio of 10:1; a pest control composition comprising any one of the present compounds 1 to 253 and carbendazim at a ratio of 0.1:1; a pest control composition comprising any one of the present compounds 1 to 253 and carbendazim at a ratio of 1:1; a pest control composition comprising any one of the present compounds 1 to 253 and carbendazim at a ratio of 10:1; a pest control composition comprising any one of the present compounds 1 to 253 and diethofencarb at a ratio of 0.1:1; a pest control composition comprising any one of the present compounds 1 to 253 and diethofencarb at a ratio of 1:1; a pest compounds 1 to 253 and diethofencarb at a ratio of 10:1; a pest control composition comprising any one of the present compounds 1 to 253 and metalaxyl at a ratio of 0.1:1; a pest control composition comprising any one of the present compounds 1 to 253 and metalaxyl at a ratio of 1:1; a pest control composition comprising any one of the present compounds 1 to 253 and metalaxyl at a ratio of 10:1;

a pest control composition comprising any one of the present compounds 1 to 253 and metalaxyl-M (mefenoxam) at a ratio of 0.1:1; a pest control composition comprising any one of the present compounds 1 to 253 and metalaxyl-M (mefenoxam) at a ratio of 1:1; a pest control composition comprising any one of the present compounds 1 to 253 and metalaxyl-M (mefenoxam) at a ratio of 10:1; a pest control composition comprising any one of the present compounds 1 to 253 and benalaxyl at a ratio of 0.1:1; a pest control composition comprising any one of the present compounds 1 to 253 and benalaxyl at a ratio of 1:1; a pest control composition comprising any one of the present compounds 1 to 253 and benalaxyl at a ratio of 10:1; a pest control composition comprising any one of the present compounds 1 to 253 and benalaxyl-M (kiralaxyl) at a ratio of 0.1:1; a pest control composition comprising any one of the present compounds 1 to 253 and benalaxyl-M (kiralaxyl) at a ratio of 1:1; a pest control composition comprising any one of the present compounds 1 to 253 and benalaxyl-M (kiralaxyl) at a ratio of 10:1; a pest control composition comprising any one of the present compounds 1 to 253 and dimethomorph at a ratio of 0.1:1; a pest control composition comprising any one of the present compounds 1 to 253 and dimethomorph at a ratio of 1:1; a pest control composition comprising any one of the present compounds 1 to 253 and dimethomorph at a ratio of 10:1; a pest control composition comprising any one of the present compounds 1 to 253 and iprovalicarb at a ratio of 0.1:1; a pest control composition comprising any one of the present compounds 1 to 253 and iprovalicarb at a ratio of 1:1; a pest control composition comprising any one of the present compounds 1 to 253 and iprovalicarb at a ratio of 10:1; a pest control composition comprising any one of the present compounds 1 to 253 and benthivalicarb-isopropyl at a ratio of 0.1:1; a pest control composition comprising any one of the present compounds 1 to 253 and benthivalicarb-isopropyl at a ratio of 1:1; a pest control composition comprising any one of the present compounds 1 to 253 and benthivalicarb-isopropyl at a ratio of 10:1; a pest control composition comprising any one of the present compounds 1 to 253 and mandipropamid at a ratio of 0.1:1;

a pest control composition comprising any one of the present compounds 1 to 253 and mandipropamid at a ratio of 1:1; a pest control composition comprising any one of the present compounds 1 to 253 and mandipropamid at a ratio of 10:1; a pest control composition comprising any one of the present compounds 1 to 253 and valifenalate at a ratio of 0.1:1; a pest control composition comprising any one of the present compounds 1 to 253 and valifenalate at a ratio of 1:1; a pest control composition comprising any one of the present compounds 1 to 253 and valifenalate at a ratio of 10:1; a pest control composition comprising any one of the present compounds 1 to 253 and cymoxanil at a ratio of 0.1:1; a pest control composition comprising any one of the present compounds 1 to 253 and cymoxanil at a ratio of 1:1; a pest control composition comprising any one of the present compounds 1 to 253 and cymoxanil at a ratio of 10:1; a pest control composition comprising any one of the present compounds 1 to 253 and fluopicolide at a ratio of 0.1:1; a pest control composition comprising any one of the present compounds 1 to 253 and fluopicolide at a ratio of 1:1; a pest control composition comprising any one of the present compounds 1 to 253 and fluopicolide at a ratio of 10:1; a pest control composition comprising any one of the present compounds 1 to 253 and cyazofamid at a ratio of 0.1:1; a pest control composition comprising any one of the present compounds 1 to 253 and cyazofamid at a ratio of 1:1; a pest control composition comprising any one of the present compounds 1 to 253 and cyazofamid at a ratio of 10:1; a pest control composition comprising any one of the present compounds 1 to 253 and amisulbrom at a ratio of 0.1:1; a pest control composition comprising any one of the present compounds 1 to 253 and amisulbrom at a ratio of 1:1; a pest control composition comprising any one of the present compounds 1 to 253 and amisulbrom at a ratio of 10:1; a pest control composition comprising any one of the present compounds 1 to 253 and ametoctradin at a ratio of 0.1:1; a pest control composition comprising any one of the present compounds 1 to 253 and ametoctradin at a ratio of 1:1;

a pest control composition comprising any one of the present compounds 1 to 253 and ametoctradin at a ratio of 10:1; a pest compounds 1 to 253 and ethaboxam at a ratio of 0.1:1; a pest control composition comprising any one of the present compounds 1 to 253 and ethaboxam at a ratio of 1:1; a pest control composition comprising any one of the present compounds 1 to 253 and ethaboxam at a ratio of 10:1; a pest control composition comprising any one of the present compounds 1 to 253 and zoxamide at a ratio of 0.1:1; a pest control composition comprising any one of the present compounds 1 to 253 and zoxamide at a ratio of 1:1; a pest control composition comprising any one of the present compounds 1 to 253 and zoxamide at a ratio of 10:1; a pest control composition comprising any one of the present compounds 1 to 253 and oxathiapiprolin at a ratio of 1:1; a pest control composition comprising any one of the present compounds 1 to 253 and oxathiapiprolin at a ratio of 10:1; a pest control composition comprising any one of the present compounds 1 to 253 and oxathiapiprolin at a ratio of 50:1; a pest control composition comprising any one of the present compounds 1 to 253 and picarbutrazox at a ratio of 0.1:1; a pest control composition comprising any one of the present compounds 1 to 253 and picarbutrazox at a ratio of 1:1; a pest control composition comprising any one of the present compounds 1 to 253 and picarbutrazox at a ratio of 10:1; a pest control composition comprising any one of the present compounds 1 to 253 and fosetylaluminum at a ratio of 0.01:1; a pest control composition comprising any one of the present compounds 1 to 253 and fosetylaluminum at a ratio of 0.1:1; a pest control composition comprising any one of the present compounds 1 to 253 and fosetylaluminum at a ratio of 1:1; a compounds 1 to 253 and a potassium salt of phosphorous acid at a ratio of 0.01:1; a pest control composition comprising any one of the present compounds 1 to 253 and a potassium salt of phosphorous acid at a ratio of 0.1:1; a pest control composition comprising any one of the present compounds 1 to 253 and a potassium salt of phosphorous acid at a ratio of 1:1; a pest control composition comprising any one of the present compounds 1 to 253 and propamocarb hydrochloride at a ratio of 0.01:1;

a pest control composition comprising any one of the present compounds 1 to 253 and propamocarb hydrochloride at a ratio of 0.1:1; a pest control composition comprising any one of the present compounds 1 to 253 and propamocarb hydrochloride at a ratio of 1:1; a pest control composition comprising any one of the present compounds 1 to 253 and fenpyrazamine at a ratio of 0.1:1; a pest control composition comprising any one of the present compounds 1 to 253 and fenpyrazamine at a ratio of 1:1; a pest control composition comprising any one of the present compounds 1 to 253 and fenpyrazamine at a ratio of 10:1; a pest control composition comprising any one of the present compounds 1 to 253 and fenhexamid at a ratio of 0.1:1; a pest control composition comprising any one of the present compounds 1 to 253 and fenhexamid at a ratio of 1:1; a pest control composition comprising any one of the present compounds 1 to 253 and fenhexamid at a ratio of 10:1; a pest control composition comprising any one of the present compounds 1 to 253 and fluazinam at a ratio of 0.1:1; a pest control composition comprising any one of the present compounds 1 to 253 and fluazinam at a ratio of 1:1; a pest control composition comprising any one of the present compounds 1 to 253 and fluazinam at a ratio of 10:1; a pest control composition comprising any one of the present compounds 1 to 253 and flusulfamide at a ratio of 0.1:1; a pest control composition comprising any one of the present compounds 1 to 253 and flusulfamide at a ratio of 1:1; a pest control composition comprising any one of the present compounds 1 to 253 and flusulfamide at a ratio of 10:1; a pest control composition comprising any one of the present compounds 1 to 253 and ferimzone at a ratio of 0.1:1; a pest control composition comprising any one of the present compounds 1 to 253 and ferimzone at a ratio of 1:1; a pest control composition comprising any one of the present compounds 1 to 253 and ferimzone at a ratio of 10:1; a pest control composition comprising any one of the present compounds 1 to 253 and quinoxyfen at a ratio of 0.1:1; a pest control composition comprising any one of the present compounds 1 to 253 and quinoxyfen at a ratio of 1:1;
a pest control composition comprising any one of the present compounds 1 to 253 and quinoxyfen at a ratio of 10:1; a pest control composition comprising any one of the present compounds 1 to 253 and metrafenone at a ratio of 0.1:1; a pest control composition comprising any one of the present compounds 1 to 253 and metrafenone at a ratio of 1:1; a pest control composition comprising any one of the present compounds 1 to 253 and metrafenone at a ratio of 10:1; a pest control composition comprising any one of the present compounds 1 to 253 and pyriofenone at a ratio of 0.1:1; a pest compounds 1 to 253 and pyriofenone at a ratio of 1:1;
a pest control composition comprising any one of the present compounds 1 to 253 and pyriofenone at a ratio of 10:1; a pest control composition comprising any one of the present compounds 1 to 253 and proquinazid at a ratio of 0.1:1; a pest control composition comprising any one of the present compounds 1 to 253 and proquinazid at a ratio of 1:1; a pest control composition comprising any one of the present compounds 1 to 253 and proquinazid at a ratio of 10:1; a pest control composition comprising any one of the present compounds 1 to 253 and cyflufenamid at a ratio of 0.1:1; a pest control composition comprising any one of the present compounds 1 to 253 and cyflufenamid at a ratio of 1:1; a pest control composition comprising any one of the present compounds 1 to 253 and cyflufenamid at a ratio of 10:1; a pest control composition comprising any one of the present compounds 1 to 253 and tolclofos-methyl at a ratio of 0.01:1; a pest control composition comprising any one of the present compounds 1 to 253 and tolclofos-methyl at a ratio of 0.1:1; a pest control composition comprising any one of the present compounds 1 to 253 and tolclofos-methyl at a ratio of 1:1; a pest control composition comprising any one of the present compounds 1 to 253 and laminaran at a ratio of 0.1:1; a pest control composition comprising any one of the present compounds 1 to 253 and laminaran at a ratio of 1:1; a pest control composition comprising any one of the present compounds 1 to 253 and laminaran at a ratio of 10:1; a pest control composition comprising any one of the present compounds 1 to 253 and pencycuron at a ratio of 0.1:1;
a pest control composition comprising any one of the present compounds 1 to 253 and pencycuron at a ratio of 1:1; a pest control composition comprising any one of the present compounds 1 to 253 and pencycuron at a ratio of 10:1; a pest control composition comprising any one of the present compounds 1 to 253 and carpropamid at a ratio of 0.1:1; a pest control composition comprising any one of the present compounds 1 to 253 and carpropamid at a ratio of 1:1; a pest control composition comprising any one of the present compounds 1 to 253 and carpropamid at a ratio of 10:1; a pest control composition comprising any one of the present compounds 1 to 253 and diclocymet at a ratio of 0.1:1; a pest control composition comprising any one of the present compounds 1 to 253 and diclocymet at a ratio of 1:1; a pest control composition comprising any one of the present compounds 1 to 253 and diclocymet at a ratio of 10:1; a pest control composition comprising any one of the present compounds 1 to 253 and tricyclazole at a ratio of 0.1:1; a pest control composition comprising any one of the present compounds 1 to 253 and tricyclazole at a ratio of 1:1; a pest control composition comprising any one of the present compounds 1 to 253 and tricyclazole at a ratio of 10:1; a pest control composition comprising any one of the present compounds 1 to 253 and pyroquilon at a ratio of 0.1:1; a pest control composition comprising any one of the present compounds 1 to 253 and pyroquilon at a ratio of 1:1; a pest control composition comprising any one of the present compounds 1 to 253 and pyroquilon at a ratio of 10:1; a pest control composition comprising any one of the present compounds 1 to 253 and fthalide at a ratio of 0.1:1; a pest control composition comprising any one of the present compounds 1 to 253 and fthalide at a ratio of 1:1; a pest control composition comprising any one of the present compounds 1 to 253 and fthalide at a ratio of 10:1; a pest control composition comprising any one of the present compounds 1 to 253 and probenazole at a ratio of 0.1:1; a pest control composition comprising any one of the present compounds 1 to 253 and probenazole at a ratio of 1:1; a pest control composition comprising any one of the present compounds 1 to 253 and probenazole at a ratio of 10:1; a pest control composition comprising any one of the present compounds 1 to 253 and isotianil at a ratio of 0.1:1;
a pest control composition comprising any one of the present compounds 1 to 253 and isotianil at a ratio of 1:1; a pest control composition comprising any one of the present compounds 1 to 253 and isotianil at a ratio of 10:1; a pest control composition comprising any one of the present compounds 1 to 253 and tiadinil at a ratio of 0.1:1; a pest control composition comprising any one of the present compounds 1 to 253 and tiadinil at a ratio of 1:1; a pest control composition comprising any one of the present compounds 1 to 253 and tiadinil at a ratio of 10:1; a pest control composition comprising any one of the present compounds 1 to 253 and tebufloquin at a ratio of 0.1:1; a pest control composition comprising any one of the present compounds 1 to 253 and tebufloquin at a ratio of 1:1; a pest control composition comprising any one of the present compounds 1 to 253 and tebufloquin at a ratio of 10:1; a pest compounds 1 to 253 and tolprocarb at a ratio of 0.1:1; a pest control composition comprising any one of the present compounds 1 to 253 and tolprocarb at a ratio of 1:1; a pest control composition comprising any one of the present compounds 1 to 253 and tolprocarb at a ratio of 10:1; a pest control composition comprising any one of the present compounds 1 to 253 and diclomezine at a ratio of 0.1:1; a pest control composition comprising any one of the present compounds 1 to 253 and diclomezine at a ratio of 1:1; a pest control composition comprising any one of the present compounds 1 to 253 and diclomezine at a ratio of 10:1; a pest control composition comprising any one of the present compounds 1 to 253 and validamycin at a ratio of 0.1:1; a pest control composition comprising any one of the present compounds 1 to 253 and validamycin at a ratio of 1:1; a pest control composition comprising any one of the present compounds 1 to 253 and validamycin at a ratio of 10:1; a pest control composition comprising any one of the present compounds 1 to 253 and isoprothiolane at a ratio of 0.1:1; a pest control composition comprising any one of the present compounds 1 to 253 and isoprothiolane at a ratio of 1:1; a pest control composition comprising any one of the present compounds 1 to 253 and isoprothiolane at a ratio of 10:1; a pest control composition comprising any one of the present compounds 1 to 253 and hydroxyisoxazole at a ratio of 0.1:1; a pest control composition comprising any one of the present compounds 1 to 253 and hydroxyisoxazole at a ratio of 1:1; a pest control composition comprising any one of the present compounds 1 to 253 and hydroxyisoxazole at a ratio of 10:1; a pest control composition comprising any one of the present compounds 1 to 253 and kasugamycin at a ratio of 0.1:1; a pest control composition comprising any one of the present compounds 1 to 253 and kasugamycin at a ratio of 1:1; a pest control composition comprising any one of the present compounds 1 to 253 and kasugamycin at a ratio of 10:1; a pest control composition comprising any one of the present compounds 1 to 253 and streptomycin at a ratio of 0.1:1; a pest control composition comprising any one of the present compounds 1 to 253 and streptomycin at a ratio of 1:1; a pest control composition comprising any one of the present compounds 1 to 253 and streptomycin at a ratio of 10:1; a pest control composition comprising any one of the present compounds 1 to 253 and oxolinic acid at a ratio of 0.1:1; a pest control composition comprising any one of the present compounds 1 to 253 and oxolinic acid at a ratio of 1:1; a pest control composition comprising any one of the present compounds 1 to 253 and oxolinic acid at a ratio of 10:1; a pest control composition comprising any one of the present compounds 1 to 253 and tetracycline at a ratio of 0.1:1; a pest control composition comprising any one of the present compounds 1 to 253 and tetracycline at a ratio of 1:1; a pest control composition comprising any one of the present compounds 1 to 253 and tetracycline at a ratio of 10:1; a pest control composition comprising any one of the present compounds 1 to 253 and oxytetracycline at a ratio of 0.1:1; a pest control composition comprising any one of the present compounds 1 to 253 and oxytetracycline at a ratio of 1:1; a pest control composition comprising any one of the present compounds 1 to 253 and oxytetracycline at a ratio of 10:1; a pest control composition comprising any one of the present compounds 1 to 253 and silthiofam at a ratio of 0.01:1;
a pest control composition comprising any one of the present compounds 1 to 253 and silthiofam at a ratio of 0.1:1; a pest control composition comprising any one of the present compounds 1 to 253 and silthiofam at a ratio of 1:1; a pest control composition comprising any one of the present compounds 1 to 253 and chlorothalonil at a ratio of 0.01:1; a pest control composition comprising any one of the present compounds 1 to 253 and chlorothalonil at a ratio of 0.1:1; a pest control composition comprising any one of the present compounds 1 to 253 and chlorothalonil at a ratio of 1:1; a pest control composition comprising any one of the present compounds 1 to 253 and mancozeb at a ratio of 0.01:1; a pest control composition comprising any one of the present compounds 1 to 253 and mancozeb at a ratio of 0.1:1; a pest control composition comprising any one of the present compounds 1 to 253 and mancozeb at a ratio of 1:1; a pest control composition comprising any one of the present compounds 1 to 253 and folpet at a ratio of 0.01:1; a pest control composition comprising any one of the present compounds 1 to 253 and folpet at a ratio of 0.1:1; a pest control composition comprising any one of the present compounds 1 to 253 and folpet at a ratio of 1:1; a pest control composition comprising any one of the present compounds 1 to 253 and captan at a ratio of 0.01:1; a pest control composition comprising any one of the present compounds 1 to 253 and captan at a ratio of 0.1:1; a pest compounds 1 to 253 and captan at a ratio of 1:1; a pest control composition comprising any one of the present compounds 1 to 253 and thiuram at a ratio of 0.01:1; a pest control composition comprising any one of the present compounds 1 to 253 and thiuram at a ratio of 0.1:1; a pest control composition comprising any one of the present compounds 1 to 253 and thiuram at a ratio of 1:1; a pest control composition comprising any one of the present compounds 1 to 253 and metiram at a ratio of 0.01:1; a pest control composition comprising any one of the present compounds 1 to 253 and metiram at a ratio of 0.1:1; a pest control composition comprising any one of the present compounds 1 to 253 and metiram at a ratio of 1:1; a pest control composition comprising any one of the present compounds 1 to 253 and maneb at a ratio of 0.01:1;
a pest control composition comprising any one of the present compounds 1 to 253 and maneb at a ratio of 0.1:1; a pest control composition comprising any one of the present compounds 1 to 253 and maneb at a ratio of 1:1; a pest control composition comprising any one of the present compounds 1 to 253 and iminoctadine acetate at a ratio of 0.1:1; a pest control composition comprising any one of the present compounds 1 to 253 and iminoctadine acetate at a ratio of 1:1; a pest control composition comprising any one of the present compounds 1 to 253 and iminoctadine acetate at a ratio of 10:1; a pest control composition comprising any one of the present compounds 1 to 253 and sulfur at a ratio of 0.01:1; a pest control composition comprising any one of the present compounds 1 to 253 and sulfur at a ratio of 0.1:1; a pest control composition comprising any one of the present compounds 1 to 253 and sulfur at a ratio of 1:1; a pest control composition comprising any one of the present compounds 1 to 253 and copper oxychloride at a ratio of 0.01:1; a pest control composition comprising any one of the present compounds 1 to 253 and copper oxychloride at a ratio of 0.1:1; a pest control composition comprising any one of the present compounds 1 to 253 and copper oxychloride at a ratio of 1:1; a pest control composition comprising any one of the present compounds 1 to 253 and copper hydroxide at a ratio of 0.01:1; a pest control composition comprising any one of the present compounds 1 to 253 and copper hydroxide at a ratio of 0.1:1; a pest control composition comprising any one of the present compounds 1 to 253 and copper hydroxide at a ratio of 1:1; a pest control composition comprising any one of the present compounds 1 to 253 and copper hydroxide sulfate at a ratio of 0.01:1; a pest control composition comprising any one of the present compounds 1 to 253 and copper hydroxide sulfate at a ratio of 0.1:1; a pest control composition comprising any one of the present compounds 1 to 253 and copper hydroxide sulfate at a ratio of 1:1; a pest control composition comprising any one of the present compounds 1 to 253 and Bordeaux mixture at a ratio of 0.01:1; a pest control composition comprising any one of the present compounds 1 to 253 and Bordeaux mixture at a ratio of 0.1:1; a pest control composition comprising any one of the present compounds 1 to 253 and Bordeaux mixture at a ratio of 1:1;
a pest control composition comprising any one of the present compounds 1 to 253 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 0.1:1; a pest control composition comprising any one of the present compounds 1 to 253 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 1:1; a pest control composition comprising any one of the present compounds 1 to 253 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 10:1; a pest control composition comprising any one of the present compounds 1 to 253 and {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 0.1:1; a pest control composition comprising any one of the present compounds 1 to 253 and carboxamide; {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 1:1; a pest control composition comprising any one of the present compounds 1 to 253 and carboxamide; {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 10:1;
a pest control composition comprising any one of the present compounds 1 to 253 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 0.1:1; a pest control composition comprising any one of the present compounds 1 to 253 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 1:1; a pest control composition comprising any one of the present compounds 1 to 253 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 10:1; a pest control composition comprising any one of the present compounds 1 to 253 and 2,6-dimethyl-1H,5H-[1,4]dithiino[2,3-c:5,6-c']dipyrrole-1,3,5,7(2H,6H)-tetrone at a ratio of 0.01:1; a pest control composition comprising any one of the present compounds 1 to 253 and 2,6-dimethyl-1H,5H-[1,4]dithiino[2,3-c:5,6-c']dipyrrole-1,3,5,7(2H,6H)-tetrone at a ratio of 0.1:1; a pest control composition comprising any one of the present compounds 1 to 253 and 2,6-dimethyl-1H,5H-[1,4]dithiino[2,3-c:5,6-c']dipyrrole-1,3,5,7(2H,6H)-tetrone at a ratio of 1:1; a pest control composition comprising any one of the present compounds 1 to 253 and 3-(4,4-difluoro-3,3-dimethyl-3,4-dihydroisoquinolin-1-yl)quinoline at a ratio of 0.1:1; a pest control composition comprising any one of the present compounds 1 to 253 and 3-(4,4-difluoro-3,3-dimethyl-3,4-dihydroisoquinolin-1-yl)quinoline at a ratio of 1:1; a pest control composition comprising any one of the present compounds 1 to 253 and 3-(4,4-difluoro-3,3-dimethyl-3,4-dihydroisoquinolin-1-yl)quinoline at a ratio of 10:1; a pest control composition comprising any one of the present compounds 1 to 253 and 3-(5-fluoro-3,3,4,4-tetramethyl-3,4-dihydroisoquinolin-1-yl)quinoline at a ratio of 0.1:1;
a pest control composition comprising any one of the present compounds 1 to 253 and 3-(5-fluoro-3,3,4,4-tetramethyl-3,4-dihydroisoquinolin-1-yl)quinoline at a ratio of 1:1; a pest control composition comprising any one of the present compounds 1 to 253 and 3-(5-fluoro-3,3,4,4-tetramethyl-3,4-dihydroisoquinolin-1-yl)quinoline at a ratio of 10:1; a pest control composition comprising any one of the present compounds 1 to 253 and 3-(4,4,5-trifluoro-3,3-dimethyl-3,4-dihydroisoquinolin-1-yl)quinoline at a ratio of 0.1:1; a pest control composition comprising any one of the present compounds 1 to 253 and 3-(4,4,5-trifluoro-3,3-dimethyl-3,4-dihydroisoquinolin-1-yl)quinoline at a ratio of 1:1; a pest control composition comprising any one of the present compounds 1 to 253 and 3-(4,4,5-trifluoro-3,3-dimethyl-3,4-dihydroisoquinolin-1-yl)quinoline at a ratio of 10:1; a pest control composition comprising any one of the present compounds 1 to 253 and [3-(4-chloro-2-fluorophenyl)-5-(2,4-difluorophenyl)-1,2-oxazol-4-yl](pyridin-3-yl)methanol at a ratio of 0.1:1; a pest control composition comprising any one of the present compounds 1 to 253 and [3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 253 and [3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 253 and s-[3-(4-chloro-2-fluorophenyl)-5-(2,4-difluorophenyl)-1,2-oxazol-4-yl](pyridin-3-yl)methanol at a ratio of 0.1:1;
a pest control composition comprising any one of the present compounds 1 to 253 and (S)-[3-(4-chloro-2-fluorophenyl)-5-(2,4-difluorophenyl)-1,2-oxazol-4-yl](pyridin-3-yl) methanol at a ratio of 1:1; a pest control composition comprising any one of the present compounds 1 to 253 and (S)-[3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 253 and (R)-[3-(4-chloro-2-fluorophenyl)-5-(2,4-difluorophenyl)-1,2-oxazol-4-yl](pyridin-3-yl) methanol at a ratio of 0.1:1; a pest control composition comprising any one of the present compounds 1 to 253 and (R)-[3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 253 and (R)-[3-(4-chloro-2-fluorophenyl)-5-(2,4-difluorophenyl)-1,2-oxazol-4-yl](pyridin-3-yl) methanol at a ratio of 10:1; a pest control composition comprising any one of the present compounds 1 to 253 and 2-{[3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 253 and 2-{[3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 253 and 2-{[3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 253 and 2-{[rel-(2R,3S)-3-(2-chlorophenyl)-2-(2,4-difluorophenyl)oxylan-2-yl]methyl}-2,4-dihydro-3H-1,2,4-triazole-3-thione at a ratio of 0.1:1;
a pest control composition comprising any one of the present compounds 1 to 253 and 2-{[rel-(2R,3S)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 253 and 2-{[rel-(2R,3S)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 253 and 2-{[rel-(2R,3R)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 253 and 2-{[rel-(2R,3R)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 253 and 2-{[rel-(2R,3R)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 253 and 2-{[(2R,3S)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 253 and 2-{[(2R,3S)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 253 and 2-{[(2R,3S)-3-(2-chlorophenyl)-2-(2,4-difluorophenyl)oxylan-2-yl]methyl}-2,4-dihydro-3H-1,2,4-triazole-3-thione at a ratio of 10:1;

a pest control composition comprising any one of the present compounds 1 to 253 and 2-{[(2S,3R)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 253 and 2-{[(2S,3R)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 253 and 2-{[(2S,3R)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 253 and 2-{[(2R,3R)-3-(2-chlorophenyl)-2-(2,4-difluorophenyl)oxylan-2-yl]methyl}-2,4-dihydro-3H-1,2,4-triazole-3-thione at a ratio of 0.1:1; a pest control composition comprising any one of the present compounds 1 to 253 and 2-{[(2R,3R)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 253 and 2-{[(2R,3R)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 253 and 2-{[(2S,3S)-3-(2-chlorophenyl)-2-(2,4-difluorophenyl)oxylan-2-yl]methyl}-2,4-dihydro-3H-1,2,4-triazole-3-thione at a ratio of 0.1:1;

a pest control composition comprising any one of the present compounds 1 to 253 and 2-{[(2S,3S)-3-(2-chlorophenyl)-2-(2,4-difluorophenyl)oxylan-2-yl]methyl}-2,4-dihydro-3H-1,2,4-triazole-3-thione at a ratio of 1:1; a pest control composition comprising any one of the present compounds 1 to 253 and 2-{[(2S,3S)-3-(2-chlorophenyl)-2-(2,4-difluorophenyl)oxylan-2-yl]methyl}-2,4-dihydro-3H-1,2,4-triazole-3-thione at a ratio of 10:1; a pest control composition comprising any one of the present compounds 1 to 253 and 1-{[3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 253 and 1-{[3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 253 and 1-{[3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 253 and 1-{[rel-(2R,3S)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 253 and 1-{[rel-(2R,3S)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 253 and 1-{[rel-(2R,3S)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 253 and 1-{[rel-(2R,3R)-3-(2-chlorophenyl)-2-(2,4-difluorophenyl)oxylan-2-yl]methyl}-1H-1,2,4-triazole-5-thiol at a ratio of 0.1:1;

a pest control composition comprising any one of the present compounds 1 to 253 and 1-{[rel-(2R,3R)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 253 and 1-{[rel-(2R,3R)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 253 and 1-{[(2R,3S)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 253 and 1-{[(2R,3S)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 253 and 1-{[(2R,3S)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 253 and 1-{[(2S,3R)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 253 and 1-{[(2S,3R)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 253 and 1-{[(2S,3R)-3-(2-chlorophenyl)-2-(2,4-difluorophenyl)oxylan-2-yl]methyl}-1H-1,2,4-triazole-5-thiol at a ratio of 10:1;

a pest control composition comprising any one of the present compounds 1 to 253 and 1-{[(2R,3R)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 253 and 1-{[(2R,3R)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 253 and 1-{[(2R,3R)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 253 and 1-{[(2S,3S)-3-(2-chlorophenyl)-2-(2,4-difluorophenyl)oxylan-2-yl]methyl}-1H-1,2,4-triazole-5-thiol at a ratio of 0.1:1; a pest control composition comprising any one of the present compounds 1 to 253 and 1-{[(2S,3S)-3-(2-chlorophenyl)-2-(2,4-difluorophenyl)oxylan-2-yl]methyl}-1H-1,2,4-triazole-5-thiol at a ratio of 1:1; a pest control composition comprising any one of the present compounds 1 to 253 and 1-{[(2S,3S)-3-(2-chlorophenyl)-2-(2,4-difluorophenyl)oxylan-2-yl]methyl}-1H-1,2,4-triazole-5-thiol at a ratio of 10:1; a pest control composition comprising any one of the present compounds 1 to 253 and 1-{[3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 253 and 1-{[3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 253 and 1-{[3-(2-chlorophenyl)-2-(2,4-difluorophenyl)oxylan-2-yl]methyl}-1H-1,2,4-triazol-5-yl thiocyanate at a ratio of 10:1;
a pest control composition comprising any one of the present compounds 1 to 253 and 1-{[rel-(2R,3S)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 253 and 1-{[rel-(2R,3S)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 253 and 1-{[rel-(2R,3S)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 253 and 1-{[rel-(2R,3R)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 253 and 1-{[rel-(2R,3R)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 253 and 1-{[rel-(2R,3R)-3-(2-chlorophenyl)-2-(2,4-difluorophenyl)oxylan-2-yl]methyl}-1H-1,2,4-triazol-5-yl thiocyanate at a ratio of 10:1; a pest compounds 1 to 253 and 1-{[(2R,3S)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 253 and 1-{[(2R,3S)-3-(2-chlorophenyl)-2-(2,4-difluorophenyl)oxylan-2-yl]methyl}-1H-1,2,4-triazol-5-yl thiocyanate at a ratio of 1:1;
a pest control composition comprising any one of the present compounds 1 to 253 and 1-{[(2R,3S)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 253 and 1-{[(2S,3R)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 253 and 1-{[(2S,3R)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 253 and 1-{[(2S,3R)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 253 and 1-{[(2R,3R)-3-(2-chlorophenyl)-2-(2,4-difluorophenyl)oxylan-2-yl]methyl}-1H-1,2,4-triazol-5-yl thiocyanate at a ratio of 0.1:1; a pest control composition comprising any one of the present compounds 1 to 253 and 1-{[(2R,3R)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 253 and 1-{[(2R,3R)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 253 and 1-{[(2S,3S)-3-(2-chlorophenyl)-2-(2,4-difluorophenyl)oxylan-2-yl]methyl}-1H-1,2,4-triazol-5-yl thiocyanate at a ratio of 0.1:1;
a pest control composition comprising any one of the present compounds 1 to 253 and 1-{[(2S,3S)-3-(2-chlorophenyl)-2-(2,4-difluorophenyl)oxylan-2-yl]methyl}-1H-1,2,4-triazol-5-yl thiocyanate at a ratio of 1:1; a pest control composition comprising any one of the present compounds 1 to 253 and 1-{[(2S,3S)-3-(2-chlorophenyl)-2-(2,4-difluorophenyl)oxylan-2-yl]methyl}-1H-1,2,4-triazol-5-yl thiocyanate at a ratio of 10:1; a pest control composition comprising any one of the present compounds 1 to 253 and 5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 253 and 5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 253 and 5-(4-chlorobenzyl)-2-chloromethyl-2-methyl-1-(1H-1,2,4-triazol-1-ylmethyl)cyclopentanol at a ratio of 10:1; a pest control composition comprising any one of the present compounds 1 to 253 and (1RS,2SR,5SR)-5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 253 and (1RS,2SR,5SR)-5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 253 and (1RS,2SR,5SR)-5-(4-chlorobenzyl)-2-chloromethyl-2-methyl-1-(1H-1,2,4-triazol-1-ylmethyl)cyclopentanol at a ratio of 10:1;
a pest control composition comprising any one of the present compounds 1 to 253 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1RS,2SR,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1RS,2SR,5RS)-2-chloromethyl-5-(4-fluorobenzyl)-2-methyl-1-(1H-1,2,4-triazol-1-ylmethyl)cyclopentanol at a ratio of 10:1;
a pest control composition comprising any one of the present compounds 1 to 253 and (1R,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2S,5S)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 253 and (1R,2S,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1S,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1R,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2R,5R)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 253 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1S,2S,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1R,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2S,5R)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 253 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1S,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and 2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and 2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 253 and 2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1RS,2SR,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1RS,2SR,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1RS,2SR,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1RS,2RS,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1;

a pest control composition comprising any one of the present compounds 1 to 253 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1RS,2SR,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1R,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1R,2S,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 253 and (1S,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1R,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1S,2S,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 253 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1R,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1R,2S,5R)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 253 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 253 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 253 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 253 and (1S,2R,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 253 and 5-amino-4-(2-chloro-4-fluorophenyl)-N-(2,6-difluorophenyl)-1,3-dimethyl-1H-pyrazole at a ratio of 0.1:1; a pest control composition comprising any one of the present compounds 1 to 253 and 5-amino-4-(2-chloro-4-fluorophenyl)-N-(2,6-difluorophenyl)-1,3-dimethyl-1H-pyrazole at a ratio of 1:1; a pest control composition comprising any one of the present compounds 1 to 253 and 5-amino-4-(2-chloro-4-fluorophenyl)-N-(2,6-difluorophenyl)-1,3-dimethyl-1H-pyrazole at a ratio of 10:1; a pest control composition comprising any one of the present compounds 1 to 253 and 5-amino-4-(2-bromo-4-fluorophenyl)-N-(2,6-difluorophenyl)-1,3-dimethyl-1H-pyrazole at a ratio of 0.1:1; a pest control composition comprising any one of the present compounds 1 to 253 and 5-amino-4-(2-bromo-4-fluorophenyl)-N-(2,6-difluorophenyl)-1,3-dimethyl-1H-pyrazole at a ratio of 1:1; a pest control composition comprising any one of the present compounds 1 to 253 and 5-amino-4-(2-bromo-4-fluorophenyl)-N-(2,6-difluorophenyl)-1,3-dimethyl-1H-pyrazole at a ratio of 10:1;

a pest control composition comprising any one of the present compounds 1 to 253 and 5-amino-4-(2-chloro-4-fluorophenyl)-N-(2-chloro-6-fluorophenyl)-1,3-dimethyl-1H-pyrazole at a ratio of 0.1:1; a pest control composition comprising any one of the present compounds 1 to 253 and 5-amino-4-(2-chloro-4-fluorophenyl)-N-(2-chloro-6-fluorophenyl)-1,3-dimethyl-1H-pyrazole at a ratio of 1:1; a pest control composition comprising any one of the present compounds 1 to 253 and 5-amino-4-(2-chloro-4-fluorophenyl)-N-(2-chloro-6-fluorophenyl)-1,3-dimethyl-1H-pyrazole at a ratio of 10:1; a pest control composition comprising any one of the present compounds 1 to 253 and 5-amino-4-(2-bromo-4-fluorophenyl)-N-(2-chloro-6-fluorophenyl)-1,3-dimethyl-1H-pyrazole at a ratio of 0.1:1; a pest control composition comprising any one of the present compounds 1 to 253 and 5-amino-4-(2-bromo-4-fluorophenyl)-N-(2-chloro-6-fluorophenyl)-1,3-dimethyl-1H-pyrazole at a ratio of 1:1; a pest control composition comprising any one of the present compounds 1 to 253 and 5-amino-4-(2-bromo-4-fluorophenyl)-N-(2-chloro-6-fluorophenyl)-1,3-dimethyl-1H-pyrazole at a ratio of 10:1;

a pest control composition comprising any one of the present compounds 1 to 253 and 5-amino-4-(2-chloro-4-fluorophenyl)-N-(2,6-difluoro-4-methylphenyl)-1,3-dimethyl-1H- pyrazole at a ratio of 0.1:1; a pest control composition comprising any one of the present compounds 1 to 253 and 5-amino-4-(2-chloro-4-fluorophenyl)-N-(2,6-difluoro-4-methylphenyl)-1,3-dimethyl-1H-pyrazole at a ratio of 1:1; a pest control composition comprising any one of the present compounds 1 to 253 and 5-amino-4-(2-chloro-4-fluorophenyl)-N-(2,6-difluoro-4-methylphenyl)-1,3-dimethyl-1H-pyrazole at a ratio of 10:1;

a pest control composition comprising any one of the present compounds 1 to 253 and 5-amino-4-(2-bromo-4-fluorophenyl)-N-(2,6-difluoro-4-methylphenyl)-1,3-dimethyl-1H-pyrazole at a ratio of 0.1:1; a pest control composition comprising any one of the present compounds 1 to 253 and 5-amino-4-(2-bromo-4-fluorophenyl)-N-(2,6-difluoro-4-methylphenyl)-1,3-dimethyl-1H-pyrazole at a ratio of 1:1; a pest control composition comprising any one of the present compounds 1 to 253 and 5-amino-4-(2-bromo-4-fluorophenyl)-N-(2,6-difluoro-4-methylphenyl)-1,3-dimethyl-1H-pyrazole at a ratio of 10:1;

a pest control composition comprising any one of the present compounds 1 to 253 and 5-amino-N-(2-chloro-6-fluoro-4-methylphenyl)-4-(2-chloro-4-fluorophenyl)-1,3-dimethyl-1H-pyrazole at a ratio of 0.1:1; a pest control composition comprising any one of the present compounds 1 to 253 and 5-amino-N-(2-chloro-6-fluoro-4-methylphenyl)-4-(2-chloro-4-fluorophenyl)-1,3-dimethyl-1H-pyrazole at a ratio of 1:1; a pest control composition comprising any one of the present compounds 1 to 253 and 5-amino-N-(2-chloro-6-fluoro-4-methylphenyl)-4-(2-chloro-4-fluorophenyl)-1,3-dimethyl-1H-pyrazole at a ratio of 10:1;

a pest control composition comprising any one of the present compounds 1 to 253 and 5-amino-4-(2-bromo-4-fluorophenyl)-N-(2-chloro-6-fluoro-4-methylphenyl)-1,3-dimethyl-1H-pyrazole at a ratio of 0.1:1; a pest control composition comprising any one of the present compounds 1 to 253 and 5-amino-4-(2-bromo-4-fluorophenyl)-N-(2-chloro-6-fluoro-4-methylphenyl)-1,3-dimethyl-1H-pyrazole at a ratio of 1:1; a pest control composition comprising any one of the present compounds 1 to 253 and 5-amino-4-(2-bromo-4-fluorophenyl)-N-(2-chloro-6-fluoro-4-methylphenyl)-1,3-dimethyl-1H-pyrazole at a ratio of 10:1;

a pest control composition comprising any one of the present compounds 1 to 253 and 9-fluoro-2,3-dihydro-2,2-dimethyl-5-(quinolin-3-yl)-1,4-benzooxazepine at a ratio of 0.1:1; a pest control composition comprising any one of the present compounds 1 to 253 and 9-fluoro-2,3-dihydro-2,2-dimethyl-5-(quinolin-3-yl)-1,4-benzooxazepine at a ratio of 1:1; a pest control composition comprising any one of the present compounds 1 to 253 and 9-fluoro-2,3-dihydro-2,2-dimethyl-5-(quinolin-3-yl)-1,4-benzooxazepine at a ratio of 10:1; a pest control composition comprising any one of the present compounds 1 to 253 and N-cyclopropyl-3-(difluoromethyl)-5-fluoro-N-(2-isopropylbenzyl)-1-methyl-1H-pyrazole-4-carboxamide at a ratio of 0.1:1; a pest control composition comprising any one of the present compounds 1 to 253 and N-cyclopropyl-3-(difluoromethyl)-5-fluoro-N-(2-isopropylbenzyl)-1-methyl-1H-pyrazole-4-carboxamide at a ratio of 1:1; a pest control composition comprising any one of the present compounds 1 to 253 and N-cyclopropyl-3-(difluoromethyl)-5-fluoro-N-(2-isopropylbenzyl)-1-methyl-1H-pyrazole-4-carboxamide at a ratio of 10:1; a pest control composition comprising any one of the present compounds 1 to 253 and N-cyclopropyl-3-(difluoromethyl)-5-fluoro-N-(5-chloro-2-isopropylbenzyl)-1-methyl-1H-pyrazole-4-carboxamide at a ratio of 0.1:1; a pest control composition comprising any one of the present compounds 1 to 253 and N-cyclopropyl-3-(difluoromethyl)-5-fluoro-N-(5-chloro-2-isopropylbenzyl)-1-methyl-1H-pyrazole-4-carboxamide at a ratio of 1:1; a pest control composition comprising any one of the present compounds 1 to 253 and N-cyclopropyl-3-(difluoromethyl)-5-fluoro-N-(5-chloro-2-isopropylbenzyl)-1-methyl-1H-pyrazole-4-carboxamide at a ratio of 10:1; a pest control composition comprising any one of the present compounds 1 to 253 and N-[1-(2,4-dichlorophenyl)-1-methoxypropan-2-yl]-3-difluoromethyl-1-methyl-1H-pyrazole-4-carboxamide at a ratio of 0.1:1;

a pest control composition comprising any one of the present compounds 1 to 253 and N-[1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1R,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1S,2R)1-(2,4-dichlorophenyl)-1-methoxypropan-2-yl]-3-difluoromethyl-1-methyl-1H-pyrazole-4-carboxamide at a ratio of 0.1:1;

a pest control composition comprising any one of the present compounds 1 to 253 and N-[(1S,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1S,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1S,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and N-[(1S,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1S,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and rel-N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and rel-N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and rel-N-[(1R,2R)1-(2,4-dichlorophenyl)-1-methoxypropan-2-yl]-3-difluoromethyl-1-methyl-1H-pyrazole-4-carboxamide at a ratio of 10:1;

a pest control composition comprising any one of the present compounds 1 to 253 and rel-N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and rel-N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and rel-N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1R,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and N-[(1R,2RS)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1R,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1S,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and N-[(1S,2RS)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1S,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1RS,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and N-[(1RS,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1RS,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 253 and N-[(1RS,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 253 and N-[(1RS,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 253 and N-[(1RS,2S)1-(2,4-dichlorophenyl)-1-methoxypropan-2-yl]-3-difluoromethyl-1-methyl-1H-pyrazole-4-carboxamide at a ratio of 10:1;

a pest control composition comprising any one of the present compounds 1 to 253 and 3-difluoromethyl-N-methoxy-1-methyl-N-[1-methyl-2-(2,4,6-trichlorophenyl)ethyl]pyrazole-4-carboxamide at a ratio of 0.1:1; a pest control composition comprising any one of the present compounds 1 to 253 and 3-difluoromethyl-N-methoxy-1-methyl-N-[1-methyl-2-(2,4,6-trichlorophenyl)ethyl]pyrazole-4-carboxamide at a ratio of 1:1; a pest control composition comprising any one of the present compounds 1 to 253 and 3-difluoromethyl-N-methoxy-1-methyl-N-[1-methyl-2-(2,4,6-trichlorophenyl)ethyl]pyrazole-4-carboxamide at a ratio of 10:1; a pest control composition comprising any one of the present compounds 1 to 253 and 3-difluoromethyl-N-methoxy-1-methyl-N-[(1R)-1-methyl-2-(2,4,6-trichlorophenyl)ethyl]pyrazole-4-carboxamide at a ratio of 0.1:1; a pest control composition comprising any one of the present compounds 1 to 253 and 3-difluoromethyl-N-methoxy-1-methyl-N-[(1R)-1-methyl-2-(2,4,6-trichlorophenyl)ethyl]pyrazole-4-carboxamide at a ratio of 1:1; a pest control composition comprising any one of the present compounds 1 to 253 and 3-difluoromethyl-N-methoxy-1-methyl-N-[(1R)-1-methyl-2-(2,4,6-trichlorophenyl)ethyl]pyrazole-4-carboxamide at a ratio of 10:1; a pest control composition comprising any one of the present compounds 1 to 253 and 3-difluoromethyl-N-methoxy-1-methyl-N-[(1S)-1-methyl-2-(2,4,6-trichlorophenyl)ethyl]pyrazole-4-carboxamide at a ratio of 0.1:1; a pest control composition comprising any one of the present compounds 1 to 253 and 3-difluoromethyl-N-methoxy-1-methyl-N-[(1S)-1-methyl-2-(2,4,6-trichlorophenyl)ethyl]pyrazole-4-carboxamide at a ratio of 1:1; a pest control composition comprising any one of the present compounds 1 to 253 and 3-difluoromethyl-N-methoxy-1-methyl-N-[(1S)-1-methyl-2-(2,4,6-trichlorophenyl)ethyl]pyrazole-4-carboxamide at a ratio of 10:1;

a pest control composition comprising any one of the present compounds 1 to 253 and 3-butyn-1-yl N-{6-[({(Z)-[(1-methyl-1H-tetrazol-5-yl)phenylmethylene]amino}oxy)methyl]-2-pyridinyl}carbamate at a ratio of 0.1:1; a pest control composition comprising any one of the present compounds 1 to 253 and 3-butyn-1-yl N-{6-[({(Z)-[(1-methyl-1H-tetrazol-5-yl)phenylmethylene]amino}oxy)methyl]-2-pyridinyl}carbamate at a ratio of 1:1; a pest control composition comprising any one of the present compounds 1 to 253 and 3-butyn-1-yl N-{6-[({(Z)-[(1-methyl-1H-tetrazol-5-yl)phenylmethylene]amino}oxy)methyl]-2-pyridinyl}carbamate at a ratio of 10:1; a pest control composition comprising any one of the present compounds 1 to 253 and 5-fluoro-2-[(4-methylphenyl)methoxy]-4-pyrimidineamine at a ratio of 0.1:1; a pest control composition comprising any one of the present compounds 1 to 253 and 5-fluoro-2-[(4-methylphenyl)methoxy]-4-pyrimidineamine at a ratio of 1:1; a pest control composition comprising any one of the present compounds 1 to 253 and 5-fluoro-2-[(4-methylphenyl)methoxy]-4-pyrimidineamine at a ratio of 10:1; a pest control composition comprising any one of the present compounds 1 to 253 and 2-[6-(3-fluoro-4-methoxyphenyl)-5-methylpyridin-2-yl]quinazoline at a ratio of 0.1:1; a pest control composition comprising any one of the present compounds 1 to 253 and 2-[6-(3-fluoro-4-methoxyphenyl)-5-methylpyridin-2-yl]quinazoline at a ratio of 1:1; a pest control composition comprising any one of the present compounds 1 to 253 and 2-[6-(3-fluoro-4-methoxyphenyl)-5-methylpyridin-2-yl]quinazoline at a ratio of 10:1; a pest control composition comprising any one of the present compounds 1 to 253 and azaconazole; a pest control composition comprising any one of the present compounds 1 to 253 and diniconazole-M; a pest control composition comprising any one of the present compounds 1 to 253 and etaconazole; a pest control composition comprising any one of the present compounds 1 to 253 and uniconazole; a pest control composition comprising any one of the present compounds 1 to 253 and (S)-(+)-N-(1,1,3-trimethylindan-4-yl)-1-methyl-3-difluoromethyl-pyrazole-4-carboxylic acid amide; a pest control composition comprising any one of the present compounds 1 to 253 and benodanil; a pest control composition comprising any one of the present compounds 1 to 253 and fenfuram; a pest compounds 1 to 253 and oxycarboxin;

a pest control composition comprising any one of the present compounds 1 to 253 and dodemorph; a pest control composition comprising any one of the present compounds 1 to 253 and piperalin; a pest control composition comprising any one of the present compounds 1 to 253 and thiabendazole; a pest control composition comprising any one of the present compounds 1 to 253 and fuberidazole; a pest control composition comprising any one of the present compounds 1 to 253 and thiophanate; a pest control composition comprising any one of the present compounds 1 to 253 and furalaxyl; a pest control composition comprising any one of the present compounds 1 to 253 and ofurace; a pest control composition comprising any one of the present compounds 1 to 253 and oxadixyl; a pest control composition comprising any one of the present compounds 1 to 253 and flumorph; a pest control composition comprising any one of the present compounds 1 to 253 and dichlofluanid; a pest control composition comprising any one of the present compounds 1 to 253 and fenoxanil; a pest control composition comprising any one of the present compounds 1 to 253 and acibenzolar-S-methyl; a pest control composition comprising any one of the present compounds 1 to 253 and anilazine; a pest control composition comprising any one of the present compounds 1 to 253 and bethoxazine; a pest control composition comprising any one of the present compounds 1 to 253 and binapacryl; a pest control composition comprising any one of the present compounds 1 to 253 and biphenyl; a pest control composition comprising any one of the present compounds 1 to 253 and blastcidin-S; a pest control composition comprising any one of the present compounds 1 to 253 and bupirimate; a pest control composition comprising any one of the present compounds 1 to 253 and captafol; a pest control composition comprising any one of the present compounds 1 to 253 and chloroneb; a pest control composition comprising any one of the present compounds 1 to 253 and dicloran; a pest control composition comprising any one of the present compounds 1 to 253 and diflumetorim; a pest control composition comprising any one of the present compounds 1 to 253 and dimethirimol; a pest control composition comprising any one of the present compounds 1 to 253 and dinocap; a pest control composition comprising any one of the present compounds 1 to 253 and dithianon; a pest control composition comprising any one of the present compounds 1 to 253 and dodine; a pest control composition comprising any one of the present compounds 1 to 253 and edifenphos; a pest control composition comprising any one of the present compounds 1 to 253 and ethirimol; a pest control composition comprising any one of the present compounds 1 to 253 and etridiazol; a pest control composition comprising any one of the present compounds 1 to 253 and fenarimol; a pest control composition comprising any one of the present compounds 1 to 253 and fentin-acetate; a pest control composition comprising any one of the present compounds 1 to 253 and fentin-hydroxide; a pest control composition comprising any one of the present compounds 1 to 253 and ferbam; a pest control composition comprising any one of the present compounds 1 to 253 and fluoroimide; a pest control composition comprising any one of the present compounds 1 to 253 and flutianil; a pest control composition comprising any one of the present compounds 1 to 253 and furmecyclox; a pest control composition comprising any one of the present compounds 1 to 253 and iodocarb; a pest control composition comprising any one of the present compounds 1 to 253 and iprobenfos; a pest control composition comprising any one of the present compounds 1 to 253 and meptyldinocap; a pest control composition comprising any one of the present compounds 1 to 253 and methasulfocarb; a pest control composition comprising any one of the present compounds 1 to 253 and metiram; a pest control composition comprising any one of the present compounds 1 to 253 and naftifine; a pest control composition comprising any one of the present compounds 1 to 253 and nuarimol; a pest control composition comprising any one of the present compounds 1 to 253 and octhilinone; a pest control composition comprising any one of the present compounds 1 to 253 and pefurazoate; a pest control composition comprising any one of the present compounds 1 to 253 and phosphorous acid; a pest control composition comprising any one of the present compounds 1 to 253 and a sodium salt of phosphorous acid; a pest control composition comprising any one of the present compounds 1 to 253 and ammonium salt of phosphorous acid; a pest control composition comprising any one of the present compounds 1 to 253 and polyoxin; a pest control composition comprising any one of the present compounds 1 to 253 and propineb; a pest control composition comprising any one of the present compounds 1 to 253 and prothiocarb; a pest control composition comprising any one of the present compounds 1 to 253 and pyrazofos; a pest control composition comprising any one of the present compounds 1 to 253 and pyributicarb; a pest control composition comprising any one of the present compounds 1 to 253 and pyrifenox; a pest control composition comprising any one of the present compounds 1 to 253 and pyrrolnitrin; a pest control composition comprising any one of the present compounds 1 to 253 and PCNB; a pest control composition comprising any one of the present compounds 1 to 253 and TCNB; a pest control composition comprising any one of the present compounds 1 to 253 and tecloftalam; a pest control composition comprising any one of the present compounds 1 to 253 and terbinafine; a pest control composition comprising any one of the present compounds 1 to 253 and tolylfluanid; a pest control composition comprising any one of the present compounds 1 to 253 and triarimol; a pest control composition comprising any one of the present compounds 1 to 253 and triazoxide; a pest control composition comprising any one of the present compounds 1 to 253 and triforine; a pest control composition comprising any one of the present compounds 1 to 253 and trimorphamide; a pest control composition comprising any one of the present compounds 1 to 253 and zineb, a pest control composition comprising any one of the present compounds 1 to 253 and ziram; a pest control composition comprising any one of the present compounds 1 to 253 and acephate at a ratio of 1:1; a pest control composition comprising any one of the present compounds 1 to 253 and acephate at a ratio of 1:10; a pest control composition comprising any one of the present compounds 1 to 253 and acephate at a ratio of 1:50; a pest compounds 1 to 253 and azamethiphos at a ratio of 1:1; a pest control composition comprising any one of the present compounds 1 to 253 and azamethiphos at a ratio of 1:10; a pest control composition comprising any one of the present compounds 1 to 253 and azamethiphos at a ratio of 1:50; a pest control composition comprising any one of the present compounds 1 to 253 and azinphos-ethyl at a ratio of 1:1; a pest control composition comprising any one of the present compounds 1 to 253 and azinphos-ethyl at a ratio of 1:10; a pest control composition comprising any one of the present compounds 1 to 253 and azinphos-ethyl at a ratio of 1:50; a pest control composition comprising any one of the present compounds 1 to 253 and azinphos-methyl at a ratio of 1:1; a pest control composition comprising any one of the present compounds 1 to 253 and azinphos-methyl at a ratio of 1:10; a pest control composition comprising any one of the present compounds 1 to 253 and azinphos-methyl at a ratio of 1:50; a pest control composition comprising any one of the present compounds 1 to 253 and cadusafos at a ratio of 1:1; a pest control composition comprising any one of the present compounds 1 to 253 and cadusafos at a ratio of 1:10; a pest control composition comprising any one of the present compounds 1 to 253 and cadusafos at a ratio of 1:50; a pest control composition comprising any one of the present compounds 1 to 253 and chlorethoxyfos at a ratio of 1:1; a pest control composition comprising any one of the present compounds 1 to 253 and chlorethoxyfos at a ratio of 1:10; a pest control composition comprising any one of the present compounds 1 to 253 and chlorethoxyfos at a ratio of 1:50; a pest control composition comprising any one of the present compounds 1 to 253 and chlorfenvinphos at a ratio of 1:1; a pest control composition comprising any one of the present compounds 1 to 253 and chlorfenvinphos at a ratio of 1:10; a pest control composition comprising any one of the present compounds 1 to 253 and chlorfenvinphos at a ratio of 1:50; a pest control composition comprising any one of the present compounds 1 to 253 and chlormephos at a ratio of 1:1; a pest control composition comprising any one of the present compounds 1 to 253 and chlormephos at a ratio of 1:10; a pest control composition comprising any one of the present compounds 1 to 253 and chlormephos at a ratio of 1:50; a pest control composition comprising any one of the present compounds 1 to 253 and chlorpyrifos at a ratio of 1:1; a pest control composition comprising any one of the present compounds 1 to 253 and chlorpyrifos at a ratio of 1:10; a pest control composition comprising any one of the present compounds 1 to 253 and chlorpyrifos at a ratio of 1:50; a pest control composition comprising any one of the present compounds 1 to 253 and chlorpyrifosmethyl at a ratio of 1:1; a pest control composition comprising any one of the present compounds 1 to 253 and chlorpyrifosmethyl at a ratio of 1:10; a pest control composition comprising any one of the present compounds 1 to 253 and chlorpyrifosmethyl at a ratio of 1:50; a pest control composition comprising any one of the present compounds 1 to 253 and coumaphos at a ratio of 1:1; a pest control composition comprising any one of the present compounds 1 to 253 and coumaphos at a ratio of 1:10; a pest compounds 1 to 253 and coumaphos at a ratio of 1:50; a pest control composition comprising any one of the present compounds 1 to 253 and cyanophos at a ratio of 1:1; a pest control composition comprising any one of the present compounds 1 to 253 and cyanophos at a ratio of 1:10; a pest control composition comprising any one of the present compounds 1 to 253 and cyanophos at a ratio of 1:50; a pest control composition comprising any one of the present compounds 1 to 253 and demeton-S-methyl at a ratio of 1:1; a pest control composition comprising any one of the present compounds 1 to 253 and demeton-S-methyl at a ratio of 1:10; a pest control composition comprising any one of the present compounds 1 to 253 and demeton-S-methyl at a ratio of 1:50; a pest control composition comprising any one of the present compounds 1 to 253 and diazinon at a ratio of 1:1; a pest control composition comprising any one of the present compounds 1 to 253 and diazinon at a ratio of 1:10; a pest control composition comprising any one of the present compounds 1 to 253 and diazinon at a ratio of 1:50; a pest control composition comprising any one of the present compounds 1 to 253 and dichlorvos at a ratio of 1:1; a pest control composition comprising any one of the present compounds 1 to 253 and dichlorvos at a ratio of 1:10; a pest control composition comprising any one of the present compounds 1 to 253 and dichlorvos at a ratio of 1:50; a pest control composition comprising any one of the present compounds 1 to 253 and dicrotophos at a ratio of 1:1; a pest control composition comprising any one of the present compounds 1 to 253 and dicrotophos at a ratio of 1:10; a pest control composition comprising any one of the present compounds 1 to 253 and dicrotophos at a ratio of 1:50; a pest control composition comprising any one of the present compounds 1 to 253 and dimethoate at a ratio of 1:1; a pest control composition comprising any one of the present compounds 1 to 253 and dimethoate at a ratio of 1:10; a pest control composition comprising any one of the present compounds 1 to 253 and dimethoate at a ratio of 1:50; a pest control composition comprising any one of the present compounds 1 to 253 and dimethylvinphos at a ratio of 1:1; a pest control composition comprising any one of the present compounds 1 to 253 and dimethylvinphos at a ratio of 1:10; a pest control composition comprising any one of the present compounds 1 to 253 and dimethylvinphos at a ratio of 1:50; a pest control composition comprising any one of the present compounds 1 to 253 and disulfoton at a ratio of 1:1; a pest control composition comprising any one of the present compounds 1 to 253 and disulfoton at a ratio of 1:10; a pest control composition comprising any one of the present compounds 1 to 253 and disulfoton at a ratio of 1:50; a pest control composition comprising any one of the present compounds 1 to 253 and EPN at a ratio of 1:1; a pest control composition comprising any one of the present compounds 1 to 253 and EPN at a ratio of 1:10; a pest control composition comprising any one of the present compounds 1 to 253 and EPN at a ratio of 1:50; a pest control composition comprising any one of the present compounds 1 to 253 and ethion at a ratio of 1:1; a pest control composition comprising any one of the present compounds 1 to 253 and ethion at a ratio of 1:10; a compounds 1 to 253 and ethion at a ratio of 1:50; a pest control composition comprising any one of the present compounds 1 to 253 and ethoprophos at a ratio of 1:1; a pest control composition comprising any one of the present compounds 1 to 253 and ethoprophos at a ratio of 1:10; a pest control composition comprising any one of the present compounds 1 to 253 and ethoprophos at a ratio of 1:50; a pest control composition comprising any one of the present compounds 1 to 253 and famphur at a ratio of 1:1; a pest control composition comprising any one of the present compounds 1 to 253 and famphur at a ratio of 1:10; a pest control composition comprising any one of the present compounds 1 to 253 and famphur at a ratio of 1:50; a pest control composition comprising any one of the present compounds 1 to 253 and fenamiphos at a ratio of 1:1; a pest control composition comprising any one of the present compounds 1 to 253 and fenamiphos at a ratio of 1:10; a pest control composition comprising any one of the present compounds 1 to 253 and fenamiphos at a ratio of 1:50; a pest control composition comprising any one of the present compounds 1 to 253 and fenitrothion at a ratio of 1:1; a pest control composition comprising any one of the present compounds 1 to 253 and fenitrothion at a ratio of 1:10; a pest control composition comprising any one of the present compounds 1 to 253 and fenitrothion at a ratio of 1:50; a pest control composition comprising any one of the present compounds 1 to 253 and fenthion at a ratio of 1:1; a pest control composition comprising any one of the present compounds 1 to 253 and fenthion at a ratio of 1:10; a pest control composition comprising any one of the present compounds 1 to 253 and fenthion at a ratio of 1:50; a pest control composition comprising any one of the present compounds 1 to 253 and heptenophos at a ratio of 1:1; a pest control composition comprising any one of the present compounds 1 to 253 and heptenophos at a ratio of 1:10; a pest control composition comprising any one of the present compounds 1 to 253 and heptenophos at a ratio of 1:50; a pest control composition comprising any one of the present compounds 1 to 253 and isofenphos at a ratio of 1:1; a pest control composition comprising any one of the present compounds 1 to 253 and isofenphos at a ratio of 1:10; a pest control composition comprising any one of the present compounds 1 to 253 and isofenphos at a ratio of 1:50; a pest control composition comprising any one of the present compounds 1 to 253 and isocarbophos at a ratio of 1:1; a pest control composition comprising any one of the present compounds 1 to 253 and isocarbophos at a ratio of 1:10; a pest control composition comprising any one of the present compounds 1 to 253 and isocarbophos at a ratio of 1:50; a pest control composition comprising any one of the present compounds 1 to 253 and isoxathion at a ratio of 1:1; a pest control composition comprising any one of the present compounds 1 to 253 and isoxathion at a ratio of 1:10; a pest control composition comprising any one of the present compounds 1 to 253 and isoxathion at a ratio of 1:50; a pest control composition comprising any one of the present compounds 1 to 253 and malathion at a ratio of 1:1; a compounds 1 to 253 and malathion at a ratio of 1:10; a pest control composition comprising any one of the present compounds 1 to 253 and malathion at a ratio of 1:50; a pest control composition comprising any one of the present compounds 1 to 253 and mecarbam at a ratio of 1:1; a pest control composition comprising any one of the present compounds 1 to 253 and mecarbam at a ratio of 1:10; a pest control composition comprising any one of the present compounds 1 to 253 and mecarbam at a ratio of 1:50; a pest control composition comprising any one of the present compounds 1 to 253 and methamidophos at a ratio of 1:1; a pest control composition comprising any one of the present compounds 1 to 253 and methamidophos at a ratio of 1:10; a pest control composition comprising any one of the present compounds 1 to 253 and methamidophos at a ratio of 1:50; a pest control composition comprising any one of the present compounds 1 to 253 and methidathion at a ratio of 1:1; a pest control composition comprising any one of the present compounds 1 to 253 and methidathion at a ratio of 1:10; a pest control composition comprising any one of the present compounds 1 to 253 and methidathion at a ratio of 1:50; a pest control composition comprising any one of the present compounds 1 to 253 and mevinphos at a ratio of 1:1; a pest control composition comprising any one of the present compounds 1 to 253 and mevinphos at a ratio of 1:10; a pest control composition comprising any one of the present compounds 1 to 253 and mevinphos at a ratio of 1:50; a pest control composition comprising any one of the present compounds 1 to 253 and monocrotophos at a ratio of 1:1; a pest control composition comprising any one of the present compounds 1 to 253 and monocrotophos at a ratio of 1:10; a pest control composition comprising any one of the present compounds 1 to 253 and monocrotophos at a ratio of 1:50; a pest control composition comprising any one of the present compounds 1 to 253 and naled at a ratio of 1:1; a pest control composition comprising any one of the present compounds 1 to 253 and naled at a ratio of 1:10; a pest control composition comprising any one of the present compounds 1 to 253 and naled at a ratio of 1:50; a pest control composition comprising any one of the present compounds 1 to 253 and omethoate at a ratio of 1:1; a pest control composition comprising any one of the present compounds 1 to 253 and omethoate at a ratio of 1:10; a pest control composition comprising any one of the present compounds 1 to 253 and omethoate at a ratio of 1:50; a pest control composition comprising any one of the present compounds 1 to 253 and oxydemeton-methyl at a ratio of 1:1; a pest control composition comprising any one of the present compounds 1 to 253 and oxydemeton-methyl at a ratio of 1:10; a pest control composition comprising any one of the present compounds 1 to 253 and oxydemeton-methyl at a ratio of 1:50; a pest control composition comprising any one of the present compounds 1 to 253 and parathion at a ratio of 1:1; a pest control composition comprising any one of the present compounds 1 to 253 and parathion at a ratio of 1:10; a pest control composition comprising any one of the present compounds 1 to 253 and parathion at a ratio of 1:50; a pest control composition comprising any one of the present compounds 1 to 253 and methylparathion at a ratio of 1:1; a compounds 1 to 253 and methylparathion at a ratio of 1:10; a pest control composition comprising any one of the present compounds 1 to 253 and methylparathion at a ratio of 1:50; a pest control composition comprising any one of the present compounds 1 to 253 and phenthoate at a ratio of 1:1; a pest control composition comprising any one of the present compounds 1 to 253 and phenthoate at a ratio of 1:10; a pest control composition comprising any one of the present compounds 1 to 253 and phenthoate at a ratio of 1:50; a pest control composition comprising any one of the present compounds 1 to 253 and phorate at a ratio of 1:1; a pest control composition comprising any one of the present compounds 1 to 253 and phorate at a ratio of 1:10; a pest control composition comprising any one of the present compounds 1 to 253 and phorate at a ratio of 1:50; a pest control composition comprising any one of the present compounds 1 to 253 and phosalone at a ratio of 1:1; a pest control composition comprising any one of the present compounds 1 to 253 and phosalone at a ratio of 1:10; a pest control composition comprising any one of the present compounds 1 to 253 and phosalone at a ratio of 1:50; a pest control composition comprising any one of the present compounds 1 to 253 and phosmet at a ratio of 1:1; a pest control composition comprising any one of the present compounds 1 to 253 and phosmet at a ratio of 1:10; a pest control composition comprising any one of the present compounds 1 to 253 and phosmet at a ratio of 1:50; a pest control composition comprising any one of the present compounds 1 to 253 and phosphamidon at a ratio of 1:1; a pest control composition comprising any one of the present compounds 1 to 253 and phosphamidon at a ratio of 1:10; a pest control composition comprising any one of the present compounds 1 to 253 and phosphamidon at a ratio of 1:50; a pest control composition comprising any one of the present compounds 1 to 253 and phoxim at a ratio of 1:1; a pest control composition comprising any one of the present compounds 1 to 253 and phoxim at a ratio of 1:10; a pest control composition comprising any one of the present compounds 1 to 253 and phoxim at a ratio of 1:50; a pest control composition comprising any one of the present compounds 1 to 253 and pirimiphos-methyl at a ratio of 1:1; a pest control composition comprising any one of the present compounds 1 to 253 and pirimiphos-methyl at a ratio of 1:10; a pest control composition comprising any one of the present compounds 1 to 253 and pirimiphos-methyl at a ratio of 1:50;
a pest control composition comprising any one of the present compounds 1 to 253 and profenofos at a ratio of 1:1; a pest control composition comprising any one of the present compounds 1 to 253 and profenofos at a ratio of 1:10; a pest control composition comprising any one of the present compounds 1 to 253 and profenofos at a ratio of 1:50; a pest control composition comprising any one of the present compounds 1 to 253 and propetamphos at a ratio of 1:1; a pest control composition comprising any one of the present compounds 1 to 253 and propetamphos at a ratio of 1:10; a pest control composition comprising any one of the present compounds 1 to 253 and propetamphos at a ratio of 1:50; a pest compounds 1 to 253 and prothiofos at a ratio of 1:1; a pest control composition comprising any one of the present compounds 1 to 253 and prothiofos at a ratio of 1:10; a pest control composition comprising any one of the present compounds 1 to 253 and prothiofos at a ratio of 1:50; a pest control composition comprising any one of the present compounds 1 to 253 and pyraclofos at a ratio of 1:1; a pest control composition comprising any one of the present compounds 1 to 253 and pyraclofos at a ratio of 1:10; a pest control composition comprising any one of the present compounds 1 to 253 and pyraclofos at a ratio of 1:50; a pest control composition comprising any one of the present compounds 1 to 253 and pyridaphenthion at a ratio of 1:1; a pest control composition comprising any one of the present compounds 1 to 253 and pyridaphenthion at a ratio of 1:10; a pest control composition comprising any one of the present compounds 1 to 253 and pyridaphenthion at a ratio of 1:50; a pest control composition comprising any one of the present compounds 1 to 253 and quinalphos at a ratio of 1:1; a pest control composition comprising any one of the present compounds 1 to 253 and quinalphos at a ratio of 1:10; a pest control composition comprising any one of the present compounds 1 to 253 and quinalphos at a ratio of 1:50; a pest control composition comprising any one of the present compounds 1 to 253 and sulfotep at a ratio of 1:1; a pest control composition comprising any one of the present compounds 1 to 253 and sulfotep at a ratio of 1:10; a pest control composition comprising any one of the present compounds 1 to 253 and sulfotep at a ratio of 1:50; a pest compounds 1 to 253 and tebupirimfos at a ratio of 1:1;
a pest control composition comprising any one of the present compounds 1 to 253 and tebupirimfos at a ratio of 1:10; a pest control composition comprising any one of the present compounds 1 to 253 and tebupirimfos at a ratio of 1:50; a pest control composition comprising any one of the present compounds 1 to 253 and temephos at a ratio of 1:1; a pest control composition comprising any one of the present compounds 1 to 253 and temephos at a ratio of 1:10; a pest control composition comprising any one of the present compounds 1 to 253 and temephos at a ratio of 1:50; a pest control composition comprising any one of the present compounds 1 to 253 and terbufos at a ratio of 1:1; a pest control composition comprising any one of the present compounds 1 to 253 and terbufos at a ratio of 1:10; a pest control composition comprising any one of the present compounds 1 to 253 and terbufos at a ratio of 1:50; a pest control composition comprising any one of the present compounds 1 to 253 and tetrachlorvinphos at a ratio of 1:1; a pest control composition comprising any one of the present compounds 1 to 253 and tetrachlorvinphos at a ratio of 1:10; a pest control composition comprising any one of the present compounds 1 to 253 and tetrachlorvinphos at a ratio of 1:50;

a pest control composition comprising any one of the present compounds 1 to 253 and thiometon at a ratio of 1:1; a pest control composition comprising any one of the present compounds 1 to 253 and thiometon at a ratio of 1:10; a pest control composition comprising any one of the present compounds 1 to 253 and thiometon at a ratio of 1:50; a pest control composition comprising any one of the present compounds 1 to 253 and triazophos at a ratio of 1:1; a pest control composition comprising any one of the present compounds 1 to 253 and triazophos at a ratio of 1:10; a pest control composition comprising any one of the present compounds 1 to 253 and triazophos at a ratio of 1:50; a pest control composition comprising any one of the present compounds 1 to 253 and trichlorfon at a ratio of 1:1; a pest control composition comprising any one of the present compounds 1 to 253 and trichlorfon at a ratio of 1:10; a pest control composition comprising any one of the present compounds 1 to 253 and trichlorfon at a ratio of 1:50;
a pest control composition comprising any one of the present compounds 1 to 253 and vamidothion at a ratio of 1:1; a pest control composition comprising any one of the present compounds 1 to 253 and vamidothion at a ratio of 1:10; a pest control composition comprising any one of the present compounds 1 to 253 and vamidothion at a ratio of 1:50; a pest control composition comprising any one of the present compounds 1 to 253 and alanycarb at a ratio of 1:1; a pest control composition comprising any one of the present compounds 1 to 253 and alanycarb at a ratio of 1:10; a pest control composition comprising any one of the present compounds 1 to 253 and alanycarb at a ratio of 1:50; a pest control composition comprising any one of the present compounds 1 to 253 and aldicarb at a ratio of 1:1; a pest control composition comprising any one of the present compounds 1 to 253 and aldicarb at a ratio of 1:10; a pest compounds 1 to 253 and aldicarb at a ratio of 1:50; a pest control composition comprising any one of the present compounds 1 to 253 and bendiocarb at a ratio of 1:1; a pest control composition comprising any one of the present compounds 1 to 253 and bendiocarb at a ratio of 1:10; a pest control composition comprising any one of the present compounds 1 to 253 and bendiocarb at a ratio of 1:50; a pest control composition comprising any one of the present compounds 1 to 253 and benfuracarb at a ratio of 1:1; a pest control composition comprising any one of the present compounds 1 to 253 and benfuracarb at a ratio of 1:10; a pest control composition comprising any one of the present compounds 1 to 253 and benfuracarb at a ratio of 1:50; a pest control composition comprising any one of the present compounds 1 to 253 and butocarboxim at a ratio of 1:1; a pest control composition comprising any one of the present compounds 1 to 253 and butocarboxim at a ratio of 1:10; a pest control composition comprising any one of the present compounds 1 to 253 and butocarboxim at a ratio of 1:50; a pest control composition comprising any one of the present compounds 1 to 253 and butoxycarboxim at a ratio of 1:1; a pest control composition comprising any one of the present compounds 1 to 253 and butoxycarboxim at a ratio of 1:10; a pest control composition comprising any one of the present compounds 1 to 253 and butoxycarboxim at a ratio of 1:50; a pest control composition comprising any one of the present compounds 1 to 253 and carbaryl at a ratio of 1:1; a pest control composition comprising any one of the present compounds 1 to 253 and carbaryl at a ratio of 1:10; a pest control composition comprising any one of the present compounds 1 to 253 and carbaryl at a ratio of 1:50; a pest control composition comprising any one of the present compounds 1 to 253 and carbofuran at a ratio of 1:1; a pest control composition comprising any one of the present compounds 1 to 253 and carbofuran at a ratio of 1:10; a pest control composition comprising any one of the present compounds 1 to 253 and carbofuran at a ratio of 1:50; a pest control composition comprising any one of the present compounds 1 to 253 and carbosulfan at a ratio of 1:1; a pest control composition comprising any one of the present compounds 1 to 253 and carbosulfan at a ratio of 1:10; a pest control composition comprising any one of the present compounds 1 to 253 and carbosulfan at a ratio of 1:50; a pest control composition comprising any one of the present compounds 1 to 253 and ethiofencarb at a ratio of 1:1; a pest control composition comprising any one of the present compounds 1 to 253 and ethiofencarb at a ratio of 1:10; a pest control composition comprising any one of the present compounds 1 to 253 and ethiofencarb at a ratio of 1:50; a pest control composition comprising any one of the present compounds 1 to 253 and fenobucarb at a ratio of 1:1; a pest control composition comprising any one of the present compounds 1 to 253 and fenobucarb at a ratio of 1:10; a pest control composition comprising any one of the present compounds 1 to 253 and fenobucarb at a ratio of 1:50; a pest control composition comprising any one of the present compounds 1 to 253 and formetanate at a ratio of 1:1; a pest control composition comprising any one of the present compounds 1 to 253 and formetanate at a ratio of 1:10; a pest control composition comprising any one of the present compounds 1 to 253 and formetanate at a ratio of 1:50; a pest control composition comprising any one of the present compounds 1 to 253 and furathiocarb at a ratio of 1:1; a pest control composition comprising any one of the present compounds 1 to 253 and furathiocarb at a ratio of 1:10; a pest control composition comprising any one of the present compounds 1 to 253 and furathiocarb at a ratio of 1:50; a pest control composition comprising any one of the present compounds 1 to 253 and isoprocarb at a ratio of 1:1; a pest control composition comprising any one of the present compounds 1 to 253 and isoprocarb at a ratio of 1:10; a pest control composition comprising any one of the present compounds 1 to 253 and isoprocarb at a ratio of 1:50; a pest control composition comprising any one of the present compounds 1 to 253 and methiocarb at a ratio of 1:1; a pest control composition comprising any one of the present compounds 1 to 253 and methiocarb at a ratio of 1:10; a pest control composition comprising any one of the present compounds 1 to 253 and methiocarb at a ratio of 1:50; a pest control composition comprising any one of the present compounds 1 to 253 and methomyl at a ratio of 1:1; a pest control composition comprising any one of the present compounds 1 to 253 and methomyl at a ratio of 1:10; a pest control composition comprising any one of the present compounds 1 to 253 and methomyl at a ratio of 1:50; a pest control composition comprising any one of the present compounds 1 to 253 and metolcarb at a ratio of 1:1; a pest compounds 1 to 253 and metolcarb at a ratio of 1:10; a pest control composition comprising any one of the present compounds 1 to 253 and metolcarb at a ratio of 1:50; a pest control composition comprising any one of the present compounds 1 to 253 and oxamyl at a ratio of 1:1; a pest control composition comprising any one of the present compounds 1 to 253 and oxamyl at a ratio of 1:10; a pest control composition comprising any one of the present compounds 1 to 253 and oxamyl at a ratio of 1:50; a pest control composition comprising any one of the present compounds 1 to 253 and pirimicarb at a ratio of 1:1; a pest control composition comprising any one of the present compounds 1 to 253 and pirimicarb at a ratio of 1:10; a pest control composition comprising any one of the present compounds 1 to 253 and pirimicarb at a ratio of 1:50; a pest control composition comprising any one of the present compounds 1 to 253 and propoxur at a ratio of 1:1; a pest control composition comprising any one of the present compounds 1 to 253 and propoxur at a ratio of 1:10; a pest control composition comprising any one of the present compounds 1 to 253 and propoxur at a ratio of 1:50; a pest control composition comprising any one of the present compounds 1 to 253 and thiodicarb at a ratio of 1:1; a pest control composition comprising any one of the present compounds 1 to 253 and thiodicarb at a ratio of 1:10; a pest control composition comprising any one of the present compounds 1 to 253 and thiodicarb at a ratio of 1:50; a pest control composition comprising any one of the present compounds 1 to 253 and thiofanox at a ratio of 1:1; a pest control composition comprising any one of the present compounds 1 to 253 and thiofanox at a ratio of 1:10; a pest control composition comprising any one of the present compounds 1 to 253 and thiofanox at a ratio of 1:50; a pest control composition comprising any one of the present compounds 1 to 253 and triazamate at a ratio of 1:1; a pest control composition comprising any one of the present compounds 1 to 253 and triazamate at a ratio of 1:10; a pest control composition comprising any one of the present compounds 1 to 253 and triazamate at a ratio of 1:50; a pest control composition comprising any one of the present compounds 1 to 253 and trimethacarb at a ratio of 1:1; a pest control composition comprising any one of the present compounds 1 to 253 and trimethacarb at a ratio of 1:10; a pest control composition comprising any one of the present compounds 1 to 253 and trimethacarb at a ratio of 1:50; a pest control composition comprising any one of the present compounds 1 to 253 and XMC at a ratio of 1:1; a pest control composition comprising any one of the present compounds 1 to 253 and XMC at a ratio of 1:10; a pest control composition comprising any one of the present compounds 1 to 253 and XMC at a ratio of 1:50;

a pest control composition comprising any one of the present compounds 1 to 253 and xylylcarb at a ratio of 1:1; a pest control composition comprising any one of the present compounds 1 to 253 and xylylcarb at a ratio of 1:10; a pest control composition comprising any one of the present compounds 1 to 253 and xylylcarb at a ratio of 1:50; a pest compounds 1 to 253 and acrinathrin at a ratio of 0.1:1; a pest control composition comprising any one of the present compounds 1 to 253 and acrinathrin at a ratio of 1:1; a pest control composition comprising any one of the present compounds 1 to 253 and acrinathrin at a ratio of 1:10; a pest control composition comprising any one of the present compounds 1 to 253 and allethrin at a ratio of 0.1:1; a pest control composition comprising any one of the present compounds 1 to 253 and allethrin at a ratio of 1:1; a pest control composition comprising any one of the present compounds 1 to 253 and allethrin at a ratio of 1:10; a pest control composition comprising any one of the present compounds 1 to 253 and bifenthrin at a ratio of 0.1:1; a pest control composition comprising any one of the present compounds 1 to 253 and bifenthrin at a ratio of 1:1; a pest control composition comprising any one of the present compounds 1 to 253 and bifenthrin at a ratio of 1:10; a pest control composition comprising any one of the present compounds 1 to 253 and bioallethrin at a ratio of 0.1:1; a pest control composition comprising any one of the present compounds 1 to 253 and bioallethrin at a ratio of 1:1; a pest control composition comprising any one of the present compounds 1 to 253 and bioallethrin at a ratio of 1:10; a pest control composition comprising any one of the present compounds 1 to 253 and bioresmethrin at a ratio of 0.1:1; a pest control composition comprising any one of the present compounds 1 to 253 and bioresmethrin at a ratio of 1:1; a pest control composition comprising any one of the present compounds 1 to 253 and bioresmethrin at a ratio of 1:10; a compounds 1 to 253 and cycloprothrin at a ratio of 0.1:1; a pest control composition comprising any one of the present compounds 1 to 253 and cycloprothrin at a ratio of 1:1; a pest control composition comprising any one of the present compounds 1 to 253 and cycloprothrin at a ratio of 1:10; a pest control composition comprising any one of the present compounds 1 to 253 and cyfluthrin at a ratio of 0.1:1; a pest control composition comprising any one of the present compounds 1 to 253 and cyfluthrin at a ratio of 1:1; a pest control composition comprising any one of the present compounds 1 to 253 and cyfluthrin at a ratio of 1:10; a pest control composition comprising any one of the present compounds 1 to 253 and beta-cyfluthrin at a ratio of 0.1:1; a pest control composition comprising any one of the present compounds 1 to 253 and beta-cyfluthrin at a ratio of 1:1; a pest control composition comprising any one of the present compounds 1 to 253 and beta-cyfluthrin at a ratio of 1:10; a pest control composition comprising any one of the present compounds 1 to 253 and cyhalothrin at a ratio of 0.1:1; a pest control composition comprising any one of the present compounds 1 to 253 and cyhalothrin at a ratio of 1:1; a pest control composition comprising any one of the present compounds 1 to 253 and cyhalothrin at a ratio of 1:10; a pest control composition comprising any one of the present compounds 1 to 253 and gamma-cyhalothrin at a ratio of 0.1:1; a pest control composition comprising any one of the present compounds 1 to 253 and gamma-cyhalothrin at a ratio of 1:1; a pest control composition comprising any one of the present compounds 1 to 253 and gamma-cyhalothrin at a ratio of 1:10; a pest control composition comprising any one of the present compounds 1 to 253 and lambda-cyhalothrin at a ratio of 0.1:1; a pest control composition comprising any one of the present compounds 1 to 253 and lambda-cyhalothrin at a ratio of 1:1; a pest control composition comprising any one of the present compounds 1 to 253 and lambda-cyhalothrin at a ratio of 1:10; a pest control composition comprising any one of the present compounds 1 to 253 and cypermethrin at a ratio of 0.1:1; a pest control composition comprising any one of the present compounds 1 to 253 and cypermethrin at a ratio of 1:1; a pest control composition comprising any one of the present compounds 1 to 253 and cypermethrin at a ratio of 1:10; a pest control composition comprising any one of the present compounds 1 to 253 and alpha-cypermethrin at a ratio of 0.1:1; a pest control composition comprising any one of the present compounds 1 to 253 and alpha-cypermethrin at a ratio of 1:1; a pest control composition comprising any one of the present compounds 1 to 253 and alpha-cypermethrin at a ratio of 1:10; a pest control composition comprising any one of the present compounds 1 to 253 and beta-cypermethrin at a ratio of 0.1:1; a pest control composition comprising any one of the present compounds 1 to 253 and beta-cypermethrin at a ratio of 1:1; a pest control composition comprising any one of the present compounds 1 to 253 and beta-cypermethrin at a ratio of 1:10; a pest control composition comprising any one of the present compounds 1 to 253 and theta-cypermethrin at a ratio of 0.1:1; a pest control composition comprising any one of the present compounds 1 to 253 and theta-cypermethrin at a ratio of 1:1; a compounds 1 to 253 and theta-cypermethrin at a ratio of 1:10; a pest control composition comprising any one of the present compounds 1 to 253 and zeta-cypermethrin at a ratio of 0.1:1; a pest control composition comprising any one of the present compounds 1 to 253 and zeta-cypermethrin at a ratio of 1:1; a pest control composition comprising any one of the present compounds 1 to 253 and zeta-cypermethrin at a ratio of 1:10; a pest control composition comprising any one of the present compounds 1 to 253 and cyphenothrin at a ratio of 0.1:1; a pest control composition comprising any one of the present compounds 1 to 253 and cyphenothrin at a ratio of 1:1; a pest control composition comprising any one of the present compounds 1 to 253 and cyphenothrin at a ratio of 1:10; a pest control composition comprising any one of the present compounds 1 to 253 and deltamethrin at a ratio of 0.1:1; a pest control composition comprising any one of the present compounds 1 to 253 and deltamethrin at a ratio of 1:1; a pest control composition comprising any one of the present compounds 1 to 253 and deltamethrin at a ratio of 1:10; a pest control composition comprising any one of the present compounds 1 to 253 and empenthrin at a ratio of 0.1:1; a pest control composition comprising any one of the present compounds 1 to 253 and empenthrin at a ratio of 1:1; a pest control composition comprising any one of the present compounds 1 to 253 and empenthrin at a ratio of 1:10; a pest control composition comprising any one of the present compounds 1 to 253 and esfenvalerate at a ratio of 0.1:1; a pest control composition comprising any one of the present compounds 1 to 253 and esfenvalerate at a ratio of 1:1; a pest control composition comprising any one of the present compounds 1 to 253 and esfenvalerate at a ratio of 1:10; a pest control composition comprising any one of the present compounds 1 to 253 and etofenprox at a ratio of 0.1:1; a pest control composition comprising any one of the present compounds 1 to 253 and etofenprox at a ratio of 1:1; a pest control composition comprising any one of the present compounds 1 to 253 and etofenprox at a ratio of 1:10; a pest control composition comprising any one of the present compounds 1 to 253 and fenpropathrin at a ratio of 0.1:1; a pest control composition comprising any one of the present compounds 1 to 253 and fenpropathrin at a ratio of 1:1; a pest control composition comprising any one of the present compounds 1 to 253 and fenpropathrin at a ratio of 1:10; a pest control composition comprising any one of the present compounds 1 to 253 and fenvalerate at a ratio of 0.1:1; a pest control composition comprising any one of the present compounds 1 to 253 and fenvalerate at a ratio of 1:1; a pest control composition comprising any one of the present compounds 1 to 253 and fenvalerate at a ratio of 1:10; a pest control composition comprising any one of the present compounds 1 to 253 and flucythrinate at a ratio of 0.1:1; a pest control composition comprising any one of the present compounds 1 to 253 and flucythrinate at a ratio of 1:1; a pest control composition comprising any one of the present compounds 1 to 253 and flucythrinate at a ratio of 1:10; a pest control composition comprising any one of the present compounds 1 to 253 and flumethrin at a ratio of 0.1:1; a pest control composition comprising any one of the present compounds 1 to 253 and flumethrin at a ratio of 1:1; a pest control composition comprising any one of the present compounds 1 to 253 and flumethrin at a ratio of 1:10; a pest control composition comprising any one of the present compounds 1 to 253 and fluvalinate at a ratio of 0.1:1; a pest control composition comprising any one of the present compounds 1 to 253 and fluvalinate at a ratio of 1:1; a pest control composition comprising any one of the present compounds 1 to 253 and fluvalinate at a ratio of 1:10; a pest control composition comprising any one of the present compounds 1 to 253 and tau-fluvalinate at a ratio of 0.1:1;

a pest control composition comprising any one of the present compounds 1 to 253 and tau-fluvalinate at a ratio of 1:1; a pest control composition comprising any one of the present compounds 1 to 253 and tau-fluvalinate at a ratio of 1:10; a pest control composition comprising any one of the present compounds 1 to 253 and halfenprox at a ratio of 0.1:1; a pest control composition comprising any one of the present compounds 1 to 253 and halfenprox at a ratio of 1:1; a pest control composition comprising any one of the present compounds 1 to 253 and halfenprox at a ratio of 1:10; a pest control composition comprising any one of the present compounds 1 to 253 and heptafluthrin at a ratio of 0.1:1; a pest control composition comprising any one of the present compounds 1 to 253 and heptafluthrin at a ratio of 1:1; a pest control composition comprising any one of the present compounds 1 to 253 and heptafluthrin at a ratio of 1:10; a pest control composition comprising any one of the present compounds 1 to 253 and imiprothrin at a ratio of 0.1:1; a pest control composition comprising any one of the present compounds 1 to 253 and imiprothrin at a ratio of 1:1; a pest control composition comprising any one of the present compounds 1 to 253 and imiprothrin at a ratio of 1:10; a pest control composition comprising any one of the present compounds 1 to 253 and kadethrin at a ratio of 0.1:1; a pest control composition comprising any one of the present compounds 1 to 253 and kadethrin at a ratio of 1:1; a pest control composition comprising any one of the present compounds 1 to 253 and kadethrin at a ratio of 1:10; a pest control composition comprising any one of the present compounds 1 to 253 and meperfluthrin at a ratio of 0.1:1; a pest control composition comprising any one of the present compounds 1 to 253 and meperfluthrin at a ratio of 1:1;

a pest control composition comprising any one of the present compounds 1 to 253 and meperfluthrin at a ratio of 1:10; a pest control composition comprising any one of the present compounds 1 to 253 and momfluorothrin at a ratio of 0.1:1; a pest control composition comprising any one of the present compounds 1 to 253 and momfluorothrin at a ratio of 1:1; a pest control composition comprising any one of the present compounds 1 to 253 and momfluorothrin at a ratio of 1:10; a pest control composition comprising any one of the present compounds 1 to 253 and permethrin at a ratio of 0.1:1; a pest control composition comprising any one of the present compounds 1 to 253 and permethrin at a ratio of 1:1; a pest control composition comprising any one of the present compounds 1 to 253 and permethrin at a ratio of 1:10; a pest control composition comprising any one of the present compounds 1 to 253 and phenothrin at a ratio of 0.1:1; a pest control composition comprising any one of the present compounds 1 to 253 and phenothrin at a ratio of 1:1; a pest control composition comprising any one of the present compounds 1 to 253 and phenothrin at a ratio of 1:10; a pest control composition comprising any one of the present compounds 1 to 253 and prallethrin at a ratio of 0.1:1; a pest control composition comprising any one of the present compounds 1 to 253 and prallethrin at a ratio of 1:1; a pest control composition comprising any one of the present compounds 1 to 253 and prallethrin at a ratio of 1:10; a pest control composition comprising any one of the present compounds 1 to 253 and pyrethrins at a ratio of 0.1:1; a pest control composition comprising any one of the present compounds 1 to 253 and pyrethrins at a ratio of 1:1; a pest control composition comprising any one of the present compounds 1 to 253 and pyrethrins at a ratio of 1:10; a pest control composition comprising any one of the present compounds 1 to 253 and resmethrin at a ratio of 0.1:1; a pest control composition comprising any one of the present compounds 1 to 253 and resmethrin at a ratio of 1:1; a pest control composition comprising any one of the present compounds 1 to 253 and resmethrin at a ratio of 1:10; a pest control composition comprising any one of the present compounds 1 to 253 and silafluofen at a ratio of 0.1:1; a pest control composition comprising any one of the present compounds 1 to 253 and silafluofen at a ratio of 1:1; a pest control composition comprising any one of the present compounds 1 to 253 and silafluofen at a ratio of 1:10; a pest control composition comprising any one of the present compounds 1 to 253 and tefluthrin at a ratio of 0.1:1; a pest control composition comprising any one of the present compounds 1 to 253 and tefluthrin at a ratio of 1:1; a pest control composition comprising any one of the present compounds 1 to 253 and tefluthrin at a ratio of 1:10; a pest control composition comprising any one of the present compounds 1 to 253 and tetramethrin at a ratio of 0.1:1; a pest control composition comprising any one of the present compounds 1 to 253 and tetramethrin at a ratio of 1:1; a pest control composition comprising any one of the present compounds 1 to 253 and tetramethrin at a ratio of 1:10; a pest control composition comprising any one of the present compounds 1 to 253 and tetramethylfluthrin at a ratio of 0.1:1; a pest control composition comprising any one of the present compounds 1 to 253 and tetramethylfluthrin at a ratio of 1:1; a pest control composition comprising any one of the present compounds 1 to 253 and tetramethylfluthrin at a ratio of 1:10; a pest control composition comprising any one of the present compounds 1 to 253 and tralomethrin at a ratio of 0.1:1; a pest control composition comprising any one of the present compounds 1 to 253 and tralomethrin at a ratio of 1:1; a pest control composition comprising any one of the present compounds 1 to 253 and tralomethrin at a ratio of 1:10; a pest control composition comprising any one of the present compounds 1 to 253 and transfluthrin at a ratio of 0.1:1; a pest control composition comprising any one of the present compounds 1 to 253 and transfluthrin at a ratio of 1:1; a pest control composition comprising any one of the present compounds 1 to 253 and transfluthrin at a ratio of 1:10; a compounds 1 to 253 and bensultap at a ratio of 1:1; a pest control composition comprising any one of the present compounds 1 to 253 and bensultap at a ratio of 1:10; a pest control composition comprising any one of the present compounds 1 to 253 and bensultap at a ratio of 1:50; a pest control composition comprising any one of the present compounds 1 to 253 and cartap at a ratio of 1:1; a pest control composition comprising any one of the present compounds 1 to 253 and cartap at a ratio of 1:10; a pest control composition comprising any one of the present compounds 1 to 253 and cartap at a ratio of 1:50; a pest control composition comprising any one of the present compounds 1 to 253 and cartap hydrochloride at a ratio of 1:1; a pest control composition comprising any one of the present compounds 1 to 253 and cartap hydrochloride at a ratio of 1:10; a pest control composition comprising any one of the present compounds 1 to 253 and cartap hydrochloride at a ratio of 1:50; a pest control composition comprising any one of the present compounds 1 to 253 and thiocyclam at a ratio of 1:1; a pest control composition comprising any one of the present compounds 1 to 253 and thiocyclam at a ratio of 1:10; a pest control composition comprising any one of the present compounds 1 to 253 and thiocyclam at a ratio of 1:50; a pest control composition comprising any one of the present compounds 1 to 253 and bisultap at a ratio of 1:1; a pest control composition comprising any one of the present compounds 1 to 253 and bisultap at a ratio of 1:10; a pest control composition comprising any one of the present compounds 1 to 253 and bisultap at a ratio of 1:50; a pest control composition comprising any one of the present compounds 1 to 253 and monosultap at a ratio of 1:1; a pest control composition comprising any one of the present compounds 1 to 253 and monosultap at a ratio of 1:10; a pest control composition comprising any one of the present compounds 1 to 253 and monosultap at a ratio of 1:50; a pest control composition comprising any one of the present compounds 1 to 253 and acetamiprid at a ratio of 1:1; a pest control composition comprising any one of the present compounds 1 to 253 and acetamiprid at a ratio of 1:10; a pest control composition comprising any one of the present compounds 1 to 253 and acetamiprid at a ratio of 1:50; a pest control composition comprising any one of the present compounds 1 to 253 and clothianidin at a ratio of 1:1; a pest control composition comprising any one of the present compounds 1 to 253 and clothianidin at a ratio of 1:10; a pest control composition comprising any one of the present compounds 1 to 253 and clothianidin at a ratio of 1:50;
a pest control composition comprising any one of the present compounds 1 to 253 and imidacloprid at a ratio of 1:1; a pest control composition comprising any one of the present compounds 1 to 253 and imidacloprid at a ratio of 1:10; a pest control composition comprising any one of the present compounds 1 to 253 and imidacloprid at a ratio of 1:50; a pest control composition comprising any one of the present compounds 1 to 253 and thiamethoxam at a ratio of 1:1; a pest control composition comprising any one of the present compounds 1 to 253 and thiamethoxam at a ratio of 1:10; a pest compounds 1 to 253 and thiamethoxam at a ratio of 1:50; a pest control composition comprising any one of the present compounds 1 to 253 and dinotefuran at a ratio of 1:1; a pest control composition comprising any one of the present compounds 1 to 253 and dinotefuran at a ratio of 1:10; a pest control composition comprising any one of the present compounds 1 to 253 and dinotefuran at a ratio of 1:50; a pest control composition comprising any one of the present compounds 1 to 253 and sulfoxaflor at a ratio of 1:1; a pest control composition comprising any one of the present compounds 1 to 253 and sulfoxaflor at a ratio of 1:10; a pest control composition comprising any one of the present compounds 1 to 253 and sulfoxaflor at a ratio of 1:50; a pest control composition comprising any one of the present compounds 1 to 253 and flupyradifurone at a ratio of 1:1; a pest control composition comprising any one of the present compounds 1 to 253 and flupyradifurone at a ratio of 1:10;
a pest control composition comprising any one of the present compounds 1 to 253 and flupyradifurone at a ratio of 1:50;
a pest control composition comprising any one of the present compounds 1 to 253 and nitenpyram at a ratio of 1:1; a pest control composition comprising any one of the present compounds 1 to 253 and nitenpyram at a ratio of 1:10; a pest control composition comprising any one of the present compounds 1 to 253 and nitenpyram at a ratio of 1:50; a pest control composition comprising any one of the present compounds 1 to 253 and thiacloprid at a ratio of 1:1;
a pest control composition comprising any one of the present compounds 1 to 253 and thiacloprid at a ratio of 1:10; a pest control composition comprising any one of the present compounds 1 to 253 and thiacloprid at a ratio of 1:50; a pest control composition comprising any one of the present compounds 1 to 253 and bistrifluron at a ratio of 0.1:1; a pest control composition comprising any one of the present compounds 1 to 253 and bistrifluron at a ratio of 1:1; a pest control composition comprising any one of the present compounds 1 to 253 and bistrifluron at a ratio of 1:10; a pest control composition comprising any one of the present compounds 1 to 253 and chlorfluazuron at a ratio of 0.1:1;
a pest control composition comprising any one of the present compounds 1 to 253 and chlorfluazuron at a ratio of 1:1; a pest control composition comprising any one of the present compounds 1 to 253 and chlorfluazuron at a ratio of 1:10; a pest control composition comprising any one of the present compounds 1 to 253 and diflubenzuron at a ratio of 0.1:1; a pest control composition comprising any one of the present compounds 1 to 253 and diflubenzuron at a ratio of 1:1; a pest control composition comprising any one of the present compounds 1 to 253 and diflubenzuron at a ratio of 1:10; a pest control composition comprising any one of the present compounds 1 to 253 and flucycloxuron at a ratio of 0.1:1; a pest control composition comprising any one of the present compounds 1 to 253 and flucycloxuron at a ratio of 1:1; a pest control composition comprising any one of the present compounds 1 to 253 and flucycloxuron at a ratio of 1:10; a pest control composition comprising any one of the present compounds 1 to 253 and flufenoxuron at a ratio of 0.1:1; a pest control composition comprising any one of the present compounds 1 to 253 and flufenoxuron at a ratio of 1:1; a pest control composition comprising any one of the present compounds 1 to 253 and flufenoxuron at a ratio of 1:10; a pest control composition comprising any one of the present compounds 1 to 253 and hexaflumuron at a ratio of 0.1:1; a pest control composition comprising any one of the present compounds 1 to 253 and hexaflumuron at a ratio of 1:1; a pest control composition comprising any one of the present compounds 1 to 253 and hexaflumuron at a ratio of 1:10;
a pest control composition comprising any one of the present compounds 1 to 253 and lufenuron at a ratio of 0.1:1; a pest control composition comprising any one of the present compounds 1 to 253 and lufenuron at a ratio of 1:1; a pest control composition comprising any one of the present compounds 1 to 253 and lufenuron at a ratio of 1:10; a pest control composition comprising any one of the present compounds 1 to 253 and novaluron at a ratio of 0.1:1; a pest control composition comprising any one of the present compounds 1 to 253 and novaluron at a ratio of 1:1; a pest control composition comprising any one of the present compounds 1 to 253 and novaluron at a ratio of 1:10; a pest control composition comprising any one of the present compounds 1 to 253 and noviflumuron at a ratio of 0.1:1; a pest control composition comprising any one of the present compounds 1 to 253 and noviflumuron at a ratio of 1:1; a pest control composition comprising any one of the present compounds 1 to 253 and noviflumuron at a ratio of 1:10; a pest control composition comprising any one of the present compounds 1 to 253 and teflubenzuron at a ratio of 0.1:1; a compounds 1 to 253 and teflubenzuron at a ratio of 1:1; a pest control composition comprising any one of the present compounds 1 to 253 and teflubenzuron at a ratio of 1:10; a pest control composition comprising any one of the present compounds 1 to 253 and triflumuron at a ratio of 0.1:1; a pest control composition comprising any one of the present compounds 1 to 253 and triflumuron at a ratio of 1:1; a pest control composition comprising any one of the present compounds 1 to 253 and triflumuron at a ratio of 1:10; a pest control composition comprising any one of the present compounds 1 to 253 and ethiprole at a ratio of 1:1; a pest control composition comprising any one of the present compounds 1 to 253 and ethiprole at a ratio of 1:10; a pest control composition comprising any one of the present compounds 1 to 253 and ethiprole at a ratio of 1:50; a pest control composition comprising any one of the present compounds 1 to 253 and fipronil at a ratio of 1:1; a pest control composition comprising any one of the present compounds 1 to 253 and fipronil at a ratio of 1:10;

a pest control composition comprising any one of the present compounds 1 to 253 and fipronil at a ratio of 1:50; a pest control composition comprising any one of the present compounds 1 to 253 and flufiprole at a ratio of 1:1; a pest control composition comprising any one of the present compounds 1 to 253 and flufiprole at a ratio of 1:10; a pest control composition comprising any one of the present compounds 1 to 253 and flufiprole at a ratio of 1:50; a pest control composition comprising any one of the present compounds 1 to 253 and chromafenozide at a ratio of 0.1:1; a pest control composition comprising any one of the present compounds 1 to 253 and chromafenozide at a ratio of 1:1; a pest control composition comprising any one of the present compounds 1 to 253 and chromafenozide at a ratio of 1:10; a pest control composition comprising any one of the present compounds 1 to 253 and halofenozide at a ratio of 0.1:1; a pest control composition comprising any one of the present compounds 1 to 253 and halofenozide at a ratio of 1:1; a pest control composition comprising any one of the present compounds 1 to 253 and halofenozide at a ratio of 1:10; a pest control composition comprising any one of the present compounds 1 to 253 and methoxyfenozide at a ratio of 0.1:1; a pest control composition comprising any one of the present compounds 1 to 253 and methoxyfenozide at a ratio of 1:1; a pest control composition comprising any one of the present compounds 1 to 253 and methoxyfenozide at a ratio of 1:10; a pest control composition comprising any one of the present compounds 1 to 253 and tebufenozide at a ratio of 0.1:1; a pest control composition comprising any one of the present compounds 1 to 253 and tebufenozide at a ratio of 1:1; a pest control composition comprising any one of the present compounds 1 to 253 and tebufenozide at a ratio of 1:10; a pest control composition comprising any one of the present compounds 1 to 253 and chlordane at a ratio of 1:1; a pest control composition comprising any one of the present compounds 1 to 253 and chlordane at a ratio of 1:10; a pest control composition comprising any one of the present compounds 1 to 253 and chlordane at a ratio of 1:50;
a pest control composition comprising any one of the present compounds 1 to 253 and endosulfan at a ratio of 1:1; a pest control composition comprising any one of the present compounds 1 to 253 and endosulfan at a ratio of 1:10; a pest control composition comprising any one of the present compounds 1 to 253 and endosulfan at a ratio of 1:50; a pest control composition comprising any one of the present compounds 1 to 253 and alpha-endosulfan at a ratio of 1:1; a pest control composition comprising any one of the present compounds 1 to 253 and alpha-endosulfan at a ratio of 1:10; a pest control composition comprising any one of the present compounds 1 to 253 and alpha-endosulfan at a ratio of 1:50; a pest control composition comprising any one of the present compounds 1 to 253 and chlorantraniliprole at a ratio of 1:0.1; a pest control composition comprising any one of the present compounds 1 to 253 and chlorantraniliprole at a ratio of 1:1; a pest control composition comprising any one of the present compounds 1 to 253 and chlorantraniliprole at a ratio of 1:10; a pest control composition comprising any one of the present compounds 1 to 253 and chlorantraniliprole at a ratio of 1:50; a pest control composition comprising any one of the present compounds 1 to 253 and cyantraniliprole at a ratio of 1:0.1; a pest control composition comprising any one of the present compounds 1 to 253 and cyantraniliprole at a ratio of 1:1; a pest control composition comprising any one of the present compounds 1 to 253 and cyantraniliprole at a ratio of 1:10; a pest control composition comprising any one of the present compounds 1 to 253 and cyantraniliprole at a ratio of 1:50; a pest control composition comprising any one of the present compounds 1 to 253 and cycloniliprole at a ratio of 1:0.1; a pest control composition comprising any one of the present compounds 1 to 253 and cycloniliprole at a ratio of 1:1; a pest control composition comprising any one of the present compounds 1 to 253 and cycloniliprole at a ratio of 1:10; a pest control composition comprising any one of the present compounds 1 to 253 and cycloniliprole at a ratio of 1:50;
a pest control composition comprising any one of the present compounds 1 to 253 and flubendiamide at a ratio of 1:0.1; a pest control composition comprising any one of the present compounds 1 to 253 and flubendiamide at a ratio of 1:1; a pest control composition comprising any one of the present compounds 1 to 253 and flubendiamide at a ratio of 1:10; a pest control composition comprising any one of the present compounds 1 to 253 and flubendiamide at a ratio of 1:50; a pest control composition comprising any one of the present compounds 1 to 253 and tetraniliprole at a ratio of 1:0.1; a pest control composition comprising any one of the present compounds 1 to 253 and tetraniliprole at a ratio of 1:1; a pest control composition comprising any one of the present compounds 1 to 253 and tetraniliprole at a ratio of 1:10; a pest control composition comprising any one of the present compounds 1 to 253 and tetraniliprole at a ratio of 1:50; a pest control composition comprising any one of the present compounds 1 to 253 and *Bacillus thuringiensis* var. *aizawai* at a ratio of 1:1; a pest control composition comprising any one of the present compounds 1 to 253 and *Bacillus thuringiensis* var. *aizawai* at a ratio of 1:10; a pest control composition comprising any one of the present compounds 1 to 253 and *Bacillus thuringiensis* var. *aizawai* at a ratio of 1:50; a pest control composition comprising any one of the present compounds 1 to 253 and *Bacillus thuringiensis* var. *Kurstaki* at a ratio of 1:1; a pest control composition comprising any one of the present compounds 1 to 253 and *Bacillus thuringiensis* var. *Kurstaki* at a ratio of 1:10; a pest control composition comprising any one of the present compounds 1 to 253 and *Bacillus thuringiensis* var. *Kurstaki* at a ratio of 1:50; a pest control composition comprising any one of the present compounds 1 to 253 and *Bacillus thuringiensis* var. *israelensis* at a ratio of 1:1; a pest control composition comprising any one of the present compounds 1 to 253 and *Bacillus thuringiensis* var. *israelensis* at a ratio of 1:10; a pest control composition comprising any one of the present compounds 1 to 253 and *Bacillus thuringiensis* var. *israelensis* at a ratio of 1:50;
a pest control composition comprising any one of the present compounds 1 to 253 and *Bacillus thuringiensis* var. *tenebriosis* at a ratio of 1:1; a pest control composition comprising any one of the present compounds 1 to 253 and *Bacillus thuringiensis* var. *tenebriosis* at a ratio of 1:10; a pest control composition comprising any one of the present compounds 1 to 253 and *Bacillus thuringiensis* var. *tenebriosis* at a ratio of 1:50; a pest control composition comprising any one of the present compounds 1 to 253 and *Bacillus firmus* at a ratio of 1:1; a pest control composition comprising any one of the present compounds 1 to 253 and *Bacillus firmus* at a ratio of 1:10; a pest control composition comprising any one of the present compounds 1 to 253 and *Bacillus firmus* at a ratio of 1:50; a pest control composition comprising any one of the present compounds 1 to 253 and *Bacillus sphaericus* at a ratio of 1:1; a pest control composition comprising any one of the present compounds 1 to 253 and *Bacillus sphaericus* at a ratio of 1:10; a pest control composition comprising any one of the present compounds 1 to 253 and *Bacillus sphaericus* at a ratio of 1:50; a pest control composition comprising any one of the present compounds 1 to 253 and *Beauveria bassiana* at a ratio of 1:1; a pest control composition comprising any one of the present compounds 1 to 253 and *Beauveria bassiana* at a ratio of 1:10; a pest control composition comprising any one of the present compounds 1 to 253 and *Beauveria bassiana* at a ratio of 1:50; a pest control composition comprising any one of the present compounds 1 to 253 and *Beauveria Brongniartii* at a ratio of 1:1; a pest control composition comprising any one of the present compounds 1 to 253 and *Beauveria Brongniartii* at a ratio of 1:10; a pest control composition comprising any one of the present compounds 1 to 253 and *Beauveria Brongniartii* at a ratio of 1:50; a pest control composition comprising any one of the present compounds 1 to 253 and *Paecilomyces fumosoroseus* at a ratio of 1:1; a pest control composition comprising any one of the present compounds 1 to 253 and *Paecilomyces fumosoroseus* at a ratio of 1:10; a pest control composition comprising any one of the present compounds 1 to 253 and *Paecilomyces fumosoroseus* at a ratio of 1:50;

a pest control composition comprising any one of the present compounds 1 to 253 and *Paecilomyces lilacinus* at a ratio of 1:1; a pest control composition comprising any one of the present compounds 1 to 253 and *Paecilomyces lilacinus* at a ratio of 1:10; a pest control composition comprising any one of the present compounds 1 to 253 and *Paecilomyces lilacinus* at a ratio of 1:50; a pest control composition comprising any one of the present compounds 1 to 253 and *Paecilomyces tenuipes* at a ratio of 1:1; a pest control composition comprising any one of the present compounds 1 to 253 and *Paecilomyces tenuipes* at a ratio of 1:10; a pest control composition comprising any one of the present compounds 1 to 253 and *Paecilomyces tenuipes* at a ratio of 1:50; a pest control composition comprising any one of the present compounds 1 to 253 and *Trichoderma harzianum* at a ratio of 1:1; a pest control composition comprising any one of the present compounds 1 to 253 and *Trichoderma harzianum* at a ratio of 1:10; a pest control composition comprising any one of the present compounds 1 to 253 and *Trichoderma harzianum* at a ratio of 1:50; a pest control composition comprising any one of the present compounds 1 to 253 and *Verticillium lecanii* at a ratio of 1:1; a pest control composition comprising any one of the present compounds 1 to 253 and *Verticillium lecanii* at a ratio of 1:10; a pest control composition comprising any one of the present compounds 1 to 253 and *Verticillium lecanii* at a ratio of 1:50; a pest control composition comprising any one of the present compounds 1 to 253 and *Pasteuria penetrans* at a ratio of 1:1; a pest control composition comprising any one of the present compounds 1 to 253 and *Pasteuria penetrans* at a ratio of 1:10; a pest control composition comprising any one of the present compounds 1 to 253 and *Pasteuria penetrans* at a ratio of 1:50; a pest control composition comprising any one of the present compounds 1 to 253 and dazomet at a ratio of 1:1; a pest control composition comprising any one of the present compounds 1 to 253 and dazomet at a ratio of 1:10; a pest control composition comprising any one of the present compounds 1 to 253 and dazomet at a ratio of 1:50; a pest control composition comprising any one of the present compounds 1 to 253 and fluensulfone at a ratio of 1:1;

a pest control composition comprising any one of the present compounds 1 to 253 and fluensulfone at a ratio of 1:10; a pest control composition comprising any one of the present compounds 1 to 253 and fluensulfone at a ratio of 1:50; a pest control composition comprising any one of the present compounds 1 to 253 and fosthiazate at a ratio of 1:1; a pest control composition comprising any one of the present compounds 1 to 253 and fosthiazate at a ratio of 1:10; a pest control composition comprising any one of the present compounds 1 to 253 and fosthiazate at a ratio of 1:50; a pest control composition comprising any one of the present compounds 1 to 253 and imicyafos at a ratio of 1:1; a pest control composition comprising any one of the present compounds 1 to 253 and imicyafos at a ratio of 1:10; a pest control composition comprising any one of the present compounds 1 to 253 and imicyafos at a ratio of 1:50; a pest control composition comprising any one of the present compounds 1 to 253 and metam at a ratio of 1:1; a pest control composition comprising any one of the present compounds 1 to 253 and metam at a ratio of 1:10; a pest control composition comprising any one of the present compounds 1 to 253 and metam at a ratio of 1:50; a pest control composition comprising any one of the present compounds 1 to 253 and tartar emetic at a ratio of 1:1; a pest control composition comprising any one of the present compounds 1 to 253 and tartar emetic at a ratio of 1:10; a pest control composition comprising any one of the present compounds 1 to 253 and tartar emetic at a ratio of 1:50; a pest control composition comprising any one of the present compounds 1 to 253 and tioxazafen at a ratio of 1:1; a pest control composition comprising any one of the present compounds 1 to 253 and tioxazafen at a ratio of 1:10; a pest control composition comprising any one of the present compounds 1 to 253 and tioxazafen at a ratio of 1:50; a pest control composition comprising any one of the present compounds 1 to 253 and *Arthrobotrys dactyloydes* at a ratio of 1:1; a pest control composition comprising any one of the present compounds 1 to 253 and *Arthrobotrys dactyloydes* at a ratio of 1:10; a pest control composition comprising any one of the present compounds 1 to 253 and *Arthrobotrys dactyloydes* at a ratio of 1:50;

a pest control composition comprising any one of the present compounds 1 to 253 and *Bacillus megaterium* at a ratio of 1:1; a pest control composition comprising any one of the present compounds 1 to 253 and *Bacillus megaterium* at a ratio of 1:10; a pest control composition comprising any one of the present compounds 1 to 253 and *Bacillus megaterium* at a ratio of 1:50; a pest control composition comprising any one of the present compounds 1 to 253 and *Hirsutella rhossiliensis* at a ratio of 1:1; a pest control composition comprising any one of the present compounds 1 to 253 and *Hirsutella rhossiliensis* at a ratio of 1:10; a pest control composition comprising any one of the present compounds 1 to 253 and *Hirsutella rhossiliensis* at a ratio of 1:50; a pest control composition comprising any one of the present compounds 1 to 253 and *Hirsutella minnesotensis* at a ratio of 1:1; a pest control composition comprising any one of the present compounds 1 to 253 and *Hirsutella minnesotensis* at a ratio of 1:10; a pest control composition comprising any one of the present compounds 1 to 253 and *Hirsutella minnesotensis* at a ratio of 1:50; a pest control composition comprising any one of the present compounds 1 to 253 and *Monacrosporium phymatopagum* at a ratio of 1:1; a pest control composition comprising any one of the present compounds 1 to 253 and *Monacrosporium phymatopagum* at a ratio of 1:10; a pest control composition comprising any one of the present compounds 1 to 253 and *Monacrosporium phymatopagum* at a ratio of 1:50; a pest control composition comprising any one of the present compounds 1 to 253 and *Pasteuria nishizawae* at a ratio of 1:1; a pest control composition comprising any one of the present compounds 1 to 253 and *Pasteuria nishizawae* at a ratio of 1:10; a pest control composition comprising any one of the present compounds 1 to 253 and *Pasteuria nishizawae* at a ratio of 1:50; a pest control composition comprising any one of the present compounds 1 to 253 and *Pasteuria usgae* at a ratio of 1:1; a pest control composition comprising any one of the present compounds 1 to 253 and *Pasteuria usgae* at a ratio of 1:10; a pest control composition comprising any one of the present compounds 1 to 253 and *Pasteuria usgae* at a ratio of 1:50;

a pest control composition comprising any one of the present compounds 1 to 253 and *Verticillium chlamydosporium* at a ratio of 1:1; a pest control composition comprising any one of the present compounds 1 to 253 and *Verticillium chlamydosporium* at a ratio of 1:10; a pest control composition comprising any one of the present compounds 1 to 253 and *Verticillium chlamydosporium* at a ratio of 1:50; a pest control composition comprising any one of the present compounds 1 to 253 and Harpin protein at a ratio of 1:1; a pest control composition comprising any one of the present compounds 1 to 253 and Harpin protein at a ratio of 1:10; a pest control composition comprising any one of the present compounds 1 to 253 and Harpin protein at a ratio of 1:50; a pest control composition comprising any one of the present compounds 1 to 253 and 6-bromo-N-{[2-chloro-5-(trifluoromethyl)phenyl]sulfonyl}-imidazo[1,2-a]pyrimidine-2-carboxamide at a ratio of 1:1; a pest control composition comprising any one of the present compounds 1 to 253 and 6-bromo-N-{[2-chloro-5-(trifluoromethyl)phenyl]sulfonyl}-imidazo[1,2-a]pyrimidine-2-carboxamide at a ratio of 1:10; a pest control composition comprising any one of the present compounds 1 to 253 and 6-bromo-N-{[2-chloro-5-(trifluoromethyl)phenyl]sulfonyl}-imidazo[1,2-a]pyrimidine-2-carboxamide at a ratio of 1:50; a pest control composition comprising any one of the present compounds 1 to 253 and 8-chloro-N-[(2-chloro-5-methoxyphenyl)sulfonyl]-6-(trifluoromethyl)-imidazo[1,2-a]pyridine-2-carboxamide at a ratio of 1:1; a pest control composition comprising any one of the present compounds 1 to 253 and 8-chloro-N-[(2-chloro-5-methoxyphenyl)sulfonyl]-6-(trifluoromethyl)-imidazo[1,2-a]pyridine-2-carboxamide at a ratio of 1:10; a pest control composition comprising any one of the present compounds 1 to 253 and 8-chloro-N-[(2-chloro-5-methoxyphenyl)sulfonyl]-6-(trifluoromethyl)-imidazo[1,2-a]pyridine-2-carboxamide at a ratio of 1:50;

a pest control composition comprising any one of the present compounds 1 to 253 and acequinocyl at a ratio of 0.1:1; a pest control composition comprising any one of the present compounds 1 to 253 and acequinocyl at a ratio of 1:1; a pest control composition comprising any one of the present compounds 1 to 253 and acequinocyl at a ratio of 1:10; a pest control composition comprising any one of the present compounds 1 to 253 and amitraz at a ratio of 0.1:1; a pest control composition comprising any one of the present compounds 1 to 253 and amitraz at a ratio of 1:1; a pest control composition comprising any one of the present compounds 1 to 253 and amitraz at a ratio of 1:10; a pest control composition comprising any one of the present compounds 1 to 253 and Benzoximate at a ratio of 0.1:1; a pest control composition comprising any one of the present compounds 1 to 253 and Benzoximate at a ratio of 1:1; a pest control composition comprising any one of the present compounds 1 to 253 and Benzoximate at a ratio of 1:10; a pest control composition comprising any one of the present compounds 1 to 253 and bifenazate at a ratio of 0.1:1; a pest control composition comprising any one of the present compounds 1 to 253 and bifenazate at a ratio of 1:1; a pest control composition comprising any one of the present compounds 1 to 253 and bifenazate at a ratio of 1:10; a pest control composition comprising any one of the present compounds 1 to 253 and bromopropylate at a ratio of 0.1:1; a pest control composition comprising any one of the present compounds 1 to 253 and bromopropylate at a ratio of 1:1; a compounds 1 to 253 and bromopropylate at a ratio of 1:10; a pest control composition comprising any one of the present compounds 1 to 253 and chinomethionat at a ratio of 0.1:1; a pest control composition comprising any one of the present compounds 1 to 253 and chinomethionat at a ratio of 1:1; a pest control composition comprising any one of the present compounds 1 to 253 and chinomethionat at a ratio of 1:10; a pest control composition comprising any one of the present compounds 1 to 253 and clofentezine at a ratio of 0.1:1; a pest control composition comprising any one of the present compounds 1 to 253 and clofentezine at a ratio of 1:1; a pest control composition comprising any one of the present compounds 1 to 253 and clofentezine at a ratio of 1:10; a pest control composition comprising any one of the present compounds 1 to 253 and cyenopyrafen at a ratio of 0.1:1; a pest control composition comprising any one of the present compounds 1 to 253 and cyenopyrafen at a ratio of 1:1; a pest control composition comprising any one of the present compounds 1 to 253 and cyenopyrafen at a ratio of 1:10; a pest control composition comprising any one of the present compounds 1 to 253 and cyflumetofen at a ratio of 0.1:1; a pest control composition comprising any one of the present compounds 1 to 253 and cyflumetofen at a ratio of 1:1; a pest control composition comprising any one of the present compounds 1 to 253 and cyflumetofen at a ratio of 1:10; a pest control composition comprising any one of the present compounds 1 to 253 and cyhexatin at a ratio of 0.1:1; a pest control composition comprising any one of the present compounds 1 to 253 and cyhexatin at a ratio of 1:1; a pest control composition comprising any one of the present compounds 1 to 253 and cyhexatin at a ratio of 1:10; a pest control composition comprising any one of the present compounds 1 to 253 and dicofol at a ratio of 0.1:1; a pest control composition comprising any one of the present compounds 1 to 253 and dicofol at a ratio of 1:1; a pest control composition comprising any one of the present compounds 1 to 253 and dicofol at a ratio of 1:10; a pest control composition comprising any one of the present compounds 1 to 253 and etoxazole at a ratio of 0.1:1; a pest control composition comprising any one of the present compounds 1 to 253 and etoxazole at a ratio of 1:1; a pest control composition comprising any one of the present compounds 1 to 253 and etoxazole at a ratio of 1:10; a pest control composition comprising any one of the present compounds 1 to 253 and fenazaquin at a ratio of 0.1:1; a pest control composition comprising any one of the present compounds 1 to 253 and fenazaquin at a ratio of 1:1; a pest control composition comprising any one of the present compounds 1 to 253 and fenazaquin at a ratio of 1:10; a pest control composition comprising any one of the present compounds 1 to 253 and fenbutatin oxide at a ratio of 0.1:1; a pest control composition comprising any one of the present compounds 1 to 253 and fenbutatin oxide at a ratio of 1:1; a pest control composition comprising any one of the present compounds 1 to 253 and fenbutatin oxide at a ratio of 1:10; a pest control composition comprising any one of the present compounds 1 to 253 and fenpyroximate at a ratio of 0.1:1; a compounds 1 to 253 and fenpyroximate at a ratio of 1:1; a pest control composition comprising any one of the present compounds 1 to 253 and fenpyroximate at a ratio of 1:10; a pest control composition comprising any one of the present compounds 1 to 253 and fluacrypyrim at a ratio of 0.1:1; a pest control composition comprising any one of the present compounds 1 to 253 and fluacrypyrim at a ratio of 1:1; a pest control composition comprising any one of the present compounds 1 to 253 and fluacrypyrim at a ratio of 1:10; a pest control composition comprising any one of the present compounds 1 to 253 and fluazuron at a ratio of 0.1:1; a pest control composition comprising any one of the present compounds 1 to 253 and fluazuron at a ratio of 1:1; a pest control composition comprising any one of the present compounds 1 to 253 and fluazuron at a ratio of 1:10; a pest control composition comprising any one of the present compounds 1 to 253 and flufenoxystrobin at a ratio of 0.1:1; a pest control composition comprising any one of the present compounds 1 to 253 and flufenoxystrobin at a ratio of 1:1; a pest control composition comprising any one of the present compounds 1 to 253 and flufenoxystrobin at a ratio of 1:10; a pest control composition comprising any one of the present compounds 1 to 253 and hexythiazox at a ratio of 0.1:1; a pest control composition comprising any one of the present compounds 1 to 253 and hexythiazox at a ratio of 1:1; a pest control composition comprising any one of the present compounds 1 to 253 and hexythiazox at a ratio of 1:10; a pest control composition comprising any one of the present compounds 1 to 253 and propargite at a ratio of 0.1:1; a pest control composition comprising any one of the present compounds 1 to 253 and propargite at a ratio of 1:1; a pest control composition comprising any one of the present compounds 1 to 253 and propargite at a ratio of 1:10; a pest control composition comprising any one of the present compounds 1 to 253 and pyflubumide at a ratio of 0.1:1; a pest control composition comprising any one of the present compounds 1 to 253 and pyflubumide at a ratio of 1:1; a pest control composition comprising any one of the present compounds 1 to 253 and pyflubumide at a ratio of 1:10; a pest control composition comprising any one of the present compounds 1 to 253 and pyridaben at a ratio of 0.1:1; a pest control composition comprising any one of the present compounds 1 to 253 and pyridaben at a ratio of 1:1; a pest control composition comprising any one of the present compounds 1 to 253 and pyridaben at a ratio of 1:10; a pest control composition comprising any one of the present compounds 1 to 253 and Pyrimidifen at a ratio of 0.1:1; a pest control composition comprising any one of the present compounds 1 to 253 and Pyrimidifen at a ratio of 1:1; a pest control composition comprising any one of the present compounds 1 to 253 and Pyrimidifen at a ratio of 1:10; a pest control composition comprising any one of the present compounds 1 to 253 and pyriminostrobin at a ratio of 0.1:1; a pest control composition comprising any one of the present compounds 1 to 253 and pyriminostrobin at a ratio of 1:1; a pest control composition comprising any one of the present compounds 1 to 253 and pyriminostrobin at a ratio of 1:10; a pest control composition comprising any one of the present compounds 1 to 253 and spirodiclofen at a ratio of 0.1:1; a pest control composition comprising any one of the present compounds 1 to 253 and spirodiclofen at a ratio of 1:1; a pest control composition comprising any one of the present compounds 1 to 253 and spirodiclofen at a ratio of 1:10; a pest control composition comprising any one of the present compounds 1 to 253 and spiromesifen at a ratio of 0.1:1; a pest control composition comprising any one of the present compounds 1 to 253 and spiromesifen at a ratio of 1:1; a pest control composition comprising any one of the present compounds 1 to 253 and spiromesifen at a ratio of 1:10; a pest control composition comprising any one of the present compounds 1 to 253 and tebufenpyrad at a ratio of 0.1:1; a pest control composition comprising any one of the present compounds 1 to 253 and tebufenpyrad at a ratio of 1:1; a pest control composition comprising any one of the present compounds 1 to 253 and tebufenpyrad at a ratio of 1:10; a pest control composition comprising any one of the present compounds 1 to 253 and tetradifon at a ratio of 0.1:1; a pest control composition comprising any one of the present compounds 1 to 253 and tetradifon at a ratio of 1:1; a pest control composition comprising any one of the present compounds 1 to 253 and tetradifon at a ratio of 1:10; a pest control composition comprising any one of the present compounds 1 to 253 and abamectin at a ratio of 1:1; a pest control composition comprising any one of the present compounds 1 to 253 and abamectin at a ratio of 1:10; a pest control composition comprising any one of the present compounds 1 to 253 and abamectin at a ratio of 1:50; a pest control composition comprising any one of the present compounds 1 to 253 and emamectin-benzoate at a ratio of 1:1; a pest control composition comprising any one of the present compounds 1 to 253 and emamectin-benzoate at a ratio of 1:10; a pest control composition comprising any one of the present compounds 1 to 253 and emamectin-benzoate at a ratio of 1:50; a pest control composition comprising any one of the present compounds 1 to 253 and lepimectin at a ratio of 1:1; a pest control composition comprising any one of the present compounds 1 to 253 and lepimectin at a ratio of 1:10; a pest control composition comprising any one of the present compounds 1 to 253 and lepimectin at a ratio of 1:50; a pest control composition comprising any one of the present compounds 1 to 253 and milbemectin at a ratio of 1:1; a pest control composition comprising any one of the present compounds 1 to 253 and milbemectin at a ratio of 1:10; a pest control composition comprising any one of the present compounds 1 to 253 and milbemectin at a ratio of 1:50; a pest control composition comprising any one of the present compounds 1 to 253 and spinetoram at a ratio of 1:1; a pest control composition comprising any one of the present compounds 1 to 253 and spinetoram at a ratio of 1:10; a pest control composition comprising any one of the present compounds 1 to 253 and spinetoram at a ratio of 1:50; a pest control composition comprising any one of the present compounds 1 to 253 and spinosad at a ratio of 1:1; a pest control composition comprising any one of the present compounds 1 to 253 and spinosad at a ratio of 1:10; a pest control composition comprising any one of the present compounds 1 to 253 and spinosad at a ratio of 1:50; a pest control composition comprising any one of the present compounds 1 to 253 and afidopyropen at a ratio of 1:1; a pest control composition comprising any one of the present compounds 1 to 253 and afidopyropen at a ratio of 1:10; a pest control composition comprising any one of the present compounds 1 to 253 and afidopyropen at a ratio of 1:50; a pest control composition comprising any one of the present compounds 1 to 253 and aluminium phosphide at a ratio of 1:1; a pest control composition comprising any one of the present compounds 1 to 253 and aluminium phosphide at a ratio of 1:10; a pest control composition comprising any one of the present compounds 1 to 253 and aluminium phosphide at a ratio of 1:50; a pest control composition comprising any one of the present compounds 1 to 253 and calcium phosphide at a ratio of 1:1; a pest control composition comprising any one of the present compounds 1 to 253 and calcium phosphide at a ratio of 1:10; a pest control composition comprising any one of the present compounds 1 to 253 and calcium phosphide at a ratio of 1:50; a pest control composition comprising any one of the present compounds 1 to 253 and hydrogen phosphide at a ratio of 1:1; a pest control composition comprising any one of the present compounds 1 to 253 and hydrogen phosphide at a ratio of 1:10; a pest control composition comprising any one of the present compounds 1 to 253 and hydrogen phosphide at a ratio of 1:50; a pest control composition comprising any one of the present compounds 1 to 253 and zinc phosphide at a ratio of 1:1; a pest control composition comprising any one of the present compounds 1 to 253 and zinc phosphide at a ratio of 1:10; a pest control composition comprising any one of the present compounds 1 to 253 and zinc phosphide at a ratio of 1:50;

a pest control composition comprising any one of the present compounds 1 to 253 and azadirachtin at a ratio of 1:1; a pest control composition comprising any one of the present compounds 1 to 253 and azadirachtin at a ratio of 1:10; a pest control composition comprising any one of the present compounds 1 to 253 and azadirachtin at a ratio of 1:50; a pest control composition comprising any one of the present compounds 1 to 253 and buprofezin at a ratio of 1:1; a pest control composition comprising any one of the present compounds 1 to 253 and buprofezin at a ratio of 1:10; a pest control composition comprising any one of the present compounds 1 to 253 and buprofezin at a ratio of 1:50; a pest control composition comprising any one of the present compounds 1 to 253 and chlorfenapyr at a ratio of 1:1; a pest control composition comprising any one of the present compounds 1 to 253 and chlorfenapyr at a ratio of 1:10; a pest control composition comprising any one of the present compounds 1 to 253 and chlorfenapyr at a ratio of 1:50; a pest control composition comprising any one of the present compounds 1 to 253 and chloropicrin at a ratio of 1:1; a pest control composition comprising any one of the present compounds 1 to 253 and chloropicrin at a ratio of 1:10; a pest control composition comprising any one of the present compounds 1 to 253 and chloropicrin at a ratio of 1:50; a pest control composition comprising any one of the present compounds 1 to 253 and cyromazine at a ratio of 1:1; a pest control composition comprising any one of the present compounds 1 to 253 and cyromazine at a ratio of 1:10; a pest compounds 1 to 253 and cyromazine at a ratio of 1:50; a pest control composition comprising any one of the present compounds 1 to 253 and diafenthiuron at a ratio of 1:1; a pest control composition comprising any one of the present compounds 1 to 253 and diafenthiuron at a ratio of 1:10; a pest control composition comprising any one of the present compounds 1 to 253 and diafenthiuron at a ratio of 1:50; a pest control composition comprising any one of the present compounds 1 to 253 and DNOC at a ratio of 1:1; a pest control composition comprising any one of the present compounds 1 to 253 and DNOC at a ratio of 1:10;

a pest control composition comprising any one of the present compounds 1 to 253 and DNOC at a ratio of 1:50; a pest control composition comprising any one of the present compounds 1 to 253 and fenoxycarb at a ratio of 1:1; a pest control composition comprising any one of the present compounds 1 to 253 and fenoxycarb at a ratio of 1:10; a pest control composition comprising any one of the present compounds 1 to 253 and fenoxycarb at a ratio of 1:50; a pest control composition comprising any one of the present compounds 1 to 253 and flometoquin at a ratio of 1:1; a pest control composition comprising any one of the present compounds 1 to 253 and flometoquin at a ratio of 1:10; a pest control composition comprising any one of the present compounds 1 to 253 and flometoquin at a ratio of 1:50; a pest control composition comprising any one of the present compounds 1 to 253 and flonicamid at a ratio of 1:1; a pest control composition comprising any one of the present compounds 1 to 253 and flonicamid at a ratio of 1:10; a pest control composition comprising any one of the present compounds 1 to 253 and flonicamid at a ratio of 1:50; a pest control composition comprising any one of the present compounds 1 to 253 and hydramethylnon at a ratio of 1:1; a pest control composition comprising any one of the present compounds 1 to 253 and hydramethylnon at a ratio of 1:10; a pest control composition comprising any one of the present compounds 1 to 253 and hydramethylnon at a ratio of 1:50; a pest control composition comprising any one of the present compounds 1 to 253 and hydroprene at a ratio of 1:1; a pest control composition comprising any one of the present compounds 1 to 253 and hydroprene at a ratio of 1:10; a pest control composition comprising any one of the present compounds 1 to 253 and hydroprene at a ratio of 1:50; a pest control composition comprising any one of the present compounds 1 to 253 and indoxacarb at a ratio of 1:1; a pest control composition comprising any one of the present compounds 1 to 253 and indoxacarb at a ratio of 1:10; a pest control composition comprising any one of the present compounds 1 to 253 and indoxacarb at a ratio of 1:50; a pest control composition comprising any one of the present compounds 1 to 253 and kinoprene at a ratio of 1:1;

a pest control composition comprising any one of the present compounds 1 to 253 and kinoprene at a ratio of 1:10; a pest control composition comprising any one of the present compounds 1 to 253 and kinoprene at a ratio of 1:50; a pest control composition comprising any one of the present compounds 1 to 253 and metaflumizone at a ratio of 1:1; a pest compounds 1 to 253 and metaflumizone at a ratio of 1:10; a pest control composition comprising any one of the present compounds 1 to 253 and metaflumizone at a ratio of 1:50; a pest control composition comprising any one of the present compounds 1 to 253 and methoprene at a ratio of 1:1; a pest control composition comprising any one of the present compounds 1 to 253 and methoprene at a ratio of 1:10; a pest control composition comprising any one of the present compounds 1 to 253 and methoprene at a ratio of 1:50; a pest control composition comprising any one of the present compounds 1 to 253 and methoxychlor at a ratio of 1:1; a pest control composition comprising any one of the present compounds 1 to 253 and methoxychlor at a ratio of 1:10; a pest control composition comprising any one of the present compounds 1 to 253 and methoxychlor at a ratio of 1:50; a pest control composition comprising any one of the present compounds 1 to 253 and methyl bromide at a ratio of 1:1; a pest control composition comprising any one of the present compounds 1 to 253 and methyl bromide at a ratio of 1:10; a pest control composition comprising any one of the present compounds 1 to 253 and methyl bromide at a ratio of 1:50; a pest control composition comprising any one of the present compounds 1 to 253 and metoxadiazone at a ratio of 1:1; a pest control composition comprising any one of the present compounds 1 to 253 and metoxadiazone at a ratio of 1:10; a pest control composition comprising any one of the present compounds 1 to 253 and metoxadiazone at a ratio of 1:50; a pest control composition comprising any one of the present compounds 1 to 253 and pymetrozine at a ratio of 1:1; a pest compounds 1 to 253 and pymetrozine at a ratio of 1:10; a pest control composition comprising any one of the present compounds 1 to 253 and pymetrozine at a ratio of 1:50; a pest control composition comprising any one of the present compounds 1 to 253 and pyrazophos at a ratio of 1:1;

a pest control composition comprising any one of the present compounds 1 to 253 and pyrazophos at a ratio of 1:10; a pest control composition comprising any one of the present compounds 1 to 253 and pyrazophos at a ratio of 1:50; a pest control composition comprising any one of the present compounds 1 to 253 and pyridalyl at a ratio of 1:1; a pest control composition comprising any one of the present compounds 1 to 253 and pyridalyl at a ratio of 1:10; a pest control composition comprising any one of the present compounds 1 to 253 and pyridalyl at a ratio of 1:50; a pest control composition comprising any one of the present compounds 1 to 253 and pyrifluquinazone at a ratio of 1:1; a pest control composition comprising any one of the present compounds 1 to 253 and pyrifluquinazone at a ratio of 1:10; a pest control composition comprising any one of the present compounds 1 to 253 and pyrifluquinazone at a ratio of 1:50; a pest control composition comprising any one of the present compounds 1 to 253 and pyriproxyfen at a ratio of 1:1; a pest control composition comprising any one of the present compounds 1 to 253 and pyriproxyfen at a ratio of 1:10; a pest control composition comprising any one of the present compounds 1 to 253 and pyriproxyfen at a ratio of 1:50; a pest control composition comprising any one of the present compounds 1 to 253 and sodium aluminum fluoride at a ratio of 1:1; a pest control composition comprising any one of the present compounds 1 to 253 and sodium aluminum fluoride at a ratio of 1:10; a pest control composition comprising any one of the present compounds 1 to 253 and sodium aluminum fluoride at a ratio of 1:50; a pest control composition comprising any one of the present compounds 1 to 253 and spirotetramat at a ratio of 1:1; a pest control composition comprising any one of the present compounds 1 to 253 and spirotetramat at a ratio of 1:10; a pest control composition comprising any one of the present compounds 1 to 253 and spirotetramat at a ratio of 1:50; a pest control composition comprising any one of the present compounds 1 to 253 and sulfluramid at a ratio of 1:1; a pest control composition comprising any one of the present compounds 1 to 253 and sulfluramid at a ratio of 1:10;

a pest control composition comprising any one of the present compounds 1 to 253 and sulfluramid at a ratio of 1:50; a pest control composition comprising any one of the present compounds 1 to 253 and sulfuryl fluoride at a ratio of 1:1; a pest control composition comprising any one of the present compounds 1 to 253 and sulfuryl fluoride at a ratio of 1:10; a pest control composition comprising any one of the present compounds 1 to 253 and sulfuryl fluoride at a ratio of 1:50; a pest control composition comprising any one of the present compounds 1 to 253 and tolfenpyrad at a ratio of 1:1; a pest control composition comprising any one of the present compounds 1 to 253 and tolfenpyrad at a ratio of 1:10; a pest control composition comprising any one of the present compounds 1 to 253 and tolfenpyrad at a ratio of 1:50; a pest compounds 1 to 253 and triflumezopyrim at a ratio of 1:1; a pest control composition comprising any one of the present compounds 1 to 253 and triflumezopyrim at a ratio of 1:10; a pest control composition comprising any one of the present compounds 1 to 253 and triflumezopyrim at a ratio of 1:50; a pest control composition comprising any one of the present compounds 1 to 253 and 4-oxo-4-(2-phenylethyl)aminobutyric acid at a ratio of 5:1; a pest control composition comprising any one of the present compounds 1 to 253 and 4-oxo-4-(2-phenylethyl)aminobutyric acid at a ratio of 1:10; a pest control composition comprising any one of the present compounds 1 to 253 and 4-oxo-4-(2-phenylethyl)aminobutyric acid at a ratio of 1:50; a pest control composition comprising any one of the present compounds 1 to 253 and methyl 5-(trifluoromethyl)benzo[b]thiophene-2-carboxylate at a ratio of 5:1; a pest control composition comprising any one of the present compounds 1 to 253 and methyl 5-(trifluoromethyl)benzo[b]thiophene-2-carboxylate at a ratio of 1:10; a pest control composition comprising any one of the present compounds 1 to 253 and methyl 5-(trifluoromethyl)benzo[b]thiophene-2-carboxylate at a ratio of 1:50;

a pest control composition comprising any one of the present compounds 1 to 253 and 5-(trifluoromethyl)benzo[b]thiophene-2-carboxylic acid at a ratio of 5:1; a pest control composition comprising any one of the present compounds 1 to 253 and 5-(trifluoromethyl)benzo[b]thiophene-2-carboxylic acid at a ratio of 1:10; a pest control composition comprising any one of the present compounds 1 to 253 and 5-(trifluoromethyl)benzo[b]thiophene-2-carboxylic acid at a ratio of 1:50; a pest control composition comprising any one of the present compounds 1 to 253 and 2,4-D at a ratio of 0.1:1; a pest control composition comprising any one of the present compounds 1 to 253 and 2,4-D at a ratio of 1:1; a pest control composition comprising any one of the present compounds 1 to 253 and 2,4-D at a ratio of 1:20; a pest control composition comprising any one of the present compounds 1 to 253 and 2,4-DB at a ratio of 0.1:1; a pest control composition comprising any one of the present compounds 1 to 253 and 2,4-DB at a ratio of 1:1; a pest control composition comprising any one of the present compounds 1 to 253 and 2,4-DB at a ratio of 1:20; a pest control composition comprising any one of the present compounds 1 to 253 and acetochlor at a ratio of 0.1:1; a pest control composition comprising any one of the present compounds 1 to 253 and acetochlor at a ratio of 1:1; a pest control composition comprising any one of the present compounds 1 to 253 and acetochlor at a ratio of 1:20; a pest control composition comprising any one of the present compounds 1 to 253 and acifluorfen at a ratio of 0.1:1; a pest control composition comprising any one of the present compounds 1 to 253 and acifluorfen at a ratio of 1:1; a pest control composition comprising any one of the present compounds 1 to 253 and acifluorfen at a ratio of 1:20; a pest control composition comprising any one of the present compounds 1 to 253 and alachlor at a ratio of 0.1:1; a pest control composition comprising any one of the present compounds 1 to 253 and alachlor at a ratio of 1:1; a pest control composition comprising any one of the present compounds 1 to 253 and alachlor at a ratio of 1:20; a pest control composition comprising any one of the present compounds 1 to 253 and ametryn at a ratio of 0.1:1; a pest control composition comprising any one of the present compounds 1 to 253 and ametryn at a ratio of 1:1; a pest control composition comprising any one of the present compounds 1 to 253 and ametryn at a ratio of 1:20;

a pest control composition comprising any one of the present compounds 1 to 253 and amicarbazone at a ratio of 0.1:1; a pest control composition comprising any one of the present compounds 1 to 253 and amicarbazone at a ratio of 1:1; a pest control composition comprising any one of the present compounds 1 to 253 and amicarbazone at a ratio of 1:20; a pest control composition comprising any one of the present compounds 1 to 253 and aminopyralid at a ratio of 0.1:1; a pest control composition comprising any one of the present compounds 1 to 253 and aminopyralid at a ratio of 1:1; a pest control composition comprising any one of the present compounds 1 to 253 and aminopyralid at a ratio of 1:20; a pest control composition comprising any one of the present compounds 1 to 253 and atrazine at a ratio of 0.1:1; a pest control composition comprising any one of the present compounds 1 to 253 and atrazine at a ratio of 1:1; a pest control composition comprising any one of the present compounds 1 to 253 and atrazine at a ratio of 1:20; a pest control composition comprising any one of the present compounds 1 to 253 and benefin at a ratio of 0.1:1; a pest control composition comprising any one of the present compounds 1 to 253 and benefin at a ratio of 1:1; a pest control composition comprising any one of the present compounds 1 to 253 and benefin at a ratio of 1:20; a pest control composition comprising any one of the present compounds 1 to 253 and bentazon at a ratio of 0.1:1; a pest control composition comprising any one of the present compounds 1 to 253 and bentazon at a ratio of 1:1; a pest control composition comprising any one of the present compounds 1 to 253 and bentazon at a ratio of 1:20; a pest control composition comprising any one of the present compounds 1 to 253 and bromoxynil at a ratio of 0.1:1; a pest control composition comprising any one of the present compounds 1 to 253 and bromoxynil at a ratio of 1:1; a pest control composition comprising any one of the present compounds 1 to 253 and bromoxynil at a ratio of 1:20; a pest control composition comprising any one of the present compounds 1 to 253 and carfentrazone at a ratio of 0.1:1; a pest control composition comprising any one of the present compounds 1 to 253 and carfentrazone at a ratio of 1:1; a pest control composition comprising any one of the present compounds 1 to 253 and carfentrazone at a ratio of 1:20; a pest control composition comprising any one of the present compounds 1 to 253 and carfentrazone-ethyl at a ratio of 0.1:1; a pest control composition comprising any one of the present compounds 1 to 253 and carfentrazone-ethyl at a ratio of 1:1; a pest control composition comprising any one of the present compounds 1 to 253 and carfentrazone-ethyl at a ratio of 1:20; a pest control composition comprising any one of the present compounds 1 to 253 and chloransulam at a ratio of 0.1:1; a pest control composition comprising any one of the present compounds 1 to 253 and chloransulam at a ratio of 1:1; a pest control composition comprising any one of the present compounds 1 to 253 and chloransulam at a ratio of 1:20; a pest control composition comprising any one of the present compounds 1 to 253 and chlorimuron at a ratio of 0.1:1; a pest control composition comprising any one of the present compounds 1 to 253 and chlorimuron at a ratio of 1:1; a pest control composition comprising any one of the present compounds 1 to 253 and chlorimuron at a ratio of 1:20; a pest control composition comprising any one of the present compounds 1 to 253 and chlorimuronethyl at a ratio of 0.1:1; a pest control composition comprising any one of the present compounds 1 to 253 and chlorimuronethyl at a ratio of 1:1; a pest control composition comprising any one of the present compounds 1 to 253 and chlorimuronethyl at a ratio of 1:20; a pest control composition comprising any one of the present compounds 1 to 253 and chloridazon at a ratio of 0.1:1; a pest control composition comprising any one of the present compounds 1 to 253 and chloridazon at a ratio of 1:1; a pest control composition comprising any one of the present compounds 1 to 253 and chloridazon at a ratio of 1:20; a pest control composition comprising any one of the present compounds 1 to 253 and clethodim at a ratio of 0.1:1; a pest control composition comprising any one of the present compounds 1 to 253 and clethodim at a ratio of 1:1; a pest control composition comprising any one of the present compounds 1 to 253 and clethodim at a ratio of 1:20; a pest control composition comprising any one of the present compounds 1 to 253 and clodinafop at a ratio of 0.1:1; a pest compounds 1 to 253 and clodinafop at a ratio of 1:1; a pest control composition comprising any one of the present compounds 1 to 253 and clodinafop at a ratio of 1:20; a pest control composition comprising any one of the present compounds 1 to 253 and clomazone at a ratio of 0.1:1; a pest control composition comprising any one of the present compounds 1 to 253 and clomazone at a ratio of 1:1; a pest control composition comprising any one of the present compounds 1 to 253 and clomazone at a ratio of 1:20; a pest control composition comprising any one of the present compounds 1 to 253 and clopyralid at a ratio of 0.1:1; a pest control composition comprising any one of the present compounds 1 to 253 and clopyralid at a ratio of 1:1; a pest control composition comprising any one of the present compounds 1 to 253 and clopyralid at a ratio of 1:20; a pest control composition comprising any one of the present compounds 1 to 253 and cloransulam-methyl at a ratio of 0.1:1; a pest control composition comprising any one of the present compounds 1 to 253 and cloransulam-methyl at a ratio of 1:1; a pest control composition comprising any one of the present compounds 1 to 253 and cloransulam-methyl at a ratio of 1:20; a pest control composition comprising any one of the present compounds 1 to 253 and desmedipham at a ratio of 0.1:1; a pest control composition comprising any one of the present compounds 1 to 253 and desmedipham at a ratio of 1:1; a pest control composition comprising any one of the present compounds 1 to 253 and desmedipham at a ratio of 1:20; a pest control composition comprising any one of the present compounds 1 to 253 and dicamba at a ratio of 0.1:1; a pest control composition comprising any one of the present compounds 1 to 253 and dicamba at a ratio of 1:1; a pest control composition comprising any one of the present compounds 1 to 253 and dicamba at a ratio of 1:20; a pest control composition comprising any one of the present compounds 1 to 253 and diclofop at a ratio of 0.1:1; a pest control composition comprising any one of the present compounds 1 to 253 and diclofop at a ratio of 1:1; a pest control composition comprising any one of the present compounds 1 to 253 and diclofop at a ratio of 1:20; a pest control composition comprising any one of the present compounds 1 to 253 and diclosulam at a ratio of 0.1:1; a pest control composition comprising any one of the present compounds 1 to 253 and diclosulam at a ratio of 1:1; a pest control composition comprising any one of the present compounds 1 to 253 and diclosulam at a ratio of 1:20; a pest control composition comprising any one of the present compounds 1 to 253 and diufenzopyr at a ratio of 0.1:1; a pest control composition comprising any one of the present compounds 1 to 253 and diufenzopyr at a ratio of 1:1; a pest control composition comprising any one of the present compounds 1 to 253 and diufenzopyr at a ratio of 1:20; a pest control composition comprising any one of the present compounds 1 to 253 and dimethenamid at a ratio of 0.1:1; a pest control composition comprising any one of the present compounds 1 to 253 and dimethenamid at a ratio of 1:1; a pest control composition comprising any one of the present compounds 1 to 253 and dimethenamid at a ratio of 1:20; a pest compounds 1 to 253 and diquat at a ratio of 0.1:1; a pest control composition comprising any one of the present compounds 1 to 253 and diquat at a ratio of 1:1; a pest control composition comprising any one of the present compounds 1 to 253 and diquat at a ratio of 1:20; a pest control composition comprising any one of the present compounds 1 to 253 and diuron at a ratio of 0.1:1; a pest control composition comprising any one of the present compounds 1 to 253 and diuron at a ratio of 1:1; a pest control composition comprising any one of the present compounds 1 to 253 and diuron at a ratio of 1:20; a pest control composition comprising any one of the present compounds 1 to 253 and EPTC at a ratio of 0.1:1; a pest control composition comprising any one of the present compounds 1 to 253 and EPTC at a ratio of 1:1; a pest control composition comprising any one of the present compounds 1 to 253 and EPTC at a ratio of 1:20; a pest control composition comprising any one of the present compounds 1 to 253 and ethalfluralin at a ratio of 0.1:1; a pest control composition comprising any one of the present compounds 1 to 253 and ethalfluralin at a ratio of 1:1; a pest control composition comprising any one of the present compounds 1 to 253 and ethalfluralin at a ratio of 1:20; a pest control composition comprising any one of the present compounds 1 to 253 and ethofumesate at a ratio of 0.1:1; a pest control composition comprising any one of the present compounds 1 to 253 and ethofumesate at a ratio of 1:1; a pest control composition comprising any one of the present compounds 1 to 253 and ethofumesate at a ratio of 1:20; a pest control composition comprising any one of the present compounds 1 to 253 and fenoxaprop at a ratio of 0.1:1; a pest control composition comprising any one of the present compounds 1 to 253 and fenoxaprop at a ratio of 1:1; a pest control composition comprising any one of the present compounds 1 to 253 and fenoxaprop at a ratio of 1:20; a pest control composition comprising any one of the present compounds 1 to 253 and fenoxaprop-P-ethyl at a ratio of 0.1:1; a pest control composition comprising any one of the present compounds 1 to 253 and fenoxaprop-P-ethyl at a ratio of 1:1; a pest control composition comprising any one of the present compounds 1 to 253 and fenoxaprop-P-ethyl at a ratio of 1:20; a pest control composition comprising any one of the present compounds 1 to 253 and florasulam at a ratio of 0.1:1; a pest control composition comprising any one of the present compounds 1 to 253 and florasulam at a ratio of 1:1; a pest control composition comprising any one of the present compounds 1 to 253 and florasulam at a ratio of 1:20; a pest control composition comprising any one of the present compounds 1 to 253 and fluazifop-P-butyl at a ratio of 0.1:1; a pest control composition comprising any one of the present compounds 1 to 253 and fluazifop-P-butyl at a ratio of 1:1; a pest control composition comprising any one of the present compounds 1 to 253 and fluazifop-P-butyl at a ratio of 1:20; a pest control composition comprising any one of the present compounds 1 to 253 and flufenacet at a ratio of 0.1:1; a pest control composition comprising any one of the present compounds 1 to 253 and flufenacet at a ratio of 1:1;

a pest control composition comprising any one of the present compounds 1 to 253 and flufenacet at a ratio of 1:20; a pest control composition comprising any one of the present compounds 1 to 253 and flumetsulam at a ratio of 0.1:1; a pest control composition comprising any one of the present compounds 1 to 253 and flumetsulam at a ratio of 1:1; a pest control composition comprising any one of the present compounds 1 to 253 and flumetsulam at a ratio of 1:20; a pest control composition comprising any one of the present compounds 1 to 253 and flumiclorac at a ratio of 0.1:1; a pest control composition comprising any one of the present compounds 1 to 253 and flumiclorac at a ratio of 1:1; a pest control composition comprising any one of the present compounds 1 to 253 and flumiclorac at a ratio of 1:20; a pest control composition comprising any one of the present compounds 1 to 253 and flumioxazin at a ratio of 0.1:1; a pest control composition comprising any one of the present compounds 1 to 253 and flumioxazin at a ratio of 1:1; a pest control composition comprising any one of the present compounds 1 to 253 and flumioxazin at a ratio of 1:20; a pest control composition comprising any one of the present compounds 1 to 253 and fluthiacet at a ratio of 0.1:1; a pest control composition comprising any one of the present compounds 1 to 253 and fluthiacet at a ratio of 1:1; a pest control composition comprising any one of the present compounds 1 to 253 and fluthiacet at a ratio of 1:20; a pest control composition comprising any one of the present compounds 1 to 253 and fomesafen at a ratio of 0.1:1; a pest control composition comprising any one of the present compounds 1 to 253 and fomesafen at a ratio of 1:1; a pest control composition comprising any one of the present compounds 1 to 253 and fomesafen at a ratio of 1:20; a pest control composition comprising any one of the present compounds 1 to 253 and foramsulfuron at a ratio of 0.1:1; a pest control composition comprising any one of the present compounds 1 to 253 and foramsulfuron at a ratio of 1:1; a pest control composition comprising any one of the present compounds 1 to 253 and foramsulfuron at a ratio of 1:20; a pest control composition comprising any one of the present compounds 1 to 253 and glufosinate at a ratio of 0.1:1; a pest control composition comprising any one of the present compounds 1 to 253 and glufosinate at a ratio of 1:1; a pest control composition comprising any one of the present compounds 1 to 253 and glufosinate at a ratio of 1:20; a pest control composition comprising any one of the present compounds 1 to 253 and glufosinateammoniumsalt at a ratio of 0.1:1; a pest control composition comprising any one of the present compounds 1 to 253 and glufosinateammoniumsalt at a ratio of 1:1; a pest control composition comprising any one of the present compounds 1 to 253 and glufosinateammoniumsalt at a ratio of 1:20; a pest control composition comprising any one of the present compounds 1 to 253 and glyphosate at a ratio of 0.1:1; a pest control composition comprising any one of the present compounds 1 to 253 and glyphosate at a ratio of 1:1; a pest control composition comprising any one of the present compounds 1 to 253 and glyphosate at a ratio of 1:20; a pest control composition comprising any one of the present compounds 1 to 253 and glyphosate trimesium salt at a ratio of 0.1:1; a pest control composition comprising any one of the present compounds 1 to 253 and glyphosate trimesium salt at a ratio of 1:1; a pest control composition comprising any one of the present compounds 1 to 253 and glyphosate trimesium salt at a ratio of 1:20; a pest control composition comprising any one of the present compounds 1 to 253 and glyphosate isopropylamine salt at a ratio of 0.1:1; a pest control composition comprising any one of the present compounds 1 to 253 and glyphosate isopropylamine salt at a ratio of 1:1; a pest control composition comprising any one of the present compounds 1 to 253 and glyphosate isopropylamine salt at a ratio of 1:20; a pest control composition comprising any one of the present compounds 1 to 253 and glyphosate potassium salt at a ratio of 0.1:1; a pest control composition comprising any one of the present compounds 1 to 253 and glyphosate potassium salt at a ratio of 1:1; a pest control composition comprising any one of the present compounds 1 to 253 and glyphosate potassium salt at a ratio of 1:20; a pest control composition comprising any one of the present compounds 1 to 253 and halosulfuron at a ratio of 0.1:1; a pest control composition comprising any one of the present compounds 1 to 253 and halosulfuron at a ratio of 1:1; a pest control composition comprising any one of the present compounds 1 to 253 and halosulfuron at a ratio of 1:20; a pest control composition comprising any one of the present compounds 1 to 253 and halosulfuron-methyl at a ratio of 0.1:1; a pest control composition comprising any one of the present compounds 1 to 253 and halosulfuron-methyl at a ratio of 1:1; a pest control composition comprising any one of the present compounds 1 to 253 and halosulfuron-methyl at a ratio of 1:20; a pest control composition comprising any one of the present compounds 1 to 253 and haloxyfop-R-methyl at a ratio of 0.1:1; a pest control composition comprising any one of the present compounds 1 to 253 and haloxyfop-R-methyl at a ratio of 1:1; a pest control composition comprising any one of the present compounds 1 to 253 and haloxyfop-R-methyl at a ratio of 1:20; a pest control composition comprising any one of the present compounds 1 to 253 and hexazinone at a ratio of 0.1:1; a pest control composition comprising any one of the present compounds 1 to 253 and hexazinone at a ratio of 1:1; a pest control composition comprising any one of the present compounds 1 to 253 and hexazinone at a ratio of 1:20; a pest control composition comprising any one of the present compounds 1 to 253 and imazamox at a ratio of 0.1:1; a pest control composition comprising any one of the present compounds 1 to 253 and imazamox at a ratio of 1:1; a pest control composition comprising any one of the present compounds 1 to 253 and imazamox at a ratio of 1:20; a pest control composition comprising any one of the present compounds 1 to 253 and imazapic at a ratio of 0.1:1; a pest control composition comprising any one of the present compounds 1 to 253 and imazapic at a ratio of 1:1; a pest control composition comprising any one of the present compounds 1 to 253 and imazapic at a ratio of 1:20; a pest control composition comprising any one of the present compounds 1 to 253 and imazaquine at a ratio of 0.1:1; a pest control composition comprising any one of the present compounds 1 to 253 and imazaquine at a ratio of 1:1; a pest control composition comprising any one of the present compounds 1 to 253 and imazaquine at a ratio of 1:20;
a pest control composition comprising any one of the present compounds 1 to 253 and imazethapyr at a ratio of 0.1:1; a pest control composition comprising any one of the present compounds 1 to 253 and imazethapyr at a ratio of 1:1; a pest control composition comprising any one of the present compounds 1 to 253 and imazethapyr at a ratio of 1:20; a pest control composition comprising any one of the present compounds 1 to 253 and iodosulfuron at a ratio of 0.1:1; a pest control composition comprising any one of the present compounds 1 to 253 and iodosulfuron at a ratio of 1:1; a pest control composition comprising any one of the present compounds 1 to 253 and iodosulfuron at a ratio of 1:20; a pest control composition comprising any one of the present compounds 1 to 253 and isoxaflutole at a ratio of 0.1:1; a pest control composition comprising any one of the present compounds 1 to 253 and isoxaflutole at a ratio of 1:1; a pest control composition comprising any one of the present compounds 1 to 253 and isoxaflutole at a ratio of 1:20; a pest control composition comprising any one of the present compounds 1 to 253 and lactofen at a ratio of 0.1:1; a pest control composition comprising any one of the present compounds 1 to 253 and lactofen at a ratio of 1:1; a pest control composition comprising any one of the present compounds 1 to 253 and lactofen at a ratio of 1:20; a pest control composition comprising any one of the present compounds 1 to 253 and lenacil at a ratio of 0.1:1; a pest control composition comprising any one of the present compounds 1 to 253 and lenacil at a ratio of 1:1; a pest control composition comprising any one of the present compounds 1 to 253 and lenacil at a ratio of 1:20; a pest control composition comprising any one of the present compounds 1 to 253 and linuron at a ratio of 0.1:1; a pest control composition comprising any one of the present compounds 1 to 253 and linuron at a ratio of 1:1; a pest control composition comprising any one of the present compounds 1 to 253 and linuron at a ratio of 1:20; a pest control composition comprising any one of the present compounds 1 to 253 and mesosulfuron at a ratio of 0.1:1; a pest control composition comprising any one of the present compounds 1 to 253 and mesosulfuron at a ratio of 1:1; a pest control composition comprising any one of the present compounds 1 to 253 and mesosulfuron at a ratio of 1:20; a pest control composition comprising any one of the present compounds 1 to 253 and mesotrione at a ratio of 0.1:1; a pest control composition comprising any one of the present compounds 1 to 253 and mesotrione at a ratio of 1:1; a pest control composition comprising any one of the present compounds 1 to 253 and mesotrione at a ratio of 1:20; a pest control composition comprising any one of the present compounds 1 to 253 and metam at a ratio of 0.1:1; a pest control composition comprising any one of the present compounds 1 to 253 and metam at a ratio of 1:1; a pest control composition comprising any one of the present compounds 1 to 253 and metam at a ratio of 1:20; a pest control composition comprising any one of the present compounds 1 to 253 and metamitron at a ratio of 0.1:1; a pest control composition comprising any one of the present compounds 1 to 253 and metamitron at a ratio of 1:1; a pest control composition comprising any one of the present compounds 1 to 253 and metamitron at a ratio of 1:20; a pest control composition comprising any one of the present compounds 1 to 253 and metolachlor at a ratio of 0.1:1; a pest control composition comprising any one of the present compounds 1 to 253 and metolachlor at a ratio of 1:1; a pest control composition comprising any one of the present compounds 1 to 253 and metolachlor at a ratio of 1:20; a pest control composition comprising any one of the present compounds 1 to 253 and metribuzin at a ratio of 0.1:1; a pest control composition comprising any one of the present compounds 1 to 253 and metribuzin at a ratio of 1:1; a pest control composition comprising any one of the present compounds 1 to 253 and metribuzin at a ratio of 1:20; a pest control composition comprising any one of the present compounds 1 to 253 and metsulfuron at a ratio of 0.1:1; a pest control composition comprising any one of the present compounds 1 to 253 and metsulfuron at a ratio of 1:1; a pest control composition comprising any one of the present compounds 1 to 253 and metsulfuron at a ratio of 1:20;
a pest control composition comprising any one of the present compounds 1 to 253 and MPCA at a ratio of 0.1:1; a pest control composition comprising any one of the present compounds 1 to 253 and MPCA at a ratio of 1:1; a pest control composition comprising any one of the present compounds 1 to 253 and MPCA at a ratio of 1:20; a pest control composition comprising any one of the present compounds 1 to 253 and MSMA at a ratio of 0.1:1; a pest control composition comprising any one of the present compounds 1 to 253 and MSMA at a ratio of 1:1; a pest control composition comprising any one of the present compounds 1 to 253 and MSMA at a ratio of 1:20; a pest control composition comprising any one of the present compounds 1 to 253 and nicosulfuron at a ratio of 0.1:1; a pest control composition comprising any one of the present compounds 1 to 253 and nicosulfuron at a ratio of 1:1; a pest control composition comprising any one of the present compounds 1 to 253 and nicosulfuron at a ratio of 1:20; a pest control composition comprising any one of the present compounds 1 to 253 and oryzalin at a ratio of 0.1:1; a pest control composition comprising any one of the present compounds 1 to 253 and oryzalin at a ratio of 1:1; a pest control composition comprising any one of the present compounds 1 to 253 and oryzalin at a ratio of 1:20; a pest control composition comprising any one of the present compounds 1 to 253 and oxyfluorfen at a ratio of 0.1:1; a pest control composition comprising any one of the present compounds 1 to 253 and oxyfluorfen at a ratio of 1:1; a pest control composition comprising any one of the present compounds 1 to 253 and oxyfluorfen at a ratio of 1:20; a pest control composition comprising any one of the present compounds 1 to 253 and paraquat at a ratio of 0.1:1; a pest control composition comprising any one of the present compounds 1 to 253 and paraquat at a ratio of 1:1; a pest control composition comprising any one of the present compounds 1 to 253 and paraquat at a ratio of 1:20; a pest control composition comprising any one of the present compounds 1 to 253 and pendimethalin at a ratio of 0.1:1; a pest control composition comprising any one of the present compounds 1 to 253 and pendimethalin at a ratio of 1:1; a pest control composition comprising any one of the present compounds 1 to 253 and pendimethalin at a ratio of 1:20; a pest control composition comprising any one of the present compounds 1 to 253 and phenmedipham at a ratio of 0.1:1; a pest control composition comprising any one of the present compounds 1 to 253 and phenmedipham at a ratio of 1:1; a pest control composition comprising any one of the present compounds 1 to 253 and phenmedipham at a ratio of 1:20; a pest control composition comprising any one of the present compounds 1 to 253 and picloram at a ratio of 0.1:1; a pest control composition comprising any one of the present compounds 1 to 253 and picloram at a ratio of 1:1; a pest control composition comprising any one of the present compounds 1 to 253 and picloram at a ratio of 1:20; a pest control composition comprising any one of the present compounds 1 to 253 and pyrimisulfuron at a ratio of 0.1:1; a pest control composition comprising any one of the present compounds 1 to 253 and pyrimisulfuron at a ratio of 1:1; a pest control composition comprising any one of the present compounds 1 to 253 and pyrimisulfuron at a ratio of 1:20; a pest control composition comprising any one of the present compounds 1 to 253 and pinoxaden at a ratio of 0.1:1; a pest control composition comprising any one of the present compounds 1 to 253 and pinoxaden at a ratio of 1:1; a pest control composition comprising any one of the present compounds 1 to 253 and pinoxaden at a ratio of 1:20; a pest control composition comprising any one of the present compounds 1 to 253 and prometryn at a ratio of 0.1:1; a pest control composition comprising any one of the present compounds 1 to 253 and prometryn at a ratio of 1:1; a pest control composition comprising any one of the present compounds 1 to 253 and prometryn at a ratio of 1:20; a pest control composition comprising any one of the present compounds 1 to 253 and pyraflufen-ethyl at a ratio of 0.1:1; a pest control composition comprising any one of the present compounds 1 to 253 and pyraflufen-ethyl at a ratio of 1:1; a pest control composition comprising any one of the present compounds 1 to 253 and pyraflufen-ethyl at a ratio of 1:20; a pest control composition comprising any one of the present compounds 1 to 253 and pyrithiobac at a ratio of 0.1:1; a pest control composition comprising any one of the present compounds 1 to 253 and pyrithiobac at a ratio of 1:1; a pest control composition comprising any one of the present compounds 1 to 253 and pyrithiobac at a ratio of 1:20; a pest control composition comprising any one of the present compounds 1 to 253 and pyroxsulam at a ratio of 0.1:1; a pest control composition comprising any one of the present compounds 1 to 253 and pyroxsulam at a ratio of 1:1; a pest control composition comprising any one of the present compounds 1 to 253 and pyroxsulam at a ratio of 1:20; a pest control composition comprising any one of the present compounds 1 to 253 and pyroxasulfone at a ratio of 0.1:1; a pest control composition comprising any one of the present compounds 1 to 253 and pyroxasulfone at a ratio of 1:1; a pest control composition comprising any one of the present compounds 1 to 253 and pyroxasulfone at a ratio of 1:20; a pest control composition comprising any one of the present compounds 1 to 253 and quizalofop-P-ethyl at a ratio of 0.1:1; a pest control composition comprising any one of the present compounds 1 to 253 and quizalofop-P-ethyl at a ratio of 1:1; a pest control composition comprising any one of the present compounds 1 to 253 and quizalofop-P-ethyl at a ratio of 1:20; a pest control composition comprising any one of the present compounds 1 to 253 and salflufenacil at a ratio of 0.1:1; a pest control composition comprising any one of the present compounds 1 to 253 and salflufenacil at a ratio of 1:1; a pest control composition comprising any one of the present compounds 1 to 253 and salflufenacil at a ratio of 1:20; a pest control composition comprising any one of the present compounds 1 to 253 and sethoxydim at a ratio of 0.1:1; a pest control composition comprising any one of the present compounds 1 to 253 and sethoxydim at a ratio of 1:1; a pest control composition comprising any one of the present compounds 1 to 253 and sethoxydim at a ratio of 1:20; a pest control composition comprising any one of the present compounds 1 to 253 and simazine at a ratio of 0.1:1; a pest control composition comprising any one of the present compounds 1 to 253 and simazine at a ratio of 1:1; a pest control composition comprising any one of the present compounds 1 to 253 and simazine at a ratio of 1:20; a pest control composition comprising any one of the present compounds 1 to 253 and sulfentrazone at a ratio of 0.1:1; a pest control composition comprising any one of the present compounds 1 to 253 and sulfentrazone at a ratio of 1:1; a pest control composition comprising any one of the present compounds 1 to 253 and sulfentrazone at a ratio of 1:20; a pest control composition comprising any one of the present compounds 1 to 253 and tebuthiuron at a ratio of 0.1:1; a pest control composition comprising any one of the present compounds 1 to 253 and tebuthiuron at a ratio of 1:1; a pest control composition comprising any one of the present compounds 1 to 253 and tebuthiuron at a ratio of 1:20; a pest control composition comprising any one of the present compounds 1 to 253 and tembotrione at a ratio of 0.1:1; a pest control composition comprising any one of the present compounds 1 to 253 and tembotrione at a ratio of 1:1; a pest control composition comprising any one of the present compounds 1 to 253 and tembotrione at a ratio of 1:20; a pest control composition comprising any one of the present compounds 1 to 253 and tepraloxydim at a ratio of 0.1:1; a pest control composition comprising any one of the present compounds 1 to 253 and tepraloxydim at a ratio of 1:1; a pest control composition comprising any one of the present compounds 1 to 253 and tepraloxydim at a ratio of 1:20; a pest control composition comprising any one of the present compounds 1 to 253 and thifensulfuron at a ratio of 0.1:1; a pest control composition comprising any one of the present compounds 1 to 253 and thifensulfuron at a ratio of 1:1; a pest control composition comprising any one of the present compounds 1 to 253 and thifensulfuron at a ratio of 1:20; a pest control composition comprising any one of the present compounds 1 to 253 and tribenuron-methyl at a ratio of 0.1:1; a pest control composition comprising any one of the present compounds 1 to 253 and tribenuron-methyl at a ratio of 1:1; a pest control composition comprising any one of the present compounds 1 to 253 and tribenuron-methyl at a ratio of 1:20; a pest control composition comprising any one of the present compounds 1 to 253 and triclopyr at a ratio of 0.1:1; a pest control composition comprising any one of the present compounds 1 to 253 and triclopyr at a ratio of 1:1; a pest control composition comprising any one of the present compounds 1 to 253 and triclopyr at a ratio of 1:20; a pest control composition comprising any one of the present compounds 1 to 253 and trifloxysulfuron at a ratio of 0.1:1; a pest control composition comprising any one of the present compounds 1 to 253 and trifloxysulfuron at a ratio of 1:1; a pest control composition comprising any one of the present compounds 1 to 253 and trifloxysulfuron at a ratio of 1:20; a pest control composition comprising any one of the present compounds 1 to 253 and trifluralin at a ratio of 0.1:1; a pest control composition comprising any one of the present compounds 1 to 253 and trifluralin at a ratio of 1:1; a pest control composition comprising any one of the present compounds 1 to 253 and trifluralin at a ratio of 1:20; a pest control composition comprising any one of the present compounds 1 to 253 and triflusulfuron-methyl at a ratio of 0.1:1; a pest control composition comprising any one of the present compounds 1 to 253 and triflusulfuron-methyl at a ratio of 1:1; and a pest control composition comprising any one of the present compounds 1 to 253 and triflusulfuron-methyl at a ratio of 1:20.

Formulation Examples will be shown below. Parts are by weight.

Formulation Example 1

Fifty parts (50 parts) of the present compounds 1 to 253, 3 parts of calcium ligninsulfoate, 2 parts of laurylmagnesium sulfate, and 45 parts of synthetic hydrated silicon oxide are thoroughly ground and mixed to obtain each formulation.

Formulation Example 2

Twenty parts (20 parts) of the present compounds 1 to 253 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of the present compounds 1 to 253, 88 parts of kaolin clay, and 10 parts of talc are thoroughly ground and mixed to obtain each formulation.

Formulation Example 4

Five parts (5 parts) the present compounds 1 to 253, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of the present compounds 1 to 253, 1 part of synthetic hydrated silicon oxide, 2 parts of calcium ligninsulfoate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of the present compounds 1 to 253, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion spots on each of test plants at the time of investigation, and comparing the area of lesion spots on a plant treated with the present control compound with that on an untreated plant.

Test Example 1

Each of plastic pots was filled with sandy loam and rice (cultivar: NIHONBARE) was sowed and grown in a greenhouse for 20 days. Then, each water dilution containing a surfactant prepared by adjusting so as to contain a predetermined concentration (500 ppm) of any one compound of the present compounds 4, 7, 13, 17, 20, 21, 22, 24, 29, 31, 37, 38, 42, 43, 44, 45, 46, 47, 48, 49, 51, 52, 53, 57, 59, 73, 83, 84, 85, 90, 91, 93, 99, 115, 117, 118, 119, 122, 123, 126, 131, 132, 136, 139, 142, 143, 145, 148, 149, 150, 151, 152, 154, 158, 159, 161, 162, 163, 165, 166, 167, 169, 170, 171, 172, 173, 174, 180, 182, 186, 187, 189, 190, 191, 193, 203, 204, 215, 218, 219, 220, 221, 222, 235, 236, and 238 was sprayed over stems and leaves so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 4, 7, 13, 17, 20, 21, 22, 24, 29, 31, 37, 38, 42, 43, 44, 45, 46, 47, 48, 49, 51, 52, 53, 57, 59, 73, 83, 84, 85, 90, 91, 93, 99, 115, 117, 118, 119, 122, 123, 126, 131, 132, 136, 139, 142, 143, 145, 148, 149, 150, 151, 152, 154, 158, 159, 161, 162, 163, 165, 166, 167, 169, 170, 171, 172, 173, 174, 180, 182, 186, 187, 189, 190, 191, 193, 203, 204, 215, 218, 219, 220, 221, 222, 235, 236, or 238 were 30% or less with respect to the lesion area on the non-treated plant.

Test Example 2

Each of plastic pots was filled with sandy loam and tomato (cultivar: PATIO) was sowed and grown in a greenhouse for 20 days. Then, each water dilution containing a surfactant prepared by adjusting so as to contain a predetermined concentration (500 ppm) of any one compound of the present compounds 7, 13, 14, 76, 93, 102, and 111 was sprayed over stems and leaves of the tomato seedling so that it sufficiently adhered to the surface of the leaves of the tomato seedling. After spraying, the plant was air-dried so as to dry the dilution on the surface of the leaves, and an aqueous suspension containing spores of tomato late blight fungus (*Phytophthora infestans*) was sprayed to inoculate the spores. After completion of the inoculation, the seedling was at first left to stand at 23° C. under high humidity condition for one day, and then cultivated in a greenhouse for 4 days. Thereafter, the area of lesion spots was investigated. As a result, it has been found that the area of lesion spots on the plant treated with the present compound 7, 13, 14, 76, 93, 102, or 111 was 30% or less of that on an untreated plant.

Test Example 3

Each of plastic pots was filled with sandy loam and wheat (cultivar: SHIROGANE) was sowed and grown in a greenhouse for 9 days. Then, each water dilution containing a surfactant prepared by adjusting so as to contain a predetermined concentration (500 ppm) of any one compound of the present compounds 6, 7, 9, 10, 36, 40, 47, 50, 52, 76, 90, 92, 138, 145, 152, 158, 160, 163, 166, 167, 169, 173, 182, 186, 187, 190, 193, 200, 203, 204, 215, 216, 217, 218, 219, 220, 221, 222, 235, and 238 was sprayed over stems and leaves of the wheat so that it sufficiently adhered to the surface of the leaves of the wheat. After spraying, the plant was air-dried so as to dry the dilution on the surface of the leaves. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 6, 7, 9, 10, 36, 40, 47, 50, 52, 76, 90, 92, 138, 145, 152, 158, 160, 163, 166, 167, 169, 173, 182, 186, 187, 190, 193, 200, 203, 204, 215, 216, 217, 218, 219, 220, 221, 222, 235, or 238 was 30% or less of that on an untreated plant.

Test Example 4

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (500 ppm) of any one compound of the present compounds 1, 2, 3, 4, 5, 6, 7, 9, 10, 11, 12, 13, 14, 15, 16, 17, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 68, 69, 72, 73, 74, 75, 76, 77, 78, 79, 80, 81, 82, 83, 84, 85, 86, 88, 90, 91, 92, 93, 94, 96, 97, 98, 99, 100, 101, 102, 103, 105, 106, 107, 109, 110, 111, 112, 113, 114, 115, 116, 117, 118, 119, 120, 122, 123, 125, 126, 127, 128, 129, 130, 131, 132, 134, 135, 136, 137, 138, 139, 140, 141, 142, 143, 144, 145, 147, 148, 149, 150, 151, 152, 153, 154, 155, 156, 157, 158, 159, 160, 161, 162, 163, 165, 166, 167, 168, 169, 170, 171, 172, 173, 174, 175, 176, 178, 179, 180, 181, 182, 183, 184, 186, 187, 188, 189, 190, 191, 192, 193, 194, 195, 196, 197, 198, 199, 200, 202, 203, 204, 205, 206, 207, 208, 209, 210, 211, 212, 213, 214, 215, 216, 217, 218, 219, 220, 221, 222, 223, 233, 234, 235, 236, 237, 238, 240, 242, 247, and 248 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 1, 2, 3, 4, 5, 6, 7, 9, 10, 11, 12, 13, 14, 15, 16, 17, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 68, 69, 72, 73, 74, 75, 76, 77, 78, 79, 80, 81, 82, 83, 84, 85, 86, 88, 90, 91, 92, 93, 94, 96, 97, 98, 99, 100, 101, 102, 103, 105, 106, 107, 109, 110, 111, 112, 113, 114, 115, 116, 117, 118, 119, 120, 122, 123, 125, 126, 127, 128, 129, 130, 131, 132, 134, 135, 136, 137, 138, 139, 140, 141, 142, 143, 144, 145, 147, 148, 149, 150, 151, 152, 153, 154, 155, 156, 157, 158, 159, 160, 161, 162, 163, 165, 166, 167, 168, 169, 170, 171, 172, 173, 174, 175, 176, 178, 179, 180, 181, 182, 183, 184, 186, 187, 188, 189, 190, 191, 192, 193, 194, 195, 196, 197, 198, 199, 200, 202, 203, 204, 205, 206, 207, 208, 209, 210, 211, 212, 213, 214, 215, 216, 217, 218, 219, 220, 221, 222, 223, 233, 234, 235, 236, 237, 238, 240, 242, 247, or 248 was 30% or less of that on an untreated plant.

Test Example 5

Each of plastic pots was filled with sandy loam and kidney bean (cultivar: NAGAUZURA NATANE) was sowed and grown in a greenhouse for 8 days. Then, each water dilution containing a surfactant prepared by adjusting so as to contain a predetermined concentration (500 ppm) of any one compound of the present compounds 1, 2, 3, 4, 5, 6, 7, 8, 9, 10, 12, 13, 14, 15, 16, 17, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 72, 73, 74, 75, 76, 77, 78, 79, 80, 81, 82, 83, 84, 85, 86, 88, 90, 91, 92, 93, 94, 96, 97, 98, 99, 100, 101, 102, 103, 106, 107, 108, 109, 110, 111, 112, 113, 114, 115, 116, 118, 119, 120, 122, 123, 125, 126, 127, 128, 130, 131, 132, 134, 136, 137, 138, 139, 140, 141, 142, 143, 145, 147, 149, 151, 152, 153, 154, 155, 157, 158, 159, 160, 162, 163, 165, 166, 168, 169, 170, 171, 172, 173, 174, 175, 176, 178, 179, 180, 182, 183, 186, 187, 188, 189, 190, 191, 192, 193, 194, 195, 196, 197, 198, 199, 200, 201, 202, 203, 204, 205, 206, 207, 208, 209, 210, 213, 214, 215, 216, 217, 218, 219, 220, 221, 222, 223, 225, 226, 227, 234, 235, 236, 237, 238, 239, 240, 242, 247, 248, and 249 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 1, 2, 3, 4, 5, 6, 7, 8, 9, 10, 12, 13, 14, 15, 16, 17, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 72, 73, 74, 75, 76, 77, 78, 79, 80, 81, 82, 83, 84, 85, 86, 88, 90, 91, 92, 93, 94, 96, 97, 98, 99, 100, 101, 102, 103, 106, 107, 108, 109, 110, 111, 112, 113, 114, 115, 116, 118, 119, 120, 122, 123, 125, 126, 127, 128, 130, 131, 132, 134, 136, 137, 138, 139, 140, 141, 142, 143, 145, 147, 149, 151, 152, 153, 154, 155, 157, 158, 159, 160, 162, 163, 165, 166, 168, 169, 170, 171, 172, 173, 174, 175, 176, 178, 179, 180, 182, 183, 186, 187, 188, 189, 190, 191, 192, 193, 194, 195, 196, 197, 198, 199, 200, 201, 202, 203, 204, 205, 206, 207, 208, 209, 210, 213, 214, 215, 216, 217, 218, 219, 220, 221, 222, 223, 225, 226, 227, 234, 235, 236, 237, 238, 239, 240, 242, 247, 248, or 249 was 30% or less of that on an untreated plant.

Test Example 6

Each of plastic pots was filled with sandy loam and wheat (cultivar: APOGEE) was sowed and grown in a greenhouse for 10 days. Then, each water dilution containing a surfactant prepared by adjusting so as to contain a predetermined concentration (500 ppm) of any one compound of the present compounds 1, 2, 4, 5, 6, 7, 8, 9, 10, 11, 12, 13, 14, 15, 16, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 72, 73, 74, 75, 76, 77, 78, 79, 80, 82, 83, 84, 88, 90, 91, 92, 93, 94, 96, 97, 99, 100, 101, 102, 105, 106, 107, 109, 110, 111, 112, 113, 114, 115, 116, 118, 119, 120, 122, 123, 126, 128, 131, 132, 134, 135, 136, 138, 140, 141, 142, 143, 144, 145, 147, 149, 151, 152, 153, 154, 155, 158, 159, 160, 161, 162, 163, 165, 166, 167, 169, 170, 171, 172, 173, 174, 176, 178, 179, 180, 181, 182, 184, 186, 187, 188, 189, 190, 192, 193, 194, 195, 196, 197, 198, 199, 203, 204, 206, 207, 208, 209, 210, 213, 214, 215, 216, 217, 218, 219, 220, 221, 222, 223, 247, and 248 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound 1, 2, 4, 5, 6, 7, 8, 9, 10, 11, 12, 13, 14, 15, 16, 18, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 72, 73, 74, 75, 76, 77, 78, 79, 80, 82, 83, 84, 88, 90, 91, 92, 93, 94, 96, 97, 99, 100, 101, 102, 105, 106, 107, 109, 110, 111, 112, 113, 114, 115, 116, 118, 119, 120, 122, 123, 126, 128, 131, 132, 134, 135, 136, 138, 140, 141, 142, 143, 144, 145, 147, 149, 151, 152, 153, 154, 155, 158, 159, 160, 161, 162, 163, 165, 166, 167, 169, 170, 171, 172, 173, 174, 176, 178, 179, 180, 181, 182, 184, 186, 187, 188, 189, 190, 192, 193, 194, 195, 196, 197, 198, 199, 203, 204, 206, 207, 208, 209, 210, 213, 214, 215, 216, 217, 218, 219, 220, 221, 222, 223, 247, or 248 was 30% or less of that on an untreated plant.

Test Example 7

Each of plastic pots was filled with sandy loam and cucumber (cultivar: SAGAMI HANJIRO) was sowed and grown in a greenhouse for 12 days. Then, each water dilution containing a surfactant prepared by adjusting so as to contain a predetermined concentration (500 ppm) of any one compound of the present compounds 1, 2, 3, 4, 5, 6, 7, 8, 9, 10, 11, 12, 13, 14, 15, 16, 17, 18, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 54, 55, 56, 57, 58, 59, 61, 64, 67, 68, 69, 72, 73, 74, 75, 76, 77, 78, 79, 80, 81, 82, 83, 84, 85, 86, 88, 90, 91, 92, 93, 94, 96, 97, 99, 100, 101, 102, 103, 105, 107, 109, 110, 111, 112, 113, 114, 115, 116, 117, 118, 119, 120, 122, 123, 126, 127, 128, 129, 130, 131, 132, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 165, 166, 167, 168, 169, 170, 171, 172, 173, 174, 175, 176, 178, 179, 180, 181, 182, 183, 184, 186, 187, 188, 189, 190, 191, 193, 194, 195, 196, 199, 200, 202, 203, 204, 205, 206, 208, 210, 213, 214, 215, 216, 217, 218, 219, 220, 221, 222, 234, 235, 236, 237, 238, 240, 247, and 248 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound 1, 2, 3, 4, 5, 6, 7, 8, 9, 10, 11, 12, 13, 14, 15, 16, 17, 18, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 54, 55, 56, 57, 58, 59, 61, 64, 67, 68, 69, 72, 73, 74, 75, 76, 77, 78, 79, 80, 81, 82, 83, 84, 85, 86, 88, 90, 91, 92, 93, 94, 96, 97, 99, 100, 101, 102, 103, 105, 107, 109, 110, 111, 112, 113, 114, 115, 116, 117, 118, 119, 120, 122, 123, 126, 127, 128, 129, 130, 131, 132, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 165, 166, 167, 168, 169, 170, 171, 172, 173, 174, 175, 176, 178, 179, 180, 181, 182, 183, 184, 186, 187, 188, 189, 190, 191, 193, 194, 195, 196, 199, 200, 202, 203, 204, 205, 206, 208, 210, 213, 214, 215, 216, 217, 218, 219, 220, 221, 222, 234, 235, 236, 237, 238, 240, 247, or 248 was 30% or less of that on an untreated plant.

Test Example 8

Each of plastic pots was filled with sandy loam and wheat (cultivar: APOGEE) was sowed and grown in a greenhouse for 10 days. Then, an aqueous suspension containing spores of wheat leaf blotch fungus (*Septoria tritici*) was sprayed to inoculate the spores. The wheat plant was left to stand at 18° C. under high humidity condition for 3 days and air-dried. Each water dilution containing a surfactant prepared by adjusting so as to contain a predetermined concentration (200 ppm) of any one compound of the present compounds 1, 4, 5, 6, 7, 8, 9, 10, 11, 12, 13, 15, 19, 20, 21, 22, 24, 26, 27, 28, 29, 33, 34, 36, 37, 38, 40, 41, 42, 43, 47, 48, 50, 51, 52, 53, 54, 59, 62, 64, 65, 71, 72, 73, 74, 76, 79, 80, 84, 85, 87, 92, 93, 94, 99, 100, 101, 110, 111, 112, 114, 115, 116, 123, 128, 131, 132, 135, 136, 137, 138, 140, 141, 142, 143, 147, 148, 151, 152, 153, 154, 158, 159, 164, 166, 169, 170, 171, 172, 173, 176, 177, 178, 179, 182, 184, 185, 186, 187, 189, 190, 193, 194, 195, 196, 197, 203, 204, 211, 212, 215, 216, 217, 219, 220, 221, 222, 233, 234, 235, 236, 237, 238, and 241 was sprayed over stems and leaves of the wheat so that it sufficiently adhered to the surface of the leaves of the wheat. After spraying, the plant was air-dried and left to stand under illumination for 14 to 18 days, and then the area of lesion spots was investigated. As a result, the area of lesion spots on the plant treated with the present compound 1, 4, 5, 6, 7, 8, 9, 10, 11, 12, 13, 15, 19, 20, 21, 22, 24, 26, 27, 28, 29, 33, 34, 36, 37, 38, 40, 41, 42, 43, 47, 48, 50, 51, 52, 53, 54, 59, 62, 64, 65, 71, 72, 73, 74, 76, 79, 80, 84, 85, 87, 92, 93, 94, 99, 100, 101, 110, 111, 112, 114, 115, 116, 123, 128, 131, 132, 135, 136, 137, 138, 140, 141, 142, 143, 147, 148, 151, 152, 153, 154, 158, 159, 164, 166, 169, 170, 171, 172, 173, 176, 177, 178, 179, 182, 184, 185, 186, 187, 189, 190, 193, 194, 195, 196, 197, 203, 204, 211, 212, 215, 216, 217, 219, 220, 221, 222, 233, 234, 235, 236, 237, 238, or 241 was 30% or less of that on an untreated plant.

Test Example 9

Each of plastic pots was filled with sandy loam and wheat (cultivar: APOGEE) was sowed and grown in a greenhouse for 10 days. Then, each water dilution containing a surfactant prepared by adjusting so as to contain a predetermined concentration (200 ppm) of any one compound of the present compounds 1, 2, 3, 4, 5, 6, 7, 8, 9, 10, 11, 12, 13, 14, 15, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 76, 77, 78, 79, 80, 82, 83, 84, 85, 86, 87, 88, 90, 91, 92, 93, 94, 96, 97, 98, 99, 100, 110, 111, 112, 113, 114, 115, 116, 118, 119, 121, 122, 123, 125, 126, 128, 129, 130, 131, 132, 133, 134, 135, 136, 137, 138, 139, 140, 141, 142, 143, 147, 148, 149, 150, 151, 152, 153, 154, 155, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 189, 190, 191, 193, 194, 195, 196, 197, 198, 199, 203, 204, 208, 209, 211, 212, 213, 214, 215, 216, 217, 219, 220, 221, 222, 247, and 248 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound 1, 2, 3, 4, 5, 6, 7, 8, 9, 10, 11, 12, 13, 14, 15, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 76, 77, 78, 79, 80, 82, 83, 84, 85, 86, 87, 88, 90, 91, 92, 93, 94, 96, 97, 98, 99, 100, 101, 102, 103, 105, 106, 107, 108, 109, 110, 111, 112, 113, 114, 115, 116, 118, 119, 121, 122, 123, 125, 126, 128, 129, 130, 131, 132, 133, 134, 135, 136, 137, 138, 139, 140, 141, 142, 143, 147, 148, 149, 150, 151, 152, 153, 154, 155, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 189, 190, 191, 193, 194, 195, 196, 197, 198, 199, 203, 204, 208, 209, 211, 212, 213, 214, 215, 216, 217, 219, 220, 221, 222, 247, or 248 was 30% or less of that on an untreated plant.

Test Example 10

Each of plastic pots was filled with sandy loam and wheat (cultivar: APOGEE) was sowed and grown in a greenhouse for 10 days. Then, each water dilution containing a surfactant prepared by adjusting so as to contain a predetermined concentration (50 ppm) of any one compound of the present compounds 89 and 104 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound 89 or 104 was 30% or less of that on an untreated plant.

Test Example 11

Each of plastic pots was filled with sandy loam and rice (cultivar: NIHONBARE) was sowed and grown in a greenhouse for 20 days. Then, each water dilution containing a surfactant prepared by adjusting so as to contain a predetermined concentration (200 ppm) of any one compound of the present compounds 3, 4, 6, 7, 9, 10, 13, 14, 15, 17, 18, 20, 21, 22, 24, 25, 28, 30, 31, 32, 33, 34, 35, 37, 38, 40, 41, 42, 43, 44, 45, 46, 47, 51, 52, 53, 54, 55, 56, 58, 59, 61, 62, 64, 65, 68, 71, 73, 74, 75, 76, 77, 83, 84, 85, 86, 87, 88, 89, 91, 92, 96, 97, 99, 100, 101, 106, 107, 114, 115, 119, 120, 121, 122, 123, 126, 127, 128, 129, 130, 131, 132, 133, 135, 136, 137, 138, 139, 140, 141, 142, 143, 147, 148, 149, 151, 152, 153, 154, 157, 158, 159, 160, 161, 162, 163, 164, 165, 166, 167, 169, 170, 171, 172, 173, 174, 176, 177, 178, 179, 181, 182, 184, 185, 186, 187, 189, 190, 191, 192, 193, 194, 196, 197, 198, 203, 204, 210, 213, 214, 215, 216, 217, 219, 220, 221, 222, 233, 234, 235, 236, 237, 238, and 241 was sprayed over stems and leaves of the rice so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 3, 4, 6, 7, 9, 10, 13, 14, 15, 17, 18, 20, 21, 22, 24, 25, 28, 30, 31, 32, 33, 34, 35, 37, 38, 40, 41, 42, 43, 44, 45, 46, 47, 51, 52, 53, 54, 55, 56, 58, 59, 61, 62, 64, 65, 68, 71, 73, 74, 75, 76, 77, 83, 84, 85, 86, 87, 88, 89, 91, 92, 96, 97, 99, 100, 101, 106, 107, 114, 115, 119, 120, 121, 122, 123, 126, 127, 128, 129, 130, 131, 132, 133, 135, 136, 137, 138, 139, 140, 141, 142, 143, 147, 148, 149, 151, 152, 153, 154, 157, 158, 159, 160, 161, 162, 163, 164, 165, 166, 167, 169, 170, 171, 172, 173, 174, 176, 177, 178, 179, 181, 182, 184, 185, 186, 187, 189, 190, 191, 192, 193, 194, 196, 197, 198, 203, 204, 210, 213, 214, 215, 216, 217, 219, 220, 221, 222, 233, 234, 235, 236, 237, 238, or 241 were 30% or less with respect to the lesion area on the non-treated plant.

Test Example 12

Each of plastic pots was filled with sandy loam and rice (cultivar: NIHONBARE) was sowed and grown in a greenhouse for 20 days. Then, each water dilution containing a surfactant prepared by adjusting so as to contain a predetermined concentration (50 ppm) of any one compound of the present compounds 19, 57, and 206 was sprayed over stems and leaves of the rice so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 19, 57, or 206 were 30% or less with respect to the lesion area on the non-treated plant.

Test Example 13

Each of plastic pots was filled with sandy loam and wheat (cultivar: SHIROGANE) was sowed and grown in a greenhouse for 9 days. Then, each water dilution containing a surfactant prepared by adjusting so as to contain a predetermined concentration (200 ppm) of any one compound of the present compounds 2, 3, 4, 5, 6, 7, 9, 10, 11, 12, 13, 15, 17, 18, 19, 20, 21, 22, 23, 24, 25, 26, 31, 33, 34, 35, 36, 38, 40, 42, 43, 44, 45, 46, 47, 48, 49, 50, 51, 52, 53, 54, 55, 56, 57, 59, 60, 61, 62, 64, 67, 68, 69, 70, 71, 72, 73, 74, 76, 78, 83, 84, 85, 87, 88, 91, 92, 94, 97, 99, 100, 101, 102, 110, 111, 112, 113, 114, 115, 116, 121, 122, 123, 126, 128, 129, 131, 132, 135, 136, 138, 139, 140, 141, 142, 143, 147, 148, 149, 150, 151, 152, 153, 154, 157, 158, 159, 160, 161, 162, 163, 164, 165, 166, 167, 168, 169, 170, 171, 172, 173, 174, 175, 176, 177, 178, 179, 180, 181, 182, 184, 185, 186, 187, 188, 189, 190, 191, 192, 193, 194, 195, 196, 197, 200, 203, 204, 205, 206, 210, 213, 215, 216, 217, 219, 220, 221, 222, 233, 234, 235, 236, 237, 238, 240, 241, 247, and 248 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 2, 3, 4, 5, 6, 7, 9, 10, 11, 12, 13, 15, 17, 18, 19, 20, 21, 22, 23, 24, 25, 26, 31, 33, 34, 35, 36, 38, 40, 42, 43, 44, 45, 46, 47, 48, 49, 50, 51, 52, 53, 54, 55, 56, 57, 59, 60, 61, 62, 64, 67, 68, 69, 70, 71, 72, 73, 74, 76, 78, 83, 84, 85, 87, 88, 91, 92, 94, 97, 99, 100, 101, 102, 110, 111, 112, 113, 114, 115, 116, 121, 122, 123, 126, 128, 129, 131, 132, 135, 136, 138, 139, 140, 141, 142, 143, 147, 148, 149, 150, 151, 152, 153, 154, 157, 158, 159, 160, 161, 162, 163, 164, 165, 166, 167, 168, 169, 170, 171, 172, 173, 174, 175, 176, 177, 178, 179, 180, 181, 182, 184, 185, 186, 187, 188, 189, 190, 191, 192, 193, 194, 195, 196, 197, 200, 203, 204, 205, 206, 210, 213, 215, 216, 217, 219, 220, 221, 222, 233, 234, 235, 236, 237, 238, 240, 241, 247, or 248 was 30% or less of that on an untreated plant.

Test Example 14

Each of plastic pots was filled with sandy loam and wheat (cultivar: SHIROGANE) was sowed and grown in a greenhouse for 9 days. Then, each water dilution containing a surfactant prepared by adjusting so as to contain a predetermined concentration (50 ppm) of any one compound of the present compounds 104 and 133 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 104 or 133 was 30% or less of that on an untreated plant.

Test Example 15

Each of plastic pots was filled with sandy loam and tomato (cultivar: PATIO) was sowed and grown in a greenhouse for 20 days. Then, each water dilution containing a surfactant prepared by adjusting so as to contain a predetermined concentration (500 ppm) of any one compound of the present compounds 20, 72, and 102 was sprayed over stems and leaves of the tomato seedling so that it sufficiently adhered to the surface of the leaves of the tomato seedling. After spraying, the plant was air-dried so as to dry the dilution on the surface of the leaves, and an aqueous suspension containing spores of tomato late blight fungus (*Phytophthora infestans*) was sprayed to inoculate the spores. After completion of the inoculation, the seedling was at first left to stand at 23° C. under high humidity condition for one day, and then cultivated in an air-conditioned room at 20° C. for 4 days. Thereafter, the area of lesion spots was investigated. As a result, it has been found that the area of lesion spots on the plant treated with the present compound 20, 72, or 102 was 30% or less of that on an untreated plant.

Test Example 16

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (200 ppm) of any one compound of the present compounds 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 105, 106, 107, 109, 110, 111, 112, 113, 114, 115, 116, 118, 119, 120, 121, 122, 123, 126, 127, 128, 129, 130, 131, 132, 133, 134, 135, 136, 137, 138, 139, 140, 141, 142, 143, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 203, 204, 205, 206, 207, 208, 209, 210, 211, 212, 213, 214, 215, 216, 217, 219, 220, 221, 222, 233, 234, 235, 236, 237, 238, 240, 241, 242, 247, and 248 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 1, 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 105, 106, 107, 109, 110, 111, 112, 113, 114, 115, 116, 118, 119, 120, 121, 122, 123, 126, 127, 128, 129, 130, 131, 132, 133, 134, 135, 136, 137, 138, 139, 140, 141, 142, 143, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 203, 204, 205, 206, 207, 208, 209, 210, 211, 212, 213, 214, 215, 216, 217, 219, 220, 221, 222, 233, 234, 235, 236, 237, 238, 240, 241, 242, 247, or 248 was 30% or less of that on an untreated plant.

Test Example 17

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (50 ppm) of any one compound of the present compounds 10 and 104 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 10 or 104 was 30% or less of that on an untreated plant.

Test Example 18

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (12.5 ppm) of the present compound 53 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 53 was 30% or less of that on an untreated plant.

Test Example 19

Each of plastic pots was filled with sandy loam and soybean (cultivar: KUROSENGOKU) was sowed and grown in a greenhouse for 13 days. Then, each water dilution containing a surfactant prepared by adjusting so as to contain a predetermined concentration (200 ppm) of any one compound of the present compounds 3, 4, 5, 6, 7, 13, 20, 21, 22, 24, 33, 38, 40, 42, 43, 44, 45, 47, 48, 49, 50, 51, 52, 71, 76, 84, 85, 87, 91, 93, 97, 100, 111, 112, 115, 116, 122, 123, 126, 139, 142, 147, 149, 151, 152, 153, 154, 157, 158, 160, 164, 165, 166, 167, 169, 170, 172, 173, 177, 186, 187, 190, 192, 193, 196, 203, 204, 215, 216, 217, 219, 220, 221, 222, 234, 235, and 238 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on the plant treated with the present compound 3, 4, 5, 6, 7, 13, 20, 21, 22, 24, 33, 38, 40, 42, 43, 44, 45, 47, 48, 49, 50, 51, 52, 71, 76, 84, 85, 87, 91, 93, 97, 100, 111, 112, 115, 116, 122, 123, 126, 139, 142, 147, 149, 151, 152, 153, 154, 157, 158, 160, 164, 165, 166, 167, 169, 170, 172, 173, 177, 186, 187, 190, 192, 193, 196, 203, 204, 215, 216, 217, 219, 220, 221, 222, 234, 235, or 238 was 30% or less of that on an untreated plant.

Test Example 20

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (200 ppm) of any one compound of the present compounds 1, 2, 3, 4, 5, 6, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 105, 106, 107, 109, 110, 111, 112, 113, 114, 115, 116, 118, 120, 121, 122, 123, 125, 126, 127, 128, 129, 130, 131, 132, 133, 134, 135, 136, 137, 138, 139, 140, 141, 142, 143, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 202, 203, 204, 205, 206, 208, 210, 211, 212, 213, 214, 215, 216, 217, 219, 220, 221, 222, 233, 234, 235, 236, 237, 238, 240, 241, 242, 247, and 248 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with of the present compound 1, 2, 3, 4, 5, 6, 7, 8, 9, 10, 11, 12, 13, 14, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 105, 106, 107, 109, 110, 111, 112, 113, 114, 115, 116, 118, 120, 121, 122, 123, 125, 126, 127, 128, 129, 130, 131, 132, 133, 134, 135, 136, 137, 138, 139, 140, 141, 142, 143, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 202, 203, 204, 205, 206, 208, 210, 211, 212, 213, 214, 215, 216, 217, 219, 220, 221, 222, 233, 234, 235, 236, 237, 238, 240, 241, 242, 247, or 248 was 30% or less of that on an untreated plant.

Test Example 21

Each of plastic pots was filled with sandy loam and barley (cultivar: NISHINOHOSHI) was sowed and grown in a greenhouse for 7 days. Then, each water dilution containing a surfactant prepared by adjusting so as to contain a predetermined concentration (50 ppm) of any one compound of the present compounds 104 and 119 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with the present compound 104 or 119 was 30% or less of that on an untreated plant.

Test Example 22

Each of plastic pots was filled with sandy loam and kidney bean (cultivar: NAGAUZURA NATANE) was sowed and grown in a greenhouse for 8 days. Then, each water dilution containing a surfactant prepared by adjusting so as to contain a predetermined concentration (200 ppm) of any one compound of the present compounds 1, 2, 3, 7, 8, 10, 13, 14, 15, 16, 17, 18, 19, 20, 21, 22, 23, 24, 25, 26, 27, 29, 30, 31, 32, 33, 35, 37, 38, 39, 40, 41, 42, 43, 44, 45, 46, 47, 48, 49, 50, 52, 53, 54, 56, 57, 58, 59, 60, 61, 62, 63, 64, 65, 66, 67, 68, 69, 70, 71, 72, 73, 74, 75, 76, 77, 78, 80, 81, 82, 83, 84, 85, 86, 87, 92, 93, 94, 95, 96, 98, 99, 100, 101, 102, 103, 104, 105, 106, 107, 109, 111, 112, 113, 114, 119, 120, 121, 122, 127, 128, 129, 130, 131, 132, 133, 134, 136, 137, 138, 139, 140, 141, 142, 143, 145, 149, 151, 152, 154, 155, 157, 158, 159, 160, 162, 163, 164, 165, 166, 168, 169, 170, 171, 172, 173, 174, 175, 176, 177, 178, 179, 180, 181, 182, 183, 184, 185, 186, 187, 189, 190, 191, 193, 194, 195, 196, 199, 200, 203, 204, 205, 206, 208, 210, 212, 213, 215, 216, 218, 219, 220, 221, 222, 223, 224, 225, 226, 234, 235, 236, 238, 239, 240, 242, 247, 248, and 249 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 1, 2, 3, 7, 8, 10, 13, 14, 15, 16, 17, 18, 19, 20, 21, 22, 23, 24, 25, 26, 27, 29, 30, 31, 32, 33, 35, 37, 38, 39, 40, 41, 42, 43, 44, 45, 46, 47, 48, 49, 50, 52, 53, 54, 56, 57, 58, 59, 60, 61, 62, 63, 64, 65, 66, 67, 68, 69, 70, 71, 72, 73, 74, 75, 76, 77, 78, 80, 81, 82, 83, 84, 85, 86, 87, 92, 93, 94, 95, 96, 98, 99, 100, 101, 102, 103, 104, 105, 106, 107, 109, 111, 112, 113, 114, 119, 120, 121, 122, 127, 128, 129, 130, 131, 132, 133, 134, 136, 137, 138, 139, 140, 141, 142, 143, 145, 149, 151, 152, 154, 155, 157, 158, 159, 160, 162, 163, 164, 165, 166, 168, 169, 170, 171, 172, 173, 174, 175, 176, 177, 178, 179, 180, 181, 182, 183, 184, 185, 186, 187, 189, 190, 191, 193, 194, 195, 196, 199, 200, 203, 204, 205, 206, 208, 210, 212, 213, 215, 216, 218, 219, 220, 221, 222, 223, 224, 225, 226, 234, 235, 236, 238, 239, 240, 242, 247, 248, or 249 was 30% or less of that on an untreated plant.

Test Example 23

Each of plastic pots was filled with sandy loam and kidney bean (cultivar: NAGAUZURA NATANE) was sowed and grown in a greenhouse for 8 days. Then, each water dilution containing a surfactant prepared by adjusting so as to contain a predetermined concentration (50 ppm) of any one compound of the present compounds 4, 5, 6, 34, 51, 55, 79, 88, 90, 91, 123, and 126 was sprayed over stems and leaves of the wheat so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 4, 5, 6, 34, 51, 55, 79, 88, 90, 91, 123, or 126 was 30% or less of that on an untreated plant.

Test Example 24

Each of plastic pots was filled with sandy loam and cucumber (cultivar: SAGAMI HANJIRO) was sowed and grown in a greenhouse for 12 days. Then, each water dilution containing a surfactant prepared by adjusting so as to contain a predetermined concentration (200 ppm) of any one compound of the present compounds 2, 3, 4, 5, 6, 7, 8, 9, 10, 11, 12, 13, 14, 15, 16, 17, 18, 19, 20, 21, 22, 23, 24, 25, 26, 27, 28, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 64, 67, 68, 69, 70, 72, 73, 74, 75, 76, 77, 78, 79, 80, 81, 82, 83, 84, 85, 86, 87, 90, 91, 92, 93, 94, 95, 96, 97, 99, 100, 101, 102, 104, 105, 107, 111, 112, 113, 114, 115, 116, 118, 119, 120, 121, 122, 123, 127, 128, 129, 130, 131, 132, 133, 135, 136, 137, 138, 139, 140, 141, 142, 143, 145, 146, 147, 148, 149, 150, 151, 152, 154, 155, 156, 157, 158, 159, 160, 161, 162, 163, 164, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 199, 201, 203, 204, 205, 206, 208, 210, 212, 213, 214, 215, 216, 218, 219, 220, 221, 222, 235, 236, 237, 238, 240, or 241 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound 2, 3, 4, 5, 6, 7, 8, 9, 10, 11, 12, 13, 14, 15, 16, 17, 18, 19, 20, 21, 22, 23, 24, 25, 26, 27, 28, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 64, 67, 68, 69, 70, 72, 73, 74, 75, 76, 77, 78, 79, 80, 81, 82, 83, 84, 85, 86, 87, 90, 91, 92, 93, 94, 95, 96, 97, 99, 100, 101, 102, 104, 105, 107, 111, 112, 113, 114, 115, 116, 118, 119, 120, 121, 122, 123, 127, 128, 129, 130, 131, 132, 133, 135, 136, 137, 138, 139, 140, 141, 142, 143, 145, 146, 147, 148, 149, 150, 151, 152, 154, 155, 156, 157, 158, 159, 160, 161, 162, 163, 164, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 199, 201, 203, 204, 205, 206, 208, 210, 212, 213, 214, 215, 216, 218, 219, 220, 221, 222, 235, 236, 237, 238, 240, or 241 was 30% or less of that on an untreated plant.

Test Example 25

Each of plastic pots was filled with sandy loam and cucumber (cultivar: SAGAMI HANJIRO) was sowed and grown in a greenhouse for 12 days. Then, each water dilution containing a surfactant prepared by adjusting so as to contain a predetermined concentration (50 ppm) of any one compound of the present compounds 55, 71, 103, and 126 was sprayed over stems and leaves of the cucumber so that it sufficiently adhered to the surface of the leaves of the cucumber. After spraying, the plant was air-dried. After 1 day, the plant was inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound 55, 71, 103, or 126 was 30% or less of that on an untreated plant.

Test Example 26

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 1, 3, 12, 13, 14, 15, 20, 21, 22, 24, 30, 33, 42, 54, 56, 57, 58, 63, 64, 65, 67, 69, 72, 73, 74, 77, 78, 82, 83, 84, 85, 86, 87, 94, 95, 96, 97, 98, 99, 102, 104, 105, 106, 107, 109, 110, 111, 112, 113, 114, 122, 123, 125, 131, 132, 135, 136, 137, 138, 139, 140, 141, 142, 143, 147, 148, 149, 152, 154, 157, 158, 159, 160, 161, 162, 163, 164, 165, 166, 167, 171, 172, 173, 174, 175, 176, 177, 178, 179, 180, 181, 184, 185, 186, 187, 189, 190, 191, 192, 193, 194, 203, 204, 208, 213, 214, 215, 216, 218, 219, 220, 221, 222, 224, 225, 226, 227, 234, 235, 236, 237, 238, 239, 240, 248, and 249 was sprayed over stems and leaves of the cucumber so that it sufficiently adhered to the surface of the leaves of the cucumber. After spraying, the plant was air-dried. After one day, the plant was inoculated by sprinkling with spores of cucumber corynespora leaf spot fungus (*Corynespora cassicola*). After the inoculation, the plant was cultivated in a greenhouse at 24° C. in the daytime and 20° C. at night for 7 days, and then the area of lesion spots was investigated. As a result, the area of lesion spots on the plant treated with the present compound 1, 3, 12, 13, 14, 15, 20, 21, 22, 24, 30, 33, 42, 54, 56, 57, 58, 63, 64, 65, 67, 69, 72, 73, 74, 77, 78, 82, 83, 84, 85, 86, 87, 94, 95, 96, 97, 98, 99, 102, 104, 105, 106, 107, 109, 110, 111, 112, 113, 114, 122, 123, 125, 131, 132, 135, 136, 137, 138, 139, 140, 141, 142, 143, 147, 148, 149, 152, 154, 157, 158, 159, 160, 161, 162, 163, 164, 165, 166, 167, 171, 172, 173, 174, 175, 176, 177, 178, 179, 180, 181, 184, 185, 186, 187, 189, 190, 191, 192, 193, 194, 203, 204, 208, 213, 214, 215, 216, 218, 219, 220, 221, 222, 224, 225, 226, 227, 234, 235, 236, 237, 238, 239, 240, 248, or 249 was 30% or less of that on an untreated plant.

Test Example 27

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (50 ppm) of any one compound of the present compounds 2, 5, 6, 7, 8, 16, 23, 31, 32, 40, 48, 51, 52, 55, 62, 76, 90, 91, 92, 93, 103, 127, 128, 145, 151, 170, and 210 was sprayed over stems and leaves of the cucumber so that it sufficiently adhered to the surface of the leaves of the cucumber. After spraying, the plant was air-dried. After one day, the plant was inoculated by sprinkling with spores of cucumber corynespora leaf spot fungus (*Corynespora cassicola*). After the inoculation, the plant was cultivated at 24° C. in the daytime and 20° C. at night for 7 days, and then the area of lesion spots was investigated. As a result, the area of lesion spots on the plant treated with the present compound 2, 5, 6, 7, 8, 16, 23, 31, 32, 40, 48, 51, 52, 55, 62, 76, 90, 91, 92, 93, 103, 127, 128, 145, 151, 170, or 210 was 30% or less of that on an untreated plant.

Test Example 28

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 1, 17, 18, 19, 23, 30, 33, 42, 43, 44, 45, 47, 56, 57, 58, 59, 60, 61, 63, 64, 66, 75, 82, 88, 97, 99, 100, 101, 104, 105, 107, 109, 112, 113, 114, 115, 116, 119, 120, 121, 122, 123, 127, 128, 129, 130, 131, 132, 135, 136, 138, 147, 148, 149, 150, 151, 152, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 189, 190, 191, 192, 193, 194, 195, 196, 203, 204, 205, 206, 207, 208, 210, 212, 213, 214, 215, 216, 218, 219, 220, 221, 222, 224, 225, 226, 234, 235, 236, 237, 238, 239, 240, 242, and 249 was sprayed over stems and leaves of the cucumber so that it sufficiently adhered to the surface of the leaves of the cucumber. After spraying, the plant was air-dried. After one day, the plant was inoculated by sprinkling with spores of cucumber anthracnose fungus (*Colletotrichum lagenarium*). After the inoculation, the plant was at first left to stand at 23° C. under high humidity condition for one day and then cultivated in a greenhouse at 24° C. in the daytime and 20° C. at night for 6 days. Thereafter, the area of lesion spots was investigated. As a result, the area of lesion spots on the plant treated with the present compound 1, 17, 18, 19, 23, 30, 33, 42, 43, 44, 45, 47, 56, 57, 58, 59, 60, 61, 63, 64, 66, 75, 82, 88, 97, 99, 100, 101, 104, 105, 107, 109, 112, 113, 114, 115, 116, 119, 120, 121, 122, 123, 127, 128, 129, 130, 131, 132, 135, 136, 138, 147, 148, 149, 150, 151, 152, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 189, 190, 191, 192, 193, 194, 195, 196, 203, 204, 205, 206, 207, 208, 210, 212, 213, 214, 215, 216, 218, 219, 220, 221, 222, 224, 225, 226, 234, 235, 236, 237, 238, 239, 240, 242, or 249 was 30% or less of that on an untreated plant.

Test Example 29

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (50 ppm) of any one compound of the present compounds 2, 5, 6, 7, 14, 20, 21, 22, 24, 31, 32, 40, 48, 51, 52, 54, 55, 71, 72, 74, 76, 77, 83, 84, 85, 86, 87, 90, 91, 93, 95, 96, 102, 103, 111, 124, 126, 133, 139, 140, 141, 142, 143, 145, and 154 was sprayed over stems and leaves of the cucumber so that it sufficiently adhered to the surface of the leaves of the cucumber. After spraying, the plant was air-dried. After one day, the plant was inoculated by sprinkling with spores of cucumber anthracnose fungus (*Colletotrichum lagenarium*). After the inoculation, the plant was at first left to stand at 23° C. under high humidity condition for one day and then cultivated in a greenhouse at 24° C. in the daytime and 20° C. at night for 6 days. Thereafter, the area of lesion spots was investigated. As a result, the area of lesion spots on the plant treated with the present compound 2, 5, 6, 7, 14, 20, 21, 22, 24, 31, 32, 40, 48, 51, 52, 54, 55, 71, 72, 74, 76, 77, 83, 84, 85, 86, 87, 90, 91, 93, 95, 96, 102, 103, 111, 124, 126, 133, 139, 140, 141, 142, 143, 145, or 154 was 30% or less of that on an untreated plant.

Test Example 30

In the present Test Example, a water dilution containing a surfactant prepared by adjusting so as to contain a predetermined concentration (500 ppm) of the present compound was used as a test chemical solution.

The above test chemical solution (0.7 mL) was added to 100 mL of deionized water to adjust the concentration of an active ingredient to 3.5 ppm. Twenty (20) heads of last instar larvae of common house mosquito (*Culex pipiens pallens*) were released in the solution and the number of dead insects was counted after 8 days.

Mortality was determined by the following equation.

Mortality (%)=(number of dead insects/number of test insects)×100

As a result, even when using any test chemical solution containing the present compound 93, 116, 215, 236, or 242, mortality of 100% was exhibited.

Test Example 31

In the present Test Example, a water dilution containing a surfactant prepared by adjusting so as to contain a predetermined concentration (500 ppm) of the present compound was used as a test chemical solution.

Cabbage was planted in each of polyethylene cups and grown until the third true leaf or the fourth true leaf was developed. The above test chemical solution was sprayed over the cabbage (*Brassicae oleracea*) at a rate of 20 mL/cup. After drying the chemical solution, the polyethylene cup having a volume of 400 mL was covered. Ten (10) heads of third instar larvae of cabbage moth (*Plutella xylostella*) were released in the cup and the cup was covered with a Tetron fabric. The cup was held at 25° C. and, after 5 days, the number of the surviving insects was counted and the mortality of insects was calculated by the following equation.

Mortality (%)=(number of dead insects/number of test insects)×100

As a result, the present compound 48 or 92 exhibited mortality of 90% or more.

Test Example 32

In the present Test Example, a water dilution containing a surfactant prepared by adjusting so as to contain a predetermined concentration (500 ppm) of the present compound was used as a test chemical solution.

Thirty (30) heads of cotton aphid (*Aphis gossypii*) (including adults and larvae) were released on the leaves of cucumber grown in a polyethylene cup until the first true leaf was developed. Next day, 20 mL of the above test chemical solution was sprayed. After 6 days, the number of the surviving insects was counted and the control value was calculated by the following equation.

Control value (%)={1−(Cb×Tai)/(Cai×Tb)}×100 wherein symbols in the equation represent the followings:
Cb: Number of insects before spraying chemical solution in untreated area;
Cai: Number of surviving insects in untreated area;
Tb: Number of insects before spraying chemical solution in treated area; and
Tai: Number of surviving insects in treated area.

As a result, the present compound 8, 20, 29, 41, 45, 59, 116, 127, 130, 131, 134, 137, 138, 148, 149, 155, 156, 157, 192, 195, 210, 219, 234, 236, or 238 showed 90% or more of the control value.

Comparative Test Example

Each of plastic pots was filled with sandy loam and wheat (cultivar: APOGEE) was sowed and grown in a greenhouse for 10 days. Then, each water dilution containing a surfactant prepared by adjusting so as to contain a predetermined concentration (500 ppm) of any one compound of 1-methyl-4-[2-(4-phenyl-phenoxymethyl)-phenyl]-1,4-dihydrotetrazol-5-one and the present compounds 223 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with 1-methyl-4-[2-(4-phenyl-phenoxymethyl)-phenyl]-1,4-dihydrotetrazol-5-one was 70% or more that on an untreated plant, whereas, the area of lesion spots on the plant treated with the present compound 223 was 30% or less of that on an untreated plant.

The invention claimed is:
1. A tetrazolinone compound represented by formula (1):

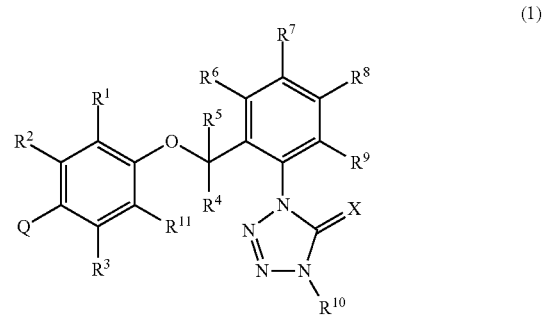

wherein Q is the following group Q4:

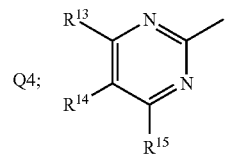

$R^1$ is a C1-C3 alkyl group optionally having one or more halogen atoms, or a halogen atom;

each of $R^2$, $R^4$, $R^5$, $R^7$, $R^8$, $R^9$, and $R^{11}$ is a hydrogen atom;

$R^3$ is a hydrogen atom or a methyl group;

$R^6$ is a C1-C3 alkyl group optionally having one or more halogen atoms, a C3-C4 cycloalkyl group, a halogen atom, or a C1-C3 alkoxy group optionally having one or more halogen atoms;

$R^{13}$, $R^{14}$, and $R^{15}$ each independently represents a C1-C3 alkyl group optionally having one or more halogen atoms, a halogen atom, a hydrogen atom, a C3-C4 cycloalkyl group optionally having one or more halogen atoms, a cyano group, or a C1-C3 alkoxy group optionally having one or more halogen atoms;

$R^{10}$ represents a C1-C3 alkyl group optionally having one or more halogen atoms, a C2-C3 alkenyl group optionally having one or more halogen atoms, a C2-C3 alkynyl group optionally having one or more halogen atoms, or a C3-C5 cycloalkyl group optionally having one or more halogen atoms; and X represents an oxygen atom or a sulfur atom.

2. A pest control agent comprising the tetrazolinone compound according to claim 1.

3. A method for controlling pests, which comprises treating plants or soil with an effective amount of the tetrazolinone compound according to claim 1.

4. The tetrazolinone compound according to claim 1, wherein X is an oxygen atom.

5. The tetrazolinone compound according to claim 4, wherein $R^{10}$ is a methyl group.

6. The tetrazolinone compound according to claim 4, wherein $R^1$ is a C1-C3 alkyl group optionally having one or more halogen atoms.

7. The tetrazolinone compound according to claim 4, wherein $R^1$ is a halogen atom.

8. The tetrazolinone compound according to claim 4, wherein $R^1$ is a methyl group.

9. The tetrazolinone compound according to claim 4, wherein $R^1$ is a chlorine atom.

10. The tetrazolinone compound according to claim 4, wherein $R^1$ is a trifluoromethyl group.

* * * * *